(12) United States Patent
Lin et al.

(10) Patent No.: US 10,160,747 B2
(45) Date of Patent: Dec. 25, 2018

(54) COMPOUNDS AND METHODS FOR KINASE MODULATION, AND INDICATIONS THEREFOR

(71) Applicant: Plexxikon Inc., Berkeley, CA (US)

(72) Inventors: Jack Lin, Hercules, CA (US); Prabha N. Ibrahim, Mountain View, CA (US); Aaron Albers, San Francisco, CA (US); John Buell, San Francisco, CA (US); Zuojun Guo, Pasadena, CA (US); Phuongly Pham, San Francisco, CA (US); Hannah Powers, San Francisco, CA (US); Songyuan Shi, Fremont, CA (US); Wayne Spevak, Berkeley, CA (US); Guoxian Wu, Foster City, CA (US); Jiazhong Zhang, Foster City, CA (US); Ying Zhang, Fremont, CA (US); Jeffrey Wu, Berkeley, CA (US)

(73) Assignee: Plexxikon Inc., Berkeley, CA (US)

( * ) Notice: Subject to any disclaimer, the term of this patent is extended or adjusted under 35 U.S.C. 154(b) by 0 days.

(21) Appl. No.: 15/460,095

(22) Filed: Mar. 15, 2017

(65) Prior Publication Data
US 2017/0267660 A1 Sep. 21, 2017

Related U.S. Application Data

(60) Provisional application No. 62/309,336, filed on Mar. 16, 2016.

(51) Int. Cl.
| | | |
|---|---|---|
| *A61K 31/506* | (2006.01) | |
| *C07D 401/14* | (2006.01) | |
| *A61K 31/437* | (2006.01) | |
| *A61K 31/444* | (2006.01) | |
| *A61K 31/4985* | (2006.01) | |
| *A61K 31/5355* | (2006.01) | |
| *A61K 45/06* | (2006.01) | |
| *C07D 401/12* | (2006.01) | |
| *C07D 471/04* | (2006.01) | |
| *C07D 487/04* | (2006.01) | |
| *C07D 498/04* | (2006.01) | |
| *C07D 417/04* | (2006.01) | |

(52) U.S. Cl.
CPC .......... *C07D 401/14* (2013.01); *A61K 31/437* (2013.01); *A61K 31/444* (2013.01); *A61K 31/4985* (2013.01); *A61K 31/506* (2013.01); *A61K 31/5355* (2013.01); *A61K 45/06* (2013.01); *C07D 401/12* (2013.01); *C07D 417/04* (2013.01); *C07D 471/04* (2013.01); *C07D 487/04* (2013.01); *C07D 498/04* (2013.01)

(58) Field of Classification Search
CPC .. C07D 401/14; C07D 401/12; C07D 417/04; C07D 471/04; C07D 487/04; C07D 498/04; A61K 31/437; A61K 31/444; A61K 31/4985; A61K 31/506; A61K 31/5355; A61K 45/06
See application file for complete search history.

(56) References Cited

U.S. PATENT DOCUMENTS

| | | |
|---|---|---|
| 7,202,266 B2 | 4/2007 | Arnold et al. |
| 7,348,338 B2 | 3/2008 | Arnold et al. |
| 7,476,746 B2 | 1/2009 | Artis et al. |
| 7,491,831 B2 | 2/2009 | Artis et al. |
| 7,498,342 B2 | 3/2009 | Ibrahim et al. |
| 7,504,509 B2 | 3/2009 | Ibrahim et al. |
| 7,517,970 B2 | 4/2009 | West et al. |
| 7,531,568 B2 | 5/2009 | Lin et al. |
| 7,572,806 B2 | 8/2009 | Arnold et al. |
| 7,585,859 B2 | 9/2009 | Ibrahim et al. |
| 7,605,168 B2 | 10/2009 | Ibrahim et al. |
| 7,723,374 B2 | 5/2010 | Artis et al. |
| 7,846,941 B2 | 12/2010 | Zhang et al. |
| 7,863,288 B2 | 1/2011 | Ibrahim et al. |
| 7,863,289 B2 | 1/2011 | Spevak et al. |
| 7,872,018 B2 | 1/2011 | Ibrahim et al. |
| 7,893,075 B2 | 2/2011 | Zhang et al. |

FOREIGN PATENT DOCUMENTS

| | | | |
|---|---|---|---|
| WO | WO-2006091671 A1 * | 8/2006 | .......... C07D 471/04 |
| WO | WO 2007/013896 | 5/2007 | |

(Continued)

OTHER PUBLICATIONS

Chemotherapy of Neoplastic Diseases in, Goodman & Gilman's: The Pharmacological Basis of Therapeutics 853-908 (L.L. Brunton et al., eds., 11th ed., 2008).*

(Continued)

*Primary Examiner* — Alexander R Pagano
(74) *Attorney, Agent, or Firm* — Sheppard Mullin Richter & Hampton LLP

(57) ABSTRACT

Disclosed are compounds of Formula I(b):

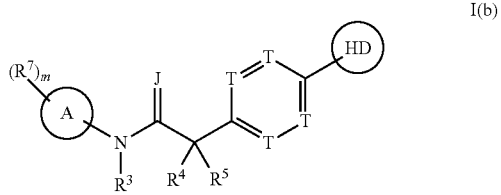

I(b)

or a pharmaceutically acceptable salt, a solvate, a tautomer, an isomer or a deuterated analog thereof, wherein Ring A, Ring HD, J, each T, $R^3$, $R^4$, $R^5$, each $R^7$, and m are as described in any of the embodiments described in this disclosure; compositions thereof; and uses thereof.

25 Claims, No Drawings
Specification includes a Sequence Listing.

(56) References Cited

U.S. PATENT DOCUMENTS

| | | |
|---|---|---|
| 7,947,708 B2 | 5/2011 | Ibrahim et al. |
| 8,053,463 B2 | 11/2011 | Lin et al. |
| 8,067,434 B2 | 11/2011 | Ibrahim et al. |
| 8,110,576 B2 | 2/2012 | Ibrahim et al. |
| 8,119,637 B2 | 2/2012 | Ibrahim et al. |
| 8,129,404 B2 | 3/2012 | Ibrahim et al. |
| 8,143,271 B2 | 3/2012 | Ibrahim et al. |
| 8,153,641 B2 | 4/2012 | Ibrahim et al. |
| 8,158,636 B2 | 4/2012 | Ibrahim et al. |
| 8,198,273 B2 | 6/2012 | Ibrahim et al. |
| 8,268,858 B2 | 9/2012 | Wu et al. |
| 8,367,828 B2 | 2/2013 | Arnold et al. |
| 8,404,700 B2 | 3/2013 | Zhang et al. |
| 8,415,469 B2 | 4/2013 | Ibrahim et al. |
| 8,461,169 B2 | 6/2013 | Zhang et al. |
| 8,470,818 B2 | 6/2013 | Ibrahim et al. |
| 8,642,606 B2 | 2/2014 | Ibrahim et al. |
| 8,673,928 B2 | 3/2014 | Ibrahim et al. |
| 8,722,702 B2 | 5/2014 | Zhang et al. |
| 8,865,735 B2 | 10/2014 | Diodone et al. |
| 8,901,118 B2 | 12/2014 | Zhang et al. |
| 8,901,301 B2 | 12/2014 | Ibrahim et al. |
| 8,912,204 B2 | 12/2014 | Ibrahim et al. |
| 9,096,593 B2 | 8/2015 | Zhang et al. |
| 9,150,570 B2 | 10/2015 | Ibrahim et al. |
| 9,169,250 B2 | 10/2015 | Zhang et al. |
| 9,260,437 B2 | 2/2016 | Ibrahim et al. |
| 9,358,235 B2 | 6/2016 | Bollag et al. |
| 9,440,969 B2 | 9/2016 | Ibrahim et al. |
| 9,447,089 B2 | 9/2016 | Desai et al. |
| 9,469,640 B2 | 10/2016 | Wu et al. |
| 9,487,515 B2 | 11/2016 | Zhang et al. |
| 9,550,768 B2 | 1/2017 | Zhang et al. |
| 9,617,267 B2 | 4/2017 | Ibrahim et al. |
| 9,624,213 B2 | 4/2017 | Ibrahim et al. |
| 2004/0142864 A1 | 7/2004 | Bremer et al. |
| 2004/0171062 A1 | 9/2004 | Hirth et al. |
| 2005/0048573 A1 | 3/2005 | Artis et al. |
| 2005/0079548 A1 | 4/2005 | Artis et al. |
| 2005/0164300 A1 | 7/2005 | Artis et al. |
| 2005/0170431 A1 | 8/2005 | Ibrahim et al. |
| 2006/0058339 A1 | 3/2006 | Ibrahim et al. |
| 2006/0135540 A1 | 6/2006 | Lin et al. |
| 2006/0160135 A1 | 7/2006 | Wang et al. |
| 2007/0066641 A1 | 3/2007 | Ibrahim et al. |
| 2007/0072904 A1 | 3/2007 | Lin et al. |
| 2008/0221127 A1 | 9/2008 | Lin et al. |
| 2008/0234349 A1 | 9/2008 | Lin et al. |
| 2008/0249137 A1 | 10/2008 | Lin et al. |
| 2010/0190777 A1 | 7/2010 | Wu et al. |
| 2011/0092538 A1 | 4/2011 | Spevak et al. |
| 2011/0112127 A1 | 5/2011 | Zhang et al. |
| 2011/0166174 A1 | 7/2011 | Ibrahim et al. |
| 2011/0183988 A1 | 7/2011 | Ibrahim et al. |
| 2012/0015966 A1 | 1/2012 | Lin et al. |
| 2012/0053177 A1 | 3/2012 | Ibrahim et al. |
| 2012/0122860 A1 | 5/2012 | Visor et al. |
| 2012/0165366 A1 | 6/2012 | Ibrahim et al. |
| 2012/0245174 A1 | 9/2012 | Ibrahim et al. |
| 2013/0237531 A1 | 9/2013 | Wu et al. |
| 2013/0261117 A1 | 10/2013 | Ibrahim et al. |
| 2013/0303534 A1 | 11/2013 | Ibrahim et al. |
| 2014/0038948 A1 | 2/2014 | Wu et al. |
| 2014/0128390 A1 | 5/2014 | Lin et al. |
| 2014/0213554 A1 | 7/2014 | Wu et al. |
| 2014/0303121 A1 | 10/2014 | Zhang et al. |
| 2014/0303187 A1 | 10/2014 | Wu et al. |
| 2014/0357612 A1 | 12/2014 | Zhang et al. |
| 2015/0133400 A1 | 5/2015 | Zhang et al. |
| 2015/0183793 A1 | 7/2015 | Zhang et al. |
| 2015/0284397 A1 | 10/2015 | Lin et al. |
| 2015/0290205 A1 | 10/2015 | Ibrahim et al. |
| 2015/0368243 A1 | 12/2015 | Ibrahim |
| 2016/0068528 A1 | 3/2016 | Zhang et al. |
| 2016/0075712 A1 | 3/2016 | Shi et al. |
| 2016/0176865 A1 | 6/2016 | Ibrahim et al. |
| 2016/0243092 A1 | 8/2016 | Bollag et al. |
| 2016/0326162 A1 | 11/2016 | Lin et al. |
| 2016/0326168 A1 | 11/2016 | Ibrahim et al. |
| 2016/0326169 A1 | 11/2016 | Ibrahim et al. |
| 2016/0339025 A1 | 11/2016 | Ibrahim et al. |
| 2016/0340357 A1 | 11/2016 | Ibrahim et al. |
| 2016/0340358 A1 | 11/2016 | Ibrahim et al. |
| 2016/0355513 A1 | 12/2016 | Desai et al. |
| 2017/0029413 A1* | 2/2017 | Holladay ............... C07B 59/002 |
| 2017/0056382 A1 | 3/2017 | Wu et al. |
| 2017/0081326 A1 | 3/2017 | Ibrahim et al. |
| 2017/0157120 A1* | 6/2017 | Ibrahim ............... A61K 31/506 |
| 2017/0283423 A1 | 10/2017 | Zhang et al. |
| 2017/0319559 A1 | 11/2017 | Wu et al. |
| 2017/0320899 A1 | 11/2017 | Zhang et al. |
| 2017/0334909 A1 | 11/2017 | Ibrahim et al. |
| 2017/0349572 A1* | 12/2017 | Wu ...................... A61K 31/519 |

FOREIGN PATENT DOCUMENTS

| | | | |
|---|---|---|---|
| WO | WO 2010/111527 | 9/2010 | |
| WO | WO 2010/129467 | 11/2010 | |
| WO | WO 2011/022473 | 2/2011 | |
| WO | WO-2012082817 A1 * | 6/2012 | ........... C07D 239/42 |
| WO | WO-2013040044 A1 * | 3/2013 | ........... C07D 403/12 |
| WO | WO 2014/141187 | 9/2014 | |
| WO | WO 2015/031613 | 3/2015 | |
| WO | WO 2017/019804 | 2/2017 | |

OTHER PUBLICATIONS

CAS Registry Nos. (2006).*
CAS Registry Nos. (2011).*
The Penguin Dictionary of Science (M.G. Clugston ed., 2009).*
K.A. Whartenby et al., 17 Expert Opinion on Investigational Drugs, 1685-1692 (2008).*
A.L. Dewar et al., 105 Blood 3127-3122 (2005).*
H. Ohno et al., 5 Molecular Cancer Therapeutics, 2634-2643 (2006).*
S. M. Pyonteck et al., 19 Nature Medicine, 1264-1272 (2013).*
C.J. Burns et al., 21 Expert Opinion on Therapeutic Patents, 147-165 (2011).*
N. Gupta et al., 185 Journal of Immunology, 2261-2272 (2010).*
W. Lin et al., 9 PLOS ONE, 1-9 (2014).*
S. Attoub et al., 62 Cancer Research, 4879-4883 (2002).*
B.P. Rubin et al., 61 Cancer Research, 8118-8121 (2001).*
R.D. Carvajal et al., 305 Journal of the American Medical Association, 2327-2334 (2011).*
A. Yasuda et al., 5 Molecular Cancer, 1-10 (2006).*
G. Di Lorenzo et al., 30 European Journal of Surgical Oncology, 987-992 (2004).*
A.Z. Al-Muhsen et al., 34 Clinical and Experimental Allergy, 911-917 (2004).*
M. Boissan, 67 Journal of Leukocyte Biology, 135-148 (2000).*
L. Reber et al., 533 European Journal of Pharmacology, 327-340 (2006).*
D.S. El Agamy et al, 690 European Journal of Pharmacology, 1-3 (2012).*
U.S. Appl. No. 15/288,558, filed Oct. 7, 2016, Zhang et al.
U.S. Appl. No. 15/370,631, filed Dec. 6, 2016, Wu et al.
U.S. Appl. No. 15/435,569, filed Feb. 17, 2017, Ibrahim et al.
U.S. Appl. No. 15/605,856, filed May 25, 2017, Ibrahim.
U.S. Appl. No. 15/606,682, filed May 26, 2017, Desai.
Liu, et al. Discovery and optimization of a highly efficacious class of 5-aryl-2-aminopyridines as FMS-like tyrosine kinase 3 (FLT3) inhibitors. Bioorg Med Chem Lett. Sep. 1, 2015;25(17):3436-41. doi: 10.1016/j.bmcl.2015.07.023. Epub Jul. 14, 2015.
U.S. Appl. No. 15/605,856, filed May 25, 2017, Ibrahim et al.
U.S. Appl. No. 15/606,682, filed May 26, 2017, Desai et al.
U.S. Appl. No. 15/669,353, filed Aug. 4, 2017, Bollag et al.
U.S. Appl. No. 15/689,931, filed Aug. 29, 2017, Ibrahim et al.
U.S. Appl. No. 15/705,097, filed Sep. 14, 2017, Ibrahim et al.

(56) References Cited

OTHER PUBLICATIONS

U.S. Appl. No. 15/713,502, filed Sep. 22, 2017, Zhang et al.
U.S. Appl. No. 15/725,197, filed Oct. 4, 2017, Ibrahim et al.
U.S. Appl. No. 15/814,179, filed Nov. 15, 2017, Zhang et al.
U.S. Appl. No. 62/473,903, filed Mar. 20, 2017, Lin et al.
U.S. Appl. No. 62/516,558, filed Jun. 7, 2017, Zhang et al.
U.S. Appl. No. 62/536,574, filed Jul. 25, 2017, Ibrahim et al.
U.S. Appl. No. 62/572,099, filed Oct. 13, 2017, Ibrahim et al.
U.S. Appl. No. 62/578,334, filed Oct. 27, 2017, Rezaei et al.
International Search Report and Written Opinion for PCT/US2017/022587 dated Jun. 22, 2017, 10 pages.
U.S. Appl. No. 15/838,268, filed Dec. 11, 2017, Zhang.
U.S. Appl. No. 15/851,639, filed Dec. 21, 2017, Wu et al.
U.S. Appl. No. 15/925,270, filed Mar. 19, 2018, Lin.
U.S. Appl. No. 15/977,772, filed May 11, 2018, Ibrahim et al.
U.S. Appl. No. 16/001,534, filed Jun. 6, 2018, Zhang et al.
Bosch et al., "Neuroinflammatory paradigms in lysosomal storage diseases", Frontiers in Neuroscience, Oct. 2015, vol. 9, Article 417, 11 pages.
Han et al., "An updated assessment of microglia depletion: current concepts and future directions", Molecular Brain, 2017, 10:25, 8 pages.
Knight et al., "Increased microglial CSF1R expression in the SIV/Macaque model of HIV CNS disease", Journal of Neuropathy & Experimental Neurology, Mar. 2018, 77(3):199-206, abstract, 7 pages.
Littlejohn, "Neurogenic neuroinflammation in fibromyalgia and complex regional pain syndrome", Nat Rev Rheumatol, Nov. 2015, 11 (11):639-48, abstract, 2 pages.
Mallard et al., "Astrocytes and microglia in acute cerebral injury underlying cerebral palsy associated with preterm birth", Pediatric Research, Jan. 2014, 75(1):234-240.
Melão "Inhibiting protein in brain cells can rejuvenate protective nerve cell coating, study shows", Multiple Sclerosis News Today, Oct. 27, 2017.
Passamonti et al., [11C]PK11195 PET in Alzheimer's disease and progressive supranuclear palsy: The NIMROD Study, Poster Session, Jun. 28, 2017.
Stefaniak et al., "Imaging of neuroinflammation in dementia: a review", J Neurol Neurosurg Psychiatry, Jan. 2016; 87(1):21-8, abstract, 2 pages.
Wong, "Immune cells in the retina can spontaneously regenerate", Science Daily, Mar. 21, 2018, 5 pages.

* cited by examiner

COMPOUNDS AND METHODS FOR KINASE MODULATION, AND INDICATIONS THEREFOR

CROSS-REFERENCE TO RELATED APPLICATIONS

This application claims the benefit under of 35 U.S.C. § 119(e) of U.S. Provisional Application 62/309,336, filed on Mar. 16, 2016, of which is hereby incorporated by reference.

SEQUENCE LISTING

The instant application contains a Sequence Listing which has been submitted electronically in ASCII format and is hereby incorporated by reference in its entirety. Said ASCII copy, created on May 15, 2017, is named 37JF-223565-US_SL.txt and is 14,769 bytes in size.

FIELD

The present disclosure relates to protein kinases and compounds which selectively modulate kinases, and uses therefor. Particular embodiments contemplate disease indications which are amenable to treatment by modulation of kinase activity by the compounds of the present disclosure.

BACKGROUND

FMS-like tyrosine kinase 3 (FLT3) is mutated in about one third of acute myeloid leukemia cases. The most frequent FLT3 mutations in acute myeloid leukemia are internal tandem duplication (ITD) mutations in the juxtamembrane domain (23%) and point mutations in the tyrosine kinase domain (10%). The most frequent kinase domain mutation is the substitution of aspartic acid at position 838 (equivalent to the human aspartic acid residue at position 835) with a tyrosine (FLT3/D835Y), converting aspartic acid to tyrosine. Even though both of these mutations constitutively activate FLT3, patients with an ITD mutation have a much poorer prognosis. It has been previously demonstrated that the FLT3/D835Y knock-in mice survive significantly longer than FLT3/ITD knock-in mice. The majority of these mice develop myeloproliferative neoplasms with a less-aggressive phenotype.

Secondary mutations in the tyrosine kinase domain (KD) is one of the most common causes of acquired clinical resistance to small molecule tyrosine kinase inhibitors (TKIs) in human cancer. Recent pharmaceutical efforts have focused on the development of "type II" kinase inhibitors, which bind to a relatively non-conserved inactive kinase conformation and exploit an allosteric site adjacent to the ATP-binding pocket as a potential means to increase kinase selectivity. Mutations in FLT3 are the common genetic alteration in patients with acute myeloid leukemia (AML) (TCGA, *N Engl J Med.* 2013, 368: 2059-74) and are primarily comprised of constitutively activating internal tandem duplication (ITD) mutations (of 1-100 amino acids) in the juxtamembrane domain, and to a lesser extent, point mutations, typically within the kinase activation loop. Secondary KD mutations in FLT3-ITD that can cause resistance to the highly potent type II FLT3 inhibitors, such as, quizartinib, which achieved a composite complete remission (CRc) rate of about 50% in relapsed or chemotherapy-refractory FLT3-ITD+AML patients treated in large phase II monotherapy studies (Tallman et al., *Blood,* 2013;122:494).

An in vitro saturation mutagenesis screen of FLT3-ITD identified five quizartinib-resistant KD mutations at three residues: the "gatekeeper" F691 residue, and two amino acid positions within the kinase activation loop (D835 and Y842), a surprisingly limited spectrum of mutations for a type II inhibitor. Mutations at two of these residues (F691L and D835V/Y/F) were subsequently identified in each of eight samples analyzed at the time of acquired clinical resistance to quizartinib (Smith et al., *Nature,* 2012;485: 260-3). This finding validated FLT3 as a therapeutic target in AML. The type II multikinase inhibitor sorafenib, which also has some clinical activity in FLT3-ITD+AML, is ineffective against all identified quizartinib resistance-causing mutants, in addition to other mutant isoforms (Smith et al.). The type I inhibitor crenolanib has been identified a type I inhibitor of quizartinib-resistant D835 mutants (Zimmerman et al. *Blood,* 2013; 122:3607-15); however, no FLT3 inhibitor has demonstrated equipotent inhibition of the F691L mutant, including the ABL/FLT3 inhibitor ponatinib, which was designed to retain activity against the problematic gatekeeper T315I mutant in BCR-ABL (Smith et al., *Blood,* 2013; 121:3165-71).

Accordingly there is a long felt need for new FLT3 inhibitors that overcome the drawbacks of the FLT3 inhibitors known in the art.

SUMMARY

The present disclosure relates to protein kinases and compounds which selectively modulate kinases, and uses therefor. Particular embodiments contemplate disease indications which are amenable to treatment by modulation of kinase activity by the compounds of the present disclosure.

One embodiment of the disclosure relates to novel compounds, as described in any of the embodiments herein, or a pharmaceutically acceptable salt, a solvate, a tautomer, an isomer or a deuterated analog thereof, wherein these novel compounds can modulate FLT3. In another embodiment the compounds described herein further modulate c-Kit, CSF-1R, or both c-Kit and CSF-1R. In another embodiment, the compounds described herein can further modulate FLT3 having an ITD mutation and optionally an F691L mutation and/or D835Y mutation.

Another embodiment of this disclosure relates to a compound of Formula I(a):

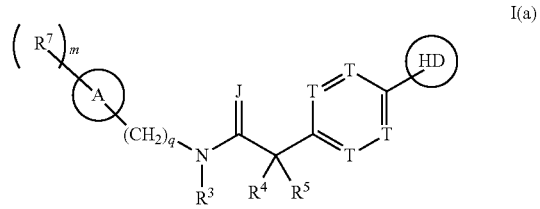

or a pharmaceutically acceptable salt, a solvate, a tautomer, an isomer or a deuterated analog thereof, wherein J is O or S;

$R^3$ is hydrogen, alkyl, or haloalkyl;

$R^4$ and $R^5$ are each independently hydrogen, halo, alkyl, haloalkyl, hydroxy, alkoxy or amino;

each T is $C(R^6)$; or one T is N and the remaining three T variables are $C(R^6)$;

each R⁶ is independently hydrogen, halo, alkyl, or alkoxy;
each R⁷ is independently halo, alkyl, haloalkyl, cycloalkyl, cycloalkylalkyl, aryl, aralkyl, heterocycloalkyl, heterocycloalkylalkyl, heteroaryl, heteroarylalkyl, cyano, —S(O)₂R²¹, or —R²⁰OR²¹, wherein each alkyl, haloalkyl, cycloalkyl, cycloalkylalkyl, aryl, aralkyl, heterocycloalkyl, heterocycloalkylalkyl, heteroaryl, heteroarylalkyl, —S(O)₂R²¹, or —R²⁰—OR²¹ is independently optionally substituted with 1 to 4 groups each independently hydroxy, halo, cyano, alkyl, or haloalkyl;

Ring A is phenyl or a 6-membered heteroaryl optionally fused to a 5- or 6-membered ring;

Ring HD is:
(i) a 9-membered fused bicyclic heterocycloalkyl or heteroaryl group having 2-3 nitrogen atoms, wherein the 9-membered fused bicyclic heterocycloalkyl or heteroaryl group is substituted with 1 to 3 groups selected from alkyl, alkoxy, cyano, —C(O)NH-alkyl, —C(O)-alkyl, —C(O)-cycloalkyl, —(CH₂)₀₋₂—N(R¹ᵇ)₂, halo, —NHC(O)-alkyl, —NHC(O)-haloalkyl, cycloalkyl, oxo, phenyl optionally substituted with 1-2 R¹¹ groups, 5-membered or 6-membered heteroaryl optionally substituted with 1-2 R¹¹ groups, or alkynyl optionally substituted with R¹⁰;

each R¹ᵇ is independently hydrogen or alkyl;

R¹⁰ is alkyl, hydroxyalkyl, alkoxyalkyl, cycloalkyl, —(CH₂)₀₋₃C(O)O-alkyl, 5- or 6-membered heteroaryl optionally substituted with 1-3 R²² or —(CH₂)₀₋₃C(O)OH;

each R¹¹ is independently a 4-6 membered heterocycloalkyl, cyano, cyanoalkyl, alkoxy, alkyl or haloalkyl;

or
(ii)

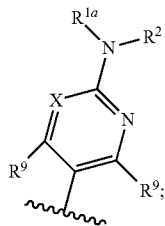

X is N or C(R⁹);
R¹ᵃ is hydrogen or alkyl;
each R⁹ is independently hydrogen, halo, amino, alkyl optionally substituted with alkoxy or hydroxy, haloalkyl or alkoxy;
R² is

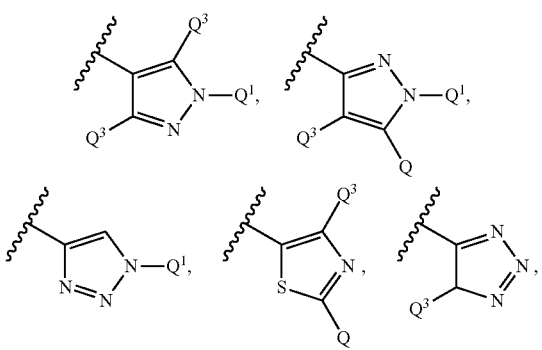

-continued

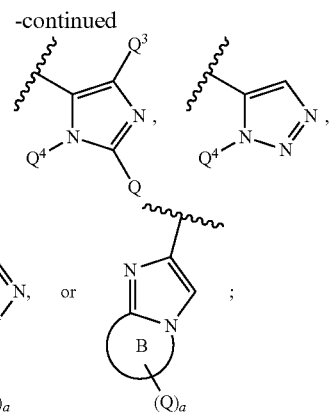

ring B is a 5 or 6-membered saturated or unsaturated ring having 0-3 heteroatoms selected from O, N, or S;

Q is hydrogen, alkyl, halo, cyano, haloalkyl, cycloalkyl, cycloalkylalkyl, heterocycloalkyl, heterocycloalkylalkyl, oxo, —R²⁰OR²¹, —R²⁰OR²³OR²¹, —R²⁰OC(O)R²¹, —R²⁰C(O)OR²¹, —R²⁰C(O)N(R²⁴)(R²⁵), —R²⁰S(O)ₜR²², —R²⁰N(R²⁴)(R²⁵), or —R²⁰N(R²⁴)C(O)R²¹, wherein each alkyl, cycloalkyl, cycloalkylalkyl, heterocycloalkyl or heterocycloalkylalkyl is independently optionally substituted with 1 to 3 groups each independently halo, oxo, amino, alkyl, haloalkyl or —R²⁰OR²¹;

Q¹ is hydrogen, alkyl, haloalkyl, cycloalkyl, cycloalkylalkyl, heterocycloalkyl, heterocycloalkylalkyl, —R²³OR²¹, —R²³OR²³OR²¹, —R²³C(O)R²¹, —R²³N(R²⁴)(R²⁵), —R²³OC(O)R²¹, —R²³C(O)OR²¹, —R²³C(O)N(R²⁴)(R²⁵), or —R²³S(O)ₜR²², wherein each alkyl, cycloalkyl, cycloalkylalkyl, heterocycloalkyl or heterocycloalkylalkyl is independently optionally substituted with 1 to 3 groups each independently halo, oxo, amino, alkyl, haloalkyl or —R²⁰OR²¹;

Q³ is hydrogen, cyano, —S—C₁-C₂ alkyl, halo, C₂-C₃ alkenyl, C₂-C₃ alkynyl, C₁-C₃ alkoxy, cyclopropyl, amino, —N(H)(C₁-C₃alkyl), —N(H)C(O)C(H)=CH₂ or C₁-C₃ alkyl, wherein each Q³ is optionally substituted with 1-3 substituents each independently halo, hydroxy or methoxy;

Q⁴ is hydrogen, cyclopropyl, C₁-C₄ alkoxy, or C₁-C₄ alkyl optionally substituted with 1-3 substituents each independently halo, hydroxy or methoxy;

a is an integer from 0 to 3;

each t is independently 0, 1 or 2;

each R²⁰ is independently alkylene, alkenylene, alkynylene or a direct bond;

each R²¹ is independently hydrogen, alkyl, haloalkyl, alkenyl, alkynyl or cycloalkyl;

each R²² is independently alkyl, haloalkyl, alkenyl, alkynyl or cycloalkyl;

each R²³ is independently alkylene, alkenylene or alkynylene;

R²⁴ and R²⁵ are each independently hydrogen or alkyl;

m is an integer from 0 to 3; and q is 0, 1, or 2.

Another embodiment of this disclosure relates to a compound of Formula I(b):

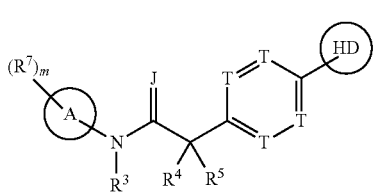

I(b)

or a pharmaceutically acceptable salt, a solvate, a tautomer, an isomer or a deuterated analog thereof, wherein
J is O or S;
$R^3$ is hydrogen, alkyl, or haloalkyl;
$R^4$ and $R^5$ are each independently hydrogen, halo, alkyl, haloalkyl, hydroxy, alkoxy or amino;
each T is $C(R^6)$; or one T is N and the remaining three T variables are $C(R^6)$;
each $R^6$ is independently hydrogen, halo, alkyl, or alkoxy;
each $R^7$ is independently halo, alkyl, haloalkyl, cycloalkyl, cycloalkylalkyl, aryl, aralkyl, heterocycloalkyl, heterocycloalkylalkyl, heteroaryl, heteroarylalkyl, cyano, —$S(O)_2R^{21}$, or —$R^{20}OR^{21}$, wherein each alkyl, haloalkyl, cycloalkyl, cycloalkylalkyl, aryl, aralkyl, heterocycloalkyl, heterocycloalkylalkyl, heteroaryl, heteroarylalkyl, —$S(O)_2R^{21}$, or —$R^{20}OR^{21}$ is independently optionally substituted with 1 to 4 groups each independently hydroxy, halo, cyano, alkyl, or haloalkyl;
Ring A is phenyl or a 6-membered heteroaryl optionally fused to a 5- or 6-membered ring;
Ring HD is:
(i) a 9-membered fused bicyclic heterocycloalkyl or heteroaryl group having 2-3 nitrogen atoms, wherein the 9-membered fused bicyclic heterocycloalkyl or heteroaryl group is substituted with 1 to 3 groups selected from alkyl, alkoxy, cyano, —C(O)NH-alkyl, —C(O)-alkyl, —C(O)-cycloalkyl, —$(CH_2)_{0-2}$—$N(R^{1b})_2$, halo, —NHC(O)-alkyl, —NHC(O)-haloalkyl, cycloalkyl, oxo, phenyl optionally substituted with 1-2 $R^{11}$ groups, 5-membered or 6-membered heteroaryl optionally substituted with 1-2 $R^{11}$ groups, or alkynyl optionally substituted with $R^{10}$);
each $R^{1b}$ is independently hydrogen or alkyl;
$R^{10}$ is alkyl, hydroxyalkyl, alkoxyalkyl, cycloalkyl, —$(CH_2)_{0-3}C(O)O$-alkyl, 5- or 6-membered heteroaryl optionally substituted with 1-3 $R^{22}$ or —$(CH_2)_{0-3}C(O)OH$;
each $R^{11}$ is independently a 4-6 membered heterocycloalkyl, cyano, cyanoalkyl, alkoxy, alkyl or haloalkyl;
or
(ii)

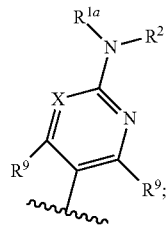

X is N or $C(R^9)$;
$R^{1a}$ is hydrogen or alkyl;
each $R^9$ is independently hydrogen, halo, amino, alkyl optionally substituted with alkoxy or hydroxy, haloalkyl or alkoxy;

$R^2$ is

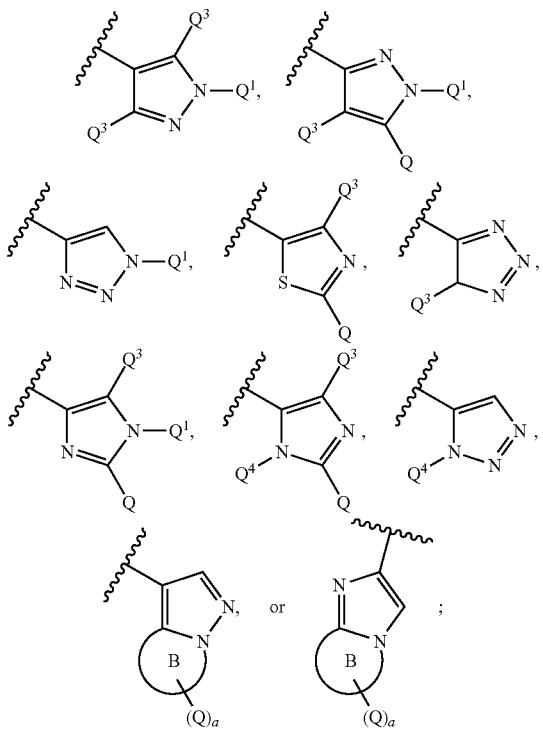

ring B is a 5 or 6-membered saturated or unsaturated ring having 0-3 heteroatoms selected from O, N, or S;
Q is hydrogen, alkyl, halo, cyano, haloalkyl, cycloalkyl, cycloalkylalkyl, heterocycloalkyl, heterocycloalkylalkyl, oxo, —$R^{20}OR^{21}$, —$R^{20}OR^{23}OR^{21}$, —$R^{20}OC(O)R^{21}$, —$R^{20}C(O)OR^{21}$, —$R^{20}C(O)N(R^{24})(R^{25})$, —$R^{20}S(O)_tR^{22}$, —$R^{20}N(R^{24})(R^{25})$, or —$R^{20}N(R^{24})C(O)R^{21}$, wherein each alkyl, cycloalkyl, cycloalkylalkyl, heterocycloalkyl or heterocycloalkylalkyl is independently optionally substituted with 1 to 3 groups each independently halo, oxo, amino, alkyl, haloalkyl or —$R^{20}OR^{21}$;
$Q^1$ is hydrogen, alkyl, haloalkyl, cycloalkyl, cycloalkylalkyl, heterocycloalkyl, heterocycloalkylalkyl, —$R^{23}OR^{21}$, —$R^{23}OR^{23}OR^{21}$, —$R^{23}C(O)R^{21}$, —$R^{23}N(R^{24})(R^{25})$, —$R^{23}OC(O)R^{21}$, —$R^{23}C(O)OR^{21}$, —$R^{23}C(O)N(R^{24})(R^{25})$, or —$R^{23}S(O)_tR^{22}$, wherein each alkyl, cycloalkyl, cycloalkylalkyl, heterocycloalkyl or heterocycloalkylalkyl is independently optionally substituted with 1 to 3 groups each independently halo, oxo, amino, alkyl, haloalkyl or —$R^{20}OR^{21}$;
$Q^3$ is hydrogen, cyano, —S—$C_1$-$C_2$ alkyl, halo, $C_2$-$C_3$ alkenyl, $C_2$-$C_3$ alkynyl, $C_1$-$C_3$ alkoxy, cyclopropyl, amino, —N(H)($C_1$-$C_3$alkyl), —N(H)C(O)C(H)=$CH_2$ or $C_1$-$C_3$ alkyl, wherein each $Q^3$ is optionally substituted with 1-3 substituents each independently halo, hydroxy or methoxy;
$Q^4$ is hydrogen, cyclopropyl, $C_1$-$C_4$ alkoxy, or $C_1$-$C_4$ alkyl optionally substituted with 1-3 substituents each independently halo, hydroxy or methoxy;
a is an integer from 0 to 3;
each t is independently 0, 1 or 2;

each $R^{20}$ is independently alkylene, alkenylene, alkynylene or a direct bond;

each $R^{21}$ is independently hydrogen, alkyl, haloalkyl, alkenyl, alkynyl or cycloalkyl;

each $R^{22}$ is independently alkyl, haloalkyl, alkenyl, alkynyl or cycloalkyl;

each $R^{23}$ is independently alkylene, alkenylene or alkynylene;

$R^{24}$ and $R^{25}$ are each independently hydrogen or alkyl; and m is an integer from 0 to 3.

Compounds of this disclosure wherein HD is defined as

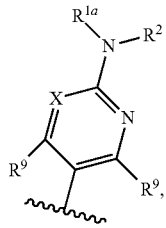

and Ring A is a phenyl or a six membered heteroaryl optionally fused to a 5- or 6-membered ring, are novel in structure and unexpectedly advantageous in function. The compounds of this disclosure overcome the deficiencies of past FLT3 inhibitors, including those disclosed in WO 2011/022473. More specifically, the compounds of this disclosure is a selection invention of WO 2011/022473 wherein the compounds of this disclosure have a novel structural motif and a moiety not specifically disclosed in WO 2011/022473, which is a cyclic group, as defined by $R^2$, attached to an amino group, and wherein the amino group is attached to a heteroaryl moiety of ring HD on the right hand side of the compounds as described herein, in combination with Ring A being defined as a phenyl or a six membered heteroaryl optionally fused to a 5 or 6 membered ring on the left hand side of the compounds as described herein. The novel compounds of this disclosure having the aforementioned novel structural motif exhibit superior and unexpectedly better potency against the mutated forms of the FLT3 tyroskine kinase enzymes, particularly the F691L mutation and/or D835Y mutation when compared to the structurally similar compounds in WO 2011/022473.

Other embodiments and subembodiments of Formula I(a) and I(b) are further described herein.

Another embodiment of the disclosure relates to a pharmaceutical composition comprising a compound according to Formula I(a) or I(b), or any embodiment and sub-embodiment of Formula I(a) or I(b) described herein, or a pharmaceutically acceptable salt, a solvate, a tautomer, an isomer or a deuterated analog of any of these compounds, and a pharmaceutically acceptable carrier or excipient.

Another embodiment of the disclosure relates to a pharmaceutical composition comprising a compound according to Formula I(a) or I(b), or any embodiment and sub-embodiment of Formula I(a) or I(b) described herein, or a pharmaceutically acceptable salt, a solvate, a tautomer, an isomer or a deuterated analog of any of these compounds, and another therapeutic agent.

Another embodiment of the disclosure relates to a method for treating a subject with a disease or condition mediated by a FLT3, c-kit, or CSF1R, said method comprising administering to the subject an effective amount of a compound according to Formula I(a) or I(b), or any embodiment and sub-embodiment of Formula I(a) or I(b) described herein, or a pharmaceutically acceptable salt, a solvate, a tautomer, an isomer or a deuterated analog of any of these compounds, wherein the disease or condition is acute myeloid leukemia, stem cell ablation and myelopreparation for stem cell transplant, primary progressive multiple sclerosis, traumatic brain injury, epilepsy, tauopathies, Erdheim-Chester Disease, Langerhans cell histocytosis, hairy cell leukemia, HIV, glioblastoma, scleroderma, anterior or posterior eye disease (including diseases of the cornea, conjunctiva, sclera or lacrimal glands), lysosomal storage diseases including mucolipodosis, alpha-mannosidosis, aspartylglucosaminuria, Batten disease, beta-mannosidosis, cystinosis, Danon disease, Fabry disease, Farber disease, fucosidosis, galactosialidosis, Gaucher disease, gangliosidosis (e.g., GM1 gangliosidosis and GM2-gangliosidosis AB variant), Krabbe disease; metachromatic leukodystrophy, mucopolysaccharidoses disorders (e.g., MPS 1—Hurler syndrome, MPS II—Hunter syndrome, MPS III—Sanfilippo (A,B,C,D), MPS IVA—Morquio, MPS IX—hyaluronidase, deficiency, MPS VI—Maroteaux-Lamy, or MPS VII—Sly syndrome), mucolipidosis type I (Sialidosis), Mucolipidosis type II (I-Cell disease), Mucolipidosis type III (Pseudo-Hurler polydystrophy), Mucolipidosis type IV, multiple sulfatase deficiency, Niemann-Pick types A, B, C; Pompe disease (glycogen storage disease), pycnodysostosis, Sandhoff disease, Schindler disease, Salla disease/sialic acid storage disease, Tay-Sachs, and Wolman disease] complex regional pain syndrome, reflex sympathetic dystrophy, muscular dystrophy, duchenne muscular dystrophy, causalgia, neuro-inflammation, neuroinflammatory disorders, benign forgetfulness, HIV, binswager type dementia, dementia with lewy bodie, prosencephaly, microencepahy, cerebral palsy, congenital hydrocephalus, abdominal dropsy, progressive supranuclear palsy, glaucoma, addiction disorders, dependencies, alcoholism, tremors, Wilson's disease, vascular dementias, multi infarct dementia, fronto temporal dementia, pseudo-dementia, bladder cancer, basal cell carcinoma, cholangiocarcinoma, colon cancer, endometrial cancer, esophageal cancer, Ewing's sarcoma, gastric cancer, glioma, hepatocellular carcinoma, Hodgkin lymphoma, laryngeal carcinoma, leukemia, liver cancer, lung cancer (such as non-small cell lung cancer and small cell lung cancer), melanoma, mesothelioma, pancreatic cancer, rectal cancer, renal cancer, squamous cell carcinoma, T cell lymphoma, thyroid cancer, monocytic leukemia, pheochromocytoma, malignant peripheral nerve cell tumors, malignant peripheral nerve sheath tumors (MPNST), cutaneous and plexiform neurofibromas, leiomyoadenomatoid tumor, fibroids, uterine fibroids, leiomyosarcoma, papillary thyroid cancer, anaplastic thyroid cancer, medullary thyroid cancer, follicular thyroid cancer, hurthle cell carcinoma, thyroid cancer, ascites, malignant ascites, mesothelioma, salivary gland tumors, mucoepidermoid carcinoma of the salivary gland, acinic cell carcinoma of the salivary gland, gastrointestinal stromal tumors (GIST), tumors that cause effusions in potential spaces of the body, pleural effusions, pericardial effusions, peritoneal effusions aka ascites, giant cell tumors (GCT), GCT of bone other sarcomas, tumor angiogenesis, paracrine tumor growth or tumors that express aberrantly or otherwise a FLT3, CSF1R, c-kit, or activating mutations or translocations of any of the foregoing.

Another embodiment of the disclosure relates to a method for treating a subject suffering from a disease or condition as described herein, said method comprising administering to the subject a pharmaceutical composition comprising a compound according to Formula I(a) or I(b), or any embodiment and sub-embodiment of Formula I(a) or I(b) described herein, or a pharmaceutically acceptable salt, a solvate, a tautomer, an isomer or a deuterated analog of any of these compounds, and another therapeutic agent, wherein the other therapeutic agent is selected from: i) an alkylating agent selected from adozelesin, altretamine, bizelesin, busulfan, carboplatin, carboquone, carmustine, chlorambucil, cisplatin, cyclophosphamide, dacarbazine, estramustine, fotemustine, hepsulfam, ifosfamide, improsulfan, irofulven, lomustine, mechlorethamine, melphalan, oxaliplatin, piposulfan, semustine, streptozocin, temozolomide, thiotepa, and treosulfan; ii) an antibiotic selected from bleomycin, dactinomycin, daunorubicin, doxorubicin, epirubicin, idarubicin, menogaril, mitomycin, mitoxantrone, neocarzinostatin, pentostatin, and plicamycin; an antimetabolite, including, but not limited to, azacitidine, capecitabine, cladribine, clofarabine, cytarabine, decitabine, floxuridine, fludarabine, 5-fluorouracil, ftorafur, gemcitabine, hydroxyurea, mercaptopurine, methotrexate, nelarabine, pemetrexed, raltitrexed, thioguanine, and trimetrexate; iii) an antibody therapy agent selected from alemtuzumab, bevacizumab, cetuximab, galiximab, gemtuzumab, panitumumab, pertuzumab, rituximab, tositumomab, trastuzumab, and 90 Y ibritumomab tiuxetan; a hormone or hormone antagonist, including, but not limited to, anastrozole, androgens, buserelin, diethylstilbestrol, exemestane, flutamide, fulvestrant, goserelin, idoxifene, letrozole, leuprolide, magestrol, raloxifene, tamoxifen, and toremifene; iv) a taxane selected from DJ-927, docetaxel, TPI 287, paclitaxel and DHA-paclitaxel; v) a retinoid selected from alitretinoin, bexarotene, fenretinide, isotretinoin, and tretinoin; vi) an alkaloid selected from etoposide, homoharringtonine, teniposide, vinblastine, vincristine, vindesine, and vinorelbine; vii) an antiangiogenic agent selected from AE-941 (GW786034, Neovastat), ABT-510, 2-methoxyestradiol, lenalidomide, and thalidomide; viii) a topoisomerase inhibitor selected from amsacrine, edotecarin, exatecan, irinotecan (also active metabolite SN-38 (7-ethyl-10-hydroxy-camptothecin)), rubitecan, topotecan, and 9-aminocamptothecin; ix) a kinase inhibitor selected from erlotinib, gefitinib, flavopiridol, imatinib mesylate, lapatinib, sorafenib, sunitinib malate, AEE-788, AG-013736, AMG 706, AMN107, BMS-354825, BMS-599626, UCN-01 (7-hydroxystaurosporine), vemurafenib, dabrafenib, trametinib, cobimetinib selumetinib and vatalanib; x) a targeted signal transduction inhibitor selected from bortezomib, geldanamycin, and rapamycin; xi) a biological response modifier selected from imiquimod, interferon-.alpha., and interleukin-2; and xii) a chemotherapeutic agent selected from 3-AP (3-amino-2-carboxyaldehyde thiosemicarbazone), altrasentan, aminoglutethimide, anagrelide, asparaginase, bryostatin-1, cilengitide, elesclomol, eribulin mesylate (E7389), ixabepilone, lonidamine, masoprocol, mitoguanazone, oblimersen, sulindac, testolactone, tiazofurin, mTOR inhibitors (e.g. sirolimus, temsirolimus, everolimus, deforolimus), PI3K inhibitors (e.g. BEZ235, GDC-0941, XL147, XL765), Cdk4 inhibitors (e.g. PD-332991), Akt inhibitors, Hsp90 inhibitors (e.g. geldanamycin, radicicol, tanespimycin), farnesyltransferase inhibitors (e.g. tipifarnib) and Aromatase inhibitors (anastrozole letrozole exemestane); xiii) a Mek inhibitor; xiv) a tyrosine kinase inhibitor as described herein; or xv) an EGFR inhibitor.

Another embodiment of the disclosure relates to a method of (1) identifying the presence of a tumor in a patient; and (2) treating the patient, identified as needing the treatment, by administering a therapeutically effective amount of a compound according to Formula I(a) or I(b), or any embodiment and sub-embodiment of Formula I(b) described herein, or a pharmaceutically acceptable salt, a solvate, a tautomer, an isomer or a deuterated analog of any of these compounds, or any composition thereof as described in the specification, wherein the step of identifying the patient includes identifying a patient having an oncogenic FLT3 mutant that is encoded by a FLT3 gene having an ITD mutation and optionally an F691L mutation and/or D835Y mutation.

DETAILED DESCRIPTION

I. Definitions

As used herein the following definitions apply unless clearly indicated otherwise:

It is noted here that as used herein and the appended claims, the singular forms "a," "an," and "the" include plural reference unless the context clearly dictates otherwise.

Unless a point of attachment indicates otherwise, the chemical moieties listed in the definitions of the variables of Formula I of this disclosure, and all the embodiments thereof, are to be read from left to right, wherein the right hand side is directly attached to the parent structure as defined. However, if a point of attachment is shown on the left hand side of the chemical moiety (e.g., -alkyloxy-($C_1$-$C_{25}$)alkyl), then the left hand side of this chemical moiety is attached directly to the parent moiety as defined. It is assumed that when considering generic descriptions of compounds of the described herein for the purpose of constructing a compound, such construction results in the creation of a stable structure. That is, one of ordinary skill in the art would recognize that theoretically some constructs which would not normally be considered as stable compounds (that is, sterically practical and/or synthetically feasible).

"Alkyl," by itself, or as part of another substituent, means, unless otherwise stated, a straight or branched chain hydrocarbon, having the number of carbon atoms designated (i.e. $C_{1-6}$ means one to six carbons). Representative alkyl groups include straight and branched chain alkyl groups having 1, 2, 3, 4, 5, 6, 7, 8, 9, 10, 11 or 12 carbon atoms. Further representative alkyl groups include straight and branched chain alkyl groups having 1, 2, 3, 4, 5, 6, 7 or 8 carbon atoms. Examples of alkyl groups include methyl, ethyl, n-propyl, isopropyl, n-butyl, t-butyl, isobutyl, sec-butyl, n-pentyl, n-hexyl, n-heptyl, n-octyl, and the like. For each of the definitions herein (e.g., alkyl, alkoxy, arylalkyl, cycloalkylalkyl, heterocycloalkylalkyl, heteroarylalkyl, etc.), when a prefix is not included to indicate the number of carbon atoms in an alkyl portion, the alkyl moiety or portion thereof will have 12 or fewer main chain carbon atoms or 8 or fewer main chain carbon atoms or 6 or fewer main chain carbon atoms. For example, $C_{1-6}$ alkyl refers to a straight or branched hydrocarbon having 1, 2, 3, 4, 5 or 6 carbon atoms and includes, but is not limited to, $C_{1-2}$ alkyl, $C_{1-4}$ alkyl, $C_{2-6}$ alkyl, $C_{2-4}$ alkyl, $C_{1-6}$ alkyl, $C_{2-8}$ alkyl, $C_{1-7}$ alkyl, $C_{2-7}$ alkyl and $C_{3-6}$ alkyl. While it is understood that substitutions are attached at any available atom to produce a stable compound, when optionally substituted alkyl is an R group of a moiety such as —OR (e.g. alkoxy), —SR (e.g. thioalkyl), —NHR (e.g. alkylamino), —C(O)NHR, and the like, substitution of the alkyl R group is such that substitution of the alkyl carbon bound to any O, S, or N of the moiety (except where N is a heteroaryl ring atom) excludes substituents that would result in any O, S, or N of the substituent (except where N is a heteroaryl ring atom) being bound to the alkyl carbon bound to any O, S, or N of the moiety.

"Alkylene" by itself or as part of another substituent means a linear or branched saturated divalent hydrocarbon moiety derived from an alkane having the number of carbon atoms indicated in the prefix. For example, (i.e., $C_{1-6}$ means one to six carbons; $C_{1-6}$ alkylene is meant to include methylene, ethylene, propylene, 2-methylpropylene, pentylene, hexylene and the like). $C_{1-4}$ alkylene includes methylene —$CH_2$—, ethylene —$CH_2CH_2$—, propylene —$CH_2CH_2CH_2$—, and isopropylene —$CH(CH_3)CH_2$—, —$CH_2CH(CH_3)$—, —$CH_2$—$(CH_2)_2CH_2$—, —$CH_2$—$CH(CH_3)CH_2$—, —$CH_2$—$C(CH_3)_2$—, —$CH_2$—$CH_2CH(CH_3)$—. Typically, an alkyl (or alkylene) group will have from 1 to 24 carbon atoms, with those groups having 10 or fewer, 8 or fewer, or 6 or fewer carbon atoms. When a prefix is not included to indicate the number of carbon atoms in an alkylene portion, the alkylene moiety or portion thereof will have 12 or fewer main chain carbon atoms or 8 or fewer main chain carbon atoms, 6 or fewer main chain carbon atoms, or 4 or fewer main chain carbon atoms, or 3 or fewer main chain carbon atoms, or 2 or fewer main chain carbon atoms, or 1 carbon atom.

"Alkenyl" refers to a linear monovalent hydrocarbon radical or a branched monovalent hydrocarbon radical having the number of carbon atoms indicated in the prefix and containing at least one double bond. For example, $C_2$-$C_6$ alkenyl is meant to include ethenyl, propenyl, and the like.

The term "alkenylene" refers to a linear monovalent hydrocarbon radical or a branched monovalent hydrocarbon radical containing at least one double bond and having the number of carbon atoms indicated in the prefix.

The term "alkynyl" refers to a monoradical of an unsaturated hydrocarbon, in some embodiments, having from 2 to 20 carbon atoms (in some embodiments, from 2 to 10 carbon atoms, e.g. 2 to 6 carbon atoms) and having from 1 to 6 carbon-carbon triple bonds e.g. 1, 2 or 3 carbon-carbon triple bonds. In some embodiments, alkynyl groups include ethynyl (—C≡CH), propargyl (or propynyl, i.e. —C≡CCH$_3$), and the like. When a prefix is not included to indicate the number of carbon atoms in an alkenyl or alkynyl portion, the alkenyl or alkynyl moiety or portion thereof will have 12 or fewer main chain carbon atoms or 8 or fewer main chain carbon atoms, 6 or fewer main chain carbon atoms or 4 or fewer main chain carbon atoms.

The term "alkynylene" refers to a linear monovalent hydrocarbon radical or a branched monovalent hydrocarbon radical containing at least one triple bond and having the number of carbon atoms indicated in the prefix. Examples of such unsaturated alkyl groups include vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers.

"Alkoxy" or "alkoxyl" refers to a —O-alkyl group, where alkyl is as defined herein. While it is understood that substitutions on alkoxy are attached at any available atom to produce a stable compound, substitution of alkoxy is such that O, S, or N (except where N is a heteroaryl ring atom), are not bound to the alkyl carbon bound to the alkoxy O. Further, where alkoxy is described as a substituent of another moiety, the alkoxy oxygen is not bound to a carbon atom that is bound to an O, S, or N of the other moiety (except where N is a heteroaryl ring atom), or to an alkene or alkyne carbon of the other moiety.

The term "alkoxyalkyl" refers to an alkyl group substituted with one or more, such as one to three alkoxy groups.

"Alkylamino" refers to a —NH-alkyl group, where alkyl is as defined herein. Exemplary alkylamino groups include $CH_3NH$—, ethylamino, and the like.

"Dialkylamino" refers to a —N(alkyl)(alkyl) group, where each alkyl is independently as defined herein. Exemplary dialkylamino groups include dimethylamino, diethylamino, ethylmethylamino, and the like. "Cycloalkylamino" denotes the group —$NR^{dd}R^{ee}$, where $R^{dd}$ and $R^{ee}$ combine with the nitrogen to form a 5-7 membered heterocycloalkyl ring, where the heterocycloalkyl may contain an additional heteroatom within the ring, such as O, N, or S, and may also be further substituted with alkyl. Alternatively, "cycloalkylamino" refers to a —NH-cycloalkyl group, where cycloalkyl is as defined herein.

"Amino" or "amine" denotes the group —$NH_2$.

"Cycloalkyl" or "Carbocycle" by itself, or as part of another substituent, unless otherwise stated, refers to saturated or unsaturated, non-aromatic monocyclic, bicyclic or tricyclic carbon ring systems having the number of carbon atoms indicated in the prefix or if unspecified having 3-10, also 3-8, and also 3-6, ring members per ring, such as cyclopropyl, cyclopentyl, cyclohexyl, 1-cyclohexenyl, adamantyl, and the like, where one or two ring carbon atoms may optionally be replaced by a carbonyl. Cycloalkyl refers to hydrocarbon rings having the indicated number of ring atoms (e.g., $C_{3-8}$ cycloalkyl means three to eight ring carbon atoms). "Cycloalkyl" or "carbocycle" may form a bridged ring or a spirocycloalkyl ring. In some embodiments, two possible points of attachment on a carbon join together to form a spirocycloalkyl ring. The cycloalkyl group may have one or more double or triple bond(s), in which case they would be termed cycloalkenyl and cycloalkynyl, respectively.

"Cycloalkylalkyl" refers to an -(alkylene)-cycloalkyl group where alkylene as defined herein has the indicated number of carbon atoms or if unspecified having six or fewer, or four or fewer main chain carbon atoms; and cycloalkyl is as defined herein has the indicated number of carbon atoms or if unspecified having 3-10, also 3-8, and also 3-6, ring members per ring. $C_{3-8}$cycloalkyl-$C_{1-2}$alkyl is meant to have 3 to 8 ring carbon atoms and 1 to 2 alkylene chain carbon atoms. Exemplary cycloalkylalkyl includes, e.g., cyclopropylmethylene, cyclobutylethylene, cyclobutylmethylene, and the like.

The term "cyano" refers to the group —CN.

The term "cyanoalkyl" or "cyanoalkylene" refers to an alkyl or alkylene as defined herein substituted by at least one cyano group as defined herein.

"Aryl" by itself, or as part of another substituent, unless otherwise stated, refers to a monocyclic, bicyclic or polycyclic polyunsaturated aromatic hydrocarbon radical containing 6 to 14 ring carbon atoms, which can be a single ring or multiple rings (up to three rings) which are fused together or linked covalently. Non-limiting examples of unsubstituted aryl groups include phenyl, 1-naphthyl and 2-naphthyl. The term "arylene" refers to a divalent aryl, wherein the aryl is as defined herein.

"Arylalkyl" or "aralkyl" refers to -(alkylene)-aryl, where the alkylene group is as defined herein and has the indicated number of carbon atoms, or if unspecified having six or fewer main chain carbon atoms or four or fewer main chain carbon atoms; and aryl is as defined herein. Examples of arylalkyl include benzyl, phenethyl, 1-methylbenzyl, and the like.

The term "haloalkyl" refers to an alkyl substituted by one to seven halogen atoms. Haloalkyl includes monohaloalkyl or polyhaloalkyl. For example, the term "$C_{1-6}$ haloalkyl" is mean to include trifluoromethyl, difluoromethyl, 2,2,2-trifluoroethyl, 4-chlorobutyl, 3-bromopropyl, and the like.

"Halogen" or "halo" refers to all halogens, that is, chloro (Cl), fluoro (F), bromo (Br), or iodo (I).

"Heteroatom" is meant to include oxygen (O), nitrogen (N), and sulfur (S).

"Heteroaryl" by itself, or as part of another substituent, refers to a monocyclic aromatic ring radical containing 5 or 6 ring atoms, or a bicyclic aromatic radical having 8 to 10 atoms, containing one or more, 1-4, 1-3, or 1-2, heteroatoms independently selected from the group consisting of O, S, and N. Heteroaryl is also intended to include oxidized S or N, such as sulfinyl, sulfonyl and N-oxide of a tertiary ring nitrogen. A carbon or nitrogen atom is the point of attachment of the heteroaryl ring structure such that a stable compound is produced. Examples of heteroaryl groups include, but are not limited to, pyridyl, pyridazinyl, pyrazinyl, indolizinyl, benzo[b]thienyl, quinazolinyl, purinyl, indolyl, quinolinyl, pyrimidinyl, pyrrolyl, pyrazolyl, oxazolyl, thiazolyl, thienyl, isoxazolyl, oxathiadiazolyl, isothiazolyl, tetrazolyl, imidazolyl, triazolyl, furanyl, benzofuryl, indolyl, triazinyl, quinoxalinyl, cinnolinyl, phthalaziniyl, benzotriazinyl, benzimidazolyl, benzopyrazolyl, benzotriazolyl, benzisoxazolyl, isobenzofuryl, isoindolyl, indolizinyl, benzotriazinyl, thienopyridyl, thienopyrimidinyl, pyrazolopyrimidinyl, imidazopyridines, benzothiaxolyl, benzothienyl, quinolyl, isoquinolyl, indazolyl, pteridinyl and thiadiazolyl. "Nitrogen containing heteroaryl" refers to heteroaryl wherein any of the heteroatoms is N.

"Heteroarylene" by itself or as part of another substituent, refers to a divalent heteroaryl, where the heteroaryl is as defined herein.

"Heteroarylalkyl" refers to -(alkylene)-heteroaryl, where the alkylene group is as defined herein and has the indicated number of carbon atoms, or if unspecified having six or fewer main chain carbon atoms or four or fewer main chain carbon atoms; and heteroaryl is as defined herein.

"Heterocycloalkyl" refers to a saturated or unsaturated non-aromatic cycloalkyl group that contains from one to five heteroatoms selected from N, O, and S, wherein the nitrogen and sulfur atoms are optionally oxidized, and the nitrogen atom(s) are optionally quaternized, the remaining ring atoms being C, where one or two C atoms may optionally be replaced by a carbonyl. The heterocycloalkyl may be a monocyclic, a bicyclic or a polycyclic ring system of 3 to 12, or 4 to 10 ring atoms, or 5 to 8 ring atoms in which one to five ring atoms are heteroatoms selected from —N=, —N—, —O—, —S—, —S(O)—, or —S(O)$_2$— and further wherein one or two ring atoms are optionally replaced by a —C(O)— group. The heterocycloalkyl can also be a heterocyclic alkyl ring fused (including spirocyclic groups) with a cycloalkyl, an aryl or a heteroaryl ring. Non limiting examples of heterocycloalkyl groups include pyrrolidinyl, piperidinyl, imidazolidinyl, benzofuranyl, pyrazolidinyl, morpholinyl, and the like. A heterocycloalkyl group can be attached to the remainder of the molecule through a ring carbon or a heteroatom.

"Heterocycloalkylalkyl" or "heterocyclylalkyl" refers to -(alkylene)-heterocycloalkyl, where the alkylene group is as defined herein and has the indicated number of carbon atoms, or if unspecified having six or fewer main chain carbon atoms or four or fewer main chain carbon atoms; and heterocycloalkyl is as defined herein.

"Hydroxyl" or "hydroxy" refers to the group —OH.

The term "hydroxyalkyl" or "hydroxyalkylene" refers to an alkyl or alkylene as defined herein substituted by at least one hydroxy group as defined herein.

The term "oxo" refers to C(=O) or (O). In some embodiments, two possible points of attachment on a carbon form an oxo group.

"Protecting group" refers to a grouping of atoms that when attached to a reactive group in a molecule masks, reduces or prevents that reactivity. Examples of protecting groups can be found in T. W. Greene and P. G. Wuts, PROTECTIVE GROUPS IN ORGANIC CHEMISTRY, (Wiley, 4th ed. 2006), Beaucage and Iyer, *Tetrahedron* 48:2223-2311 (1992), and Harrison and Harrison et al., COMPENDIUM OF SYNTHETIC ORGANIC METHODS, Vols. 1-8 (John Wiley and Sons. 1971-1996). Representative amino protecting groups include formyl, acetyl, trifluoroacetyl, benzyl, benzyloxycarbonyl (CBZ), tert-butoxycarbonyl (Boc), trimethyl silyl (TMS), 2-trimethylsilyl-ethanesulfonyl (SES), trityl and substituted trityl groups, allyloxycarbonyl, 9-fluorenylmethyloxycarbonyl (FMOC), nitro-veratryloxycarbonyl (NVOC), tri-isopropylsilyl (TIPS), phenylsulphonyl and the like (see also, Boyle, A. L. (Editor), carbamates, amides, N-sulfonyl derivatives, groups of formula —C(O)OR$^a$, wherein R$^a$ is, for example, methyl, ethyl, t-butyl, benzyl, phenylethyl, CH$_2$=CHCH$_2$—, and the like, groups of the formula —C(O)R', wherein R' is, for example, methyl, phenyl, trifluoromethyl, and the like, groups of the formula —SO$_2$R", wherein R" is, for example, tolyl, phenyl, trifluoromethyl, 2,2,5,7,8-pentamethylchroman-6-yl, 2,3,6-trimethyl-4-methoxyphenyl, and the like, and silanyl containing groups, such as 2-trimethylsilylethoxymethyl, t-butyldimethylsilyl, triisopropylsilyl, and the like, CURRENT PROTOCOLS IN NUCLEIC ACID CHEMISTRY, John Wiley and Sons, New York, Volume 1, 2000).

"Optional" or "Optionally" as used throughout the disclosure means that the subsequently described event or circumstance may or may not occur, and that the description includes instances where the event or circumstance occurs and instances in which it does not. For example, the phrase "the aromatic group" is optionally substituted with one or two alkyl substituents" means that the alkyl may but need not be present, and the description includes situations where the aromatic group is substituted with an alkyl group and situations where the aromatic group is not substituted with the alkyl group.

As used herein, the term "composition" refers to a formulation suitable for administration to an intended animal subject for therapeutic purposes that contains at least one pharmaceutically active compound and at least one pharmaceutically acceptable carrier or excipient.

The term "pharmaceutically acceptable" indicates that the indicated material does not have properties that would cause a reasonably prudent medical practitioner to avoid administration of the material to a patient, taking into consideration the disease or conditions to be treated and the respective route of administration. For example, it is commonly required that such a material be essentially sterile, e.g., for injectables.

"Pharmaceutically acceptable salt" refers to a salt which is acceptable for administration to a patient, such as a mammal (e.g., salts having acceptable mammalian safety for a given dosage regime). Such salts can be derived from pharmaceutically acceptable inorganic or organic bases and from pharmaceutically-acceptable inorganic or organic acids, depending on the particular substituents found on the compounds described herein. When compounds of the present disclosure contain relatively acidic functionalities, base addition salts can be obtained by contacting the neutral form of such compounds with a sufficient amount of the desired base, either neat or in a suitable inert solvent. Salts derived from pharmaceutically acceptable inorganic bases include aluminum, ammonium, calcium, copper, ferric, ferrous, lithium, magnesium, manganic, manganous, potassium, sodium, zinc and the like. Salts derived from pharmaceutically acceptable organic bases include salts of primary, secondary, tertiary and quaternary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, N,N'-dibenzylethylenediamine, chloroprocaine, choline, diethanolamine, meglumine (N-methyl-glucamine) and the like. When compounds of the present disclosure contain relatively basic functionalities, acid addition salts can be obtained by contacting the neutral form of such compounds with a sufficient amount of the desired acid, either neat or in a suitable inert solvent. Salts derived from pharmaceutically acceptable acids include acetic, trifluoroacetic, propionic, ascorbic, benzenesulfonic, benzoic, camphosulfonic, citric, ethanesulfonic, fumaric, glycolic, gluconic, glucoronic, glutamic, hippuric, hydrobromic, hydrochloric, isethionic, lactic, lactobionic, maleic, malic, mandelic, methanesulfonic, mucic, naphthalenesulfonic, nicotinic, nitric, pamoic, pantothenic, phosphoric, succinic, sulfuric, hydroiodic, carbonic, tartaric, p-toluenesulfonic, pyruvic, aspartic, benzoic, anthranilic, mesylic, salicylic, p-hydroxybenzoic, phenylacetic, embonic (pamoic), ethanesulfonic, benzenesulfonic, 2-hydroxyethanesulfonic, sulfanilic, stearic, cyclohexylaminosulfonic, algenic, hydroxybutyric, galactaric and galacturonic acid and the like.

Also included are salts of amino acids such as arginate and the like, and salts of organic acids like glucuronic or galactunoric acids and the like (see, for example, Berge, S. M. et al, "Pharmaceutical Salts," J. Pharmaceutical Science, 1977, 66:1-19). Certain specific compounds of the present disclosure contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present disclosure.

As used herein in connection with compounds of the disclosure, the term "synthesizing" and like terms means chemical synthesis from one or more precursor materials.

The compounds of the present disclosure may also contain unnatural proportions of atomic isotopes at one or more of the atoms that constitute such compounds. For example, the compounds may be radiolabeled with radioactive isotopes, such as for example tritium ($^3H$), iodine-125 ($^{125}I$), carbon-14 ($^{14}C$), carbon-11 ($^{11}C$) or fluorine-18 ($^{18}F$). All isotopic variations of the compounds of the present disclosure, whether radioactive or not, are intended to be encompassed within the scope of the present disclosure.

The term deuterated" as used herein alone or as part of a group, means substituted deuterium atoms. The term "deuterated analog" as used herein alone or as part of a group, means substituted deuterium atoms in place of hydrogen. The deuterated analog of the disclosure may be a fully or partially deuterium substituted derivative. In some embodiments, the deuterium substituted derivative of the disclosure holds a fully or partially deuterium substituted alkyl, aryl or heteroaryl group.

The disclosure also embraces isotopically-labeled compounds of the present disclosure which are identical to those recited herein, but for the fact that one or more atoms are replaced by an atom having an atomic mass or mass number different from the atomic mass or mass number usually found in nature. Examples of isotopes that can be incorporated into compounds of the disclosure include isotopes of hydrogen, carbon, nitrogen, oxygen, phosphorous, fluorine, and chlorine, such as, but not limited to $^2H$ (deuterium, D), $^3H$ (tritium), $^{11}C$, $^{13}C$, $^{14}C$, $^{15}N$, $^{18}F$, $^{31}F$, $^{32}F$, $^{35}S$, $^{36}Cl$, and $^{125}I$. Unless otherwise stated, when a position is designated specifically as "H" or "hydrogen," the position is understood to have hydrogen at its natural abundance isotopic composition or its isotopes, such as deuterium (D) or tritium ($^3H$). Certain isotopically-labeled compounds of the present disclosure (e.g., those labeled with $^3H$ and $^{14}C$) are useful in compound and/or substrate tissue distribution assays. Tritiated (i.e., $^3H$) and carbon-14 (i.e., $^{14}C$) and fluorine-18 ($^{18}F$) isotopes are useful for their ease of preparation and detectability. Further, substitution with heavier isotopes such as deuterium (i.e., $^2H$) may afford certain therapeutic advantages resulting from greater metabolic stability (e.g., increased in vivo half-life or reduced dosage requirements) and hence may be preferred in some circumstances. Isotopically labeled compounds of the present disclosure can generally be prepared by following procedures analogous to those described in the Schemes and in the Examples herein below, by substituting an isotopically labeled reagent for a non-isotopically labeled reagent.

"Prodrugs" means any compound which releases an active parent drug according to Formula I in vivo when such prodrug is administered to a mammalian subject. Prodrugs of a compound of Formula I are prepared by modifying functional groups present in the compound of Formula I in such a way that the modifications may be cleaved in vivo to release the parent compound. Prodrugs may be prepared by modifying functional groups present in the compounds in such a way that the modifications are cleaved, either in routine manipulation or in vivo, to the parent compounds. Prodrugs include compounds of Formula I wherein a hydroxy, amino, carboxyl or sulfhydryl group in a compound of Formula I is bonded to any group that may be cleaved in vivo to regenerate the free hydroxyl, amino, or sulfhydryl group, respectively. Examples of prodrugs include, but are not limited to esters (e.g., acetate, formate, and benzoate derivatives), amides, guanidines, carbamates (e.g., N,N-dimethylaminocarbonyl) of hydroxy functional groups in compounds of Formula I, and the like. Preparation, selection, and use of prodrugs is discussed in T. Higuchi and V. Stella, "Pro-drugs as Novel Delivery Systems," Vol. 14 of the A.C.S. Symposium Series; "Design of Prodrugs," ed. H. Bundgaard, Elsevier, 1985; and in Bioreversible Carriers in Drug Design, ed. Edward B. Roche, American Pharmaceutical Association and Pergamon Press, 1987, each of which are hereby incorporated by reference in their entirety.

"Tautomer" means compounds produced by the phenomenon wherein a proton of one atom of a molecule shifts to another atom. See, March, *Advanced Organic Chemistry: Reactions, Mechanisms and Structures*, Fourth Edition, John Wiley & Sons, pages 69-74 (1992). The tautomers also refer to one of two or more structural isomers that exist in equilibrium and are readily converted from one isomeric form to another. Examples of include keto-enol tautomers, such as acetone/propen-2-ol, imine-enamine tautomers and the like, ring-chain tautomers, such as glucose/2,3,4,5,6-pentahydroxy-hexanal and the like, the tautomeric forms of heteroaryl groups containing a —N=C(H)—NH— ring atom arrangement, such as pyrazoles, imidazoles, benzimidazoles, triazoles, and tetrazoles. Where the compound contains, for example, a keto or oxime group or an aromatic moiety, tautomeric isomerism (tautomerism) can occur. The compounds described herein may have one or more tautomers and therefore include various isomers. A person of ordinary skill in the art would recognize that other tautomeric ring atom arrangements are possible. All such isomeric forms of these compounds are expressly included in the present disclosure.

"Isomers" mean compounds having identical molecular Formulae but differ in the nature or sequence of bonding of their atoms or in the arrangement of their atoms in space. Isomers that differ in the arrangement of their atoms in space are termed "stereoisomers." "Stereoisomer" and "stereoisomers" refer to compounds that exist in different stereoisomeric forms if they possess one or more asymmetric centers or a double bond with asymmetric substitution and, therefore, can be produced as individual stereoisomers or as mixtures. Stereoisomers include enantiomers and diastereomers. Stereoisomers that are not mirror images of one another are termed "diastereomers" and those that are non-superimposable mirror images of each other are termed "enantiomers." When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture." Unless otherwise indicated, the description is intended to include individual stereoisomers as well as mixtures. The methods for the determination of stereochemistry and the separation of stereoisomers are well-known in the art (see discussion in Chapter 4 of ADVANCED ORGANIC CHEMISTRY, 6th edition J. March, John Wiley and Sons, New York, 2007) differ in the chirality of one or more stereocenters.

Certain compounds of the present disclosure can exist in unsolvated forms as well as solvated forms, including hydrated forms. "Hydrate" refers to a complex formed by combination of water molecules with molecules or ions of the solute. "Solvate" refers to a complex formed by combination of solvent molecules with molecules or ions of the solute. The solvent can be an organic compound, an inorganic compound, or a mixture of both. Solvate is meant to include hydrate. Some examples of solvents include, but are not limited to, methanol, N,N-dimethylformamide, tetrahydrofuran, dimethylsulfoxide, and water. In general, the solvated forms are equivalent to unsolvated forms and are encompassed within the scope of the present disclosure. Certain compounds of the present disclosure may exist in multiple crystalline or amorphous forms. In general, all physical forms are equivalent for the uses contemplated by the present disclosure and are intended to be within the scope of the present disclosure.

"Solid form" refers to a solid preparation (i.e. a preparation that is neither gas nor liquid) of a pharmaceutically active compound that is suitable for administration to an intended animal subject for therapeutic purposes. The solid form includes any complex, such as a salt, co-crystal or an amorphous complex, as well as any polymorph of the compound. The solid form may be substantially crystalline, semi-crystalline or substantially amorphous. The solid form may be administered directly or used in the preparation of a suitable composition having improved pharmaceutical properties. For example, the solid form may be used in a formulation comprising at least one pharmaceutically acceptable carrier or excipient.

As used herein in connection with amino acid or nucleic acid sequence, the term "isolate" indicates that the sequence is separated from at least a portion of the amino acid and/or nucleic acid sequences with which it would normally be associated.

In connection with amino acid or nucleic sequences, the term "purified" indicates that the subject molecule constitutes a significantly greater proportion of the biomolecules in a composition than the proportion observed in a prior composition, e.g., in a cell culture. The greater proportion can be 2-fold, 5-fold, 10-fold, or more than 10-fold, with respect to the proportion found in the prior composition.

In the context of the use, testing, or screening of compounds that are or may be modulators, the term "contacting" means that the compound(s) are caused to be in sufficient proximity to a particular molecule, complex, cell, tissue, organism, or other specified material that potential binding interactions and/or chemical reaction between the compound and other specified material can occur.

As used herein, the term "subject" refers to a living organism that is treated with compounds as described herein, including, but not limited to, any mammal, such as a human, other primates, sports animals, animals of commercial interest such as cattle, farm animals such as horses, or pets such as dogs and cats.

The term "administering" refers to oral administration, administration as a suppository, topical contact, intravenous, intraperitoneal, intramuscular, intralesional, intranasal or subcutaneous administration, or the implantation of a slow-release device e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc.

In the present context, the term "therapeutically effective" or "effective amount" indicates that a compound or material or amount of the compound or material when administered is sufficient or effective to prevent, alleviate, or ameliorate one or more symptoms of a disease, disorder or medical condition being treated, and/or to prolong the survival of the subject being treated. The therapeutically effective amount will vary depending on the compound, the disease, disorder or condition and its severity and the age, weight, etc., of the mammal to be treated. In general, satisfactory results in subjects are indicated to be obtained at a daily dosage of from about 0.1 to about 10 g/kg subject body weight. In some embodiments, a daily dose ranges from about 0.10 to 10.0 mg/kg of body weight, from about 1.0 to 3.0 mg/kg of body weight, from about 3 to 10 mg/kg of body weight, from about 3 to 150 mg/kg of body weight, from about 3 to 100 mg/kg of body weight, from about 10 to 100 mg/kg of body weight, from about 10 to 150 mg/kg of body weight, or from about 150 to 1000 mg/kg of body weight. The dosage can be conveniently administered, e.g., in divided doses up to four times a day or in sustained-release form.

By "assaying" is meant the creation of experimental conditions and the gathering of data regarding a particular result of the exposure to specific experimental conditions. For example, enzymes can be assayed based on their ability to act upon a detectable substrate. A compound can be assayed based on its ability to bind to a particular target molecule or molecules.

As used herein, the terms "ligand" and "modulator" are used equivalently to refer to a compound that changes (i.e., increases or decreases) the activity of a target biomolecule, e.g., an enzyme such as a kinase. Generally a ligand or modulator will be a small molecule, where "small molecule" refers to a compound with a molecular weight of 1500 Daltons or less, 1000 Daltons or less, 800 Daltons or less, or 600 Daltons or less. Thus, an "improved ligand" is one that possesses better pharmacological and/or pharmacokinetic properties than a reference compound, where "better" can be defined by one skilled in the relevant art for a particular biological system or therapeutic use.

The term "binds" in connection with the interaction between a target and a potential binding compound indicates that the potential binding compound associates with the target to a statistically significant degree as compared to association with proteins generally (i.e., non-specific binding). Thus, the term "binding compound" refers to a compound that has a statistically significant association with a target molecule. In some embodiments, a binding compound interacts with a specified target with a dissociation constant ($K_D$) of 1 mM or less, 1 µM or less, 100 nM or less, 10 nM or less, or 1 nM or less. In the context of compounds binding to a target, the terms "greater affinity" and "selective" indicates that the compound binds more tightly than a reference compound, or than the same compound in a reference condition, i.e., with a lower dissociation constant. In some embodiments, the greater affinity is at least 2, 3, 4, 5, 8, 10, 50, 100, 200, 400, 500, 1000, or 10,000-fold greater affinity.

The terms "prevent," "preventing," "prevention" and grammatical variations thereof as used herein, refers to a method of partially or completely delaying or precluding the onset or recurrence of a disease, disorder or condition and/or one or more of its attendant symptoms or barring a subject from acquiring or reacquiring a disorder or condition or reducing a subject's risk of acquiring or requiring a disorder or condition or one or more of its attendant symptoms.

"Unit dosage form" refers to a composition intended for a single administration to treat a subject suffering from a disease or medical condition. Each unit dosage form typically comprises each of the active ingredients of this disclosure plus pharmaceutically acceptable excipients. Examples of unit dosage forms are individual tablets, individual capsules, bulk powders, liquid solutions, ointments, creams, eye drops, suppositories, emulsions or suspensions. Treatment of the disease or condition may require periodic administration of unit dosage forms, for example: one unit dosage form two or more times a day, one with each meal, one every four hours or other interval, or only one per day. The expression "oral unit dosage form" indicates a unit dosage form designed to be taken orally.

In addition, abbreviations as used herein have respective meanings as follows:

| | |
|---|---|
| ° C. | Degree Celsius |
| ATP | Adenosine triphosphate |
| BOC | tert-Butoxycarbonyl |
| BSA | Bovine serum albumin |
| DEAE | Diethylaminoethyl |
| DMEM | Dulbecco's Modified Eagle's Medium |
| DMF | Dimethylformamide |
| DMSO | Dimethylsulfoxide |
| DTT | Dithiothreitol |
| EDTA | Ethylenediaminetetraacetic acid |
| Et | Ethyl |
| FBS | Fetal bovine serum |
| g | Gram |
| Hepes | 4-(2-hydroxyethyl)-1-piperazineethanesulfonic acid |
| M | Molar |
| [M + H⁺]⁺ | Mass peak plus hydrogen |
| MEM | Minimum essential medium |
| mg | Milligram |
| mL/ml | Milliliter |
| mM | Millimolar |
| mmol | Millimole |
| MS ESI | Mass spectrometry electrospray ionization |
| nM | Nanomolar |
| NEAA | Non-Essential Amino Acids |
| ng | nanogram |
| NMP | N-Methyl-2-pyrrolidone |
| PBS | Phosphate buffered saline |
| PBST | Phosphate buffered saline with Tween |
| Ph | Phenyl |
| PMB | p-Methoxybenzyl |
| RP-HPLC | Reverse phase high performance liquid chromatography |
| rpm | Revolutions per minute |
| s | Second(s) |
| SEM | trimethylsilylethoxymethyl |
| TBAF | Tetra-n-butylammonium fluoride |
| TFA | Trifluoroacetic acid |
| THF | Tetrahydrofuran |
| wt | weight |
| µg | Microgram |
| µL/µl | Microliter |
| µM | Micromolar |

II. Compounds

Embodiment 1 of this disclosure relates to a compound of Formula I(a):

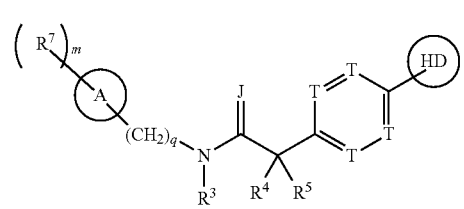

I(a)

or a pharmaceutically acceptable salt, a solvate, a tautomer, an isomer or a deuterated analog thereof, wherein:

J is O or S;

$R^3$ is hydrogen, alkyl, or haloalkyl;

$R^4$ and $R^5$ are each independently hydrogen, halo, alkyl, haloalkyl, hydroxy, alkoxy or amino;

each T is $C(R^6)$; or one T is N and the remaining three T variables are $C(R^6)$;

each $R^6$ is independently hydrogen, halo, alkyl, or alkoxy;

each $R^7$ is independently halo, alkyl, haloalkyl, cycloalkyl, cycloalkylalkyl, aryl, aralkyl, heterocycloalkyl, heterocycloalkylalkyl, heteroaryl, heteroarylalkyl, cyano, —$S(O)_2R^{21}$, or —$R^{20}OR^{21}$, wherein each alkyl, haloalkyl, cycloalkyl, cycloalkylalkyl, aryl, aralkyl, heterocycloalkyl, heterocycloalkylalkyl, heteroaryl, heteroarylalkyl, —$S(O)_2R^{21}$, or —$R^{20}OR^{21}$ is independently optionally substituted with 1 to 4 groups each independently hydroxy, halo, cyano, alkyl, or haloalkyl;

Ring A is phenyl or a 6-membered heteroaryl optionally fused to a 5- or 6-membered ring;

Ring HD is:

(i) a 9-membered fused bicyclic heterocycloalkyl or heteroaryl group having 2-3 nitrogen atoms, wherein the 9-membered fused bicyclic heterocycloalkyl or heteroaryl group is substituted with 1 to 3 groups selected from alkyl, alkoxy, cyano, —C(O)NH-alkyl, —C(O)-alkyl, —C(O)-cycloalkyl, —(CH$_2$)$_{0-2}$—N(R$^{1b}$)$_2$, halo, —NHC(O)-alkyl, —NHC(O)-haloalkyl, cycloalkyl, oxo, phenyl optionally substituted with 1-2 R$^{11}$ groups, 5-membered or 6-membered heteroaryl optionally substituted with 1-2 R$^{11}$ groups, or alkynyl optionally substituted with R$^{10}$;

each R$^{1b}$ is independently hydrogen or alkyl;

R$^{10}$ is alkyl, hydroxyalkyl, alkoxyalkyl, cycloalkyl, —(CH$_2$)$_{0-3}$C(O)O-alkyl, 5- or 6-membered heteroaryl optionally substituted with 1-3 R$^{22}$ or —(CH$_2$)$_{0-3}$C(O)OH;

each R$^{11}$ is independently a 4-6 membered heterocycloalkyl, cyano, cyanoalkyl, alkoxy, alkyl or haloalkyl;

or (ii)

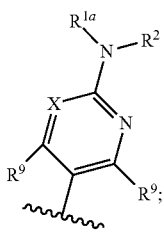

X is N or C(R$^9$);

R$^{1a}$ is hydrogen or alkyl;

each R$^9$ is independently hydrogen, halo, amino, alkyl optionally substituted with alkoxy or hydroxy, haloalkyl or alkoxy;

R$^2$ is

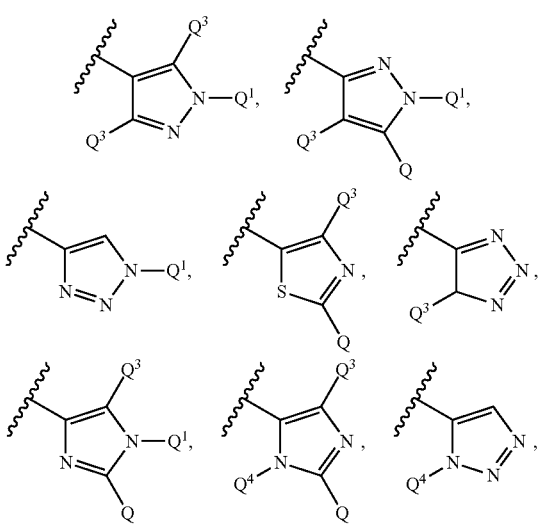

-continued

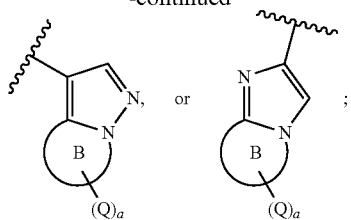

ring B is a 5 or 6-membered saturated or unsaturated ring having 0-3 heteroatoms selected from O, N, or S;

Q is hydrogen, alkyl, halo, cyano, haloalkyl, cycloalkyl, cycloalkylalkyl, heterocycloalkyl, heterocycloalkylalkyl, oxo, —R$^{20}$OR$^{21}$, —R$^{20}$OR$^{23}$OR$^{21}$, —R$^{20}$OC(O)R$^{21}$, —R$^{20}$C(O)OR$^{21}$, —R$^{20}$C(O)N(R$^{24}$)(R$^{25}$), —R$^{20}$S(O)$_t$R$^{22}$, —R$^{20}$N(R$^{24}$)(R$^{25}$), or —R$^{20}$N(R$^{24}$)C(O)R$^{21}$, wherein each alkyl, cycloalkyl, cycloalkylalkyl, heterocycloalkyl or heterocycloalkylalkyl is independently optionally substituted with 1 to 3 groups each independently halo, oxo, amino, alkyl, haloalkyl or —R$^{20}$OR$^{21}$;

Q$^1$ is hydrogen, alkyl, haloalkyl, cycloalkyl, cycloalkylalkyl, heterocycloalkyl, heterocycloalkylalkyl, —R$^{23}$OR$^{21}$, —R$^{23}$OR$^{23}$OR$^{21}$, —R$^{23}$C(O)R$^{21}$, —R$^{23}$N(R$^{24}$)(R$^{25}$), —R$^{23}$OC(O)R$^{21}$, —R$^{23}$C(O)OR$^{21}$, —R$^{23}$C(O)N(R$^{24}$)(R$^{25}$), or —R$^{23}$S(O)$_t$R$^{22}$, wherein each alkyl, cycloalkyl, cycloalkylalkyl, heterocycloalkyl or heterocycloalkylalkyl is independently optionally substituted with 1 to 3 groups each independently halo, oxo, amino, alkyl, haloalkyl or —R$^{20}$OR$^{21}$;

Q$^3$ is hydrogen, cyano, —S—C$_1$-C$_2$ alkyl, halo, C$_2$-C$_3$ alkenyl, C$_2$-C$_3$ alkynyl, C$_1$-C$_3$ alkoxy, cyclopropyl, amino, —N(H)(C$_1$-C$_3$alkyl), —N(H)C(O)C(H)=CH$_2$ or C$_1$-C$_3$ alkyl, wherein each Q$^3$ is optionally substituted with 1-3 substituents each independently halo, hydroxy or methoxy;

Q$^4$ is hydrogen, cyclopropyl, C$_1$-C$_4$ alkoxy, or C$_1$-C$_4$ alkyl optionally substituted with 1-3 substituents each independently halo, hydroxy or methoxy;

a is an integer from 0 to 3;

each t is independently 0, 1 or 2;

each R$^{20}$ is independently alkylene, alkenylene, alkynylene or a direct bond;

each R$^{21}$ is independently hydrogen, alkyl, haloalkyl, alkenyl, alkynyl or cycloalkyl;

each R$^{22}$ is independently alkyl, haloalkyl, alkenyl, alkynyl or cycloalkyl;

each R$^{23}$ is independently alkylene, alkenylene or alkynylene;

R$^{24}$ and R$^{25}$ are each independently hydrogen or alkyl; and m is an integer from 0 to 3; and q is 0, 1, or 2.

Embodiment 1(a) of this disclosure relates Formula I(b) of Embodiment 1, having Formula I(b):

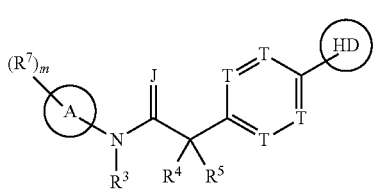

I(b)

or a pharmaceutically acceptable salt, a solvate, a tautomer, an isomer or a deuterated analog thereof, wherein:

J is O or S;

$R^3$ is hydrogen, alkyl, or haloalkyl;

$R^4$ and $R^5$ are each independently hydrogen, halo, alkyl, haloalkyl, hydroxy, alkoxy or amino;

each T is $C(R^6)$; or one T is N and the remaining three T variables are $C(R^6)$;

each $R^6$ is independently hydrogen, halo, alkyl, or alkoxy;

each $R^7$ is independently halo, alkyl, haloalkyl, cycloalkyl, cycloalkylalkyl, aryl, aralkyl, heterocycloalkyl, heterocycloalkylalkyl, heteroaryl, heteroarylalkyl, cyano, —$S(O)_2R^{21}$, or —$R^{20}OR^{21}$, wherein each alkyl, haloalkyl, cycloalkyl, cycloalkylalkyl, aryl, aralkyl, heterocycloalkyl, heterocycloalkylalkyl, heteroaryl, heteroarylalkyl, —$S(O)_2 R^{21}$, or —$R^{20}OR^{21}$ is independently optionally substituted with 1 to 4 groups each independently hydroxy, halo, cyano, alkyl, or haloalkyl;

Ring A is phenyl or a 6-membered heteroaryl optionally fused to a 5- or 6-membered ring;

Ring HD is:
(i) a 9-membered fused bicyclic heterocycloalkyl or heteroaryl group having 2-3 nitrogen atoms, wherein the 9-membered fused bicyclic heterocycloalkyl or heteroaryl group is substituted with 1 to 3 groups selected from alkyl, alkoxy, cyano, —C(O)NH-alkyl, —C(O)-alkyl, —C(O)-cycloalkyl, —$(CH_2)_{0-2}$—$N(R^{1b})_2$, halo, —NHC(O)-alkyl, —NHC(O)-haloalkyl, cycloalkyl, oxo, phenyl optionally substituted with 1-2 $R^{11}$ groups, 5-membered or 6-membered heteroaryl optionally substituted with 1-2 $R^{11}$ groups, or alkynyl optionally substituted with $R^{10}$;

each $R^{1b}$ is independently hydrogen or alkyl;

$R^{10}$ is alkyl, hydroxyalkyl, alkoxyalkyl, cycloalkyl, —$(CH_2)_{0-3}C(O)O$-alkyl, 5- or 6-membered heteroaryl optionally substituted with 1-3 $R^{22}$ or —$(CH_2)_{0-3}C(O)OH$;

each $R^{11}$ is independently a 4-6 membered heterocycloalkyl, cyano, cyanoalkyl, alkoxy, alkyl or haloalkyl;

or (ii)

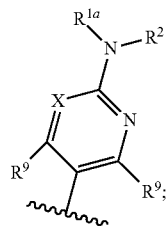

X is N or $C(R^9)$;

$R^{1a}$ is hydrogen or alkyl;

each $R^9$ is independently hydrogen, halo, amino, alkyl optionally substituted with alkoxy or hydroxy, haloalkyl or alkoxy;

$R^2$ is

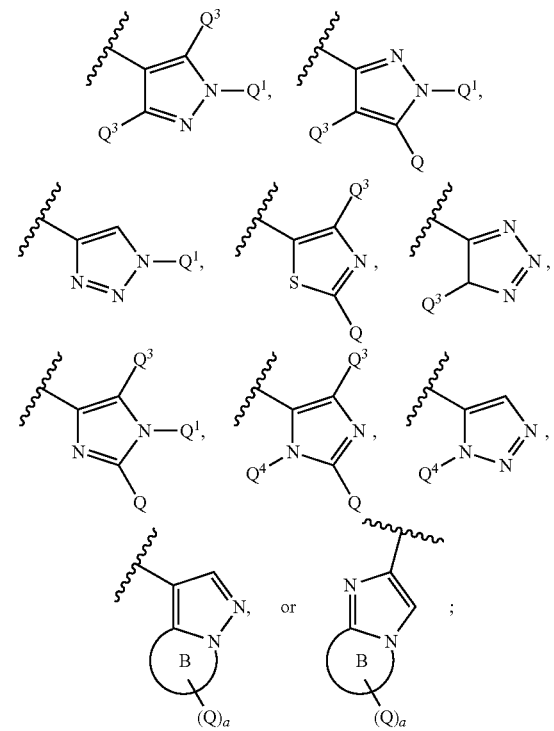

ring B is a 5 or 6-membered saturated or unsaturated ring having 0-3 heteroatoms selected from O, N, or S;

Q is hydrogen, alkyl, halo, cyano, haloalkyl, cycloalkyl, cycloalkylalkyl, heterocycloalkyl, heterocycloalkylalkyl, oxo, —$R^{20}OR^{21}$, —$R^{20}OR^{23}OR^{21}$, —$R^{20}OC(O)R^{21}$, —$R^{20}C(O)OR^{21}$, —$R^{20}C(O)N(R^{24})(R^{25})$, —$R^{20}S(O)_tR^{22}$, —$R^{20}N(R^{24})(R^{25})$, or —$R^{20}N(R^{24})C(O)R^{21}$, wherein each alkyl, cycloalkyl, cycloalkylalkyl, heterocycloalkyl or heterocycloalkylalkyl is independently optionally substituted with 1 to 3 groups each independently halo, oxo, amino, alkyl, haloalkyl or —$R^{20}OR^{21}$;

$Q^1$ is hydrogen, alkyl, haloalkyl, cycloalkyl, cycloalkylalkyl, heterocycloalkyl, heterocycloalkylalkyl, —$R^{23}OR^{21}$, —$R^{23}OR^{23}OR^{21}$, —$R^{23}C(O)R^{21}$, —$R^{23}N(R^{24})(R^{25})$, —$R^{23}OC(O)R^{21}$, —$R^{23}C(O)OR^{21}$, —$R^{23}C(O)N(R^{24})(R^{25})$, or —$R^{23}S(O)_tR^{22}$, wherein each alkyl, cycloalkyl, cycloalkylalkyl, heterocycloalkyl or heterocycloalkylalkyl is independently optionally substituted with 1 to 3 groups each independently halo, oxo, amino, alkyl, haloalkyl or —$R^{20}OR^{21}$;

$Q^3$ is hydrogen, cyano, —S—$C_1$-$C_2$ alkyl, halo, $C_2$-$C_3$ alkenyl, $C_2$-$C_3$ alkynyl, $C_1$-$C_3$ alkoxy, cyclopropyl, amino, —$N(H)(C_1$-$C_3$alkyl), —$N(H)C(O)C(H)$=$CH_2$ or $C_1$-$C_3$ alkyl, wherein each $Q^3$ is optionally substituted with 1-3 substituents each independently halo, hydroxy or methoxy;

$Q^4$ is hydrogen, cyclopropyl, $C_1$-$C_4$ alkoxy, or $C_1$-$C_4$ alkyl optionally substituted with 1-3 substituents each independently halo, hydroxy or methoxy;

a is an integer from 0 to 3;

each t is independently 0, 1 or 2;

each $R^{20}$ is independently alkylene, alkenylene, alkynylene or a direct bond;

each $R^{21}$ is independently hydrogen, alkyl, haloalkyl, alkenyl, alkynyl or cycloalkyl;

each $R^{22}$ is independently alkyl, haloalkyl, alkenyl, alkynyl or cycloalkyl;

each $R^{23}$ is independently alkylene, alkenylene or alkynylene;

$R^{24}$ and $R^{25}$ are each independently hydrogen or alkyl; and m is an integer from 0 to 3.

Embodiment 1(b) of this disclosure relates to Formula I(a) or Formula I(b) of Embodiment 1, wherein Ring A is phenyl; and Ring HD is a 9-membered fused bicyclic heterocycloalkyl group having 2-3 nitrogen atoms, wherein the 9 membered fused bicyclic heterocycloalkyl group is substituted with 1-3 groups selected from alkyl, alkoxy, —C(O)-alkyl, —(CH$_2$)$_{0-2}$—N(R$^{1b}$)$_2$, halo, —NHC(O)-alkyl, —NHC(O)-haloalkyl, cycloalkyl, oxo, spirocycloalkyl, C(O)-cycloalkyl, phenyl optionally substituted with 1-2 $R^{11}$ groups; 5-6 membered heteroaryl optionally substituted with 1-2 $R^{11}$ groups; alkynyl optionally substituted with $R^{10}$.

Embodiment 1(c) of this disclosure relates to Formula I(a) or Formula I(b) of Embodiment 1, wherein Ring A is a 6-membered heteroaryl optionally fused to a 5 or 6 membered ring; and Ring HD is a 9-membered fused bicyclic heterocycloalkyl or heteroaryl group having 2-3 nitrogen atoms, wherein the 9-membered fused bicyclic heterocycloalkyl or heteroaryl group is substituted with 1 to 3 groups selected from alkyl, alkoxy, —C(O)-alkyl, —C(O)-cycloalkyl, —(CH$_2$)$_{0-2}$—N (R$^{1b}$)$_2$, halo, —NHC(O)-alkyl, —NHC(O)-haloalkyl, cycloalkyl, oxo, phenyl optionally substituted with 1-2 $R^{11}$ groups, 5-membered or 6-membered heteroaryl optionally substituted with 1-2 $R^{11}$ groups, or alkynyl optionally substituted with $R^{10}$.

Embodiment 1(d) of this disclosure relates to Formula I(a) or Formula I(b) of Embodiment 1, wherein Ring A is phenyl; and Ring HD is

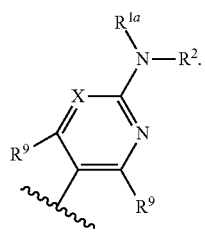

Embodiment 1(e) of this disclosure relates to Formula I(a) or Formula I(b) of Embodiment 1, wherein Ring A is a 6-membered heteroaryl optionally fused to a 5- or 6-membered ring; and Ring HD is:

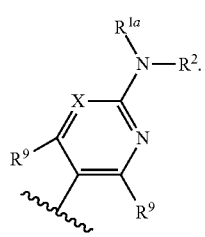

Embodiment 2 of this disclosure relates to Formula I(a) or Formula I(b) of Embodiment 1 or 1(a) having Formula II(a) or II(b):

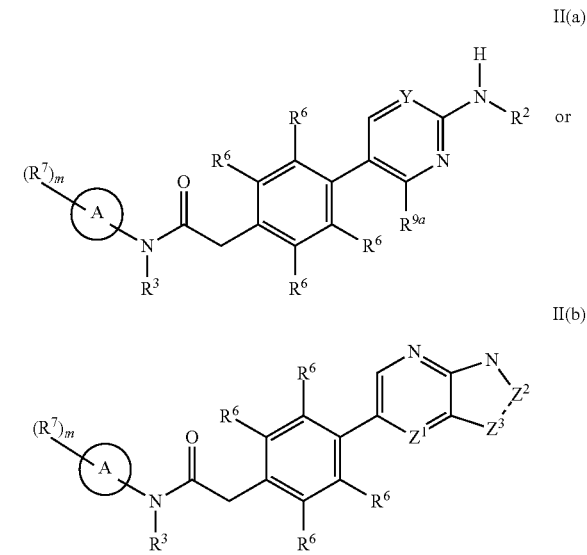

or a pharmaceutically acceptable salt, a solvate, a tautomer, an isomer or a deuterated analog thereof, wherein:

Ring A is phenyl, pyridyl, pyrimidinyl, or pyridazinyl;

Y is N or CR$^9$;

(i) --- is a single bond, wherein:

$Z^1$ is CH or N, $Z^2$ is C(R$^{12}$)(R$^{12a}$) and $Z^3$ is C(R$^{13}$)(R$^{13a}$); or $Z^1$ is CH, $Z^2$ is N(R$^{12}$) and $Z^3$ is C(R$^{13}$)(R$^{13a}$); or $Z^1$ is CH, $Z^2$ is C(R$^{12}$)(R$^{12a}$) and $Z^3$ is N(R$^{13}$);

or (ii) --- is a double bond, wherein:

$Z^1$ is CH or N, $Z^2$ is C(R$^{12}$) and $Z^3$ is C(R$^{13}$); or $Z^1$ is CH, $Z^2$ is N and $Z^3$ is C(R$^{13}$); or $Z^1$ is CH, $Z^2$ is C(R$^{12}$) and $Z^3$ is N;

$R^3$ is hydrogen or C$_1$-C$_6$ alkyl;

each $R^6$ is independently hydrogen, halo, C$_1$-C$_3$alkyl, or C$_1$-C$_3$ alkoxy;

each $R^7$ is independently C$_1$-C$_6$ alkyl, C$_1$-C$_6$ haloalkyl, C$_1$-C$_6$alkoxy, C$_3$-C$_6$ cycloalkyl, 4-6 membered heterocycloalkyl, C$_3$-C$_6$cycloalkylalkyl, —S(O)$_2$alkyl, or a 4-6 membered heterocycloalkyl-C$_1$-C$_6$ alkyl, wherein each $R^7$ is optionally substituted with 1 to 3 groups each independently hydroxy, halo, C$_1$-C$_6$ alkyl, cyano or C$_1$-C$_6$ haloalkyl;

$R^{9a}$ is hydrogen, halo, hydroxy-C$_1$-C$_6$ alkyl, C$_1$-C$_6$ alkyl, or C$_1$-C$_6$ alkoxy-C$_1$-C$_6$ alkyl;

each $R^{11}$ is independently a 5-6 membered heterocycloalkyl, cyano, C$_1$-C$_6$ alkoxy, C$_1$-C$_6$alkyl, C$_1$-C$_6$ haloalkyl, —C(O)OCH$_3$, or —C(O)OH;

$R^{10}$ is C$_1$-C$_6$ alkyl, hydroxy-C$_1$-C$_6$ alkyl, C$_1$-C$_6$alkoxy-C$_1$-C$_6$ alkyl, 5-membered heteroaryl optionally substituted with alkyl, C$_3$-C$_6$ cycloalkyl, —C(O)OCH$_3$, or —C(O)OH;

$R^{12}$ is hydrogen, C$_1$-C$_4$ alkyl, C$_1$-C$_4$ alkoxy, —(CH$_2$)$_{0-2}$—N(R$^{1b}$)$_2$, halo, C$_3$-C$_6$ cycloalkyl, —C(O)—C$_3$-C$_6$cycloalkyl, phenyl optionally substituted with 1-2 $R^{11}$ groups, 5-6 membered heteroaryl optionally substituted with 1-2 $R^{11}$ groups, or alkynyl optionally substituted with $R^{10}$;

$R^{13}$ is hydrogen, C$_1$-C$_4$ alkyl, C$_1$-C$_4$ alkoxy, —C(O)—C$_1$-C$_4$ alkyl, halo, cyano, —(CH$_2$)$_{0-2}$—N(R$^{1b}$)$_2$, —C(O)NHCH$_3$, amino, —NHC(O)CF$_3$, C$_3$-C$_6$ cycloalkyl, —C(O)—$C_3$-$C_6$ cycloalkyl, phenyl optionally substituted with 1-2 $R^{11}$ groups, 5-6 membered heteroaryl optionally substituted with 1-2 $R^{11}$ groups, or alkynyl optionally substituted with $R^{10}$;

$R^{12a}$ is hydrogen; or $R^{12}$ and $R^{12a}$, together with the carbon to which they are attached, join to form a $C_{3-6}$ spirocycloalkyl; or $R^{12}$ and $R^{12a}$ form an oxo group;

$R^{13a}$ is hydrogen; or $R^{13}$ and $R^{13a}$, together with the carbon to which they are attached, join to form a $C_{3-6}$ spirocycloalkyl; or $R^{13}$ and $R^{13a}$ form an oxo group;

each $R^{1b}$ is independently hydrogen or alkyl; and m is 0, 1 or 2.

Embodiment 2(a) of this disclosure relates to Formula II(a) or II(b) of Embodiment 2, wherein Ring A is phenyl, and Y is N.

Embodiment 2(b) of this disclosure relates to Formula II(a) or II(b) of Embodiment 2, wherein Ring A is phenyl, and Y is $CR^9$.

Embodiment 2(c) of this disclosure relates to Formula II(a) or II(b) of Embodiment 2, wherein Ring A is pyridyl, and Y is N.

Embodiment 2(d) of this disclosure relates to Formula II(a) or II(b) of Embodiment 2, wherein Ring A is pyridyl, and Y is $CR^9$.

Embodiment 2(e) of this disclosure relates to Formula II(a) or II(b) of Embodiment 2, wherein Ring A is pyrimidinyl, and Y is N.

Embodiment 2(f) of this disclosure relates to Formula II(a) or II(b) of Embodiment 2, wherein Ring A is pyrimidinyl, and Y is $CR^9$.

Embodiment 2(g) of this disclosure relates to Formula II(a) or II(b) of Embodiment 2, wherein Ring A is pyridazinyl, and Y is N.

Embodiment 2(h) of this disclosure relates to Formula II(a) or II(b) of Embodiment 2, wherein Ring A is pyridazinyl, Y is $CR^9$.

Embodiment 3 of this disclosure relates to Formula I(a) or I(b) of Embodiment 1 or 1(a), or Formula II(a) or II(b) of Embodiment 2, wherein:

$R^3$ is hydrogen;

each $R^6$ is independently chloro, fluoro, methoxy, or methyl;

each $R^7$ is independently $C_1$-$C_3$ alkyl, $C_1$-$C_3$ haloalkyl, $C_1$-$C_3$ alkoxy, hydroxy-$C_1$-$C_4$ alkyl, $C_1$-$C_3$alkoxy-$C_1$-$C_3$alkyl, $C_3$-$C_6$ cycloalkyl, 4-6 membered heterocycloalkyl, $C_3$-$C_6$ cycloalkylalkyl, or a 4-6 membered heterocycloalkyl-$C_1$-$C_6$ alkyl;

m is 1 or 2.

Embodiment 4 of this disclosure relates to any one of Embodiments 1-3 having Formula III(a):

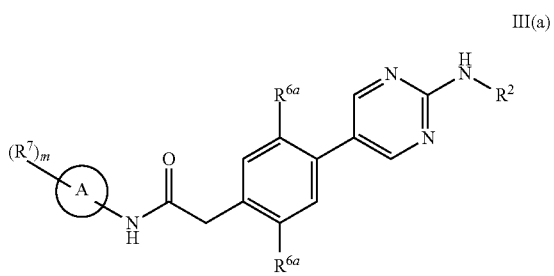

III(a)

or a pharmaceutically acceptable salt, a solvate, a tautomer, an isomer or a deuterated analog thereof, wherein each $R^{6a}$ is independently hydrogen or fluoro.

Embodiment 4(a) of this disclosure relates to Formula III(a) of Embodiment 4, wherein one $R^{6a}$ is hydrogen, and the other $R^{6a}$ is fluoro.

Embodiment 4(b) of this disclosure relates to Formula III(a) of Embodiment 4, wherein both $R^{6a}$ groups are hydrogen.

Embodiment 4(c) of this disclosure relates to Formula III(a) of Embodiment 4, wherein both $R^{6a}$ groups are fluoro.

Embodiment 5 of this disclosure relates to any one of Embodiments 1-3 having Formula III(b) or III(c):

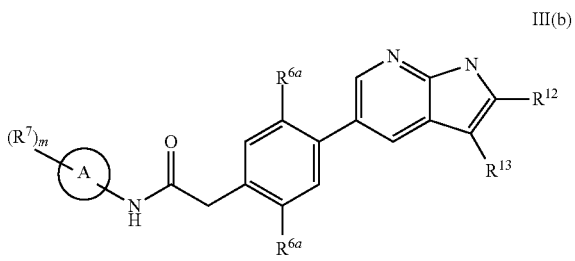

III(b)

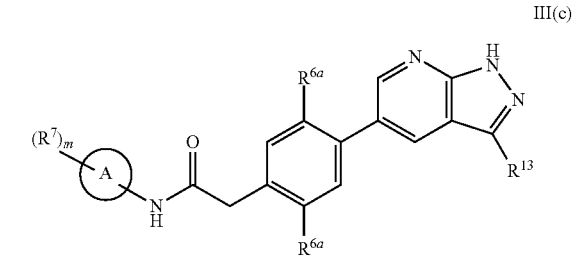

III(c)

or a pharmaceutically acceptable salt, a solvate, a tautomer, an isomer or a deuterated analog thereof, wherein each $R^{6a}$ is independently hydrogen or fluoro.

Embodiment 5(a) of this disclosure relates to Formula III(b) or III(c) of Embodiment 5, wherein Ring A is phenyl; one $R^{6a}$ is hydrogen, and the remaining $R^{6a}$ is fluoro.

Embodiment 5(b) of this disclosure relates to Formula III(b) or III(c) of Embodiment 5, wherein Ring A is phenyl; and both $R^{6a}$ groups are hydrogen.

Embodiment 5(c) of this disclosure relates to Formula III(b) or III(c) of Embodiment 5, wherein Ring A is phenyl; and both $R^{6a}$ groups are fluoro.

Embodiment 5(d) of this disclosure relates to Formula III(b) or III(c) of Embodiment 5, wherein Ring A is pyridyl; one $R^{6a}$ is hydrogen, and the remaining $R^{6a}$ is fluoro.

Embodiment 5(e) of this disclosure relates to Formula III(b) or III(c) of Embodiment 5, wherein Ring A is pyridyl; and both $R^{6a}$ groups are hydrogen.

Embodiment 5(f) of this disclosure relates to Formula III(b) or III(c) of Embodiment 5, wherein Ring A is pyridyl; and both $R^{6a}$ groups are fluoro.

Embodiment 5(g) of this disclosure relates to Formula III(b) or III(c) of Embodiment 5, wherein Ring A is pyrimidinyl; one $R^{6a}$ is hydrogen, and the remaining $R^{6a}$ is fluoro.

Embodiment 5(h) of this disclosure relates to Formula III(b) or III(c) of Embodiment 5, wherein Ring A is pyrimidinyl; and both $R^{6a}$ groups are hydrogen.

Embodiment 5(i) of this disclosure relates to Formula III(b) or III(c) of Embodiment 5, wherein Ring A is pyrimidinyl; and both $R^{6a}$ groups are fluoro.

Embodiment 5(j) of this disclosure relates to Formula III(b) or III(c) of Embodiment 5, wherein Ring A is pyridazinyl; one $R^{6a}$ is hydrogen, and the remaining $R^{6a}$ is fluoro.

Embodiment 5(k) of this disclosure relates to Formula III(b) or III(c) of Embodiment 5, wherein Ring A is pyridazinyl; and both $R^{6a}$ groups are hydrogen.

Embodiment 5(l) of this disclosure relates to Formula III(b) or III(c) of Embodiment 5, wherein Ring A is pyridazinyl; and both $R^{6a}$ groups are fluoro.

Embodiment 5(m) of this disclosure relates to Formula III(b) of Embodiment 5.

Embodiment 5(n) of this disclosure relates to Formula III(c) of Embodiment 5.

Embodiment 5(o) of this disclosure relates to Formula III(b) of Embodiment 5, wherein Ring A is phenyl; one $R^{6a}$ is hydrogen, and the remaining $R^{6a}$ is fluoro.

Embodiment 5(p) of this disclosure relates to Formula III(b) of Embodiment 5, wherein Ring A is phenyl; and both $R^{6a}$ groups are hydrogen.

Embodiment 5(q) of this disclosure relates to Formula III(b) of Embodiment 5, wherein Ring A is phenyl; and both $R^{6a}$ groups are fluoro.

Embodiment 5(r) of this disclosure relates to Formula III(b) of Embodiment 5, wherein Ring A is pyridyl; one $R^{6a}$ is hydrogen, and the remaining $R^{6a}$ is fluoro.

Embodiment 5(s) of this disclosure relates to Formula III(b) of Embodiment 5, wherein Ring A is pyridyl; and both $R^{6a}$ groups are hydrogen.

Embodiment 5(t) of this disclosure relates to Formula III(b) of Embodiment 5, wherein Ring A is pyridyl; and both $R^{6a}$ groups are fluoro.

Embodiment 5(u) of this disclosure relates to Formula III(b) of Embodiment 5, wherein Ring A is pyrimidinyl; one $R^{6a}$ is hydrogen, and the remaining $R^{6a}$ is fluoro.

Embodiment 5(v) of this disclosure relates to Formula III(b) of Embodiment 5, wherein Ring A is pyrimidinyl; and both $R^{6a}$ groups are hydrogen.

Embodiment 5(w) of this disclosure relates to Formula III(b) of Embodiment 5, wherein Ring A is pyrimidinyl; and both $R^{6a}$ groups are fluoro.

Embodiment 5(x) of this disclosure relates to Formula III(b) of Embodiment 5, wherein Ring A is pyridazinyl; one $R^{6a}$ is hydrogen, and the remaining $R^{6a}$ is fluoro.

Embodiment 5(y) of this disclosure relates to Formula III(b) of Embodiment 5, wherein Ring A is pyridazinyl; and both $R^{6a}$ groups are hydrogen.

Embodiment 5(z) of this disclosure relates to Formula III(b) of Embodiment 5, wherein Ring A is pyridazinyl; and both $R^{6a}$ groups are fluoro.

Embodiment 5(aa) of this disclosure relates to Formula III(c) of Embodiment 5, wherein Ring A is phenyl; one $R^{6a}$ is hydrogen, and the remaining $R^{6a}$ is fluoro.

Embodiment 5(bb) of this disclosure relates to Formula III(c) of Embodiment 5, wherein Ring A is phenyl; and both $R^{6a}$ groups are hydrogen.

Embodiment 5(cc) of this disclosure relates to Formula III(c) of Embodiment 5, wherein Ring A is phenyl; and both $R^{6a}$ groups are fluoro.

Embodiment 5(dd) of this disclosure relates to Formula III(c) of Embodiment 5, wherein Ring A is pyridyl; one $R^{6a}$ is hydrogen, and the remaining $R^{6a}$ is fluoro.

Embodiment 5(ee) of this disclosure relates to Formula III(c) of Embodiment 5, wherein Ring A is pyridyl; and both $R^{6a}$ groups are hydrogen.

Embodiment 5(ff) of this disclosure relates to Formula III(c) of Embodiment 5, wherein Ring A is pyridyl; and both $R^{6a}$ groups are fluoro.

Embodiment 5(gg) of this disclosure relates to Formula III(c) of Embodiment 5, wherein Ring A is pyrimidinyl; one $R^{6a}$ is hydrogen, and the remaining $R^{6a}$ is fluoro.

Embodiment 5(hh) of this disclosure relates to Formula III(c) of Embodiment 5, wherein Ring A is pyrimidinyl; and both $R^{6a}$ groups are hydrogen.

Embodiment 5(ii) of this disclosure relates to Formula III(c) of Embodiment 5, wherein Ring A is pyrimidinyl; and both $R^{6a}$ groups are fluoro.

Embodiment 5(jj) of this disclosure relates to Formula III(c) of Embodiment 5, wherein Ring A is pyridazinyl; one $R^{6a}$ is hydrogen, and the remaining $R^{6a}$ is fluoro.

Embodiment 5(kk) of this disclosure relates to Formula III(c) of Embodiment 5, wherein Ring A is pyridazinyl; and both $R^{6a}$ groups are hydrogen.

Embodiment 5(ll) of this disclosure relates to Formula III(c) of Embodiment 5, wherein Ring A is pyridazinyl; and both $R^{6a}$ groups are fluoro.

Embodiment 6 of this disclosure relates to any one of Embodiments 1-5, wherein:

Ring A is pyridyl or phenyl; and each $R^6$ is hydrogen or one $R^6$ is halo, alkyl or alkoxy.

Embodiment 7 of this disclosure relates to any one of Embodiments 1-4, 5, 5(a), 5(b), 5(c), 5(d), 5(e), 5(f), 5(m), 5(n), 5(o), 5(p), 5(q), 5(r), 5(s), 5(t), 5(aa), 5(bb), 5(cc), 5(dd), 5(ee), 5(ff), or 6, wherein:

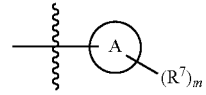

is:

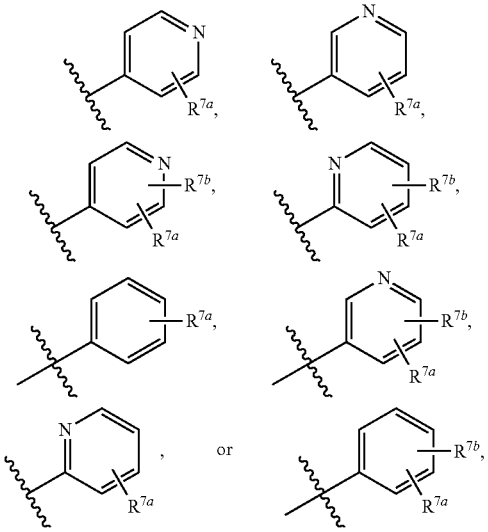

wherein:

$R^{7a}$ is $C_1$-$C_4$ alkoxy, $C_1$-$C_4$ alkyl optionally substituted with cyano, $C_1$-$C_4$ haloalkyl, cyclopropyl, halo, morpholinyl or cyano; and $R^{7b}$ is $C_1$-$C_4$ alkoxy, $C_1$-$C_4$ alkyl optionally substituted with cyano, $C_1$-$C_4$ haloalkyl, halo or cyano.

Embodiment 7(a) of this disclosure relates to Embodiments 7, wherein:

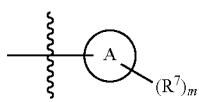

is:

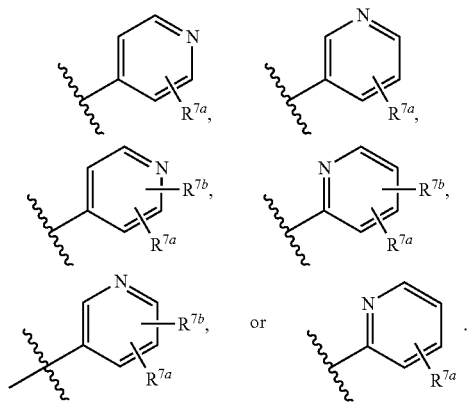

Embodiment 7(b) of this disclosure relates to Embodiment 7, wherein:

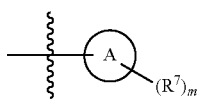

is:

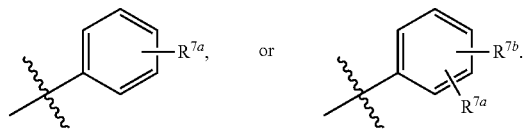

Embodiment 8 of this disclosure relates to any one of Embodiments 1, 1(a), 1(b), 1(c), 1(d), 1(e), 2, 2(c), 2(d), 3, 4, 4(a), 4(b), 4(c), 5, 5(d), 5(e), 5(f), 5(m), 5(n), 5(r), 5(s), 5(t), 5(dd), 5(ee), 5(ff), 6, 7, or 7(a), wherein:

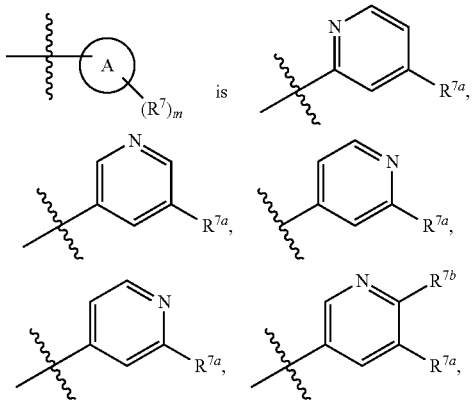

-continued

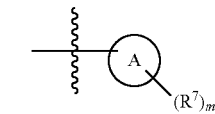

wherein:

$R^{7a}$ is cyclopropyl, —OCH$_3$, —CH$_3$, —CH$_2$F, —CHF$_2$, —CF$_3$, —OCF$_3$, —C(CH$_3$)$_3$, —C(CN)(CH$_3$)$_2$, F, Cl, Br, or cyano; and 'R$^{7b}$ is cyclopropyl, —OCH$_3$, —CH$_3$, —CH$_2$F, —CHF$_2$, —CF$_3$, —C(CH$_3$)$_3$, —C(CN)(CH$_3$)$_2$, —OCF$_3$, F, Cl, Br or cyano.

Embodiment 9 of this disclosure relates to any one of Embodiments 1, 1(a), 1(b), 1(c), 1(d), 1(e), 2, 2(c), 2(d), 3, 4, 4(a), 4(b), 4(c), 5, 5(d), 5(e), 5(f), 5(m), 5(n), 5(r), 5(s), 5(t), 5(dd), 5(ee), 5(ff), 6, 7, 7(a), or 8, wherein:

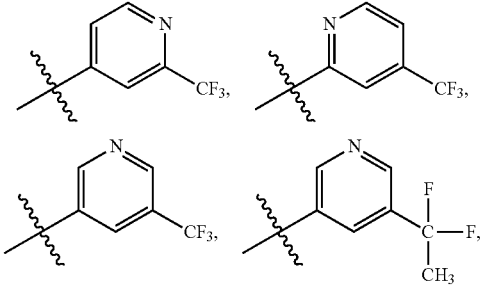

is:

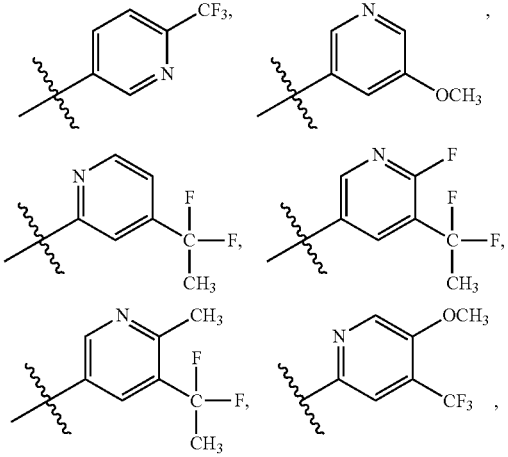

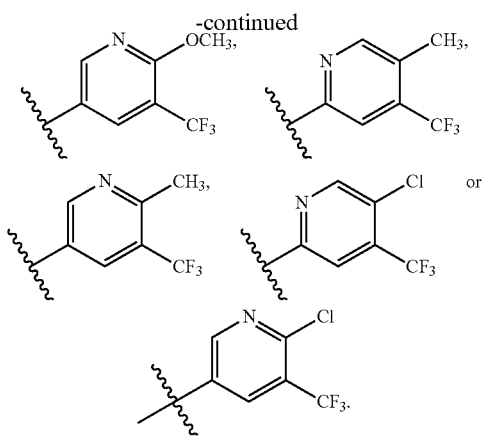

Embodiment 10 of this disclosure relates to any one of Embodiments 1, 1(a), 1(b), 1(c), 1(d), 1(e), 2, 2(a), 2(b), 2(c), 2(d), 2(e), 2(f), 2(g), 2(h), 3, 4, 4(a), 4(b), 4(c), 6, 7, 7(a), 7(b), 8 or 9 wherein $R^2$ is:

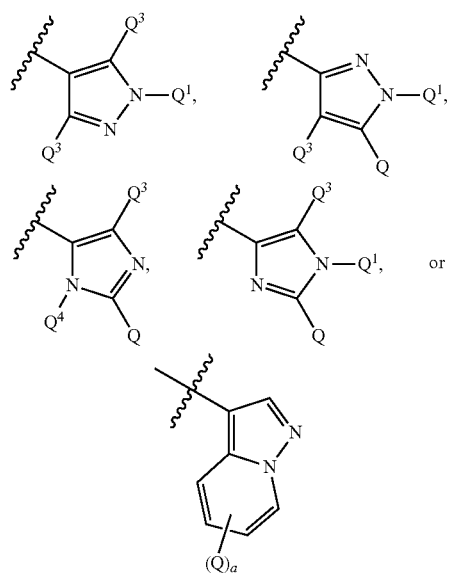

Embodiment 11 of this disclosure relates to any one of Embodiments 1, 1(a), 1(b), 1(c), 1(d), 1(e), 2, 2(a), 2(b), 2(c), 2(d), 2(e), 2(f), 2(g), 2(h), 3, 4, 4(a), 4(b), 4(c), 6, 7, 7(a), 7(b), 8, 9, or 10, wherein $R^2$ is:

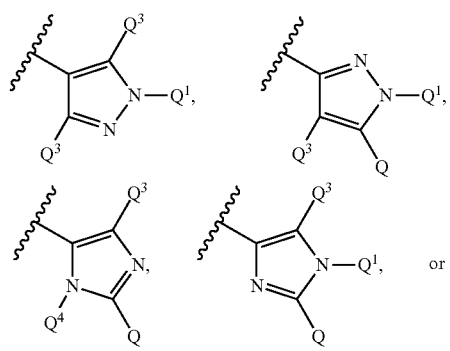

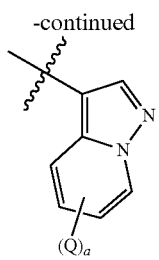

wherein:
Q is hydrogen, —OCH$_3$, hydroxy-C$_1$-C$_4$ alkyl, —CF$_3$, —CHF$_2$, —CH$_2$F, —CH$_2$CH$_3$, or —CH$_3$;
Q$^1$ is hydrogen, hydroxy-C$_1$-C$_4$ alkyl, —CF$_3$, —CHF$_2$, —CH$_2$F, —CH$_2$CH$_3$, or —CH$_3$;
Q$^3$ is hydrogen, —OCH$_3$, hydroxy-C$_1$-C$_3$ alkyl, —CF$_3$, —CHF$_2$, —CH$_2$F, —CH$_2$CH$_3$, or —CH$_3$; and
Q$^4$ is hydrogen, hydroxy-C$_1$-C$_4$ alkyl, —CF$_3$, —CHF$_2$, —CH$_2$F, —CH$_2$CH$_3$, or —CH$_3$.

Embodiment 12 of this disclosure relates to any one of Embodiments 1, 1(a), 1(b), 1(c), 1(d), 1(e), 2, 2(a), 2(b), 2(c), 2(d), 2(e), 2(f), 2(g), 2(h), 3, 4, 4(a), 4(b), 4(c), 6, 7, 7(a), 7(b), 8, 9, 10 or 11 wherein $R^2$ is

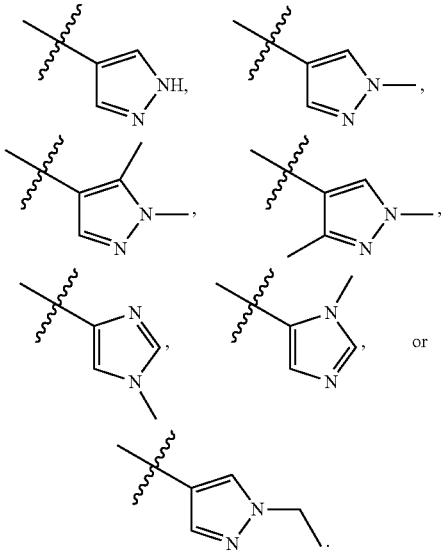

Embodiment 13 of this disclosure relates to any one of Embodiments 1, 1(a), 1(b), 1(c), 1(d), 1(e), 2, 2(a), 2(b), 2(c), 2(d), 2(e), 2(f), 2(g), 2(h), 3, 5, 5(a), 5(b) 5(c), 5(d), 5(e), 5(f), 5(g), 5(h), 5(i), 5(j), 5(k), 5(l), 5(m), 5(n), 5(o), 5(p) 5(q), 5(r), 5(s), 5(t), 5(u), 5(v), 5(w), 5(x), 5(y), 5(z), 5(aa), 5(bb) 5(cc), 5(dd), 5(ee), 5(ff), 5(gg), 5(hh), 5(ii), 5(jj), 5(kk), 5(ll), 6, 7, 7(a), 7(b), 8 or 9, wherein:
$R^{12}$ is hydrogen; —CH$_3$; Cl; F; Br; cyclopropyl; phenyl; pyridyl optionally substituted with morpholinyl, ethoxy, methoxy, cyano, —CF$_3$, —CHF$_2$, —CH$_2$F or —CH$_3$; ethynyl optionally substituted with —C(CH$_3$)$_3$, —C(CH$_3$)$_2$OH, cyclopropyl, —C(O)OCH$_3$, —C(O)OH, or methoxymethyl; or imidazolyl optionally substituted with methyl, —C(O)OCH$_3$, or —C(O)OH; and
$R^{13}$ is hydrogen, —C(O)CH$_3$, —C(O)CH$_2$CH$_3$, F, Cl, Br, cyano, cyclopropyl, —C(O)-cyclopropyl, —C(O)NHCH$_3$, —OCH$_3$, —OCH$_2$CH$_3$, —CH$_2$CH$_3$, amino, or —NHC(O)CF$_3$.

Embodiment 14 of this disclosure relates to any one of Embodiments 1, 1(a), 1(b), 1(c), 1(d), 1(e), 2, 2(a), 2(b), 2(c), 2(d), 2(e), 2(f), 2(g), 2(h), 3, 5, 5(a), 5(b) 5(c), 5(d), 5(e), 5(f), 5(g), 5(h), 5(i), 5(j), 5(k), 5(l), 5(m), 5(n), 5(o), 5(p) 5(q), 5(r), 5(s), 5(t), 5(u), 5(v), 5(w), 5(x), 5(y), 5(z), 5(aa), 5(bb) 5(cc), 5(dd), 5(ee), 5(ff), 5(gg), 5(hh), 5(ii), 5(jj), 5(kk), 5(ll), 6, 7, 7(a), 7(b), 8, 9, or 13 wherein:

$R^{12}$ is phenyl; pyridyl optionally substituted with morpholinyl, ethoxy, methoxy, cyano, —$CF_3$, —$CHF_2$, —$CH_2F$, or —$CH_3$; or ethynyl optionally substituted with —$C(CH_3)_3$, —$C(CH_3)_2OH$, cyclopropyl, —$C(O)OCH_3$, —$C(O)OH$, or methoxymethyl; and $R^{13}$ is hydrogen, —$C(O)CH_3$, —$C(O)CH_2CH_3$, F, Cl, Br, cyano, cyclopropyl, —$C(O)$-cyclopropyl, —$C(O)NHCH_3$, —$OCH_3$, —$OCH_2CH_3$, —$CH_2CH_3$, amino, or —$NHCOCF_3$.

Embodiment 14(a) of this disclosure relates to any one of Embodiments 5(m), 5(o), 5(p) 5(q), 5(r), 5(s), 5(t), 5(u), 5(v), 5(w), 5(x), 5(y) or 5(z), wherein:

$R^{12}$ is phenyl; pyridyl optionally substituted with morpholinyl, ethoxy, methoxy, cyano, —$CF_3$, —$CHF_2$, —$CH_2F$, or —$CH_3$; or ethynyl optionally substituted with —$C(CH_3)_3$, —$C(CH_3)_2OH$, cyclopropyl, —$C(O)OCH_3$, —$C(O)OH$, or methoxymethyl; and $R^{13}$, when present, is hydrogen, —$C(O)CH_3$, —$C(O)CH_2CH_3$, F, Cl, Br, cyano, cyclopropyl, —$C(O)$-cyclopropyl, —$C(O)NHCH_3$, —$OCH_3$, —$OCH_2CH_3$, —$CH_2CH_3$, amino, or $NHCOCF_3$.

Embodiment 14(b) of this disclosure relates to any one of Embodiments 5(m), 5(o), 5(p) 5(q), 5(r), 5(s), 5(t), 5(u), 5(v), 5(w), 5(x), 5(y) or 5(z), wherein:

$R^{12}$ is phenyl; pyridyl optionally substituted with morpholinyl, ethoxy, methoxy, cyano, —$CF_3$, —$CHF_2$, —$CH_2F$, or —$CH_3$; or ethynyl optionally substituted with —$C(CH_3)_3$, —$C(CH_3)_2OH$, cyclopropyl, —$C(O)OCH_3$, —$C(O)OH$, or methoxymethyl; and $R^{13}$ is hydrogen.

Embodiment 14(c) of this disclosure relates to any one of Embodiments 5(m), 5(o), 5(p) 5(q), 5(r), 5(s), 5(t), 5(u), 5(v), 5(w), 5(x), 5(y) or 5(z), wherein:

$R^{12}$ is phenyl; and
$R^{13}$ is hydrogen.

Embodiment 14(d) of this disclosure relates to any one of Embodiments 5(m), 5(o), 5(p) 5(q), 5(r), 5(s), 5(t), 5(u), 5(v), 5(w), 5(x), 5(y), or 5(z), wherein:

$R^{12}$ pyridyl optionally substituted with morpholinyl; and
$R^{13}$ is hydrogen.

Embodiment 14(e) of this disclosure relates to any one of Embodiments 5(m), 5(o), 5(p) 5(q), 5(r), 5(s), 5(t), 5(u), 5(v), 5(w), 5(x), 5(y) or 5(z), wherein:

$R^{12}$ is ethoxy; and
$R^{13}$ is hydrogen.

Embodiment 14(f) of this disclosure relates to any one of Embodiments 5(m), 5(o), 5(p) 5(q), 5(r), 5(s), 5(t), 5(u), 5(v), 5(w), 5(x), 5(y) or 5(z), wherein:

$R^{12}$ is methoxy; and
$R^{13}$ is hydrogen.

Embodiment 14(g) of this disclosure relates to any one of Embodiments 5(m), 5(o), 5(p) 5(q), 5(r), 5(s), 5(t), 5(u), 5(v), 5(w), 5(x), 5(y) or 5(z), wherein:

$R^{12}$ is cyano; and
$R^{13}$ is hydrogen.

Embodiment 14(h) of this disclosure relates to any one of Embodiments 5(m), 5(o), 5(p) 5(q), 5(r), 5(s), 5(t), 5(u), 5(v), 5(w), 5(x), 5(y) or 5(z), wherein:

$R^{12}$ is —$CF_3$, —$CHF_2$, —$CH_2F$, or —$CH_3$; and
$R^{13}$ is hydrogen.

Embodiment 14(i) of this disclosure relates to any one of Embodiments 5(m), 5(o), 5(p) 5(q), 5(r), 5(s), 5(t), 5(u), 5(v), 5(w), 5(x), 5(y) or 5(z), wherein:

$R^{12}$ is ethynyl substituted with —$C(CH_3)_3$, —$C(CH_3)_2OH$, cyclopropyl, —$C(O)OCH_3$, —$C(O)OH$, or methoxymethyl; and
$R^{13}$ is hydrogen.

Embodiment 14(j) of this disclosure relates to any one of Embodiments 5(m), 5(o), 5(p) 5(q), 5(r), 5(s), 5(t), 5(u), 5(v), 5(w), 5(x), 5(y) or 5(z), wherein:

$R^{12}$ is ethynyl substituted with —$C(CH_3)_3$; and
$R^{13}$ is hydrogen.

Embodiment 14(k) of this disclosure relates to any one of Embodiments 5(m), 5(o), 5(p) 5(q), 5(r), 5(s), 5(t), 5(u), 5(v), 5(w), 5(x), 5(y) or 5(z), wherein:

$R^{12}$ is ethynyl substituted —$C(CH_3)_2OH$; and
$R^{13}$ is hydrogen.

Embodiment 14(l) of this disclosure relates to any one of Embodiments 5(m), 5(o), 5(p) 5(q), 5(r), 5(s), 5(t), 5(u), 5(v), 5(w), 5(x), 5(y) or 5(z), wherein:

$R^{12}$ is ethynyl substituted with cyclopropyl; and
$R^{13}$ is hydrogen.

Embodiment 14(m) of this disclosure relates to any one of Embodiments 5(m), 5(o), 5(p) 5(q), 5(r), 5(s), 5(t), 5(u), 5(v), 5(w), 5(x), 5(y) or 5(z), wherein:

$R^{12}$ is ethynyl substituted with —$C(O)OCH_3$; and
$R^{13}$ is hydrogen.

Embodiment 14(n) of this disclosure relates to any one of Embodiments 5(m), 5(o), 5(p) 5(q), 5(r), 5(s), 5(t), 5(u), 5(v), 5(w), 5(x), 5(y) or 5(z), wherein:

$R^{12}$ is ethynyl substituted with —$C(O)OH$; and
$R^{13}$ is hydrogen.

Embodiment 14(o) of this disclosure relates to any one of Embodiments 5(m), 5(o), 5(p) 5(q), 5(r), 5(s), 5(t), 5(u), 5(v), 5(w), 5(x), 5(y) or 5(z), wherein:

$R^{12}$ is ethynyl substituted with methoxymethyl; and
$R^{13}$ is hydrogen.

Embodiment 14(p) of this disclosure relates to any one of Embodiments 5(n), 5(aa), 5(bb) 5(cc), 5(dd), 5(ee), 5(ff), 5(gg), 5(hh), 5(ii), 5(jj), 5(kk) or 5(ll) wherein $R^{13}$ is —$C(O)CH_3$, —$C(O)CH_2CH_3$, F, Cl, Br, —CN, cyclopropyl, —$C(O)$-cyclopropyl, —$C(O)NHCH_3$, —$OCH_3$, —$OCH_2CH_3$, —$CH_2CH_3$, amino, or —$NHC(O)CF_3$.

Embodiment 14(q) of this disclosure relates to any one of Embodiments 5(n), 5(aa), 5(bb) 5(cc), 5(dd), 5(ee), 5(ff), 5(gg), 5(hh), 5(ii), 5(jj), 5(kk) or 5(ll) wherein $R^{13}$ is —$C(O)CH_3$.

Embodiment 14(r) of this disclosure relates to any one of Embodiments 5(n), 5(aa), 5(bb) 5(cc), 5(dd), 5(ee), 5(ff), 5(gg), 5(hh), 5(ii), 5(jj), 5(kk) or 5(ll) wherein $R^{13}$ is —$C(O)CH_2CH_3$.

Embodiment 14(s) of this disclosure relates to any one of Embodiments 5(n), 5(aa), 5(bb) 5(cc), 5(dd), 5(ee), 5(ff), 5(gg), 5(hh), 5(ii), 5(jj), 5(kk) or 5(ll) wherein $R^{13}$ is F, Cl, or Br.

Embodiment 14(t) of this disclosure relates to any one of Embodiments 5(n), 5(aa), 5(bb) 5(cc), 5(dd), 5(ee), 5(ff), 5(gg), 5(hh), 5(ii), 5(jj), 5(kk) or 5(ll) wherein $R^{13}$ is cyano.

Embodiment 14(u) of this disclosure relates to any one of Embodiments 5(n), 5(aa), 5(bb) 5(cc), 5(dd), 5(ee), 5(ff), 5(gg), 5(hh), 5(ii), 5(jj), 5(kk) or 5(ll) wherein $R^{13}$ is cyclopropyl.

Embodiment 14(v) of this disclosure relates to any one of Embodiments 5(n), 5(aa), 5(bb) 5(cc), 5(dd), 5(ee), 5(ff), 5(gg), 5(hh), 5(ii), 5(jj), 5(kk) or 5(ll) wherein $R^{13}$ is —$C(O)$-cyclopropyl.

Embodiment 14(w) of this disclosure relates to any one of Embodiments 5(n), 5(aa), 5(bb) 5(cc), 5(dd), 5(ee), 5(ff), 5(gg), 5(hh), 5(ii), 5(jj), 5(kk) or 5(ll) wherein R$^{13}$ is —C(O)NHCH$_3$.

Embodiment 14(x) of this disclosure relates to any one of Embodiments 5(n), 5(aa), 5(bb) 5(cc), 5(dd), 5(ee), 5(ff), 5(gg), 5(hh), 5(ii), 5(jj), 5(kk) or 5(ll) wherein R$^{13}$ is —OCH$_3$.

Embodiment 14(y) of this disclosure relates to any one of Embodiments 5(n), 5(aa), 5(bb) 5(cc), 5(dd), 5(ee), 5(ff), 5(gg), 5(hh), 5(ii), 5(jj), 5(kk) or 5(ll) wherein R$^{13}$ is —OCH$_2$CH$_3$.

Embodiment 14(z) of this disclosure relates to any one of Embodiments 5(n), 5(aa), 5(bb) 5(cc), 5(dd), 5(ee), 5(ff), 5(gg), 5(hh), 5(ii), 5(jj), 5(kk) or 5(ll) wherein R$^{13}$ is —CH$_2$CH$_3$.

Embodiment 14(aa) of this disclosure relates to any one of Embodiments 5(n), 5(aa), 5(bb) 5(cc), 5(dd), 5(ee), 5(ff), 5(gg), 5(hh), 5(ii), 5(jj), 5(kk) or 5(ll) wherein R$^{13}$ is amino.

Embodiment 14(bb) of this disclosure relates to any one of Embodiments 5(n), 5(aa), 5(bb) 5(cc), 5(dd), 5(ee), 5(ff), 5(gg), 5(hh), 5(ii), 5(jj), 5(kk) or 5(ll) wherein R$^{13}$ is —NHC(O)CF$_3$.

Embodiment 15 of this disclosure relates to any one of Embodiments 5-9, and 13 having Formula III(b):

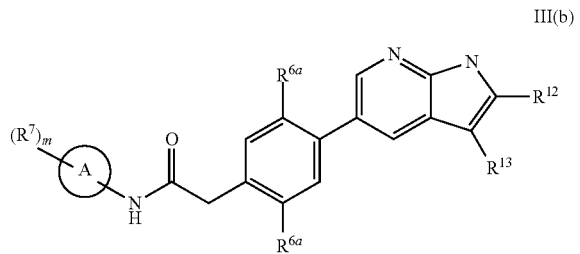

III(b)

or a pharmaceutically acceptable salt, a solvate, a tautomer, an isomer or a deuterated analog thereof, wherein:

R$^{12}$ is phenyl; pyridyl optionally substituted with morpholinyl, ethoxy, methoxy, cyano, —CF$_3$, —CHF$_2$, —CH$_2$F, or —CH$_3$; or ethynyl optionally substituted with —C(CH$_3$)$_3$, —C(CH$_3$)$_2$OH, cyclopropyl, —C(O)OCH$_3$, —C(O)OH, or methoxymethyl; and R$^{13}$ is hydrogen.

Embodiment 16 of this disclosure relates to any one of Embodiments 5-9, and 13 having Formula III(c):

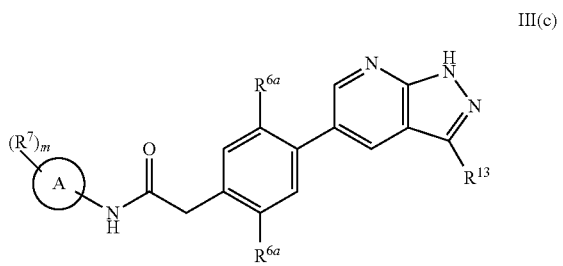

III(c)

or a pharmaceutically acceptable salt, a solvate, a tautomer, an isomer or a deuterated analog thereof, wherein R$^{13}$ is —C(O)CH$_3$, —C(O)CH$_2$CH$_3$, F, Cl, Br, cyano, cyclopropyl, —C(O)-cyclopropyl, —C(O)NHCH$_3$, —OCH$_3$, —OCH$_2$CH$_3$, —CH$_2$CH$_3$, amino, or —NHC(O)CF$_3$.

Embodiment 17 of this disclosure relates to Embodiment 1 selected from any one of compounds P-0001-P-0274 in Table 1, or a pharmaceutically acceptable salt, a solvate, a tautomer, an isomer or a deuterated analog of any of the compounds in Table 1.

Embodiment 18 of this disclosure relates to a pharmaceutical composition comprising a compound of any of Embodiments 1, 1(a), 1(b), 1(c), 1(d), 1(e), 2, 2(a), 2(b), 2(c), 2(d), 2(e), 2(f), 2(g), 2(h), 3, 4, 4(a), 4(b), 4(c), 5, 5(a), 5(b) 5(c), 5(d), 5(e), 5(f), 5(g), 5(h), 5(i), 5(j), 5(k), 5(l), 5(m), 5(n), 5(o), 5(p), 5(q), 5(r), 5(s), 5(t), 5(u), 5(v), 5(w), 5(x), 5(z), 5(aa), 5(bb), 5(cc), 5(dd), 5(ee), 5(ff), 5(gg), 5(hh), 5(ii), 5(kk), 5(ll) 6, 7, 7(a), 7(b), 8, 9, 10 or 11, 12, 13, 14, 14(a), 14(b), 14(c), 14(d), 14(e), 14(f), 14(g), 14(h), 14(i), 14(j), 14(k), 14(l), 14(m), 14(n), 14(o), 14(p), 14(q), 14(r), 14(s), 14(t), 14(u), 14(v), 14(w), 14(x), 14(z), 14(aa), 14(bb), 15, 16 or 17, and a pharmaceutically acceptable carrier.

Embodiment 19 of this disclosure relates to a pharmaceutical composition of Embodiment 18, further comprising a second pharmaceutical agent selected from the group consisting of an anti-proliferative agent, an anti-inflammatory agent, an immunomodulatory agent and an immunosuppressive agent.

Embodiment 20 of this disclosure relates to a pharmaceutical composition according to Embodiment 18, further comprising a second pharmaceutical agent, wherein the second pharmaceutical agent is i) an alkylating agent selected from adozelesin, altretamine, bizelesin, busulfan, carboplatin, carboquone, carmustine, chlorambucil, cisplatin, cyclophosphamide, dacarbazine, estramustine, fotemustine, hepsulfam, ifosfamide, improsulfan, irofulven, lomustine, mechlorethamine, melphalan, oxaliplatin, piposulfan, semustine, streptozocin, temozolomide, thiotepa, and treosulfan; ii) an antibiotic selected from bleomycin, dactinomycin, daunorubicin, doxorubicin, epirubicin, idarubicin, menogaril, mitomycin, mitoxantrone, neocarzinostatin, pentostatin, and plicamycin; iii) an antimetabolite selected from the group consisting of azacitidine, capecitabine, cladribine, clofarabine, cytarabine, decitabine, floxuridine, fludarabine, 5-fluorouracil, ftorafur, gemcitabine, hydroxyurea, mercaptopurine, methotrexate, nelarabine, pemetrexed, raltitrexed, thioguanine, and trimetrexate; iv) an antibody therapy agent selected from alemtuzumab, bevacizumab, cetuximab, galiximab, gemtuzumab, nivolumab, panitumumab, pembrolizumab, pertuzumab, rituximab, tositumomab, trastuzumab, and 90 Y ibritumomab tiuxetan; v) a hormone or hormone antagonist selected from the group consisting of anastrozole, androgens, buserelin, diethylstilbestrol, exemestane, flutamide, fulvestrant, goserelin, idoxifene, letrozole, leuprolide, magestrol, raloxifene, tamoxifen, and toremifene; vi) a taxane selected from DJ-927, docetaxel, TPI 287, paclitaxel and DHA-paclitaxel; vii) a retinoid selected from alitretinoin, bexarotene, fenretinide, isotretinoin, and tretinoin; viii) an alkaloid selected from etoposide, homoharringtonine, teniposide, vinblastine, vincristine, vindesine, and vinorelbine; ix) an antiangiogenic agent selected from AE-941 (GW786034, Neovastat), ABT-510, 2-methoxyestradiol, lenalidomide, and thalidomide; x) a topoisomerase inhibitor selected from amsacrine, edotecarin, exatecan, irinotecan, SN-38 (7-ethyl-10-hydroxy-camptothecin), rubitecan, topotecan, and 9-aminocamptothecin; xi) a kinase inhibitor selected from erlotinib, gefitinib, flavopiridol, imatinib mesylate, lapatinib, sorafenib, sunitinib malate, AEE-788, AG-013736, AMG 706, AMN107, BMS-354825, BMS-599626, UCN-01 (7-hydroxystaurosporine), vemurafenib, dabrafenib, trametinib, cobimetinib selumetinib and vatalanib; xii) a targeted signal transduction inhibitor selected from bortezomib, geldanamycin, and rapamycin; xiii) a biological response modifier selected from imiquimod, interferon-α and interleukin-2; xiv) an IDO inhibitor; and xv) a chemotherapeutic agent selected from 3-AP (3-amino-2-carboxyaldehyde thiosemicarbazone), altrasentan, aminoglutethimide, anagrelide, asparaginase, bryostatin-1, cilengitide, elesclomol, eribulin mesylate (E7389), ixabepilone, lonidamine, masoprocol, mitoguanazone, oblimersen, sulindac, testolactone, tiazofurin, a mTOR inhibitor, a PI3K inhibitor, a Cdk4 inhibitor, an Akt inhibitor, a Hsp90 inhibitor, a farnesyltransferase inhibitor or an aromatase inhibitor (anastrozole letrozole exemestane); xvi) a Mek inhibitor; xvii) a tyrosine kinase inhibitor; or xviii) an EGFR inhibitor.

Embodiment 21 of this disclosure relates to a method for treatment of a disease or condition modulated by a FLT3, CSF1R, or c-kit, wherein the disease is an inflammatory disease, an inflammatory condition, an autoimmune disease, or cancer, said method comprising administering to a subject suffering from the disease a therapeutically effective amount of a compound according to any one of Embodiments 1-17, or a pharmaceutical composition of any one of Embodiments 18-20.

Embodiment 22 of this disclosure relates to a method for treating a subject with a disease or condition mediated by FLT3, CSF1R, or c-ki, said method comprising administering to the subject an effective one or more compounds in Embodiments 1, 1(a), 1(b), 1(c), 1(d), 1(e), 2, 2(a), 2(b), 2(c), 2(d), 2(e), 2(f), 2(g), 2(h), 3, 4, 4(a), 4(b), 4(c), 5, 5(a), 5(b) 5(c), 5(d), 5(e), 5(f), 5(g), 5(h), 5(i), 5(j), 5(k), 5(l), 5(m), 5(n), 5(o), 5(p), 5(q), 5(r), 5(s), 5(t), 5(u), 5(v), 5(w), 5(x), 5(z), 5(aa), 5(bb), 5(cc), 5(dd), 5(ee), 5(ff), 5(gg), 5(hh), 5(ii), 5(kk), 5(ll) 6, 7, 7(a), 7(b), 8, 9, 10 or 11, 12, 13, 14, 14(a), 14(b), 14(c), 14(d), 14(e), 14(f), 14(g), 14(h), 14(i), 14(j), 14(k), 14(l), 14(m), 14(n), 14(o), 14(p), 14(q), 14(r), 14(s), 14(t), 14(u), 14(v), 14(w), 14(x), 14(z), 14(aa), 14(bb), 15, 16 or 17, or a pharmaceutical composition according to Embodiments 18, 19 or 20, wherein the disease or condition is acute myeloid leukemia, stem cell ablation and myelopreparation for stem cell transplant, primary progressive multiple sclerosis, traumatic brain injury, epilepsy, tauopathies, Erdheim-Chester Disease, Langerhans cell histocytosis, hairy cell leukemia, HIV, glioblastoma, scleroderma, anterior or posterior eye disease (including diseases of the cornea, conjunctiva, sclera or lacrimal glands), lysosomal storage diseases [including mucolipodosis, alpha-mannosidosis, aspartylglucosaminuria, Batten disease, beta-mannosidosis, cystinosis, Danon disease, Fabry disease, Farber disease, fucosidosis, galactosialidosis, Gaucher disease, gangliosidosis (e.g., GM1 gangliosidosis and GM2-gangliosidosis AB variant), Krabbe disease; metachromatic leukodystrophy, mucopolysaccharidoses disorders (e.g., MPS 1—Hurler syndrome, MPS II—Hunter syndrome, MPS III—Sanfilippo (A,B,C,D), MPS IVA—Morquio, MPS IX—hyaluronidase, deficiency, MPS VI—Maroteaux-Lamy, or MPS VII—Sly syndrome), mucolipidosis type I (Sialidosis), Mucolipidosis type II (I-Cell disease), Mucolipidosis type III (Pseudo-Hurler polydystrophy), Mucolipidosis type IV, multiple sulfatase deficiency, Niemann-Pick types A, B, C; Pompe disease (glycogen storage disease), pycnodysostosis, Sandhoff disease, Schindler disease, Salla disease/sialic acid storage disease, Tay-Sachs, and Wolman disease] complex regional pain syndrome, reflex sympathetic dystrophy, muscular dystrophy, duchenne muscular dystrophy, causalgia, neuro-inflammation, neuroinflammatory disorders, benign forgetfulness, HIV, binswager type dementia, dementia with lewy bodie, prosencephaly, micro-encepahy, cerebral palsy, congenital hydrocephalus, abdominal dropsy, progressive supranuclear palsy, glaucoma, addiction disorders, dependencies, alcoholism, tremors, Wilson's disease, vascular dementias, multi infarct dementia, fronto temporal dementia, pseudo-dementia, bladder cancer, basal cell carcinoma, cholangiocarcinoma, colon cancer, endometrial cancer, esophageal cancer, Ewing's sarcoma, gastric cancer, glioma, hepatocellular carcinoma, Hodgkin lymphoma, laryngeal carcinoma, leukemia, liver cancer, lung cancer (such as non-small cell lung cancer and small cell lung cancer), melanoma, mesothelioma, pancreatic cancer, rectal cancer, renal cancer, squamous cell carcinoma, T cell lymphoma, thyroid cancer, monocytic leukemia, pheochromocytoma, malignant peripheral nerve cell tumors, malignant peripheral nerve sheath tumors (MPNST), cutaneous and plexiform neurofibromas, leiomyoadenomatoid tumor, fibroids, uterine fibroids, leiomyosarcoma, papillary thyroid cancer, anaplastic thyroid cancer, medullary thyroid cancer, follicular thyroid cancer, hurthle cell carcinoma, thyroid cancer, ascites, malignant ascites, mesothelioma, salivary gland tumors, mucoepidermoid carcinoma of the salivary gland, acinic cell carcinoma of the salivary gland, gastrointestinal stromal tumors (GIST), tumors that cause effusions in potential spaces of the body, pleural effusions, pericardial effusions, peritoneal effusions aka ascites, giant cell tumors (GCT), GCT of bone other sarcomas, tumor angiogenesis, paracrine tumor growth or tumors that express aberrantly or otherwise a FLT3 ligand, or activating mutations or translocations of any of the foregoing.

Embodiment 23 of this disclosure relates to a method for treating a subject with a disease or condition mediated by FLT3, CSF1R, or c-ki, said method comprising administering to the subject an effective amount of a compound according to any one of Embodiments 1, 1(a), 1(b), 1(c), 1(d), 1(e), 2, 2(a), 2(b), 2(c), 2(d), 2(e), 2(f), 2(g), 2(h), 3, 4, 4(a), 4(b), 4(c), 5, 5(a), 5(b) 5(c), 5(d), 5(e), 5(f), 5(g), 5(h), 5(i), 5(j), 5(k), 5(l), 5(m), 5(n), 5(o), 5(p), 5(q), 5(r), 5(s), 5(t), 5(u), 5(v), 5(w), 5(x), 5(z), 5(aa), 5(bb), 5(cc), 5(dd), 5(ee), 5(ff), 5(gg), 5(hh), 5(ii), 5(kk), 5(ll) 6, 7, 7(a), 7(b), 8, 9, 10 or 11, 12, 13, 14, 14(a), 14(b), 14(c), 14(d), 14(e), 14(f), 14(g), 14(h), 14(i), 14(j), 14(k), 14(l), 14(m), 14(n), 14(o), 14(p), 14(q), 14(r), 14(s), 14(t), 14(u), 14(v), 14(w), 14(x), 14(z), 14(aa), 14(bb), 15, 16 or 17, or a pharmaceutical composition according to any one of Embodiments 18-20, wherein the disease or condition is lysosomal storage selected from the group consisting of mucolipodosis, alpha-mannosidosis; aspartylglucosaminuria; Batten disease; beta-mannosidosis; cystinosis; Danon disease; Fabry disease; Farber disease; fucosidosis; galactosialidosis; Gaucher disease; gangliosidosis; Krabbe disease; metachromatic leukodystrophy; mucopolysaccharidoses disorders; aspartylglucosaminuria; Batten disease; beta-mannosidosis; cystinosis; Danon disease; Fabry disease; Farber disease; fucosidosis; galactosialidosis; Gaucher disease; gangliosidosis; Krabbe disease; metachromatic leukodystrophy; mucopolysaccharidoses disorders; mucolipidosis type I (Sialidosis); Mucolipidosis type II (I-Cell disease); Mucolipidosis type III (Pseudo-Hurler polydystrophy); Mucolipidosis type IV; multiple sulfatase deficiency; Niemann-Pick types A, B, C; Pompe disease (glycogen storage disease); pycnodysostosis; Sandhoff disease; Schindler disease; Salla disease/sialic acid storage disease; Tay-Sachs; and Wolman disease.

Embodiment 24 of this disclosure relates to any one of Embodiments 21-23, wherein the FLT3 kinase is a mutated form comprising a FLT3 internal tandem duplication (ITD) mutation.

Embodiment 25 of this disclosure relates to Embodiment 24, wherein mutated FLT3 kinase further comprises a D835 mutation, a F691L mutation, or both D835 and F691L mutations.

Embodiment 26 of this disclosure relates to Embodiment 25, wherein mutated FLT3 kinase further comprises a D835Y mutation, a F691L mutation, or both D835Y and F691L mutations.

"Selected from one or more of a group of specific Formulae" for purposes of this disclosure is intended to have the following meaning:

When any selection from any particular group in any embodiment described this disclosure, this embodiment includes embodiments where the selection can be from all listed groups in the particular embodiment as well as all possible subgroups of this embodiment.

For illustrative purposes, when embodiments include more than one formulae, this embodiment is meant to include any one or more of the formulae listed in said embodiment. For example, in an embodiment that would include Formulae I(a), I(b), II(a), or II(b), this embodiment is meant to include all of the following groups from which the Formula is selected from:

1. one of Formulae I(a), I(b), II(a), or II(b);
2. one of Formulae I(a) or I(b);
3. one of Formula II(a) or II(b);
4. Formula I(a);
5. Formula I(b);
6. Formula II(a); or
7. Formula II(b).

III. General

In one aspect, the present disclosure relates to compounds of Formula I(a) and I(b), all embodiments and sub-embodiments thereof including any one or more of compounds P-0001-P-0274, and any other compounds as described herein, that are useful as inhibitors of an oncogenic FLT3 or a FLT3 mutant, and the use of the compounds in treating a subject suffering from diseases that are mediated by a mutated FLT3kinase.

FLT3 kinase is a tyrosine kinase receptor involved in the regulation and stimulation of cellular proliferation. See e.g., Gilliland et al., Blood 100: 1532-42 (2002). The FLT3 kinase is a member of the class III receptor tyrosine kinase (RTKIII) receptor family and belongs to the same subfamily of tyrosine kinases as c-kit, c-fms, and the platelet-derived growth factor α and β receptors. See e.g., Lyman et al., FLT3 Ligand in THE CYTOKINE HANDBOOK 989 (Thomson et al., eds. 4th Ed.) (2003). The FLT3 kinase has five immunoglobulin-like domains in its extracellular region as well as an insert region of 75-100 amino acids in the middle of its cytoplasmic domain. FLT3 kinase is activated upon the binding of the FLT3 ligand, which causes receptor dimerization. Dimerization of the FLT3 kinase by FLT3 ligand activates the intracellular kinase activity as well as a cascade of downstream substrates including Stat5, Ras, phosphatidylinositol-3-kinase (PI3K), PLCγ, Erk2, Akt, MAPK, SHC, SHP2, and SHIP. See e.g., Rosnet et al., Acta Haematol. 95: 218 (1996); Hayakawa et al., Oncogene 19: 624 (2000); Mizuki et al., Blood 96: 3907 (2000); and Gilliland et al., Curr. Opin. Hematol. 9: 274-81 (2002). Both membrane-bound and soluble FLT3 ligand bind, dimerize, and subsequently activate the FLT3 kinase.

In normal cells, immature hematopoietic cells, typically CD34+ cells, placenta, gonads, and brain express FLT3 kinase. See, e.g., Rosnet, et al., Blood 82: 1110-19 (1993); Small et al., Proc. Natl. Acad. Sci. U.S.A. 91: 459-63 (1994); and Rosnet et al., Leukemia 10: 238-48 (1996). However, efficient stimulation of proliferation via FLT3 kinase typically requires other hematopoietic growth factors or interleukins. FLT3 kinase also plays a critical role in immune function through its regulation of dendritic cell proliferation and differentiation. See e.g., McKenna et al., Blood 95: 3489-97 (2000).

Numerous hematologic malignancies express FLT3 kinase, the most prominent of which is AML. See e.g., Yokota et al., Leukemia 11: 1605-09 (1997). Other FLT3 expressing malignancies include B-precursor cell acute lymphoblastic leukemias, myelodysplastic leukemias, T-cell acute lymphoblastic leukemias, and chronic myelogenous leukemias. See e.g., Rasko et al., Leukemia 9: 2058-66 (1995).

FLT3 kinase mutations associated with hematologic malignancies are activating mutations. In other words, the FLT3 kinase is constitutively activated without the need for binding and dimerization by FLT3 ligand, and therefore stimulates the cell to grow continuously.

Several studies have identified inhibitors of FLT3 kinase activity that also inhibit the kinase activity of related receptors, e.g., VEGF receptor (VEGFR), PDGF receptor (PDGFR), and kit receptor kinases. See e.g., Mendel et al., Clin. Cancer Res. 9: 327-37 (2003); O'Farrell et al., Blood 101: 3597-605 (2003); and Sun et al., J. Med. Chem. 46: 1116-19 (2003). Such compounds effectively inhibit FLT3 kinase-mediated phosphorylation, cytokine production, cellular proliferation, resulting in the induction of apoptosis. See e.g., Spiekermann et al., Blood 101: 1494-1504 (2003). Moreover, such compounds have potent antitumor activity in vitro and in vivo.

In some embodiments, the oncogenic FLT3 or FLT3 mutant is encoded by a FLT3 gene with an internal tandem duplication (ITD) mutation in the juxtamembrane as described in U.S. Pat. No. 6,846,630, which is herein incorporated by reference. In certain embodiments, the oncogenic FLT3 or FLT3 mutant encoded by FLT3 with ITD mutations has one or more mutations at residues F691, D835, Y842 or combinations thereof. In some embodiments, the oncogenic FLT3 or FLT3 mutant has one or more mutations selected from F691L, D835V/Y, Y842C/H or combinations thereof.

In some embodiments, a subject has a FLT3 gene mutation encoding an FLT3 mutant having an amino acid substitution at residues F691, D835, Y842 or combinations thereof. In certain instances, the amino acid substitution is selected from F691L, D835V/Y, Y842C/H or combinations thereof.

In some embodiments, the disclosure provides a method of inhibiting an oncogenic FLT3 or a mutant FLT3. The method includes contacting the FLT3 kinase with a compound as described herein. In some embodiments, the oncogenic FLT3 or FLT3 mutant is encoded by a FLT3 gene having an ITD mutation. In some embodiments, the oncogenic FLT3 or FLT3 mutant encoded by an FLT3 gene with an ITD mutation has one or more mutations at residues F691, D835, Y842 or combinations thereof. In some embodiments, the oncogenic FLT3 or FLT3 mutant has one or more mutations are selected from F691L, D835V/Y, Y842C/H or combinations thereof. In another embodiment, the oncogenic FLT3 mutant is encoded by a FLT3 gene having an ITD mutation. In another embodiment, the oncogenic FLT3 mutant is encoded by a FLT3 gene having an ITD mutation and a F691L mutation. In another embodiment, the oncogenic FLT3 mutant is encoded by a FLT3 gene having an ITD mutation and a D835Y mutation. In another embodiment, the oncogenic FLT3 mutant is encoded by a FLT3 gene having an ITD mutation, a F691L mutation, and a D835Y mutation.

Hematologic cancers, also known as hematologic or hematopoietic malignancies, are cancers of the blood or bone marrow; including leukemia and lymphoma. Acute myelogenous leukemia (AML) is a clonal hematopoietic stem cell leukemia that represents about 90% of all acute leukemias in adults with an incidence of 3.9 per 100,000 (See e.g., Lowenberg et al., N. Eng. J. Med. 341: 1051-62 (1999) and Lopesde Menezes, et al, Clin. Cancer Res. (2005), 11(14):5281-5291). While chemotherapy can result in complete remissions, the long term disease-free survival rate for AML is about 14% with about 7,400 deaths from AML each year in the United States. Approximately 70% of AML blasts express wild type FLT3 and about 25% to about 35% express FLT3 kinase receptor mutations which result in constitutively active FLT3. Two types of activating mutations have been identified, in AML patients: internal tandem duplications (ITDs) and point mutation in the activating loop of the kinase domain. FLT3-ITD mutations in AML patients is indicative of a poor prognosis for survival, and in patients who are in remission, FLT3-ITD mutations are the most significant factor adversely affecting relapse rate with 64% of patients having the mutation relapsing within 5 years (see Current Pharmaceutical Design (2005), 11:3449-3457. The prognostic significance of FLT3 mutations in clinical studies suggests that FLT3 plays a driving role in AML and may be necessary for the development and maintenance of the disease. Mixed Lineage Leukemia (MLL) involve translocations of chromosome 11 band q23 (11q23) and occur in approximately 80% of infant hematological malignancies and 10% of adult acute leukemias. Although certain 11q23 translocation have been shown to be essential to immortalization of hematopoietic progenitors in vitro, a secondary genotoxic event is required to develop leukemia. There is a strong concordance between FLT3 and MLL fusion gene expression, and the most consistently overexpressed gene in MLL is FLT3. Moreover, it has been shown that activated FLT3 together with MLL fusion gene expression induces acute leukemia with a short latency period (see Ono, et al., J. of Clinical Investigation (2005), 115:919-929). Therefore, it is believed that FLT3 signaly is involved in the development and maintenance of MLL (see Armstrong, et al., Cancer Cell (2003), 3:173-183).

The FLT3-ITD mutation is also present in about 3% of cases of adult myelodysplastic syndrome and some cases of acute lymphocytic leukemia (ALL) (Current Pharmaceutical Design (2005), 11:3449-3457).

FLT3 has been shown to be a client protein of Hsp90, and 17AAG, a benzoquinone ansamycin antibiotic that inhibits Hsp90 activity, has been shown to disrupts the association of FLT3 with Hsp90. The growth of leukemia cell that express either wild type FLT3 or FLT3-ITD mutations was found to be inhibited by treatment with 17"AAG (Yao, et al., Clinical Cancer Research (2003), 9:4483-4493).

The compounds as described herein are useful for the treatment or prevention of haematological malignancies, including, but not limiting to, acute myeloic leukemia (AML); mixed lineage leukemia (MLL); acute promyelocytic leukemia; acute lymphocytic leukemia, acute lymphoblastic leukemia, myeloid sarcoma; T-cell type acute lymphocytic leukemia (T-ALL); B-cell type acute lymphocytic leukemia (B-ALL); chronic myelomonocytic leukemia (CMML); myelodysplastic syndrome; myeloproliferative disorders; other proliferative disorders, including, but not limiting to, cancer; autoimmune disorders; and skin disorders, such as psoriasis and atopic dermatitis.

In another aspect, the present disclosure also provides a method for modulating FLT3 activity by contacting a FLT3 or a mutant FLT3 by administering an effective amount of any of the compounds described in Embodiments 1, 1(a), 1(b), 1(c), 1(d), 1(e), 2, 2(a), 2(b), 2(c), 2(d), 2(e), 2(f), 2(g), 2(h), 3, 4, 4(a), 4(b), 4(c), 5, 5(a), 5(b) 5(c), 5(d), 5(e), 5(f), 5(g), 5(h), 5(i), 5(j), 5(k), 5(l), 5(m), 5(n), 5(o), 5(p), 5(q), 5(r), 5(s), 5(t), 5(u), 5(v), 5(w), 5(x), 5(z), 5(aa), 5(bb), 5(cc), 5(dd), 5(ee), 5(ff), 5(gg), 5(hh), 5(ii), 5(kk), 5(ll) 6, 7, 7(a), 7(b), 8, 9, 10 or 11, 12, 13, 14, 14(a), 14(b), 14(c), 14(d), 14(e), 14(f), 14(g), 14(h), 14(i), 14(j), 14(k), 14(l), 14(m), 14(n), 14(o), 14(p), 14(q), 14(r), 14(s), 14(t), 14(u), 14(v), 14(w), 14(x), 14(z), 14(aa), 14(bb), 15, 16 or 17. The compound is, in some embodiments, provided at a level sufficient to modulate the activity of the FLT3 by at least 10%, 20%, 30%, 40%, 50%, 60%, 70%, 80%, or 90%, or greater than 90%. In many embodiments, the compound will be at a concentration of about 1 µM, 100 µM, or 1 mM, or in a range of 1-100 nM, 100-500 nM, 500-1000 nM, 1-100 µM, 100-500 µM, or 500-1000 µM. In some embodiments, the contacting is carried out in vitro. In other embodiments, the contacting is carried out in vivo.

In another aspect, the present disclosure also provides a method for modulating c-Kit activity by contacting c-Kit by administering an effective amount of any of the compounds described in Embodiments 1, 1(a), 1(b), 1(c), 1(d), 1(e), 2, 2(a), 2(b), 2(c), 2(d), 2(e), 2(f), 2(g), 2(h), 3, 4, 4(a), 4(b), 4(c), 5, 5(a), 5(b) 5(c), 5(d), 5(e), 5(f), 5(g), 5(h), 5(i), 5(j), 5(k), 5(l), 5(m), 5(n), 5(o), 5(p), 5(q), 5(r), 5(s), 5(t), 5(u), 5(v), 5(w), 5(x), 5(z), 5(aa), 5(bb), 5(cc), 5(dd), 5(ee), 5(ff), 5(gg), 5(hh), 5(ii), 5(kk), 5(ll) 6, 7, 7(a), 7(b), 8, 9, 10 or 11, 12, 13, 14, 14(a), 14(b), 14(c), 14(d), 14(e), 14(f), 14(g), 14(h), 14(i), 14(j), 14(k), 14(l), 14(m), 14(n), 14(o), 14(p), 14(q), 14(r), 14(s), 14(t), 14(u), 14(v), 14(w), 14(x), 14(z), 14(aa), 14(bb), 15, 16 or 17. The compound is, in some embodiments, provided at a level sufficient to modulate the activity of the c-Kit by at least 10%, 20%, 30%, 40%, 50%, 60%, 70%, 80%, or 90%, or greater than 90%. In many embodiments, the compound will be at a concentration of about 1 µM, 100 µM, or 1 mM, or in a range of 1-100 nM, 100-500 nM, 500-1000 nM, 1-100 µM, 100-500 µM, or 500-1000 µM. In some embodiments, the contacting is carried out in vitro. In other embodiments, the contacting is carried out in vivo.

In another embodiment, the present disclosure also provides a method for modulating CSFR1 activity by contacting CSFR1 by administering an effective amount of any of the compounds described in Embodiments 1, 1(a), 1(b), 1(c), 1(d), 1(e), 2, 2(a), 2(b), 2(c), 2(d), 2(e), 2(f), 2(g), 2(h), 3, 4, 4(a), 4(b), 4(c), 5, 5(a), 5(b) 5(c), 5(d), 5(e), 5(f), 5(g), 5(h), 5(i), 5(j), 5(k), 5(l), 5(m), 5(n), 5(o), 5(p), 5(q), 5(r), 5(s), 5(t), 5(u), 5(v), 5(w), 5(x), 5(z), 5(aa), 5(bb), 5(cc), 5(dd), 5(ee), 5(ff), 5(gg), 5(hh), 5(ii), 5(kk), 5(ll) 6, 7, 7(a), 7(b), 8, 9, 10 or 11, 12, 13, 14, 14(a), 14(b), 14(c), 14(d), 14(e), 14(f), 14(g), 14(h), 14(i), 14(j), 14(k), 14(l), 14(m), 14(n), 14(o), 14(p), 14(q), 14(r), 14(s), 14(t), 14(u), 14(v), 14(w), 14(x), 14(z), 14(aa), 14(bb), 15, 16 or 17. The compound is, in some embodiments, provided at a level sufficient to modulate the activity of the CSF1R by at least 10%, 20%, 30%, 40%, 50%, 60%, 70%, 80%, or 90%, or greater than 90%. In many embodiments, the compound will be at a concentration of about 1 µM, 100 µM, or 1 mM, or in a range of 1-100 nM, 100-500 nM, 500-1000 nM, 1-100 µM, 100-500 µM, or 500-1000 µM. In some embodiments, the contacting is carried out in vitro. In other embodiments, the contacting is carried out in vivo.

In another aspect, the present disclosure also provides a method for modulating one or more of FLT3, c-Kit and/or CSF1R activity by contacting one or more of FLT3, c-Kit and/or CSF1R by administering an effective amount of any of the compounds described in Embodiments 1, 1(a), 1(b), 1(c), 1(d), 1(e), 2, 2(a), 2(b), 2(c), 2(d), 2(e), 2(f), 2(g), 2(h), 3, 4, 4(a), 4(b), 4(c), 5, 5(a), 5(b) 5(c), 5(d), 5(e), 5(f), 5(g), 5(h), 5(i), 5(j), 5(k), 5(l), 5(m), 5(n), 5(o), 5(p), 5(q), 5(r), 5(s), 5(t), 5(u), 5(v), 5(w), 5(x), 5(z), 5(aa), 5(bb), 5(cc), 5(dd), 5(ee), 5(ff), 5(gg), 5(hh), 5(ii), 5(kk), 5(ll) 6, 7, 7(a), 7(b), 8, 9, 10 or 11, 12, 13, 14, 14(a), 14(b), 14(c), 14(d), 14(e), 14(f), 14(g), 14(h), 14(i), 14(j), 14(k), 14(l), 14(m), 14(n), 14(o), 14(p), 14(q), 14(r), 14(s), 14(t), 14(u), 14(v), 14(w), 14(x), 14(z), 14(aa), 14(bb), 15, 16 or 17. The compound is, in some embodiments, provided at a level sufficient to modulate the activity of one or more of FLT3, c-Kit and/or CSF1R by at least 10%, 20%, 30%, 40%, 50%, 60%, 70%, 80%, or 90%, or greater than 90%. In many embodiments, the compound will be at a concentration of about 1 µM, 100 µM, or 1 mM, or in a range of 1-100 nM, 100-500 nM, 500-1000 nM, 1-100 µM, 100-500 µM, or 500-1000 µM. In some embodiments, the contacting is carried out in vitro. In other embodiments, the contacting is carried out in vivo.

In another aspect, the present disclosure also provides a method for modulating FLT3 activity and c-Kit activity by contacting both c-Kit and FLT3 or a mutant FLT3 by administering an effective amount of any of the compounds described in Embodiments 1, 1(a), 1(b), 1(c), 1(d), 1(e), 2, 2(a), 2(b), 2(c), 2(d), 2(e), 2(f), 2(g), 2(h), 3, 4, 4(a), 4(b), 4(c), 5, 5(a), 5(b) 5(c), 5(d), 5(e), 5(f), 5(g), 5(h), 5(i), 5(j), 5(k), 5(l), 5(m), 5(n), 5(o), 5(p), 5(q), 5(r), 5(s), 5(t), 5(u), 5(v), 5(w), 5(x), 5(z), 5(aa), 5(bb), 5(cc), 5(dd), 5(ee), 5(ff), 5(gg), 5(hh), 5(ii), 5(kk), 5(ll) 6, 7, 7(a), 7(b), 8, 9, 10 or 11, 12, 13, 14, 14(a), 14(b), 14(c), 14(d), 14(e), 14(f), 14(g), 14(h), 14(i), 14(j), 14(k), 14(l), 14(m), 14(n), 14(o), 14(p), 14(q), 14(r), 14(s), 14(t), 14(u), 14(v), 14(w), 14(x), 14(z), 14(aa), 14(bb), 15, 16 or 17. The compound is, in some embodiments, provided at a level sufficient to modulate the activity of c-Kit and FLT3 by at least 10%, 20%, 30%, 40%, 50%, 60%, 70%, 80%, or 90%, or greater than 90%. In many embodiments, the compound will be at a concentration of about 1 µM, 100 µM, or 1 mM, or in a range of 1-100 nM, 100-500 nM, 500-1000 nM, 1-100 µM, 100-500 µM, or 500-1000 µM. In some embodiments, the contacting is carried out in vitro. In other embodiments, the contacting is carried out in vivo.

As used herein, the term FLT3 mediated disease or condition refers to a disease or condition in which the biological function of FLT3 affects the development and/or course of the disease or condition, and/or in which modulation of FLT3 alters the development, course, and/or symptoms. These mutations attenuate the intrinsic tyrosine kinase activity of the receptor to different degrees and are models for the effect of modulation of FLT3 activity. A FLT3 mediated disease or condition includes a disease or condition for which FLT3 inhibition provides a therapeutic benefit, e.g. wherein treatment with FLT3 inhibitors, including compounds described herein, provides a therapeutic benefit to the subject suffering from or at risk of the disease or condition.

As used herein, the term c-Kit mediated disease or condition refers to a disease or condition in which the biological function of c-Kit affects the development and/or course of the disease or condition, and/or in which modulation of c-Kit alters the development, course, and/or symptoms. These mutations attenuate the intrinsic tyrosine kinase activity of the receptor to different degrees and are models for the effect of modulation of c-Kit activity. A c-Kit mediated disease or condition includes a disease or condition for which c-Kit inhibition provides a therapeutic benefit, e.g. wherein treatment with c-Kit inhibitors, including compounds described herein, provides a therapeutic benefit to the subject suffering from or at risk of the disease or condition.

As used herein, the term CSF1R mediated disease or condition refers to a disease or condition in which the biological function of CSF1R affects the development and/or course of the disease or condition, and/or in which modulation of CSF1R alters the development, course, and/or symptoms. These mutations attenuate the intrinsic tyrosine kinase activity of the receptor to different degrees and are models for the effect of modulation of CSF1R activity. A CSF1R mediated disease or condition includes a disease or condition for which CSF1R inhibition provides a therapeutic benefit, e.g. wherein treatment with CSF1R inhibitors, including compounds described herein, provides a therapeutic benefit to the subject suffering from or at risk of the disease or condition.

Reference to particular amino acid residues in human FLT3 polypeptide is defined by the numbering corresponding to the FLT3 sequence in GenBank NP004110.2 (SEQ ID NO:1). Reference to particular nucleotide positions in a nucleotide sequence encoding all or a portion of FLT3 is defined by the numbering corresponding to the sequence provided in GenBank NM_44119 (SEQ ID NO:2).

The terms "Flt3," also referred to herein as "FLT3," mean an enzymatically active kinase that contains a portion with greater than 90% amino acid sequence identity to amino acid residues including the ATP binding site of full-length FLT3 (e.g., human FLT3, e.g., the sequence NP_004110.2, SEQ ID NO:1), for a maximal alignment over an equal length segment; or that contains a portion with greater than 90% amino acid sequence identity to at least 200 contiguous amino acids of native FLT3 and retains kinase activity. In some embodiments, the sequence identity is at least 95, 97, 98, 99, or even 100%. In some embodiments, the specified level of sequence identity is over a sequence at least 100-500, at least 200-400, or at least 300 contiguous amino acid residues in length. Unless indicated to the contrary, the term includes reference to wild-type c-FLT3, allelic variants, and mutated forms (e.g., having activating mutations).

The terms "FLT-mediated diseases or disorders" shall include diseases associated with or implicating FLT3 activity, for example, the overactivity of FLT3, and conditions that accompany with these diseases. The term "overactivity of FLT3" refers to either 1) FLT3 expression in cells which normally do not express FLT3; 2) FLT3 expression by cells which normally do not express v; 3) increased FLT3 expression leading to unwanted cell proliferation; or 4) mutations leading to constitutive activation of FLT3. Examples of "FLT-mediated diseases or disorders" include disorders resulting from over stimulation of FLT3 or from abnormally high amount of FLT3 activity, due to abnormally high amount of FLT3 or mutations in FLT3. It is known that overactivity of FLT3 has been implicated in the pathogenesis of a number of diseases, including inflammatory and autoimmune diseases, cell proliferative disorders, neoplastic disorders and cancers as described herein.

The term "FLT3-ITD allelic ratio" refers to the percentage of tumor DNA alleles harboring the FLT3-ITD mutation normalized to the percent blast cells in a patient sample. In one embodiment, a low FLT3-ITD allelic ratio is where less than 25% of normalized tumor DNA alleles is a FLT3-ITD allele. In certain embodiments, an intermediate FLT3-ITD allelic ratio is where between 25% and 50% of normalized tumor DNA alleles is a FLT3-ITD allele. In certain embodiments, a high FLT3-ITD allelic ratio is where greater than 50% of normalized tumor DNA alleles is a FLT3-ITD allele.

The "FLT3/ITD mutation-containing cells" include any of cells having tandem duplication mutation absent in healthy humans in a region of exons 14 to 15 in a juxtamembrane region of FLT3, that is, cells highly expressing mRNA derived from the mutation, cells having increased FLT3-derived growth signals caused by the mutation, cells highly expressing the mutant FLT3 protein, etc. The "FLT3/ITD mutation-containing cancerous cells" include any of cancerous cells having tandem duplication mutation absent in healthy humans in a region of exons 14 to 15 in a juxtamembrane region of FLT3, that is, cancerous cells highly expressing mRNA derived from the mutation, cancerous cells having increased FLT3-derived growth signals caused by the mutation, cancerous cells highly expressing the mutant FLT3 protein, etc. The "FLT3/ITD mutation-containing leukemic cells" include any of leukemic cells having tandem duplication mutation absent in healthy humans in a region of exons 14 to 15 in a juxtamembrane region of FLT3, that is, leukemic cells highly expressing mRNA derived from the mutation, leukemic cells having increased FLT3-derived growth signals caused by the mutation, leukemic cells highly expressing the mutant FLT3 protein, etc.

The terms "modulate," "modulation," and the like refer to the ability of a compound to increase or decrease the function and/or expression of a protein kinase such as FLT3, where such function may include transcription regulatory activity and/or protein-binding. Modulation may occur in vitro or in vivo. Modulation, as described herein, includes the inhibition, antagonism, partial antagonism, activation, agonism or partial agonism of a function or characteristic associated with FLT3, either directly or indirectly, and/or the upregulation or downregulation of the expression of FLT3, either directly or indirectly. In another embodiment, the modulation is direct. Inhibitors or antagonists are compounds that, e.g., bind to, partially or totally block stimulation, decrease, prevent, inhibit, delay activation, inactivate, desensitize, or downregulate signal transduction. Activators or agonists are compounds that, e.g., bind to, stimulate, increase, open, activate, facilitate, enhance activation, activate, sensitize or upregulate signal transduction.

The ability of a compound to inhibit the function of FLT3 can be demonstrated in a biochemical assay, e.g., binding assay, or a cell-based assay.

Also in the context of compounds binding to a biomolecular target, the term "greater specificity" indicates that a compound binds to a specified target to a greater extent than to another biomolecule or biomolecules that may be present under relevant binding conditions, where binding to such other biomolecules produces a different biological activity than binding to the specified target. Typically, the specificity is with reference to a limited set of other biomolecules, e.g., in the case of FLT3, other tyrosine kinases or even other type of enzymes. In particular embodiments, the greater specificity is at least 2, 3, 4, 5, 8, 10, 50, 100, 200, 400, 500, or 1000-fold greater specificity.

As used herein in connection with binding compounds or ligands, the term "specific for FLT3 kinase," "specific for FLT3", and terms of like import mean that a particular compound binds to FLT3 to a statistically greater extent than to other kinases that may be present in a particular sample. Also, where biological activity other than binding is indicated, the term "specific for FLT3" indicates that a particular compound has greater biological effect associated with binding FLT3 than to other tyrosine kinases, e.g., kinase activity inhibition. The specificity is also with respect to other biomolecules (not limited to tyrosine kinases) that may be present in a particular sample.

The term "first line cancer therapy" refers to therapy administered to a subject as an initial regimen to reduce the number of cancer cells. First line therapy is also referred to as induction therapy, primary therapy and primary treatment. Commonly administered first-line therapy for AML is cytarabine-based therapy in which cytarabine is administered often in combination with one or more agents selected from daunorubicin, idarubicin, doxorubicin, mitoxantrone, tipifarnib, thioguanine or gemtuzumab ozogamicin. Common regimens used in cytarabine-based therapy include the "7+3" or "5+2" therapy comprising administration of cytarabine with an anthracycline such as daunorubicin or idarubicin. Another first-line therapy is clofarabine-based therapy in which clofarabine is administered, often in combination with an anthracycline such as daunorubicin, idarubicin or doxorubicin. Other first-line therapy for AML are etoposide-based therapy in which etoposide is administered, often in combination with mitoxantrone, and optionally, with cytarabine. Another first-line therapy for AML (for subtype M3, also called acute promyelocytic leukemia) is all-trans-retinoic acid (ATRA). It is recognized that what is considered "first line therapy" by those of ordinary skill in the art will continue to evolve as new anti-cancer agents are developed and tested in the clinics. A summary of the currently accepted approaches to first line treatment is described in NCCN Clinical Practice Guidelines in Oncology for acute myeloid leukemia and the NCI guidelines on acute myeloid leukemia treatment (see, e.g., http://www.cancer.gov/cancertopics/pdq/treatment/adultAML/Health-Professional/page7).

The term "second line cancer therapy" refers to a cancer treatment that is administered to a subject who does not respond to first line therapy, that is, often first line therapy is administered or who has a recurrence of cancer after being in remission. In certain embodiments, second line therapy that may be administered includes a repeat of the initial successful cancer therapy, which may be any of the treatments described under "first line cancer therapy". In certain embodiments, second line therapy is the administration of gemtuzumab ozogamicin. In certain embodiments, investigational drugs may also be administered as second line therapy in a clinical trial setting. A summary of the currently accepted approaches to second line treatment is described in the NCCN Clinical Practice Guidelines in Oncology for acute myeloid leukemia and the NCI guidelines on acute myeloid leukemia treatment (see, e.g., http://www.cancer.gov/cancertopics/pdq/treatment/adultAML/HealthProfessional/page5).

The term "refractory" refers to wherein a subject fails to respond or is otherwise resistant to cancer therapy or treatment. The cancer therapy may be first-line, second-line or any subsequently administered treatment. In certain embodiments, refractory refers to a condition where a subject fails to achieve complete remission after two induction attempts. A subject may be refractory due to a cancer cell's intrinsic resistance to a particular therapy, or the subject may be refractory due to an acquired resistance that develops during the course of a particular therapy.

IV. Binding Assays

The methods of the present disclosure can involve assays that are able to detect the binding of compounds to a target molecule. Such binding is at a statistically significant level, with a confidence level of at least 90%, or at least 95, 97, 98, 99% or greater confidence level that the assay signal represents binding to the target molecule, i.e., is distinguished from background. In some embodiments, controls are used to distinguish target binding from non-specific binding. A large variety of assays indicative of binding are known for different target types and can be used for this disclosure.

Binding compounds can be characterized by their effect on the activity of the target molecule. Thus, a "low activity" compound has an inhibitory concentration ($IC_{50}$) or effective concentration ($EC_{50}$) of greater than 1 µM under standard conditions. By "very low activity" is meant an $IC_{50}$ or $EC_{50}$ of above 100 µM under standard conditions. By "extremely low activity" is meant an $IC_{50}$ or $EC_{50}$ of above 1 mM under standard conditions. By "moderate activity" is meant an $IC_{50}$ or $EC_{50}$ of 200 nM to 1 µM under standard conditions. By "moderately high activity" is meant an $IC_{50}$ or $EC_{50}$ of 1 nM to 200 nM. By "high activity" is meant an $IC_{50}$ or $EC_{50}$ of below 1 nM under standard conditions. The $IC_{50}$ or $EC_{50}$ is defined as the concentration of compound at which 50% of the activity of the target molecule (e.g. enzyme or other protein) activity being measured is lost or gained relative to the range of activity observed when no compound is present. Activity can be measured using methods known to those of ordinary skill in the art, e.g., by measuring any detectable product or signal produced by occurrence of an enzymatic reaction, or other activity by a protein being measured.

By "background signal" in reference to a binding assay is meant the signal that is recorded under standard conditions for the particular assay in the absence of a test compound, molecular scaffold, or ligand that binds to the target molecule. Persons of ordinary skill in the art will realize that accepted methods exist and are widely available for determining background signal.

By "standard deviation" is meant the square root of the variance. The variance is a measure of how spread out a distribution is. It is computed as the average squared deviation of each number from its mean. For example, for the numbers 1, 2, and 3, the mean is 2 and the variance is:

$$\sigma^2 = \frac{(1-2)^2 + (2-2)^2 + (3-2)^2}{3} = 0.667.$$

Surface Plasmon Resonance

Binding parameters can be measured using surface plasmon resonance, for example, with a BIAcore® chip (Biacore, Japan) coated with immobilized binding components. Surface plasmon resonance is used to characterize the microscopic association and dissociation constants of reaction between an sFv or other ligand directed against target molecules. Such methods are generally described in the following references which are incorporated herein by reference. Vely F. et al., (2000) BIAcore® analysis to test phosphopeptide-SH2 domain interactions, Methods in Molecular Biology. 121:313-21; Liparoto et al., (1999) Biosensor analysis of the interleukin-2 receptor complex, Journal of Molecular Recognition. 12:316-21; Lipschultz et al., (2000) Experimental design for analysis of complex kinetics using surface plasmon resonance, Methods. 20(3): 310-8; Malmqvist., (1999) BIACORE: an affinity biosensor system for characterization of biomolecular interactions, Biochemical Society Transactions 27:335-40; Alfthan, (1998) Surface plasmon resonance biosensors as a tool in antibody engineering, Biosensors & Bioelectronics. 13:653-63; Fivash et al., (1998) BIAcore for macromolecular interaction, Current Opinion in Biotechnology. 9:97-101; Price et al.; (1998) Summary report on the ISOBM TD-4 Workshop: analysis of 56 monoclonal antibodies against the MUC1 mucin. Tumour Biology 19 Suppl 1:1-20; Malmqvist et al, (1997) Biomolecular interaction analysis: affinity biosensor technologies for functional analysis of proteins, Current Opinion in Chemical Biology. 1:378-83; O'Shannessy et al., (1996) Interpretation of deviations from pseudo-first-order kinetic behavior in the characterization of ligand binding by biosensor technology, Analytical Biochemistry. 236:275-83; Malmborg et al., (1995) BIAcore as a tool in antibody engineering, Journal of Immunological Methods. 183:7-13; Van Regenmortel, (1994) Use of biosensors to characterize recombinant proteins, Developments in Biological Standardization. 83:143-51; and O'Shannessy, (1994) Determination of kinetic rate and equilibrium binding constants for macromolecular interactions: a critique of the surface plasmon resonance literature, Current Opinions in Biotechnology. 5:65-71.

BIAcore® uses the optical properties of surface plasmon resonance (SPR) to detect alterations in protein concentration bound to a dextran matrix lying on the surface of a gold/glass sensor chip interface, a dextran biosensor matrix. In brief, proteins are covalently bound to the dextran matrix at a known concentration and a ligand for the protein is injected through the dextran matrix. Near infrared light, directed onto the opposite side of the sensor chip surface is reflected and also induces an evanescent wave in the gold film, which in turn, causes an intensity dip in the reflected light at a particular angle known as the resonance angle. If the refractive index of the sensor chip surface is altered (e.g. by ligand binding to the bound protein) a shift occurs in the resonance angle. This angle shift can be measured and is expressed as resonance units (RUs) such that 1000 RUs is equivalent to a change in surface protein concentration of 1 ng/mm$^2$. These changes are displayed with respect to time along the y-axis of a sensorgram, which depicts the association and dissociation of any biological reaction.

High Throughput Screening (HTS) Assays

HTS typically uses automated assays to search through large numbers of compounds for a desired activity. Typically HTS assays are used to find new drugs by screening for chemicals that act on a particular enzyme or molecule. For example, if a chemical inactivates an enzyme it might prove to be effective in preventing a process in a cell which causes a disease. High throughput methods enable researchers to assay thousands of different chemicals against each target molecule very quickly using robotic handling systems and automated analysis of results.

As used herein, "high throughput screening" or "HTS" refers to the rapid in vitro screening of large numbers of compounds (libraries); generally tens to hundreds of thousands of compounds, using robotic screening assays. Ultra high-throughput Screening (uHTS) generally refers to the high-throughput screening accelerated to greater than 100,000 tests per day.

To achieve high-throughput screening, it is advantageous to house samples on a multicontainer carrier or platform. A multicontainer carrier facilitates measuring reactions of a plurality of candidate compounds simultaneously. Multi-well microplates may be used as the carrier. Such multi-well microplates, and methods for their use in numerous assays, are both known in the art and commercially available.

Screening assays may include controls for purposes of calibration and confirmation of proper manipulation of the components of the assay. Blank wells that contain all of the reactants but no member of the chemical library are usually included. As another example, a known inhibitor (or activator) of an enzyme for which modulators are sought, can be incubated with one sample of the assay, and the resulting decrease (or increase) in the enzyme activity used as a comparator or control. It will be appreciated that modulators can also be combined with the enzyme activators or inhibitors to find modulators which inhibit the enzyme activation or repression that is otherwise caused by the presence of the known the enzyme modulator.

Measuring Enzymatic and Binding Reactions During Screening Assays

Techniques for measuring the progression of enzymatic and binding reactions, e.g., in multicontainer carriers, are known in the art and include, but are not limited to, the following.

Spectrophotometric and spectrofluorometric assays are well known in the art. Examples of such assays include the use of colorimetric assays for the detection of peroxides, as described in Gordon, A. J. and Ford, R. A., (1972) The Chemist's Companion: A Handbook Of Practical Data, Techniques, And References, John Wiley and Sons, N.Y., Page 437.

Fluorescence spectrometry may be used to monitor the generation of reaction products. Fluorescence methodology is generally more sensitive than the absorption methodology. The use of fluorescent probes is well known to those skilled in the art. For reviews, see Bashford et al., (1987) Spectrophotometry and Spectrofluorometry: A Practical Approach, pp. 91-114, IRL Press Ltd.; and Bell, (1981) Spectroscopy In Biochemistry, Vol. I, pp. 155-194, CRC Press.

In spectrofluorometric methods, enzymes are exposed to substrates that change their intrinsic fluorescence when processed by the target enzyme. Typically, the substrate is nonfluorescent and is converted to a fluorophore through one or more reactions. As a non-limiting example, SMase activity can be detected using the Amplex® Red reagent (Molecular Probes, Eugene, Oreg.). In order to measure sphingomyelinase activity using Amplex® Red, the following reactions occur. First, SMase hydrolyzes sphingomyelin to yield ceramide and phosphorylcholine. Second, alkaline phosphatase hydrolyzes phosphorylcholine to yield choline. Third, choline is oxidized by choline oxidase to betaine. Finally, $H_2O_2$, in the presence of horseradish peroxidase, reacts with Amplex® Red to produce the fluorescent product, Resorufin, and the signal therefrom is detected using spectrofluorometry.

Fluorescence polarization (FP) is based on a decrease in the speed of molecular rotation of a fluorophore that occurs upon binding to a larger molecule, such as a receptor protein, allowing for polarized fluorescent emission by the bound ligand. FP is empirically determined by measuring the vertical and horizontal components of fluorophore emission following excitation with plane polarized light. Polarized emission is increased when the molecular rotation of a fluorophore is reduced. A fluorophore produces a larger polarized signal when it is bound to a larger molecule (i.e. a receptor), slowing molecular rotation of the fluorophore. The magnitude of the polarized signal relates quantitatively to the extent of fluorescent ligand binding. Accordingly, polarization of the "bound" signal depends on maintenance of high affinity binding.

FP is a homogeneous technology and reactions are very rapid, taking seconds to minutes to reach equilibrium. The reagents are stable, and large batches may be prepared, resulting in high reproducibility. Because of these properties, FP has proven to be highly automatable, often performed with a single incubation with a single, premixed, tracer-receptor reagent. For a review, see Owickiet al., (1997), Application of Fluorescence Polarization Assays in High-Throughput Screening, Genetic Engineering News, 17:27.

FP is particularly desirable since its readout is independent of the emission intensity (Checovich, W. J., et al., (1995) Nature 375:254-256; Dandliker, W. B., et al., (1981) Methods in Enzymology 74:3-28) and is thus insensitive to the presence of colored compounds that quench fluorescence emission. FP and FRET (see below) are well-suited for identifying compounds that block interactions between sphingolipid receptors and their ligands. See, for example, Parker et al., (2000) Development of high throughput screening assays using fluorescence polarization: nuclear receptor-ligand-binding and kinase/phosphatase assays, J Biomol Screen 5:77-88.

Fluorophores derived from sphingolipids that may be used in FP assays are commercially available. For example, Molecular Probes (Eugene, Oreg.) currently sells sphingomyelin and one ceramide flurophores. These are, respectively, N-(4,4-difluoro-5,7-dimethyl-4-bora-3a,4a-diaza-s-indacene-3-pentanoyl)sphingosyl phosphocholine (BODIPY® FL C5-sphingomyelin); N-(4,4-difluoro-5,7-dimethyl-4-bora-3a,4a-diaza-s-indacene-3-dodecanoyl)sphingosyl phosphocholine (BODIPY® FL C12-sphingomyelin); and N-(4,4-difluoro-5,7-dimethyl-4-bora-3a,4a-diaza-s-indacene-3-pentanoyl)sphingosine (BODIPY® FL $C_5$-ceramide). U.S. Pat. No. 4,150,949, (Immunoassay for gentamicin), discloses fluorescein-labelled gentamicins, including fluoresceinthiocarbanyl gentamicin. Additional fluorophores may be prepared using methods well known to the skilled artisan.

Exemplary normal-and-polarized fluorescence readers include the POLARION® fluorescence polarization system (Tecan AG, Hombrechtikon, Switzerland). General multiwell plate readers for other assays are available, such as the VERSAMAX® reader and the SPECTRAMAX® multiwell plate spectrophotometer (both from Molecular Devices).

Fluorescence resonance energy transfer (FRET) is another useful assay for detecting interaction and has been described. See, e.g., Heim et al., (1996) Curr. Biol. 6:178-182; Mitra et al., (1996) Gene 173:13-17; and Selvin et al., (1995) Meth. Enzymol. 246:300-345. FRET detects the transfer of energy between two fluorescent substances in close proximity, having known excitation and emission wavelengths. As an example, a protein can be expressed as a fusion protein with green fluorescent protein (GFP). When two fluorescent proteins are in proximity, such as when a protein specifically interacts with a target molecule, the resonance energy can be transferred from one excited molecule to the other. As a result, the emission spectrum of the sample shifts, which can be measured by a fluorometer, such as a fMAX multiwell fluorometer (Molecular Devices, Sunnyvale Calif.).

Scintillation proximity assay (SPA) is a particularly useful assay for detecting an interaction with the target molecule. SPA is widely used in the pharmaceutical industry and has been described (Hanselman et al., (1997) J. Lipid Res. 38:2365-2373; Kahl et al., (1996) Anal. Biochem. 243:282-283; Undenfriend et al., (1987) Anal. Biochem. 161:494-500). See also U.S. Pat. Nos. 4,626,513 and 4,568,649, and European Patent No. 0,154,734. One commercially available system uses FLASHPLATE® scintillant-coated plates (NEN Life Science Products, Boston, Mass.).

The target molecule can be bound to the scintillator plates by a variety of well known means. Scintillant plates are available that are derivatized to bind to fusion proteins such as GST, His6 (SEQ ID NO: 3) or Flag fusion proteins. Where the target molecule is a protein complex or a multimer, one protein or subunit can be attached to the plate first, then the other components of the complex added later under binding conditions, resulting in a bound complex.

In a typical SPA assay, the gene products in the expression pool will have been radiolabeled and added to the wells, and allowed to interact with the solid phase, which is the immobilized target molecule and scintillant coating in the wells. The assay can be measured immediately or allowed to reach equilibrium. Either way, when a radiolabel becomes sufficiently close to the scintillant coating, it produces a signal detectable by a device such as a TOPCOUNT NXT® microplate scintillation counter (Packard BioScience Co., Meriden Conn.). If a radiolabeled expression product binds to the target molecule, the radiolabel remains in proximity to the scintillant long enough to produce a detectable signal.

In contrast, the labeled proteins that do not bind to the target molecule, or bind only briefly, will not remain near the scintillant long enough to produce a signal above background. Any time spent near the scintillant caused by random Brownian motion will also not result in a significant amount of signal. Likewise, residual unincorporated radiolabel used during the expression step may be present, but will not generate significant signal because it will be in solution rather than interacting with the target molecule. These non-binding interactions will therefore cause a certain level of background signal that can be mathematically removed. If too many signals are obtained, salt or other modifiers can be added directly to the assay plates until the desired specificity is obtained (Nichols et al., (1998) Anal. Biochem. 257:112-119).

V. Kinase Activity Assays

A number of different assays for kinase activity can be utilized for assaying for active modulators and/or determining specificity of a modulator for a particular kinase or group or kinases. In addition to the assay mentioned in the Examples below, one of ordinary skill in the art will know of other assays that can be utilized and can modify an assay for a particular application. For example, numerous papers concerning kinases described assays that can be used.

Additional alternative assays can employ binding determinations. For example, this sort of assay can be formatted either in a fluorescence resonance energy transfer (FRET) format, or using an AlphaScreen (amplified/uminescent-proximity homogeneous assay) format by varying the donor and acceptor reagents that are attached to streptavidin or the phospho-specific antibody.

VI. Alternative Compound Forms or Derivatives (a) Isomers, Prodrugs, and Active Metabolites Compounds contemplated herein are described with reference to both generic formulae and specific compounds. In addition, the compounds described herein may exist in a number of different forms or derivatives, all within the scope of the present disclosure. These include, for example, tautomers, stereoisomers, racemic mixtures, regioisomers, salts, prodrugs (e.g. carboxylic acid esters), solvated forms, different crystal forms or polymorphs, and active metabolites.

(b) Tautomers, Stereoisomers, Regioisomers, and Solvated Forms

It is understood that some compounds may exhibit tautomerism. In such cases, the formulae provided herein expressly depict only one of the possible tautomeric forms. It is therefore to be understood that the formulae provided herein are intended to represent any tautomeric form of the depicted compounds and are not to be limited merely to the specific tautomeric form depicted by the drawings of the formulae.

Likewise, some of the compounds according to the present disclosure may exist as stereoisomers, i.e. having the same atomic connectivity of covalently bonded atoms yet differing in the spatial orientation of the atoms. For example, compounds may be optical stereoisomers, which contain one or more chiral centers, and therefore, may exist in two or more stereoisomeric forms (e.g. enantiomers or diastereomers). Thus, such compounds may be present as single stereoisomers (i.e., essentially free of other stereoisomers), racemates, and/or mixtures of enantiomers and/or diastereomers. As another example, stereoisomers include geometric isomers, such as cis- or trans-orientation of substituents on adjacent carbons of a double bond. All such single stereoisomers, racemates and mixtures thereof are intended to be within the scope of the present disclosure. Unless specified to the contrary, all such steroisomeric forms are included within the formulae provided herein.

In some embodiments, a chiral compound of the present disclosure is in a form that contains at least 80% of a single isomer (60% enantiomeric excess ("e.e.") or diastereomeric excess ("d.e.")), or at least 85% (70% e.e. or d.e.), 90% (80% e.e. or d.e.), 95% (90% e.e. or d.e.), 97.5% (95% e.e. or d.e.), or 99% (98% e.e. or d.e.). As generally understood by those skilled in the art, an optically pure compound having one chiral center is one that consists essentially of one of the two possible enantiomers (i.e., is enantiomerically pure), and an optically pure compound having more than one chiral center is one that is both diastereomerically pure and enantiomerically pure. In some embodiments, the compound is present in optically pure form.

For compounds in which synthesis involves addition of a single group at a double bond, particularly a carbon-carbon double bond, the addition may occur at either of the double bond-linked atoms. For such compounds, the present disclosure includes both such regioisomers.

(c) Prodrugs and Metabolites

In addition to the present formulae and compounds described herein, the disclosure also includes prodrugs (generally pharmaceutically acceptable prodrugs), active metabolic derivatives (active metabolites), and their pharmaceutically acceptable salts.

Prodrugs are compounds or pharmaceutically acceptable salts thereof which, when metabolized under physiological conditions or when converted by solvolysis, yield the desired active compound. Prodrugs include, without limitation, esters, amides, carbamates, carbonates, ureides, solvates, or hydrates of the active compound. Typically, the prodrug is inactive, or less active than the active compound, but may provide one or more of advantageous handling, administration, and/or metabolic properties. For example, some prodrugs are esters of the active compound; during metabolysis, the ester group is cleaved to yield the active drug. Also, some prodrugs are activated enzymatically to yield the active compound, or a compound which, upon further chemical reaction, yields the active compound.

In this context, a common example of a prodrug is an alkyl ester of a carboxylic acid. Relative to compounds in any of Embodiments 1, 1(a), 1(b), 1(c), 1(d), 1(e), 2, 2(a), 2(b), 2(c), 2(d), 2(e), 2(f), 2(g), 2(h), 3, 4, 4(a), 4(b), 4(c), 5, 5(a), 5(b) 5(c), 5(d), 5(e), 5(f), 5(g), 5(h), 5(i), 5(j), 5(k), 5(l), 5(m), 5(n), 5(o), 5(p), 5(q), 5(r), 5(s), 5(t), 5(u), 5(v), 5(w), 5(x), 5(z), 5(aa), 5(bb), 5(cc), 5(dd), 5(ee), 5(ff), 5(gg), 5(hh), 5(ii), 5(kk), 5(ll) 6, 7, 7(a), 7(b), 8, 9, 10 or 11, 12, 13, 14, 14(a), 14(b), 14(c), 14(d), 14(e), 14(f), 14(g), 14(h), 14(i), 14(j), 14(k), 14(l), 14(m), 14(n), 14(o), 14(p), 14(q), 14(r), 14(s), 14(t), 14(u), 14(v), 14(w), 14(x), 14(z), 14(aa), 14(bb), 15, 16 or 17, further examples include, without limitation, an amide or carbamate derivative at the pyrrole nitrogen (i.e. $N^1$) of the azaindole core.

As described in The Practice of Medicinal Chemistry, Ch. 31-32 (Ed. Wermuth, Academic Press, San Diego, Calif., 2001), prodrugs can be conceptually divided into two non-exclusive categories, bioprecursor prodrugs and carrier prodrugs. Generally, bioprecursor prodrugs are compounds that are inactive or have low activity compared to the corresponding active drug compound, that contain one or more protective groups and are converted to an active form by metabolism or solvolysis. Both the active drug form and any released metabolic products should have acceptably low toxicity. Typically, the formation of active drug compound involves a metabolic process or reaction that is one of the follow types:

Oxidative reactions: Oxidative reactions are exemplified without limitation to reactions such as oxidation of alcohol, carbonyl, and acid functionalities, hydroxylation of aliphatic carbons, hydroxylation of alicyclic carbon atoms, oxidation of aromatic carbon atoms, oxidation of carbon-carbon double bonds, oxidation of nitrogen-containing functional groups, oxidation of silicon, phosphorus, arsenic, and sulfur, oxidative N-dealkylation, oxidative O- and S-dealkylation, oxidative deamination, as well as other oxidative reactions.

Reductive reactions: Reductive reactions are exemplified without limitation to reactions such as reduction of carbonyl functionalities, reduction of alcohol functionalities and carbon-carbon double bonds, reduction of nitrogen-containing functional groups, and other reduction reactions.

Reactions without change in the oxidation state: Reactions without change in the state of oxidation are exemplified without limitation to reactions such as hydrolysis of esters and ethers, hydrolytic cleavage of carbon-nitrogen single bonds, hydrolytic cleavage of non-aromatic heterocycles, hydration and dehydration at multiple bonds, new atomic linkages resulting from dehydration reactions, hydrolytic dehalogenation, removal of hydrogen halide molecule, and other such reactions.

Carrier prodrugs are drug compounds that contain a transport moiety, e.g., that improves uptake and/or localized delivery to a site(s) of action. Desirably for such a carrier prodrug, the linkage between the drug moiety and the transport moiety is a covalent bond, the prodrug is inactive or less active than the drug compound, the prodrug and any release transport moiety are acceptably non-toxic. For prodrugs where the transport moiety is intended to enhance uptake, typically the release of the transport moiety should be rapid. In other cases, it is desirable to utilize a moiety that provides slow release, e.g., certain polymers or other moieties, such as cyclodextrins. (See, e.g., Cheng et al., U.S. Patent Publ. No. 2004/0077595, incorporated herein by reference.) Such carrier prodrugs are often advantageous for orally administered drugs. Carrier prodrugs can, for example, be used to improve one or more of the following properties: increased lipophilicity, increased duration of pharmacological effects, increased site-specificity, decreased toxicity and adverse reactions, and/or improvement in drug formulation (e.g. stability, water solubility, suppression of an undesirable organoleptic or physiochemical property). For example, lipophilicity can be increased by esterification of hydroxyl groups with lipophilic carboxylic acids, or of carboxylic acid groups with alcohols, e.g., aliphatic alcohols. Wermuth, supra.

Prodrugs may proceed from prodrug form to active form in a single step or may have one or more intermediate forms which may themselves have activity or may be inactive.

Metabolites, e.g., active metabolites, overlap with prodrugs as described above, e.g., bioprecursor prodrugs. Thus, such metabolites are pharmacologically active compounds or compounds that further metabolize to pharmacologically active compounds that are derivatives resulting from metabolic process in the body of a subject. Of these, active metabolites are such pharmacologically active derivative compounds. For prodrugs, the prodrug compound is generally inactive or of lower activity than the metabolic product. For active metabolites, the parent compound may be either an active compound or may be an inactive prodrug.

Prodrugs and active metabolites may be identified using routine techniques known in the art. See, e.g., Bertolini et al., 1997, *J. Med. Chem.*, 40:2011-2016; Shan et al., 1997, *J Pharm Sci* 86(7):756-757; Bagshawe, 1995, *Drug Dev. Res.*, 34:220-230; Wermuth, supra.

(d) Pharmaceutically Acceptable Salts

Compounds can be formulated as or be in the form of pharmaceutically acceptable salts. Contemplated pharmaceutically acceptable salt forms include, without limitation, mono, bis, tris, tetrakis, and so on. Pharmaceutically acceptable salts are non-toxic in the amounts and concentrations at which they are administered. The preparation of such salts can facilitate the pharmacological use by altering the physical characteristics of a compound without preventing it from exerting its physiological effect. Useful alterations in physical properties include lowering the melting point to facilitate transmucosal administration and increasing the solubility to facilitate administering higher concentrations of the drug.

Pharmaceutically acceptable salts include acid addition salts such as those containing sulfate, chloride, hydrochloride, fumarate, maleate, phosphate, sulfamate, acetate, citrate, lactate, tartrate, methanesulfonate, ethanesulfonate, benzenesulfonate, p-toluenesulfonate, cyclohexylsulfamate and quinate. Pharmaceutically acceptable salts can be obtained from acids such as hydrochloric acid, maleic acid, sulfuric acid, phosphoric acid, sulfamic acid, acetic acid, citric acid, lactic acid, tartaric acid, malonic acid, methanesulfonic acid, ethanesulfonic acid, benzenesulfonic acid, p-toluenesulfonic acid, cyclohexylsulfamic acid, fumaric acid, and quinic acid.

Pharmaceutically acceptable salts also include basic addition salts such as those containing benzathine, chloroprocaine, choline, diethanolamine, ethanolamine, t-butylamine, ethylenediamine, meglumine, procaine, aluminum, calcium, lithium, magnesium, potassium, sodium, ammonium, alkylamine, and zinc, when acidic functional groups, such as carboxylic acid or phenol are present. For example, see Remington's Pharmaceutical Sciences, 19th ed., Mack Publishing Co., Easton, Pa., Vol. 2, p. 1457, 1995. Such salts can be prepared using the appropriate corresponding bases.

Pharmaceutically acceptable salts can be prepared by standard techniques. For example, the free-base form of a compound can be dissolved in a suitable solvent, such as an aqueous or aqueous-alcohol solution containing the appropriate acid and then isolated by evaporating the solution. In another example, a salt can be prepared by reacting the free base and acid in an organic solvent.

Thus, for example, if the particular compound is a base, the desired pharmaceutically acceptable salt may be prepared by any suitable method available in the art, for example, treatment of the free base with an inorganic acid, such as hydrochloric acid, hydrobromic acid, sulfuric acid, nitric acid, phosphoric acid, and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha-hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

Similarly, if the particular compound is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include organic salts derived from amino acids, such as L-glycine, L-lysine, and L-arginine, ammonia, primary, secondary, and tertiary amines, and cyclic amines, such as hydroxyethylpyrrolidine, piperidine, morpholine or piperazine, and inorganic salts derived from sodium, calcium, potassium, magnesium, manganese, iron, copper, zinc, aluminum and lithium.

The pharmaceutically acceptable salt of the different compounds may be present as a complex. Examples of complexes include 8-chlorotheophylline complex (analogous to, e. g., dimenhydrinate: diphenhydramine 8-chlorotheophylline (1:1) complex; Dramamine) and various cyclodextrin inclusion complexes.

Unless specified to the contrary, specification of a compound herein includes pharmaceutically acceptable salts of such compound.

(e) Other Compound Forms

In the case of agents that are solids, it is understood by those skilled in the art that the compounds and salts may exist in different crystal or polymorphic forms, or may be formulated as co-crystals, or may be in an amorphous form, or may be any combination thereof (e.g. partially crystalline, partially amorphous, or mixtures of polymorphs) all of which are intended to be within the scope of the present disclosure and specified formulae. Whereas salts are formed by acid/base addition, i.e. a free base or free acid of the compound of interest forms an acid/base reaction with a corresponding addition base or addition acid, respectively, resulting in an ionic charge interaction, co-crystals are a new chemical species that is formed between neutral compounds, resulting in the compound and an additional molecular species in the same crystal structure.

In some instances, compounds of the disclosure are complexed with an acid or a base, including base addition salts such as ammonium, diethylamine, ethanolamine, ethylenediamine, diethanolamine, t-butylamine, piperazine, meglumine; acid addition salts, such as acetate, acetylsalicylate, besylate, camsylate, citrate, formate, fumarate, glutarate, hydrochlorate, maleate, mesylate, nitrate, oxalate, phosphate, succinate, sulfate, tartrate, thiocyanate and tosylate; and amino acids such as alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine or valine. In combining the compound of the disclosure with the acid or base, an amorphous complex is formed rather than a crystalline material such as a typical salt or co-crystal. In some instances, the amorphous form of the complex is facilitated by additional processing, such as by spray-drying, mechanochemical methods such as roller compaction, or microwave irradiation of the parent compound mixed with the acid or base. Such methods may also include addition of ionic and/or non-ionic polymer systems, including, but not limited to, hydroxypropyl methyl cellulose acetate succinate (HPMCAS) and methacrylic acid copolymer (e.g. Eudragit® L100-55), that further stabilize the amorphous nature of the complex. Such amorphous complexes provide several advantages. For example, lowering of the melting temperature relative to the free base facilitates additional processing, such as hot melt extrusion, to further improve the biopharmaceutical properties of the compound. Also, the amorphous complex is readily friable, which provides improved compression for loading of the solid into capsule or tablet form.

Additionally, the formulae are intended to cover hydrated or solvated as well as unhydrated or unsolvated forms of the identified structures. For example, the indicated compounds include both hydrated and non-hydrated forms. Other examples of solvates include the structures in combination with a suitable solvent, such as isopropanol, ethanol, methanol, dimethyl sulfoxide, ethyl acetate, acetic acid, or ethanolamine.

VII. Formulations and Administration

The methods and compounds will typically be used in therapy for human subjects. However, they may also be used to treat similar or identical indications in other animal subjects. In this context, the terms "subject," "animal subject," and the like refer to human and non-human vertebrates, e.g. mammals, such as non-human primates, sports and commercial animals, e.g., equines, bovines, porcines, ovines, rodents, and pets, e.g., canines and felines.

Suitable dosage forms, in part, depend upon the use or the route of administration, for example, oral, transdermal, transmucosal, inhalant, or by injection (parenteral). Such dosage forms should allow the compound to reach target cells. Other factors are well known in the art, and include considerations such as toxicity and dosage forms that retard the compound or composition from exerting its effects. Techniques and formulations generally may be found in The Science and Practice of Pharmacy, 21st edition, Lippincott, Williams and Wilkins, Philadelphia, Pa., 2005 (hereby incorporated by reference herein).

Compounds of the present disclosure (i.e. any of the compounds described in Embodiments 1, 1(a), 1(b), 1(c), 1(d), 1(e), 2, 2(a), 2(b), 2(c), 2(d), 2(e), 2(f), 2(g), 2(h), 3, 4, 4(a), 4(b), 4(c), 5, 5(a), 5(b) 5(c), 5(d), 5(e), 5(f), 5(g), 5(h), 5(i), 5(j), 5(k), 5(l), 5(m), 5(n), 5(o), 5(p), 5(q), 5(r), 5(s), 5(t), 5(u), 5(v), 5(w), 5(x), 5(z), 5(aa), 5(bb), 5(cc), 5(dd), 5(ee), 5(ff), 5(gg), 5(hh), 5(ii), 5(kk), 5(ll) 6, 7, 7(a), 7(b), 8, 9, 10 or 11, 12, 13, 14, 14(a), 14(b), 14(c), 14(d), 14(e), 14(f), 14(g), 14(h), 14(i), 14(j), 14(k), 14(l), 14(m), 14(n), 14(o), 14(p), 14(q), 14(r), 14(s), 14(t), 14(u), 14(v), 14(w), 14(x), 14(z), 14(aa), 14(bb), 15, 16 or 17) can be formulated as pharmaceutically acceptable salts.

Carriers or excipients can be used to produce compositions. The carriers or excipients can be chosen to facilitate administration of the compound. Examples of carriers include calcium carbonate, calcium phosphate, various sugars such as lactose, glucose, or sucrose, or types of starch, cellulose derivatives, gelatin, vegetable oils, polyethylene glycols and physiologically compatible solvents. Examples of physiologically compatible solvents include sterile solutions of water for injection (WFI), saline solution, and dextrose.

The compounds can be administered by different routes including intravenous, intraperitoneal, subcutaneous, intramuscular, oral, transmucosal, rectal, transdermal, or inhalant. In some embodiments, the compounds can be administered by oral administration. For oral administration, for example, the compounds can be formulated into conventional oral dosage forms such as capsules, tablets, and liquid preparations such as syrups, elixirs, and concentrated drops.

For inhalants, compounds of the disclosure may be formulated as dry powder or a suitable solution, suspension, or aerosol. Powders and solutions may be formulated with suitable additives known in the art. For example, powders may include a suitable powder base such as lactose or starch, and solutions may comprise propylene glycol, sterile water, ethanol, sodium chloride and other additives, such as acid, alkali and buffer salts. Such solutions or suspensions may be administered by inhaling via spray, pump, atomizer, or nebulizer, and the like. The compounds of the disclosure may also be used in combination with other inhaled therapies, for example corticosteroids such as fluticasone propionate, beclomethasone dipropionate, triamcinolone acetonide, budesonide, and mometasone furoate; beta agonists such as albuterol, salmeterol, and formoterol; anticholinergic agents such as ipratropium bromide or tiotropium; vasodilators such as treprostinal and iloprost; enzymes such as DNAase; therapeutic proteins; immunoglobulin antibodies; an oligonucleotide, such as single or double stranded DNA or RNA, siRNA; antibiotics such as tobramycin; muscarinic receptor antagonists; leukotriene antagonists; cytokine antagonists; protease inhibitors; cromolyn sodium; nedocril sodium; and sodium cromoglycate.

Pharmaceutical preparations for oral use can be obtained, for example, by combining the active compounds with solid excipients, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations, for example, maize starch, wheat starch, rice starch, potato starch, gelatin, gum tragacanth, methyl cellulose, hydroxypropylmethyl-cellulose, sodium carboxymethylcellulose (CMC), and/or polyvinylpyrrolidone (PVP: povidone). If desired, disintegrating agents may be added, such as the cross-linked polyvinylpyrrolidone, agar, or alginic acid, or a salt thereof such as sodium alginate.

Dragee cores are provided with suitable coatings. For this purpose, concentrated sugar solutions may be used, which may optionally contain, for example, gum arabic, talc, poly-vinylpyrrolidone, carbopol gel, polyethylene glycol (PEG), and/or titanium dioxide, lacquer solutions, and suitable organic solvents or solvent mixtures. Dye-stuffs or pigments may be added to the tablets or dragee coatings for identification or to characterize different combinations of active compound doses.

Pharmaceutical preparations that can be used orally include push-fit capsules made of gelatin ("gelcaps"), as well as soft, sealed capsules made of gelatin, and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols (PEGs). In addition, stabilizers may be added.

Alternatively, injection (parenteral administration) may be used, e.g., intramuscular, intravenous, intraperitoneal, and/or subcutaneous. For injection, the compounds of the disclosure are formulated in sterile liquid solutions, such as in physiologically compatible buffers or solutions, such as saline solution, Hank's solution, or Ringer's solution. In addition, the compounds may be formulated in solid form and redissolved or suspended immediately prior to use. Lyophilized forms can also be produced.

Administration can also be by transmucosal, topical, transdermal, or inhalant means. For transmucosal, topical or transdermal administration, penetrants appropriate to the barrier to be permeated are used in the formulation. Such penetrants are generally known in the art, and include, for example, for transmucosal administration, bile salts and fusidic acid derivatives. In addition, detergents may be used to facilitate permeation. Transmucosal administration, for example, may be through nasal sprays or suppositories (rectal or vaginal).

The topical compositions of this disclosure are formulated as oils, creams, lotions, ointments, and the like by choice of appropriate carriers known in the art. Suitable carriers include vegetable or mineral oils, white petrolatum (white soft paraffin), branched chain fats or oils, animal fats and high molecular weight alcohol (greater than $C_{12}$). In another embodiment, the carriers are those in which the active ingredient is soluble. Emulsifiers, stabilizers, humectants and antioxidants may also be included as well as agents imparting color or fragrance, if desired. Creams for topical application are formulated from a mixture of mineral oil, self-emulsifying beeswax and water in which mixture the active ingredient, dissolved in a small amount solvent (e.g. an oil), is admixed. Additionally, administration by transdermal means may comprise a transdermal patch or dressing such as a bandage impregnated with an active ingredient and optionally one or more carriers or diluents known in the art. To be administered in the form of a transdermal delivery system, the dosage administration will, of course, be continuous rather than intermittent throughout the dosage regimen.

The amounts of various compounds to be administered can be determined by standard procedures taking into account factors such as the compound $IC_{50}$, the biological half-life of the compound, the age, size, and weight of the subject, and the indication being treated. The importance of these and other factors are well known to those of ordinary skill in the art. Generally, a dose will be between about 0.01 and 50 mg/kg, or 0.1 and 20 mg/kg of the subject being treated. Multiple doses may be used.

The compounds of the disclosure may also be used in combination with other therapies for treating the same disease. Such combination use includes administration of the compounds and one or more other therapeutics at different times, or co-administration of the compound and one or more other therapies. In some embodiments, dosage may be modified for one or more of the compounds of the disclosure or other therapeutics used in combination, e.g., reduction in the amount dosed relative to a compound or therapy used alone, by methods well known to those of ordinary skill in the art.

It is understood that use in combination includes use with other therapies, drugs, medical procedures etc., where the other therapy or procedure may be administered at different times (e.g. within a short time, such as within hours (e.g. 1, 2, 3, 4-24 hours), or within a longer time (e.g. 1-2 days, 2-4 days, 4-7 days, 1-4 weeks)) than a compound of the present disclosure, or at the same time as a compound of the disclosure. Use in combination also includes use with a therapy or medical procedure that is administered once or infrequently, such as surgery, along with a compound of the disclosure administered within a short time or longer time before or after the other therapy or procedure. In some embodiments, the present disclosure provides for delivery of compounds of the disclosure and one or more other drug therapeutics delivered by a different route of administration or by the same route of administration. The use in combination for any route of administration includes delivery of compounds of the disclosure and one or more other drug therapeutics delivered by the same route of administration together in any formulation, including formulations where the two compounds are chemically linked in such a way that they maintain their therapeutic activity when administered. In one aspect, the other drug therapy may be co-administered with one or more compounds of the disclosure. Use in combination by co-administration includes administration of co-formulations or formulations of chemically joined compounds, or administration of two or more compounds in separate formulations within a short time of each other (e.g. within an hour, 2 hours, 3 hours, up to 24 hours), administered by the same or different routes. Co-administration of separate formulations includes co-administration by delivery via one device, for example the same inhalant device, the same syringe, etc., or administration from separate devices within a short time of each other. Co-formulations of compounds of the disclosure and one or more additional drug therapies delivered by the same route includes preparation of the materials together such that they can be administered by one device, including the separate compounds combined in one formulation, or compounds that are modified such that they are chemically joined, yet still maintain their biological activity. Such chemically joined compounds may have a linkage that is substantially maintained in vivo, or the linkage may break down in vivo, separating the two active components.

In certain embodiments, the patient is 60 years or older and relapsed after a first line cancer therapy. In certain embodiments, the patient is 18 years or older and is relapsed or refractory after a second line cancer therapy. In certain embodiments, the patient is 60 years or older and is primary refractory to a first line cancer therapy. In certain embodiments, the patient is 70 years or older and is previously untreated. In certain embodiments, the patient is 70 years or older and is ineligible and/or unlikely to benefit from cancer therapy.

In certain embodiments, the therapeutically effective amount used in the methods provided herein is at least 10 mg per day. In certain embodiments, the therapeutically effective amount is 10, 50, 90, 100, 135, 150, 200, 250, 300, 350, 400, 450, 500, 600, 700, 800, 900, 1000, 1200, 1300, 1400, 1500, 1600, 1700, 1800, 1900, 2000, 2200, 2500 mg per dosage. In other embodiments, the therapeutically effective amount is 10, 50, 90, 100, 135, 150, 200, 250, 300, 350, 400, 450, 500, 600, 700, 800, 900, 1000, 1200, 1300, 1400, 1500, 1600, 1700, 1800, 1900, 2000, 2200, 2500, 3000, 3500, 4000, 4500, 5000 mg per day or more. In certain embodiments, the compound is administered continuously.

In certain embodiments, provided herein is a method for treating a diseases or condition mediated by FLT3 or oncogenic FLT3 by administering to a mammal having a disease or condition at least 10, 50, 90, 100, 135, 150, 200, 250, 300, 350, 400, 450, 500, 600, 700, 800, 900, 1000, 1200, 1300, 1400, 1500, 1600, 1700, 1800, 1900, 2000, 2200, 2500, 3000, 3500, 4000, 4500, 5000 mg per day of any of the compounds described in Embodiments 1, 1(a), 1(b), 1(c), 1(d), 1(e), 2, 2(a), 2(b), 2(c), 2(d), 2(e), 2(f), 2(g), 2(h), 3, 4, 4(a), 4(b), 4(c), 5, 5(a), 5(b) 5(c), 5(d), 5(e), 5(f), 5(g), 5(h), 5(i), 5(j), 5(k), 5(l), 5(m), 5(n), 5(o), 5(p), 5(q), 5(r), 5(s), 5(t), 5(u), 5(v), 5(w), 5(x), 5(z), 5(aa), 5(bb), 5(cc), 5(dd), 5(ee), 5(ff), 5(gg), 5(hh), 5(ii), 5(kk), 5(ll) 6, 7, 7(a), 7(b), 8, 9, 10 or 11, 12, 13, 14, 14(a), 14(b), 14(c), 14(d), 14(e), 14(f), 14(g), 14(h), 14(i), 14(j), 14(k), 14(l), 14(m), 14(n), 14(o), 14(p), 14(q), 14(r), 14(s), 14(t), 14(u), 14(v), 14(w), 14(x), 14(z), 14(aa), 14(bb), 15, 16 or 17, and wherein the compound is administered on an empty stomach.

In certain embodiments, the disease or condition in the methods provided herein is cancer. In certain embodiments, the disease or condition in the methods provided herein is a solid tumor. In yet another embodiment, the disease or condition in the methods provided herein is a blood-borne tumor. In yet another embodiment, the disease or condition is leukemia. In certain embodiments, the leukemia is acute myeloid leukemia. In certain embodiments, the leukemia is acute lymphocytic leukemia. In still another embodiment, the leukemia is a refractory or drug resistant leukemia.

In certain embodiments, the drug resistant leukemia is drug resistant acute myeloid leukemia. In certain embodiments, the mammal having the drug resistant acute myeloid leukemia has an activating FLT3 mutation. In still another embodiment, the drug resistant acute myeloid leukemia has a FLT3 internal tandem duplication (ITD) mutation. In still another embodiment, the drug resistant acute myeloid leukemia has a FLT3 internal tandem duplication (ITD) mutation and a drug resistant D835Y mutation. In still another embodiment, the drug resistant acute myeloid leukemia has a FLT3 internal tandem duplication (ITD) mutation and a drug resistant F691L mutation. In still another embodiment, the drug resistant acute myeloid leukemia has a FLT3 internal tandem duplication (ITD) mutation and drug resistant D835Y and F691L mutations.

Each method provided herein may further comprise administering a second therapeutic agent. In certain embodiments, the second therapeutic agent is an anticancer agent. In certain embodiments, the second therapeutic agent is a protein kinase inhibitor; In certain embodiments, a tyrosine kinase inhibitorincluding, but not limiting to, sunitinib, cediranib, cabozantinib, trametinib, dabrafenib, cobimetinib, ponatinib (AP24534), PHA-665752, Dovitinib (TKI258, CHIR-258), AC220 (quizartinib), TG101209, KW-2449, AEE788 (NVP-AEE788), MP-470 (amuvatinib), TSU-68 (SU6668, orantinib, ENMD-2076, vatalanib dihydrochloride (PTK787) and tandutinib (MLN518).

VIII. Methods for Treating Conditions Mediated by FLT3 Kinases

In another aspect, the present disclosure provides a method for treating a subject suffering from or at risk of FLT3 protein kinase mediated diseases or conditions. The method includes administering to the subject an effective amount of one or more compounds described in Embodiments 1, 1(a), 1(b), 1(c), 1(d), 1(e), 2, 2(a), 2(b), 2(c), 2(d), 2(e), 2(f), 2(g), 2(h), 3, 4, 4(a), 4(b), 4(c), 5, 5(a), 5(b) 5(c), 5(d), 5(e), 5(f), 5(g), 5(h), 5(i), 5(j), 5(k), 5(l), 5(m), 5(n), 5(o), 5(p), 5(q), 5(r), 5(s), 5(t), 5(u), 5(v), 5(w), 5(x), 5(z), 5(aa), 5(bb), 5(cc), 5(dd), 5(ee), 5(ff), 5(gg), 5(hh), 5(ii), 5(kk), 5(ll) 6, 7, 7(a), 7(b), 8, 9, 10 or 11, 12, 13, 14, 14(a), 14(b), 14(c), 14(d), 14(e), 14(f), 14(g), 14(h), 14(i), 14(j), 14(k), 14(l), 14(m), 14(n), 14(o), 14(p), 14(q), 14(r), 14(s), 14(t), 14(u), 14(v), 14(w), 14(x), 14(z), 14(aa), 14(bb), 15, 16 or 17, or a pharmaceutical composition of one or more compounds in any of the aforementioned embodiments. In certain embodiments, the method involves administering to the subject an effective amount of any one or more compound(s) as described herein in combination with one or more other therapies for the disease or condition. Non-limiting examples of a disease or condition mediated by a FLT3 protein kinase include acute myeloid leukemia, stem cell ablation and myelopreparation for stem cell transplant, primary progressive multiple sclerosis, complex regional pain syndrome, reflex sympathetic dystrophy, muscular dystrophy, duchenne muscular dystrophy, causalgia, neuroinflammation, neuroinflammatory disorders, benign forgetfulness, HIV, binswager type dementia, dementia with lewy bodie, prosencepahy, microencepahy, cerebral palsy, congenital hydrocephalus, abdominal dropsy, progressive supranuclear palsy, glaucoma, addiction disorders, dependencies, alcoholism, tremors, Wilson's disease, vascular dementias, multi infarct dementia, fronto temporal dementia, pseudo-dementia, bladder cancer, basal cell carcinoma, cholangiocarcinoma, colon cancer, endometrial cancer, esophageal cancer, Ewing's sarcoma, gastric cancer, glioma, hepatocellular carcinoma, Hodgkin lymphoma, laryngeal carcinoma, leukemia, liver cancer, lung cancer, melanoma, mesothelioma, pancreatic cancer, rectal cancer, renal cancer, squamous cell carcinoma, t cell lymphoma, thyroid cancer, monocytic leukemia, pheochromocytoma, malignant peripheral nerve cell tumors, malignant peripheral nerve sheath tumors (MPNST), cutaneous and plexiform neurofibromas, leiomyoadenomatoid tumor, fibroids, uterine fibroids, leiomyosarcoma, papillary thyroid cancer, anaplastic thyroid cancer, medullary thyroid cancer, follicular thyroid cancer, hurthle cell carcinoma, thyroid cancer, ascites, malignant ascites, mesothelioma, salivary gland tumors, mucoepidermoid carcinoma of the salivary gland, acinic cell carcinoma of the salivary gland, gastrointestinal stromal tumors (GIST), tumors that cause effusions in potential spaces of the body, pleural effusions, pericardial effusions, peritoneal effusions aka ascites, giant cell tumors (GCT), GCT of bone other sarcomas, tumor angiogenesis, paracrine tumor growth or tumors that express aberrantly or otherwise Fms, CSF1R, CSF1 or IL-34, or activating mutations or translocations of any of the foregoing.

Further methods and uses of the compounds and compositions described in the embodiments of this disclosure are set forth below.

In another embodiment of this disclosure, the disease or condition that can be treated by one or more compounds in Embodiments 1, 1(a), 1(b), 1(c), 1(d), 1(e), 2, 2(a), 2(b), 2(c), 2(d), 2(e), 2(f), 2(g), 2(h), 3, 4, 4(a), 4(b), 4(c), 5, 5(a), 5(b) 5(c), 5(d), 5(e), 5(f), 5(g), 5(h), 5(i), 5(j), 5(k), 5(l), 5(m), 5(n), 5(o), 5(p), 5(q), 5(r), 5(s), 5(t), 5(u), 5(v), 5(w), 5(x), 5(z), 5(aa), 5(bb), 5(cc), 5(dd), 5(ee), 5(ff), 5(gg), 5(hh), 5(ii), 5(kk), 5(ll) 6, 7, 7(a), 7(b), 8, 9, 10 or 11, 12, 13, 14, 14(a), 14(b), 14(c), 14(d), 14(e), 14(f), 14(g), 14(h), 14(i), 14(j), 14(k), 14(l), 14(m), 14(n), 14(o), 14(p), 14(q), 14(r), 14(s), 14(t), 14(u), 14(v), 14(w), 14(x), 14(z), 14(aa), 14(bb), 15, 16 or 17, or a pharmaceutical composition according to Embodiments 18, 19 or 20, is a lysosomal storage disorder. Non-limiting examples of lysosomal storage disorders include mucolipodosis, alpha-mannosidosis; aspartylglucosaminuria; Batten disease; beta-mannosidosis; cystinosis; Danon disease; Fabry disease; Farber disease; fucosidosis; galactosialidosis; Gaucher disease; gangliosidosis (e.g., GM1 gangliosidosis and GM2-gangliosidosis AB variant); Krabbe disease; metachromatic leukodystrophy; mucopolysaccharidoses disorders (e.g., MPS 1—Hurler syndrome, MPS II—Hunter syndrome, MPS III—Sanfilippo (A,B,C,D), MPS IVA—Morquio, MPS IX—hyaluronidase, deficiency, MPS VI—Maroteaux-Lamy, or MPS VII—Sly syndrome); mucolipidosis type I (Sialidosis); Mucolipidosis type II (I-Cell disease); Mucolipidosis type III (Pseudo-Hurler polydystrophy); Mucolipidosis type IV; multiple sulfatase deficiency; Niemann-Pick types A, B, C; Pompe disease (glycogen storage disease); pycnodysostosis; Sandhoff disease; Schindler disease; Salla disease/sialic acid storage disease; Tay-Sachs; and Wolman disease.

In other embodiments, the disclosure provides a method for treating a subject suffering from a disease or condition mediated by CSF1R, c-kit, FLT3, infiltration or activation of macrophages and/or microglias or combinations thereof. The method includes administering to the subject an effective amount of one or more compounds in Embodiments 1, 1(a), 1(b), 1(c), 1(d), 1(e), 2, 2(a), 2(b), 2(c), 2(d), 2(e), 2(f), 2(g), 2(h), 3, 4, 4(a), 4(b), 4(c), 5, 5(a), 5(b) 5(c), 5(d), 5(e), 5(f), 5(g), 5(h), 5(i), 5(j), 5(k), 5(l), 5(m), 5(n), 5(o), 5(p), 5(q), 5(r), 5(s), 5(t), 5(u), 5(v), 5(w), 5(x), 5(z), 5(aa), 5(bb), 5(cc), 5(dd), 5(ee), 5(ff), 5(gg), 5(hh), 5(ii), 5(kk), 5(ll) 6, 7, 7(a), 7(b), 8, 9, 10 or 11, 12, 13, 14, 14(a), 14(b), 14(c), 14(d), 14(e), 14(f), 14(g), 14(h), 14(i), 14(j), 14(k), 14(l), 14(m), 14(n), 14(o), 14(p), 14(q), 14(r), 14(s), 14(t), 14(u), 14(v), 14(w), 14(x), 14(z), 14(aa), 14(bb), 15, 16 or 17, or a pharmaceutical composition according to Embodiments 18, 19 or 20.

In other embodiments of this disclosure, the method involves administering to the subject an effective amount of a compound as described herein in combination with one or more other suitable therapies for the disease or condition. In some embodiments, the disclosure provides a method for treating a subject suffering from a disease or condition mediated by tumor-associated macrophages (TAM). In certain embodiments, the disclosure provides a method for treating a subject suffering from a disease or condition, such as a tumor, where tumor-associated macrophages play a role in tumor proliferation, survival, and metastasis. In some embodiments, the disclosure provides a method for treating a subject suffering from a disease or condition, where reduction/depletion of macrophages or microglia provides a benefit. In certain instances, the disease or condition is as described herein. The method includes administering to the subject an effective amount of one or more compounds in Embodiments 1, 1(a), 1(b), 1(c), 1(d), 1(e), 2, 2(a), 2(b), 2(c), 2(d), 2(e), 2(f), 2(g), 2(h), 3, 4, 4(a), 4(b), 4(c), 5, 5(a), 5(b) 5(c), 5(d), 5(e), 5(f), 5(g), 5(h), 5(i), 5(j), 5(k), 5(l), 5(m), 5(n), 5(o), 5(p), 5(q), 5(r), 5(s), 5(t), 5(u), 5(v), 5(w), 5(x), 5(z), 5(aa), 5(bb), 5(cc), 5(dd), 5(ee), 5(ff), 5(gg), 5(hh), 5(ii), 5(kk), 5(ll) 6, 7, 7(a), 7(b), 8, 9, 10 or 11, 12, 13, 14, 14(a), 14(b), 14(c), 14(d), 14(e), 14(f), 14(g), 14(h), 14(i), 14(j), 14(k), 14(l), 14(m), 14(n), 14(o), 14(p), 14(q), 14(r), 14(s), 14(t), 14(u), 14(v), 14(w), 14(x), 14(z), 14(aa), 14(bb), 15, 16 or 17, or a pharmaceutical composition according to Embodiments 18, 19 or 20. In some embodiments, the disclosure provides methods for treating a subject suffering from tumors that express aberrantly or otherwise CSF1R, or activating mutations or translocations thereof.

In other embodiments of this disclosure, a disease treatable with one or more compounds in Embodiments 1, 1(a), 1(b), 1(c), 1(d), 1(e), 2, 2(a), 2(b), 2(c), 2(d), 2(e), 2(f), 2(g), 2(h), 3, 4, 4(a), 4(b), 4(c), 5, 5(a), 5(b) 5(c), 5(d), 5(e), 5(f), 5(g), 5(h), 5(i), 5(j), 5(k), 5(l), 5(m), 5(n), 5(o), 5(p), 5(q), 5(r), 5(s), 5(t), 5(u), 5(v), 5(w), 5(x), 5(z), 5(aa), 5(bb), 5(cc), 5(dd), 5(ee), 5(ff), 5(gg), 5(hh), 5(ii), 5(kk), 5(ll) 6, 7, 7(a), 7(b), 8, 9, 10 or 11, 12, 13, 14, 14(a), 14(b), 14(c), 14(d), 14(e), 14(f), 14(g), 14(h), 14(i), 14(j), 14(k), 14(l), 14(m), 14(n), 14(o), 14(p), 14(q), 14(r), 14(s), 14(t), 14(u), 14(v), 14(w), 14(x), 14(z), 14(aa), 14(bb), 15, 16 or 17, or a pharmaceutical composition according to Embodiments 18, 19 or 20, is a CSF1R mediated disease selected from the group consisting of immune disorders, including, but not limiting to, rheumatoid arthritis, systemic lupus erythematosis (SLE), and transplant rejection; stem cell ablation and myelopreparation for stem cell transplant; inflammatory diseases including, but not limited to, osteoarthritis, inflammatory bowel syndrome, ulcerative colitis, Crohn's disease, chronic obstructive pulmonary disease (COPD), emphysema, Kawasaki's Disease, hemophagocytic syndrome (macrophage activation syndrome), multicentric reticulohistiocytosis, and atherosclerosis; metabolic disorders, including, but not limited to, Type I diabetes, Type II diabetes, insulin resistance, hyperglycemia, obesity, and lipolysis; disorders of bone structure, mineralization and bone formation and resorption, including, but not limited to, osteoporosis, increased risk of fracture, Paget's disease, hypercalcemia, infection-mediated osteolysis (e.g. osteomyelitis), pen-prosthetic or wear-debris-mediated osteolysis, and metastasis of cancer to bone; kidney and genitourinary diseases, including, but not limited to, endometriosis, nephritis (e.g. glomerulonephritis, interstitial nephritis, Lupus nephritis), tubular necrosis, diabetes-associated renal complications (e.g. diabetic nephropathy), and renal hypertrophy; disorders of the central nervous system, including, but not limited to, multiple sclerosis, stroke, Alzheimer's disease and Parkinson's disease; inflammatory and chronic pain, including, but not limited to, bone pain; and cancers, including, but not limited to, multiple myeloma, acute myeloid leukemia (AML), chronic myeloid leukemia (CML), monocytic leukemia, prostate cancer, breast cancer, ovarian cancer, melanoma, glioblastoma multiforme, metastasis of tumors to other tissues, and other chronic myeloproliferative diseases such as myelofibrosis. In some embodiments, the CSF1R mediated diseases include tumors that express aberrantly or otherwise CSF1R, or activating mutations or translocations thereof In other embodiments of this disclosure, the disease or condition is mediated by CSF1R and c-kit and is selected from the group consisting of mast cell tumors, small cell lung cancer, testicular cancer, gastrointestinal stromal tumors, glioblastoma, astrocytoma, neuroblastoma, carcinomas of the female genital tract, sarcomas of neuroectodermal origin, colorectal carcinoma, carcinoma in situ, Schwann cell neoplasia, malignant peripheral nerve cell tumors, malignant peripheral nerve sheath tumors, pheochromocytomas cutaneous and plexiform neurofibromas, neurofibromatosis, neurofibromatosis-1 (NF1), leiomyo-adenomatoid tumor, leiomyo sarcoma, acute myeloid leukemia, acute lymphocytic leukemia, chronic myelogenous leukemia, multiple myeloma, mastocytosis, melanoma, breast cancer, ovarian cancer, prostate cancer, canine mast cell tumors, metastasis of cancer to bone or other tissues, chronic myeloproliferative diseases such as myelofibrosis, renal hypertrophy, asthma, rheumatoid arthritis, allergic rhinitis, multiple sclerosis, osteoarthritis, inflammatory bowel syndrome, transplant rejection, systemic lupus erythematosis, ulcerative colitis, Crohn's disease, chronic obstructive pulmonary disease, emphysema, Kawasaki's Disease, hemophagocytic syndrome (macrophage activation syndrome), multicentric reticulohistiocytosis, atherosclerosis, Type I diabetes, Type II diabetes, insulin resistance, hyperglycemia, obesity, lipolysis, hypereosinophilia, osteoporosis, increased risk of fracture, Paget's disease, hypercalcemia, infection-mediated osteolysis (e.g. osteomyelitis), peri-prosthetic or wear-debris-mediated osteolysis, endometriosis, glomerulonephritis, interstitial nephritis, Lupus nephritis, tubular necrosis, diabetic nephropathy, stroke, Alzheimer's disease, Parkinson's disease, inflammatory pain, chronic pain, and bone pain.

In other embodiments of this disclosure, the disease or condition treatable with the compounds or compositions as described herein is selected from stem cell ablation and myelopreparation for stem cell transplant, primary progressive multiple sclerosis, complex regional pain syndrome, reflex sympathetic dystrophy, muscular dystrophy, duchenne muscular dystrophy, causalgia, neuro-inflammation, neuroinflammatory disorders, benign forgetfulness, binswager type dementia, dementia with lewy bodie, prosencephaly, microencepahy, cerebral palsy, congenital hydrocephalus, abdominal dropsy, progressive supranuclear palsy, glaucoma, addiction disorders, dependencies, alcoholism, tremors, Wilson's disease, vascular dementias, multi infarct dementia, frontotemporal dementia, pseudo-dementia, bladder cancer, basal cell carcinoma, cholangiocarcinoma, colon cancer, endometrial cancer, esophageal cancer, Ewing's sarcoma, gastric cancer, glioma, hepatocellular carcinoma, Hodgkin lymphoma, laryngeal carcinoma, leukemia, liver cancer, lung cancer, melanoma, mesothelioma, pancreatic cancer, rectal cancer, renal cancer, squamous cell carcinoma, t cell lymphoma, thyroid cancer, monocytic leukemia, pheochromocytoma, malignant peripheral nerve cell tumors, malignant peripheral nerve sheath tumors (MPNST), cutaneous and plexiform neurofibromas, leiomyoadenomatoid tumor, fibroids, uterine fibroids, leiomyosarcoma, papillary thyroid cancer, anaplastic thyroid cancer, medullary thyroid cancer, follicular thyroid cancer, hurthle cell carcinoma, thyroid cancer, ascites, malignant ascites, mesothelioma, salivary gland tumors, mucoepidermoid carcinoma of the salivary gland, acinic cell carcinoma of the salivary gland, gastrointestinal stromal tumors (GIST), tumors that cause effusions in potential spaces of the body, pleural effusions, pericardial effusions, peritoneal effusions aka ascites, giant cell tumors (GCT), GCT of bone, pigmented villonodular synovitis (PVNS), tenosynovial giant cell tumor (TGCT), TCGT of tendon sheath (TGCT-TS), other sarcomas; tumor angiogenesis and paracrine tumor growth; and tumors that express aberrantly or otherwise CSF1R, or an activating mutation or translocation of any of the foregoing.

Other embodiments of this disclosure relate to the treatment of a Kit-mediated disease or condition in a subject in need thereof (e.g. a mammal such as a human, other primates, sports animals, animals of commercial interest such as cattle, farm animals such as horses, or pets such as dogs and cats), e.g., a disease or condition characterized by abnormal Kit activity (e.g. kinase activity) by administering to the subject one or more compounds in Embodiments 1, 1(a), 1(b), 1(c), 1(d), 1(e), 2, 2(a), 2(b), 2(c), 2(d), 2(e), 2(f), 2(g), 2(h), 3, 4, 4(a), 4(b), 4(c), 5, 5(a), 5(b) 5(c), 5(d), 5(e), 5(f), 5(g), 5(h), 5(i), 5(j), 5(k), 5(l), 5(m), 5(n), 5(o), 5(p), 5(q), 5(r), 5(s), 5(t), 5(u), 5(v), 5(w), 5(x), 5(z), 5(aa), 5(bb), 5(cc), 5(dd), 5(ee), 5(ff), 5(gg), 5(hh), 5(ii), 5(kk), 5(ll) 6, 7, 7(a), 7(b), 8, 9, 10 or 11, 12, 13, 14, 14(a), 14(b), 14(c), 14(d), 14(e), 14(f), 14(g), 14(h), 14(i), 14(j), 14(k), 14(l), 14(m), 14(n), 14(o), 14(p), 14(q), 14(r), 14(s), 14(t), 14(u), 14(v), 14(w), 14(x), 14(z), 14(aa), 14(bb), 15, 16 or 17, or a pharmaceutical composition according to Embodiments 18, 19 or 20. In one embodiment, the Kit mediated disease is selected from the group consisting of malignancies, including, but not limited to, mast cell tumors, small cell lung cancer, non-small cell lung cancer (NSCLC), testicular cancer, pancreatic cancer, breast cancer, merkel cell carcinoma, carcinomas of the female genital tract, sarcomas of neuroectodermal origin, colorectal carcinoma, carcinoma in situ, gastrointestinal stromal tumors (GISTs), tumor angiogenesis, glioblastoma, astrocytoma, neuroblastoma, neurofibromatosis (including Schwann cell neoplasia associated with neurofibromatosis), acute myeloid leukemia, acute lymphocytic leukemia, chronic myeloid leukemia, mastocytosis, melanoma, and canine mast cell tumors; cardiovascular disease, including but not limited to atherosclerosis, cardiomyopathy, heart failure, pulmonary arterial hypertension and pulmonary fibrosis; inflammatory and autoimmune indications, including, but not limited to, allergy, anaphylaxis, asthma, rheumatoid arthritis, allergic rhinitis, multiple sclerosis, inflammatory bowel disease, transplant rejection, hypereosinophilia, urticaria and dermatitis; gastrointestinal indications, including but not limited to gastroesophageal reflux disease (GERD), esophagitis, and gastrointestinal tract ulcers; ophthalmic indications, including but not limited to uveitis and retinitis; and neurologic indications, including, but not limiting to migraine and tumors that express aberrantly or otherwise Kit or an activating mutation or translocation thereof In embodiments of this disclosure involving treatment of a disease or condition with one or more of the compounds described herein, the disclosure provides methods for treating a CSF1R-mediated disease or condition in a subject in need thereof (e.g. a mammal such as a human, other primates, sports animals, animals of commercial interest such as cattle, farm animals such as horses, or pets such as dogs and cats), e.g., a disease or condition characterized by abnormal CSF1R activity. In some embodiments, the methods may involve administering to the subject suffering from or at risk of a CSF1R-mediated disease or condition an effective amount of one or more compounds in Embodiments 1, 1(a), 1(b), 1(c), 1(d), 1(e), 2, 2(a), 2(b), 2(c), 2(d), 2(e), 2(f), 2(g), 2(h), 3, 4, 4(a), 4(b), 4(c), 5, 5(a), 5(b) 5(c), 5(d), 5(e), 5(f), 5(g), 5(h), 5(i), 5(j), 5(k), 5(l), 5(m), 5(n), 5(o), 5(p), 5(q), 5(r), 5(s), 5(t), 5(u), 5(v), 5(w), 5(x), 5(z), 5(aa), 5(bb), 5(cc), 5(dd), 5(ee), 5(ff), 5(gg), 5(hh), 5(ii), 5(kk), 5(ll) 6, 7, 7(a), 7(b), 8, 9, 10 or 11, 12, 13, 14, 14(a), 14(b), 14(c), 14(d), 14(e), 14(f), 14(g), 14(h), 14(i), 14(j), 14(k), 14(l), 14(m), 14(n), 14(o), 14(p), 14(q), 14(r), 14(s), 14(t), 14(u), 14(v), 14(w), 14(x), 14(z), 14(aa), 14(bb), 15, 16 or 17, or a pharmaceutical composition according to Embodiments 18, 19 or 20. In one embodiment, the CSF1R mediated disease is selected from the group consisting of inflammatory and autoimmune indications, including, but not limited to, rheumatoid arthritis, osteoarthritis, psoriatic arthritis, psoriasis, dermatitis, ankylosing spondylitis, polymyositis, dermatomyositis, systemic sclerosis, juvenile idiopathic arthritis, polymyalgia rheumatica, Sjogren's disease, Langerhan's cell histiocytosis (LCH), Still's disease, inflammatory bowel disease, ulcerative colitis, Crohn's disease, systemic lupus erythematosis (SLE), immune thrombocytopenic purpura (ITP), myelopreparation for autologous transplantation, transplant rejection, chronic obstructive pulmonary disease (COPD), emphysema, Kawasaki's Disease, hemophagocytic syndrome (macrophage activation syndrome), multicentric reticulohistiocytosis, and atherosclerosis; metabolic disorders, including, but not limited to, Type I diabetes, Type II diabetes, insulin resistance, hyperglycemia, obesity, and lipolysis; disorders of bone structure, mineralization and bone formation and resorption, including, but not limited to, osteoporosis, osteodystrophy, increased risk of fracture, Paget's disease, hypercalcemia, infection-mediated osteolysis (e.g. osteomyelitis), and periprosthetic or wear-debris-mediated osteolysis; kidney and genitourinary diseases, including, but not limited to, endometriosis, nephritis (e.g. glomerulonephritis, interstitial nephritis, Lupus nephritis), tubular necrosis, diabetes-associated renal complications (e.g. diabetic nephropathy), and renal hypertrophy; disorders of the nervous system, including, but not limited to, demyelinating disorders (e.g. multiple sclerosis, Charcot Marie Tooth syndrome), amyotrophic lateral sclerosis (ALS), myasthenia gravis, chronic demyelinating polyneuropathy, other demyelinating disorders, stroke, Alzheimer's disease and Parkinson's disease; pain, including, but not limited to, chronic pain, acute pain, inflammatory pain, neuropathic pain, bone pain; malignancies, including, but not limited to, multiple myeloma, acute myeloid leukemia (AML), chronic myeloid leukemia (CML), lung cancer, pancreatic cancer, prostate cancer, breast cancer, ovarian cancer, neuroblastoma, sarcoma, osteosarcoma, giant cell tumors, (e.g. giant cell tumor of bone, giant cell tumor of tendon sheath (TGCT)), pigmented villonodular synovitis (PVNS), tumor angiogenesis, melanoma, glioblastoma multiforme, a subset of glioblastoma, proneural subset of glioblastoma, glioma, other tumors of the central nervous system, metastasis of tumors to other tissues, osteolytic bone metastases, and other chronic myeloproliferative diseases such as myelofibrosis; vasculitis, including but not limited to collagen vascular disease, polyarteritis nodosa, Behcet's disease, sarcoidosis, familiar Mediterranean fever, Churg-Strauss vasculitis, temporal arteritis, giant cell arteritis, Takayasu's arteritis; ophthalmic indications, including but not limited to uveitis, scleritis, retinitis, age related macular degeneration, choroidal neovascularization, diabetic retinopathy; inherited disorders, including but not limited to cherubism, neurofibromatosis; infectious disease indications, including but not limited to infections associated with human immunodeficiency virus, hepatitis B virus, hepatitis C virus, human granulocytic anaplasmosis; lysosomal storage disorders, including but not limited to Gaucher's disease, Fabry's disease, Niemann-Pick disease; gastrointestinal indications, including but not limited to liver cirrhosis; pulmonary indications, including but not limited to pulmonary fibrosis, acute lung injury (e.g. ventilator-induced, smoke- or toxin-induced); surgical indications, including but not limited to (cardiopulmonary) bypass surgery, vascular surgery, and vascular grafts; and tumors that express aberrantly or otherwise CSF1R or an activating mutation or translocation thereof.

Another embodiment of this disclosure relate to methods for treating a disease or condition mediated by CSF1R and Kit in a subject in need thereof (e.g. a mammal such as a human, other primates, sports animals, animals of commercial interest such as cattle, farm animals such as horses, or pets such as dogs and cats), e.g., a disease or condition characterized by abnormal CSF1R activity and Kit activity (e.g. kinase activity). In some embodiments, the methods may involve administering to the subject suffering from or at risk of a disease or condition mediated by CSF1R and Kit an effective amount of one or more compounds in Embodiments 1, 1(a), 1(b), 1(c), 1(d), 1(e), 2, 2(a), 2(b), 2(c), 2(d), 2(e), 2(f), 2(g), 2(h), 3, 4, 4(a), 4(b), 4(c), 5, 5(a), 5(b) 5(c), 5(d), 5(e), 5(f), 5(g), 5(h), 5(i), 5(j), 5(k), 5(l), 5(m), 5(n), 5(o), 5(p), 5(q), 5(r), 5(s), 5(t), 5(u), 5(v), 5(w), 5(x), 5(z), 5(aa), 5(bb), 5(cc), 5(dd), 5(ee), 5(ff), 5(gg), 5(hh), 5(ii), 5(kk), 5(ll) 6, 7, 7(a), 7(b), 8, 9, 10 or 11, 12, 13, 14, 14(a), 14(b), 14(c), 14(d), 14(e), 14(f), 14(g), 14(h), 14(i), 14(j), 14(k), 14(l), 14(m), 14(n), 14(o), 14(p), 14(q), 14(r), 14(s), 14(t), 14(u), 14(v), 14(w), 14(x), 14(z), 14(aa), 14(bb), 15, 16 or 17, or a pharmaceutical composition according to Embodiments 18, 19 or 20. In one embodiment, the condition mediated by CSF1R and Kit is selected from the group consisting of rheumatoid arthritis, osteoarthritis, psoriatic arthritis, psoriasis, dermatitis, allergy, anaphylaxis, asthma, allergic rhinitis, ankylosing spondylitis, polymyositis, dermatomyositis, systemic sclerosis, juvenile idiopathic arthritis, polymyalgia rheumatica, Sjogren's disease, Langerhan's cell histiocytosis, Still's disease, inflammatory bowel disease, ulcerative colitis, Crohn's disease, systemic lupus erythematosis, immune thrombocytopenic purpura, myelopreparation for autologous transplantation, transplant rejection, chronic obstructive pulmonary disease, emphysema, Kawasaki's Disease, hemophagocytic syndrome, multicentric reticulohistiocytosis, hypereosinophilia, and urticaria type I diabetes, type II diabetes, insulin resistance, hyperglycemia, obesity, and lipolysis, osteoporosis, osteodystrophy, increased risk of fracture, Paget's disease, hypercalcemia, infection-mediated osteolysis, and pen-prosthetic or wear-debris-mediated osteolysis, endometriosis, nephritis, tubular necrosis, diabetes-associated renal complications, and renal hypertrophy, multiple sclerosis, Charcot Marie Tooth syndrome, amyotrophic lateral sclerosis, myasthenia gravis, chronic demyelinating polyneuropathy, other demyelinating disorders, stroke, Alzheimer's disease and Parkinson's disease, acute pain, neuropathic pain, inflammatory pain, chronic pain, migraine, multiple myeloma, acute lymphocytic leukemia, acute myeloid leukemia, chronic myeloid leukemia, mast cell tumors, canine mast cell tumors, lung cancer, testicular cancer, pancreatic cancer, prostate cancer, breast cancer, ovarian cancer, merkel cell carcinoma, carcinomas of the female genital tract, colorectal carcinoma, carcinoma in situ, gastrointestinal stromal tumors, tumor angiogenesis, astrocytoma, neuroblastoma, sarcoma, osteosarcoma, sarcomas of neuroectodermal origin, giant cell tumor of bone, giant cell tumor of tendon sheath, pigmented villonodular synovitis, melanoma, glioblastoma, glioblastoma multiforme, glioma, other tumors of the central nervous system, neurofibromatosis (including Schwann cell neoplasia associated with neurofibromatosis), mastocytosis, metastasis of tumors to other tissues, osteolytic bone metastases, and other chronic myeloproliferative diseases such as myelofibrosis, collagen vascular disease, polyarteritis nodosa, Behcet's disease, sarcoidosis, familiar Mediterranean fever, Churg-Strauss vasculitis, temporal arteritis, giant cell arteritis, Takayasu's arteritis, uveitis, scleritis, retinitis, age related macular degeneration, choroidal neovascularization, diabetic retinopathy, cherubism, neurofibromatosis, infections associated with human immunodeficiency virus, hepatitis B virus, hepatitis C virus, human granulocytic anaplasmosis, Gaucher's disease, Fabry's disease, Niemann-Pick disease, liver cirrhosis, gastroesophageal reflux disease, esophagitis, and gastrointestinal tract ulcers, pulmonary fibrosis, acute lung injury, bypass surgery, vascular surgery, and vascular grafts, atherosclerosis, cardiomyopathy, heart failure, and pulmonary arterial hypertension.

Another embodiment of this disclosure relates to the treatment of a disease or condition mediated by CSF1R and Flt-3 in a subject in need thereof (e.g. a mammal such as a human, other primates, sports animals, animals of commercial interest such as cattle, farm animals such as horses, or pets such as dogs and cats), e.g., a disease or condition characterized by abnormal CSF1R activity and flt-3 activity, with one or more of the compounds described herein, the disclosure provides methods for treating a disease or condition In some embodiments, the methods may involve administering to the subject suffering from or at risk of a disease or condition mediated by CSF1R and Flt-3 with an effective amount of one or more compounds in Embodiments 1, 1(a), 1(b), 1(c), 1(d), 1(e), 2, 2(a), 2(b), 2(c), 2(d), 2(e), 2(f), 2(g), 2(h), 3, 4, 4(a), 4(b), 4(c), 5, 5(a), 5(b) 5(c), 5(d), 5(e), 5(f), 5(g), 5(h), 5(i), 5(j), 5(k), 5(l), 5(m), 5(n), 5(o), 5(p), 5(q), 5(r), 5(s), 5(t), 5(u), 5(v), 5(w), 5(x), 5(z), 5(aa), 5(bb), 5(cc), 5(dd), 5(ee), 5(ff), 5(gg), 5(hh), 5(ii), 5(kk), 5(ll) 6, 7, 7(a), 7(b), 8, 9, 10 or 11, 12, 13, 14, 14(a), 14(b), 14(c), 14(d), 14(e), 14(f), 14(g), 14(h), 14(i), 14(j), 14(k), 14(l), 14(m), 14(n), 14(o), 14(p), 14(q), 14(r), 14(s), 14(t), 14(u), 14(v), 14(w), 14(x), 14(z), 14(aa), 14(bb), 15, 16 or 17, or a pharmaceutical composition according to Embodiments 18, 19 or 20.

Another embodiment of this disclosure relates to the treatment of a disease or condition comprising administering an effective amount of one or more compounds in Embodiments 1, 1(a), 1(b), 1(c), 1(d), 1(e), 2, 2(a), 2(b), 2(c), 2(d), 2(e), 2(f), 2(g), 2(h), 3, 4, 4(a), 4(b), 4(c), 5, 5(a), 5(b) 5(c), 5(d), 5(e), 5(f), 5(g), 5(h), 5(i), 5(j), 5(k), 5(l), 5(m), 5(n), 5(o), 5(p), 5(q), 5(r), 5(s), 5(t), 5(u), 5(v), 5(w), 5(x), 5(z), 5(aa), 5(bb), 5(cc), 5(dd), 5(ee), 5(ff), 5(gg), 5(hh), 5(ii), 5(kk), 5(ll) 6, 7, 7(a), 7(b), 8, 9, 10 or 11, 12, 13, 14, 14(a), 14(b), 14(c), 14(d), 14(e), 14(f), 14(g), 14(h), 14(i), 14(j), 14(k), 14(l), 14(m), 14(n), 14(o), 14(p), 14(q), 14(r), 14(s), 14(t), 14(u), 14(v), 14(w), 14(x), 14(z), 14(aa), 14(bb), 15, 16 or 17, or a pharmaceutical composition according to Embodiments 18, 19 or 20, to a subject in need thereof suffering from or at risk of a disease or condition selected from the group consisting of rheumatoid arthritis, osteoarthritis, osteoporosis, peri-prosthetic osteolysis, systemic sclerosis, demyelinating disorders, multiple sclerosis, Charcot Marie Tooth syndrome, amyotrophic lateral sclerosis, Alzheimer's disease, Parkinson's disease, ulcerative colitis, Crohn's disease, immune thrombocytopenic purpura, atherosclerosis, systemic lupus erythematosis, myelopreparation for autologous transplantation, transplant rejection, glomerulonephritis, interstitial nephritis, Lupus nephritis, tubular necrosis, diabetic nephropathy, renal hypertrophy, type I diabetes, acute pain, inflammatory pain, neuropathic pain, acute myeloid leukemia, melanoma, multiple myeloma, metastatic breast cancer, prostate cancer, pancreatic cancer, lung cancer, ovarian cancer, gliomas, glioblastomas, neurofibromatosis, osteolytic bone metastases, brain metastases, gastrointestinal stromal tumors, and giant cell tumors.

Another embodiment of this disclosure relates to methods of modulating the various activities of kinases including dimerization, ligand binding and phosphotransferase activities or methods of modulating the expression of kinases, in a cell, tissue or whole organism, using the compounds and compositions provided herein, or pharmaceutically acceptable derivatives thereof. In one embodiment, provided herein are methods of modulating the activity of FLT3 activity in a cell, tissue or whole organism using one or more compounds in Embodiments 1, 1(a), 1(b), 1(c), 1(d), 1(e), 2, 2(a), 2(b), 2(c), 2(d), 2(e), 2(f), 2(g), 2(h), 3, 4, 4(a), 4(b), 4(c), 5, 5(a), 5(b) 5(c), 5(d), 5(e), 5(f), 5(g), 5(h), 5(i), 5(j), 5(k), 5(l), 5(m), 5(n), 5(o), 5(p), 5(q), 5(r), 5(s), 5(t), 5(u), 5(v), 5(w), 5(x), 5(z), 5(aa), 5(bb), 5(cc), 5(dd), 5(ee), 5(ff), 5(gg), 5(hh), 5(ii), 5(kk), 5(ll) 6, 7, 7(a), 7(b), 8, 9, 10 or 11, 12, 13, 14, 14(a), 14(b), 14(c), 14(d), 14(e), 14(f), 14(g), 14(h), 14(i), 14(j), 14(k), 14(l), 14(m), 14(n), 14(o), 14(p), 14(q), 14(r), 14(s), 14(t), 14(u), 14(v), 14(w), 14(x), 14(z), 14(aa), 14(bb), 15, 16 or 17, or a pharmaceutical composition according to Embodiments 18, 19 or 20. In one embodiment, the methods provided herein are for treating tumor-associated osteolysis, osteoporosis including ovariectomy-induced bone loss, orthopedic implant failure, renal inflammation and glomerulonephritis, transplant rejection including renal and bone marrow allografts and skin xenograft, obesity, Alzheimer's Disease and Langerhans cell histiocytosis.

In another embodiment of this disclosure, the methods provided herein are for treating chronic skin disorders including psoriasis.

In another embodiment of this disclosure, the methods provided herein are for treating periodontitis, Langerhans cell histiocytosis, osteoporosis, Paget's disease of bone (PDB), bone loss due to cancer therapy, periprosthetic osteolysis, glucocorticoid-induced osteoporosis, rheumatoid arthritis, psoriatic arthritis, osteoarthritis, and/or inflammatory arthritis is provided herein.

In another embodiment of this disclosure, the methods provided herein are for treating bone diseases including disorders relating to the mineralization, formation and resorption of the bone, including but not limited to osteoporosis, Paget's disease, hypercalcemia, osteolysis, osteomyelitis, and bone pain.

In another embodiment of this disclosure, the methods provided herein are for treating cancers, including, but not limited to head and neck cancer, (originating in lip, oral cavity, oropharynx, hypopharynx, larynx, nasopharynx, nasal cavity and paranasal sinuses or salivary glands); lung cancer, including small cell lung cancer, non-small cell lung cancer; gastrointestinal tract cancers, including esophageal cancer, gastric cancer, colorectal cancer, anal cancer, pancreatic cancer, liver cancer, gallbladder cancer, extrahepatic bile duct cancer, cancer of the ampulla of vater; breast cancer; gynecologic cancers, including, cancer of uterine cervix, cancer of the uterine body, vaginal cancer, vulvar cancer, ovarian cancer, gestational trophoblastic cancer neoplasia; testicular cancer; urinary tract cancers, including, renal cancer, urinary bladder cancer, prostate cancer, penile cancer, urethral cancer; neurologic tumors; endocrine neoplasms, including carcinoid and islet cell tumors, pheochromocytoma, adrenal cortical carcinoma, parathyroid carcinoma and metastases to endocrine glands. In another embodiment, the methods provided herein are for treating carcinoma, breast cancer, ovarian cancer, bone metastases, osteoporosis, Paget's disease, hypercalcemia, osteolysis, osteomyelitis, bone pain, inflammatory bowel disease (IBD), Crohn's disease, ulcerative colitis (UC), systemic lupus erythematosis (SLE), arthritis, osteoarthritis, rheumatoid arthritis, osteoporosis, asthma, chronic obstructive pulmonary disease (COPD), psoriasis and multiple sclerosis. In another embodiment, provided herein are methods for treating inflammatory diseases of the eye including conjunctivitis, uveitis, iritis, scleritis, blepheritis, meibomitis and optical neuritis. In yet another embodiment, provided herein are methods for treating glaucoma, diabetic retinopathy and macular degeneration.

Further examples of cancers are basal cell carcinoma; squamous cell carcinoma; chondrosarcoma (a cancer arising in cartilage cells); mesenchymal-chondrosarcoma; soft tissue sarcomas, including, malignant tumours that may arise in any of the mesodermal tissues (muscles, tendons, vessels that carry blood or lymph, joints and fat); soft tissue sarcomas include; alveolar soft-part sarcoma, angiosarcoma, fibrosarcoma, leiomyosarcoma, liposarcoma, malignant fibrous histiocytoma, hemangiopericytoma, mesenchymoma, schwannoma, peripheral neuroectodermal tumours, rhabdomyosarcoma, synovial sarcoma; gestational trophoblastic tumour (malignancy in which the tissues formed in the uterus following conception become cancerous); Hodgkin's lymphoma and laryngeal cancer. In another embodiment, the cancer is a leukemia. In one embodiment, the leukemia is chronic lymphocytic leukemia, chronic myelocytic leukemia, acute lymphoblastic leukemia, acute myeloid leukemia, and acute myeloblastic leukemia.

In another embodiment of this disclosure, the leukemia is acute leukemia In another embodiment of this disclosure, the acute leukemia is acute myeloid leukemia (AML). In another embodiment of this disclosure, the acute myeloid leukemia is undifferentiated AML (M0), myeloblastic leukemia (M1), myeloblastic leukemia (M2), promyelocytic leukemia (M3 or M3 variant [M3V]), myelomonocytic leukemia (M4 or M4 variant with eosinophilia [M4E]), monocytic leukemia (M5), erythroleukemia (M6), or megakaryoblastic leukemia (M7). In another embodiment of this disclosure, the acute myeloid leukemia is undifferentiated AML (M0). In another embodiment of this disclosure, the acute myeloid leukemia is myeloblastic leukemia (M1). In another embodiment of this disclosure, the acute myeloid leukemia is myeloblastic leukemia (M2). In another embodiment of this disclosure, the acute myeloid leukemia is promyelocytic leukemia (M3 or M3 variant [M3V]). In another embodiment of this disclosure, the acute myeloid leukemia is myelomonocytic leukemia (M4 or M4 variant with eosinophilia [M4E]). In another embodiment of this disclosure, the acute myeloid leukemia is monocytic leukemia (M5). In another embodiment of this disclosure, the acute myeloid leukemia is erythroleukemia (M6). In another embodiment of this disclosure, the acute myeloid leukemia is megakaryoblastic leukemia (M7). In another embodiment of this disclosure, the acute myeloid leukemia is promyelocytic leukemia [000187] In another embodiment of this disclosure, the acute leukemia is acute lymphoblastic leukemia (also known as acute lymphocytic leukemia or ALL). In another embodiment of this disclosure, the acute lymphocytic leukemia is leukemia that originates in the blast cells of the bone marrow (B-cells), thymus (T-cells), or lymph nodes. The acute lymphocytic leukemia is categorized according to the French-American-British (FAB) Morphological Classification Scheme as L1—Mature-appearing lymphoblasts (T-cells or pre-B-cells), L2—Immature and pleomorphic (variously shaped) lymphoblasts (T-cells or pre-B-cells), and L3—Lymphoblasts (B-cells; Burkitt's cells). In another embodiment of this disclosure, the acute lymphocytic leukemia originates in the blast cells of the bone marrow (B-cells). In another embodiment of this disclosure, the acute lymphocytic leukemia originates in the thymus (T-cells). In another embodiment of this disclosure, the acute lymphocytic leukemia originates in the lymph nodes. In another embodiment of this disclosure, the acute lymphocytic leukemia is L1 type characterized by mature-appearing lymphoblasts (T-cells or pre-B-cells). In another embodiment of this disclosure, the acute lymphocytic leukemia is L2 type characterized by immature and pleomorphic (variously shaped) lymphoblasts (T-cells or pre-B-cells). In another embodiment of this disclosure, the acute lymphocytic leukemia is L3 type characterized by lymphoblasts (B-cells; Burkitt's cells).

In another embodiment of this disclosure, the leukemia is T-cell leukemia. In another embodiment of this disclosure, the T-cell leukemia is peripheral T-cell leukemia, T-cell lymphoblastic leukemia, cutaneous T-cell leukemia, and adult T-cell leukemia. In another embodiment, the T-cell leukemia is peripheral T-cell leukemia. In another embodiment of this disclosure, the T-cell leukemia is T-cell lymphoblastic leukemia. In another embodiment of this disclosure, the T-cell leukemia is cutaneous T-cell leukemia. In another embodiment of this disclosure, the T-cell leukemia is adult T-cell leukemia.

In another embodiment of this disclosure, FLT3 inhibition of any one or more of the compounds in this disclosure can be used in combination with autophagy inhibition to active the chaperone-mediated autophagy (CMA) pathway in cancer cells to induce metabolic catastrophe and promote cancer cell death. CMA eliminates cancer cells by activating the degradation of the pro-oncogenic proteins, such as HK2. The ability of CMA to promote the degradation of HK2 and mutant p53 suggests the utility of CMA in manipulating cellular metabolism as a means of anticancer therapeutics.

Another embodiment of this disclosure relates to one or more compounds in Embodiments 1, 1(a), 1(b), 1(c), 1(d), 1(e), 2, 2(a), 2(b), 2(c), 2(d), 2(e), 2(f), 2(g), 2(h), 3, 4, 4(a), 4(b), 4(c), 5, 5(a), 5(b) 5(c), 5(d), 5(e), 5(f), 5(g), 5(h), 5(i), 5(j), 5(k), 5(l), 5(m), 5(n), 5(o), 5(p), 5(q), 5(r), 5(s), 5(t), 5(u), 5(v), 5(w), 5(x), 5(z), 5(aa), 5(bb), 5(cc), 5(dd), 5(ee), 5(ff), 5(gg), 5(hh), 5(ii), 5(kk), 5(ll) 6, 7, 7(a), 7(b), 8, 9, 10 or 11, 12, 13, 14, 14(a), 14(b), 14(c), 14(d), 14(e), 14(f), 14(g), 14(h), 14(i), 14(j), 14(k), 14(l), 14(m), 14(n), 14(o), 14(p), 14(q), 14(r), 14(s), 14(t), 14(u), 14(v), 14(w), 14(x), 14(z), 14(aa), 14(bb), 15, 16 or 17, or a pharmaceutical composition according to Embodiments 18, 19 or 20, for the treatment, prevention, or amelioration of a disease selected from an inflammatory disease, an autoimmune disease and cancer that is associated with or is mediated by overexpression of FLT3 or the FLT3 ligand. In certain embodiments, the disease is mediated by overexpression of wildtype FLT3. In certain embodiments, provided herein are methods of using the compounds and compositions disclosed herein, or pharmaceutically acceptable salts, solvates, hydrates, clathrates, single stereoisomers, mixture of stereoisomers, racemic mixture of stereoisomers or prodrugs thereof, for the treatment, prevention, or amelioration of a hematological cancer associated with or is mediated by one or more FLT3 tyrosine kinase domain mutation. In certain embodiments, the hematological cancer is associated with or is mediated by one or more FLT3 mutations selected from FLT3-ITD mutations and FLT3 tyrosine kinase domain mutations. In certain embodiments, the hematological cancer is associated with or is mediated by one or more FLT3-ITD mutations and one or more FLT3 tyrosine kinase domain mutations. In certain embodiments, the hematological cancer is leukemia or myelodysplastic syndromes (MDS). In yet another embodiment, the hematological cancer is acute myeloid leukemia (AML), acute lymphoblastic leukemia (ALL) or myelodysplastic syndromes. In yet another embodiment, the FLT3 tyrosine kinase domain mutation confers drug resistance to FLT3-targeted therapy. In yet another embodiment, the FLT3 tyrosine kinase domain mutation comprises one or more point mutations at any one of positions E608, N676, F691, C828, D835, D839, N841, Y842 and M855. In yet another embodiment, the FLT3 tyrosine kinase domain mutation comprises one or more point mutations selected from E608K, N676D, N676I, N676S, F691 I, F691L, C828S, D835Y, D835V, D835H, D835F, D835E, D839, N841, Y842C, Y842D, Y842H, Y842N, Y842S and M855T. In certain embodiments, the FLT3 tyrosine kinase domain mutation comprises one or more FLT3-ITD mutations and one or more point mutations at positions selected from E608, F691, D835 and Y842. In yet another embodiment, the tyrosine kinase domain mutation of FLT3 comprises one or more FLT3-ITD mutations and one or more point mutations selected from E608K, F691L, D835Y, D835V, D835F, Y842C and Y842H. In certain embodiments, the tyrosine kinase domain mutation of FLT3 comprises one or more FLT3-ITD mutations and a point mutation at one or both of F691 and D835. In yet another embodiment, the tyrosine kinase domain mutation of FLT3 comprises the FLT3-ITD mutation and one or more point mutation selected from F691L, D835Y, D835V and D835F. In yet another embodiment, the acquired mutation confers drug resistance to one or more of sorafenib, midostaurin (PKC-412), SU5614 and quizartinib (AC220).

In another embodiment of this disclosure, the resistance to quizartinib (AC220) is associated with, attributable to or mediated by a mutation in FLT3 comprising at least one point mutation at positions E608, F691, D835 and Y842. In another embodiment, the resistance to quizartinib (AC220) associated with, attributable to or mediated by polyclonal mutations in FLT3 comprising at least two point mutations selected from positions E608, F691, D835 and Y842. In one embodiment, the resistance to quizartinib (AC220) is associated with, attributable to or mediated by a mutation in FLT3 comprising at least one point mutation at positions F691, D835 and Y842. In one embodiment, the resistance to quizartinib (AC220) is associated with, attributable to or mediated by a mutation in FLT3 comprising at least one point mutation at positions F691 and D835. In yet another embodiment, the resistance to quizartinib (AC220) is associated with, attributable to or mediated by a mutation in FLT3 comprising at least one point mutation selected from E608K, F691L, D835F, D835Y, D835V, Y842C and Y842H. In yet another embodiment, the mutation in FLT3 further comprises a FLT3-ITD mutation.

In another embodiment of this disclosure, the resistance to sorafenib is associated with, attributable to or mediated by a mutation in FLT3 comprising at least one point mutation selected from F691L, Y842H, Y842N and Y842S. In one embodiment, the resistance to PKC-412 is associated with, attributable to or mediated by a mutation in FLT3 comprising at least one point mutation selected from N676D, N676I, N676S and F691L. In one embodiment, the resistance to SU5614 is associated with, attributable to or mediated by a mutation in FLT3 comprising at least one point mutation selected from C 828S, D835Y, D835V, D835H, D835F, D835E, D839G, D839H, N841C, Y842C, Y842D, and M855T.

In another embodiment, the FLT3 kinase is a mutated form. In another embodiment, the FLT3 Kinase mutation is FLT3 internal tandem duplication (ITD) mutation. In another embodiment, the FLT3 mutation further includes D835Y, F691L or both D835Y and F691L. In another embodiment, the disease or condition is selected from acute myeloid leukemia, acute lymphocytic leukemia or chronic myelogenous leukemia.

In some embodiments, the present disclosure provides a method for inhibiting mutant FLT3 kinase, such as FLT3 ITD and drug resistant FLT3 mutants such as D835Y and F691L. The method includes contacting one or more of any of the compounds described in Embodiments 1, 1(a), 1(b), 1(c), 1(d), 1(e), 2, 2(a), 2(b), 2(c), 2(d), 2(e), 2(f), 2(g), 2(h), 3, 4, 4(a), 4(b), 4(c), 5, 5(a), 5(b) 5(c), 5(d), 5(e), 5(f), 5(g), 5(h), 5(i), 5(j), 5(k), 5(l), 5(m), 5(n), 5(o), 5(p), 5(q), 5(r), 5(s), 5(t), 5(u), 5(v), 5(w), 5(x), 5(z), 5(aa), 5(bb), 5(cc), 5(dd), 5(ee), 5(ff), 5(gg), 5(hh), 5(ii), 5(kk), 5(ll) 6, 7, 7(a), 7(b), 8, 9, 10 or 11, 12, 13, 14, 14(a), 14(b), 14(c), 14(d), 14(e), 14(f), 14(g), 14(h), 14(i), 14(j), 14(k), 14(l), 14(m), 14(n), 14(o), 14(p), 14(q), 14(r), 14(s), 14(t), 14(u), 14(v), 14(w), 14(x), 14(z), 14(aa), 14(bb), 15, 16 or 17, or a pharmaceutical composition thereof, with a cell or a FLT3 mutant protein kinase either in vitro or in vivo.

In certain embodiments, the present disclosure provides use of one or more compounds of any of the compounds described in Embodiments 1, 1(a), 1(b), 1(c), 1(d), 1(e), 2, 2(a), 2(b), 2(c), 2(d), 2(e), 2(f), 2(g), 2(h), 3, 4, 4(a), 4(b), 4(c), 5, 5(a), 5(b) 5(c), 5(d), 5(e), 5(f), 5(g), 5(h), 5(i), 5(j), 5(k), 5(l), 5(m), 5(n), 5(o), 5(p), 5(q), 5(r), 5(s), 5(t), 5(u), 5(v), 5(w), 5(x), 5(z), 5(aa), 5(bb), 5(cc), 5(dd), 5(ee), 5(ff), 5(gg), 5(hh), 5(ii), 5(kk), 5(ll) 6, 7, 7(a), 7(b), 8, 9, 10 or 11, 12, 13, 14, 14(a), 14(b), 14(c), 14(d), 14(e), 14(f), 14(g), 14(h), 14(i), 14(j), 14(k), 14(l), 14(m), 14(n), 14(o), 14(p), 14(q), 14(r), 14(s), 14 (t), 14(u), 14(v), 14(w), 14(x), 14(z), 14(aa), 14(bb), 15, 16 or 17, or a pharmaceutical composition thereof, in the manufacture of a medicament for the treatment of a disease or condition as described herein. In other embodiments, the present disclosure provides a compound as described in any of Embodiments 1, 1(a), 1(b), 1(c), 1(d), 1(e), 2, 2(a), 2(b), 2(c), 2(d), 2(e), 2(f), 2(g), 2(h), 3, 4, 4(a), 4(b), 4(c), 5, 5(a), 5(b) 5(c), 5(d), 5(e), 5(f), 5(g), 5(h), 5(i), 5(j), 5(k), 5(l), 5(m), 5(n), 5(o), 5(p), 5(q), 5(r), 5(s), 5(t), 5(u), 5(v), 5(w), 5(x), 5(z), 5(aa), 5(bb), 5(cc), 5(dd), 5(ee), 5(ff), 5(gg), 5(hh), 5(ii), 5(kk), 5(ll) 6, 7, 7(a), 7(b), 8, 9, 10 or 11, 12, 13, 14, 14(a), 14(b), 14(c), 14(d), 14(e), 14(f), 14(g), 14(h), 14(i), 14(j), 14(k), 14(l), 14(m), 14(n), 14(o), 14(p), 14(q), 14(r), 14(s), 14(t), 14(u), 14(v), 14(w), 14(x), 14(z), 14(aa), 14(bb), 15, 16 or 17, or a pharmaceutical composition thereof, for use in treating a disease or condition as described herein.

VII. Combination Therapy

Protein kinase modulators may be usefully combined with another pharmacologically active compound, or with two or more other pharmacologically active compounds, particularly in the treatment of cancer. In one embodiment, the composition includes any one or more compound(s) as described herein along with one or more compounds that are therapeutically effective for the same disease indication, wherein the compounds have a synergistic effect on the disease indication. In one embodiment, the composition includes any one or more compound(s) as described herein effective in treating a cancer and one or more other compounds that are effective in treating the same cancer, further wherein the compounds are synergistically effective in treating the cancer.

In some embodiments, the present disclosure provides a composition comprising one or more compounds as described in any of Embodiments 1, 1(a), 1(b), 1(c), 1(d), 1(e), 2, 2(a), 2(b), 2(c), 2(d), 2(e), 2(f), 2(g), 2(h), 3, 4, 4(a), 4(b), 4(c), 5, 5(a), 5(b) 5(c), 5(d), 5(e), 5(f), 5(g), 5(h), 5(i), 5(j), 5(k), 5(l), 5(m), 5(n), 5(o), 5(p), 5(q), 5(r), 5(s), 5(t), 5(u), 5(v), 5(w), 5(x), 5(z), 5(aa), 5(bb), 5(cc), 5(dd), 5(ee), 5(ff), 5(gg), 5(hh), 5(ii), 5(kk), 5(ll) 6, 7, 7(a), 7(b), 8, 9, 10 or 11, 12, 13, 14, 14(a), 14(b), 14(c), 14(d), 14(e), 14(f), 14(g), 14(h), 14(i), 14(j), 14(k), 14(l), 14(m), 14(n), 14(o), 14(p), 14(q), 14(r), 14(s), 14(t), 14(u), 14(v), 14(w), 14(x), 14(z), 14(aa), 14(bb), 15, 16 or 17, or a pharmaceutical composition thereof, and one or more agents. In some embodiments, the one or more agents are selected from an alkylating agent, including, but not limited to, adozelesin, altretamine, bendamustine, bizelesin, busulfan, carboplatin, carboquone, carmofur, carmustine, chlorambucil, cisplatin, cyclophosphamide, dacarbazine, estramustine, etoglucid, fotemustine, hepsulfam, ifosfamide, improsulfan, irofulven, lomustine, mannosulfan, mechlorethamine, melphalan, mitobronitol, nedaplatin, nimustine, oxaliplatin, piposulfan, prednimustine, procarbazine, ranimustinc, satraplatin, semustine, streptozocin, temozolomide, thiotepa, treosulfan, triaziquone, triethylenemelamine, triplatin tetranitrate, trofosphamide, and uramustine; an antibiotic, including, but not limited to, aclarubicin, amrubicin, bleomycin, dactinomycin, daunorubicin, doxorubicin, elsamitrucin, epirubicin, idarubicin, menogaril, mitomycin, neocarzinostatin, pentostatin, pirarubicin, plicamycin, valrubicin, and zorubicin; an antimetabolite, including, but not limited to, aminopterin, azacitidine, azathioprine, capecitabine, cladribine, clofarabine, cytarabine, decitabine, floxuridine, fludarabine, 5-fluorouracil, gemcitabine, hydroxyurea, mercaptopurine, methotrexate, nelarabine, pemetrexed, azathioprine, raltitrexed, tegafur-uracil, thioguanine, trimethoprim, trimetrexate, and vidarabine; an immunotherapy, including, but not limited to, alemtuzumab, bevacizumab, cetuximab, galiximab, gemtuzumab, panitumumab, pertuzumab, rituximab, tositumomab, trastuzumab, 90 Y ibritumomab tiuxetan, ipilimumab, and tremelimumab; a hormone or hormone antagonist, including, but not limited to, anastrozole, androgens, buserelin, diethylstilbestrol, exemestane, flutamide, fulvestrant, goserelin, idoxifene, letrozole, leuprolide, magestrol, raloxifene, tamoxifen, and toremifene; a taxane, including, but not limited to, DJ-927, docetaxel, TPI 287, larotaxel, ortataxel, paclitaxel, DHA-paclitaxel, and tesetaxel; a retinoid, including, but not limited to, alitretinoin, bexarotene, fenretinide, isotretinoin, and tretinoin; an alkaloid, including, but not limited to, demecolcine, homoharringtonine, vinblastine, vincristine, vindesine, vinflunine, and vinorelbine; an antiangiogenic agent, including, but not limited to, AE-941 (GW786034, Neovastat), ABT-510, 2-methoxyestradiol, lenalidomide, and thalidomide; a topoisomerase inhibitor, including, but not limited to, amsacrine, belotecan, edotecarin, etoposide, etoposide phosphate, exatecan, irinotecan (also active metabolite SN-38 (7-ethyl-10-hydroxy-camptothecin)), lucanthone, mitoxantrone, pixantrone, rubitecan, teniposide, topotecan, and 9-aminocamptothecin; a kinase inhibitor, including, but not limited to, axitinib (AG 013736), dasatinib (BMS 354825), erlotinib, gefitinib, flavopiridol, imatinib mesylate, lapatinib, motesanib diphosphate (AMG 706), nilotinib (AMN107), seliciclib, sorafenib, sunitinib malate, AEE-788, BMS-599626, UCN-01 (7-hydroxystaurosporine), and vatalanib; a targeted signal transduction inhibitor including, but not limited to bortezomib, geldanamycin, and rapamycin; a biological response modifier, including, but not limited to, imiquimod, interferon-.alpha., and interleukin-2; IDO inhibitors, including, but not limited to, indoximod, and other chemotherapeutics, including, but not limited to 3-AP (3-amino-2-carboxyaldehyde thiosemicarbazone), altrasentan, aminoglutethimide, anagrelide, asparaginase, bryostatin-1, cilengitide, elesclomol, eribulin mesylate (E7389), ixabepilone, lonidamine, masoprocol, mitoguanazone, oblimersen, sulindac, testolactone, tiazofurin, mTOR inhibitors (e.g. temsirolimus, everolimus, deforolimus), PI3K inhibitors (e.g. BEZ235, GDC-0941, XL147, XL765), Cdk4 inhibitors (e.g. PD-332991), Akt inhibitors, Hsp90 inhibitors (e.g. tanespimycin) and farnesyltransferase inhibitors (e.g. tipifarnib); and MEK inhibitors (e.g., AS703026, AZD6244 (selumetinib), AZD8330, BIX02188, C11040 (PD184352), D-87503, GSK1120212 (JTP-74057), PD0325901, PD318088, PD98059, PDEA119 (BAY 869766), TAK-733).

In another embodiment, each method provided herein may further comprise administering a second therapeutic agent. In certain embodiments, the second therapeutic agent is an anticancer agent. In certain embodiments, the second therapeutic agent is a protein kinase inhibitor; In certain embodiments, a tyrosine kinase inhibitor; and in yet another embodiment, a second FLT3 kinase inhibitor, including, but not limiting to, Sunitinib, Cediranib, XL-184 free base (Cabozantinib, Ponatinib (AP24534), PHA-665752, Dovitinib (TKI258, CHIR-258), AC220 (Quizartinib), TG101209, KW-2449, AEE788 (NVP-AEE788), MP-470 (Amuvatinib), TSU-68 (SU6668, Orantinib, ENMD-2076, Vatalanib dihydrochloride (PTK787) and Tandutinib (MLN518).

In one embodiment, the present disclosure provides methods for treating a disease or condition mediated by FLT3 kinase, including mutant FLT3 kinase (such as FLT3 ITD and drug resistant FLT3 mutants such as D835Y and F691L), by administering to the subject an effective amount of a composition including any one or more compound(s) as described herein in combination with one or more other suitable therapies for treating the disease.

In another embodiment, the present disclosure provides a method of treating a cancer in a subject in need thereof by administering to the subject an effective amount of a composition including any one or more compound(s) as described herein in combination with one or more other therapies or medical procedures effective in treating the cancer. Other therapies or medical procedures include suitable anticancer therapy (e.g. drug therapy, vaccine therapy, gene therapy, photodynamic therapy) or medical procedure (e.g. surgery, radiation treatment, hyperthermia heating, bone marrow or stem cell transplant). In one embodiment, the one or more suitable anticancer therapies or medical procedures is selected from treatment with a chemotherapeutic agent (e.g. chemotherapeutic drug), radiation treatment (e.g. x-ray, .gamma.-ray, or electron, proton, neutron, or .alpha. particle beam), hyperthermia heating (e.g. microwave, ultrasound, radiofrequency ablation), Vaccine therapy (e.g. AFP gene hepatocellular carcinoma vaccine, AFP adenoviral vector vaccine, AG-858, allogeneic GM-CSF-secretion breast cancer vaccine, dendritic cell peptide vaccines), gene therapy (e.g. Ad5CMV-p53 vector, adenovector encoding MDA7, adenovirus 5-tumor necrosis factor alpha), photodynamic therapy (e.g. aminolevulinic acid, motexatin lutetium), surgery, or bone marrow and stem cell transplantation.

VIII. Kits

In another aspect, the present disclosure provides kits that include one or more compounds as described in any one of Embodiments 1, 1(a), 1(b), 1(c), 1(d), 1(e), 2, 2(a), 2(b), 2(c), 2(d), 2(e), 2(f), 2(g), 2(h), 3, 4, 4(a), 4(b), 4(c), 5, 5(a), 5(b) 5(c), 5(d), 5(e), 5(f), 5(g), 5(h), 5(i), 5(j), 5(k), 5(l), 5(m), 5(n), 5(o), 5(p), 5(q), 5(r), 5(s), 5(t), 5(u), 5(v), 5(w), 5(x), 5(z), 5(aa), 5(bb), 5(cc), 5(dd), 5(ee), 5(ff), 5(gg), 5(hh), 5(ii), 5(kk), 5(ll) 6, 7, 7(a), 7(b), 8, 9, 10 or 11, 12, 13, 14, 14(a), 14(b), 14(c), 14(d), 14(e), 14(f), 14(g), 14(h), 14(i), 14(j), 14(k), 14(l), 14(m), 14(n), 14(o), 14(p), 14(q), 14(r), 14(s), 14(t), 14(u), 14(v), 14(w), 14(x), 14(z), 14(aa), 14(bb), 15, 16 or 17, or a pharmaceutical composition thereof. In some embodiments, the compound or composition is packaged, e.g., in a vial, bottle, flask, which may be further packaged, e.g., within a box, envelope, or bag; the compound or composition is approved by the U.S. Food and Drug Administration or similar regulatory agency for administration to a mammal, e.g., a human; the compound or composition is approved for administration to a mammal, e.g., a human, for a protein kinase mediated disease or condition; the kits described herein may include written instructions for use and/or other indication that the compound or composition is suitable or approved for administration to a mammal, e.g., a human, for a Raf protein kinase-mediated disease or condition; and the compound or composition may be packaged in unit dose or single dose form, e.g., single dose pills, capsules, or the like.

IX. Companion Diagnostics

Another aspect of the disclosure relates to a method of (1) identifying the presence of a tumor in a patient; and (2) treating the patient, identified as needing the treatment, by administering a therapeutically effective amount of one or more compounds as described in any one of Embodiments 1, 1(a), 1(b), 1(c), 1(d), 1(e), 2, 2(a), 2(b), 2(c), 2(d), 2(e), 2(f), 2(g), 2(h), 3, 4, 4(a), 4(b), 4(c), 5, 5(a), 5(b) 5(c), 5(d), 5(e), 5(f), 5(g), 5(h), 5(i), 5(j), 5(k), 5(l), 5(m), 5(n), 5(o), 5(p), 5(q), 5(r), 5(s), 5(t), 5(u), 5(v), 5(w), 5(x), 5(z), 5(aa), 5(bb), 5(cc), 5(dd), 5(ee), 5(ff), 5(gg), 5(hh), 5(ii), 5(kk), 5(ll) 6, 7, 7(a), 7(b), 8, 9, 10 or 11, 12, 13, 14, 14(a), 14(b), 14(c), 14(d), 14(e), 14(f), 14(g), 14(h), 14(i), 14(j), 14(k), 14(l), 14(m), 14(n), 14(o), 14(p), 14(q), 14(r), 14(s), 14(t), 14(u), 14(v), 14(w), 14(x), 14(z), 14(aa), 14(bb), 15, 16 or 17, or a pharmaceutical composition thereof. In one embodiment, the tumor can be identified by employing a tumor biomarker. Tumor biomarkers can also be useful in establishing a specific diagnosis, such as determining whether tumors are of primary or metastatic origin. To make this distinction, chromosomal alterations found on cells located in the primary tumor site can be screened against those found in the secondary site. If the alterations match, the secondary tumor can be identified as metastatic; whereas if the alterations differ, the secondary tumor can be identified as a distinct primary tumor.

In another embodiment, the tumor can be identified by a biopsy. Non-limiting examples of biopsies that can be employed include fine needle aspiration biopsy, a core needle biopsy, a vacuum-assisted biopsy, an image-guided biopsy, a surgical biopsy, an incisional biopsy, an endoscopic biopsy, a bone marrow biopsy.

In another embodiment, the identification of tumor can be by magnetic resonance imaging (MRI) is a test that uses magnetic fields to produce detailed images of the body.

In another embodiment, the identification of tumor can be by a bone scan. In another embodiment, the identification of tumor can be a computed tomography (CT) scan, also called a CAT scan.

In another embodiment, the identification of tumor can be by an integrated PET-CT scan combines images from a positron emission tomography (PET) scan and a computed tomography (CT) scan that have been performed at the same time using the same machine.

In another embodiment, the identification of tumor can be by an ultrasound, which is an imaging test that uses high-frequency sound waves to locate a tumor inside the body.

In more specific embodiments, companion diagnostics that can be used to help treat patients, as a form of personalized medicine, can be employed by identifying a patient having a FLT3 mutant that is encoded by a FLT3 gene having an ITD mutation. In another embodiment, the companion diagnostic that can be used to help treat patients, as a form of personalized medicine, can be employed by identifying a patient having an oncogenic FLT3 mutant that is encoded by a FLT3 gene having an ITD mutation and a drug resistant F691L mutation. In another embodiment, the companion diagnostic that can be used to help treat patients, as a form of personalized medicine, can be employed by identifying a patient having an oncogenic FLT3 mutant that is encoded by a FLT3 gene having an ITD mutation and a D835Y drug resistant mutation. In another embodiment, the companion diagnostic that can be used to help treat patients, as a form of personalized medicine, can be employed by identifying a patient having an oncogenic FLT3 mutant that is encoded by a FLT3 gene having an ITD mutation, a drug resistant F691L mutation, and a D835Y drug resistant mutation.

X. Manipulation of FLT3, c-Kit and/or CSF1R

Techniques for the manipulation of nucleic acids, such as, e.g., subcloning, labeling probes (e.g. random-primer labeling using Klenow polymerase, nick translation, amplification), sequencing, hybridization and the like are well described in the scientific and patent literature, see, e.g., Sambrook, ed., Molecular Cloning: a Laboratory Manual (2nd ed.), Vols. 1-3, Cold Spring Harbor Laboratory, (1989); Current Protocols in Molecular Biology, Ausubel, ed. John Wiley & Sons, Inc., New York (1997); Laboratory Techniques in Biochemistry and Molecular Biology: Hybridization With Nucleic Acid Probes, Part I. Theory and Nucleic Acid Preparation, Tijssen, ed. Elsevier, N.Y. (1993).

Nucleic acid sequences can be amplified as necessary for further use using amplification methods, such as PCR, isothermal methods, rolling circle methods, etc., are well known to the skilled artisan. See, e.g., Saiki, "Amplification of Genomic DNA" in PCR Protocols, Innis et al., Eds., Academic Press, San Diego, Calif. 1990, pp 13-20; Wharam et al., Nucleic Acids Res. 2001 Jun 1;29(11):E54-E54; Hafner et al., Biotechniques 2001 Apr;30(4):852-6, 858, 860 passim; Zhong et al., Biotechniques 2001 Apr;30(4):852-6, 858, 860 passim.

Nucleic acids, vectors, capsids, polypeptides, and the like can be analyzed and quantified by any of a number of general means well known to those of skill in the art. These include, e.g., analytical biochemical methods such as NMR, spectrophotometry, radiography, electrophoresis, capillary electrophoresis, high performance liquid chromatography (HPLC), thin layer chromatography (TLC), and hyperdiffusion chromatography, various immunological methods, e.g. fluid or gel precipitin reactions, immunodiffusion, immunoelectrophoresis, radioimmunoassays (RIAs), enzyme-linked immunosorbent assays (ELISAs), immuno-fluorescent assays, Southern analysis, Northern analysis, dot-blot analysis, gel electrophoresis (e.g. SDS-PAGE), nucleic acid or target or signal amplification methods, radiolabeling, scintillation counting, and affinity chromatography.

Obtaining and manipulating nucleic acids used to practice the methods of the disclosure can be performed by cloning from genomic samples, and, if desired, screening and re-cloning inserts isolated or amplified from, e.g., genomic clones or cDNA clones. Sources of nucleic acid used in the methods of the present disclosure include genomic or cDNA libraries contained in, e.g., mammalian artificial chromosomes (MACs), see, e.g., U.S. Pat. Nos. 5,721,118; 6,025,155; human artificial chromosomes, see, e.g., Rosenfeld (1997) Nat. Genet. 15:333-335; yeast artificial chromosomes (YAC); bacterial artificial chromosomes (BAC); P1 artificial chromosomes, see, e.g., Woon (1998) Genomics 50:306-316; P1-derived vectors (PACs), see, e.g., Kern (1997) Biotechniques 23:120-124; cosmids, recombinant viruses, phages or plasmids.

The nucleic acids used to practice the methods of the present disclosure can be operatively linked to a promoter. A promoter can be one motif or an array of nucleic acid control sequences which direct transcription of a nucleic acid. A promoter can include necessary nucleic acid sequences near the start site of transcription, such as, in the case of a polymerase II type promoter, a TATA element. A promoter also optionally includes distal enhancer or repressor elements which can be located as much as several thousand base pairs from the start site of transcription. A "constitutive" promoter is a promoter which is active under most environmental and developmental conditions. An "inducible" promoter is a promoter which is under environmental or developmental regulation. A "tissue specific" promoter is active in certain tissue types of an organism, but not in other tissue types from the same organism. The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

The nucleic acids used to practice the methods of the present disclosure can also be provided in expression vectors and cloning vehicles, e.g., sequences encoding the polypeptides used to practice the methods of the present disclosure. Expression vectors and cloning vehicles used to practice the methods of the present disclosure can comprise viral particles, baculovirus, phage, plasmids, phagemids, cosmids, fosmids, bacterial artificial chromosomes, viral DNA (e.g. vaccinia, adenovirus, foul pox virus, pseudorabies and derivatives of SV40), P1-based artificial chromosomes, yeast plasmids, yeast artificial chromosomes, and any other vectors specific for specific hosts of interest (such as *bacillus, Aspergillus* and yeast). Vectors used to practice the methods of the present disclosure can include chromosomal, non-chromosomal and synthetic DNA sequences. Large numbers of suitable vectors are known to those of skill in the art, and are commercially available.

The nucleic acids used to practice the methods of the present disclosure can be cloned, if desired, into any of a variety of vectors using routine molecular biological methods; methods for cloning in vitro amplified nucleic acids are described, e.g., U.S. Pat. No. 5,426,039. To facilitate cloning of amplified sequences, restriction enzyme sites can be "built into" a PCR primer pair. Vectors may be introduced into a genome or into the cytoplasm or a nucleus of a cell and expressed by a variety of conventional techniques, well described in the scientific and patent literature. See, e.g., Roberts (1987) Nature 328:731; Schneider (1995) Protein Expr. Purif. 6435:10; Sambrook, Tijssen or Ausubel. The vectors can be isolated from natural sources, obtained from such sources as ATCC or GenBank libraries, or prepared by synthetic or recombinant methods. For example, the nucleic acids used to practice the methods of the present disclosure can be expressed in expression cassettes, vectors or viruses which are stably or transiently expressed in cells (e.g. episomal expression systems). Selection markers can be incorporated into expression cassettes and vectors to confer a selectable phenotype on transformed cells and sequences. For example, selection markers can code for episomal maintenance and replication such that integration into the host genome is not required.

In one aspect, the nucleic acids used to practice the methods of the present disclosure are administered in vivo for in situ expression of the peptides or polypeptides used to practice the methods of the disclosure. The nucleic acids can be administered as "naked DNA" (see, e.g., U.S. Pat. No. 5,580,859) or in the form of an expression vector, e.g., a recombinant virus. The nucleic acids can be administered by any route, including peri- or intra-tumorally, as described below. Vectors administered in vivo can be derived from viral genomes, including recombinantly modified enveloped or non-enveloped DNA and RNA viruses, selected from baculoviridiae, parvoviridiae, picornoviridiae, herpesveridiae, poxviridae, adenoviridiae, or picornnaviridiae. Chimeric vectors may also be employed which exploit advantageous merits of each of the parent vector properties (See e.g., Feng (1997) Nature Biotechnology 15:866-870). Such viral genomes may be modified by recombinant DNA techniques to include the nucleic acids used to practice the methods of the present disclosure; and may be further engineered to be replication deficient, conditionally replicating or replication competent. In alternative aspects, vectors are derived from the adenoviral (e.g. replication incompetent vectors derived from the human adenovirus genome, see, e.g., U.S. Pat. Nos. 6,096,718; 6,110,458; 6,113,913; 5,631,236); adeno-associated viral and retroviral genomes. Retroviral vectors can include those based upon murine leukemia virus (MuLV), gibbon ape leukemia virus (GaLV), Simian Immuno deficiency virus (SIV), human immuno deficiency virus (HIV), and combinations thereof; see, e.g., U.S. Pat. Nos. 6,117,681; 6,107,478; 5,658,775; 5,449,614; Buchscher (1992) J. Virol. 66:2731-2739; Johann (1992) J. Virol. 66:1635-1640). Adeno-associated virus (AAV)-based vectors can be used to transduce cells with target nucleic acids, e.g., in the in vitro production of nucleic acids and peptides, and in in vivo and ex vivo gene therapy procedures; see, e.g., U.S. Pat. Nos. 6,110,456; 5,474,935; Okada (1996) Gene Ther. 3:957-964.

The present disclosure also relates to use of fusion proteins, and nucleic acids encoding them. A polypeptide used to practice the methods of the present disclosure can be fused to a heterologous peptide or polypeptide, such as N-terminal identification peptides which impart desired characteristics, such as increased stability or simplified purification. Peptides and polypeptides used to practice the methods of the present disclosure can also be synthesized and expressed as fusion proteins with one or more additional domains linked thereto for, e.g., producing a more immunogenic peptide, to more readily isolate a recombinantly synthesized peptide, to identify and isolate antibodies and antibody-expressing B cells, and the like. Detection and purification facilitating domains include, e.g., metal chelating peptides such as polyhistidine tracts and histidine-tryptophan modules that allow purification on immobilized metals, protein A domains that allow purification on immobilized immunoglobulin, and the domain utilized in the FLAGS extension/affinity purification system (Immunex Corp, Seattle WA). The inclusion of a cleavable linker sequences such as Factor Xa or enterokinase (Invitrogen, San Diego CA) between a purification domain and the motif-comprising peptide or polypeptide to facilitate purification. For example, an expression vector can include an epitope-encoding nucleic acid sequence linked to six histidine residues (SEQ ID NO: 3) followed by a thioredoxin and an enterokinase cleavage site (see e.g., Williams (1995) Biochemistry 34:1787-1797; Dobeli (1998) Protein Expr. Purif. 12:404-414). The histidine residues facilitate detection and purification while the enterokinase cleavage site provides a means for purifying the epitope from the remainder of the fusion protein. In one aspect, a nucleic acid encoding a polypeptide used to practice the methods of the present disclosure is assembled in appropriate phase with a leader sequence capable of directing secretion of the translated polypeptide or fragment thereof. Technology pertaining to vectors encoding fusion proteins and application of fusion proteins are well described in the scientific and patent literature, see e.g., Kroll (1993) DNA Cell. Biol. 12:441-53.

The nucleic acids and polypeptides used to practice the methods of the present disclosure can be bound to a solid support, e.g., for use in screening and diagnostic methods. Solid supports can include, e.g., membranes (e.g. nitrocellulose or nylon), a microtiter dish (e.g. PVC, polypropylene, or polystyrene), a test tube (glass or plastic), a dip stick (e.g. glass, PVC, polypropylene, polystyrene, latex and the like), a microfuge tube, or a glass, silica, plastic, metallic or polymer bead or other substrate such as paper. One solid support uses a metal (e.g. cobalt or nickel)-comprising column which binds with specificity to a histidine tag engineered onto a peptide.

Adhesion of molecules to a solid support can be direct (i.e., the molecule contacts the solid support) or indirect (a "linker" is bound to the support and the molecule of interest binds to this linker). Molecules can be immobilized either covalently (e.g. utilizing single reactive thiol groups of cysteine residues (see, e.g., Colliuod (1993) Bioconjugate Chem. 4:528-536) or non-covalently but specifically (e.g. via immobilized antibodies (see, e.g., Schuhmann (1991) Adv. Mater. 3:388-391; Lu (1995) Anal. Chem. 67:83-87; the biotin/strepavidin system (see, e.g., Iwane (1997) Biophys. Biochem. Res. Comm. 230:76-80); metal chelating, e.g., Langmuir-Blodgett films (see, e.g., Ng (1995) Langmuir 11:4048-55); metal-chelating self-assembled monolayers (see, e.g., Sigal (1996) Anal. Chem. 68:490-497) for binding of polyhistidine fusions.

Indirect binding can be achieved using a variety of linkers which are commercially available. The reactive ends can be any of a variety of functionalities including, but not limited to: amino reacting ends such as N-hydroxysuccinimide (NHS) active esters, imidoesters, aldehydes, epoxides, sulfonyl halides, isocyanate, isothiocyanate, and nitroaryl halides; and thiol reacting ends such as pyridyl disulfides, maleimides, thiophthalimides, and active halogens. The heterobifunctional crosslinking reagents have two different reactive ends, e.g., an amino-reactive end and a thiol-reactive end, while homobifunctional reagents have two similar reactive ends, e.g., bismaleimidohexane (BMH) which permits the crosslinking of sulfhydryl-containing compounds. The spacer can be of varying length and be aliphatic or aromatic. Examples of commercially available homobifunctional crosslinking reagents include, but are not limited to, the imidoesters such as dimethyl adipimidate dihydrochloride (DMA); dimethyl pimelimidate dihydrochloride (DMP); and dimethyl suberimidate dihydrochloride (DMS). Heterobifunctional reagents include commercially available active halogen-NHS active esters coupling agents such as N-succinimidyl bromoacetate and N-succinimidyl (4-iodoacetyl)aminobenzoate (SIAB) and the sulfosuccinimidyl derivatives such as sulfosuccinimidyl(4-iodoacetyl) aminobenzoate (sulfo-SIAB) (Pierce). Another group of coupling agents is the heterobifunctional and thiol cleavable agents such as N-succinimidyl 3-(2-pyridyidithio)propionate (SPDP) (Pierce Chemicals, Rockford, Ill.).

Antibodies can also be used for binding polypeptides and peptides used to practice the methods of the present disclosure to a solid support. This can be done directly by binding peptide-specific antibodies to the column or it can be done by creating fusion protein chimeras comprising motif-containing peptides linked to, e.g., a known epitope (e.g. a tag (e.g. FLAG, myc) or an appropriate immunoglobulin constant domain sequence (an "immunoadhesin," see, e.g., Capon (1989) Nature 377:525-531 (1989).

Nucleic acids or polypeptides used to practice the methods of the present disclosure can be immobilized to or applied to an array. Arrays can be used to screen for or monitor libraries of compositions (e.g. small molecules, antibodies, nucleic acids, etc.) for their ability to bind to or modulate the activity of a nucleic acid or a polypeptide used to practice the methods of the present disclosure. For example, in one aspect of the disclosure, a monitored parameter is transcript expression of a gene comprising a nucleic acid used to practice the methods of the present disclosure. One or more, or all the transcripts of a cell can be measured by hybridization of a sample comprising transcripts of the cell, or nucleic acids representative of or complementary to transcripts of a cell, by hybridization to immobilized nucleic acids on an array, or "biochip." By using an "array" of nucleic acids on a microchip, some or all of the transcripts of a cell can be simultaneously quantified. Alternatively, arrays comprising genomic nucleic acid can also be used to determine the genotype of a newly engineered strain made by the methods of the present disclosure. Polypeptide arrays" can also be used to simultaneously quantify a plurality of proteins.

The terms "array" or "microarray" or "biochip" or "chip" as used herein is a plurality of target elements, each target element comprising a defined amount of one or more polypeptides (including antibodies) or nucleic acids immobilized onto a defined area of a substrate surface. In practicing the methods of the present disclosure, any known array and/or method of making and using arrays can be incorporated in whole or in part, or variations thereof, as described, for example, in U.S. Pat. Nos. 6,277,628; 6,277,489; 6,261,776; 6,258,606; 6,054,270; 6,048,695; 6,045,996; 6,022,963; 6,013,440; 5,965,452; 5,959,098; 5,856,174; 5,830,645; 5,770,456; 5,632,957; 5,556,752; 5,143,854; 5,807,522; 5,800,992; 5,744,305; 5,700,637; 5,556,752; 5,434,049; see also, e.g., WO 99/51773; WO 99/09217; WO 97/46313; WO 96/17958; see also, e.g., Johnston (1998) Curr. Biol. 8:R171-R174; Schummer (1997) Biotechniques 23:1087-1092; Kern (1997) Biotechniques 23:120-124; Solinas-Toldo (1997) Genes, Chromosomes & Cancer 20:399-407; Bowtell (1999) Nature Genetics Supp. 21:25-32. See also published U.S. patent application Nos. 20010018642; 20010019827; 20010016322; 20010014449; 20010014448; 20010012537; 20010008765.

Host Cells and Transformed Cells

The present disclosure also provides a transformed cell comprising a nucleic acid sequence used to practice the methods of the present disclosure, e.g., a sequence encoding a polypeptide used to practice the methods of the present disclosure, or a vector used to practice the methods of the present disclosure. The host cell may be any of the host cells familiar to those skilled in the art, including prokaryotic cells, eukaryotic cells, such as bacterial cells, fungal cells, yeast cells, mammalian cells, insect cells, or plant cells. Exemplary bacterial cells include *E. coli, Streptomyces, Bacillus subtilis, Salmonella typhimurium* and various species within the genera *Pseudomonas, Streptomyces*, and *Staphylococcus*. Exemplary insect cells include *Drosophila* S2 and *Spodoptera* Sf9. Exemplary animal cells include CHO, COS or Bowes melanoma or any mouse or human cell line. The selection of an appropriate host is within the abilities of those skilled in the art.

Vectors may be introduced into the host cells using any of a variety of techniques, including transformation, transfection, transduction, viral infection, gene guns, or Ti-mediated gene transfer. Particular methods include calcium phosphate transfection, DEAE-Dextran mediated transfection, lipofection, or electroporation.

Engineered host cells can be cultured in conventional nutrient media modified as appropriate for activating promoters, selecting transformants or amplifying the genes used to practice the methods of the present disclosure. Following transformation of a suitable host strain and growth of the host strain to an appropriate cell density, the selected promoter may be induced by appropriate means (e.g. temperature shift or chemical induction) and the cells may be cultured for an additional period to allow them to produce the desired polypeptide or fragment thereof Cells can be harvested by centrifugation, disrupted by physical or chemical means, and the resulting crude extract is retained for further purification. Microbial cells employed for expression of proteins can be disrupted by any convenient method, including freeze-thaw cycling, sonication, mechanical disruption, or use of cell lysing agents. Such methods are well known to those skilled in the art. The expressed polypeptide or fragment can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the polypeptide. If desired, high performance liquid chromatography (HPLC) can be employed for final purification steps.

Various mammalian cell culture systems can also be employed to express recombinant protein. Examples of mammalian expression systems include the COS-7 lines of monkey kidney fibroblasts and other cell lines capable of expressing proteins from a compatible vector, such as the C127, 3T3, CHO, HeLa and BHK cell lines.

The constructs in host cells can be used in a conventional manner to produce the gene product encoded by the recombinant sequence. Depending upon the host employed in a recombinant production procedure, the polypeptides produced by host cells containing the vector may be glycosylated or may be non-glycosylated. Polypeptides used to practice the methods of the present disclosure may or may not also include an initial methionine amino acid residue.

Cell-free translation systems can also be employed to produce a polypeptide used to practice the methods of the present disclosure. Cell-free translation systems can use mRNAs transcribed from a DNA construct comprising a promoter operably linked to a nucleic acid encoding the polypeptide or fragment thereof. In some aspects, the DNA construct may be linearized prior to conducting an in vitro transcription reaction. The transcribed mRNA is then incubated with an appropriate cell-free translation extract, such as a rabbit reticulocyte extract, to produce the desired polypeptide or fragment thereof The expression vectors can contain one or more selectable marker genes to provide a phenotypic trait for selection of transformed host cells such as dihydrofolate reductase or neomycin resistance for eukaryotic cell culture, or such as tetracycline or ampicillin resistance in *E. coli*.

For transient expression in mammalian cells, cDNA encoding a polypeptide of interest may be incorporated into a mammalian expression vector, e.g. pcDNA1, which is available commercially from Invitrogen Corporation (San Diego, Calif., U.S.A.; catalogue number V490-20). This is a multifunctional 4.2 kb plasmid vector designed for cDNA expression in eukaryotic systems, and cDNA analysis in prokaryotes, incorporated on the vector are the CMV promoter and enhancer, splice segment and polyadenylation signal, an SV40 and Polyoma virus origin of replication, and M13 origin to rescue single strand DNA for sequencing and mutagenesis, Sp6 and T7 RNA promoters for the production of sense and anti-sense RNA transcripts and a Col E1-like high copy plasmid origin. A polylinker is located appropriately downstream of the CMV promoter (and 3' of the T7 promoter).

The cDNA insert may be first released from the above phagemid incorporated at appropriate restriction sites in the pcDNAI polylinker. Sequencing across the junctions may be performed to confirm proper insert orientation in pcDNAI. The resulting plasmid may then be introduced for transient expression into a selected mammalian cell host, for example, the monkey-derived, fibroblast like cells of the COS-1 lineage (available from the American Type Culture Collection, Rockville, Md. as ATCC CRL 1650).

For transient expression of the protein-encoding DNA, for example, COS-1 cells may be transfected with approximately 8 μg DNA per $10^6$ COS cells, by DEAE-mediated DNA transfection and treated with chloroquine according to the procedures described by Sambrook et al, Molecular Cloning: A Laboratory Manual, 1989, Cold Spring Harbor Laboratory Press, Cold Spring Harbor N.Y., pp. 16.30-16.37. An exemplary method is as follows. Briefly, COS-1 cells are plated at a density of $5 \times 10^6$ cells/dish and then grown for 24 hours in FBS-supplemented DMEM/F12 medium. Medium is then removed and cells are washed in PBS and then in medium. A transfection solution containing DEAE dextran (0.4 mg/mL), 100 µM chloroquine, 10% NuSerum, DNA (0.4 mg/mL) in DMEM/F12 medium is then applied on the cells 10 mL volume. After incubation for 3 hours at 37° C., cells are washed in PBS and medium as just described and then shocked for 1 minute with 10% DMSO in DMEM/F12 medium. Cells are allowed to grow for 2-3 days in 10% FBS-supplemented medium, and at the end of incubation dishes are placed on ice, washed with ice cold PBS and then removed by scraping. Cells are then harvested by centrifugation at 1000 rpm for 10 minutes and the cellular pellet is frozen in liquid nitrogen, for subsequent use in protein expression. Northern blot analysis of a thawed aliquot of frozen cells may be used to confirm expression of receptor-encoding cDNA in cells under storage.

In a like manner, stably transfected cell lines can also prepared, for example, using two different cell types as host: CHO K1 and CHO Pro5. To construct these cell lines, cDNA coding for the relevant protein may be incorporated into the mammalian expression vector pRC/CMV (Invitrogen), which enables stable expression. Insertion at this site places the cDNA under the expression control of the cytomegalovirus promoter and upstream of the polyadenylation site and terminator of the bovine growth hormone gene, and into a vector background comprising the neomycin resistance gene (driven by the SV40 early promoter) as selectable marker.

An exemplary protocol to introduce plasmids constructed as described above is as follows. The host CHO cells are first seeded at a density of $5 \times 10^5$ in 10% FBS-supplemented MEM medium. After growth for 24 hours, fresh medium is added to the plates and three hours later, the cells are transfected using the calcium phosphate-DNA co-precipitation procedure (Sambrook et al, supra). Briefly, 3 µg of DNA is mixed and incubated with buffered calcium solution for 10 minutes at room temperature. An equal volume of buffered phosphate solution is added and the suspension is incubated for 15 minutes at room temperature. Next, the incubated suspension is applied to the cells for 4 hours, removed and cells were shocked with medium containing 15% glycerol. Three minutes later, cells are washed with medium and incubated for 24 hours at normal growth conditions. Cells resistant to neomycin are selected in 10% FBS-supplemented alpha-MEM medium containing G418 (1 mg/mL). Individual colonies of G418-resistant cells are isolated about 2-3 weeks later, clonally selected and then propagated for assay purposes.

EXAMPLES

The examples below depict the general synthetic procedure for the compounds described herein. Synthesis of the compounds described herein is not limited by these examples and schemes. One skilled in the art will know that other procedures can be used to synthesize the compounds described herein, and that the procedures described in the examples and schemes is only one such procedure. In the descriptions below, one of ordinary skill in the art would recognize that specific reaction conditions, added reagents, solvents, and reaction temperatures can be modified for the synthesis of specific compounds that fall within the scope of this disclosure. Unless otherwise specified, intermediate compounds in the examples below, that do not contain a description of how they are made, are either commercially available to one skilled in the art, or can otherwise be synthesized by the skilled artisan using commercially available precursor molecules and synthetic methods known in the art.

The examples are intended to be illustrative and are not limiting or restrictive to the scope of the disclosure.

Synthetic Examples

Standard abbreviations and acronyms as defined in *J. Org. Chem.* 2007 72(1): 23A-24A are used herein. Other abbreviations and acronyms used herein are described above.

Example 1

Compound P-0138 is prepared in three steps from 5-bromo-2-fluoro-pyrimidine 1, 1-methylpyrazol-4-amine 2, 2-[4-(4,4,5,5-tetramethyl-1,3,2-dioxaborolan-2-yl)phenyl]acetic acid 4 and 6-methoxy-5-(trifluoromethyl)pyridin-3-amine 5 as shown in Scheme 1.

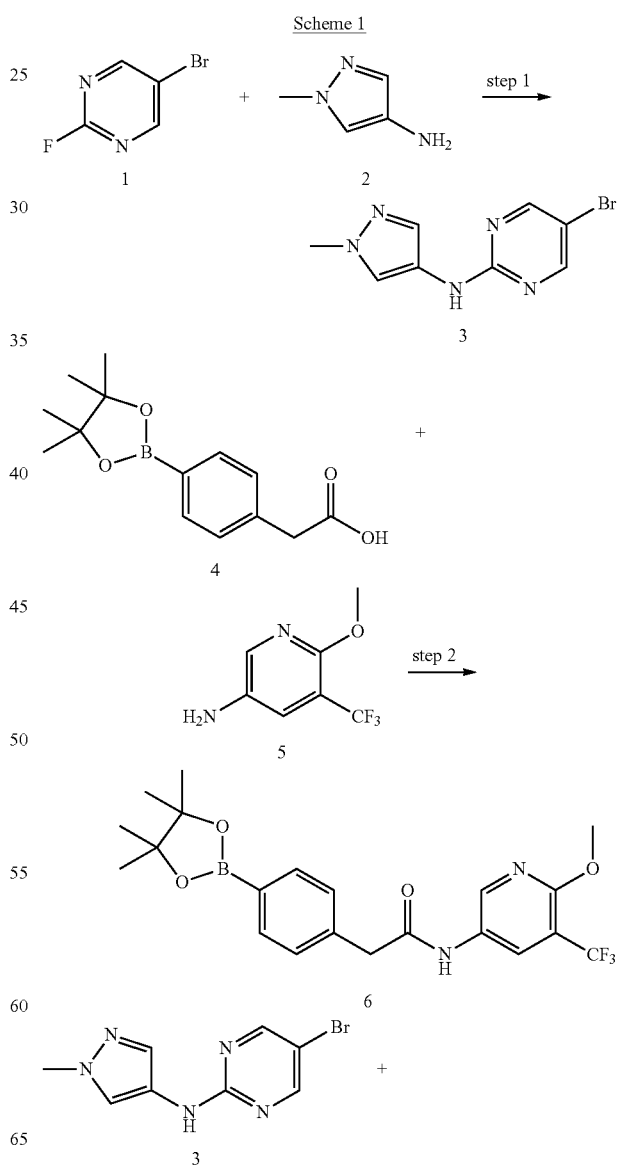

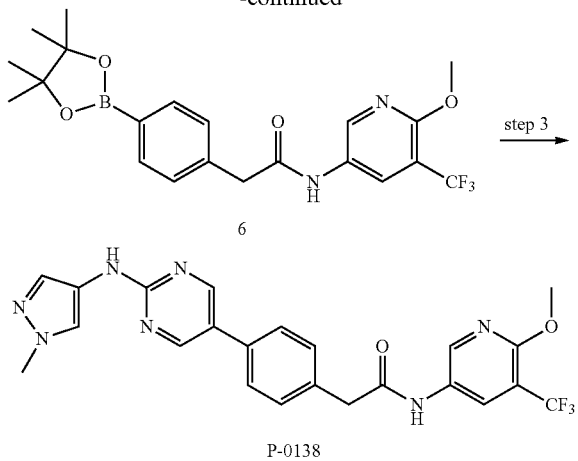

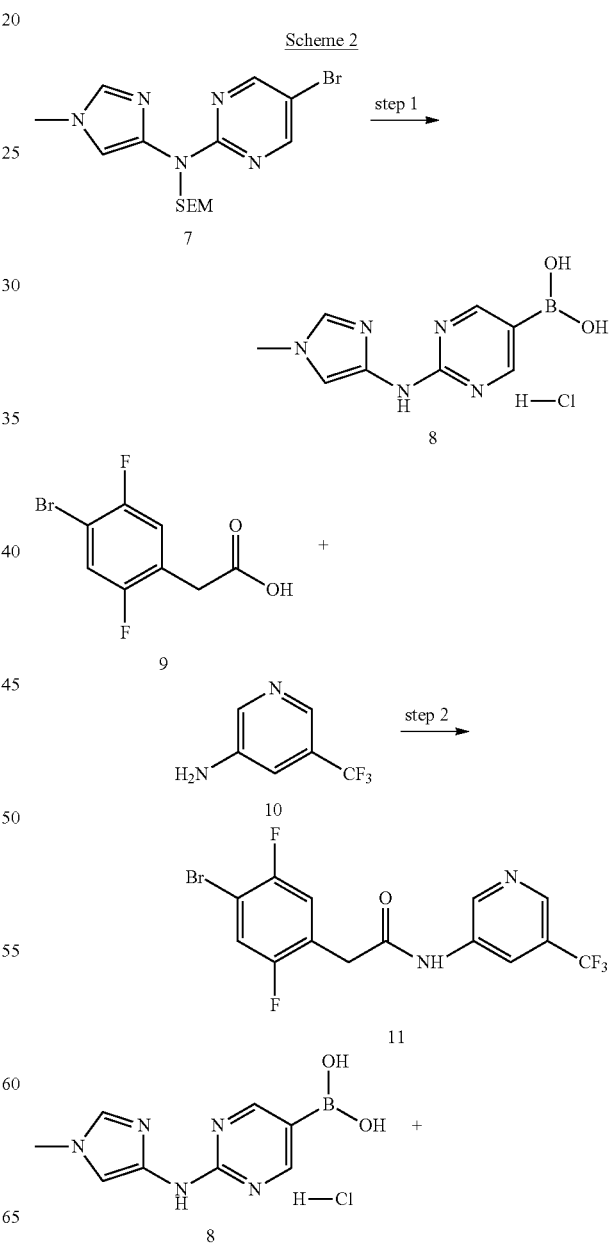

addition of 2.5 M aqueous potassium carbonate (0.72 ml). The mixture was allowed to stir at 90° C. for 3 hours. The reaction was diluted with ethyl acetate and was dried over anhydrous magnesium sulfate, filtered and concentrated down under a reduced atmosphere. The residue was purified by silica gel flash column chromatography eluting with 5% methanol in ethyl acetate, followed by triturating with acetonitrile to provide compound P-0138. MS ESI [M+H$^+$]$^+$=484.30.

Example 2

Compound P-0078 is prepared in 3 steps from 5-bromo-N-(1-methylimidazol-4-yl)-N-(2-trimethylsilylethoxymethyl)pyrimidine-2-amine 7 (prepared from compound 12 using standard SEM protection conditions), 2-(4-bromo-2,5-difluoro-phenyl)acetic acid 9, and 5-(trifluoromethyl)pyridin-3-amine 10 as shown in Scheme 2.

Step 1—Preparation of 5-bromo-N-(1-methyl-1H-pyrazol-4-yl)pyrimidin-2-amine, 3: To 1-methylpyrazol-4-amine (2, 2.43 g, 25.0 mmol), 5-bromo-2-fluoro-pyrimidine (1, 5.31 g, 30.0 mmol) and N,N-diisopropylethylamine (9.69 g, 75.0 mmol) was added dimethyl sulfoxide (12.5 mL). The reaction flask was placed under nitrogen gas and allowed to stir at 120° C. for 19 hours. The brownish solution was diluted with water (200 mL) and extracted with ethyl acetate (5×100 mL). The combined organic layers were washed with water (2×100 mL) and 5 M sodium chloride (1×100 mL) and the aqueous layer back extracted with ethyl acetate (1×100 mL). The combined organic layers were dried over anhydrous sodium sulfate and filtered. The filtrate was concentrated under reduced pressure and the product triturated with diethyl ether (1×100 mL). The precipitate was collected by vacuum filtration and washed with diethyl ether (1×100 mL), giving 5.58 g of compound 3 as a yellow solid. MS ESI [M+H$^+$]$^+$=254.05. The brownish orange filtrate was evaporated and purified by silica gel flash column chromatography eluting with 0-10% methanol in dichloromethane. This provided an additional 762 mg of compound 3. MS ESI [M+H$^+$]$^+$=254.05.

Step 2—Preparation of N-[6-methoxy-5-(trifluoromethyl)-3-pyridyl]-2-[4-(4,4,5,5-tetramethyl-1,3,2-dioxaborolan-2-yl)phenyl]acetamide, 6: To a mixture of 2-[4-(4,4,5,5-tetramethyl-1,3,2-dioxaborolan-2-yl)phenyl]acetic acid (4, 2.02 g, 7.71 mmol), 6-methoxy-5-(trifluoromethyl)pyridin-3-amine (5, 1.48 g, 7.70 mmol) and pyridine (1.83 g, 23.1 mmol) in ethyl acetate (80 ml) was added slowly propylphosphonic anhydride (50 wt % solution in ethyl acetate, 9.1 ml, 15.4 mmol). The reaction mixture was allowed to stir at room temperature for 3 hours. The reaction was diluted with ethyl acetate and was washed with saturated aqueous ammonium chloride, water and brine. The organic layer was dried over anhydrous magnesium sulfate, filtered and concentrated down under reduced pressure to provide 3.10 g (92% yield) of compound 6, which was used for the next step without purification. MS ESI [M+H$^+$]$^+$=437.25.

Step 3—Preparation of N-[6-methoxy-5-(trifluoromethyl)-3-pyridyl]-2-[4-[2-[(1-methylpyrazol-4-yl)amino]pyrimidin-5-yl]phenyl]acetamide, P-0138: A mixture of 5-bromo-N-(1-methylpyrazol-4-yl)pyrimidin-2-amine (3, 152 mg, 0.598 mmol), N-[6-methoxy-5-(trifluoromethyl)-3-pyridyl]-2-[4-(4,4,5,5-tetramethyl-1,3,2-dioxaborolan-2-yl)phenyl]acetamide (6, 314 mg, 0.720 mmol) and [1,1'-bis(diphenylphosphino)ferrocene] dichloropalladium(II) dichloromethane complex (44 mg, 0.054 mmol) in dioxane (6 ml) was purged with nitrogen gas, followed by the

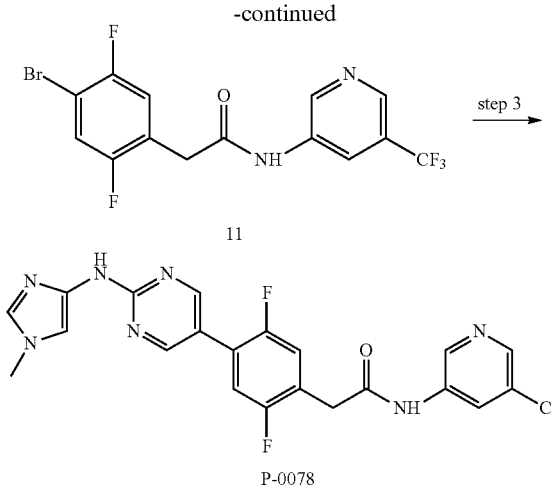

Step 1—Preparation of (2-((1-methyl-1H-imidazol-4-yl)amino)pyrimidin-5-yl)boronic acid hydrochloride, 8: To a dried 50 mL pressure vessel equipped with a magnetic stir bar was added 5-bromo-N-(1-methylimidazol-4-yl)-N-(2-trimethylsilylethoxymethyl)pyrimidin-2-amine (7, 2.69 g, 7.00 mmol), bis(pinacolato)diboron (3.56 g, 14.0 mmol), [1,1'Bis(diphenylphosphino)ferrocene] dichloropalladium (II) dichloromethane complex (572 mg, 0.700 mmol), potassium acetate (3.44 g, 35.1 mmol) and anhydrous 1,4-dioxane (21.0 mL). The reaction vessel was placed under nitrogen gas, sealed, and allowed to stir at 100° C. for 15 hours. The resulting opaque brown solution was filtered and diluted with ethyl acetate and water. The organic layer was washed with water, 5 M aqueous sodium chloride and dried over anhydrous sodium sulfate. The drying agent was removed by filtration and the filtrate was concentrated under a reduced atmosphere to provide a viscous oil that was purified by reverse phase silica gel flash column chromatography eluting with 0-100% acetonitrile in water with 0.1% formic acid. This provided 1.51 g of a mixture of SEM protected and deprotected products. This material was treated with 4 M HCl in dioxane (10 ml) and allowed to stir at ambient temperature for 4 hours to form a precipitate. The solid was collected by filtration to provide 1.23 g (50% yield) of compound 8. MS ESI [M+H$^+$]$^+$=220.15.

Step 2—Preparation of 2-(4-bromo-2,5-difluoro-phenyl)-N-[5-(trifluoromethyl)-3-pyridyl]acetamide, 11: To a mixture of 2-(4-bromo-2,5-difluoro-phenyl)acetic acid (9, 2.16 g, 8.60 mmol), 5-(trifluoromethyl)pyridin-3-amine (10, 1.39 g, 8.57 mmol) and pyridine (2.09 ml, 25.8 mmol) in ethyl acetate (85 ml) was added slowly propylphosphonic anhydride (50 wt % solution in ethyl acetate, 10.1 ml, 17.2 mmol). The reaction mixture was allowed to stir at room temperature for 3 hours. The reaction was diluted with ethyl acetate and was washed with saturated aqueous ammonium chloride, water and brine. The organic layer was dried over anhydrous magnesium sulfate, filtered and concentrated under reduced pressure to provide 3.29 g (97% yield) of compound 11 that was used in the next step without further purification. MS ESI [M+H$^+$]$^+$=397.05.

Step 3—Preparation of 2-(2,5-difluoro-4-(2-((1-methyl-1H-imidazol-4-yl)amino)pyrimidin-5-yl)phenyl)-N-(5-(trifluoromethyl)pyridin-3-yl)acetamide, P-0078: To a 5 mL microwaveable vial containing a magnetic stir bar was added 2- (4-bromo-2,5-difluoro-phenyl)-N-[5-(trifluoromethyl)-3-pyridyl]acetamide (11, 195 mg, 0.494 mmol), [2-[(1-methylimidazol-4-yl)amino]pyrimidin-5-yl]boronic acid hydrochloride (8, 133 mg, 0.521 mmol), [1,1'-bis(diphenylphosphino)ferrocene]dichloropalladium(II) dichloromethane complex (41 mg, 0.050 mmol), 2.0 M aqueous potassium carbonate (1.2 mL), and anhydrous acetonitrile (5 mL). The reaction vial was placed under nitrogen, sealed, and heated at 120° C. in a microwave reactor for 2 hours. The resulting dark brown solution was added to ethyl acetate and was washed with water and 5 M aqueous sodium chloride. The organic layer was dried over anhydrous sodium sulfate, filtered and evaporated under reduced pressure. The resulting residue was purified by silica gel flash column chromatography eluting with 0-15% methanol in dichloromethane) to provide compound P-0078. MS ESI [M+H$^+$]$^+$=490.30.

Example 3

Compound P-0167 is prepared in 3 steps from 5-bromo-N-(1-methylimidazol-4-yl)pyrimidin-2-amine 12 (prepared in a manner analogous to compound 3 in scheme 1 using 1-methyl-1H-imidazol-4-amine in place of 1-methylpyrazol-4-amine), ethyl 2-[4-(4,4,5,5-tetramethyl-1,3,2-dioxaborolan-2-yl)phenyl]acetate 4 and 5-(trifluoromethyl)pyridin-3-amine 10 as shown in Scheme 3.

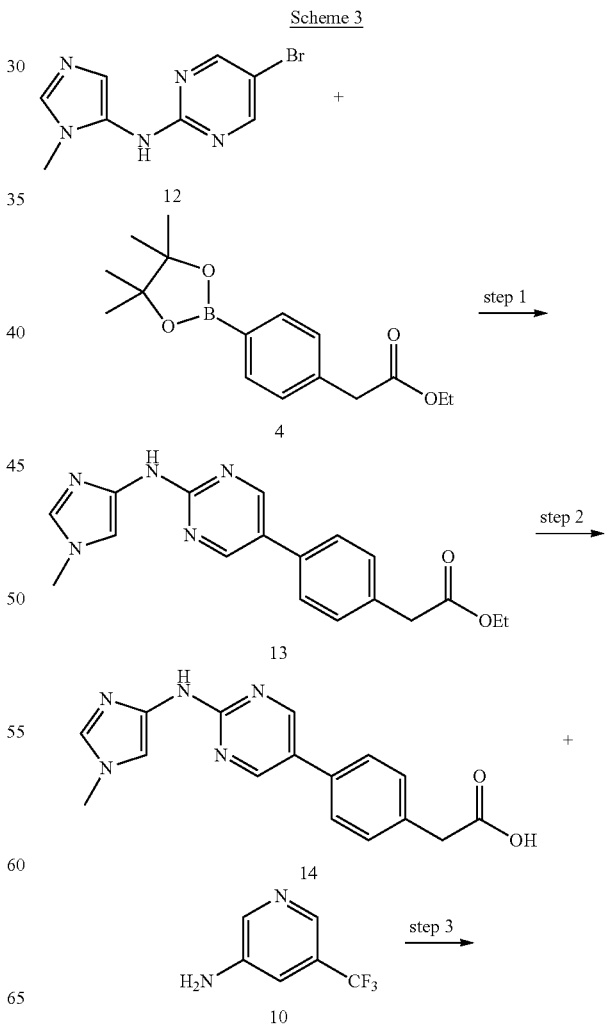

Scheme 3

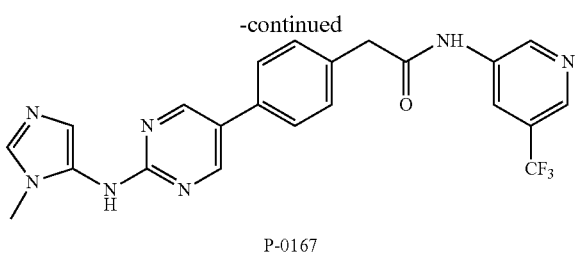

P-0167

Step 1—Preparation of ethyl 2-(4-(2-((1-methyl-1H-imidazol-4-yl)amino)pyrimidin-5-yl)phenyl)acetate, 13: To a 500 ml round bottom flask was added 5-bromo-N-(1-methylimidazol-4-yl)pyrimidin-2-amine (12, 2.00 g, 7.87 mmol) followed by THF (100 ml). The solid was allowed to dissolve and to the resulting solution was added ethyl 2-[4-(4,4,5,5-tetramethyl-1,3,2-dioxaborolan-2-yl)phenyl]acetate (4, 2.40 g, 8.27 mmol) followed by 1 M aqueous potassium carbonate (50 ml). The mixture was de-gassed and purged with nitrogen. To the mixture was then added [1,1'-bis(diphenylphosphino)ferrocene]dichloropalladium (II) dichloromethane complex (0.62 g, 0.76 mmol) and the reaction was allowed to stir at 70° C. for 4 hours. Upon completion, the reaction mixture was filtered through celite, poured into water and extracted with ethyl acetate. The organic layer was dried over anhydrous sodium sulfate and filtered. The solvent was removed under reduced pressure in the presence of silica and the resulting crude material was purified by silica gel flash column chromatography eluting with 0-50% ethyl acetate in hexane to provide 750 mg of compound 13.

Step 2—Preparation of 2-(4-(2-((1-methyl-1H-imidazol-4-yl)amino)pyrimidin-5-yl)phenyl)acetic acid, 14: To a 50 ml round bottom flask was added ethyl 2-(4-(2-((1-methyl-1H-imidazol-4-yl)amino)pyrimidin-5-yl)phenyl)acetate (13, 0.220 g, 0.652 mmol) followed by THF (10 ml) and 1 M aqueous lithium hydroxide (5 ml). The mixture was allowed to stir at 70° C. overnight. Upon completion, the reaction mixture was acidified with 1 M aqueous HCl (5 ml), poured into water and extracted with ethyl acetate. The organic layer was washed with brine, dried over anhydrous sodium sulfate and filtered. The solvent was removed under reduced pressure to provide 205 mg of compound 14.

Step 3—Preparation of 2-(4-(2-((1-methyl-1H-imidazol-5-yl)amino)pyrimidin-5-yl)phenyl)-N-(5-(trifluoromethyl) pyridin-3-yl)acetamide, P-0167: To a 5 ml reaction vial was added 2-[4-[2-[(1-methylimidazol-4-yl)amino]pyrimidin-5-yl]phenyl]acetic acid (14, 160 mg, 0.050 mmol) followed by anhydrous NMP (1.5 ml), 5-(trifluoromethyl)pyridin-3-amine (10, 8 mg, 0.05 mmol) and pyridine (80 µl). To the mixture was slowly added propylphosphonic anhydride (50 wt % solution in ethyl acetate, 0.25 ml, 0.42 mmol). The reaction was allowed to stir at room temperature for three hours. Upon completion, the reaction was poured into water and extracted with ethyl acetate. The organic phase was washed with saturated aqueous ammonium chloride and brine, dried over anhydrous sodium sulfate and filtered. The solvent was removed under reduced pressure in the presence of silica. The resulting crude material was purified by silica gel flash column chromatography eluting with 0-15% methanol in dichloromethane. This provided compound P-0167. MS ESI [M+H$^+$]$^+$=452.00.

Example 4

Compound P-0213 is prepared in 4 steps from 5-bromo-1H-pyrazolo[3,4-b]pyridin-3-ol 15 and N-[6-methoxy-5-(trifluoromethyl)-3-pyridyl]-2-[4-(4,4,5,5-tetramethyl-1,3,2-dioxaborolan-2-yl)phenyl]acetamide 6 as shown in Scheme 4.

Scheme 4

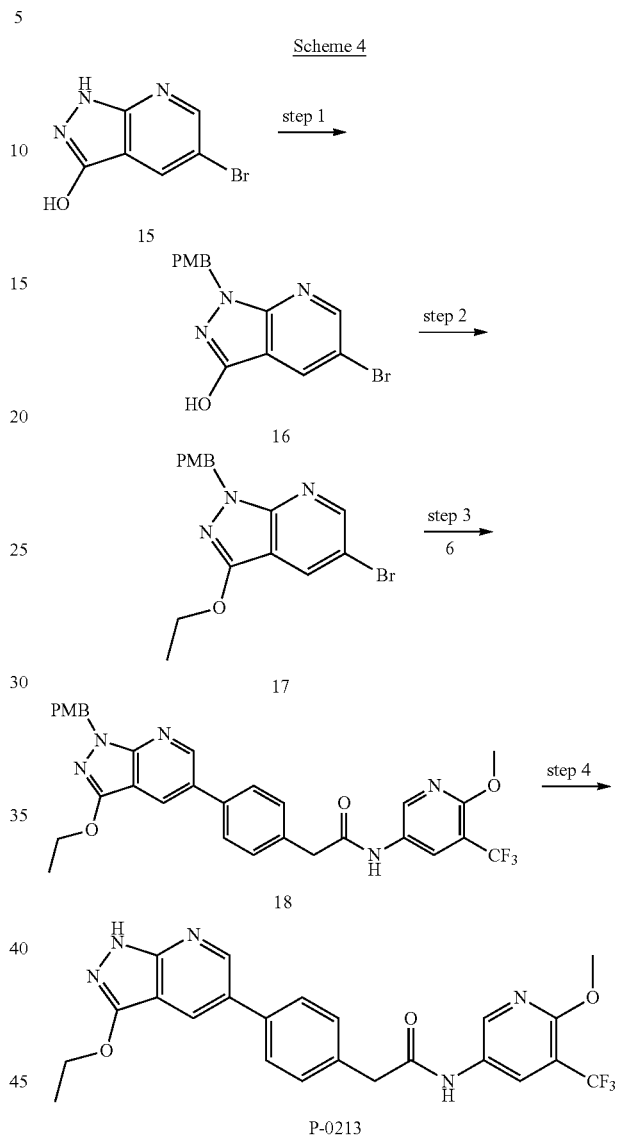

Step 1—Preparation of 5-bromo-1-(4-methoxybenzyl)-1H-pyrazolo[3,4-b]pyridin-3-ol, 16: To the mixture of 5-bromo-1H-pyrazolo[3,4-b]pyridin-3-ol (15, 4.28 g, 20.0 mmol) and 1-(chloromethyl)-4-methoxy-benzene (3.45 g, 22.0 mmol) in DMSO (100 ml) was added sodium hydroxide (1.20 g, 30 mmol). The mixture was allowed to stir at room temperature for one hour. The reaction mixture was partitioned between ethyl acetate and water. The ethyl acetate layer was collected and washed with water, brine and then dried over anhydrous magnesium sulfate. The drying agent was removed by filtration and concentrated down under reduced pressure. The residue was triturated with ethyl acetate to provide 3.66 g (55% yield) of compound 16 that was used in the next step without further purification. MS ESI [M+H$^+$]$^+$=334.05.

Step 2—Preparation of 5-bromo-3-ethoxy-1-(4-methoxybenzyl)-1H-pyrazolo[3,4-b]pyridine, 17: To a mixture of 5-bromo-1-[(4-methoxyphenyl)methyl]pyrazolo[3,4-b]pyridin-3-ol (16, 1.27 g, 3.80 mmol) in N,N-dimethylformamide (40 ml) was added slowly 60% sodium hydride in mineral oil (182 mg, 4.55 mmol). After stirring for 15 minutes, iodoethane (0.59 g, 3.8 mmol) was added. The mixture was allowed to stir at room temperature for one hour. The reaction mixture was partitioned between ethyl acetate and water. The ethyl acetate layer was collected and washed with water, brine and then dried over anhydrous magnesium sulfate. The drying agent was removed by filtration and concentrated down under reduced pressure. The sample was purified by silica gel flash column chromatography eluting with 20% ethyl acetate in hexane to provide 1.06 g (77% yield) of compound 17. MS ESI [M+H$^+$]$^+$=364.10.

Step 3—Preparation of 2-(4-(3-ethoxy-1-(4-methoxybenzyl)-1H-pyrazolo[3,4-b]pyridin-5-yl)phenyl)-N-(6-methoxy-5-(trifluoromethyl)pyridin-3-yl)acetamide, 18: To a mixture of 5-bromo-3-ethoxy-1-[(4-methoxyphenyl) methyl]pyrazolo[3,4-b]pyridine (17, 163 mg, 0.450 mmol), N-[6-methoxy-5-(trifluoromethyl)-3-pyridyl]-2-[4-(4,4,5,5-tetramethyl-1,3,2-dioxaborolan-2-yl)phenyl]acetamide (6, 236 mg, 0.541 mmol) and [1,1'-bis(diphenylphosphino)ferrocene] dichloropalladium(II) dichloromethane complex (33 mg, 0.040 mmol) in dioxane (5 ml) that was purged with nitrogen gas, was added 2.5 M aqueous potassium carbonate (0.540 ml). The mixture was allowed to stir at 100° C. for 2 hours. The reaction was diluted with ethyl acetate and was dried over anhydrous magnesium sulfate. The drying agent was removed by filtration and concentrated down under reduced pressure. The crude sample was purified by silica gel flash column chromatography eluting with 50% ethyl acetate in hexane to provide 257 mg (97% yield) of compound 18. MS ESI [M+H$^+$]$^+$=592.4.

Step 4—Preparation of 2-(4-(3-ethoxy-1H-pyrazolo[3,4-b]pyridin-5-yl)phenyl)-N-(6-methoxy-5-(trifluoromethyl) pyridin-3-yl)acetamide, P-0213: A mixture of 2-[4-[3-ethoxy-1-[(4-methoxyphenyl)methyl]pyrazolo[3,4-b] pyridin-5-yl] phenyl]-N-[6-methoxy-5-(trifluoromethyl)-3-pyridyl]acetamide (18, 257 mg, 0.434 mmol) in trifluoroacetic acid (5 ml) was allowed to stir at 100° C. for 5 hours. The reaction mixture was concentrated down under reduced pressure. The crude sample was purified by silica gel flash column chromatography eluting with 60% ethyl acetate in dichloromethane, followed by triturating with acetonitrile to provide compound P-0213. MS ESI [M+H$^+$]$^+$=472.30.

Example 5

Compound P-0214 is prepared in 3 steps from 5-bromo-2-iodo-1-(phenylsulfonyl)-1H-pyrrolo[2,3-b] pyridine 19 and N-[6-methoxy-5-(trifluoromethyl)-3-pyridyl]-2-[4-(4,4, 5,5-tetramethyl-1,3,2-dioxaborolan-2-yl)phenyl]acetamide 6 as shown in Scheme 5.

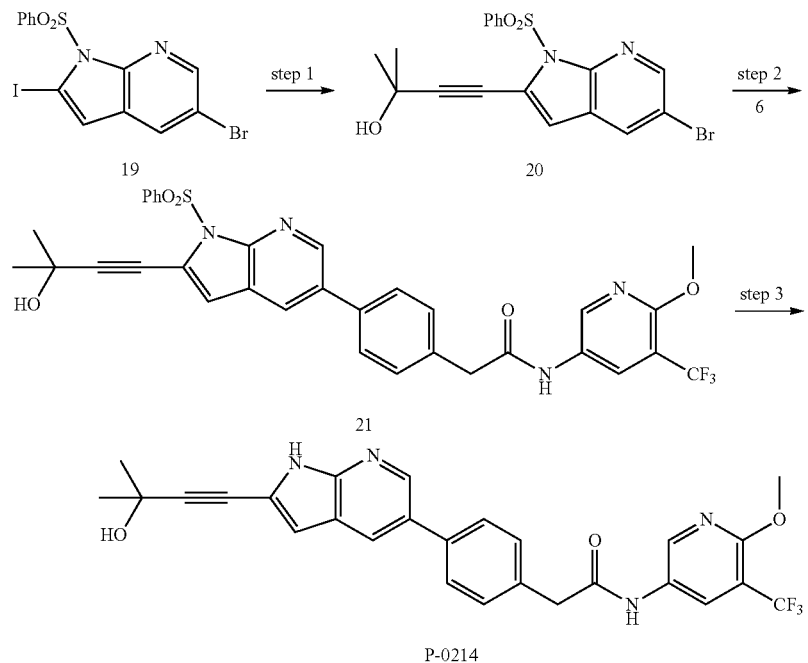

Step 1—Preparation of 4-(5-bromo-1-(phenylsulfonyl)-1H-pyrrolo[2,3-b]pyridin-2-yl)-2-methylbut-3-yn-2-ol, 20: A mixture of 1-(benzenesulfonyl)-5-bromo-2-iodo-pyrrolo [2,3-b]pyridine (19, 2.04 g, 4.41 mmol), 2-methylbut-3-yn-2-ol (389 mg, 4.62 mmol), bis(triphenylphosphine) palladium(II) dichloride (93 mg, 0.13 mmol) and copper(I) iodide (25 mg, 0.13 mmol) in triethylamine (20 ml) was purged with nitrogen gas, then allowed to stir at 100° C. for 2 hours. The reaction mixture was concentrated down under reduced pressure and purified by silica gel flash column chromatography eluting with 30% ethyl acetate in hexane to provide 994 mg (54% yield) of compound 20. MS ESI [M+H$^+$]$^+$=421.05.

Step 2—Preparation of 2-(4-(2-(3-hydroxy-3-methylbut-1-yn-1-yl)-1-(phenylsulfonyl)-1H-pyrrolo[2,3-b]pyridin-5-yl)phenyl)-N-(6-methoxy-5-(trifluoromethyl)pyridin-3-yl) acetamide, 21: A mixture of 4-[1-(benzenesulfonyl)-5-bromo-pyrrolo[2,3-b]pyridin-2-yl]-2-methyl-but-3-yn-2-ol (20, 189 mg, 0.451 mmol), N-[6-methoxy-5-(trifluoromethyl)-3-pyridyl]-2-[4-(4,4,5,5-tetramethyl-1,3,2-dioxa-borolan-2-yl)phenyl]acetamide (6, 236 mg, 0.541 mmol), and [1,1'-bis(diphenylphosphino)ferrocene] dichloropalladium(II) dichloromethane complex (33 mg, 0.040 mmol) in acetonitrile (5 ml) was purged with nitrogen gas, followed by the addition of 2.5 M aqueous potassium carbonate (0.54 ml). The mixture was allowed to stir at 90° C. for 3 hours. The sample was diluted with ethyl acetate and was dried over anhydrous magnesium sulfate, filtered and concentrated down under reduced pressure. The crude sample was purified by silica gel flash column chromatography eluting with 80% ethyl acetate to provide 198 mg (68% yield) of compound 21. MS ESI [M+H$^+$]$^+$=649.30.

Step 3—Preparation of 2-(4-(2-(3-hydroxy-3-methylbut-1-yn-1-yl)-1H-pyrrolo[2,3-b]pyridin-5-yl)phenyl)-N-(6-methoxy-5-(trifluoromethyl)pyridin-3-yl)acetamide, P-0214: To a mixture of 2-[4-[1-(benzenesulfonyl)-2-(3-hydroxy-3-methyl-but-1-ynyl)pyrrolo[2,3-b]pyridin-5-yl]phenyl]-N-[6-methoxy-5-(trifluoromethyl)-3-pyridyl]acetamide (21, 198 mg, 0.305 mmol) in tetrahydrofuran (4 ml) was added 1 M TBAF in tetrahydrofuran (1.0 ml). The mixture was allowed to stir at 50° C. for 2 hours or upon completion. The crude reaction was diluted with ethyl acetate which was washed with saturated aqueous sodium bicarbonate, water and then brine. The organic layer was dried over anhydrous magnesium sulfate, filtered and concentrated down under reduced pressure. The crude sample was purified by silica gel flash column chromatography eluting with 100% ethyl acetate, followed by triturating with acetonitrile to provide compound P-0214. MS ESI [M+H$^+$]$^+$=509.35.

Example 6

Compound P-0200 is prepared in 5 steps from 5-bromo-2-iodo-1-(phenylsulfonyl)-1H-pyrrolo[2,3-b]pyridine 19, 2-(4-bromo-3-fluorophenyl)acetic acid 22, 5-(trifluoromethyl)pyridin-3-amine 23 and (2-methoxypyridin-4-yl)boronic acid 25 as shown in Scheme 6.

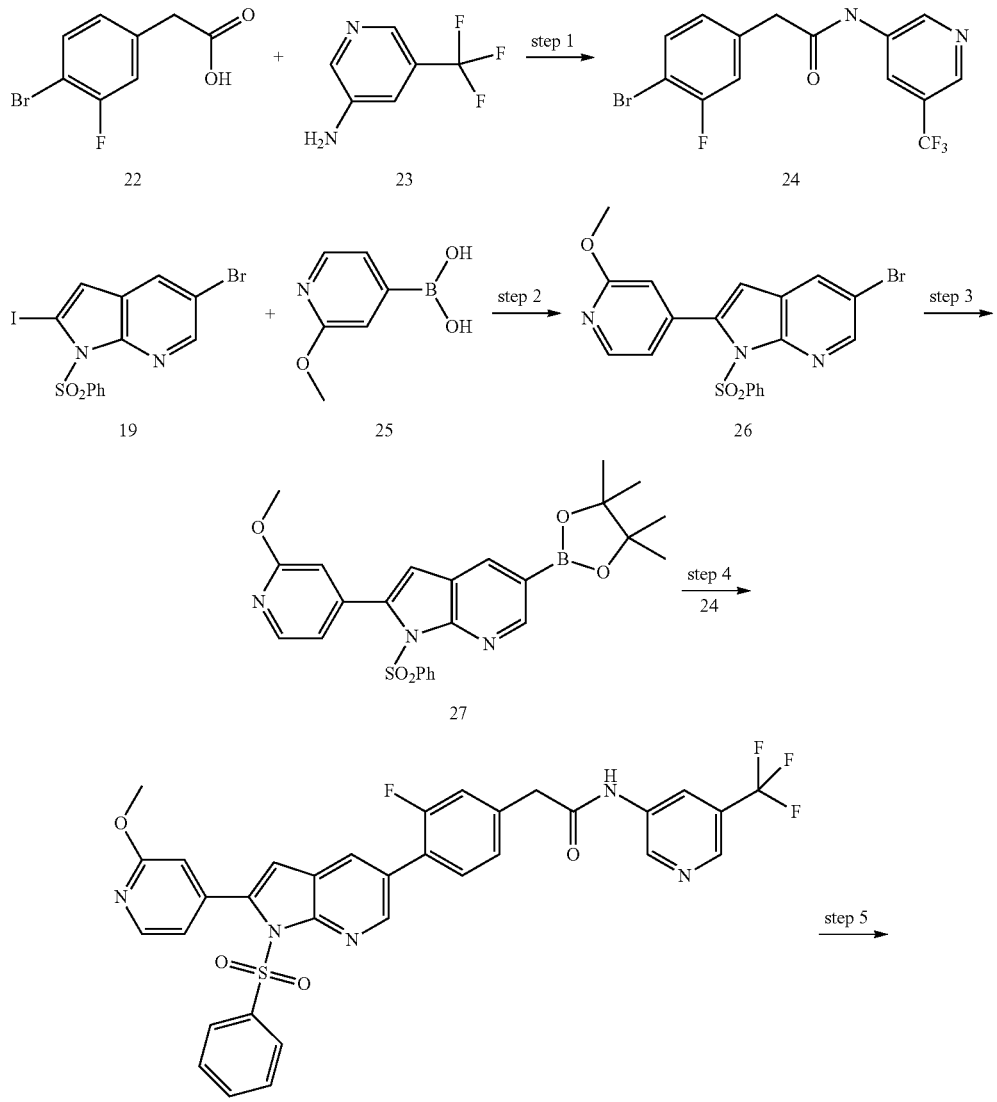

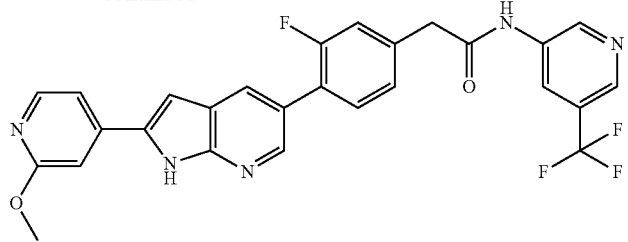

P-200

Step 1—Preparation of 2-(4-bromo-3-fluorophenyl)-N-(5-(trifluoromethyl)pyridin-3-yl)acetamide, 24: To a mixture of 2-(4-bromo-3-fluoro-phenyl)acetic acid (22, 1.00 g, 4.29 mmol), 5-(trifluoromethyl)pyridin-3-amine (23, 697 mg, 4.30 mmol) and pyridine (1.0 ml) in ethyl acetate (40 ml) was added slowly propylphosphonic anhydride (50 wt % solution in ethyl acetate, 5.1 ml, 8.6 mmol). The reaction mixture was allowed to stir at room temperature for 15 hours. The mixture was diluted with ethyl acetate and was washed with saturated aqueous ammonium chloride, water and brine. The organic layer was dried over anhydrous sodium sulfate, filtered and concentrated under reduced pressure to provide 1.50 g (93% yield) of compound 24 that was used in the next step without further purification.

Step 2—Preparation of 5-bromo-2-(2-methoxypyridin-4-yl)-1-(phenylsulfonyl)-1H-pyrrolo[2,3-b]pyridine, 26: A mixture of 1-(benzenesulfonyl)-5-bromo-2-iodo-pyrrolo[2,3-b]pyridine (19, 2.01 g, 4.34 mmol), (2-methoxy-4-pyridyl)boronic acid (25, 665 mg, 4.35 mmol) and [1,1'-bis(diphenylphosphino)ferrocene] dichloropalladium(II) dichloromethane complex (318 mg, 0.389 mmol) in acetonitrile (45 ml) was purged with nitrogen gas followed by the addition of 2.5 M aqueous potassium carbonate (5.2 ml).The mixture was allowed to stir at 70° C. for 2 hours. The reaction was diluted with ethyl acetate and was washed with water and brine. The organic layer was dried over anhydrous sodium sulfate, filtered and concentrated under reduced pressure. The sample was purified by silica gel flash column chromatography eluting with 30% ethyl acetate in hexane to provide 1.37 g (71% yield) of compound 26.

Step 3—Preparation of 2-(2-methoxypyridin-4-yl)-1-(phenylsulfonyl)-5-(4,4,5,5-tetramethyl-1,3,2-dioxaborolan-2-yl)-1H-pyrrolo[2,3-b]pyridine 27: A mixture of 1-(benzenesulfonyl)-5-bromo-2-(2-methoxy-4-pyridyl)pyrrolo[2,3-b]pyridine (26, 1.02 g, 2.30 mmol), bis(pinacolato)diboron (876 mg, 3.45 mmol), [1,1'-bis(diphenylphosphino)ferrocene] dichloropalladium(II) dichloromethane complex (168 mg, 0.206 mmol), and potassium acetate (677 mg, 6.90 mmol) in dioxane (25 ml) was allowed to stir at 120° C. for 15 hours. The mixture was diluted with ethyl acetate and was filtered through a short bed of celite and concentrated down under reduced pressure. The sample was purified by silica gel flash column chromatography eluting with 30-50% ethyl acetate in hexane to provide 1.08 g (96% yield) of compound 27.

Step 4—Preparation of 2-(3-fluoro-4-(2-(2-methoxypyridin-4-yl)-1-(phenylsulfonyl)-1H-pyrrolo[2,3-b]pyridin-5-yl)phenyl)-N-(5-(trifluoromethyl)pyridin-3-yl)acetamide, 28: A mixture of 2-(4-bromo-3-fluoro-phenyl)-N-[5-(trifluoromethyl)-3-pyridyl]acetamide (24, 196 mg, 0.520 mmol), 1-(benzenesulfonyl)-2-(2-methoxy-4-pyridyl)-5-(4,4,5,5-tetramethyl-1,3,2-dioxaborolan-2-yl)pyrrolo[2,3-b]pyridine (27, 307 mg, 0.625 mmol) and [1,1'-bis(diphenylphosphino)ferrocene] dichloropalladium(II) dichloromethane complex (38 mg, 0.047 mmol) in acetonitrile (5 ml) was purged with nitrogen gas, followed by the addition of 2.5 M aqueous potassium carbonate (0.62 ml). The mixture was allowed to stir at 100° C. for 2 hours. The reaction was diluted with ethyl acetate and was dried over anhydrous sodium sulfate, filtered and concentrated down under reduced pressure. The product was purified by silica gel flash column chromatography eluting with 80% ethyl acetate in hexane to provide 208 mg (61% yield) of compound 28 as a brittle foam.

Step 5—Preparation of 2-(3-fluoro-4-(2-(2-methoxypyridin-4-yl)-1H-pyrrolo[2,3-b]pyridin-5-yl)phenyl)-N-(5-(trifluoromethyl)pyridin-3-yl)acetamide, P-0200: To a mixture of 2-[4-[1-(benzenesulfonyl)-2-(2-methoxy-4-pyridyl)pyrrolo[2,3-b]pyridin-5-yl]-3-fluoro-phenyl]-N-[5-(trifluoromethyl)-3-pyridyl]acetamide (28, 208 mg, 0.314 mmol) in tetrahydrofuran (3 ml) was added 1 M TBAF in tetrahydrofuran (0.950 ml). The mixture was allowed to stir at 50° C. for 2 hours. The crude reaction was diluted with ethyl acetate and was washed with water followed by brine. This solution was dried over anhydrous sodium sulfate, filtered and concentrated under reduced pressure. The product was purified by silica gel flash column chromatography eluting with 100% ethyl acetate, followed by triturating with acetonitrile to provide compound P-0200. MS ESI [M+H$^+$]$^+$=522.25.

Example 7

Compound P-0042 is prepared in 2 steps from 5-bromo-3-fluoro-1H-pyrrolo[2,3-b]pyridine 29, methyl 2-(2-fluoro-4-(4,4,5,5-tetramethyl-1,3,2-dioxaborolan-2-yl)phenyl)acetate 30, and 2-(5-aminopyridin-2-yl)-2-methylpropanenitrile 32 as shown in Scheme 7.

Scheme 7

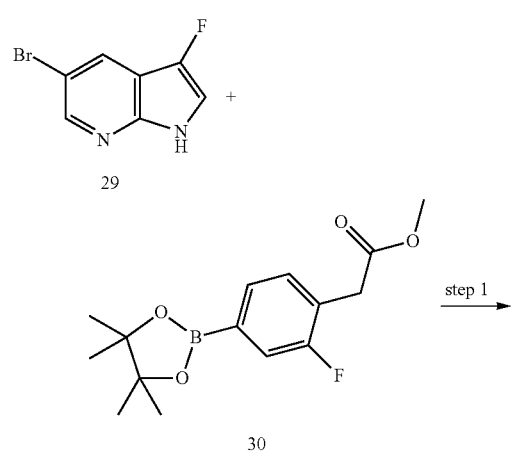

Example 8

Compound P-0040 is prepared in 2 steps from 2-chloro-5-iodo-1-(phenylsulfonyl)-1H-pyrrolo[2,3-b]pyridine 33, 2-(2-fluoro-4-(4,4,5,5-tetramethyl-1,3,2-dioxaborolan-2-yl)phenyl)acetic acid 34 and 4-(trifluoromethyl)pyridin-2-amine 35 as shown in Scheme 8.

Scheme 8

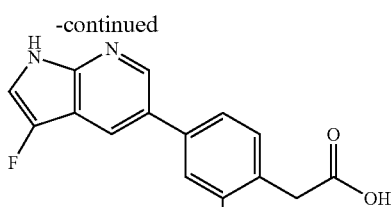

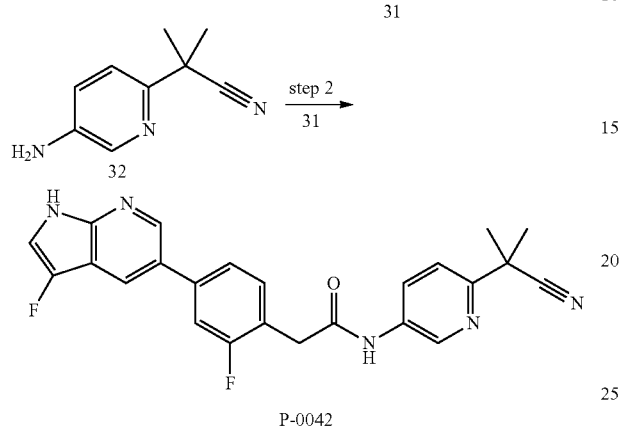

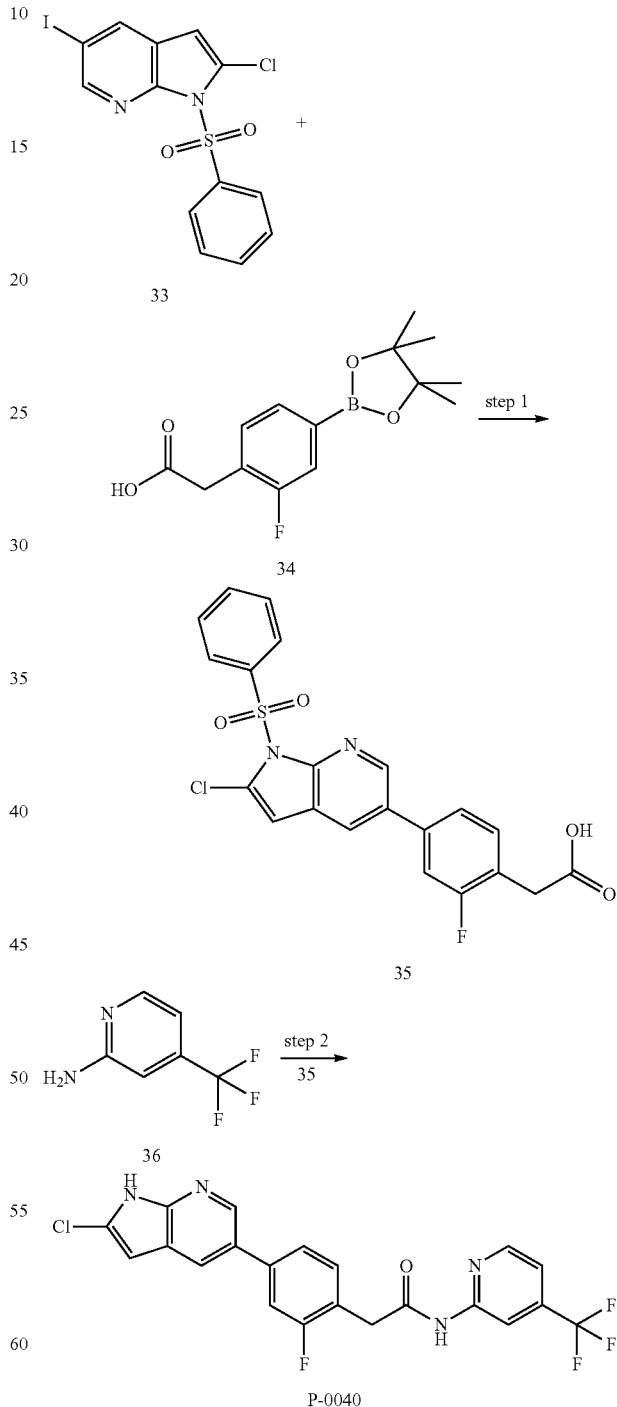

Step 1—Preparation of 2-(2-fluoro-4-(3-fluoro-1H-pyrrolo[2,3-b]pyridin-5-yl)phenyl)acetic acid, 31: A mixture of 5-bromo-3-fluoro-1H-pyrrolo[2,3-b]pyridine (29, 0.250 g, 1.16 mmol), methyl 2-[2-fluoro-4-(4,4,5,5-tetramethyl-1,3,2-dioxaborolan-2-yl)phenyl]acetate (30, 0.360 g, 1.22 mmol), 2.5 M aqueous potassium carbonate (1.4 ml) and [1,1'-bis(diphenylphosphino)ferrocene] dichloropalladium (II) dichloromethane complex (0.114 g, 0.14 mmol) in acetonitrile and DMF was flushed with nitrogen and allowed to stir at 85° C. for 3 hours. The reaction mixture was filtered through celite and then partitioned between saturated aqueous ammonium chloride and ethyl acetate. The organic layer was separated, washed with brine, dried over anhydrous magnesium sulfate and filtered. Then, this crude material was suspended in 1 M lithium hydroxide in THF (2.3 ml) at room temperature. After 20 min, the reaction was heated to 40° C. for 2 hours. The reaction mixture was partitioned between aqueous ammonium chloride and ethyl acetate and the organic layer was separated and dried over anhydrous magnesium sulfate. This material was used in the next reaction without further purification.

Step 2—Preparation of N-(6-(2-cyanopropan-2-yl)pyridin-3-yl)-2-(2-fluoro-4-(3-fluoro-1H-pyrrolo[2,3-b]pyridin-5-yl)phenyl)acetamide, P-0042: To a mixture of 2-[2-fluoro-4-(3-fluoro-1H-pyrrolo[2,3-b]pyridin-5-yl)phenyl]acetic acid (31, 90 mg, 0.31 mmol), 2-(5-amino-2-pyridyl)-2-methyl-propanenitrile (32, 58 mg, 0.36 mmol), and pyridine (0.09 ml) in ethyl acetate (3.7 ml) was added propylphosphonic anhydride (50 wt % solution in ethyl acetate, 0.28 mL, 0.47 mmol). The reaction was allowed to stir at ambient temperature for 18 hours. The reaction mixture was then partitioned between ethyl acetate and aqueous ammonium chloride. The organic layer was separated, washed with brine, dried over anhydrous magnesium sulfate, filtered, and concentrated. The material was purified by silica gel flash column chromatography eluting with 0-5% methanol in dichloromethane to provide compound P-0042. MS ESI [M+H$^+$]$^+$=432.25.

Step 1—Preparation of 2-(4-(2-chloro-1-(phenylsulfonyl)-1H-pyrrolo[2,3-b]pyridin-5-yl)-2-fluorophenyl)acetic acid, 35: To 2-(2-fluoro-4-(4,4,5,5-tetramethyl-1,3,2-dioxaborolan-2-yl)phenyl)acetic acid (34, 112 mg, 0.400 mmol)

in acetonitrile (10 ml) was added 1-(benzenesulfonyl)-2-chloro-5-iodo-pyrrolo[2,3-b]pyridine (33, 130 mg, 0.311 mmol), 1 M aqueous potassium carbonate (5 ml) and [1,1'-bis(diphenylphosphino)ferrocene] dichloropalladium(II) dichloromethane complex (90 mg, 0.11 mmol). The reaction mixture was allowed to stir at ambient temperature for 2 hours. The reaction mixture was poured into water and extracted with ethyl acetate. The organic layer was washed with water and brine and then dried over anhydrous magnesium sulfate, filtered and concentrated under reduced pressure. The volatiles were removed under reduced pressure. The crude material was purified by silica gel flash column chromatography eluting with 0-80% ethyl acetate in hexane to provide 42 mg of compound 35. MS ESI [M+H+]+=589.2.

Step 2—Preparation of 2-(4-(2-chloro-1H-pyrrolo[2,3-b]pyridin-5-yl)-2-fluorophenyl)-N-(4-(trifluoromethyl)pyridin-2-yl)acetamide, P-0040: To a mixture of 2-[4-[1-(benzenesulfonyl)-2-chloro-pyrrolo[2,3-b]pyridin-5-yl]-2-fluoro-phenyl]acetic acid (35, 80 mg, 0.18 mmol) in THF (10 ml) were added 4-(trifluoromethyl)pyridin-2-amine (36, 42 mg, 0.26 mmol), triethylamine (1 ml) and propylphosphonic anhydride (50 wt % solution in ethyl acetate, 0.5 ml, 0.8 mmol). The mixture was allowed to stir at ambient temperature for 24 hours. The reaction mixture was diluted with water and extracted with ethyl acetate. The organic layer was washed with water and brine, and then dried over anhydrous magnesium sulfate. The drying agent was removed by filtration and the filtrate was concentrated under reduced pressure. The residue was treated with 1M aqueous potassium hydroxide (10 ml) and was allowed to stir at ambient temperature for 2 hours. The reaction mixture was acidified with 1 N aqueous HCl and extracted with ethyl acetate. The organic layer was washed with water and brine, and then dried over anhydrous magnesium sulfate. The drying agent was removed by filtration and the filtrate was concentrated under reduced pressure. The crude material was purified by silica gel flash column chromatography eluting with 0-100% ethyl acetate in hexane. This provided compound P-0040. MS ESI [M+H+]+=449.2.

Example 9

Compound P-0031 is prepared in 2 steps from 2-(2-fluoro-4-(4,4,5,5-tetramethyl-1,3,2-dioxaborolan-2-yl)phenyl)acetic acid 34, 2-(trifluoromethyl)pyridin-4-amine 37, and 1-(5-bromo-1H-pyrrolo[2,3-b]pyridin-3-yl)ethan-1-one 39 as shown in Scheme 9.

Scheme 9

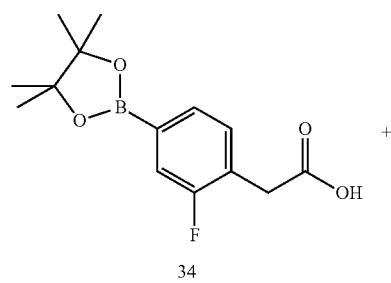

34

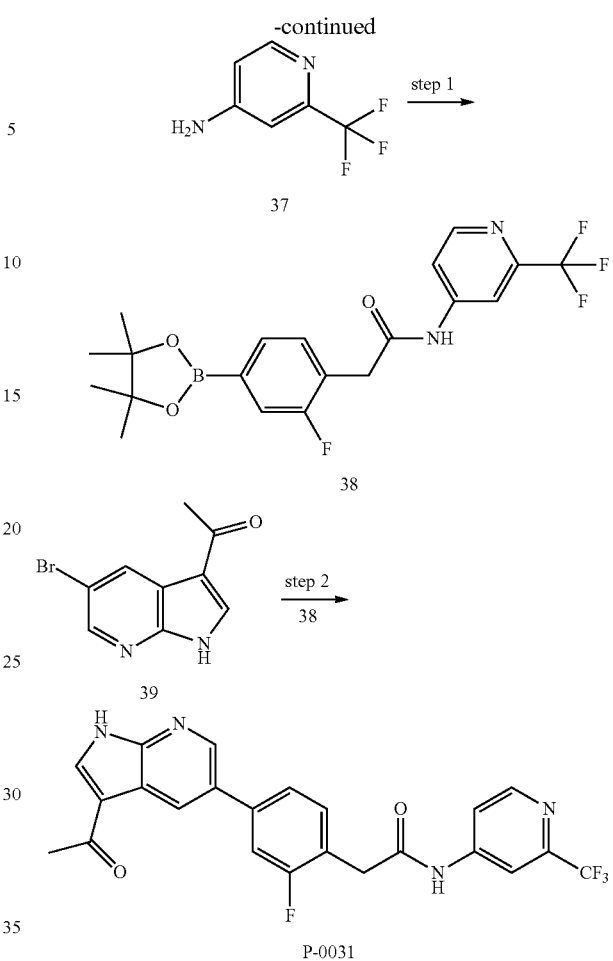

Step 1—Preparation of 2-(2-fluoro-4-(4,4,5,5-tetramethyl-1,3,2-dioxaborolan-2-yl)phenyl)-N-(2-(trifluoromethyl)pyridin-4-yl)acetamide, 38: A mixture of 2-[2-fluoro-4-(4,4,5,5-tetramethyl-1,3,2-dioxaborolan-2-yl)phenyl]acetic acid (34, 0.85 g, 3.0 mmol), 2-(trifluoromethyl)pyridin-4-amine (37, 0.504 g, 3.11 mmol) and pyridine (0.74 ml) in ethyl acetate (30 ml) was allowed to stir at ambient temperature for 2 minutes followed by addition of propylphosphonic anhydride (50 wt % solution in ethyl acetate, 2.7 ml, 4.5 mmol). The reaction was allowed to stir at ambient temperature for 18 hours. The reaction mixture was then partitioned between ethyl acetate and aqueous ammonium chloride. The organic layer was separated, washed with brine and dried over anhydrous magnesium sulfate. The drying agent was removed by filtration and the filtrate was concentrated under reduced pressure. This provided compound 37 which was used in the next reaction without further purification.

Step 2—Preparation of 2-(4-(3-acetyl-1H-pyrrolo[2,3-b]pyridin-5-yl)-2-fluorophenyl)-N-(2-(trifluoromethyl)pyridin-4-yl)acetamide, P-0031: A mixture of 1-(5-bromo-1H-pyrrolo[2,3-b]pyridin-3-yl)ethanone (39, 0.10 g, 0.42 mmol), 2-[2-fluoro-4-(4,4,5,5-tetramethyl-1,3,2-dioxaborolan-2-yl)phenyl]-N-[2-(trifluoromethyl)-4-pyridyl]acetamide (38, 0.19 g, 0.45 mmol), 2.5 M aqueous potassium carbonate (0.5 ml) and [1,1'-bis(diphenylphosphino)ferrocene] dichloropalladium(II) dichloromethane complex (0.04 g, 0.05 mmol) in acetonitrile/DMF was flushed with argon and allowed to stir at 105° C. for 12 hours. The reaction mixture was filtered through celite and then concentrated under reduced pressure. The crude material was dissolved in ethyl acetate and washed with aqueous ammonium chloride followed by brine. The organic layer was dried over anhydrous magnesium sulfate, filtered and concentrated under reduced pressure. The crude material was suspended in diethyl ether, sonicated, and heated. The liquid was removed and a brown solid remained. This material was purified by silica gel flash column chromatography eluting with 0-10% methanol in dichloromethane to provide compound P-0031. MS ESI [M+H$^+$]$^+$=457.25.

Example 10

Compound P-0065 is prepared in 3 steps from 2-(2-fluoro-4-(4,4,5,5-tetramethyl-1,3,2-dioxaborolan-2-yl)phenyl)acetic acid 34, 6-methyl-5-(trifluoromethyl)pyridin-3-amine 40, 5-bromo-2-fluoropyrimidine 1 and pyrazolo[1,5-a]pyridin-3-amine 42 as shown in Scheme 10.

Scheme 10

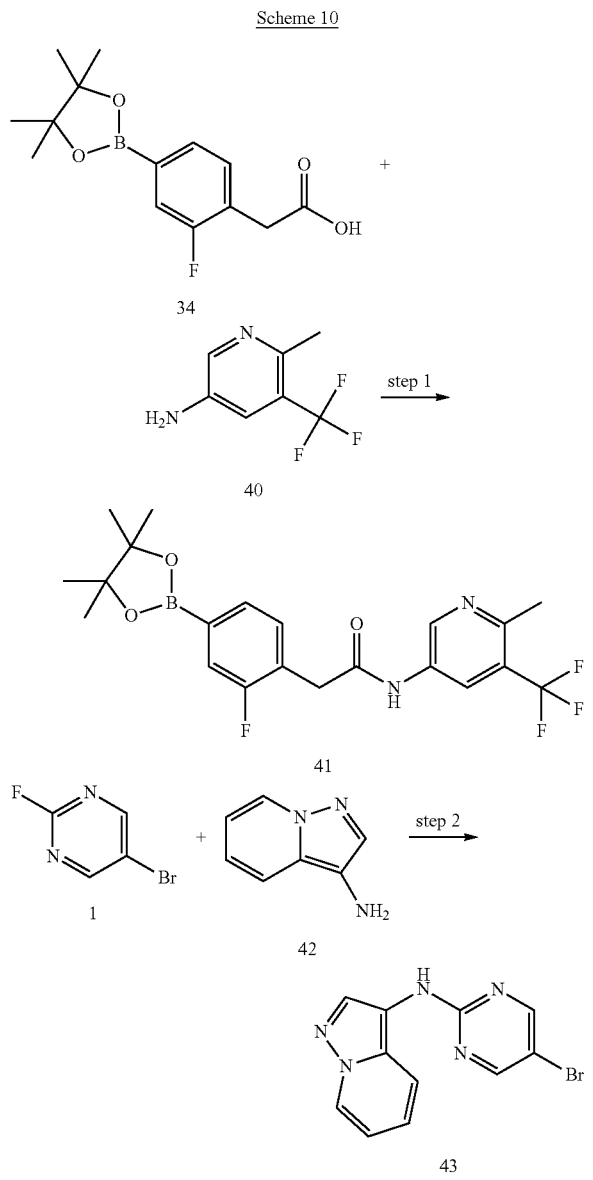

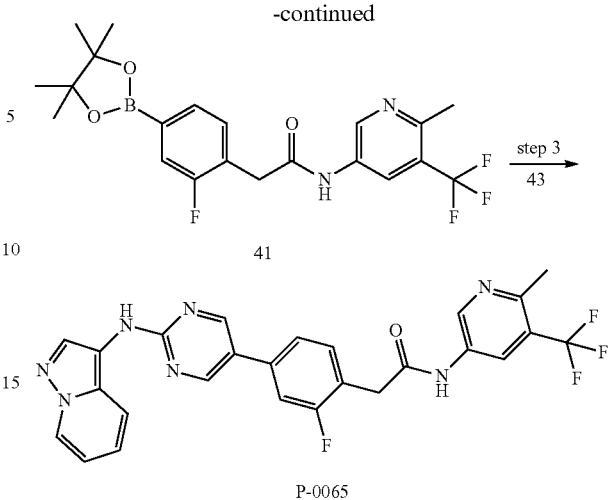

P-0065

Step 1—Preparation of 2-(2-fluoro-4-(4,4,5,5-tetramethyl-1,3,2-dioxaborolan-2-yl)phenyl)-N-(6-methyl-5-(trifluoromethyl)pyridin-3-yl)acetamide, 41: To a mixture of 2-[2-fluoro-4-(4,4,5,5-tetramethyl-1,3,2-dioxaborolan-2-yl)phenyl]acetic acid (34, 1.60 g, 5.71 mmol), 6-methyl-5-(trifluoromethyl)pyridin-3-amine (40, 1.00 g, 5.68 mmol) and pyridine (1.38 ml) in ethyl acetate (60 ml) was added propylphosphonic anhydride (50 wt % solution in ethyl acetate, 6.70 ml, 11.3 mmol). The reaction mixture was allowed to stir at ambient temperature for 3 hours. The mixture was diluted with ethyl acetate and was washed with saturated aqueous ammonium chloride, water and brine. The organic layer was dried over anhydrous magnesium sulfate, filtered and concentrated under reduced pressure to provide 2.50 g (99% yield) of compound 41 which was used in next step without further purification.

Step 2—Preparation of N-(5-bromopyrimidin-2-yl)pyrazolo[1,5-a]pyridin-3-amine, 43: To 5-bromo-2-fluoro-pyrimidine (1, 0.600 g, 3.39 mmol) in NMP (10 ml) was added pyrazolo[1,5-a]pyridin-3-amine dihydrochloride (42, 0.301 g, 1.46 mmol) and triethylamine (1 mL). The reaction mixture was allowed to stir at 180° C. for 30 minutes. The reaction mixture was diluted with water and saturated aqueous sodium bicarbonate and extracted with ethyl acetate. The organic layer was washed with water and brine, and then dried over anhydrous magnesium sulfate, filtered and concentrated under reduced pressure. This provided 0.4 g (94% yield) of compound 43 as brownish viscous liquid that solidified after several days. MS ESI [M+H$^+$]$^+$=292.00.

Step 3—Preparation of 2-(2-fluoro-4-(2-(pyrazolo[1,5-a]pyridin-3-ylamino)pyrimidin-5-yl)phenyl)-N-(6-methyl-5-(trifluoromethyl)pyridin-3-yl)acetamide, P-0065: To a mixture of N-(5-bromopyrimidin-2-yl)pyrazolo[1,5-a]pyridin-3-amine (43, 78 mg, 0.27 mmol), 2-[2-fluoro-4-(4,4,5,5-tetramethyl-1,3,2-dioxaborolan-2-yl)phenyl]-N-[6-methyl-5-(trifluoromethyl)-3-pyridyl]acetamide (41, 100 mg, 0.23 mmol) and [1,1'-bis(diphenylphosphino)ferrocene] dichloropalladium(II) dichloromethane complex (22 mg, 0.027 mmol) in dimethylformamide (1 ml) was added 1 M aqueous potassium carbonate (1 ml) and then acetonitrile (2 mL). The mixture was purged with nitrogen and was allowed to stir at 120° C. for 30 minutes. The reaction mixture was poured into water and extracted with ethyl acetate. The organic layer was separated, washed with brine, and dried over anhydrous sodium sulfate. After removal of the drying agent and solvent, the residue was purified with silica gel flash column chromatography, followed by preparative RP-HPLC to provide compound P-0065. MS ESI [M+H⁺]⁺=522.05.

Example 11

Compound P-0079 is prepared in 1 step from 2-bromo-7-chloro-5H-pyrrolo[2,3-b]pyrazine 44 and N-(6-methyl-5-(trifluoromethyl)pyridin-3-yl)-2-(4-(4,4,5,5-tetramethyl-1,3,2-dioxaborolan-2-yl)phenyl)acetamide 45 (prepared in a manner analogous to compound 6 in example 1) as shown in Scheme 11.

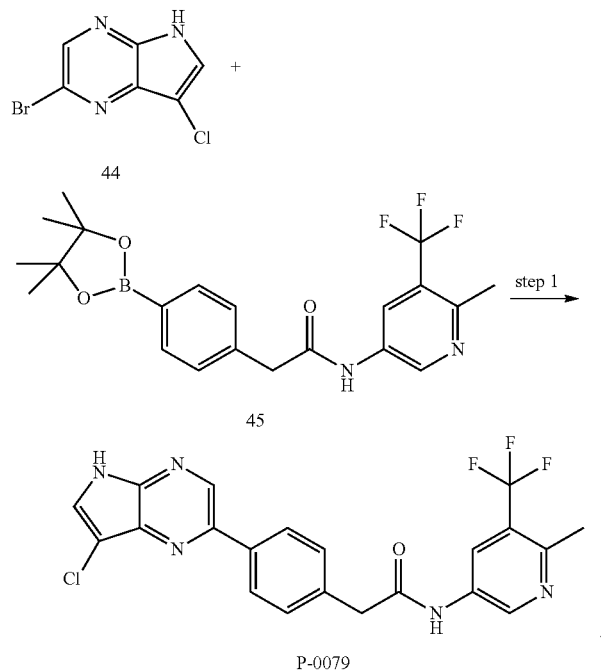

Step 1—Preparation of 2-(4-(7-chloro-5H-pyrrolo[2,3-b]pyrazin-2-yl)phenyl)-N-(6-methyl-5-(trifluoromethyl)pyridin-3-yl)acetamide, P-0079: To N-[6-methyl-5-(trifluoromethyl)-3-pyridyl]-2-[4-(4,4,5,5-tetramethyl-1,3,2-dioxaborolan-2-yl)phenyl]acetamide (45, 0.12 g, 0.29 mmol) in acetonitrile (4 ml) was added 2-bromo-7-chloro-5H-pyrrolo[2,3-b]pyrazine (44, 0.079 g, 0.34 mmol), 1M aqueous potassium carbonate (2 ml) and [1,1'-bis(diphenylphosphino)ferrocene] dichloropalladium(II) dichloromethane complex (0.073 g, 0.090 mmol). The reaction mixture was allowed to stir at 110° C. for 2 hours. The reaction mixture was poured into water and extracted with ethyl acetate. The organic layer was washed with water and brine, and then the organic layer was dried over anhydrous magnesium sulfate, filtered and concentrated under reduced pressure. The crude material was purified by silica gel flash column chromatography eluting with 0-85% ethyl acetate in dichloromethane. This provided compound P-0079. MS ESI [M+H⁺]⁺=446.2.

Example 12

Compound P-0064 is prepared in 2 steps from 2-(2-fluoro-4-(4,4,5,5-tetramethyl-1,3,2-dioxaborolan-2-yl)phenyl)acetic acid 34, 5-(trifluoromethyl)pyridin-3-amine 10, and 5'-bromospiro[cyclopropane-1,3'-pyrrolo[2,3-b]pyridin]-2'(1'H)-one 47 as shown in Scheme 12.

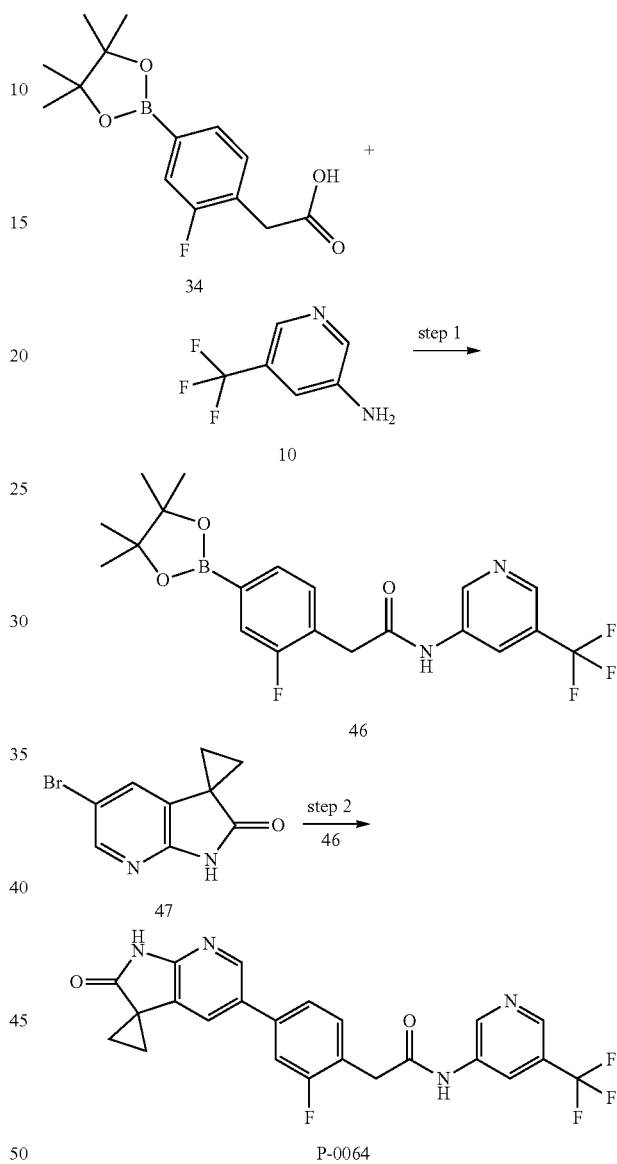

Step 1—Preparation of 2-(2-fluoro-4-(4,4,5,5-tetramethyl-1,3,2-dioxaborolan-2-yl)phenyl)-N-(5-(trifluoromethyl)pyridin-3-yl)acetamide, 46: To a mixture of 2-[2-fluoro-4-(4,4,5,5-tetramethyl-1,3,2-dioxaborolan-2-yl)phenyl]acetic acid (34, 0.899 g, 3.21 mmol) in ethyl acetate (20 ml) was added 5-(trifluoromethyl)pyridin-3-amine (10, 0.520 g, 3.21 mmol), triethylamine (1.0 ml) and propylphosphonic anhydride (50 wt % solution in ethyl acetate, 2.51 ml, 4.22 mmol). The mixture was allowed to stir at room temperature for 2 hours. The reaction mixture was diluted with water and extracted with ethyl acetate. The organic layer was washed with water and brine, and then dried over anhydrous magnesium sulfate, filtered and concentrated under reduced pressure. The residue was suspended in a mixture of ethyl acetate and hexane. The solid precipitate was collected by filtration and washed with hexane. After drying, this provided 1.03 g of compound 46. MS ESI [M+H⁺]⁺=425.2.

Step 2—Preparation of 2-(2-fluoro-4-(2'-oxo-1',2'-dihydrospiro[cyclopropane-1,3'-pyrrolo[2,3-b]pyridin]-5'-yl)phenyl)-N-(5-(trifluoromethyl)pyridin-3-yl)acetamide, P-0064: To a mixture of 5-bromospiro[1H-pyrrolo[2,3-b]pyridine-3,1'-cyclopropane]-2-one (47, 66 mg, 0.28 mmol), 2-[2-fluoro-4-(4,4,5,5-tetramethyl-1,3,2-dioxaborolan-2-yl)phenyl]-N-[5-(trifluoromethyl)-3-pyridyl]acetamide (46, 100 mg, 0.236 mmol) and [1,1'-bis(diphenylphosphino)ferrocene] dichloropalladium(II) dichloromethane complex (18 mg, 0.022 mmol) in dimethylformamide (1 ml) was added 1 M aqueous potassium carbonate (1 ml) and acetonitrile (2 mL). The mixture was purged with nitrogen and was then allowed to stir at 80° C. for 5 hours. The reaction mixture was poured into water and extracted with ethyl acetate. The organic layer was collected, washed with brine, and dried under anhydrous sodium sulfate. After removal of drying agent and solvent, the residue was purified by silica gel flash column chromatography, followed by preparative RP-HPLC, to provide compound P-0064. MS ESI [M+H⁺]⁺=457.20.

Example 13

Compound P-0066 is prepared in 1 step from 2-(2-fluoro-4-(4,4,5,5-tetramethyl-1,3,2-dioxaborolan-2-yl)phenyl)-N-(6-methyl-5-(trifluoromethyl)pyridin-3-yl)acetamide 41 and tert-butyl 5-bromo-3-cyclopropyl-1H-pyrazolo[3,4-b]pyridine-1-carboxylate 48 (prepared from 5-bromo-3-cyclopropyl-1H-pyrazolo[3,4-b]pyridine using a typical BOC protection procedure) as shown in Scheme 13.

Step 1—Preparation of 2-(4-(3-cyclopropyl-1H-pyrazolo[3,4-b]pyridin-5-yl)-2-fluorophenyl)-N-(6-methyl-5-(trifluoromethyl)pyridin-3-yl)acetamide, P-0066: To tert-butyl 5-bromo-3-cyclopropyl-pyrazolo[3,4-b]pyridine-1-carboxylate (48, 0.18 g, 0.53 mmol) in acetonitrile (8 ml) was added 2-[2-fluoro-4-(4,4,5,5-tetramethyl-1,3,2-dioxaborolan-2-yl)phenyl]-N-[6-methyl-5-(trifluoromethyl)-3-pyridyl]acetamide (41, 0.28 g, 0.64 mmol), 1M aqueous potassium carbonate (4 ml), and [1,1'-bis(diphenylphosphino)ferrocene] dichloropalladium(II) dichloromethane complex (0.10 g, 0.12 mmol). The reaction mixture was allowed to stir at 100° C. for 2 hours. The reaction mixture was poured into water and extracted with ethyl acetate. The organic layer was washed with water and brine. The organic layer was dried over anhydrous magnesium sulfate, filtered and concentrated under reduced pressure. The crude material was purified by silica gel flash column chromatography eluting with 0-80% ethyl acetate in dichloromethane. This provided compound P-0066. MS ESI [M+H⁺]⁺=470.25.

Example 14

Compound P-0080 is prepared in 1 step from 2-(2-fluoro-4-(4,4,5,5-tetramethyl-1,3,2-dioxaborolan-2-yl)phenyl)-N-(5-(trifluoromethyl)pyridin-3-yl)acetamide 46 and 5-bromo-2-cyclopropyl-1H-pyrrolo[2,3-b]pyridine 49 as shown in Scheme 14.

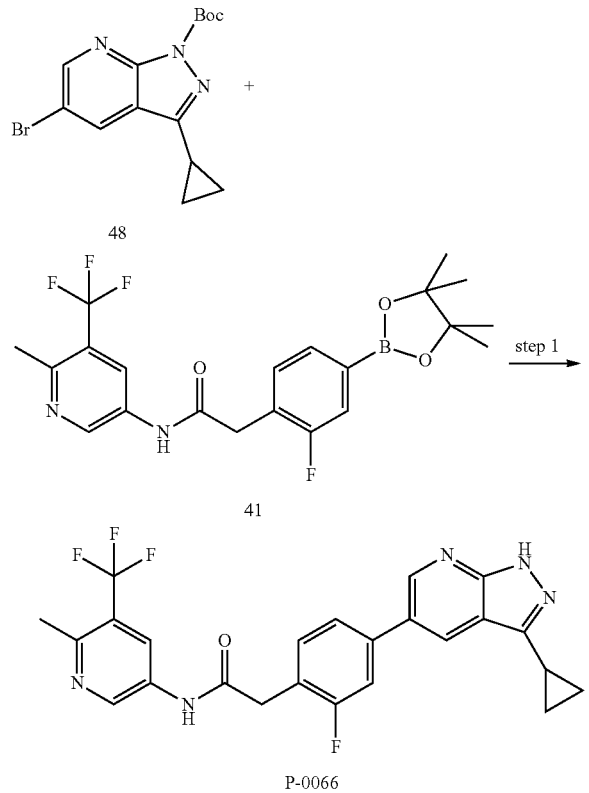

Scheme 13

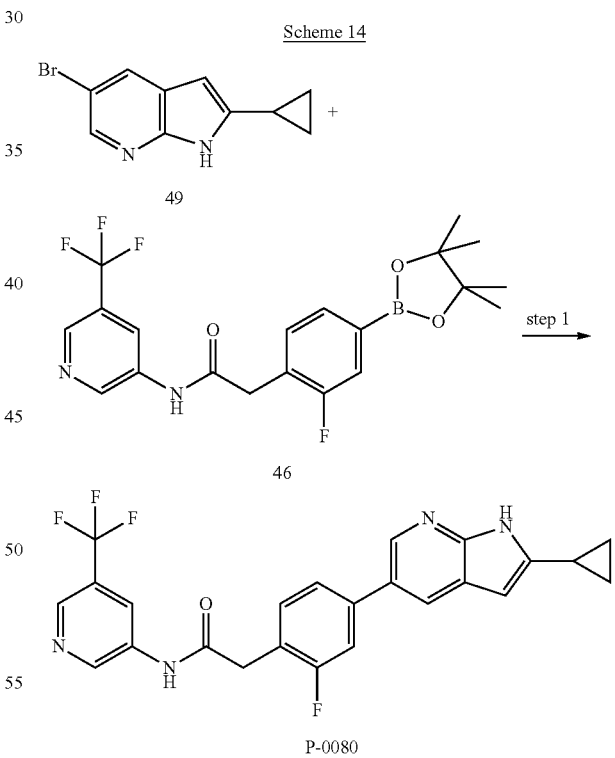

Scheme 14

Step 1—Preparation of 2-(4-(2-cyclopropyl-1H-pyrrolo[2,3-b]pyridin-5-yl)-2-fluorophenyl)-N-(5-(trifluoromethyl)pyridin-3-yl)acetamide, P-0080: To 2-[2-fluoro-4-(4,4,5,5-tetramethyl-1,3,2-dioxaborolan-2-yl)phenyl]-N-[5-(trifluoromethyl)-3-pyridyl]acetamide (46, 0.23 g, 0.54 mmol) in acetonitrile (8 ml) was added 5-bromo-2-cyclopropyl-1H-pyrrolo[2,3-b]pyridine (48, 0.11 g, 0.46 mmol), 1 M aqueous potassium carbonate (4 ml), and [1,1'-bis(diphenylphosphino)ferrocene] dichloropalladium(II) dichloromethane complex (0.10 g, 0.12 mmol). The reaction mixture was allowed to stir at 110° C. for 2 hours. The reaction mixture was poured into water and extracted with ethyl acetate. The organic layer was washed with water and brine. The organic layer was dried over anhydrous sodium sulfate, filtered and concentrated under reduced pressure. The crude material was purified by silica gel flash column chromatography eluting with 0-80% ethyl acetate in hexane followed by a second purification eluting with 0-10% metha nol in dichloromethane. This provided compound P-0080. MS ESI [M+H⁺]⁺=455.25.

Example 15

Compound P-0175 is prepared in 5 steps from 5-bromo-3-methyl-1H-pyrazolo[3,4-b]pyridine 50, 2-(4-bromo-2,5-difluorophenyl)acetic acid 9 and 6-methyl-5-(trifluoromethyl)pyridin-3-amine 40 as shown in Scheme 15.

Scheme 15

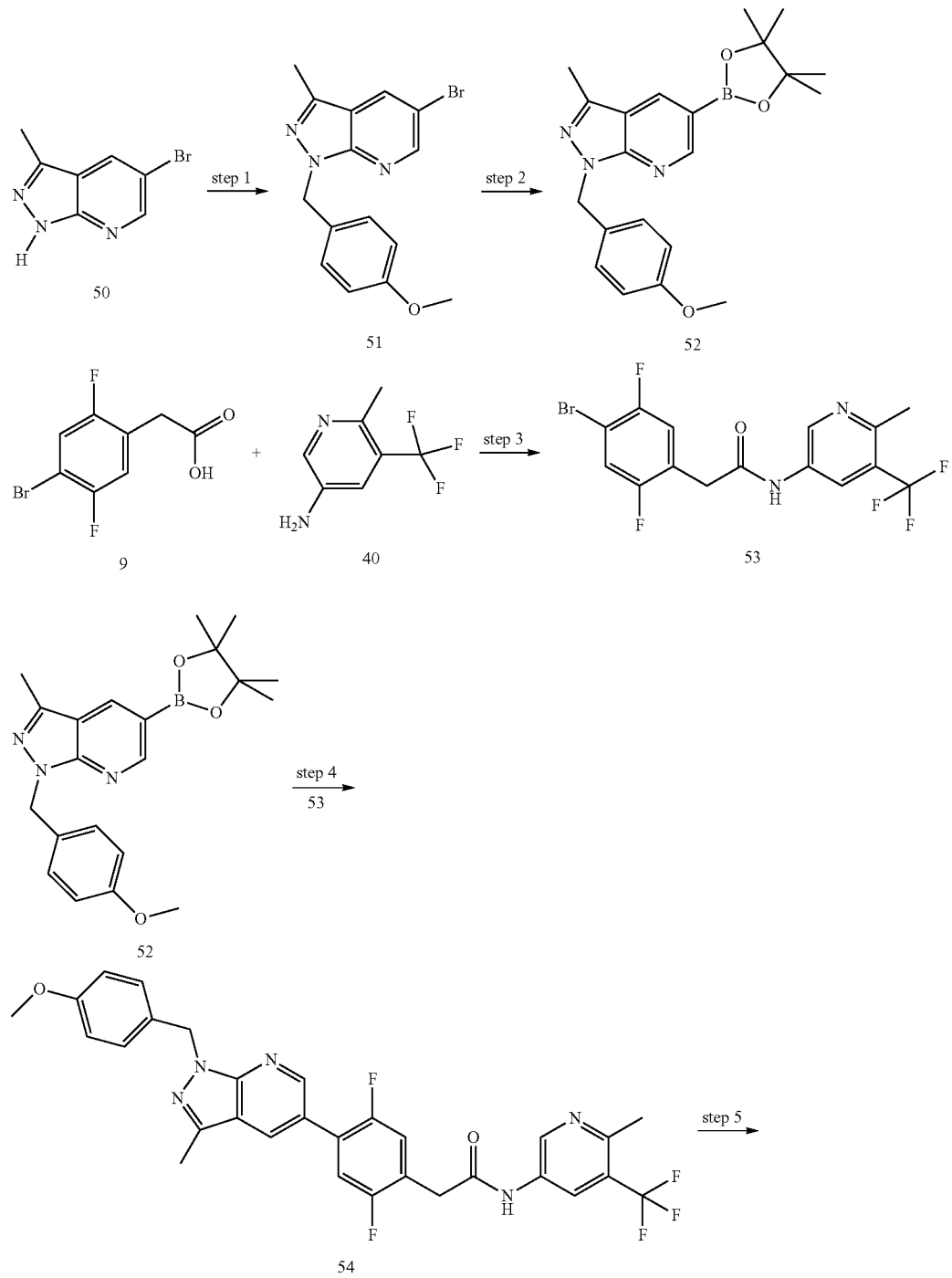

-continued

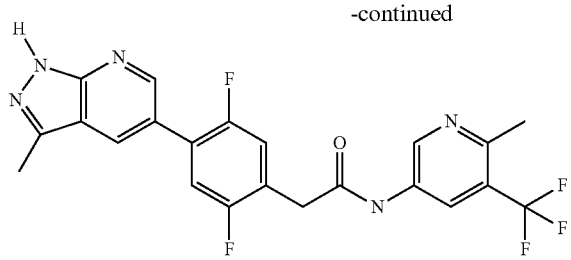

P-0175

Step 1—Preparation of 5-bromo-1-(4-methoxybenzyl)-3-methyl-1H-pyrazolo[3,4-b]pyridine, 51: To 5-bromo-3-methyl-1H-pyrazolo[3,4-b] pyridine (49, 0.500 g, 2.36 mmol) in DMSO (15 ml) was added NaOH (0.15 g, 3.8 mmol). After 10 minutes, 1-(chloromethyl)-4-methoxy-benzene (0.370 g, 2.36 mmol) was added. The reaction was allowed to stir at room temperature for 4 hours. The reaction was poured into water and extracted with ethyl acetate. The organic layer was washed with brine. The organic layer was dried over anhydrous sodium sulfate, filtered and concentrated under reduced pressure. The material was purified by silica gel flash column chromatography eluting with 10-50% ethyl acetate in hexane. This provided 430 mg of compound 51.

Step 2—Preparation of 1-(4-methoxybenzyl)-3-methyl-5-(4,4,5,5-tetramethyl-1,3,2-dioxaborolan-2-yl)-1H-pyrazolo[3,4-b]pyridine, 52: To 5-bromo-1-[(4-methoxyphenyl)methyl]-3-methyl-pyrazolo[3,4-b]pyridine (51, 0.41 g, 1.2 mmol) in 1,4-dioxane (4 ml) was added bis(pinacolato)diboron (0.47 g, 1.9 mmol), potassium acetate (0.36 g, 3.7 mmol) and [1,1'-bis(diphenylphosphino)ferrocene] dichloropalladium(II) dichloromethane complex (0.09 g, 0.11 mmol). The reaction mixture was allowed to stir at 110° C. for 2 hours. Upon completion, the reaction was diluted with ethyl acetate and filtered through a short bed of celite. The solvent was removed in the presence of silica. The resulting crude material was purified by silica gel flash column chromatography eluting with 10-50% ethyl acetate in hexane. This provided 350 mg (75% yield) of compound 52.

Step 3—Preparation of 2-(4-bromo-2,5-difluorophenyl)-N-(6-methyl-5-(trifluoromethyl)pyridin-3-yl)acetamide, 53: To 2-(4-bromo-2,5-difluoro-phenyl)acetic acid (9, 1.43 g, 5.70 mmol), 6-methyl-5-(trifluoromethyl)pyridin-3-amine (40, 1.00 g, 5.68 mmol) and pyridine (1.38 ml) in ethyl acetate (60 ml) was added slowly propylphosphonic anhydride (50 wt % solution in ethyl acetate, 6.70 ml, 11.4 mmol). The reaction mixture was allowed to stir at room temperature for 3 hours. The mixture was diluted with ethyl acetate and was washed with saturated aqueous ammonium chloride, water and brine. The organic layer was dried over anhydrous sodium sulfate, filtered and concentrated under reduced pressure. This provided 2.18 g (94% yield) of compound 53 that was used in the next step without further purification.

Step 4—Preparation of 2-(2,5-difluoro-4-(1-(4-methoxybenzyl)-3-methyl-1H-pyrazolo[3,4-b]pyridin-5-yl)phenyl)-N-(6-methyl-5-(trifluoromethyl)pyridin-3-yl)acetamide, 54: To 1-[(4-methoxyphenyl)methyl]-3-methyl-5-(4,4,5,5-tetramethyl-1,3,2-dioxaborolan-2-yl)pyrazolo[3,4-b]pyridine (52, 0.050 g, 0.13 mmol) in NMP (3 ml) was added 2-(4-bromo-2,5-difluoro-phenyl)-N-[6-methyl-5-(trifluoromethyl)-3-pyridyl]acetamide (53, 65 mg, 0.16 mmol) followed by 1 M aqueous potassium carbonate (550 µl). The reaction mixture was degassed and purged with nitrogen and [1,1'-bis(diphenylphosphino)ferrocene] dichloropalladium (II) dichloromethane complex (0.010 g, 0.012 mmol) was added. The reaction mixture was allowed to stir at 120° C. for 90 minutes. Upon completion, the reaction was filtered through a short bed of celite, poured into water and extracted with ethyl acetate. The organic phase was washed with brine, dried over anhydrous sodium sulfate, filtered and concentrated under reduced pressure. The resulting material was purified by silica gel flash column chromatography eluting with 0-20% methanol in dichloromethane. This provided 32 mg (42% yield) of compound 54.

Step 5—Preparation of 2-(2,5-difluoro-4-(3-methyl-1H-pyrazolo[3,4-b]pyridin-5-yl)phenyl)-N-(6-methyl-5-(trifluoromethyl)pyridin-3-yl)acetamide, P-0175: To 2-(2,5-difluoro-4-(1-(4-methoxybenzyl)-3-methyl-1H-pyrazolo[3,4-b]pyridin-5-yl)phenyl)-N-(6-methyl-5-(trifluoromethyl)pyridin-3-yl)acetamide (54, 30 mg, 0.052 mmol) was added TFA (2.3 ml) and the solution was allowed to stir at 80° C. for 3 hours. Upon completion, the reaction mixture was poured into water and extracted with ethyl acetate. The organic layer was washed with brine, dried over anhydrous sodium sulfate and filtered. The solvent was removed in the presence of silica and the resulting crude material was purified by silica gel flash column chromatography eluting with 0-15% methanol in dichloromethane. This provided compound P-0175. MS ESI $[M+H^+]^+$=462.25.

Example 16

Compound P-0216 was prepared in 3 steps from 5-bromo-1H-pyrazolo[3,4-b]pyridin-3-amine 55 and N-[6-methoxy-5-(trifluoromethyl)-3-pyridyl]-2-[4-(4,4,5,5-tetramethyl-1,3,2-dioxaborolan-2-yl)phenyl]acetamide 6 as shown in Scheme 16.

Scheme 16

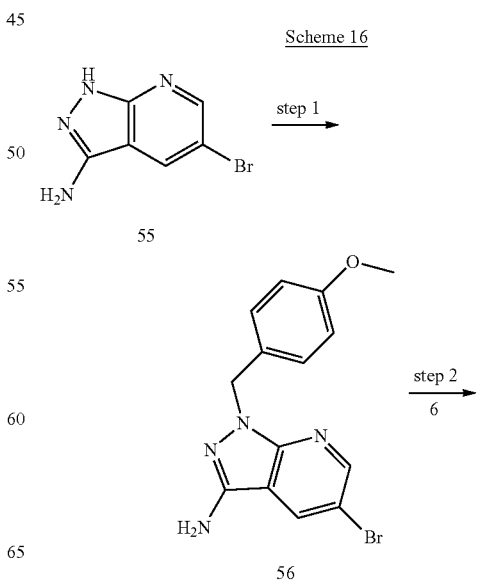

-continued

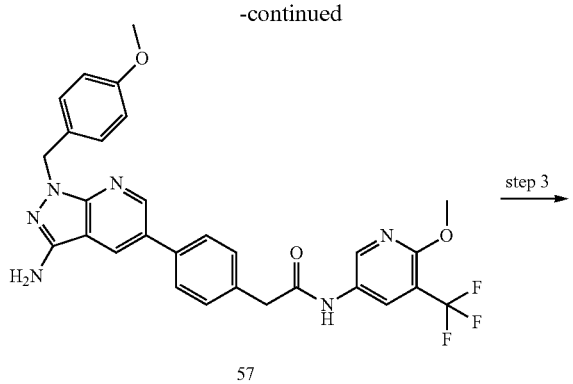

57

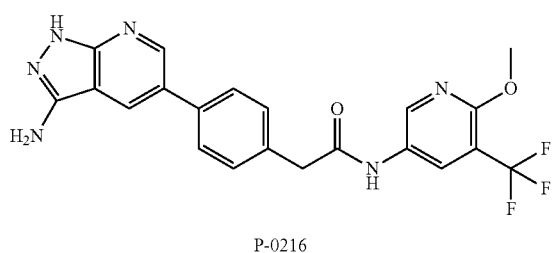

P-0216

Step 1—Preparation of 5-bromo-1-(4-methoxybenzyl)-1H-pyrazolo[3,4-b]pyridin-3-amine, 56: To an ice cold mixture of 5-bromo-1H-pyrazolo[3,4-b]pyridin-3-amine (55, 2.00 g, 9.39 mmol) in DMF (50 ml) was added slowly NaH in mineral oil (60%, 564 mg, 14.1 mmol). After stirring for 15 minutes, 1-(chloromethyl)-4-methoxy-benzene (4.42 g, 28.2 mmol) was added slowly. The mixture was allowed to stir and warm to ambient temperature for 1 hour. The reaction mixture was partitioned between ethyl acetate and water and was washed with water and brine. The organic layer was dried over anhydrous sodium sulfate, filtered and concentrated under reduced pressure. The material was purified by silica gel flash column chromatography eluting with 50% ethyl acetate in hexane to provide 1.57 g (50% yield) of compound 56.

Step 2—Preparation of 2-(4-(3-amino-1-(4-methoxybenzyl)-1H-pyrazolo[3,4-b]pyridin-5-yl)phenyl)-N-(6-methoxy-5-(trifluoromethyl)pyridin-3-yl)acetamide, 57: A mixture of 5-bromo-1-[(4-methoxyphenyl)methyl]pyrazolo[3,4-b]pyridin-3-amine (56, 149 mg, 0.447 mmol), N-[6-methoxy-5-(trifluoromethyl)-3-pyridyl]-2-[4-(4,4,5,5-tetramethyl-1,3,2-dioxaborolan-2-yl)phenyl]acetamide (6, 236 mg, 0.541 mmol) and [1,1'-bis(diphenylphosphino)ferrocene] dichloropalladium(II) dichloromethane complex (33 mg, 0.040 mmol) in dioxane (5 ml) was purged with nitrogen gas and then 2.5 M aqueous potassium carbonate (0.540 ml) was added. The mixture was allowed to stir at 100° C. for 3 hours. The reaction was diluted with ethyl acetate and was dried over anhydrous magnesium sulfate, filtered and concentrated under reduced pressure. The material was purified by silica gel flash column chromatography eluting with 80% ethyl acetate in dichloromethane to provide 150 mg (60% yield) of compound 57. MS ESI [M+H$^+$]$^+$=563.30.

Step 3—Preparation of 2-(4-(3-amino-1H-pyrazolo[3,4-b]pyridin-5-yl)phenyl)-N-(6-methoxy-5-(trifluoromethyl)pyridin-3-yl)acetamide, P-0216: A mixture of 2-[4-[3-amino-1-[(4-methoxyphenyl)methyl]pyrazolo[3,4-b]pyridin-5-yl]phenyl]-N[6-methoxy-5(trifluoromethyl)-3-pyridyl]acetamide (57, 150 mg, 0.267 mmol) in TFA (4 ml) was allowed to stir at 80° C. for 1 hour. The reaction mixture was concentrated down under reduced pressure. The material was purified by silica gel flash column chromatography eluting with 10% methanol in ethyl acetate, followed by triturating with acetonitrile to provide compound P-0216. MS ESI [M+H$^+$]$^+$=443.25

All compounds in Table 1 listed below can be made according to the synethetic examples described in this disclosure, and by making any necessary substitutions of starting materials that the skilled artisan would be able to obtain either commercially or otherwise.

All compounds below have a mass spectrometry (MH)+ value unless specifically indicated otherwise as (MH)-.

TABLE 1

| Number | Compound Name | Compound Structure | (MH)+ |
|---|---|---|---|
| P-0001 | 2-[2-methyl-4-(2-phenyl-1H-pyrrolo[2,3-b]pyridin-5-yl)phenyl]-N-[3-(trifluoromethyl)phenyl]acetamide | 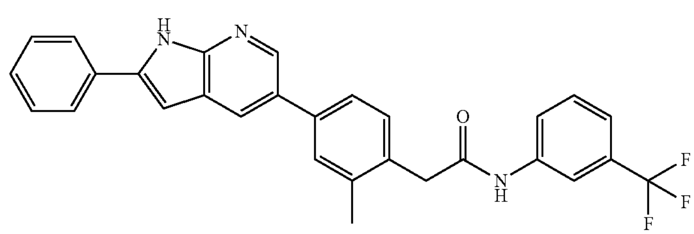 [SMILES: Cc1cc(-c2cnc3[nH]c(-c4ccccc4)cc3c2)ccc1CC(=O)Nc1cccc(C(F)(F)F)c1] | 486.3 |
| P-0002 | 2-[3-methyl-4-(2-phenyl-1H-pyrrolo[2,3-b]pyridin-5-yl)phenyl]-N-[3-(trifluoromethyl)phenyl]acetamide | 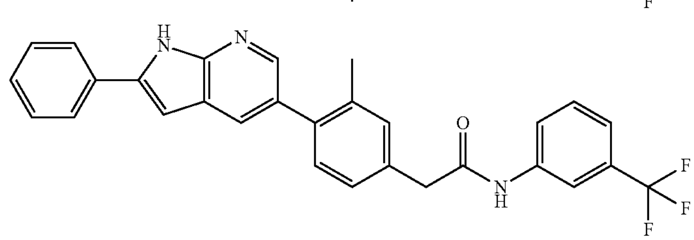 | 486.3 |

TABLE 1-continued

| Number | Compound Name | Compound Structure | (MH)+ |
|---|---|---|---|
| P-0003 | 2-[3-fluoro-4-(2-phenyl-1H-pyrrolo[2,3-b]pyridin-5-yl)phenyl]-N-[3-(trifluoromethyl)phenyl]acetamide | 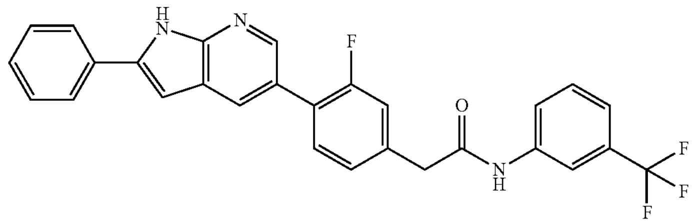 [SMILES: O=C(Cc1ccc(-c2cnc3[nH]c(-c4ccccc4)cc3c2)c(F)c1)Nc1cccc(C(F)(F)F)c1] | 490.3 |
| P-0004 | 2-[2-fluoro-4-(2-phenyl-1H-pyrrolo[2,3-b]pyridin-5-yl)phenyl]-N-[2-(trifluoromethyl)-4-pyridyl]acetamide | 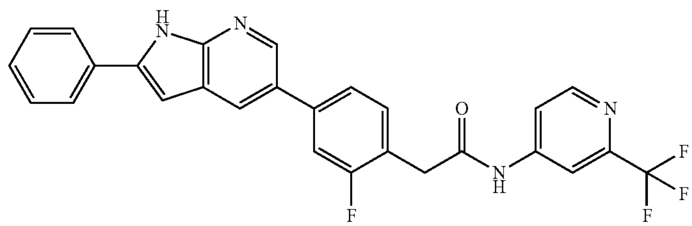 [SMILES: O=C(Cc1ccc(-c2cnc3[nH]c(-c4ccccc4)cc3c2)cc1F)Nc1ccnc(C(F)(F)F)c1] | 491.3 |
| P-0005 | 2-[5-(2-phenyl-1H-pyrrolo[2,3-b]pyridin-5-yl)-2-pyridyl]-N-[2-(trifluoromethyl)-4-pyridyl]acetamide | 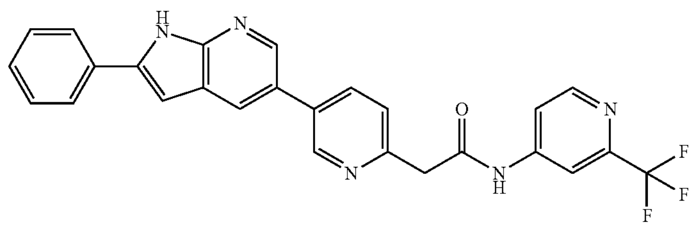 [SMILES: O=C(Cc1ccc(-c2cnc3[nH]c(-c4ccccc4)cc3c2)cn1)Nc1ccnc(C(F)(F)F)c1] | 474.3 |
| P-0006 | 2-[6-[2-(2-cyano-4-pyridyl)-1H-pyrrolo[2,3-b]pyridin-5-yl]-3-pyridyl]-N-[6-methoxy-5-(trifluoromethyl)-3-pyridyl]acetamide | 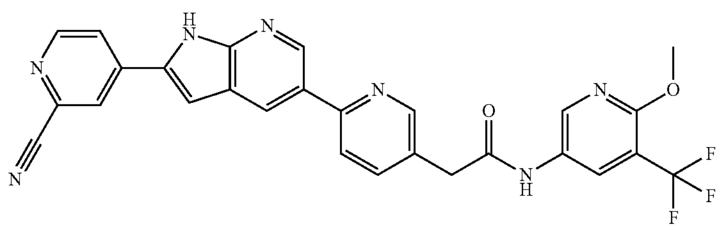 [SMILES: COc1ncc(NC(=O)Cc2ccc(-c3cnc4[nH]c(-c5ccnc(C#N)c5)cc4c3)nc2)cc1C(F)(F)F] | 530.05 |
| P-0007 | 2-[2-fluoro-4-[2-(6-methoxy-3-pyridyl)-1H-pyrrolo[2,3-b]pyridin-5-yl]phenyl]-N-[6-methoxy-5-(trifluoromethyl)-3-pyridyl]acetamide | 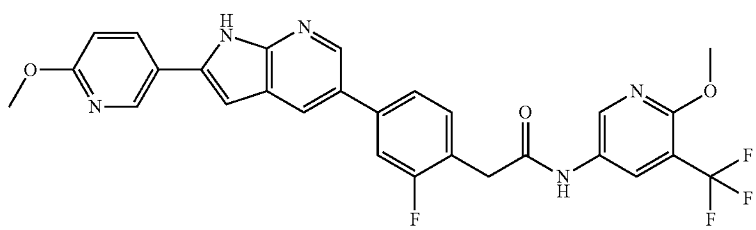 [SMILES: COc1ccc(-c2cc3cc(-c4ccc(CC(=O)Nc5cnc(OC)c(C(F)(F)F)c5)c(F)c4)cnc3[nH]2)cn1] | 552.3 |
| P-0008 | 2-[4-[2-(2-cyclopropylethynyl)-1H-pyrrolo[2,3-b]pyridin-5-yl]phenyl]-N-[6-methoxy-5-(trifluoromethyl)-3-pyridyl]acetamide | 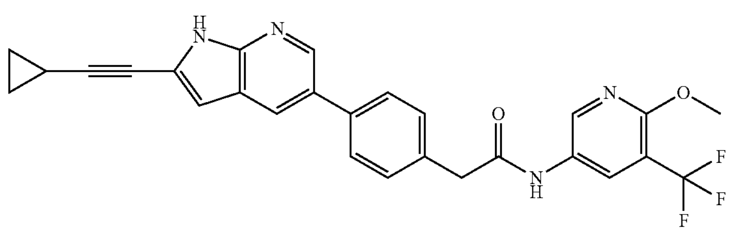 [SMILES: COc1ncc(NC(=O)Cc2ccc(-c3cnc4[nH]c(C#CC5CC5)cc4c3)cc2)cc1C(F)(F)F] | 491.4 |
| P-0009 | 2-[2-fluoro-4-[2-(2-methoxy-4-pyridyl)-1H-pyrrolo[2,3-b]pyridin-5-yl]phenyl]-N-[6-methoxy-5-(trifluoromethyl)-3-pyridyl]acetamide | 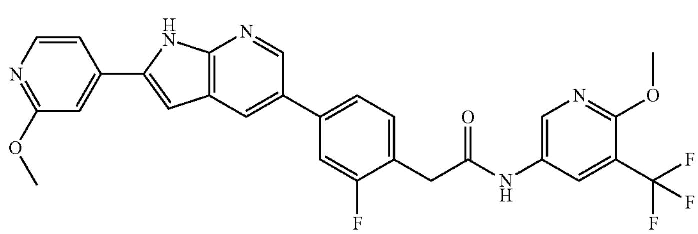 [SMILES: COc1cc(-c2cc3cc(-c4ccc(CC(=O)Nc5cnc(OC)c(C(F)(F)F)c5)c(F)c4)cnc3[nH]2)ccn1] | 552.1 |

TABLE 1-continued

| Number | Compound Name | Compound Structure | (MH)+ |
|---|---|---|---|
| P-0010 | 2-[2-fluoro-4-[2-(6-morpholino-3-pyridyl)-1H-pyrrolo[2,3-b]pyridin-5-yl]phenyl]-N-[6-methoxy-5-(trifluoromethyl)-3-pyridyl]acetamide | 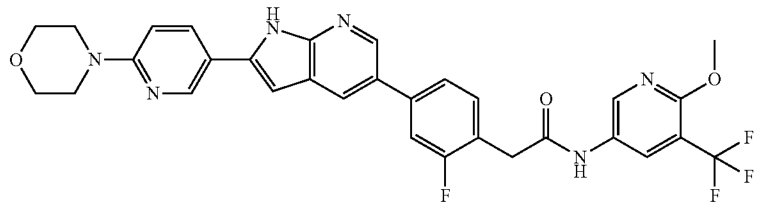 [SMILES: COc1ncc(NC(=O)Cc2ccc(-c3cnc4[nH]c(-c5ccc(N6CCOCC6)nc5)cc4c3)cc2F)cc1C(F)(F)F] | 607.4 |
| P-0011 | 2-[4-[2-(6-cyano-3-pyridyl)-1H-pyrrolo[2,3-b]pyridin-5-yl]-2-fluoro-phenyl]-N-[6-methoxy-5-(trifluoromethyl)-3-pyridyl]acetamide | 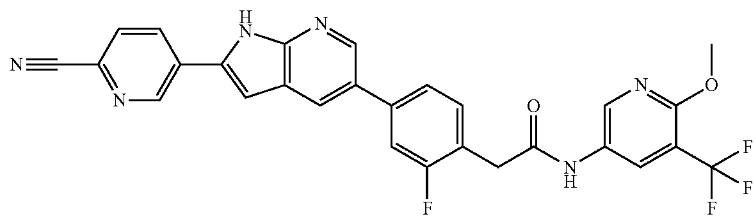 [SMILES: COc1ncc(NC(=O)Cc2ccc(-c3cnc4[nH]c(-c5ccc(C#N)nc5)cc4c3)cc2F)cc1C(F)(F)F] | 547.3 |
| P-0012 | 2-[3-fluoro-4-[2-(6-methoxy-3-pyridyl)-1H-pyrrolo[2,3-b]pyridin-5-yl]phenyl]-N-[6-methoxy-5-(trifluoromethyl)-3-pyridyl]acetamide | 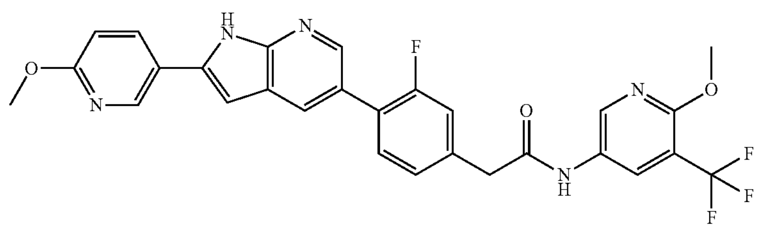 [SMILES: COc1ccc(-c2cc3cc(-c4ccc(CC(=O)Nc5cnc(OC)c(C(F)(F)F)c5)cc4F)cnc3[nH]2)cn1] | 552.3 |
| P-0013 | 2-[4-[2-(2-cyano-4-pyridyl)-1H-pyrrolo[2,3-b]pyridin-5-yl]-2-fluoro-phenyl]-N-[6-methoxy-5-(trifluoromethyl)-3-pyridyl]acetamide | 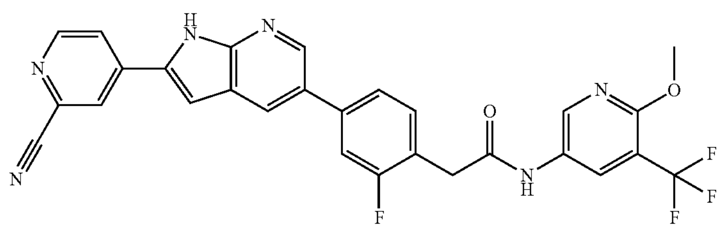 [SMILES: COc1ncc(NC(=O)Cc2ccc(-c3cnc4[nH]c(-c5ccnc(C#N)c5)cc4c3)cc2F)cc1C(F)(F)F] | 547.3 |
| P-0014 | 2-[4-[2-(6-cyano-3-pyridyl)-1H-pyrrolo[2,3-b]pyridin-5-yl]-3-fluoro-phenyl]-N-[6-methoxy-5-(trifluoromethyl)-3-pyridyl]acetamide | 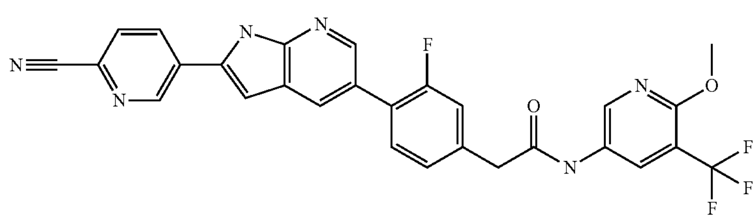 [SMILES: COc1ncc(NC(=O)Cc2ccc(-c3cnc4[nH]c(-c5ccc(C#N)nc5)cc4c3)c(F)c2)cc1C(F)(F)F] | 547.3 |
| P-0015 | 2-[4-[2-[1-(difluoromethyl)pyrazol-4-yl]-1H-pyrrolo[2,3-b]pyridin-5-yl]-2-fluoro-phenyl]-N-[6-methoxy-5-(trifluoromethyl)-3-pyridyl]acetamide | 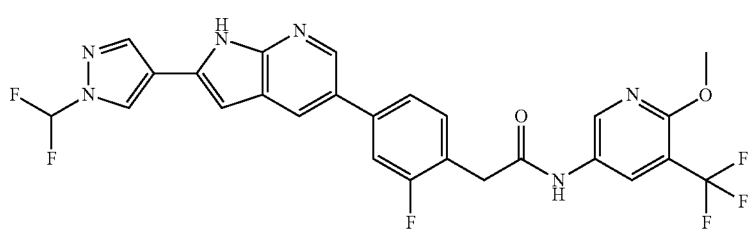 [SMILES: COc1ncc(NC(=O)Cc2ccc(-c3cnc4[nH]c(-c5cnn(C(F)F)c5)cc4c3)cc2F)cc1C(F)(F)F] | 561.3 |
| P-0016 | 2-[4-[2-(2-cyano-4-pyridyl)-1H-pyrrolo[2,3-b]pyridin-5-yl]-3-fluoro-phenyl]-N-[6-methoxy-5-(trifluoromethyl)-3-pyridyl]acetamide | 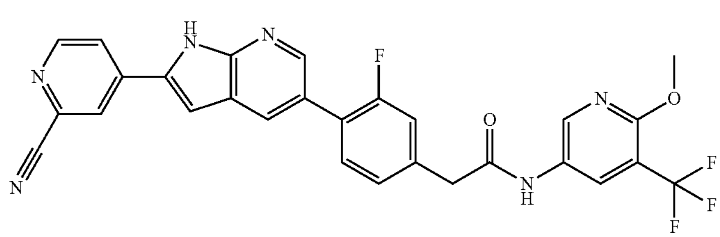 [SMILES: COc1ncc(NC(=O)Cc2ccc(-c3cnc4[nH]c(-c5ccnc(C#N)c5)cc4c3)c(F)c2)cc1C(F)(F)F] | 547.3 |

US 10,160,747 B2

TABLE 1-continued

| Number | Compound Name | Compound Structure | (MH)+ |
|---|---|---|---|
| P-0017 | 2-[3-fluoro-4-[2-[(1-methylpyrazol-4-yl)amino]pyrimidin-5-yl]phenyl]-N-[4-(trifluoromethyl)-2-pyridyl]acetamide | 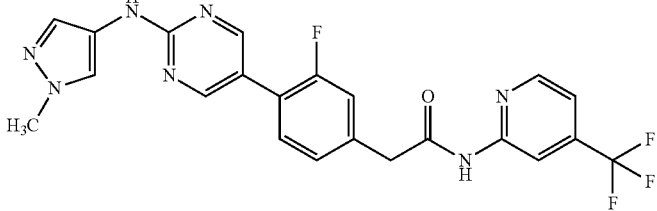 | 472.3 |
| P-0018 | 2-[3-fluoro-4-[2-[(1-methylimidazol-4-yl)amino]pyrimidin-5-yl]phenyl]-N-[4-(trifluoromethyl)-2-pyridyl]acetamide | 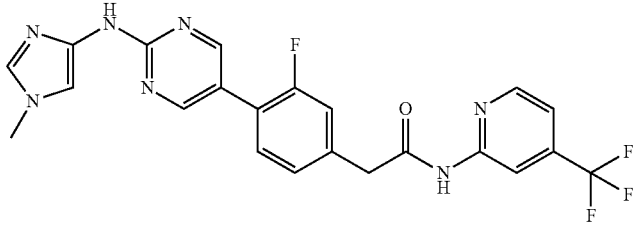 | 472.3 |
| P-0019 | 2-[2,5-difluoro-4-[2-[(1-methylpyrazol-4-yl)amino]pyrimidin-5-yl]phenyl]-N-[4-(trifluoromethyl)-2-pyridyl]acetamide | 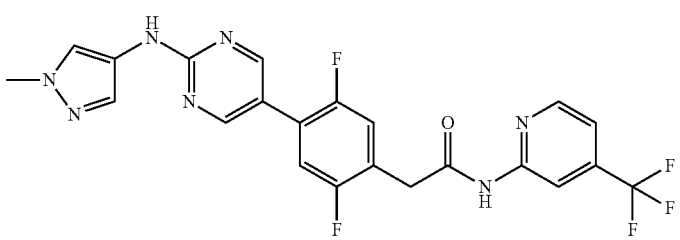 [SMILES: Cn1cc(Nc2ncc(-c3cc(F)c(CC(=O)Nc4cc(C(F)(F)F)ccn4)cc3F)cn2)cn1] | 490.3 |
| P-0020 | 2-[2,5-difluoro-4-[2-[(1-methylimidazol-4-yl)amino]pyrimidin-5-yl]phenyl]-N-[4-(trifluoromethyl)-2-pyridyl]acetamide | 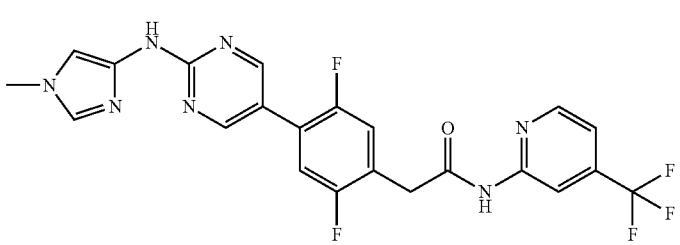 [SMILES: Cn1cnc(Nc2ncc(-c3cc(F)c(CC(=O)Nc4cc(C(F)(F)F)ccn4)cc3F)cn2)c1] | 490.3 |
| P-0021 | 2-[4-[2-[[1-(difluoromethyl)pyrazol-4-yl]amino]pyrimidin-5-yl]-2,5-difluoro-phenyl]-N-[4-(trifluoromethyl)-2-pyridyl]acetamide | 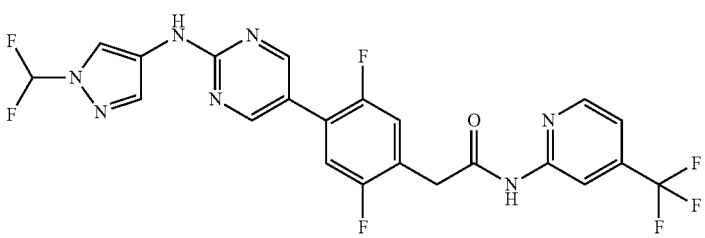 [SMILES: O=C(Cc1cc(F)c(-c2cnc(Nc3cnn(C(F)F)c3)nc2)cc1F)Nc1cc(C(F)(F)F)ccn1] | 526.3 |
| P-0022 | 2-[4-[2-[(1-methylimidazol-4-yl)amino]pyrimidin-5-yl]phenyl]-N-[4-(trifluoromethyl)-2-pyridyl]acetamide | 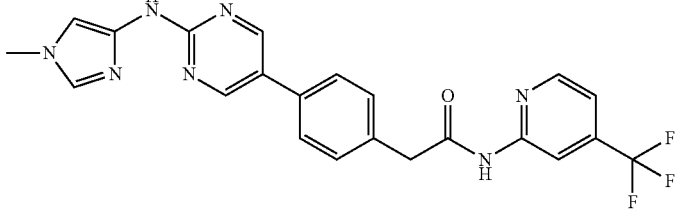 | 454.3 |

TABLE 1-continued

| Number | Compound Name | Compound Structure | (MH)+ |
|---|---|---|---|
| P-0023 | 2-[4-[2-[[1-(difluoromethyl)pyrazol-4-yl]amino]pyrimidin-5-yl]phenyl]-N-[4-(trifluoromethyl)-2-pyridyl]acetamide | 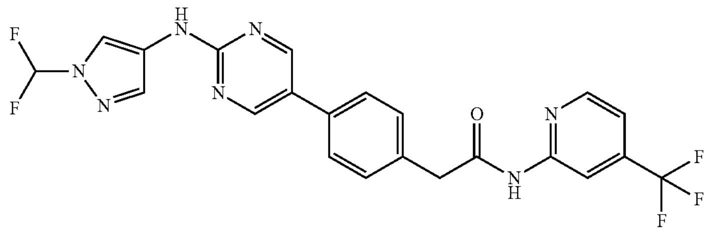 [SMILES: O=C(Cc1ccc(-c2cnc(Nc3cnn(C(F)F)c3)nc2)cc1)Nc1cc(C(F)(F)F)ccn1] | 490.3 |
| P-0024 | 2-[4-[2-[[1-(difluoromethyl)pyrazol-4-yl]amino]pyrimidin-5-yl]-3-fluoro-phenyl]-N-[4-(trifluoromethyl)-2-pyridyl]acetamide | 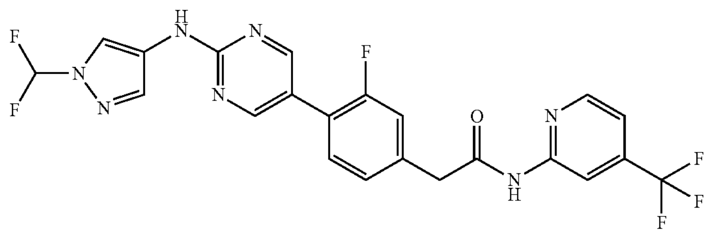 [SMILES: O=C(Cc1ccc(-c2cnc(Nc3cnn(C(F)F)c3)nc2)c(F)c1)Nc1cc(C(F)(F)F)ccn1] | 508.3 |
| P-0025 | N-[6-methoxy-5-(trifluoromethyl)-3-pyridyl]-2-[4-[2-(1H-pyrazol-4-ylamino)pyrimidin-5-yl]phenyl]acetamide | 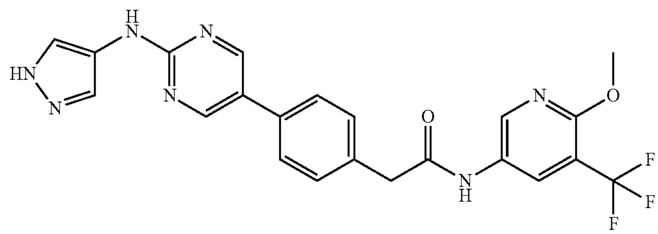 [SMILES: COc1ncc(NC(=O)Cc2ccc(-c3cnc(Nc4cn[nH]c4)nc3)cc2)cc1C(F)(F)F] | 470.3 |
| P-0026 | 2-[2-fluoro-4-[2-(1H-pyrazol-4-ylamino)pyrimidin-5-yl]phenyl]-N-[6-methoxy-5-(trifluoromethyl)-3-pyridyl]acetamide | 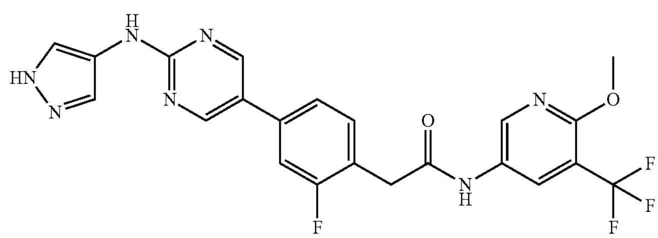 [SMILES: COc1ncc(NC(=O)Cc2ccc(-c3cnc(Nc4cn[nH]c4)nc3)cc2F)cc1C(F)(F)F] | 488.3 |
| P-0027 | 2-[2-fluoro-4-[2-(1H-pyrazol-4-ylamino)pyrimidin-5-yl]phenyl]-N-[6-methyl-5-(trifluoromethyl)-3-pyridyl]acetamide | 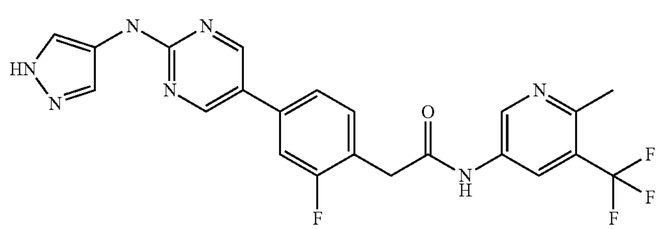 [SMILES: Cc1ncc(NC(=O)Cc2ccc(-c3cnc(Nc4cn[nH]c4)nc3)cc2F)cc1C(F)(F)F] | 472.3 |
| P-0028 | 2-[3-fluoro-4-[2-(1H-pyrazol-4-ylamino)pyrimidin-5-yl]phenyl]-N-[6-methoxy-5-(trifluoromethyl)-3-pyridyl]acetamide | 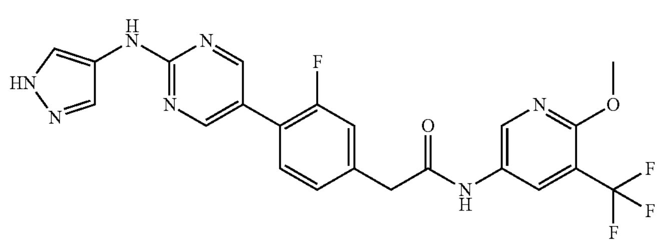 [SMILES: COc1ncc(NC(=O)Cc2ccc(-c3cnc(Nc4cn[nH]c4)nc3)c(F)c2)cc1C(F)(F)F] | 488.3 |

TABLE 1-continued

| Number | Compound Name | Compound Structure | (MH)+ |
|---|---|---|---|
| P-0029 | 2-[2-fluoro-4-(3-fluoro-1H-pyrrolo[2,3-b]pyridin-5-yl)phenyl]-N-[2-(trifluoromethyl)-4-pyridyl]acetamide | 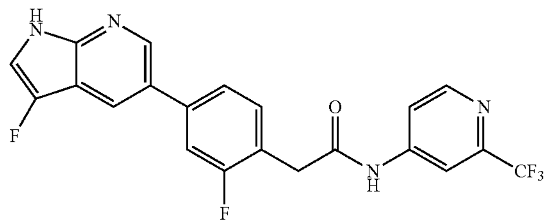 [SMILES: O=C(Cc1ccc(-c2cnc3[nH]cc(F)c3c2)cc1F)Nc1ccnc(C(F)(F)F)c1] | 433 |
| P-0030 | 2-[4-(2-chloro-1H-pyrrolo[2,3-b]pyridin-5-yl)-2-fluoro-phenyl]-N-[2-(trifluoromethyl)-4-pyridyl]acetamide | 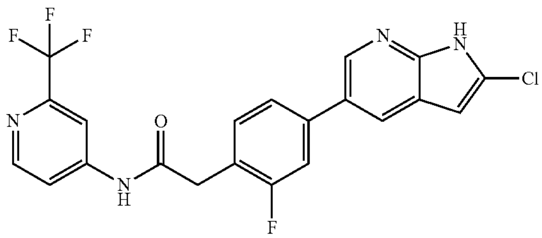 [SMILES: O=C(Cc1ccc(-c2cnc3[nH]c(Cl)cc3c2)cc1F)Nc1ccnc(C(F)(F)F)c1] | 449.2 |
| P-0031 | 2-[4-(3-acetyl-1H-pyrrolo[2,3-b]pyridin-5-yl)-2-fluoro-phenyl]-N-[2-(trifluoromethyl)-4-pyridyl]acetamide | 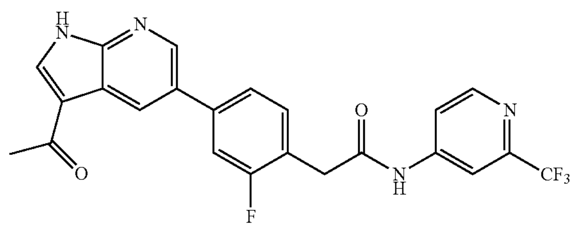 [SMILES: CC(=O)c1c[nH]c2ncc(-c3ccc(CC(=O)Nc4ccnc(C(F)(F)F)c4)c(F)c3)cc12] | 457.3 |
| P-0032 | 2-[4-[3-(cyclopropanecarbonyl)-1H-pyrrolo[2,3-b]pyridin-5-yl]-2-fluoro-phenyl]-N-[2-(trifluoromethyl)-4-pyridyl]acetamide | 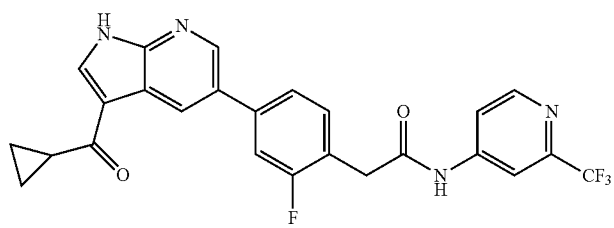 [SMILES: O=C(Cc1ccc(-c2cnc3[nH]cc(C(=O)C4CC4)c3c2)cc1F)Nc1ccnc(C(F)(F)F)c1] | 483.3 |
| P-0033 | 2-[2-fluoro-4-[2-(pyrazolo[1,5-a]pyridin-3-ylamino)pyrimidin-5-yl]phenyl]-N-[2-(trifluoromethyl)-4-pyridyl]acetamide | 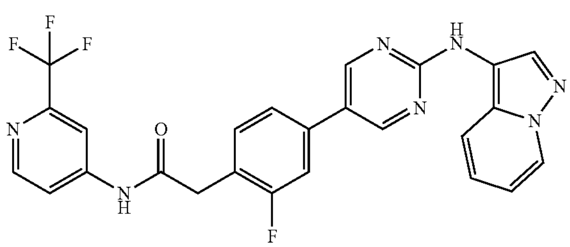 [SMILES: O=C(Cc1ccc(-c2cnc(Nc3cnn4ccccc34)nc2)cc1F)Nc1ccnc(C(F)(F)F)c1] | 508.3 |
| P-0034 | 2-[2-fluoro-4-(3-fluoro-1H-pyrrolo[2,3-b]pyridin-5-yl)phenyl]-N-[6-methoxy-5-(trifluoromethyl)-3-pyridyl]acetamide | 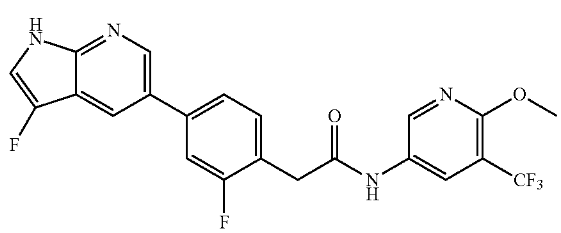 [SMILES: COc1ncc(NC(=O)Cc2ccc(-c3cnc4[nH]cc(F)c4c3)cc2F)cc1C(F)(F)F] | 463.3 |

TABLE 1-continued

| Number | Compound Name | Compound Structure | (MH)+ |
|---|---|---|---|
| P-0035 | 2-[4-(3-acetyl-1H-pyrrolo[2,3-b]pyridin-5-yl)-2-fluoro-phenyl]-N-[6-methoxy-5-(trifluoromethyl)-3-pyridyl]acetamide | 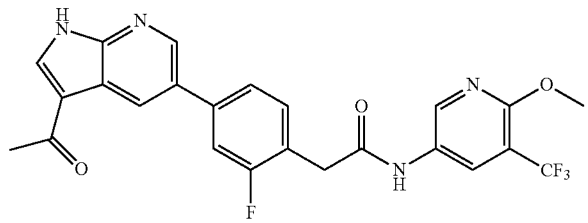 [SMILES: COc1ncc(NC(=O)Cc2ccc(-c3cnc4[nH]cc(C(C)=O)c4c3)cc2F)cc1C(F)(F)F] | 487.3 |
| P-0036 | 2-[4-[3-(cyclopropanecarbonyl)-1H-pyrrolo[2,3-b]pyridin-5-yl]-2-fluoro-phenyl]-N-[6-methoxy-5-(trifluoromethyl)-3-pyridyl]acetamide | 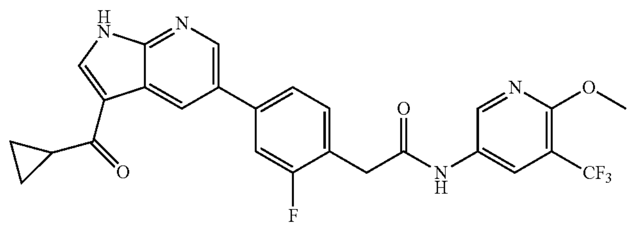 [SMILES: COc1ncc(NC(=O)Cc2ccc(-c3cnc4[nH]cc(C(=O)C5CC5)c4c3)cc2F)cc1C(F)(F)F] | 513.3 |
| P-0037 | 2-[2-fluoro-4-[2-(pyrazolo[1,5-a]pyridin-3-ylamino)pyrimidin-5-yl]phenyl]-N-[6-methoxy-5-(trifluoromethyl)-3-pyridyl]acetamide | 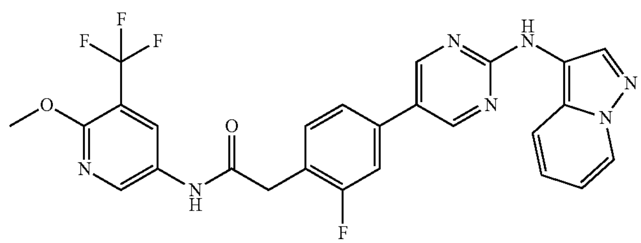 [SMILES: COc1ncc(NC(=O)Cc2ccc(-c3cnc(Nc4cnn5ccccc45)nc3)cc2F)cc1C(F)(F)F] | 538.3 |
| P-0038 | 2-[4-(2-chloro-1H-pyrrolo[2,3-b]pyridin-5-yl)-2-fluoro-phenyl]-N-[6-methoxy-5-(trifluoromethyl)-3-pyridyl]acetamide | 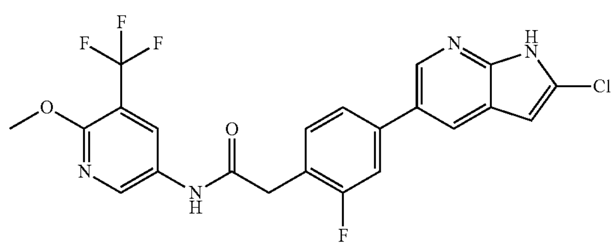 [SMILES: COc1ncc(NC(=O)Cc2ccc(-c3cnc4[nH]c(Cl)cc4c3)cc2F)cc1C(F)(F)F] | 479.2 |
| P-0039 | 2-[4-[2-[[1-(difluoromethyl)-5-methyl-pyrazol-4-yl]amino]pyrimidin-5-yl]phenyl]-N-[6-methoxy-5-(trifluoromethyl)-3-pyridyl]acetamide | 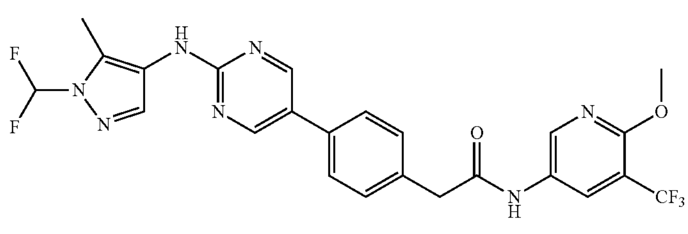 [SMILES: COc1ncc(NC(=O)Cc2ccc(-c3cnc(Nc4cnn(C(F)F)c4C)nc3)cc2)cc1C(F)(F)F] | 534.1 |
| P-0040 | 2-[4-(2-chloro-1H-pyrrolo[2,3-b]pyridin-5-yl)-2-fluoro-phenyl]-N-[4-(trifluoromethyl)-2-pyridyl]acetamide | 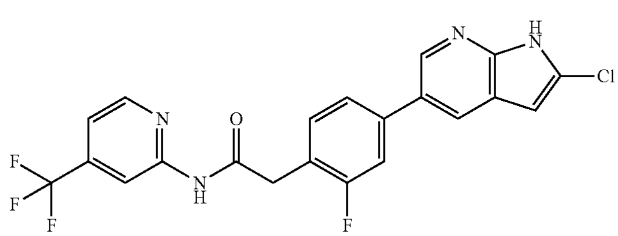 [SMILES: O=C(Cc1ccc(-c2cnc3[nH]c(Cl)cc3c2)cc1F)Nc1cc(C(F)(F)F)ccn1] | 449.2 |

TABLE 1-continued

| Number | Compound Name | Compound Structure | (MH)+ |
|---|---|---|---|
| P-0041 | 2-[4-(2-chloro-1H-pyrrolo[2,3-b]pyridin-5-yl)-2-fluoro-phenyl]-N-[5-(trifluoromethyl)-2-pyridyl]acetamide | 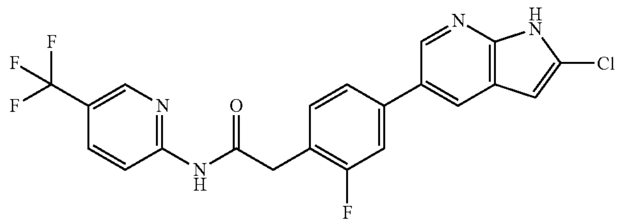 [SMILES: O=C(Cc1ccc(-c2cnc3[nH]c(Cl)cc3c2)cc1F)Nc1ccc(C(F)(F)F)cn1] | 449.2 |
| P-0042 | N-[6-(1-cyano-1-methyl-ethyl)-3-pyridyl]-2-[2-fluoro-4-(3-fluoro-1H-pyrrolo[2,3-b]pyridin-5-yl)phenyl]acetamide | 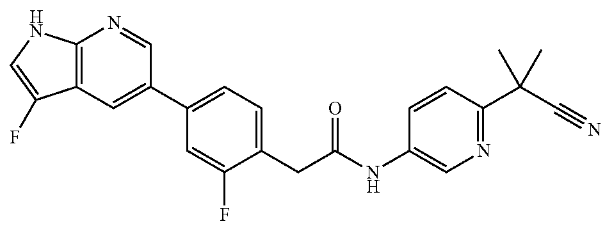 [SMILES: CC(C)(C#N)c1ccc(NC(=O)Cc2ccc(-c3cnc4[nH]cc(F)c4c3)cc2F)cn1] | 432.3 |
| P-0043 | N-(6-tert-butyl-3-pyridyl)-2-[2-fluoro-4-(3-fluoro-1H-pyrrolo[2,3-b]pyridin-5-yl)phenyl]acetamide | 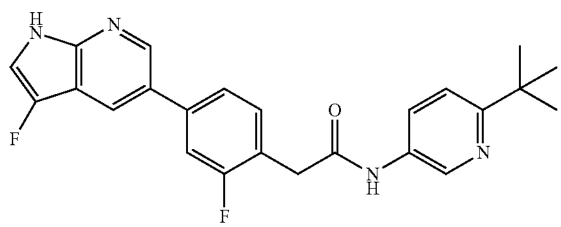 [SMILES: CC(C)(C)c1ccc(NC(=O)Cc2ccc(-c3cnc4[nH]cc(F)c4c3)cc2F)cn1] | 421.3 |
| P-0044 | N-(4-chloro-5-cyclopropyl-2-pyridyl)-2-[2-fluoro-4-(3-fluoro-1H-pyrrolo[2,3-b]pyridin-5-yl)phenyl]acetamide | 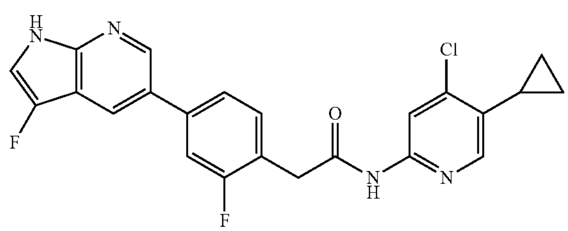 [SMILES: O=C(Cc1ccc(-c2cnc3[nH]cc(F)c3c2)cc1F)Nc1cc(Cl)c(C2CC2)cn1] | 439.3 |
| P-0045 | 2-[4-(2-chloro-1H-pyrrolo[2,3-b]pyridin-5-yl)-2,5-difluoro-phenyl]-N-[6-methoxy-5-(trifluoromethyl)-3-pyridyl]acetamide | 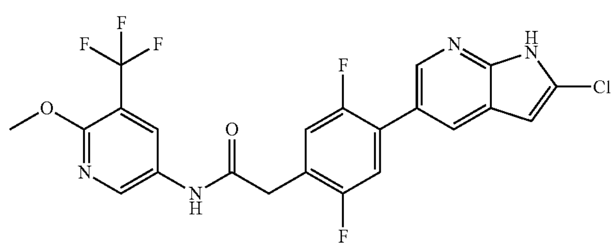 [SMILES: COc1ncc(NC(=O)Cc2cc(F)c(-c3cnc4[nH]c(Cl)cc4c3)cc2F)cc1C(F)(F)F] | 497.2 |
| P-0046 | 2-[4-(2-chloro-1H-pyrrolo[2,3-b]pyridin-5-yl)-3-fluoro-phenyl]-N-[6-methoxy-5-(trifluoromethyl)-3-pyridyl]acetamide | 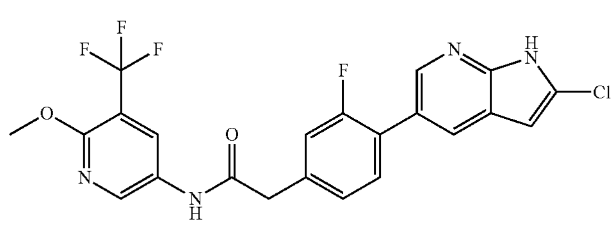 [SMILES: COc1ncc(NC(=O)Cc2ccc(-c3cnc4[nH]c(Cl)cc4c3)c(F)c2)cc1C(F)(F)F] | 479.2 |

TABLE 1-continued

| Number | Compound Name | Compound Structure | (MH)+ |
|---|---|---|---|
| P-0047 | 2-[4-(7-chloro-5H-pyrrolo[2,3-b]pyrazin-2-yl)-2-fluoro-phenyl]-N-[6-methoxy-5-(trifluoromethyl)-3-pyridyl]acetamide | 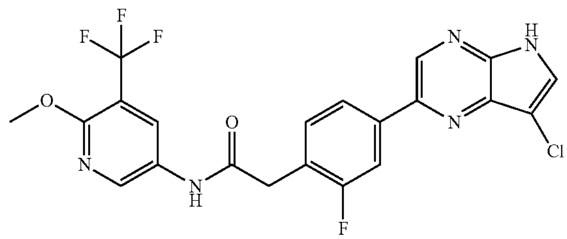 [SMILES: COc1ncc(NC(=O)Cc2ccc(-c3cnc4[nH]cc(Cl)c4n3)cc2F)cc1C(F)(F)F] | 480.3 |
| P-0048 | 2-[3-fluoro-4-(3-fluoro-1H-pyrrolo[2,3-b]pyridin-5-yl)phenyl]-N-[6-methoxy-5-(trifluoromethyl)-3-pyridyl]acetamide | 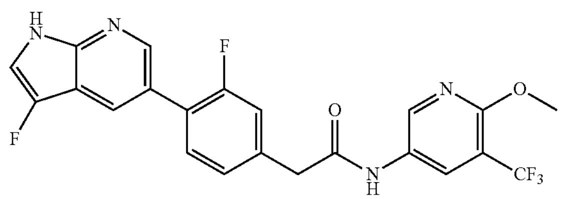 [SMILES: COc1ncc(NC(=O)Cc2ccc(-c3cnc4[nH]cc(F)c4c3)c(F)c2)cc1C(F)(F)F] | 463.2 |
| P-0049 | 2-[2-fluoro-4-(3-propanoyl-1H-pyrrolo[2,3-b]pyridin-5-yl)phenyl]-N-[6-methoxy-5-(trifluoromethyl)-3-pyridyl]acetamide | 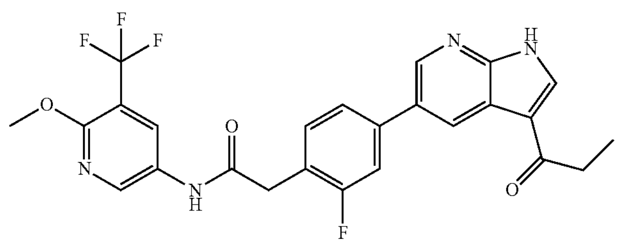 [SMILES: CCC(=O)c1c[nH]c2ncc(-c3ccc(CC(=O)Nc4cnc(OC)c(C(F)(F)F)c4)c(F)c3)cc12] | 501.3 |
| P-0050 | 2-[2-fluoro-4-[2-[[1-[(2S)-2-hydroxypropyl]-3-methoxy-pyrazol-4-yl]amino]pyrimidin-5-yl]phenyl]-N-[5-(trifluoromethyl)-3-pyridyl]acetamide | 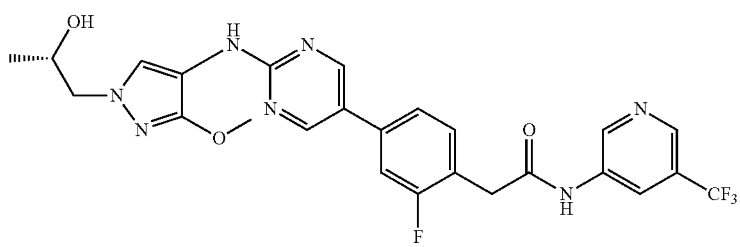 [SMILES: COc1nn(C[C@H](C)O)cc1Nc1ncc(-c2ccc(CC(=O)Nc3cncc(C(F)(F)F)c3)c(F)c2)cn1] | 546.3 |
| P-0051 | 2-[2,5-difluoro-4-(3-fluoro-1H-pyrrolo[2,3-b]pyridin-5-yl)phenyl]-N-[6-methoxy-5-(trifluoromethyl)-3-pyridyl]acetamide | 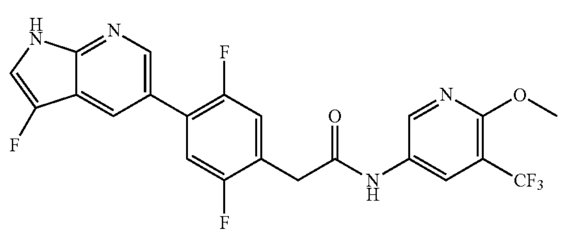 | 481.2 |
| P-0052 | 2-[2-fluoro-4-[2-[(1-methylimidazol-4-yl)amino]pyrimidin-5-yl]phenyl]-N-[5-(trifluoromethyl)-3-pyridyl]acetamide | 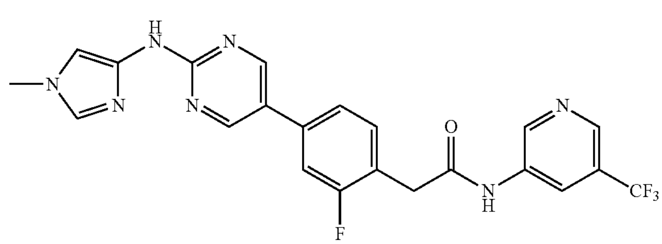 [SMILES: Cn1cnc(Nc2ncc(-c3ccc(CC(=O)Nc4cncc(C(F)(F)F)c4)c(F)c3)cn2)c1] | 472.3 |

TABLE 1-continued

| Number | Compound Name | Compound Structure | (MH)+ |
|---|---|---|---|
| P-0053 | 2-[2-fluoro-4-(3-fluoro-1H-pyrrolo[2,3-b]pyridin-5-yl)phenyl]-N-[5-(trifluoromethyl)-3-pyridyl]acetamide | 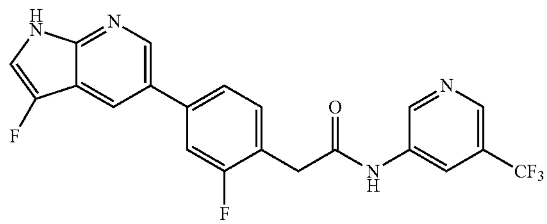 [SMILES: O=C(Cc1ccc(-c2cnc3[nH]cc(F)c3c2)cc1F)Nc1cncc(C(F)(F)F)c1] | 433.3 |
| P-0054 | 2-[4-[2-[[1-(difluoromethyl)-3-methyl-pyrazol-4-yl]amino]pyrimidin-5-yl]phenyl]-N-[6-methoxy-5-(trifluoromethyl)-3-pyridyl]acetamide | 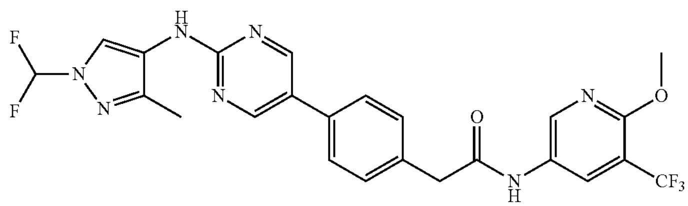 [SMILES: COc1ncc(NC(=O)Cc2ccc(-c3cnc(Nc4cn(C(F)F)nc4C)nc3)cc2)cc1C(F)(F)F] | 534.1 |
| P-0055 | 2-[4-(3-acetyl-1H-pyrrolo[2,3-b]pyridin-5-yl)-2-fluoro-phenyl]-N-[5-(trifluoromethyl)-3-pyridyl]acetamide | 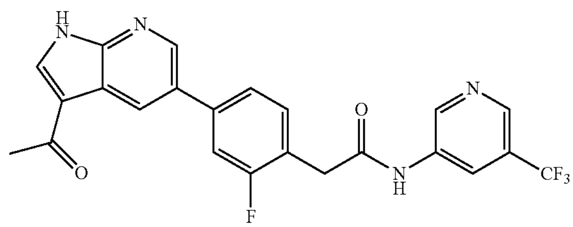 [SMILES: CC(=O)c1c[nH]c2ncc(-c3ccc(CC(=O)Nc4cncc(C(F)(F)F)c4)c(F)c3)cc12] | 457.3 |
| P-0056 | 2-[4-[2-(3-methoxyprop-1-ynyl)-1H-pyrrolo[2,3-b]pyridin-5-yl]phenyl]-N-[6-methoxy-5-(trifluoromethyl)-3-pyridyl]acetamide | 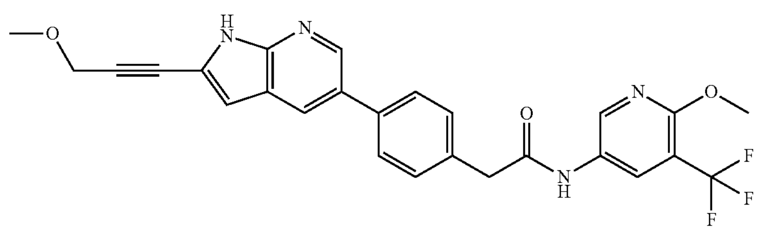 [SMILES: COCC#Cc1cc2cc(-c3ccc(CC(=O)Nc4cnc(OC)c(C(F)(F)F)c4)cc3)cnc2[nH]1] | 495.3 |
| P-0057 | 2-[2-fluoro-4-(2-oxospiro[1H-pyrrolo[2,3-b]pyridine-3,1'-cyclopropane]-5-yl)phenyl]-N-[6-methyl-5-(trifluoromethyl)-3-pyridyl]acetamide | 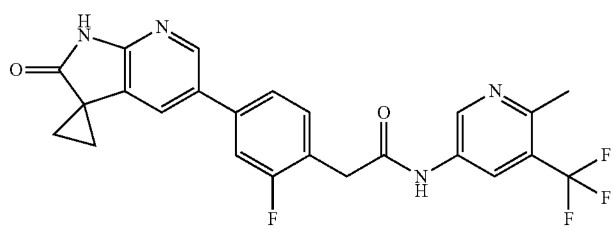 [SMILES: Cc1ncc(NC(=O)Cc2ccc(-c3cnc4c(c3)C3(CC3)C(=O)N4)cc2F)cc1C(F)(F)F] | 471.3 |
| P-0058 | 2-[2-fluoro-4-[2-(pyrazolo[1,5-a]pyridin-3-ylamino)pyrimidin-5-yl]phenyl]-N-[5-(trifluoromethyl)-3-pyridyl]acetamide | 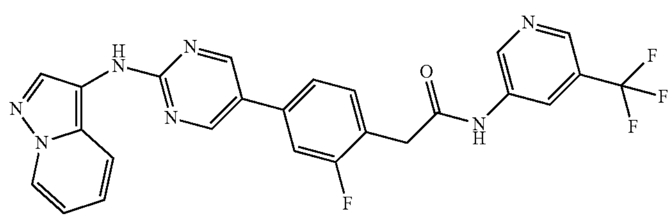 [SMILES: O=C(Cc1ccc(-c2cnc(Nc3cnn4ccccc34)nc2)cc1F)Nc1cncc(C(F)(F)F)c1] | 507.4 |
| P-0059 | 2-[4-(7-chloro-5H-pyrrolo[2,3-b]pyrazin-2-yl)-2-fluoro-phenyl]-N-[6-methyl-5-(trifluoromethyl)-3-pyridyl]acetamide | 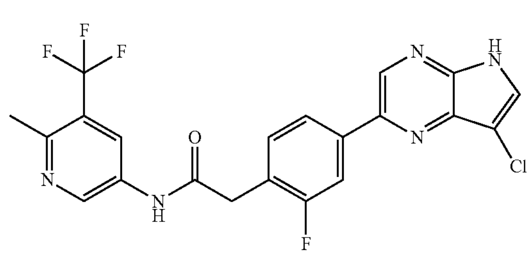 [SMILES: Cc1ncc(NC(=O)Cc2ccc(-c3cnc4[nH]cc(Cl)c4n3)cc2F)cc1C(F)(F)F] | 464.2 |

TABLE 1-continued

| Number | Compound Name | Compound Structure | (MH)+ |
|---|---|---|---|
| P-0060 | 2-[4-(7-chloro-5H-pyrrolo[2,3-b]pyrazin-2-yl)-2-fluoro-phenyl]-N-[6-chloro-5-(trifluoromethyl)-3-pyridyl]acetamide | 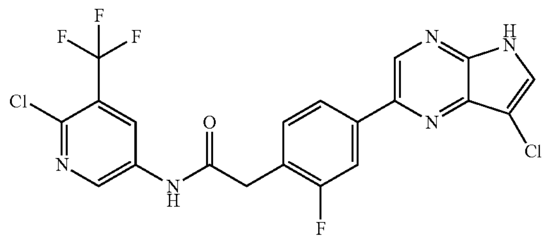 [SMILES: O=C(Cc1ccc(-c2cnc3[nH]cc(Cl)c3n2)cc1F)Nc1cnc(Cl)c(C(F)(F)F)c1] | 484.2 |
| P-0061 | 2-[4-(7-chloro-5H-pyrrolo[2,3-b]pyrazin-2-yl)-2-fluoro-phenyl]-N-[5-(trifluoromethyl)-3-pyridyl]acetamide | 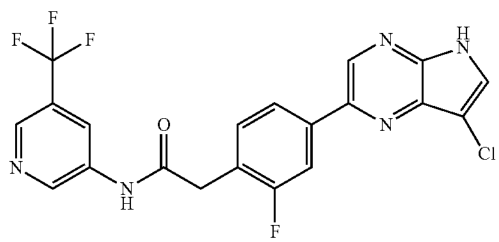 [SMILES: O=C(Cc1ccc(-c2cnc3[nH]cc(Cl)c3n2)cc1F)Nc1cncc(C(F)(F)F)c1] | 450.2 |
| P-0062 | 2-[2-fluoro-4-(3-fluoro-1H-pyrrolo[2,3-b]pyridin-5-yl)phenyl]-N-[6-methyl-5-(trifluoromethyl)-3-pyridyl]acetamide | 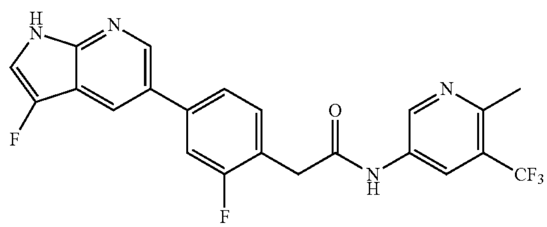 [SMILES: Cc1ncc(NC(=O)Cc2ccc(-c3cnc4[nH]cc(F)c4c3)cc2F)cc1C(F)(F)F] | 447.3 |
| P-0063 | 2-[4-(3-acetyl-1H-pyrrolo[2,3-b]pyridin-5-yl)-2-fluoro-phenyl]-N-[6-methyl-5-(trifluoromethyl)-3-pyridyl]acetamide | 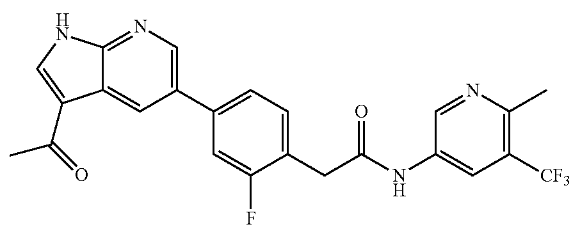 [SMILES: CC(=O)c1c[nH]c2ncc(-c3ccc(CC(=O)Nc4cnc(C)c(C(F)(F)F)c4)c(F)c3)cc12] | 471.3 |
| P-0064 | 2-[2-fluoro-4-(2-oxospiro[1H-pyrrolo[2,3-b]pyridine-3,1'-cyclopropane]-5-yl)phenyl]-N-[5-(trifluoromethyl)-3-pyridyl]acetamide | 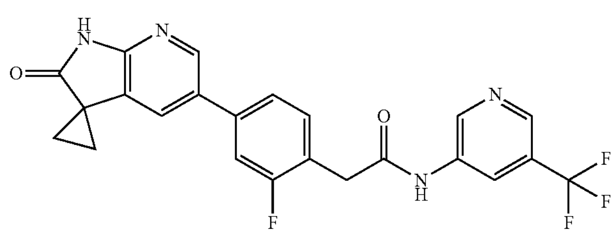 [SMILES: O=C(Cc1ccc(-c2cnc3c(c2)C2(CC2)C(=O)N3)cc1F)Nc1cncc(C(F)(F)F)c1] | 457.2 |
| P-0065 | 2-[2-fluoro-4-[2-(pyrazolo[1,5-a]pyridin-3-ylamino)pyrimidin-5-yl]phenyl]-N-[6-methyl-5-(trifluoromethyl)-3-pyridyl]acetamide | 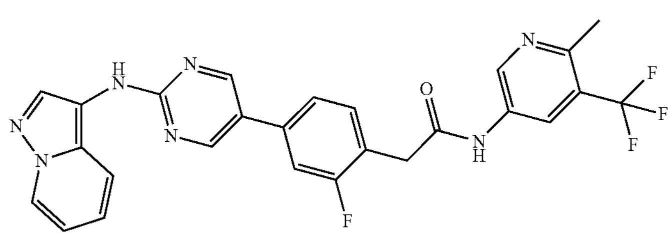 [SMILES: Cc1ncc(NC(=O)Cc2ccc(-c3cnc(Nc4cnn5ccccc45)nc3)cc2F)cc1C(F)(F)F] | 522.1 |

TABLE 1-continued

| Number | Compound Name | Compound Structure | (MH)+ |
|---|---|---|---|
| P-0066 | 2-[4-(3-cyclopropyl-1H-pyrazolo[3,4-b]pyridin-5-yl)-2-fluoro-phenyl]-N-[6-methyl-5-(trifluoromethyl)-3-pyridyl]acetamide | 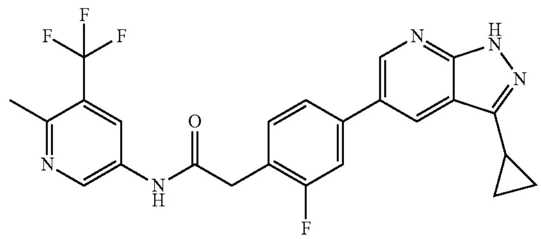 [SMILES: Cc1ncc(NC(=O)Cc2ccc(-c3cnc4[nH]nc(C5CC5)c4c3)cc2F)cc1C(F)(F)F] | 470.3 |
| P-0067 | 2-[4-(2-chloro-1H-pyrrolo[2,3-b]pyridin-5-yl)-2-fluoro-phenyl]-N-[6-methyl-5-(trifluoromethyl)-3-pyridyl]acetamide | 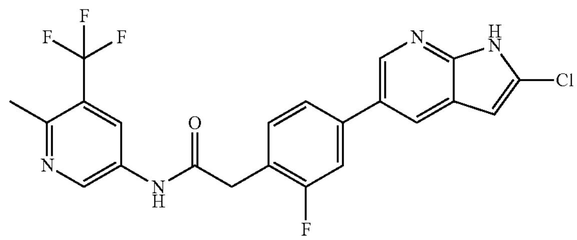 [SMILES: Cc1ncc(NC(=O)Cc2ccc(-c3cnc4[nH]c(Cl)cc4c3)cc2F)cc1C(F)(F)F] | 463.2 |
| P-0068 | 2-[2-fluoro-4-(3-propanoyl-1H-pyrrolo[2,3-b]pyridin-5-yl)phenyl]-N-[5-(trifluoromethyl)-3-pyridyl]acetamide | 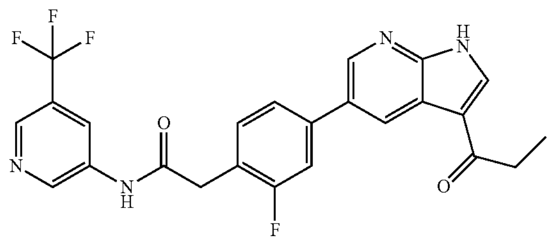 [SMILES: CCC(=O)c1c[nH]c2ncc(-c3ccc(CC(=O)Nc4cncc(C(F)(F)F)c4)c(F)c3)cc12] | 471.3 |
| P-0069 | 2-[6-[2-(2-morpholino-4-pyridyl)-1H-pyrrolo[2,3-b]pyridin-5-yl]-3-pyridyl]-N-[2-(trifluoromethyl)-4-pyridyl]acetamide | 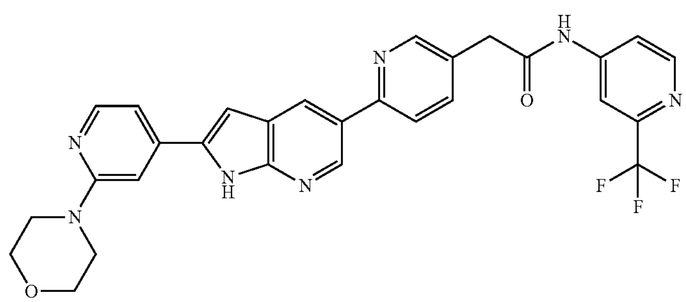 [SMILES: O=C(Cc1ccc(-c2cnc3[nH]c(-c4ccnc(N5CCOCC5)c4)cc3c2)nc1)Nc1ccnc(C(F)(F)F)c1] | 560.4 |
| P-0070 | 2-[2-fluoro-4-(3-propanoyl-1H-pyrrolo[2,3-b]pyridin-5-yl)phenyl]-N-[6-methyl-5-(trifluoromethyl)-3-pyridyl]acetamide | 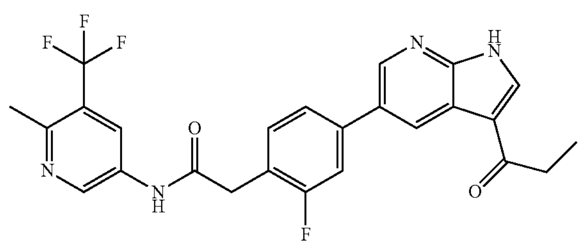 [SMILES: CCC(=O)c1c[nH]c2ncc(-c3ccc(CC(=O)Nc4cnc(C)c(C(F)(F)F)c4)c(F)c3)cc12] | 485.3 |
| P-0071 | 2-[3-fluoro-4-[2-(pyrazolo[1,5-a]pyridin-3-ylamino)pyrimidin-5-yl]phenyl]-N-[5-(trifluoromethyl)-3-pyridyl]acetamide | 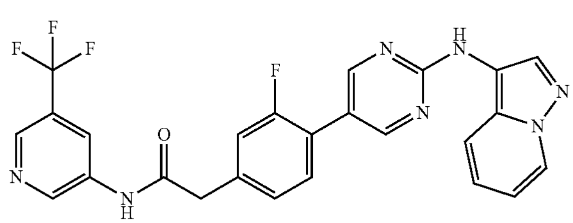 [SMILES: O=C(Cc1ccc(-c2cnc(Nc3cnn4ccccc34)nc2)c(F)c1)Nc1cncc(C(F)(F)F)c1] | 508.3 |

TABLE 1-continued

| Number | Compound Name | Compound Structure | (MH)+ |
|---|---|---|---|
| P-0072 | 2-[4-(3-cyclopropyl-1H-pyrazolo[3,4-b]pyridin-5-yl)-2-fluoro-phenyl]-N-[5-(trifluoromethyl)-3-pyridyl]acetamide | 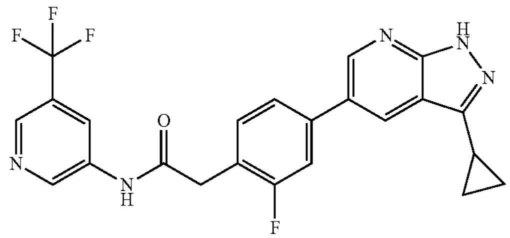 [SMILES: O=C(Cc1ccc(-c2cnc3[nH]nc(C4CC4)c3c2)cc1F)Nc1cncc(C(F)(F)F)c1] | 456.3 |
| P-0073 | 2-[4-(3-cyclopropyl-1H-pyrazolo[3,4-b]pyridin-5-yl)phenyl]-N-[5-(trifluoromethyl)-3-pyridyl]acetamide | 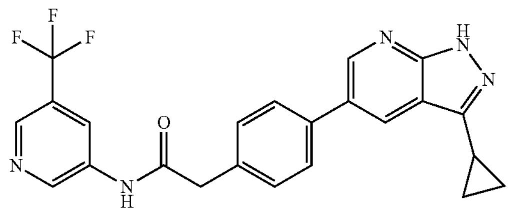 [SMILES: O=C(Cc1ccc(-c2cnc3[nH]nc(C4CC4)c3c2)cc1)Nc1cncc(C(F)(F)F)c1] | 438.3 |
| P-0074 | 2-[4-[2-(pyrazolo[1,5-a]pyridin-3-ylamino)pyrimidin-5-yl]phenyl]-N-[5-(trifluoromethyl)-3-pyridyl]acetamide | 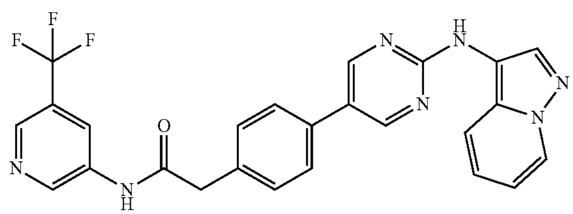 [SMILES: O=C(Cc1ccc(-c2cnc(Nc3cnn4ccccc34)nc2)cc1)Nc1cncc(C(F)(F)F)c1] | 490.3 |
| P-0075 | 2-[2,5-difluoro-4-[2-(pyrazolo[1,5-a]pyridin-3-ylamino)pyrimidin-5-yl]phenyl]-N-[5-(trifluoromethyl)-3-pyridyl]acetamide | 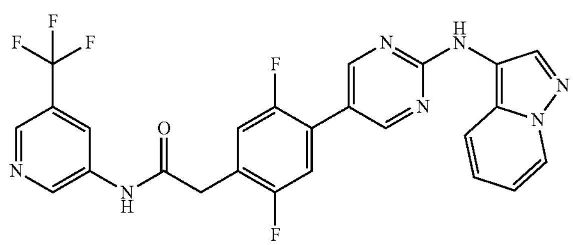 [SMILES: O=C(Cc1cc(F)c(-c2cnc(Nc3cnn4ccccc34)nc2)cc1F)Nc1cncc(C(F)(F)F)c1] | 526.3 |
| P-0076 | 2-[4-[2-[(1,5-dimethylpyrazol-4-yl)amino]pyrimidin-5-yl]-2-fluoro-phenyl]-N-[6-methyl-5-(trifluoromethyl)-3-pyridyl]acetamide | 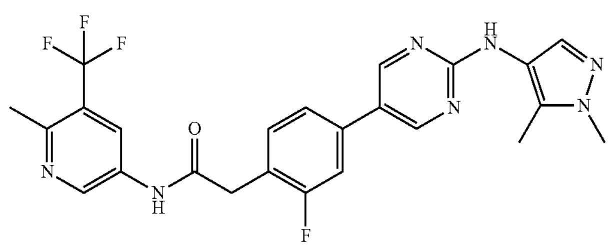 | 500.3 |
| P-0077 | 2-[4-[2-[(1,3-dimethylpyrazol-4-yl)amino]pyrimidin-5-yl]-2-fluoro-phenyl]-N-[6-methyl-5-(trifluoromethyl)-3-pyridyl]acetamide | 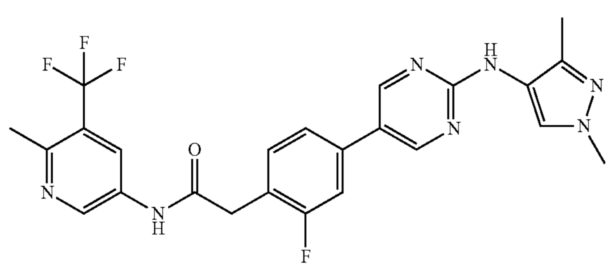 | 500.3 |

TABLE 1-continued

| Number | Compound Name | Compound Structure | (MH)+ |
|---|---|---|---|
| P-0078 | 2-(2,5-difluoro-4-(2-((1-methyl-1H-imidazol-4-yl)amino)pyrimidin-5-yl)phenyl)-N-(5-(trifluoromethyl)pyridin-3-yl)acetamide | 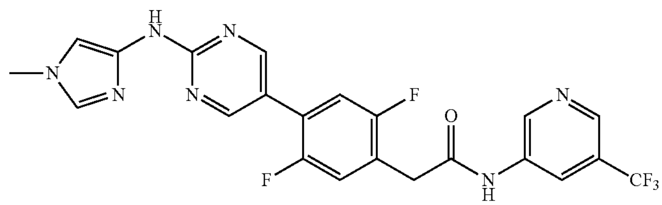 [SMILES: Cn1cnc(Nc2ncc(-c3cc(F)c(CC(=O)Nc4cncc(C(F)(F)F)c4)cc3F)cn2)c1] | 490.3 |
| P-0079 | 2-[4-(7-chloro-5H-pyrrolo[2,3-b]pyrazin-2-yl)phenyl]-N-[6-methyl-5-(trifluoromethyl)-3-pyridyl]acetamide | 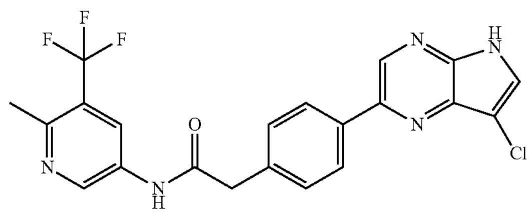 [SMILES: Cc1ncc(NC(=O)Cc2ccc(-c3cnc4[nH]cc(Cl)c4n3)cc2)cc1C(F)(F)F] | 446.2 |
| P-0080 | 2-[4-(2-cyclopropyl-1H-pyrrolo[2,3-b]pyridin-5-yl)-2-fluoro-phenyl]-N-[5-(trifluoromethyl)-3-pyridyl]acetamide | 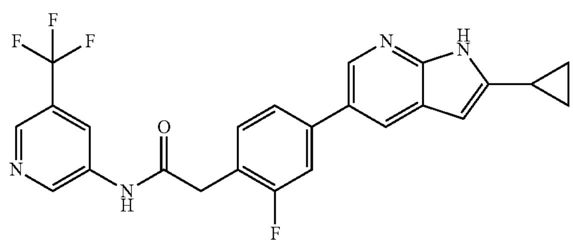 [SMILES: O=C(Cc1ccc(-c2cnc3[nH]c(C4CC4)cc3c2)cc1F)Nc1cncc(C(F)(F)F)c1] | 455.3 |
| P-0081 | N-(5-cyclopropyl-3-pyridyl)-2-[2-fluoro-4-[2-[(1-methylpyrazol-4-yl)amino]pyrimidin-5-yl]phenyl]acetamide | 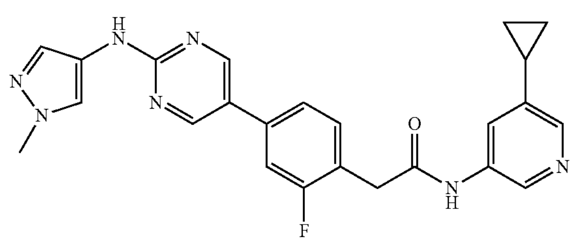 [SMILES: Cn1cc(Nc2ncc(-c3ccc(CC(=O)Nc4cncc(C5CC5)c4)c(F)c3)cn2)cn1] | 444.2 |
| P-0082 | 2-[2-fluoro-4-[2-[(1-methylpyrazol-4-yl)amino]pyrimidin-5-yl]phenyl]-N-[4-(trifluoromethyl)-2-pyridyl]acetamide | 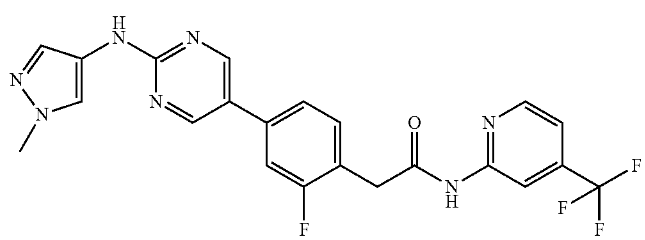 [SMILES: Cn1cc(Nc2ncc(-c3ccc(CC(=O)Nc4cc(C(F)(F)F)ccn4)c(F)c3)cn2)cn1] | 472.3 |
| P-0083 | 2-[2-fluoro-4-[2-[(1-methylpyrazol-4-yl)amino]pyrimidin-5-yl]phenyl]-N-[2-(trifluoromethyl)-4-pyridyl]acetamide | 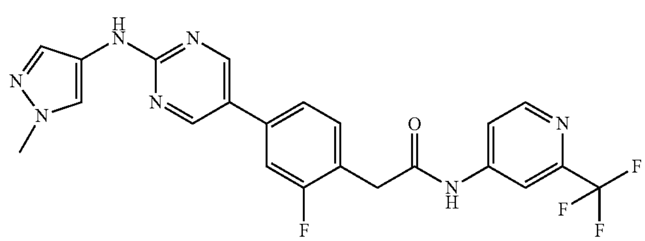 [SMILES: Cn1cc(Nc2ncc(-c3ccc(CC(=O)Nc4ccnc(C(F)(F)F)c4)c(F)c3)cn2)cn1] | 472.1 |

TABLE 1-continued

| Number | Compound Name | Compound Structure | (MH)+ |
|---|---|---|---|
| P-0084 | 2-[2-fluoro-4-[2-[(1-methylpyrazol-4-yl)amino]pyrimidin-5-yl]phenyl]-N-[5-(trifluoromethyl)-3-pyridyl]acetamide | 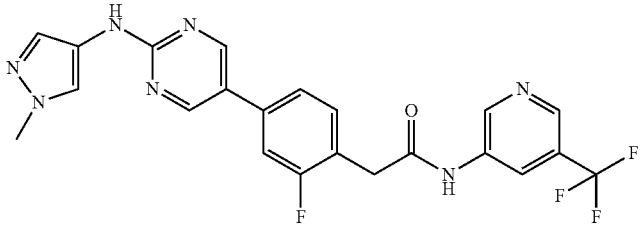 [SMILES: Cn1cc(Nc2ncc(-c3ccc(CC(=O)Nc4cncc(C(F)(F)F)c4)c(F)c3)cn2)cn1] | 472.1 |
| P-0085 | 2-[2-fluoro-4-[2-[(1-methylimidazol-4-yl)amino]pyrimidin-5-yl]phenyl]-N-(5-methoxy-3-pyridyl)acetamide | 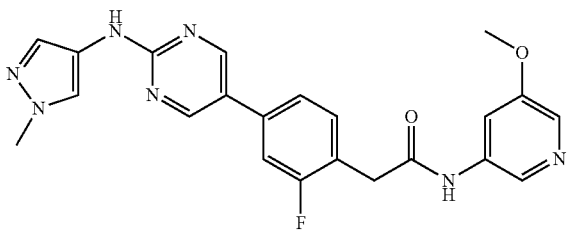 [SMILES: COc1cncc(NC(=O)Cc2ccc(-c3cnc(Nc4cnn(C)c4)nc3)cc2F)c1] | 434.1 |
| P-0086 | 2-[2-fluoro-4-[2-[(1-methylpyrazol-4-yl)amino]pyrimidin-5-yl]phenyl]-N-(5-methoxy-3-pyridyl)acetamide | 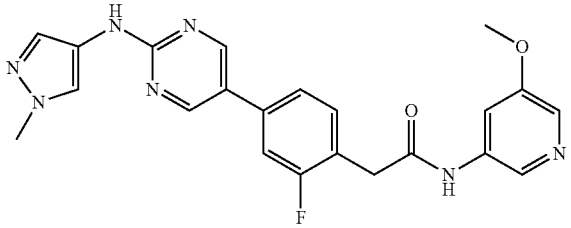 [SMILES: COc1cncc(NC(=O)Cc2ccc(-c3cnc(Nc4cnn(C)c4)nc3)cc2F)c1] | 434.3 |
| P-0087 | 2-[2-fluoro-4-[2-[(1-methylpyrazol-4-yl)amino]pyrimidin-5-yl]phenyl]-N-[[6-(trifluoromethyl)-3-pyridyl]methyl]acetamide | 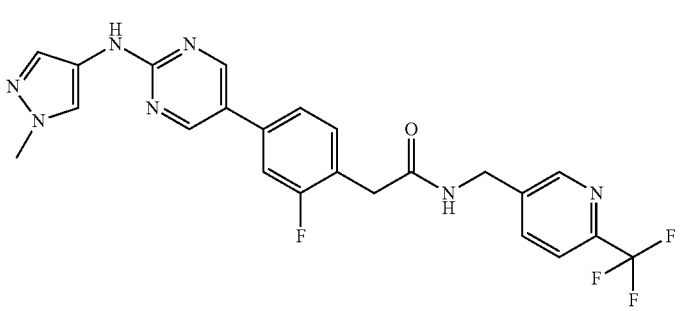 [SMILES: Cn1cc(Nc2ncc(-c3ccc(CC(=O)NCc4ccc(C(F)(F)F)nc4)c(F)c3)cn2)cn1] | 486.3 |
| P-0088 | 2-[2-fluoro-4-[2-[(1-methylpyrazol-4-yl)amino]pyrimidin-5-yl]phenyl]-N-(2-pyridylmethyl)acetamide | 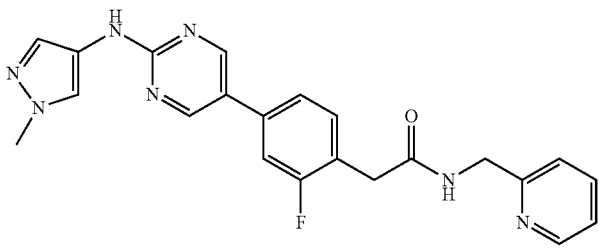 [SMILES: Cn1cc(Nc2ncc(-c3ccc(CC(=O)NCc4ccccn4)c(F)c3)cn2)cn1] | 418.3 |
| P-0089 | 2-[2-fluoro-4-[2-[(1-methylpyrazol-4-yl)amino]pyrimidin-5-yl]phenyl]-N-[6-methoxy-5-(trifluoromethyl)-3-pyridyl]acetamide | 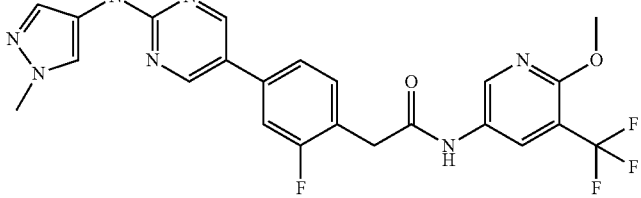 | 502.2 |

TABLE 1-continued

| Number | Compound Name | Compound Structure | (MH)+ |
|---|---|---|---|
| P-0090 | N-[5-(1,1-difluoroethyl)-3-pyridyl]-2-[2-fluoro-4-[2-[(1-methylpyrazol-4-yl)amino]pyrimidin-5-yl]phenyl]acetamide | 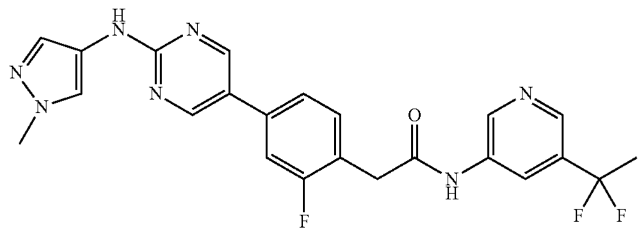 [SMILES: Cn1cc(Nc2ncc(-c3ccc(CC(=O)Nc4cncc(C(C)(F)F)c4)c(F)c3)cn2)cn1] | 468.2 |
| P-0091 | 2-[2-fluoro-4-[2-[(1-methylpyrazol-4-yl)amino]pyrimidin-5-yl]phenyl]-N-[6-methyl-5-(trifluoromethyl)-3-pyridyl]acetamide | 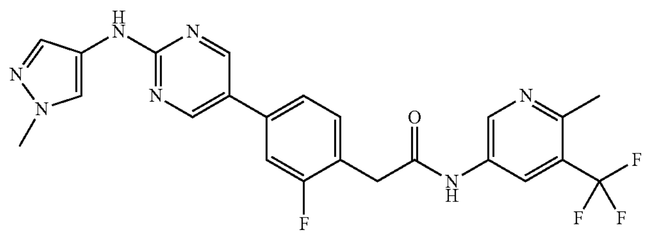 [SMILES: Cc1ncc(NC(=O)Cc2ccc(-c3cnc(Nc4cnn(C)c4)nc3)cc2F)cc1C(F)(F)F] | 486.2 |
| P-0092 | N-[6-chloro-5-(trifluoromethyl)-3-pyridyl]-2-[2-fluoro-4-[2-[(1-methylpyrazol-4-yl)amino]pyrimidin-5-yl]phenyl]acetamide | 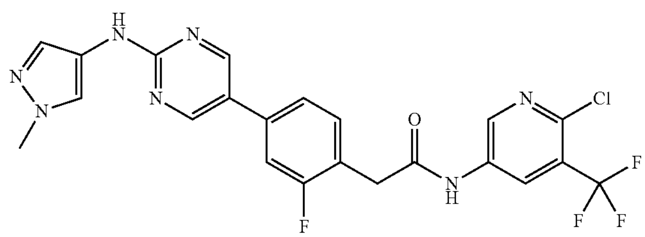 [SMILES: Cn1cc(Nc2ncc(-c3ccc(CC(=O)Nc4cnc(Cl)c(C(F)(F)F)c4)c(F)c3)cn2)cn1] | 506.3 |
| P-0093 | N-[4-(1,1-difluoroethyl)-2-pyridyl]-2-[2-fluoro-4-[2-[(1-methylpyrazol-4-yl)amino]pyrimidin-5-yl]phenyl]acetamide | 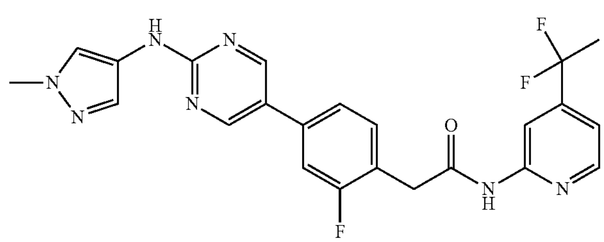 [SMILES: Cn1cc(Nc2ncc(-c3ccc(CC(=O)Nc4cc(C(C)(F)F)ccn4)c(F)c3)cn2)cn1] | 468.1 |
| P-0094 | 2-[2-fluoro-4-[2-[(1-methylpyrazol-4-yl)amino]pyrimidin-5-yl]phenyl]-N-(2-isopropyl-4-pyridyl)acetamide | 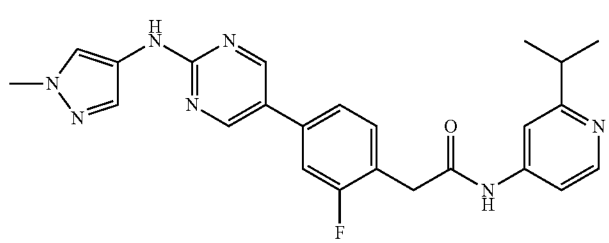 [SMILES: CC(C)c1cc(NC(=O)Cc2ccc(-c3cnc(Nc4cnn(C)c4)nc3)cc2F)ccn1] | 446.1 |

TABLE 1-continued

| Number | Compound Name | Compound Structure | (MH)+ |
|---|---|---|---|
| P-0095 | 2-[4-[2-[(1-methylpyrazol-4-yl)amino]pyrimidin-5-yl]phenyl]-N-[6-(trifluoromethyl)-3-pyridyl]acetamide | 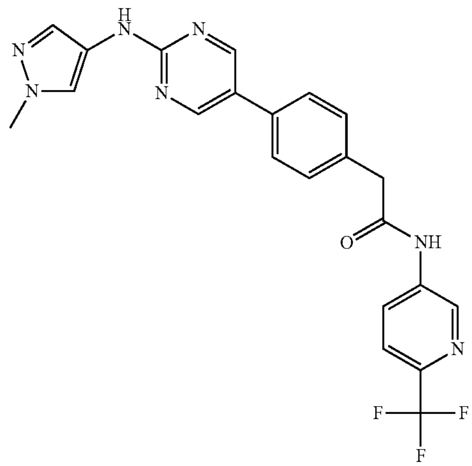 [SMILES: Cn1cc(Nc2ncc(-c3ccc(CC(=O)Nc4ccc(C(F)(F)F)nc4)cc3)cn2)cn1] | 454.1 |
| P-0096 | 2-[2-fluoro-4-[2-[(1-methylimidazol-4-yl)amino]pyrimidin-5-yl]phenyl]-N-[4-(trifluoromethyl)-2-pyridyl]acetamide | 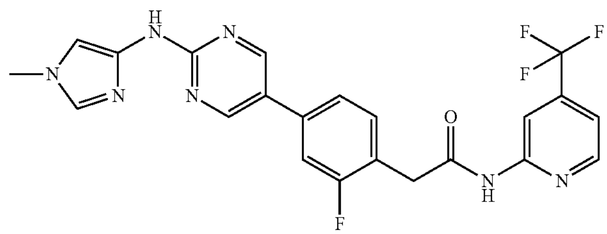 [SMILES: Cn1cnc(Nc2ncc(-c3ccc(CC(=O)Nc4cc(C(F)(F)F)ccn4)c(F)c3)cn2)c1] | 472.1 |
| P-0097 | N-(2-cyclopropyl-4-pyridyl)-2-[4-[2-[(1-methylpyrazol-4-yl)amino]pyrimidin-5-yl]phenyl]acetamide | 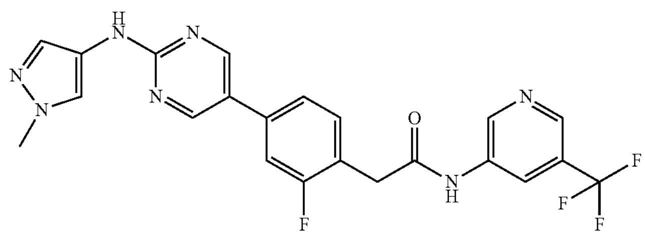 [SMILES: Cn1cc(Nc2ncc(-c3ccc(CC(=O)Nc4cncc(C(F)(F)F)c4)c(F)c3)cn2)cn1] | 426.1 |
| P-0098 | N-(2-cyclopropyl-4-pyridyl)-2-[2-fluoro-4-[2-[(1-methylpyrazol-4-yl)amino]pyrimidin-5-yl]phenyl]acetamide | 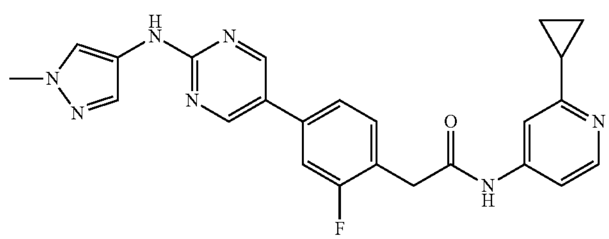 [SMILES: Cn1cc(Nc2ncc(-c3ccc(CC(=O)Nc4ccnc(C5CC5)c4)c(F)c3)cn2)cn1] | 444.1 |
| P-0099 | 2-[2-fluoro-4-[2-[(1-methylimidazol-4-yl)amino]pyrimidin-5-yl]phenyl]-N-[6-methyl-5-(trifluoromethyl)-3-pyridyl]acetamide | 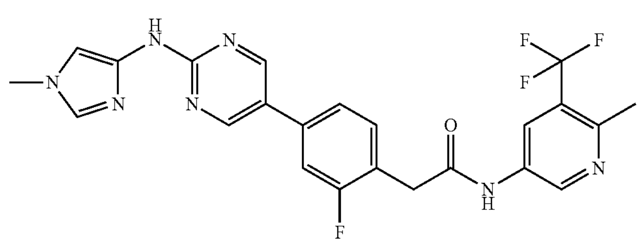 | 486.1 |

TABLE 1-continued

| Number | Compound Name | Compound Structure | (MH)+ |
|---|---|---|---|
| P-0100 | N-[6-chloro-5-(trifluoromethyl)-3-pyridyl]-2-[2-fluoro-4-[2-[(1-methylimidazol-4-yl)amino]pyrimidin-5-yl]phenyl]acetamide | 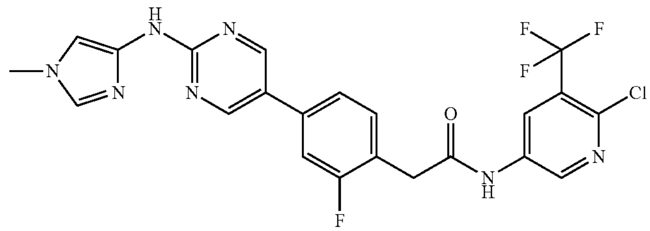 [SMILES: Cn1cnc(Nc2ncc(-c3ccc(CC(=O)Nc4cnc(Cl)c(C(F)(F)F)c4)c(F)c3)cn2)c1] | 506.0 |
| P-0101 | 2-[2-fluoro-4-[2-[(1-methylimidazol-4-yl)amino]pyrimidin-5-yl]phenyl]-N-[6-methoxy-5-(trifluoromethyl)-3-pyridyl]acetamide | 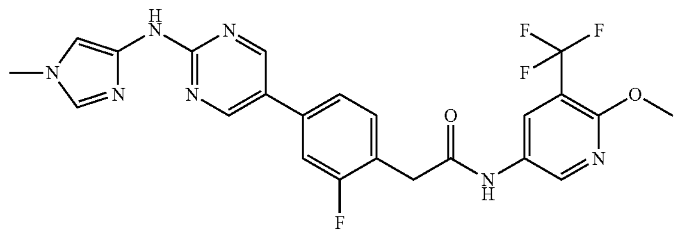 | 502.2 |
| P-0102 | N-[4-(1,1-difluoroethyl)-2-pyridyl]-2-[2-fluoro-4-[2-[(1-methylimidazol-4-yl)amino]pyrimidin-5-yl]phenyl]acetamide | 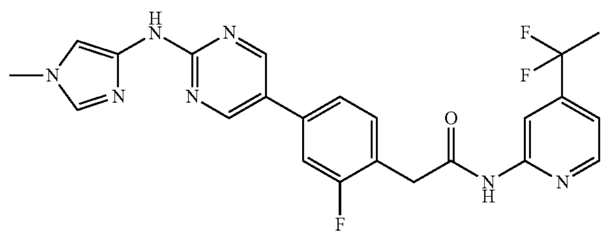 [SMILES: Cn1cnc(Nc2ncc(-c3ccc(CC(=O)Nc4cc(C(C)(F)F)ccn4)c(F)c3)cn2)c1] | 468.1 |
| P-0103 | N-[5-(1,1-difluoroethyl)-3-pyridyl]-2-[2-fluoro-4-[2-[(1-methylimidazol-4-yl)amino]pyrimidin-5-yl]phenyl]acetamide | 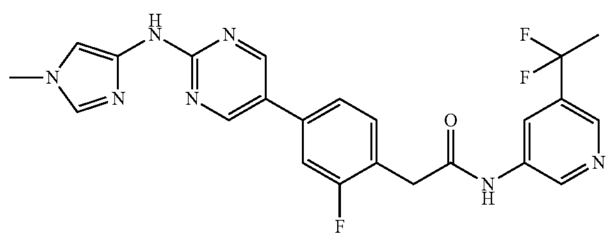 [SMILES: Cn1cnc(Nc2ncc(-c3ccc(CC(=O)Nc4cncc(C(C)(F)F)c4)c(F)c3)cn2)c1] | 468.1 |
| P-0104 | N-[5-(1,1-difluoroethyl)-6-fluoro-3-pyridyl]-2-[4-[2-[(1-methylpyrazol-4-yl)amino]pyrimidin-5-yl]phenyl]acetamide | 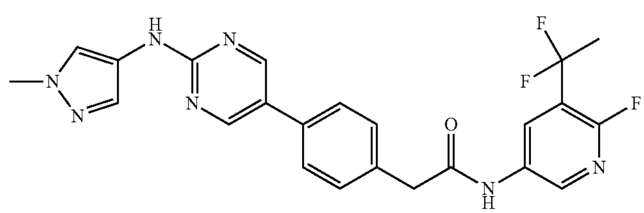 [SMILES: Cn1cc(Nc2ncc(-c3ccc(CC(=O)Nc4cnc(F)c(C(C)(F)F)c4)cc3)cn2)cn1] | 466.1 MH(−) |
| P-0105 | N-[5-(1,1-difluoroethyl)-6-fluoro-3-pyridyl]-2-[2-fluoro-4-[2-[(1-methylpyrazol-4-yl)amino]pyrimidin-5-yl]phenyl]acetamide | 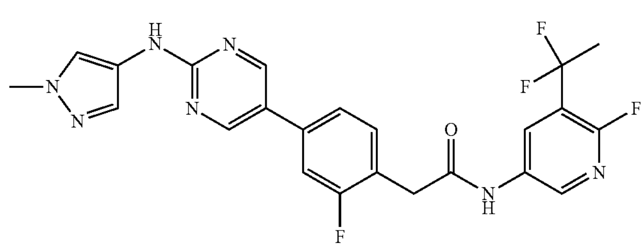 [SMILES: Cn1cc(Nc2ncc(-c3ccc(CC(=O)Nc4cnc(F)c(C(C)(F)F)c4)c(F)c3)cn2)cn1] | 486.1 |

TABLE 1-continued

| Number | Compound Name | Compound Structure | (MH)+ |
|---|---|---|---|
| P-0106 | 2-[2-fluoro-4-[2-[(1-methylpyrazol-4-yl)amino]pyrimidin-5-yl]phenyl]-N-[5-(trifluoromethyl)-2-pyridyl]acetamide | 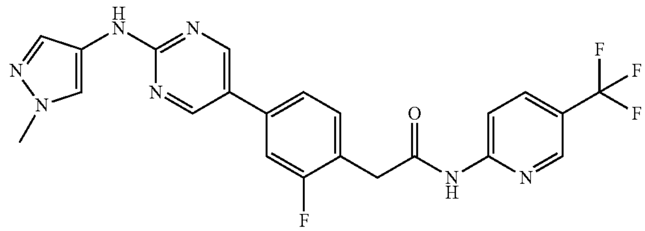 [SMILES: Cn1cc(Nc2ncc(-c3ccc(CC(=O)Nc4ccc(C(F)(F)F)cn4)c(F)c3)cn2)cn1] | 472.1 |
| P-0107 | N-(4-chloro-5-cyclopropyl-2-pyridyl)-2-[2-fluoro-4-[2-[(1-methylpyrazol-4-yl)amino]pyrimidin-5-yl]phenyl]acetamide | 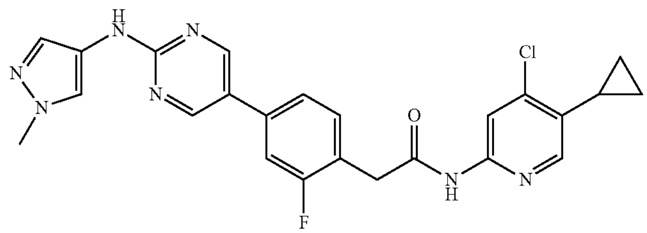 [SMILES: Cn1cc(Nc2ncc(-c3ccc(CC(=O)Nc4cc(Cl)c(C5CC5)cn4)c(F)c3)cn2)cn1] | 478.1 |
| P-0108 | N-[6-(1-cyano-1-methyl-ethyl)-3-pyridyl]-2-[2-fluoro-4-[2-[(1-methylpyrazol-4-yl)amino]pyrimidin-5-yl]phenyl]acetamide | 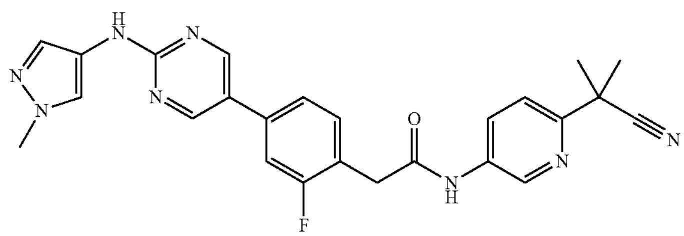 [SMILES: Cn1cc(Nc2ncc(-c3ccc(CC(=O)Nc4ccc(C(C)(C)C#N)nc4)c(F)c3)cn2)cn1] | 471.1 |
| P-0109 | 2-[4-[2-[(1-methylpyrazol-4-yl)amino]pyrimidin-5-yl]phenyl]-N-[5-(trifluoromethyl)-2-pyridyl]acetamide | 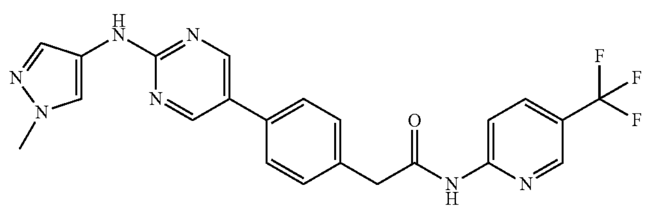 [SMILES: Cn1cc(Nc2ncc(-c3ccc(CC(=O)Nc4ccc(C(F)(F)F)cn4)cc3)cn2)cn1] | 452.0 MH(−) |
| P-0110 | 2-[2-fluoro-4-[2-[(1-methylpyrazol-4-yl)amino]pyrimidin-5-yl]phenyl]-N-[6-(trifluoromethyl)-3-pyridyl]acetamide | 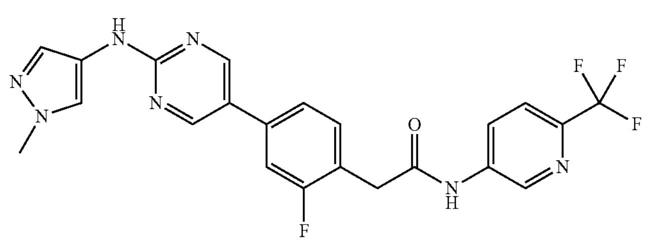 [SMILES: Cn1cc(Nc2ncc(-c3ccc(CC(=O)Nc4ccc(C(F)(F)F)nc4)c(F)c3)cn2)cn1] | 472.0 |
| P-0111 | N-(5-ethyl-3-pyridyl)-2-[2-fluoro-4-[2-[(1-methylpyrazol-4-yl)amino]pyrimidin-5-yl]phenyl]acetamide | 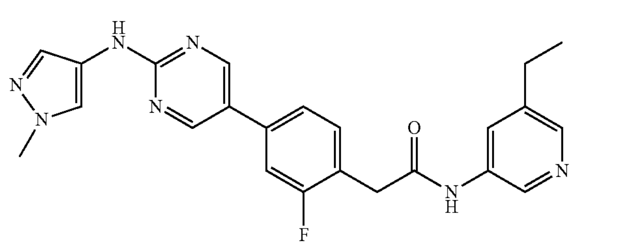 [SMILES: CCc1cncc(NC(=O)Cc2ccc(-c3cnc(Nc4cnn(C)c4)nc3)cc2F)c1] | 432.1 |

TABLE 1-continued

| Number | Compound Name | Compound Structure | (MH)+ |
|---|---|---|---|
| P-0112 | N-(2-tert-butyl-4-pyridyl)-2-[4-[2-[(1-methylpyrazol-4-yl)amino]pyrimidin-5-yl]phenyl]acetamide | 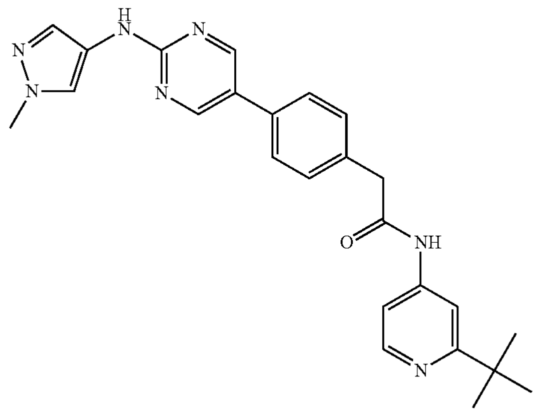 [SMILES: Cn1cc(Nc2ncc(-c3ccc(CC(=O)Nc4ccnc(C(C)(C)C)c4)cc3)cn2)cn1] | 442.3 |
| P-0113 | N-[4-cyano-3-(trifluoromethyl)phenyl]-2-[4-[2-[(1-methylpyrazol-4-yl)amino]pyrimidin-5-yl]phenyl]acetamide | 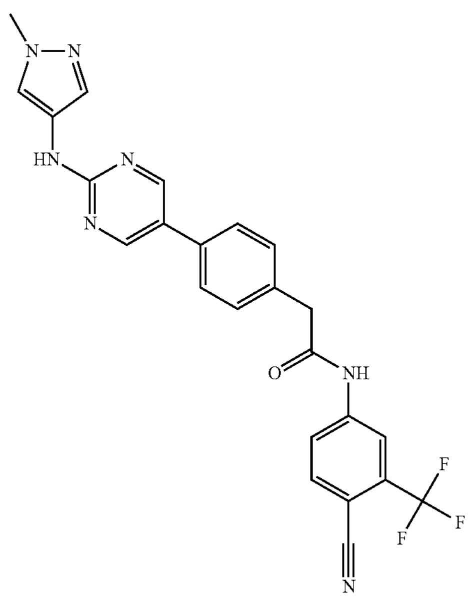 [SMILES: Cn1cc(Nc2ncc(-c3ccc(CC(=O)Nc4ccc(C#N)c(C(F)(F)F)c4)cc3)cn2)cn1] | 478.0 |
| P-0114 | N-[(5-chloro-2-pyridyl)methyl]-2-[4-[2-[(1-methylpyrazol-4-yl)amino]pyrimidin-5-yl]phenyl]acetamide | 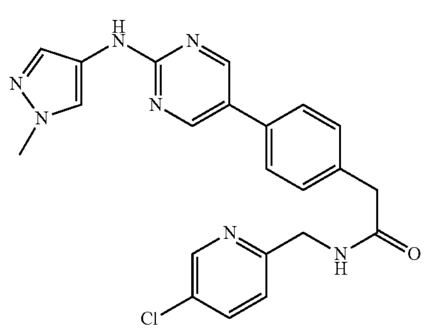 [SMILES: Cn1cc(Nc2ncc(-c3ccc(CC(=O)NCc4ccc(Cl)cn4)cc3)cn2)cn1] | 434.2 |

TABLE 1-continued

| Number | Compound Name | Compound Structure | (MH)+ |
|---|---|---|---|
| P-0115 | 2-[4-[2-[(1-methylpyrazol-4-yl)amino]pyrimidin-5-yl]phenyl]-N-[(4-methyl-2-pyridyl)methyl]acetamide | 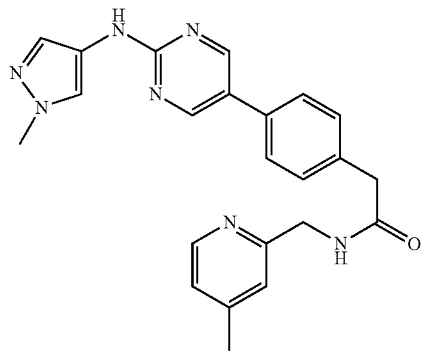 [SMILES: Cc1ccnc(CNC(=O)Cc2ccc(-c3cnc(Nc4cnn(C)c4)nc3)cc2)c1] | 414.1 |
| P-0116 | N-(5,6-dichloro-3-pyridyl)-2-[4-[2-[(1-methylpyrazol-4-yl)amino]pyrimidin-5-yl]phenyl]acetamide | 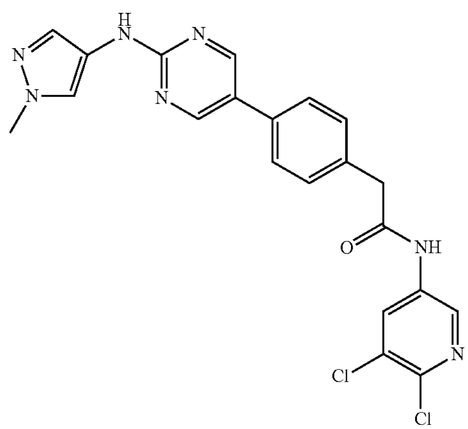 [SMILES: Cn1cc(Nc2ncc(-c3ccc(CC(=O)Nc4cnc(Cl)c(Cl)c4)cc3)cn2)cn1] | 454.0 |
| P-0117 | N-(5-bromo-6-chloro-3-pyridyl)-2-[4-[2-[(1-methylpyrazol-4-yl)amino]pyrimidin-5-yl]phenyl]acetamide | 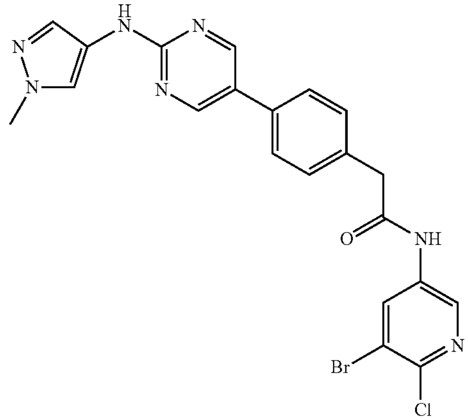 [SMILES: Cn1cc(Nc2ncc(-c3ccc(CC(=O)Nc4cnc(Cl)c(Br)c4)cc3)cn2)cn1] | 498.4 |

TABLE 1-continued

| Number | Compound Name | Compound Structure | (MH)+ |
|---|---|---|---|
| P-0118 | N-(5-bromo-6-methoxy-3-pyridyl)-2-[4-[2-[(1-methylpyrazol-4-yl)amino]pyrimidin-5-yl]phenyl]acetamide | 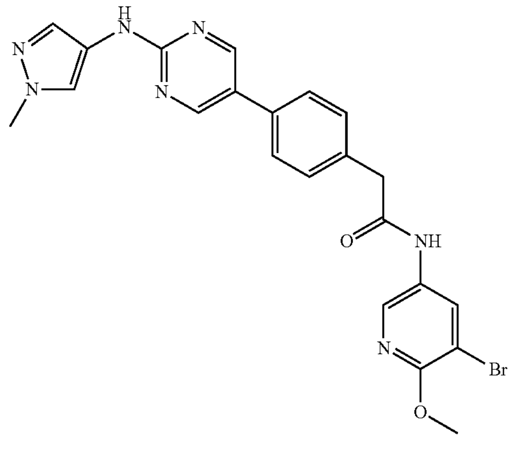 [SMILES: COc1ncc(NC(=O)Cc2ccc(-c3cnc(Nc4cnn(C)c4)nc3)cc2)cc1Br] | 494.2 |
| P-0119 | 2-[4-[2-[(1-methylpyrazol-4-yl)amino]pyrimidin-5-yl]phenyl]-N-(1H-pyrrolo[2,3-b]pyridin-5-yl)acetamide | 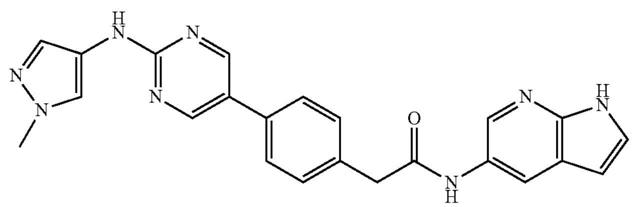 [SMILES: Cn1cc(Nc2ncc(-c3ccc(CC(=O)Nc4cnc5[nH]ccc5c4)cc3)cn2)cn1] | 425.2 |
| P-0120 | N-(3-methyl-1H-pyrazolo[3,4-b]pyridin-5-yl)-2-[4-[2-[(1-methylpyrazol-4-yl)amino]pyrimidin-5-yl]phenyl]acetamide | 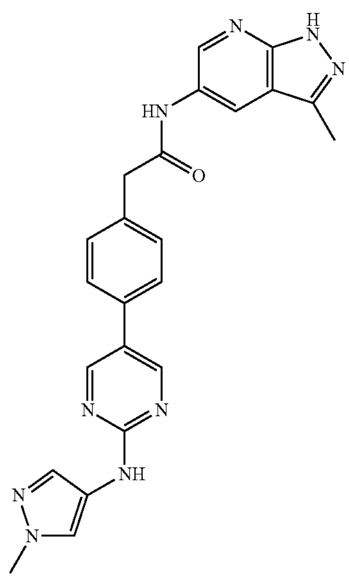 [SMILES: Cc1n[nH]c2ncc(NC(=O)Cc3ccc(-c4cnc(Nc5cnn(C)c5)nc4)cc3)cc12] | 440.2 |
| P-0121 | 2-[4-[2-[(1-methylpyrazol-4-yl)amino]pyrimidin-5-yl]phenyl]-N-[2-(trifluoromethyl)-3-pyridyl]acetamide | 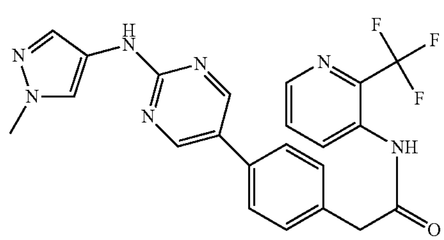 [SMILES: Cn1cc(Nc2ncc(-c3ccc(CC(=O)Nc4cccnc4C(F)(F)F)cc3)cn2)cn1] | 454.0 |

TABLE 1-continued

| Number | Compound Name | Compound Structure | (MH)+ |
|---|---|---|---|
| P-0122 | 2-[4-[2-[(1-methylpyrazol-4-yl)amino]pyrimidin-5-yl]phenyl]-N-[3-(trifluoromethyl)-4-pyridyl]acetamide | 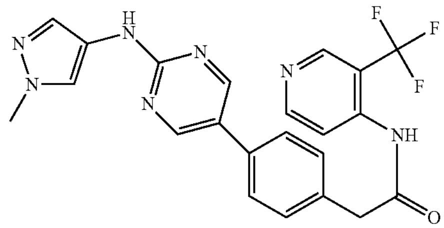 [SMILES: Cn1cc(Nc2ncc(-c3ccc(CC(=O)Nc4ccncc4C(F)(F)F)cc3)cn2)cn1] | 454.0 |
| P-0123 | N-[(2,6-dichlorophenyl)methyl]-2-[4-[2-[(1-methylpyrazol-4-yl)amino]pyrimidin-5-yl]phenyl]acetamide | 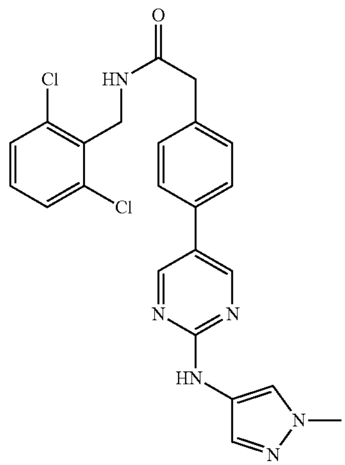 [SMILES: Cn1cc(Nc2ncc(-c3ccc(CC(=O)NCc4c(Cl)cccc4Cl)cc3)cn2)cn1] | 467.2 |
| P-0124 | N-[(2-chloro-5-fluorophenyl)methyl]-2-[4-[2-[(1-methylpyrazol-4-yl)amino]pyrimidin-5-yl]phenyl]acetamide | 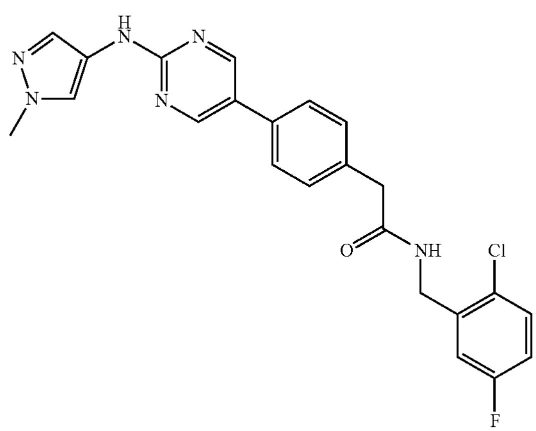 [SMILES: Cn1cc(Nc2ncc(-c3ccc(CC(=O)NCc4cc(F)ccc4Cl)cc3)cn2)cn1] | 451.0 |
| P-0125 | N-[(2-chloro-4-fluorophenyl)methyl]-2-[4-[2-[(1-methylpyrazol-4-yl)amino]pyrimidin-5-yl]phenyl]acetamide | 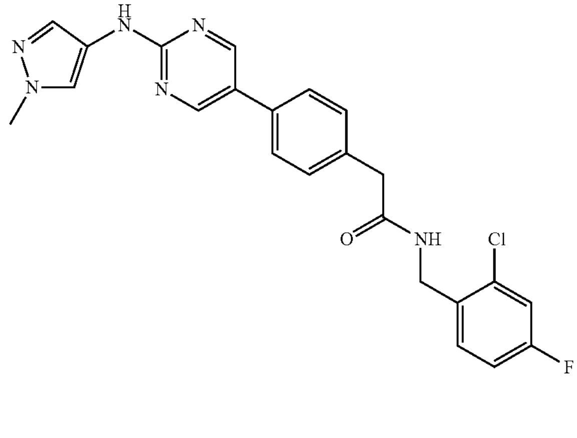 [SMILES: Cn1cc(Nc2ncc(-c3ccc(CC(=O)NCc4ccc(F)cc4Cl)cc3)cn2)cn1] | 451.0 |

TABLE 1-continued

| Number | Compound Name | Compound Structure | (MH)+ |
|---|---|---|---|
| P-0126 | N-[(2,5-dichlorophenyl)methyl]-2-[4-[2-[(1-methylpyrazol-4-yl)amino]pyrimidin-5-yl]phenyl]acetamide | 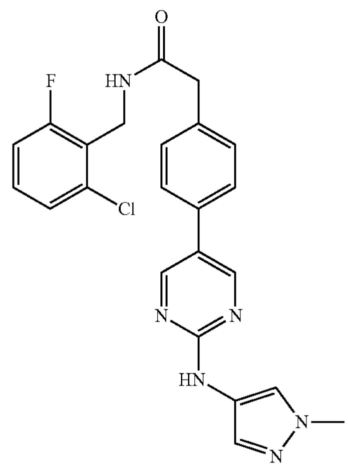 [SMILES: Cn1cc(Nc2ncc(-c3ccc(CC(=O)NCc4c(F)cccc4Cl)cc3)cn2)cn1] | 467.2 |
| P-0127 | N-[(2-chloro-6-fluoro-phenyl)methyl]-2-[4-[2-[(1-methylpyrazol-4-yl)amino]pyrimidin-5-yl]phenyl]acetamide | 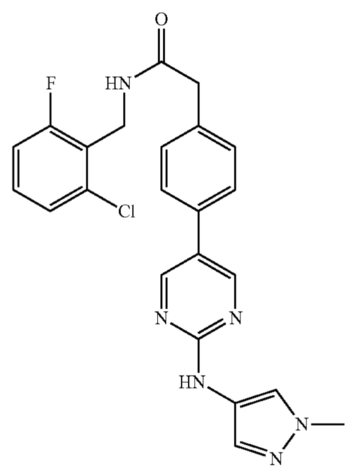 [SMILES: Cn1cc(Nc2ncc(-c3ccc(CC(=O)NCc4c(F)cccc4Cl)cc3)cn2)cn1] | 451.0 |
| P-0128 | 2-[4-[2-[(1-methylpyrazol-4-yl)amino]pyrimidin-5-yl]phenyl]-N-[[3-(trifluoromethyl)phenyl]methyl]acetamide | 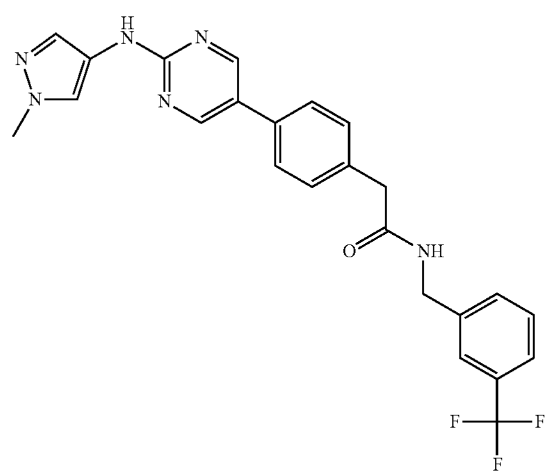 [SMILES: Cn1cc(Nc2ncc(-c3ccc(CC(=O)NCc4cccc(C(F)(F)F)c4)cc3)cn2)cn1] | 467.2 |

TABLE 1-continued

| Number | Compound Name | Compound Structure | (MH)+ |
|---|---|---|---|
| P-0129 | 2-[4-[2-[(1-methylpyrazol-4-yl)amino]pyrimidin-5-yl]phenyl]-N-[[4-(trifluoromethyl)phenyl]methyl]acetamide | 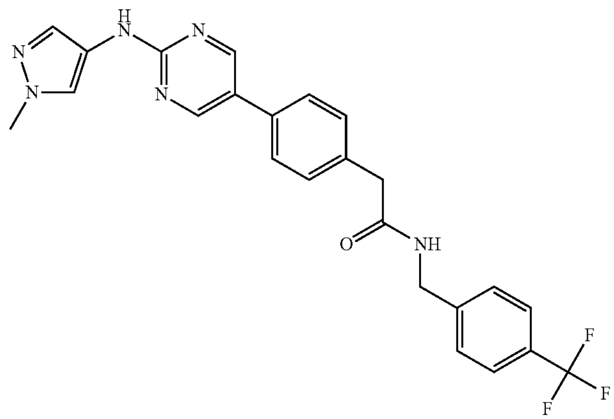 [SMILES: Cn1cc(Nc2ncc(-c3ccc(CC(=O)NCc4ccc(C(F)(F)F)cc4)cc3)cn2)cn1] | 467.2 |
| P-0130 | N-(3-methylisoxazolo[5,4-b]pyridin-5-yl)-2-[4-[2-[(1-methylpyrazol-4-yl)amino]pyrimidin-5-yl]phenyl]acetamide | 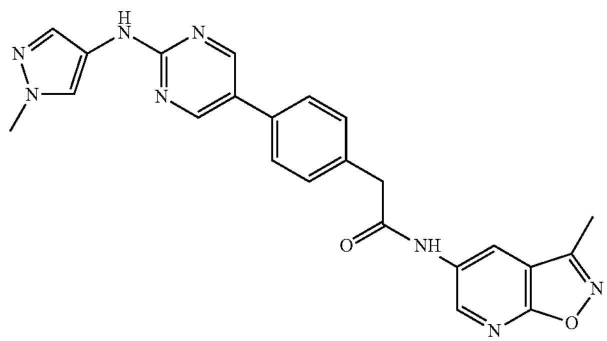 [SMILES: Cc1noc2ncc(NC(=O)Cc3ccc(-c4cnc(Nc5cnn(C)c5)nc4)cc3)cc12] | 441.1 |
| P-0131 | 2-[4-[2-[(1-methylpyrazol-4-yl)amino]pyrimidin-5-yl]phenyl]-N-(3-pyridyl)acetamide | 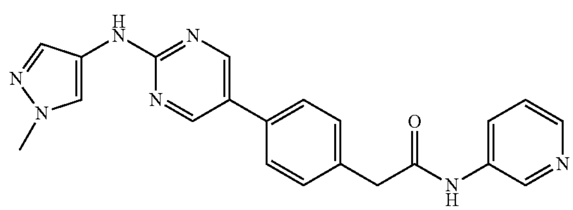 [SMILES: Cn1cc(Nc2ncc(-c3ccc(CC(=O)Nc4cccnc4)cc3)cn2)cn1] | 386.1 |
| P-0132 | 2-[4-[2-[(1-methylpyrazol-4-yl)amino]pyrimidin-5-yl]phenyl]-N-(3-pyridylmethyl)acetamide | 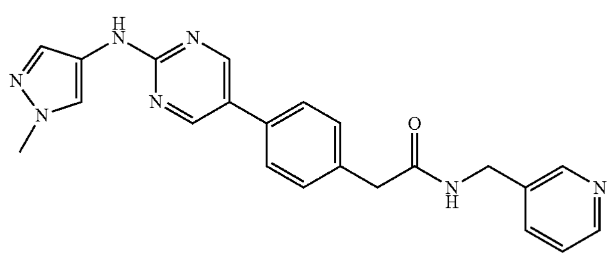 [SMILES: Cn1cc(Nc2ncc(-c3ccc(CC(=O)NCc4cccnc4)cc3)cn2)cn1] | 400.1 |
| P-0133 | N-(5-methoxy-3-pyridyl)-2-[4-[2-[(1-methylpyrazol-4-yl)amino]pyrimidin-5-yl]phenyl]acetamide | 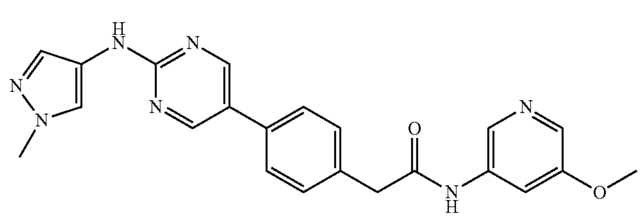 [SMILES: COc1cncc(NC(=O)Cc2ccc(-c3cnc(Nc4cnn(C)c4)nc3)cc2)c1] | 414.1 MH(−) |

TABLE 1-continued

| Number | Compound Name | Compound Structure | (MH)+ |
|---|---|---|---|
| P-0134 | 2-[4-[2-[(1-methylpyrazol-4-yl)amino]pyrimidin-5-yl]phenyl]-N-[2-(trifluoromethyl)-4-pyridyl]acetamide | 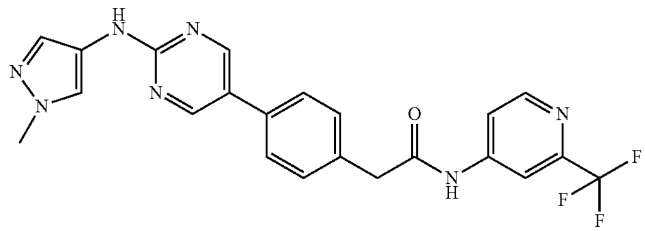 [SMILES: Cn1cc(Nc2ncc(-c3ccc(CC(=O)Nc4ccnc(C(F)(F)F)c4)cc3)cn2)cn1] | 452.2 MH(−) |
| P-0135 | 2-[4-[2-[(1-methylpyrazol-4-yl)amino]pyrimidin-5-yl]phenyl]-N-[6-(trifluoromethyl)pyrimidin-4-yl]acetamide | 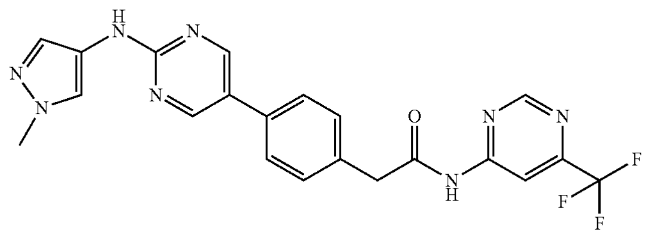 | 455.10 |
| P-0136 | 2-[4-[2-[(1-methylpyrazol-4-yl)amino]pyrimidin-5-yl]phenyl]-N-[5-(trifluoromethyl)-3-pyridyl]acetamide | 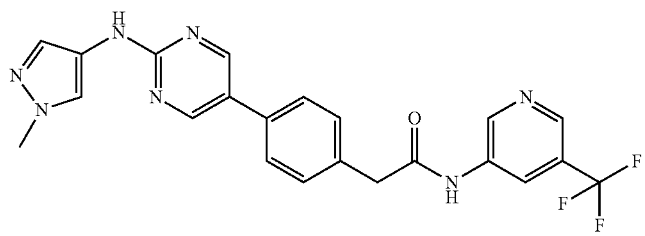 [SMILES: Cn1cc(Nc2ncc(-c3ccc(CC(=O)Nc4cncc(C(F)(F)F)c4)cc3)cn2)cn1] | 452.1 MH(−) |
| P-0137 | 2-[4-[2-[(1-methylpyrazol-4-yl)amino]pyrimidin-5-yl]phenyl]-N-[2-(trifluoromethyl)pyrimidin-4-yl]acetamide | 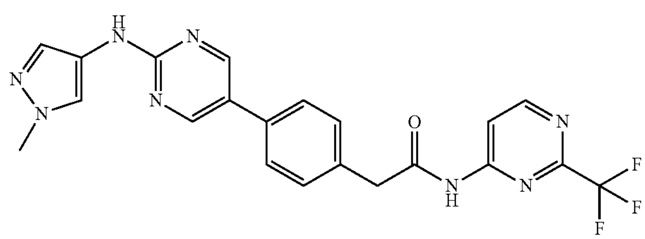 [SMILES: Cn1cc(Nc2ncc(-c3ccc(CC(=O)Nc4ccnc(C(F)(F)F)n4)cc3)cn2)cn1] | 453.1 MH(−) |
| P-0138 | N-[6-methoxy-5-(trifluoromethyl)-3-pyridyl]-2-[4-[2-[(1-methylpyrazol-4-yl)amino]pyrimidin-5-yl]phenyl]acetamide | 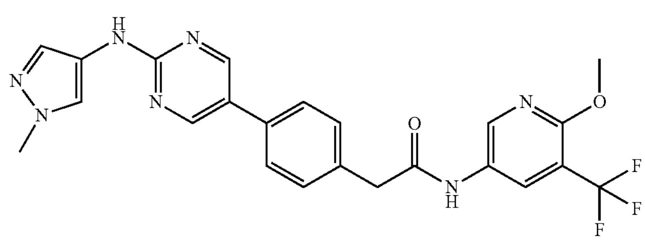 [SMILES: COc1ncc(NC(=O)Cc2ccc(-c3cnc(Nc4cnn(C)c4)nc3)cc2)cc1C(F)(F)F] | 484.15 |
| P-0139 | 2-[4-[2-[(1-methylpyrazol-4-yl)amino]pyrimidin-5-yl]phenyl]-N-[4-(trifluoromethyl)-2-pyridyl]acetamide | 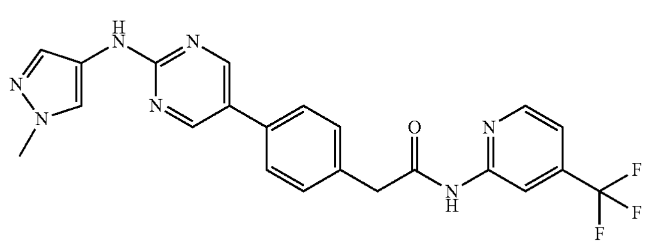 [SMILES: Cn1cc(Nc2ncc(-c3ccc(CC(=O)Nc4cc(C(F)(F)F)ccn4)cc3)cn2)cn1] | 454.10 |

TABLE 1-continued

| Number | Compound Name | Compound Structure | (MH)+ |
|---|---|---|---|
| P-0140 | 2-[4-[2-[(1-methylpyrazol-4-yl)amino]pyrimidin-5-yl]phenyl]-N-[6-methyl-5-(trifluoromethyl)-3-pyridyl]acetamide | 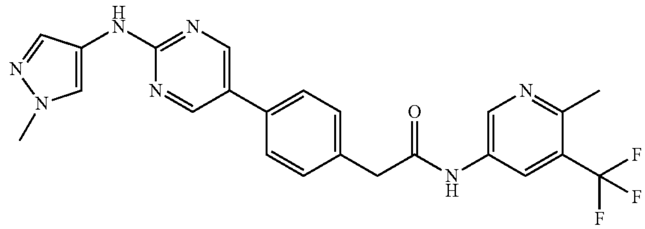 [SMILES: Cc1ncc(NC(=O)Cc2ccc(-c3cnc(Nc4cnn(C)c4)nc3)cc2)cc1C(F)(F)F] | 468.3 |
| P-0141 | 2-[4-[2-[(1-methylpyrazol-4-yl)amino]pyrimidin-5-yl]phenyl]-N-[3-(trifluoromethyl)phenyl]acetamide | 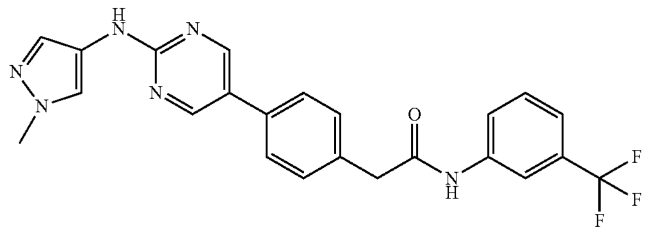 [SMILES: Cn1cc(Nc2ncc(-c3ccc(CC(=O)Nc4cccc(C(F)(F)F)c4)cc3)cn2)cn1] | 451.1 MH(−) |
| P-0142 | N-[3-fluoro-4-(trifluoromethyl)phenyl]-2-[4-[2-[(1-methylpyrazol-4-yl)amino]pyrimidin-5-yl]phenyl]acetamide | 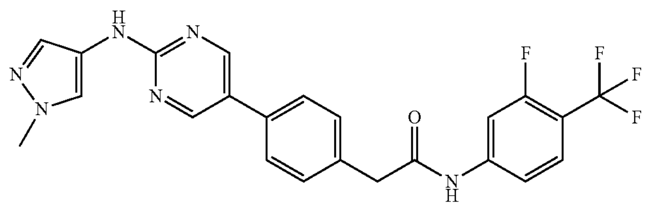 [SMILES: Cn1cc(Nc2ncc(-c3ccc(CC(=O)Nc4ccc(C(F)(F)F)c(F)c4)cc3)cn2)cn1] | 469.1 MH(−) |
| P-0143 | N-(6-tert-butyl-3-pyridyl)-2-[4-[2-[(1-methylpyrazol-4-yl)amino]pyrimidin-5-yl]phenyl]acetamide | 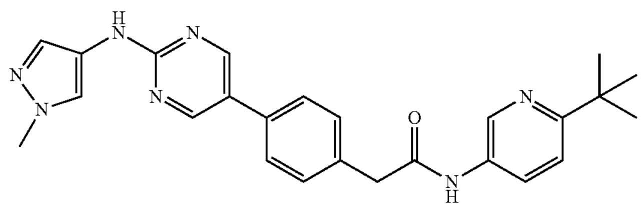 [SMILES: Cn1cc(Nc2ncc(-c3ccc(CC(=O)Nc4ccc(C(C)(C)C)nc4)cc3)cn2)cn1] | 442.2 |
| P-0144 | N-[5-(1,1-difluoroethyl)-3-pyridyl]-2-[4-[2-[(1-methylpyrazol-4-yl)amino]pyrimidin-5-yl]phenyl]acetamide | 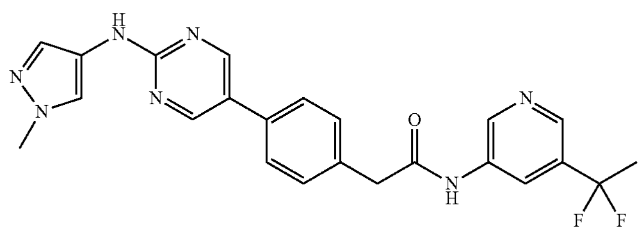 [SMILES: Cn1cc(Nc2ncc(-c3ccc(CC(=O)Nc4cncc(C(C)(F)F)c4)cc3)cn2)cn1] | 450.3 |
| P-0145 | N-[6-chloro-5-(trifluoromethyl)-3-pyridyl]-2-[4-[2-[(1-methylpyrazol-4-yl)amino]pyrimidin-5-yl]phenyl]acetamide | 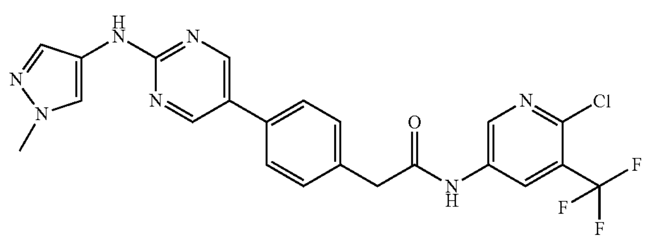 [SMILES: Cn1cc(Nc2ncc(-c3ccc(CC(=O)Nc4cnc(Cl)c(C(F)(F)F)c4)cc3)cn2)cn1] | 488.3 |
| P-0146 | N-[6-(1-cyano-1-methyl-ethyl)-3-pyridyl]-2-[4-[2-[(1-methylpyrazol-4-yl)amino]pyrimidin-5-yl]phenyl]acetamide | 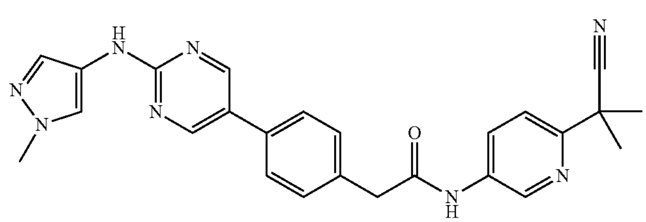 [SMILES: Cn1cc(Nc2ncc(-c3ccc(CC(=O)Nc4ccc(C(C)(C)C#N)nc4)cc3)cn2)cn1] | 451.1 MH(−) |

TABLE 1-continued

| Number | Compound Name | Compound Structure | (MH)+ |
|---|---|---|---|
| P-0147 | N-[4-(1,1-difluoroethyl)-2-pyridyl]-2-[4-[2-[(1-methylpyrazol-4-yl)amino]pyrimidin-5-yl]phenyl]acetamide | 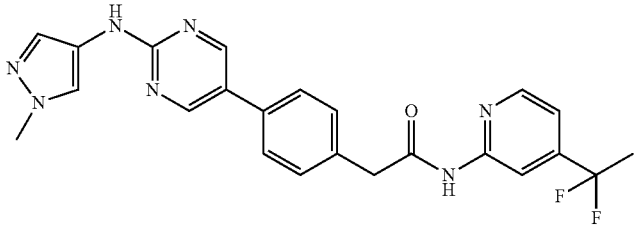 [SMILES: Cn1cc(Nc2ncc(-c3ccc(CC(=O)Nc4cc(C(C)(F)F)ccn4)cc3)cn2)cn1] | 450.1 |
| P-0148 | N-[6-chloro-5-(trifluoromethyl)-3-pyridyl]-2-[4-[2-[(1-methylimidazol-4-yl)amino]pyrimidin-5-yl]phenyl]acetamide | 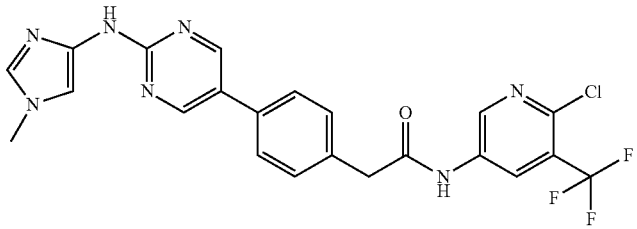 [SMILES: Cn1cnc(Nc2ncc(-c3ccc(CC(=O)Nc4cnc(Cl)c(C(F)(F)F)c4)cc3)cn2)c1] | 488.0 |
| P-0149 | N-[6-methoxy-5-(trifluoromethyl)-3-pyridyl]-2-[4-[2-[(1-methylimidazol-4-yl)amino]pyrimidin-5-yl]phenyl]acetamide | 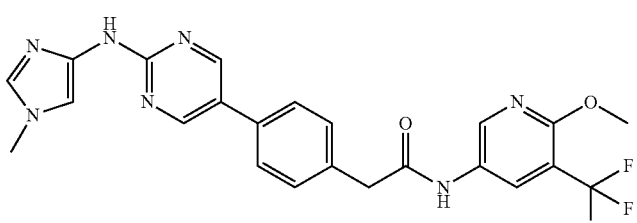 | 482.05 |
| P-0150 | 2-[4-[2-[(1-methylimidazol-4-yl)amino]pyrimidin-5-yl]phenyl]-N-[6-methyl-5-(trifluoromethyl)-3-pyridyl]acetamide | 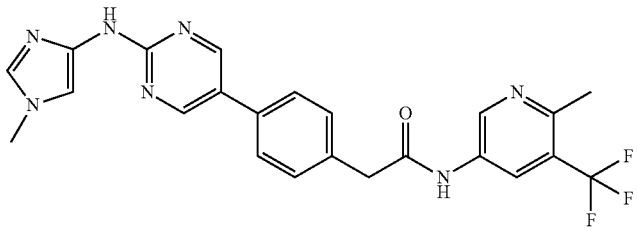 [SMILES: Cc1ncc(NC(=O)Cc2ccc(-c3cnc(Nc4cn(C)cn4)nc3)cc2)cc1C(F)(F)F] | 466.05 MH(−) |
| P-0151 | N-(6-chloropyridazin-4-yl)-2-[4-[2-[(1-methylpyrazol-4-yl)amino]pyrimidin-5-yl]phenyl]acetamide | 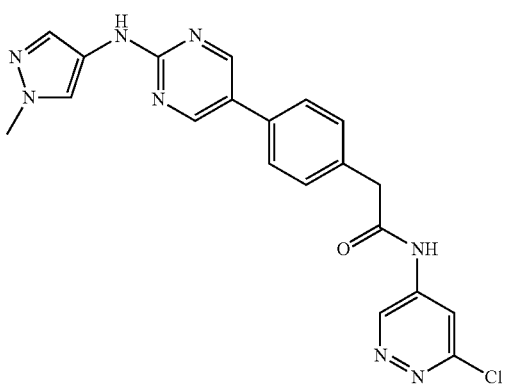 [SMILES: Cn1cc(Nc2ncc(-c3ccc(CC(=O)Nc4cnnc(Cl)c4)cc3)cn2)cn1] | 421.0 |

TABLE 1-continued

| Number | Compound Name | Compound Structure | (MH)+ |
|---|---|---|---|
| P-0152 | 2-[4-[2-[(1-methylpyrazol-4-yl)amino]pyrimidin-5-yl]phenyl]-N-[6-(trifluoromethyl)-2-pyridyl]acetamide | 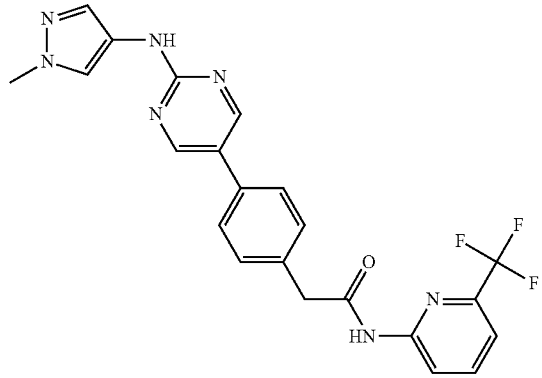 [SMILES: Cn1cc(Nc2ncc(-c3ccc(CC(=O)Nc4cccc(C(F)(F)F)n4)cc3)cn2)cn1] | 454.0 |
| P-0153 | N-(2-methoxy-4-pyridyl)-2-[4-[2-[(1-methylpyrazol-4-yl)amino]pyrimidin-5-yl]phenyl]acetamide | 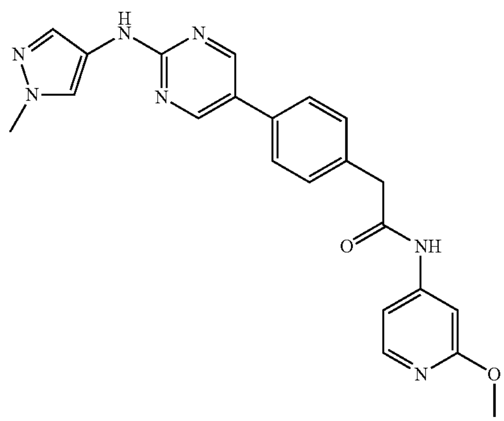 | 416.2 |
| P-0154 | 2-[4-[2-[(1-methylpyrazol-4-yl)amino]pyrimidin-5-yl]phenyl]-N-(2-methylsulfonyl-4-pyridyl)acetamide | 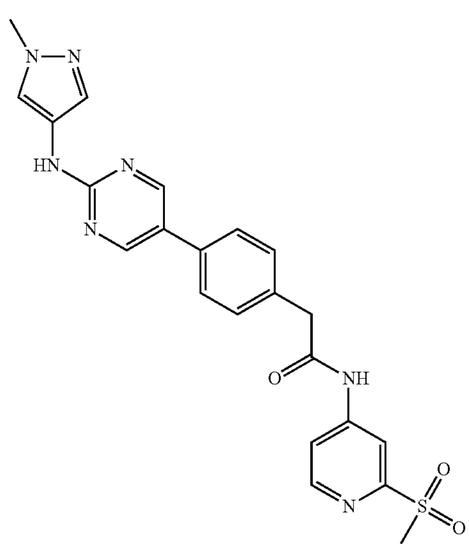 [SMILES: Cn1cc(Nc2ncc(-c3ccc(CC(=O)Nc4ccnc(S(C)(=O)=O)c4)cc3)cn2)cn1] | 464.2 |

TABLE 1-continued

| Number | Compound Name | Compound Structure | (MH)+ |
|---|---|---|---|
| P-0155 | 2-[4-[2-[(1-methylpyrazol-4-yl)amino]pyrimidin-5-yl]phenyl]-N-(3-methylsulfonylphenyl)acetamide | 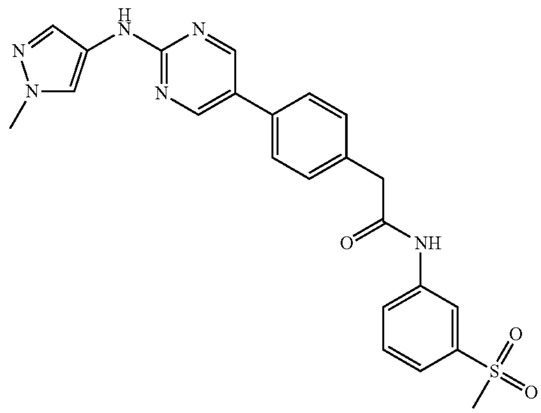 [SMILES: Cn1cc(Nc2ncc(-c3ccc(CC(=O)Nc4cccc(S(C)(=O)=O)c4)cc3)cn2)cn1] | 463.3 |
| P-0156 | 2-[4-[2-[(1-methylpyrazol-4-yl)amino]pyrimidin-5-yl]phenyl]-N-(4-methylsulfonylphenyl)acetamide | 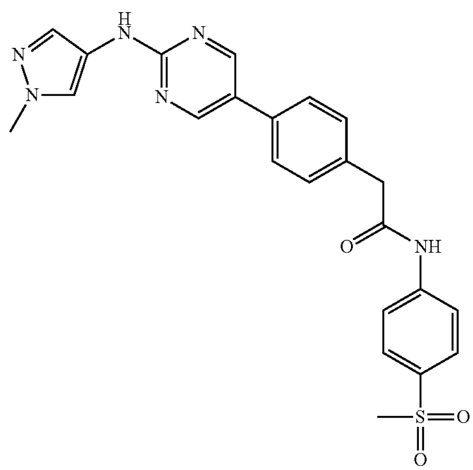 [SMILES: Cn1cc(Nc2ncc(-c3ccc(CC(=O)Nc4ccc(S(C)(=O)=O)cc4)cc3)cn2)cn1] | 463.3 |
| P-0157 | 2-[4-[2-[(1-methylpyrazol-4-yl)amino]pyrimidin-5-yl]phenyl]-N-[3-(trifluoromethoxy)phenyl]acetamide | 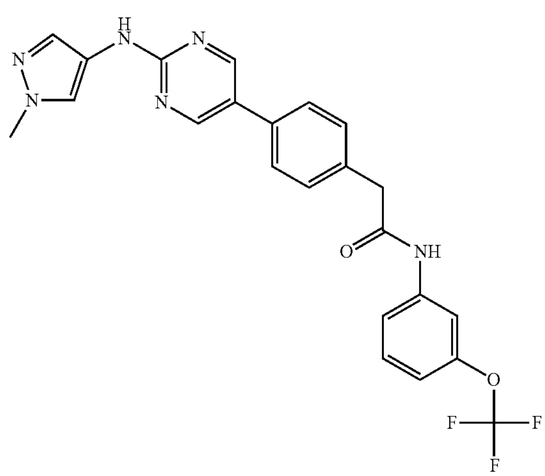 [SMILES: Cn1cc(Nc2ncc(-c3ccc(CC(=O)Nc4cccc(OC(F)(F)F)c4)cc3)cn2)cn1] | 469.3 |

TABLE 1-continued

| Number | Compound Name | Compound Structure | (MH)+ |
|---|---|---|---|
| P-0158 | N-[3-(1-cyano-1-methyl-ethyl)phenyl]-2-[4-[2-[(1-methylpyrazol-4-yl)amino]pyrimidin-5-yl]phenyl]acetamide | 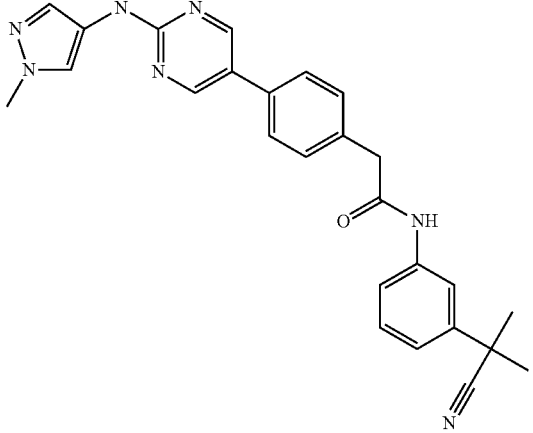 | 452.2 |
| P-0159 | 2-[4-[2-[(1-methylpyrazol-4-yl)amino]pyrimidin-5-yl]phenyl]-N-[[3-(trifluoromethyl)-2-pyridyl]methyl]acetamide | 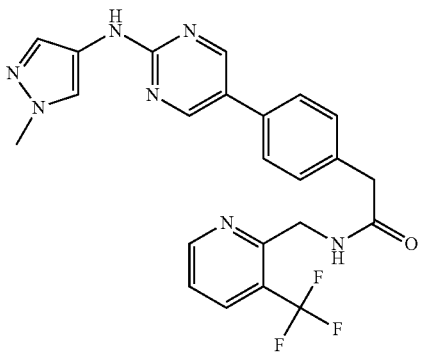 [SMILES: Cn1cc(Nc2ncc(-c3ccc(CC(=O)NCc4ncccc4C(F)(F)F)cc3)cn2)cn1] | 468.1 |
| P-0160 | N-[(2-methoxyphenyl)methyl]-2-[4-[2-[(1-methylpyrazol-4-yl)amino]pyrimidin-5-yl]phenyl]acetamide | 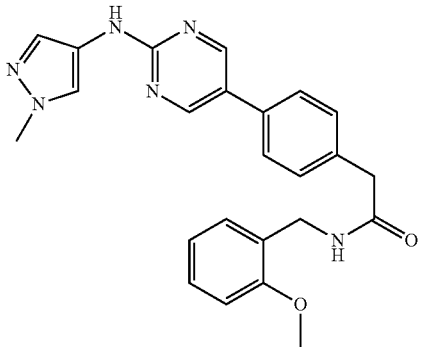 [SMILES: COc1ccccc1CNC(=O)Cc1ccc(-c2cnc(Nc3cnn(C)c3)nc2)cc1] | 429.1 |
| P-0161 | 2-[4-[2-[(1-methylpyrazol-4-yl)amino]pyrimidin-5-yl]phenyl]-N-[[5-(trifluoromethyl)-3-pyridyl]methyl]acetamide | 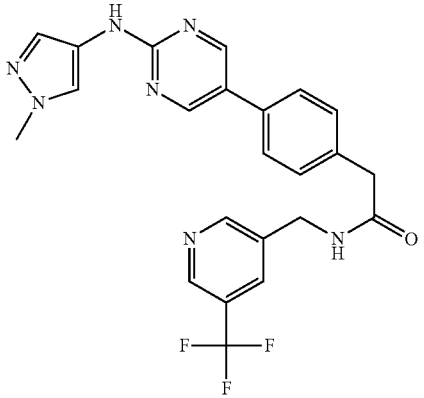 [SMILES: Cn1cc(Nc2ncc(-c3ccc(CC(=O)NCc4cncc(C(F)(F)F)c4)cc3)cn2)cn1] | 468.1 |

TABLE 1-continued

| Number | Compound Name | Compound Structure | (MH)+ |
|---|---|---|---|
| P-0162 | 2-[4-[2-[(1-methylpyrazol-4-yl)amino]pyrimidin-5-yl]phenyl]-N-[[5-(trifluoromethyl)-2-pyridyl]methyl]acetamide | 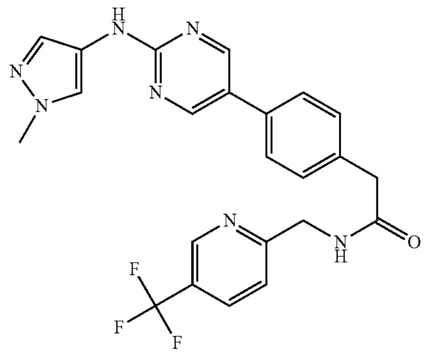 [SMILES: Cn1cc(Nc2ncc(-c3ccc(CC(=O)NCc4ccc(C(F)(F)F)cn4)cc3)cn2)cn1] | 468.1 |
| P-0163 | N-(4,5-difluoro-2-pyridyl)-2-[4-[2-[(1-methylpyrazol-4-yl)amino]pyrimidin-5-yl]phenyl]acetamide | 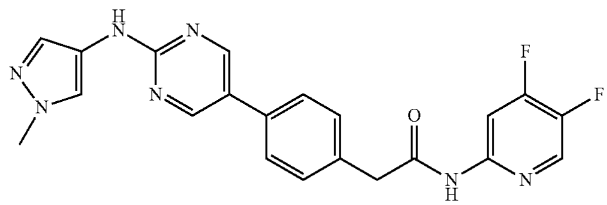 [SMILES: Cn1cc(Nc2ncc(-c3ccc(CC(=O)Nc4cc(F)c(F)cn4)cc3)cn2)cn1] | 422.1 |
| P-0164 | N-(4-chloro-5-cyclopropyl-2-pyridyl)-2-[4-[2-[(1-methylpyrazol-4-yl)amino]pyrimidin-5-yl]phenyl]acetamide | 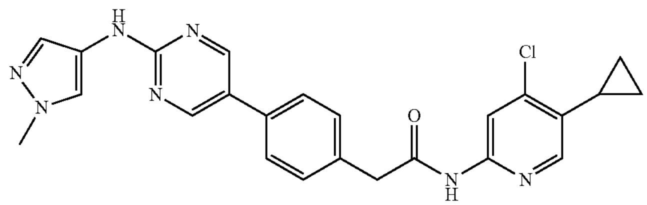 [SMILES: Cn1cc(Nc2ncc(-c3ccc(CC(=O)Nc4cc(Cl)c(C5CC5)cn4)cc3)cn2)cn1] | 460.1 |
| P-0165 | N-[6-chloro-5-(trifluoromethyl)-3-pyridyl]-2-[4-[2-[(1-ethylpyrazol-4-yl)amino]pyrimidin-5-yl]phenyl]acetamide | 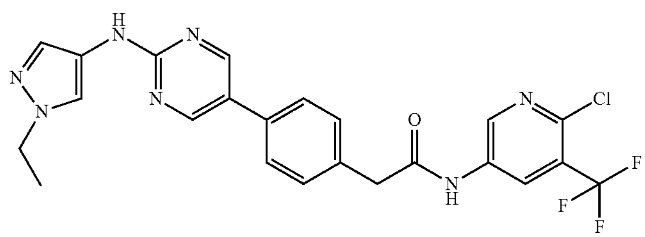 [SMILES: CCn1cc(Nc2ncc(-c3ccc(CC(=O)Nc4cnc(Cl)c(C(F)(F)F)c4)cc3)cn2)cn1] | 502.0 |
| P-0166 | 2-[4-[2-[(1-ethylpyrazol-4-yl)amino]pyrimidin-5-yl]phenyl]-N-[5-(trifluoromethyl)-3-pyridyl]acetamide | 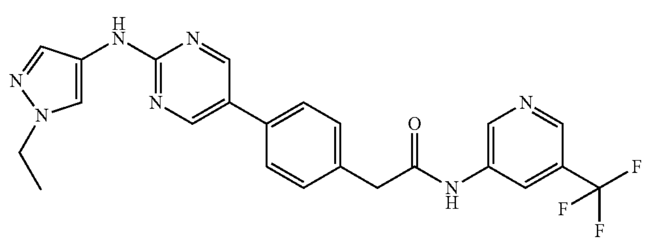 [SMILES: CCn1cc(Nc2ncc(-c3ccc(CC(=O)Nc4cncc(C(F)(F)F)c4)cc3)cn2)cn1] | 468.1 |
| P-0167 | 2-[4-[2-[(1-methylimidazol-4-yl)amino]pyrimidin-5-yl]phenyl]-N-[5-(trifluoromethyl)-3-pyridyl]acetamide | 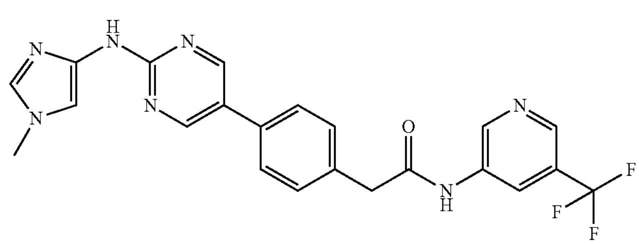 [SMILES: Cn1cnc(Nc2ncc(-c3ccc(CC(=O)Nc4cncc(C(F)(F)F)c4)cc3)cn2)c1] | 454.0 |

TABLE 1-continued

| Number | Compound Name | Compound Structure | (MH)+ |
|---|---|---|---|
| P-0168 | N-[5-(1,1-difluoroethyl)-6-fluoro-3-pyridyl]-2-[4-[2-[(1-methylimidazol-4-yl)amino]pyrimidin-5-yl]phenyl]acetamide | 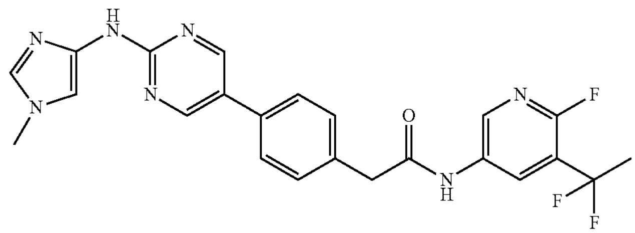 [SMILES: Cn1cnc(Nc2ncc(-c3ccc(CC(=O)Nc4cnc(F)c(C(C)(F)F)c4)cc3)cn2)c1] | 468.1 |
| P-0169 | N-[4-(1,1-difluoroethyl)-2-pyridyl]-2-[4-[2-[(1-methylimidazol-4-yl)amino]pyrimidin-5-yl]phenyl]acetamide | 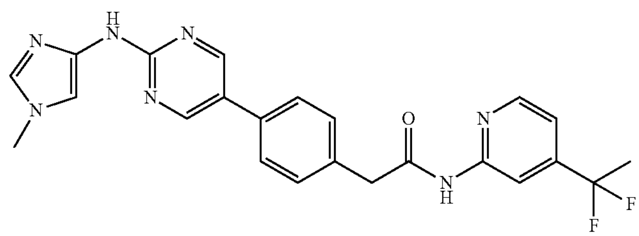 [SMILES: Cn1cnc(Nc2ncc(-c3ccc(CC(=O)Nc4cc(C(C)(F)F)ccn4)cc3)cn2)c1] | 450.1 |
| P-0170 | N-[5-(1,1-difluoroethyl)-6-fluoro-3-pyridyl]-2-[3-fluoro-4-[2-[(1-methylimidazol-4-yl)amino]pyrimidin-5-yl]phenyl]acetamide | 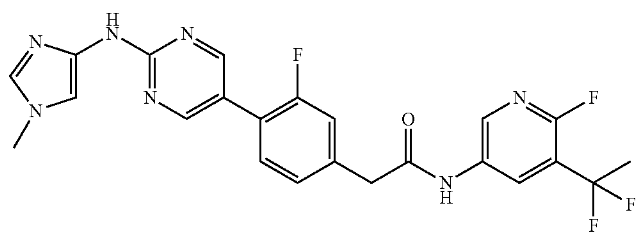 [SMILES: Cn1cnc(Nc2ncc(-c3ccc(CC(=O)Nc4cnc(F)c(C(C)(F)F)c4)cc3F)cn2)c1] | 486.1 |
| P-0171 | N-[4-(1,1-difluoroethyl)-2-pyridyl]-2-[3-fluoro-4-[2-[(1-methylimidazol-4-yl)amino]pyrimidin-5-yl]phenyl]acetamide | 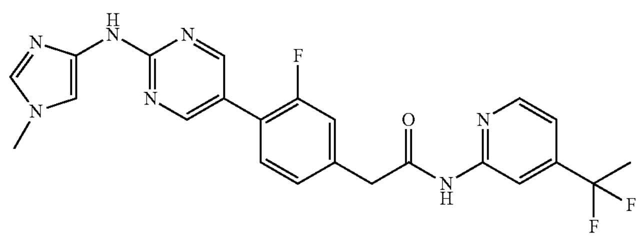 [SMILES: Cn1cnc(Nc2ncc(-c3ccc(CC(=O)Nc4cc(C(C)(F)F)ccn4)cc3F)cn2)c1] | 468.1 |
| P-0172 | 2-[3-fluoro-4-(3-methyl-1H-pyrazolo[3,4-b]pyridin-5-yl)phenyl]-N-[6-methyl-5-(trifluoromethyl)-3-pyridyl]acetamide | 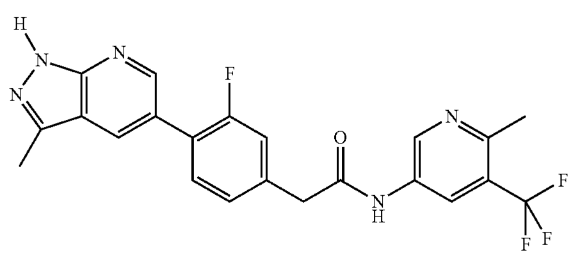 [SMILES: Cc1ncc(NC(=O)Cc2ccc(-c3cnc4[nH]nc(C)c4c3)c(F)c2)cc1C(F)(F)F] | 444.2 |
| P-0173 | 2-[2,5-difluoro-4-(3-methyl-1H-pyrazolo[3,4-b]pyridin-5-yl)phenyl]-N-[5-(trifluoromethyl)-3-pyridyl]acetamide | 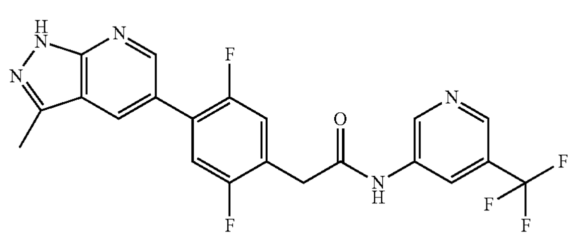 [SMILES: Cc1n[nH]c2ncc(-c3cc(F)c(CC(=O)Nc4cncc(C(F)(F)F)c4)cc3F)cc12] | 448.3 |

TABLE 1-continued

| Number | Compound Name | Compound Structure | (MH)+ |
|---|---|---|---|
| P-0174 | 2-[3-fluoro-4-(3-methyl-1H-pyrazolo[3,4-b]pyridin-5-yl)phenyl]-N-[6-methoxy-5-(trifluoromethyl)-3-pyridyl]acetamide | 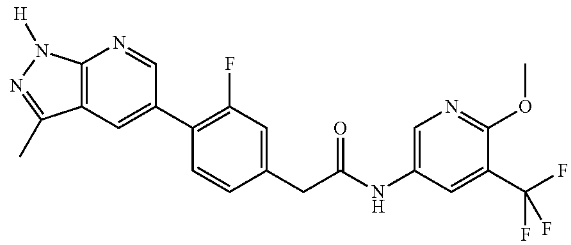 [SMILES: COc1ncc(NC(=O)Cc2ccc(-c3cnc4[nH]nc(C)c4c3)c(F)c2)cc1C(F)(F)F] | 460.3 |
| P-0175 | 2-[2,5-difluoro-4-(3-methyl-1H-pyrazolo[3,4-b]pyridin-5-yl)phenyl]-N-[6-methyl-5-(trifluoromethyl)-3-pyridyl]acetamide | 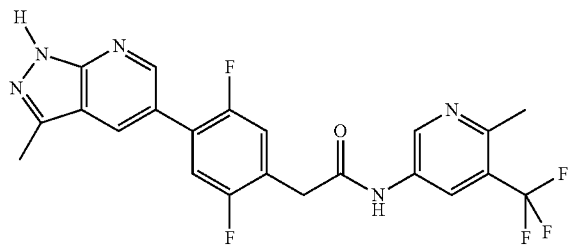 [SMILES: Cc1ncc(NC(=O)Cc2cc(F)c(-c3cnc4[nH]nc(C)c4c3)cc2F)cc1C(F)(F)F] | 462.3 |
| P-0176 | 2-[2,5-difluoro-4-(3-methyl-1H-pyrazolo[3,4-b]pyridin-5-yl)phenyl]-N-[6-methoxy-5-(trifluoromethyl)-3-pyridyl]acetamide | 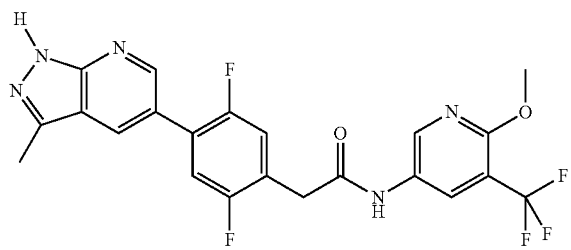 | 478.2 |
| P-0177 | 2-[3-fluoro-4-(3-methyl-1H-pyrazolo[3,4-b]pyridin-5-yl)phenyl]-N-[5-(trifluoromethyl)-3-pyridyl]acetamide | 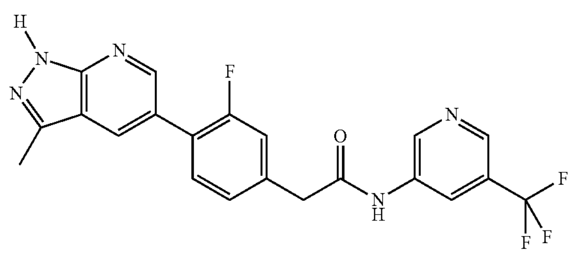 [SMILES: Cc1n[nH]c2ncc(-c3ccc(CC(=O)Nc4cncc(C(F)(F)F)c4)cc3F)cc12] | 430.3 |
| P-0178 | 2-[4-[2-[[1-(2-methoxyethyl)pyrazol-4-yl]amino]pyrimidin-5-yl]phenyl]-N-[5-(trifluoromethyl)-3-pyridyl]acetamide | 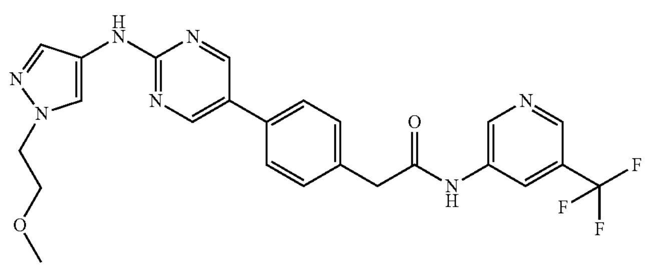 [SMILES: COCCn1cc(Nc2ncc(-c3ccc(CC(=O)Nc4cncc(C(F)(F)F)c4)cc3)cn2)cn1] | 498.4 |
| P-0179 | 2-[4-[2-[[1-(2-methoxyethyl)pyrazol-4-yl]amino]pyrimidin-5-yl]phenyl]-N-[6-methyl-5-(trifluoromethyl)-3-pyridyl]acetamide | 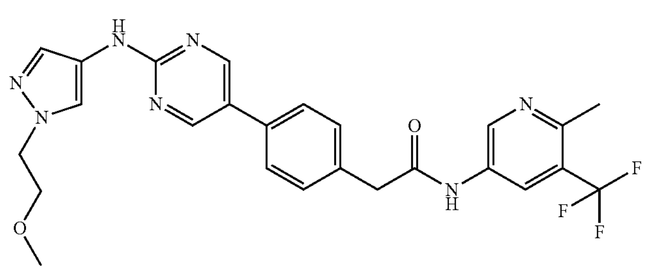 [SMILES: COCCn1cc(Nc2ncc(-c3ccc(CC(=O)Nc4cnc(C)c(C(F)(F)F)c4)cc3)cn2)cn1] | 512.5 |

TABLE 1-continued

| Number | Compound Name | Compound Structure | (MH)+ |
|---|---|---|---|
| P-0180 | 2-[4-[2-[[1-[(2S)-2-hydroxypropyl]-3-methoxy-pyrazol-4-yl]amino]pyrimidin-5-yl]phenyl]-N-[6-methyl-5-(trifluoromethyl)-3-pyridyl]acetamide | 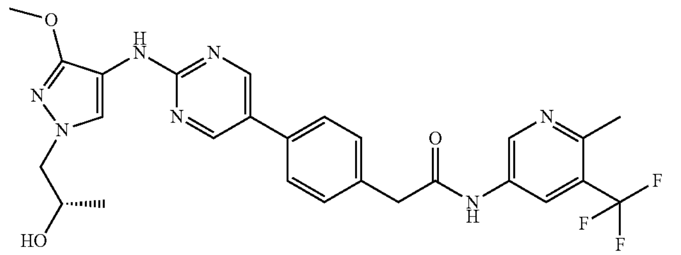 [SMILES: COc1nn(C[C@H](C)O)cc1Nc1ncc(-c2ccc(CC(=O)Nc3cnc(C)c(C(F)(F)F)c3)cc2)cn1] | 540.2 MH(−) |
| P-0181 | 2-[5-[2-(2-morpholino-4-pyridyl)-1H-pyrrolo[2,3-b]pyridin-5-yl]-2-pyridyl]-N-[2-(trifluoromethyl)-4-pyridyl]acetamide | 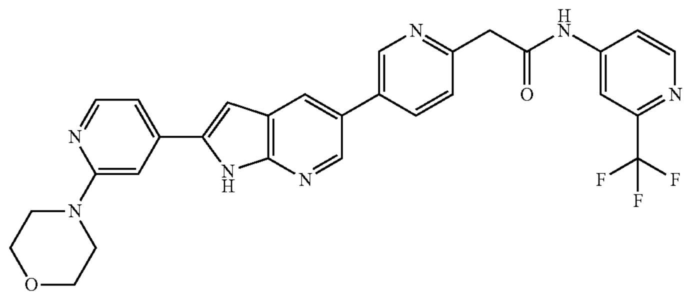 [SMILES: O=C(Cc1ccc(-c2cnc3[nH]c(-c4ccnc(N5CCOCC5)c4)cc3c2)cn1)Nc1ccnc(C(F)(F)F)c1] | 560.4 |
| P-0182 | 2-[5-[2-(2-cyano-4-pyridyl)-1H-pyrrolo[2,3-b]pyridin-5-yl]-2-pyridyl]-N-[2-(trifluoromethyl)-4-pyridyl]acetamide | 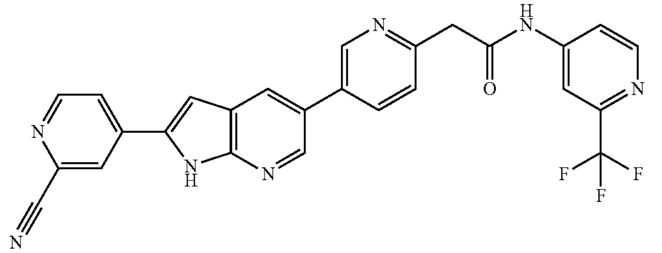 [SMILES: N#Cc1cc(-c2cc3cc(-c4ccc(CC(=O)Nc5ccnc(C(F)(F)F)c5)nc4)cnc3[nH]2)ccn1] | 500.3 |
| P-0183 | 2-[5-[2-(6-morpholino-3-pyridyl)-1H-pyrrolo[2,3-b]pyridin-5-yl]-2-pyridyl]-N-[2-(trifluoromethyl)-4-pyridyl]acetamide | 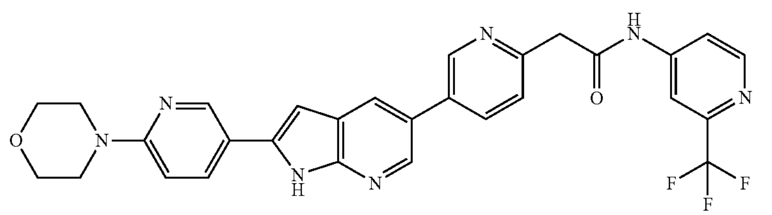 [SMILES: O=C(Cc1ccc(-c2cnc3[nH]c(-c4ccc(N5CCOCC5)nc4)cc3c2)cn1)Nc1ccnc(C(F)(F)F)c1] | 560.3 |
| P-0184 | 2-[5-[2-(6-cyano-3-pyridyl)-1H-pyrrolo[2,3-b]pyridin-5-yl]-2-pyridyl]-N-[2-(trifluoromethyl)-4-pyridyl]acetamide | 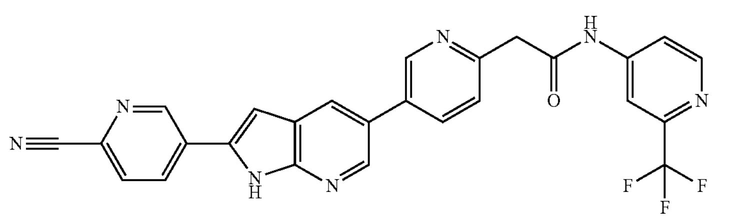 [SMILES: N#Cc1ccc(-c2cc3cc(-c4ccc(CC(=O)Nc5ccnc(C(F)(F)F)c5)nc4)cnc3[nH]2)cn1] | 500.3 |
| P-0185 | 2-[6-[2-(2-cyano-4-pyridyl)-1H-pyrrolo[2,3-b]pyridin-5-yl]-3-pyridyl]-N-[2-(trifluoromethyl)-4-pyridyl]acetamide | 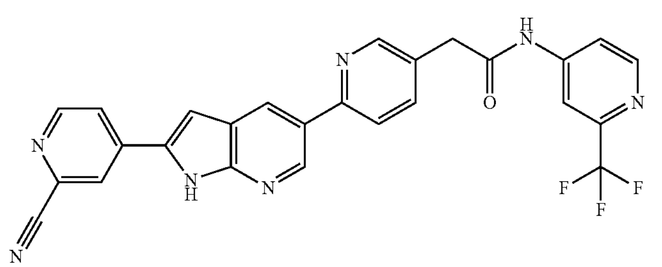 [SMILES: N#Cc1cc(-c2cc3cc(-c4ccc(CC(=O)Nc5ccnc(C(F)(F)F)c5)cn4)cnc3[nH]2)ccn1] | 500.3 |

TABLE 1-continued

| Number | Compound Name | Compound Structure | (MH)+ |
|---|---|---|---|
| P-0186 | 2-[6-[2-(2-methoxy-4-pyridyl)-1H-pyrrolo[2,3-b]pyridin-5-yl]-3-pyridyl]-N-[2-(trifluoromethyl)-4-pyridyl]acetamide | 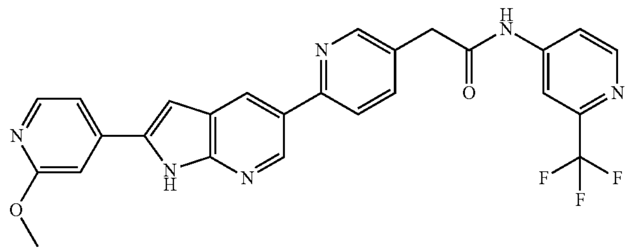 [SMILES: COc1cc(-c2cc3cc(-c4ccc(CC(=O)Nc5ccnc(C(F)(F)F)c5)cn4)cnc3[nH]2)ccn1] | 505.3 |
| P-0187 | 2-[5-[2-(2-methoxy-4-pyridyl)-1H-pyrrolo[2,3-b]pyridin-5-yl]-2-pyridyl]-N-[2-(trifluoromethyl)-4-pyridyl]acetamide | 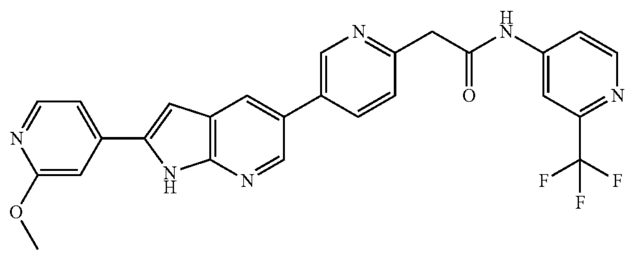 [SMILES: COc1cc(-c2cc3cc(-c4ccc(CC(=O)Nc5ccnc(C(F)(F)F)c5)nc4)cnc3[nH]2)ccn1] | 505.3 |
| P-0188 | 2-[4-[2-(2-cyano-4-pyridyl)-1H-pyrrolo[2,3-b]pyridin-5-yl]-2,5-difluoro-phenyl]-N-[4-(trifluoromethyl)-2-pyridyl]acetamide | 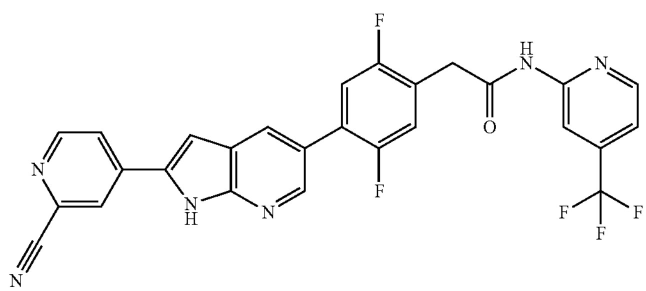 [SMILES: N#Cc1cc(-c2cc3cc(-c4cc(F)c(CC(=O)Nc5cc(C(F)(F)F)ccn5)cc4F)cnc3[nH]2)ccn1] | 535.3 |
| P-0189 | 2-[2,5-difluoro-4-[2-(2-methoxy-4-pyridyl)-1H-pyrrolo[2,3-b]pyridin-5-yl]phenyl]-N-[4-(trifluoromethyl)-2-pyridyl]acetamide | 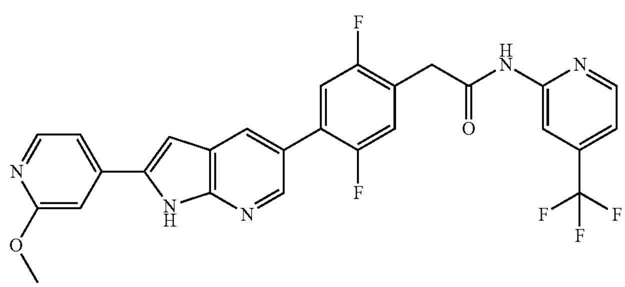 [SMILES: COc1cc(-c2cc3cc(-c4cc(F)c(CC(=O)Nc5cc(C(F)(F)F)ccn5)cc4F)cnc3[nH]2)ccn1] | 540.3 |
| P-0190 | 2-[2,5-difluoro-4-[2-(2-morpholino-4-pyridyl)-1H-pyrrolo[2,3-b]pyridin-5-yl]phenyl]-N-[4-(trifluoromethyl)-2-pyridyl]acetamide | 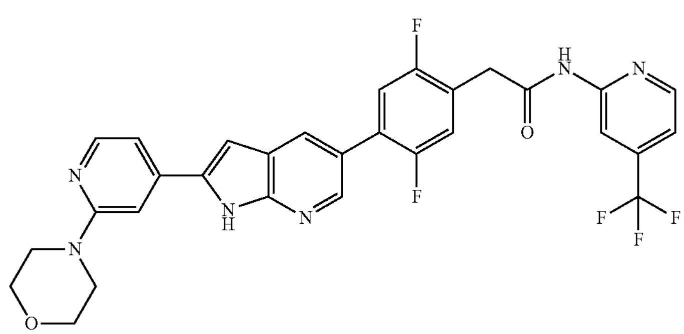 [SMILES: O=C(Cc1cc(F)c(-c2cnc3[nH]c(-c4ccnc(N5CCOCC5)c4)cc3c2)cc1F)Nc1cc(C(F)(F)F)ccn1] | 595.4 |

TABLE 1-continued

| Number | Compound Name | Compound Structure | (MH)+ |
|---|---|---|---|
| P-0191 | 2-[3-fluoro-4-[2-(6-methoxy-3-pyridyl)-1H-pyrrolo[2,3-b]pyridin-5-yl]phenyl]-N-[4-(trifluoromethyl)-2-pyridyl]acetamide | 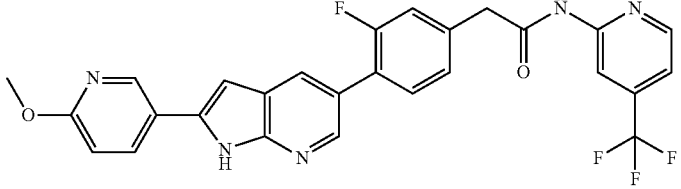 | 522.3 |
| P-0192 | 2-[3-fluoro-4-[2-(6-morpholino-3-pyridyl)-1H-pyrrolo[2,3-b]pyridin-5-yl]phenyl]-N-[4-(trifluoromethyl)-2-pyridyl]acetamide | 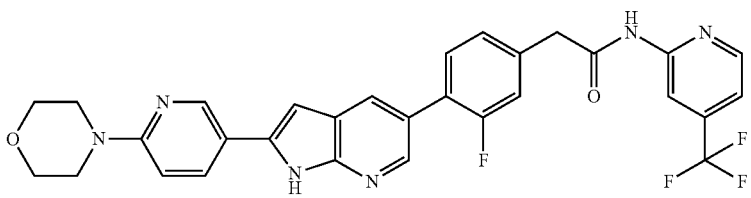 [SMILES: O=C(Cc1ccc(-c2cnc3[nH]c(-c4ccc(N5CCOCC5)nc4)cc3c2)c(F)c1)Nc1cc(C(F)(F)F)ccn1] | 577.4 |
| P-0193 | 2-[3-fluoro-4-[2-(6-morpholino-3-pyridyl)-1H-pyrrolo[2,3-b]pyridin-5-yl]phenyl]-N-[6-methoxy-5-(trifluoromethyl)-3-pyridyl]acetamide | 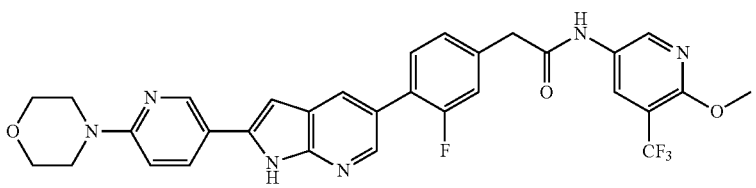 [SMILES: COc1ncc(NC(=O)Cc2ccc(-c3cnc4[nH]c(-c5ccc(N6CCOCC6)nc5)cc4c3)c(F)c2)cc1C(F)(F)F] | 607.4 |
| P-0194 | 2-[4-[2-(2-cyano-4-pyridyl)-1H-pyrrolo[2,3-b]pyridin-5-yl]-3-fluoro-phenyl]-N-[4-(trifluoromethyl)-2-pyridyl]acetamide | 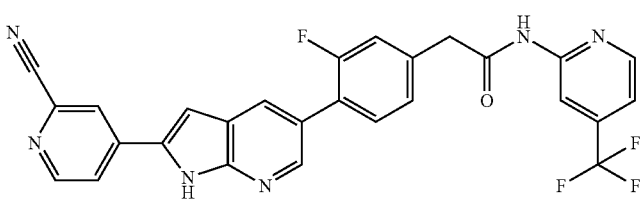 [SMILES: N#Cc1cc(-c2cc3cc(-c4ccc(CC(=O)Nc5cc(C(F)(F)F)ccn5)cc4F)cnc3[nH]2)ccn1] | 517.3 |
| P-0195 | 2-[4-[2-(6-cyano-3-pyridyl)-1H-pyrrolo[2,3-b]pyridin-5-yl]-3-fluoro-phenyl]-N-[5-(trifluoromethyl)-3-pyridyl]acetamide | 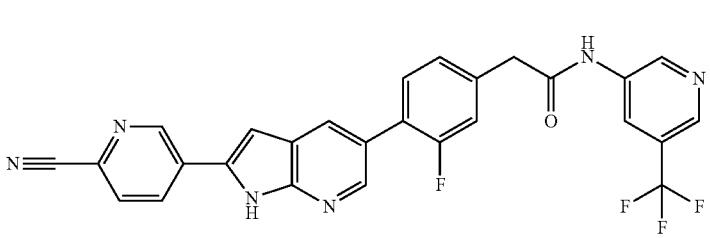 [SMILES: N#Cc1ccc(-c2cc3cc(-c4ccc(CC(=O)Nc5cncc(C(F)(F)F)c5)cc4F)cnc3[nH]2)cn1] | 517.3 |
| P-0196 | 2-[3-fluoro-4-[2-(6-methoxy-3-pyridyl)-1H-pyrrolo[2,3-b]pyridin-5-yl]phenyl]-N-[5-(trifluoromethyl)-3-pyridyl]acetamide | 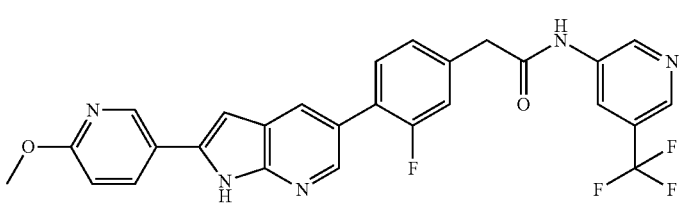 [SMILES: COc1ccc(-c2cc3cc(-c4ccc(CC(=O)Nc5cncc(C(F)(F)F)c5)cc4F)cnc3[nH]2)cn1] | 522.3 |
| P-0197 | 2-[4-[2-[1-(difluoromethyl)pyrazol-4-yl]-1H-pyrrolo[2,3-b]pyridin-5-yl]-3-fluoro-phenyl]-N-[5-(trifluoromethyl)-3-pyridyl]acetamide | 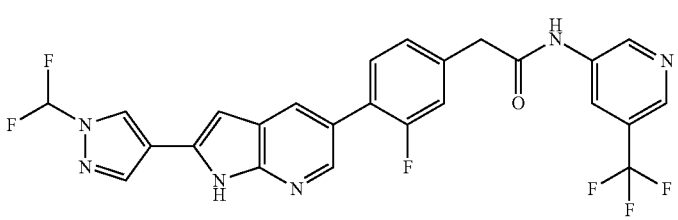 [SMILES: O=C(Cc1ccc(-c2cnc3[nH]c(-c4cnn(C(F)F)c4)cc3c2)c(F)c1)Nc1cncc(C(F)(F)F)c1] | 531.3 |

TABLE 1-continued

| Number | Compound Name | Compound Structure | (MH)+ |
|---|---|---|---|
| P-0198 | 2-[3-fluoro-4-[2-(6-morpholino-3-pyridyl)-1H-pyrrolo[2,3-b]pyridin-5-yl]phenyl]-N-[5-(trifluoromethyl)-3-pyridyl]acetamide | 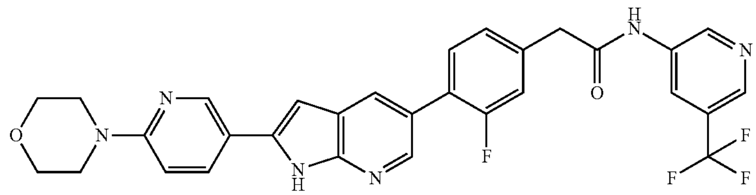 [SMILES: O=C(Cc1ccc(-c2cnc3[nH]c(-c4ccc(N5CCOCC5)nc4)cc3c2)c(F)c1)Nc1cncc(C(F)(F)F)c1] | 577.4 |
| P-0199 | 2-[4-[2-(2-cyano-4-pyridyl)-1H-pyrrolo[2,3-b]pyridin-5-yl]-3-fluoro-phenyl]-N-[5-(trifluoromethyl)-3-pyridyl]acetamide | 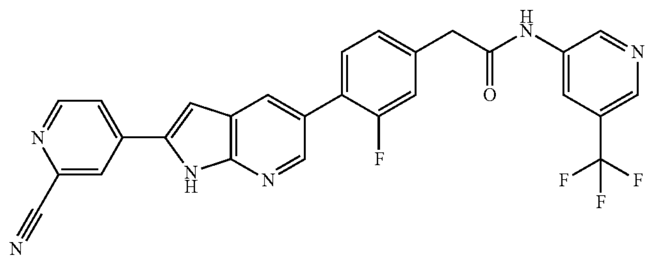 [SMILES: N#Cc1cc(-c2cc3cc(-c4ccc(CC(=O)Nc5cncc(C(F)(F)F)c5)cc4F)cnc3[nH]2)ccn1] | 517.3 |
| P-0200 | 2-[3-fluoro-4-[2-(2-methoxy-4-pyridyl)-1H-pyrrolo[2,3-b]pyridin-5-yl]phenyl]-N-[5-(trifluoromethyl)-3-pyridyl]acetamide | 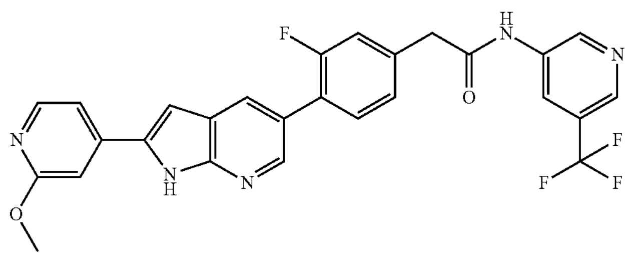 [SMILES: COc1cc(-c2cc3cc(-c4ccc(CC(=O)Nc5cncc(C(F)(F)F)c5)cc4F)cnc3[nH]2)ccn1] | 522.3 |
| P-0201 | 2-[3-fluoro-4-[2-(2-morpholino-4-pyridyl)-1H-pyrrolo[2,3-b]pyridin-5-yl]phenyl]-N-[5-(trifluoromethyl)-3-pyridyl]acetamide | 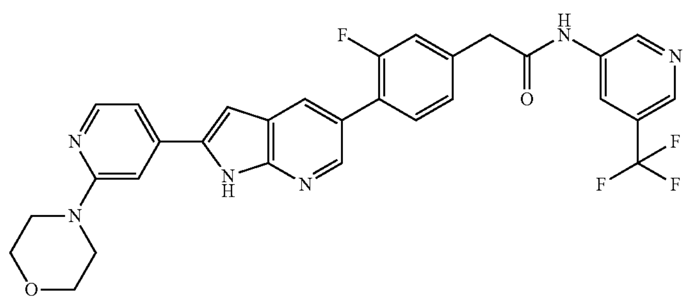 [SMILES: O=C(Cc1ccc(-c2cnc3[nH]c(-c4ccnc(N5CCOCC5)c4)cc3c2)c(F)c1)Nc1cncc(C(F)(F)F)c1] | 577.4 |
| P-0202 | 2-[4-(3-ethoxy-1H-pyrazolo[3,4-b]pyridin-5-yl)-3-fluoro-phenyl]-N-[6-methoxy-5-(trifluoromethyl)-3-pyridyl]acetamide | 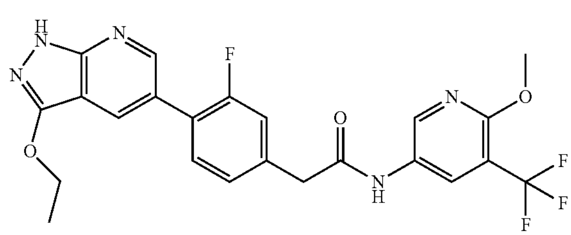 [SMILES: CCOc1n[nH]c2ncc(-c3ccc(CC(=O)Nc4cnc(OC)c(C(F)(F)F)c4)cc3F)cc12] | 490.3 |
| P-0203 | 2-[4-(3-amino-1H-pyrazolo[3,4-b]pyridin-5-yl)-3-fluoro-phenyl]-N-[6-methoxy-5-(trifluoromethyl)-3-pyridyl]acetamide | 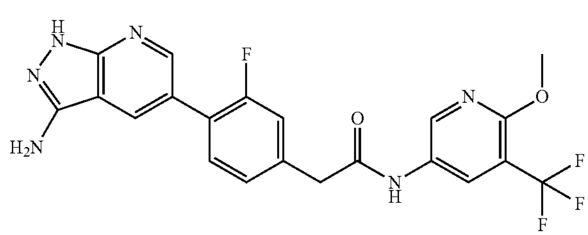 [SMILES: COc1ncc(NC(=O)Cc2ccc(-c3cnc4[nH]nc(N)c4c3)c(F)c2)cc1C(F)(F)F] | 461.2 |

TABLE 1-continued

| Number | Compound Name | Compound Structure | (MH)+ |
|---|---|---|---|
| P-0204 | 2-[4-[2-(3-hydroxy-3-methyl-but-1-ynyl)-1H-pyrrolo[2,3-b]pyridin-5-yl]phenyl]-N-[5-(trifluoromethyl)-3-pyridyl]acetamide | 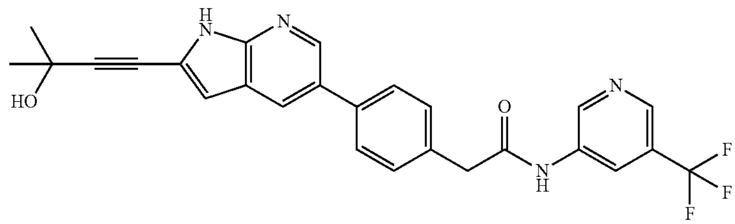 [SMILES: CC(C)(O)C#Cc1cc2cc(-c3ccc(CC(=O)Nc4cncc(C(F)(F)F)c4)cc3)cnc2[nH]1] | 479.23 |
| P-0205 | 2-[3-fluoro-4-[2-[(1-methylpyrazol-4-yl)amino]pyrimidin-5-yl]phenyl]-N-[5-(trifluoromethyl)-3-pyridyl]acetamide | 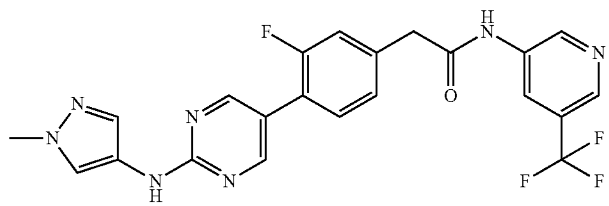 [SMILES: Cn1cc(Nc2ncc(-c3ccc(CC(=O)Nc4cncc(C(F)(F)F)c4)cc3F)cn2)cn1] | 472.3 |
| P-0206 | 2-[3-fluoro-4-[2-[(1-methylpyrazol-4-yl)amino]pyrimidin-5-yl]phenyl]-N-[6-methoxy-5-(trifluoromethyl)-3-pyridyl]acetamide | 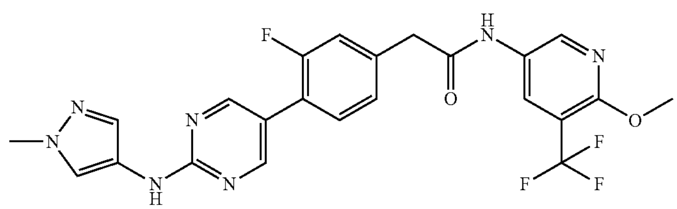 | 502.3 |
| P-0207 | 2-[2,5-difluoro-4-[2-[(1-methylpyrazol-4-yl)amino]pyrimidin-5-yl]phenyl]-N-[5-(trifluoromethyl)-3-pyridyl]acetamide | 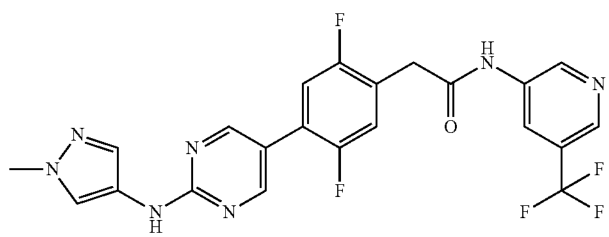 [SMILES: Cn1cc(Nc2ncc(-c3cc(F)c(CC(=O)Nc4cncc(C(F)(F)F)c4)cc3F)cn2)cn1] | 490.3 |
| P-0208 | 2-[2,5-difluoro-4-[2-[(1-methylpyrazol-4-yl)amino]pyrimidin-5-yl]phenyl]-N-[6-methoxy-5-(trifluoromethyl)-3-pyridyl]acetamide | 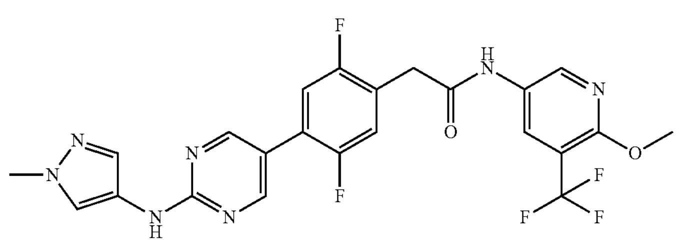 | 520.3 |
| P-0209 | 2-[4-[2-[[1-(difluoromethyl)pyrazol-4-yl]amino]pyrimidin-5-yl]phenyl]-N-[5-(trifluoromethyl)-3-pyridyl]acetamide | 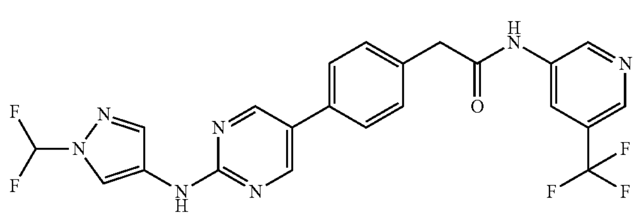 [SMILES: O=C(Cc1ccc(-c2cnc(Nc3cnn(C(F)F)c3)nc2)cc1)Nc1cncc(C(F)(F)F)c1] | 490.3 |
| P-0210 | 2-[4-[2-[[1-(difluoromethyl)pyrazol-4-yl]amino]pyrimidin-5-yl]phenyl]-N-[6-methyl-5-(trifluoromethyl)-3-pyridyl]acetamide | 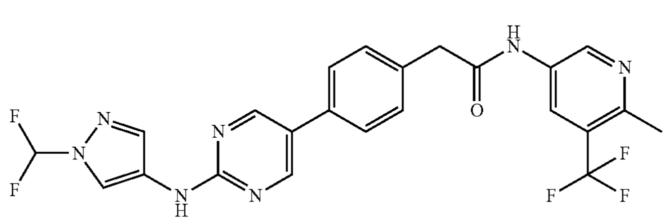 [SMILES: Cc1ncc(NC(=O)Cc2ccc(-c3cnc(Nc4cnn(C(F)F)c4)nc3)cc2)cc1C(F)(F)F] | 504.3 |

TABLE 1-continued

| Number | Compound Name | Compound Structure | (MH)+ |
|---|---|---|---|
| P-0211 | 2-[4-[2-[[1-(difluoromethyl)pyrazol-4-yl]amino]pyrimidin-5-yl]phenyl]-N-[6-methoxy-5-(trifluoromethyl)-3-pyridyl]acetamide | 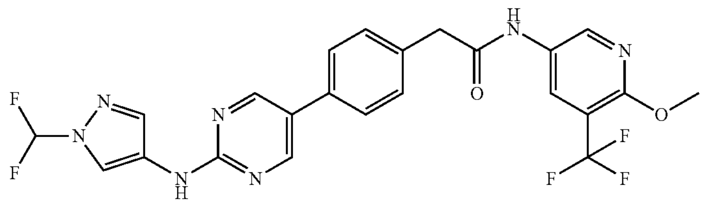 [SMILES: COc1ncc(NC(=O)Cc2ccc(-c3cnc(Nc4cnn(C(F)F)c4)nc3)cc2)cc1C(F)(F)F] | 520.3 |
| P-0212 | 2-[4-(3-methoxy-1H-pyrazolo[3,4-b]pyridin-5-yl)phenyl]-N-[6-methoxy-5-(trifluoromethyl)-3-pyridyl]acetamide | 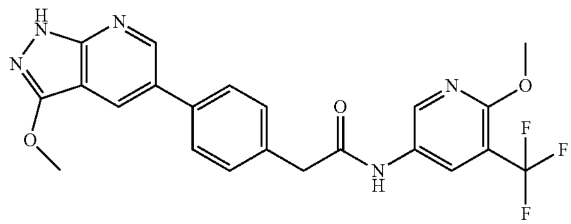 [SMILES: COc1ncc(NC(=O)Cc2ccc(-c3cnc4[nH]nc(OC)c4c3)cc2)cc1C(F)(F)F] | 458.3 |
| P-0213 | 2-[4-(3-ethoxy-1H-pyrazolo[3,4-b]pyridin-5-yl)phenyl]-N-[6-methoxy-5-(trifluoromethyl)-3-pyridyl]acetamide | 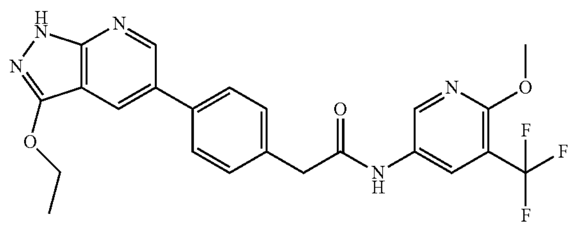 [SMILES: CCOc1n[nH]c2ncc(-c3ccc(CC(=O)Nc4cnc(OC)c(C(F)(F)F)c4)cc3)cc12] | 472.3 |
| P-0214 | 2-[4-[2-(3-hydroxy-3-methyl-but-1-ynyl)-1H-pyrrolo[2,3-b]pyridin-5-yl]phenyl]-N-[6-methoxy-5-(trifluoromethyl)-3-pyridyl]acetamide | 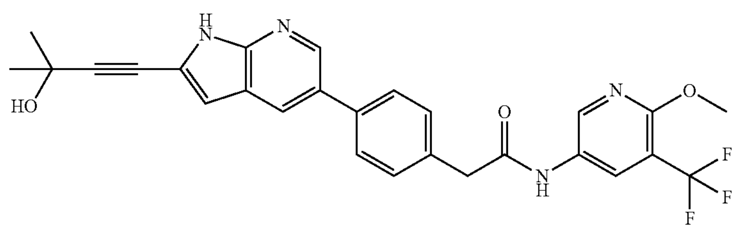 [SMILES: COc1ncc(NC(=O)Cc2ccc(-c3cnc4[nH]c(C#CC(C)(C)O)cc4c3)cc2)cc1C(F)(F)F] | 509.4 |
| P-0215 | 2,2,2-trifluoro-N-[5-[4-[2-[[6-methoxy-5-(trifluoromethyl)-3-pyridyl]amino]-2-oxo-ethyl]phenyl]-1H-pyrazolo[3,4-b]pyridin-3-yl]acetamide | 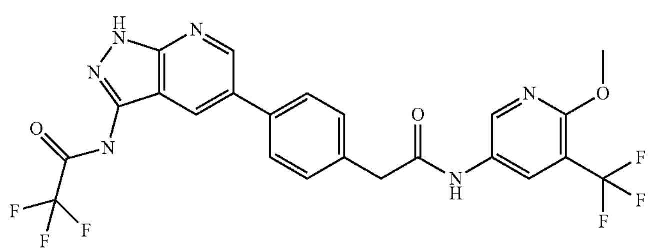 [SMILES: COc1ncc(NC(=O)Cc2ccc(-c3cnc4[nH]nc(NC(=O)C(F)(F)F)c4c3)cc2)cc1C(F)(F)F] | 539.3 |
| P-0216 | 2-[4-(3-amino-1H-pyrazolo[3,4-b]pyridin-5-yl)phenyl]-N-[6-methoxy-5-(trifluoromethyl)-3-pyridyl]acetamide | 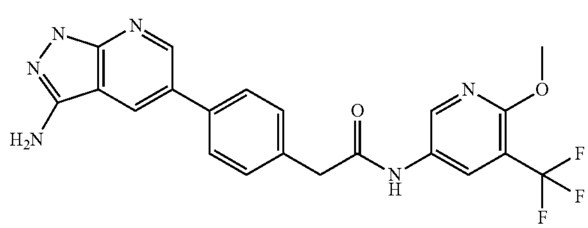 [SMILES: COc1ncc(NC(=O)Cc2ccc(-c3cnc4[nH]nc(N)c4c3)cc2)cc1C(F)(F)F] | 443.3 |
| P-0217 | 2-[4-(3-ethoxy-1H-pyrazolo[3,4-b]pyridin-5-yl)phenyl]-N-[6-methyl-5-(trifluoromethyl)-3-pyridyl]acetamide | 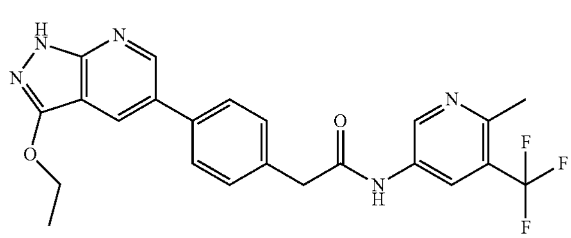 [SMILES: CCOc1n[nH]c2ncc(-c3ccc(CC(=O)Nc4cnc(C)c(C(F)(F)F)c4)cc3)cc12] | 456.3 |

TABLE 1-continued

| Number | Compound Name | Compound Structure | (MH)+ |
|---|---|---|---|
| P-0218 | 2-[4-(3-methoxy-1H-pyrazolo[3,4-b]pyridin-5-yl)phenyl]-N-[6-methyl-5-(trifluoromethyl)-3-pyridyl]acetamide | 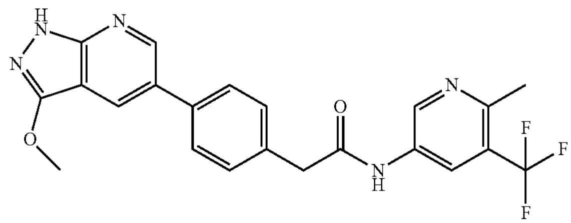 [SMILES: COc1n[nH]c2ncc(-c3ccc(CC(=O)Nc4cnc(C)c(C(F)(F)F)c4)cc3)cc12] | 442.3 |
| P-0219 | 2-[4-[2-(3,3-dimethylbut-1-ynyl)-1H-pyrrolo[2,3-b]pyridin-5-yl]phenyl]-N-[6-methoxy-5-(trifluoromethyl)-3-pyridyl]acetamide | 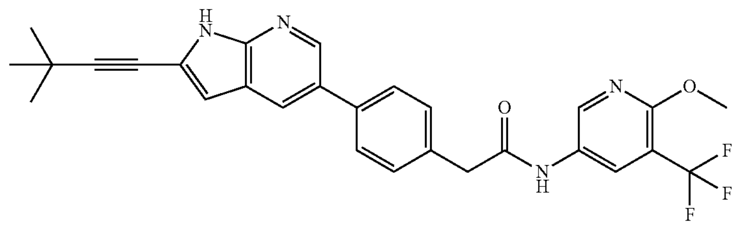 [SMILES: COc1ncc(NC(=O)Cc2ccc(-c3cnc4[nH]c(C#CC(C)(C)C)cc4c3)cc2)cc1C(F)(F)F] | 507.4 |
| P-0220 | 2-[4-[2-(3-hydroxy-3-methyl-but-1-ynyl)-1H-pyrrolo[2,3-b]pyridin-5-yl]phenyl]-N-[6-methyl-5-(trifluoromethyl)-3-pyridyl]acetamide | 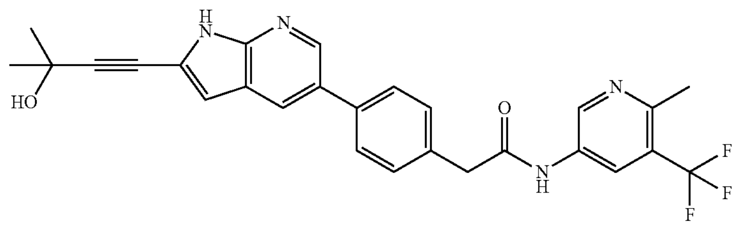 [SMILES: Cc1ncc(NC(=O)Cc2ccc(-c3cnc4[nH]c(C#CC(C)(C)O)cc4c3)cc2)cc1C(F)(F)F] | 493.4 |
| P-0221 | N-[6-methoxy-5-(trifluoromethyl)-3-pyridyl]-2-[4-[2-[(5-methyl-1H-pyrazol-4-yl)amino]pyrimidin-5-yl]phenyl]acetamide | 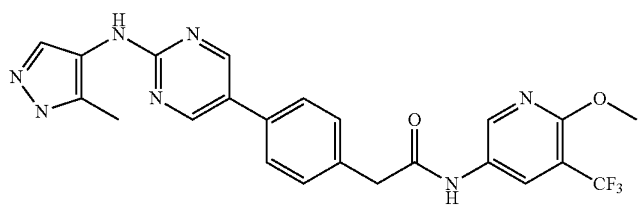 [SMILES: COc1ncc(NC(=O)Cc2ccc(-c3cnc(Nc4cn[nH]c4C)nc3)cc2)cc1C(F)(F)F] | 484.3 |
| P-0222 | 2-[4-[2-[[1-(2-methoxyethyl)pyrazol-4-yl]amino]pyrimidin-5-yl]phenyl]-N-[4-(trifluoromethyl)-2-pyridyl]acetamide | 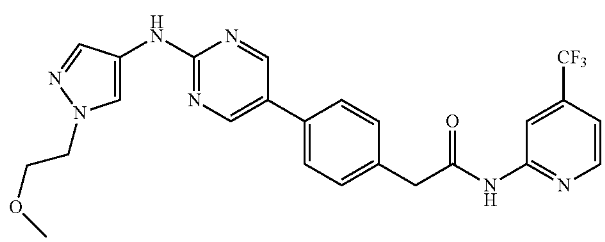 [SMILES: COCCn1cc(Nc2ncc(-c3ccc(CC(=O)Nc4cc(C(F)(F)F)ccn4)cc3)cn2)cn1] | 498.4 |
| P-0223 | 2-[4-[2-[[1-(difluoromethyl)pyrazol-4-yl]amino]pyrimidin-5-yl]phenyl]-N-(5-ethyl-3-pyridyl)acetamide | 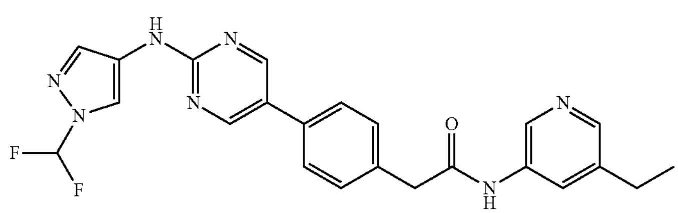 [SMILES: CCc1cncc(NC(=O)Cc2ccc(-c3cnc(Nc4cnn(C(F)F)c4)nc3)cc2)c1] | 450.3 |
| P-0224 | N-(5-cyclopropyl-3-pyridyl)-2-[4-[2-[[1-(difluoromethyl)pyrazol-4-yl]amino]pyrimidin-5-yl]phenyl]acetamide | 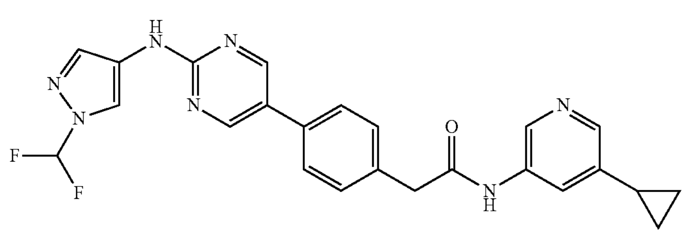 [SMILES: O=C(Cc1ccc(-c2cnc(Nc3cnn(C(F)F)c3)nc2)cc1)Nc1cncc(C2CC2)c1] | 462.3 |

TABLE 1-continued

| Number | Compound Name | (MH)+ |
|---|---|---|
| P-0225 | 2-[3-fluoro-4-[2-(1H-pyrazol-4-ylamino)pyrimidin-5-yl]phenyl]-N-[6-methyl-5-(trifluoromethyl)-3-pyridyl]acetamide | 472.3 |
| P-0226 | 2-[2,5-difluoro-4-[2-(1H-pyrazol-4-ylamino)pyrimidin-5-yl]phenyl]-N-[6-methoxy-5-(trifluoromethyl)-3-pyridyl]acetamide | 506.1 |
| P-0227 | N-[6-methoxy-5-(trifluoromethyl)-3-pyridyl]-2-[4-[2-[2-(3-methylimidazol-4-yl)ethynyl]-1H-pyrrolo[2,3-b]pyridin-5-yl]phenyl]acetamide | 531.2 |
| P-0228 | 2-[4-[2-[(1,3-dimethylpyrazol-4-yl)amino]pyrimidin-5-yl]phenyl]-N-[6-methyl-5-(trifluoromethyl)-3-pyridyl]acetamide | 482.4 |
| P-0229 | 2-[4-[2-[(1,5-dimethylpyrazol-4-yl)amino]pyrimidin-5-yl]phenyl]-N-[6-methyl-5-(trifluoromethyl)-3-pyridyl]acetamide | 482.4 |
| P-0230 | 2-[4-(3-chloro-1H-pyrazolo[3,4-b]pyridin-5-yl)phenyl]-N-[6-methoxy-5-(trifluoromethyl)-3-pyridyl]acetamide | 462.2 |
| P-0231 | 2-[4-[2-[(1-cyclopropylpyrazol-4-yl)amino]pyrimidin-5-yl]phenyl]-N-[5-(trifluoromethyl)-3-pyridyl]acetamide | 480.1 |

TABLE 1-continued

| Number | Compound Name | Compound Structure | (MH)+ |
|---|---|---|---|
| P-0232 | 2-[4-[2-[(1-cyclopropylpyrazol-4-yl)amino]pyrimidin-5-yl]phenyl]-N-[6-methyl-5-(trifluoromethyl)-3-pyridyl]acetamide | 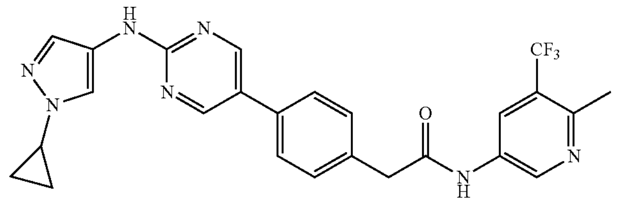 [SMILES: Cc1ncc(NC(=O)Cc2ccc(-c3cnc(Nc4cnn(C5CC5)c4)nc3)cc2)cc1C(F)(F)F] | 494.2 |
| P-0233 | N-[6-chloro-5-(trifluoromethyl)-3-pyridyl]-2-[4-[2-[(1-cyclopropylpyrazol-4-yl)amino]pyrimidin-5-yl]phenyl]acetamide | 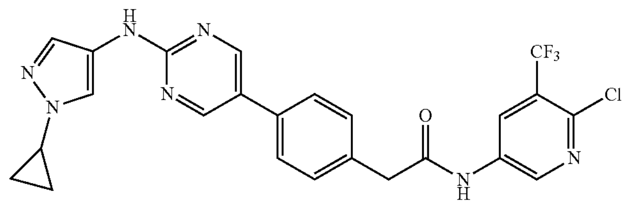 [SMILES: O=C(Cc1ccc(-c2cnc(Nc3cnn(C4CC4)c3)nc2)cc1)Nc1cnc(Cl)c(C(F)(F)F)c1] | 514.3 |
| P-0234 | 2-[4-[2-[(1-cyclopropylpyrazol-4-yl)amino]pyrimidin-5-yl]phenyl]-N-[6-methoxy-5-(trifluoromethyl)-3-pyridyl]acetamide | 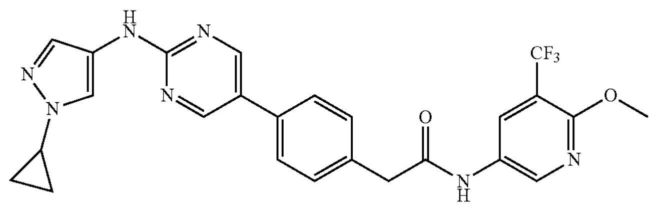 [SMILES: COc1ncc(NC(=O)Cc2ccc(-c3cnc(Nc4cnn(C5CC5)c4)nc3)cc2)cc1C(F)(F)F] | 510.1 |
| P-0235 | 2-[4-[2-[(1-cyclopropylpyrazol-4-yl)amino]pyrimidin-5-yl]phenyl]-N-[6-(trifluoromethyl)-3-pyridyl]acetamide | 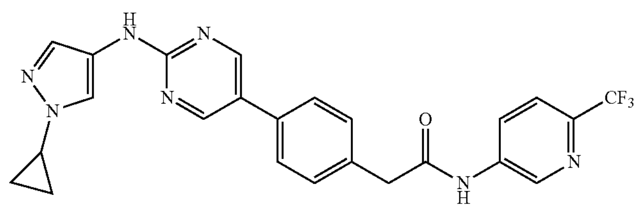 [SMILES: O=C(Cc1ccc(-c2cnc(Nc3cnn(C4CC4)c3)nc2)cc1)Nc1ccc(C(F)(F)F)nc1] | 480.1 |
| P-0236 | 2-[4-[2-[(1-cyclopropylpyrazol-4-yl)amino]pyrimidin-5-yl]phenyl]-N-[5-(trifluoromethyl)-2-pyridyl]acetamide | 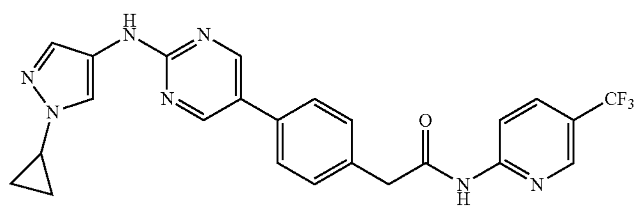 [SMILES: O=C(Cc1ccc(-c2cnc(Nc3cnn(C4CC4)c3)nc2)cc1)Nc1ccc(C(F)(F)F)cn1] | 480.1 |
| P-0237 | 2-[4-[2-[(1-cyclopropylpyrazol-4-yl)amino]pyrimidin-5-yl]phenyl]-N-[4-(trifluoromethyl)-2-pyridyl]acetamide | 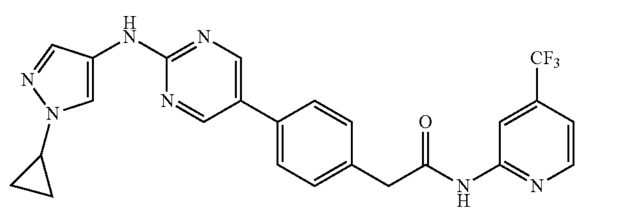 [SMILES: O=C(Cc1ccc(-c2cnc(Nc3cnn(C4CC4)c3)nc2)cc1)Nc1cc(C(F)(F)F)ccn1] | 480.1 |
| P-0238 | 2-[4-[2-[(1-cyclopropylpyrazol-4-yl)amino]pyrimidin-5-yl]-2-fluoro-phenyl]-N-[5-(trifluoromethyl)-3-pyridyl]acetamide | 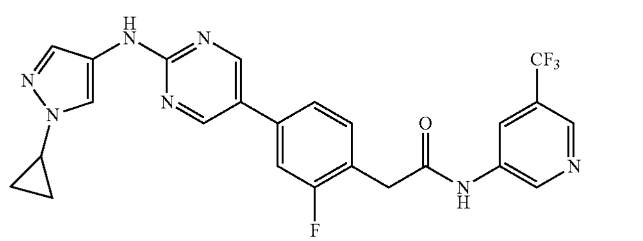 [SMILES: O=C(Cc1ccc(-c2cnc(Nc3cnn(C4CC4)c3)nc2)cc1F)Nc1cncc(C(F)(F)F)c1] | 498.4 |

TABLE 1-continued

| Number | Compound Name | Compound Structure | (MH)+ |
|---|---|---|---|
| P-0239 | 2-[4-[2-[(1-cyclopropylpyrazol-4-yl)amino]pyrimidin-5-yl]-2-fluoro-phenyl]-N-[6-methyl-5-(trifluoromethyl)-3-pyridyl]acetamide | 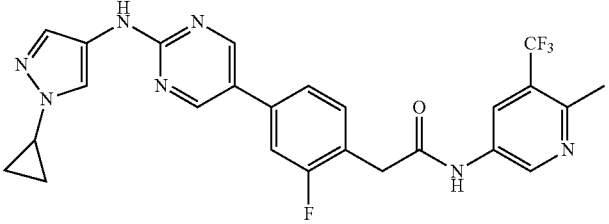 [SMILES: Cc1ncc(NC(=O)Cc2ccc(-c3cnc(Nc4cnn(C5CC5)c4)nc3)cc2F)cc1C(F)(F)F] | 512.5 |
| P-0240 | N-[6-chloro-5-(trifluoromethyl)-3-pyridyl]-2-[4-[2-[(1-cyclopropylpyrazol-4-yl)amino]pyrimidin-5-yl]-2-fluoro-phenyl]acetamide | 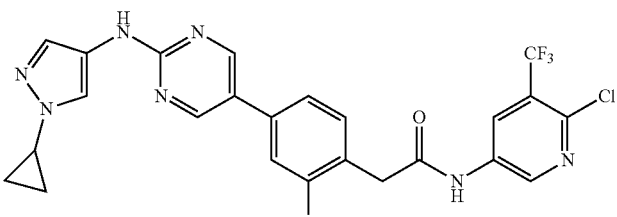 | 532.0 |
| P-0241 | 2-[4-[2-[(1-cyclopropylpyrazol-4-yl)amino]pyrimidin-5-yl]-2-fluoro-phenyl]-N-[6-methoxy-5-(trifluoromethyl)-3-pyridyl]acetamide | 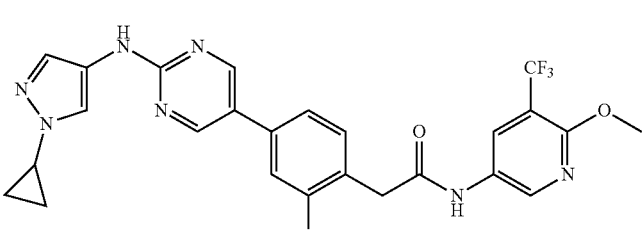 | 528.1 |
| P-0242 | 2-[4-[2-[(1-cyclopropylpyrazol-4-yl)amino]pyrimidin-5-yl]-2-fluoro-phenyl]-N-[6-(trifluoromethyl)-3-pyridyl]acetamide | 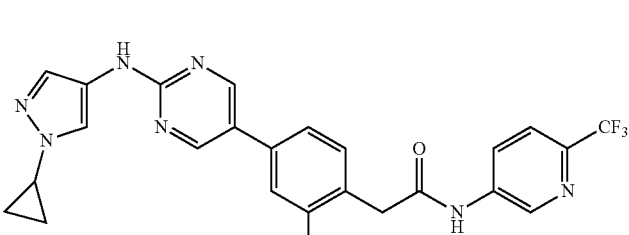 | 498.4 |
| P-0243 | 2-[4-[2-[(1-cyclopropylpyrazol-4-yl)amino]pyrimidin-5-yl]-2-fluoro-phenyl]-N-[5-(trifluoromethyl)-2-pyridyl]acetamide | 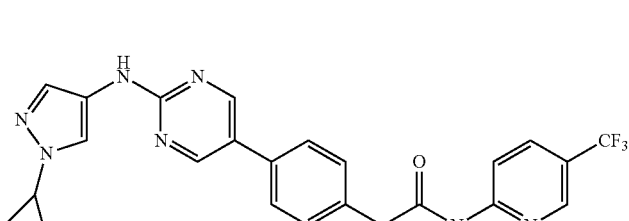 | 498.4 |
| P-0244 | 2-[4-[2-[(1-cyclopropylpyrazol-4-yl)amino]pyrimidin-5-yl]-2-fluoro-phenyl]-N-[4-(trifluoromethyl)-2-pyridyl]acetamide | 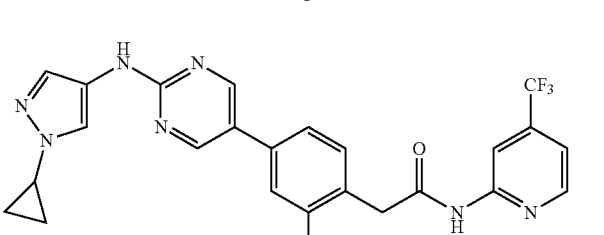 | 498.4 |

TABLE 1-continued

| Number | Compound Name | Compound Structure | (MH)+ |
|---|---|---|---|
| P-0245 | 2-[4-(3-fluoro-1H-pyrazolo[3,4-b]pyridin-5-yl)phenyl]-N-[6-methoxy-5-(trifluoromethyl)-3-pyridyl]acetamide | 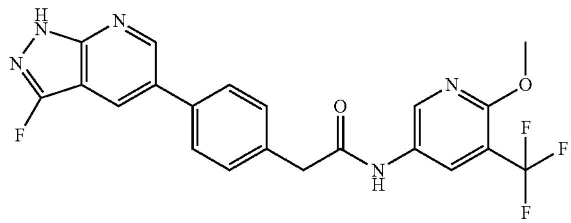 [SMILES: COc1ncc(NC(=O)Cc2ccc(-c3cnc4[nH]nc(F)c4c3)cc2)cc1C(F)(F)F] | 446.3 |
| P-0246 | 2-[4-[2-[(1-ethylpyrazol-4-yl)amino]pyrimidin-5-yl]-3-fluoro-phenyl]-N-[6-methoxy-5-(trifluoromethyl)-3-pyridyl]acetamide | 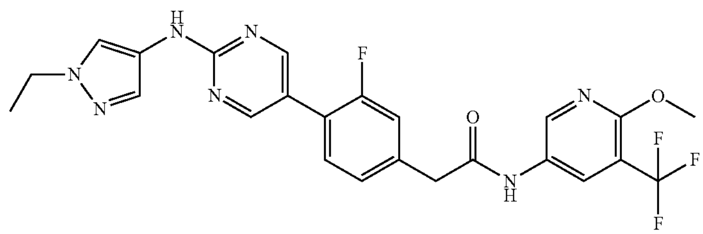 [SMILES: CCn1cc(Nc2ncc(-c3ccc(CC(=O)Nc4cnc(OC)c(C(F)(F)F)c4)cc3F)cn2)cn1] | 516.3 |
| P-0247 | 2-[4-[2-[(1-ethylpyrazol-4-yl)amino]pyrimidin-5-yl]-2,5-difluoro-phenyl]-N-[6-methoxy-5-(trifluoromethyl)-3-pyridyl]acetamide | 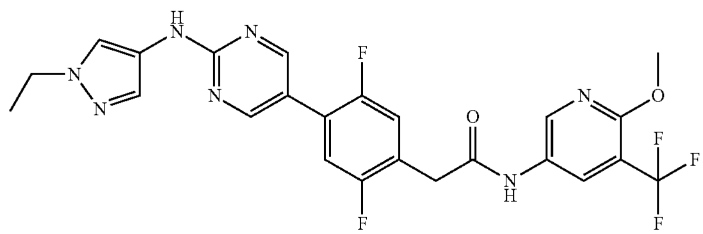 [SMILES: CCn1cc(Nc2ncc(-c3cc(F)c(CC(=O)Nc4cnc(OC)c(C(F)(F)F)c4)cc3F)cn2)cn1] | 534.3 |
| P-0248 | 2-[4-[2-[(1-ethylpyrazol-4-yl)amino]pyrimidin-5-yl]-3-fluoro-phenyl]-N-[6-methyl-5-(trifluoromethyl)-3-pyridyl]acetamide | 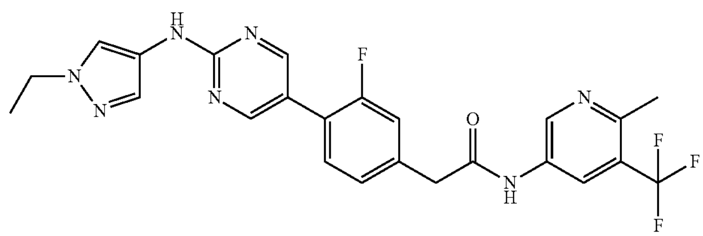 [SMILES: CCn1cc(Nc2ncc(-c3ccc(CC(=O)Nc4cnc(C)c(C(F)(F)F)c4)cc3F)cn2)cn1] | 500.3 |
| P-0249 | 2-[4-[2-[(1-ethylpyrazol-4-yl)amino]pyrimidin-5-yl]-2,5-difluoro-phenyl]-N-[6-methyl-5-(trifluoromethyl)-3-pyridyl]acetamide | 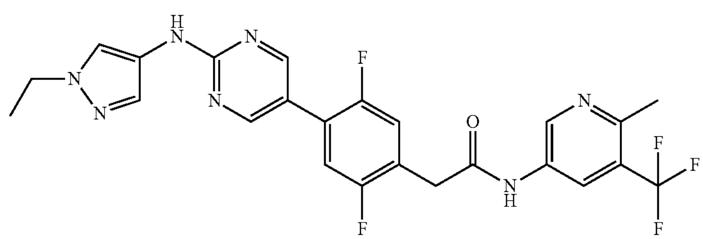 [SMILES: CCn1cc(Nc2ncc(-c3cc(F)c(CC(=O)Nc4cnc(C)c(C(F)(F)F)c4)cc3F)cn2)cn1] | 518.3 |
| P-0250 | 2-[4-[2-[(1-ethylpyrazol-4-yl)amino]pyrimidin-5-yl]phenyl]-N-[4-(trifluoromethyl)-2-pyridyl]acetamide | 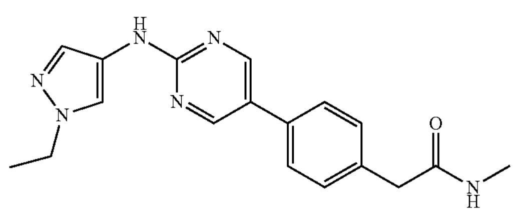 [SMILES: CCn1cc(Nc2ncc(-c3ccc(CC(=O)NC)cc3)cn2)cn1] | 468.1 |
| P-0251 | 2-[4-[2-[(1-ethylpyrazol-4-yl)amino]pyrimidin-5-yl]phenyl]-N-[5-(trifluoromethyl)-2-pyridyl]acetamide | 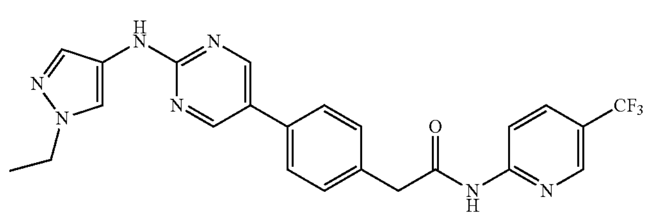 [SMILES: CCn1cc(Nc2ncc(-c3ccc(CC(=O)Nc4ccc(C(F)(F)F)cn4)cc3)cn2)cn1] | 468.4 |

TABLE 1-continued

| Number | Compound Name | Compound Structure | (MH)+ |
|---|---|---|---|
| P-0252 | 2-[4-[2-[(1-ethylpyrazol-4-yl)amino]pyrimidin-5-yl]phenyl]-N-[6-(trifluoromethyl)-3-pyridyl]acetamide | 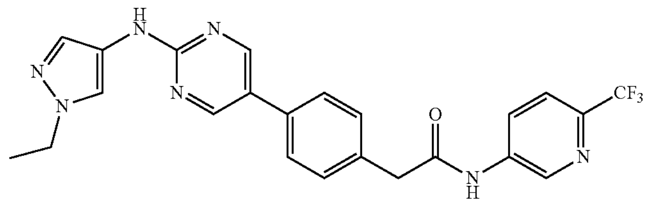 [SMILES: CCn1cc(Nc2ncc(-c3ccc(CC(=O)Nc4ccc(C(F)(F)F)nc4)cc3)cn2)cn1] | 468.1 |
| P-0253 | 2-[4-[2-[(1-ethylpyrazol-4-yl)amino]pyrimidin-5-yl]phenyl]-N-[6-methoxy-5-(trifluoromethyl)-3-pyridyl]acetamide | 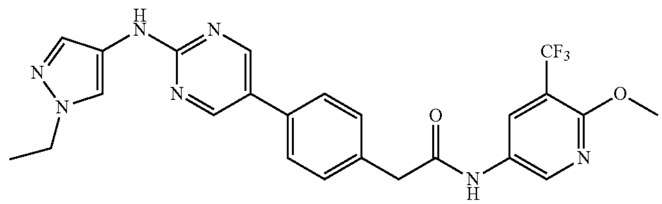 [SMILES: CCn1cc(Nc2ncc(-c3ccc(CC(=O)Nc4cnc(OC)c(C(F)(F)F)c4)cc3)cn2)cn1] | 498.4 |
| P-0254 | 2-[4-[2-[(1-ethylpyrazol-4-yl)amino]pyrimidin-5-yl]phenyl]-N-[6-methyl-5-(trifluoromethyl)-3-pyridyl]acetamide | 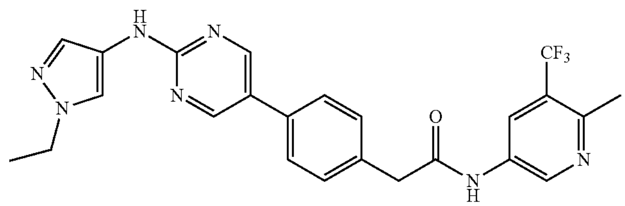 [SMILES: CCn1cc(Nc2ncc(-c3ccc(CC(=O)Nc4cnc(C)c(C(F)(F)F)c4)cc3)cn2)cn1] | 482.2 |
| P-0255 | 2-[4-[2-[(1-ethylpyrazol-4-yl)amino]pyrimidin-5-yl]-2-fluoro-phenyl]-N-[4-(trifluoromethyl)-2-pyridyl]acetamide | 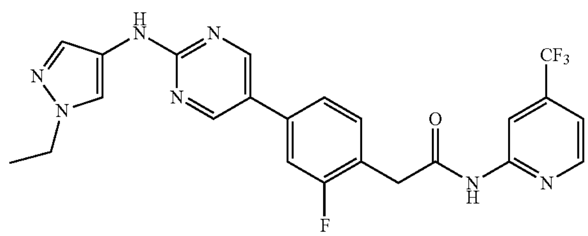 [SMILES: CCn1cc(Nc2ncc(-c3ccc(CC(=O)Nc4cc(C(F)(F)F)ccn4)c(F)c3)cn2)cn1] | 486.1 |
| P-0256 | 2-[4-[2-[(1-ethylpyrazol-4-yl)amino]pyrimidin-5-yl]-2-fluoro-phenyl]-N-[5-(trifluoromethyl)-2-pyridyl]acetamide | 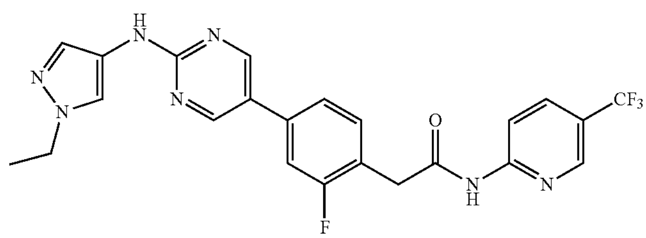 [SMILES: CCn1cc(Nc2ncc(-c3ccc(CC(=O)Nc4ccc(C(F)(F)F)cn4)c(F)c3)cn2)cn1] | 486.4 |
| P-0257 | 2-[4-[2-[(1-ethylpyrazol-4-yl)amino]pyrimidin-5-yl]-2-fluoro-phenyl]-N-[6-(trifluoromethyl)-3-pyridyl]acetamide | 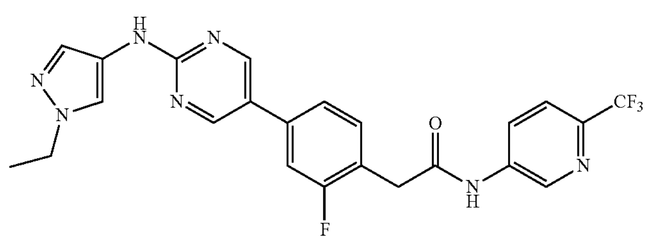 [SMILES: CCn1cc(Nc2ncc(-c3ccc(CC(=O)Nc4ccc(C(F)(F)F)nc4)c(F)c3)cn2)cn1] | 486.4 |
| P-0258 | 2-[4-[2-[(1-ethylpyrazol-4-yl)amino]pyrimidin-5-yl]-2-fluoro-phenyl]-N-[5-(trifluoromethyl)-3-pyridyl]acetamide | 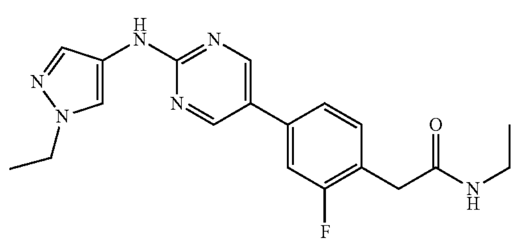 [SMILES: CCNC(=O)Cc1ccc(-c2cnc(Nc3cnn(CC)c3)nc2)cc1F] | 486.4 |

TABLE 1-continued

| Number | Compound Name | Compound Structure | (MH)+ |
|---|---|---|---|
| P-0259 | 2-[4-[2-[(1-ethylpyrazol-4-yl)amino]pyrimidin-5-yl]-2-fluoro-phenyl]-N-[6-methoxy-5-(trifluoromethyl)-3-pyridyl]acetamide | 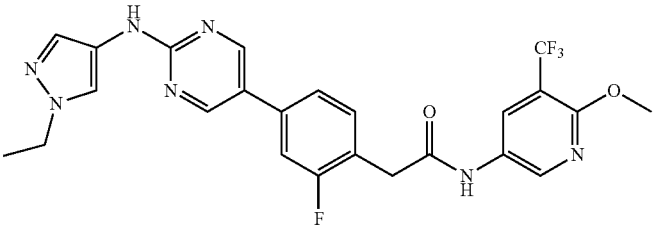 [SMILES: CCn1cc(Nc2ncc(-c3ccc(CC(=O)Nc4cnc(OC)c(C(F)(F)F)c4)c(F)c3)cn2)cn1] | 516.1 |
| P-0260 | N-[6-chloro-5-(trifluoromethyl)-3-pyridyl]-2-[4-[2-[(1-ethylpyrazol-4-yl)amino]pyrimidin-5-yl]-2-fluoro-phenyl]acetamide | 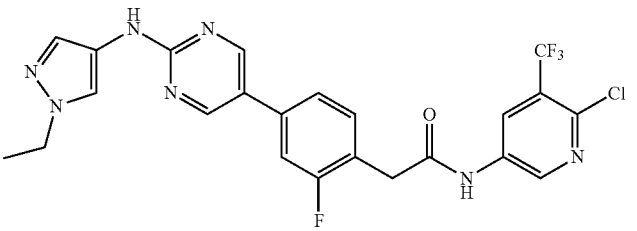 [SMILES: CCn1cc(Nc2ncc(-c3ccc(CC(=O)Nc4cnc(Cl)c(C(F)(F)F)c4)c(F)c3)cn2)cn1] | 520.3 |
| P-0261 | 2-[4-[2-[(1-ethylpyrazol-4-yl)amino]pyrimidin-5-yl]-2-fluoro-phenyl]-N-[6-methyl-5-(trifluoromethyl)-3-pyridyl]acetamide | 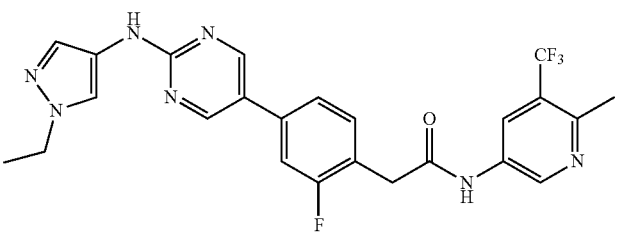 [SMILES: CCn1cc(Nc2ncc(-c3ccc(CC(=O)Nc4cnc(C)c(C(F)(F)F)c4)c(F)c3)cn2)cn1] | 500.2 |
| P-0262 | 2-[4-(3-cyclopropyl-1H-pyrazolo[3,4-b]pyridin-5-yl)-2-fluoro-phenyl]-N-[6-methoxy-5-(trifluoromethyl)-3-pyridyl]acetamide | 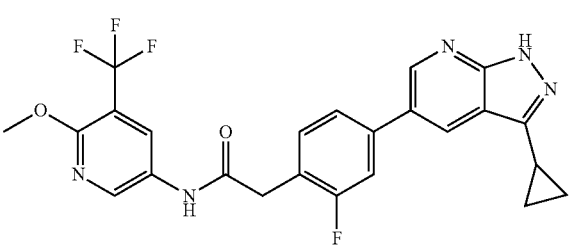 [SMILES: COc1ncc(NC(=O)Cc2ccc(-c3cnc4[nH]nc(C5CC5)c4c3)cc2F)cc1C(F)(F)F] | 486.3 |
| P-0263 | 2-[4-(3-cyclopropyl-1H-pyrazolo[3,4-b]pyridin-5-yl)phenyl]-N-[6-methoxy-5-(trifluoromethyl)-3-pyridyl]acetamide | 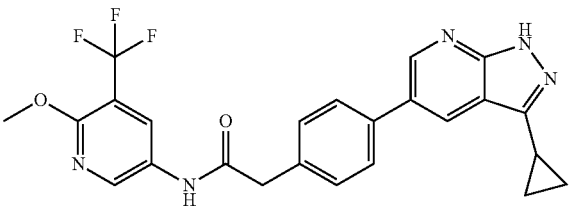 [SMILES: COc1ncc(NC(=O)Cc2ccc(-c3cnc4[nH]nc(C5CC5)c4c3)cc2)cc1C(F)(F)F] | 468.3 |
| P-0264 | 2-[2-fluoro-4-[2-[[1-(2-methoxyethyl)pyrazol-4-yl]amino]pyrimidin-5-yl]phenyl]-N-[6-methyl-5-(trifluoromethyl)-3-pyridyl]acetamide | 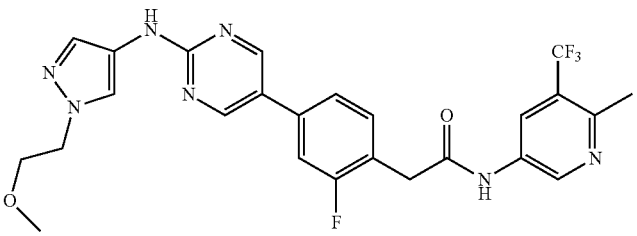 [SMILES: COCCn1cc(Nc2ncc(-c3ccc(CC(=O)Nc4cnc(C)c(C(F)(F)F)c4)c(F)c3)cn2)cn1] | 530.2 |

TABLE 1-continued

| Number | Compound Name | Compound Structure | (MH)+ |
|---|---|---|---|
| P-0265 | 2-[2-fluoro-4-[2-[[1-(2-methoxyethyl)pyrazol-4-yl]amino]pyrimidin-5-yl]phenyl]-N-[6-methoxy-5-(trifluoromethyl)-3-pyridyl]acetamide | 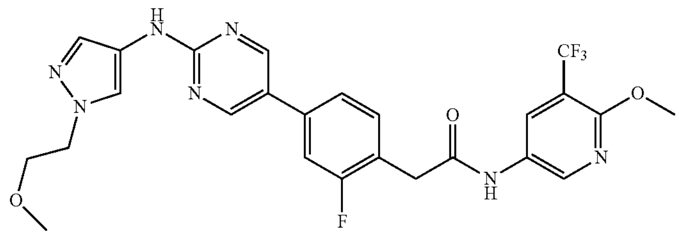 [SMILES: COCCn1cc(Nc2ncc(-c3ccc(CC(=O)Nc4cnc(OC)c(C(F)(F)F)c4)c(F)c3)cn2)cn1] | 546.1 |
| P-0266 | N-[6-chloro-5-(trifluoromethyl)-3-pyridyl]-2-[2-fluoro-4-[2-[[1-(2-methoxyethyl)pyrazol-4-yl]amino]pyrimidin-5-yl]phenyl]acetamide | 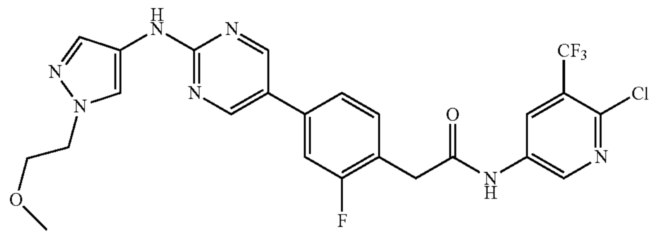 [SMILES: COCCn1cc(Nc2ncc(-c3ccc(CC(=O)Nc4cnc(Cl)c(C(F)(F)F)c4)c(F)c3)cn2)cn1] | 550.3 |
| P-0267 | 2-[2-fluoro-4-[2-[[1-(2-methoxyethyl)pyrazol-4-yl]amino]pyrimidin-5-yl]phenyl]-N-[5-(trifluoromethyl)-3-pyridyl]acetamide | 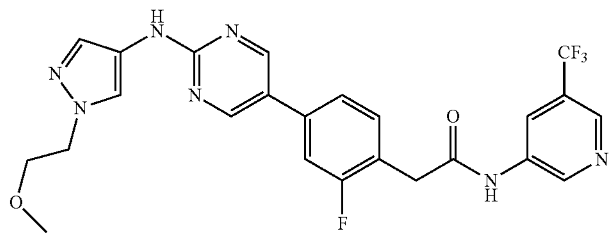 [SMILES: COCCn1cc(Nc2ncc(-c3ccc(CC(=O)Nc4cncc(C(F)(F)F)c4)c(F)c3)cn2)cn1] | 516.4 |
| P-0268 | 2-[2-fluoro-4-[2-[[1-(2-methoxyethyl)pyrazol-4-yl]amino]pyrimidin-5-yl]phenyl]-N-[6-(trifluoromethyl)-3-pyridyl]acetamide | 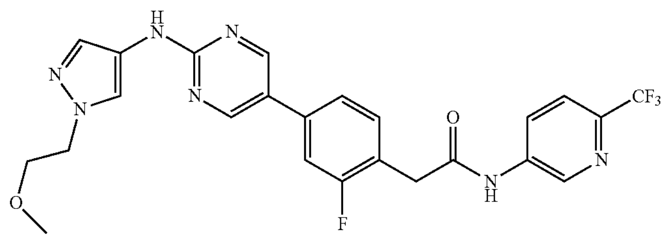 [SMILES: COCCn1cc(Nc2ncc(-c3ccc(CC(=O)Nc4ccc(C(F)(F)F)nc4)c(F)c3)cn2)cn1] | 516.1 |
| P-0269 | 2-[2-fluoro-4-[2-[[1-(2-methoxyethyl)pyrazol-4-yl]amino]pyrimidin-5-yl]phenyl]-N-[5-(trifluoromethyl)-2-pyridyl]acetamide | 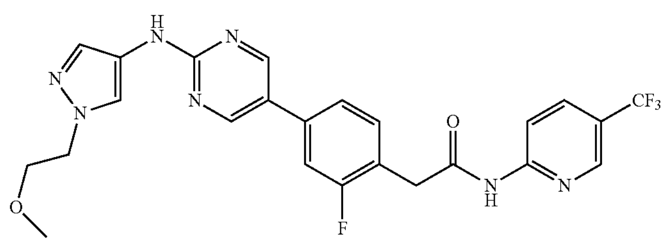 [SMILES: COCCn1cc(Nc2ncc(-c3ccc(CC(=O)Nc4ccc(C(F)(F)F)cn4)c(F)c3)cn2)cn1] | 516.4 |
| P-0270 | 2-[2-fluoro-4-[2-[[1-(2-methoxyethyl)pyrazol-4-yl]amino]pyrimidin-5-yl]phenyl]-N-[4-(trifluoromethyl)-2-pyridyl]acetamide | 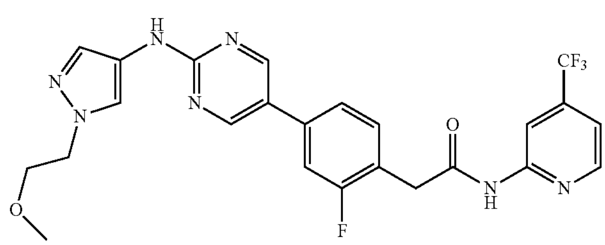 [SMILES: COCCn1cc(Nc2ncc(-c3ccc(CC(=O)Nc4cc(C(F)(F)F)ccn4)c(F)c3)cn2)cn1] | 516.4 |

TABLE 1-continued

| Number | Compound Name | Compound Structure | (MH)+ |
|---|---|---|---|
| P-0271 | 2-[4-[2-[[1-(2-methoxyethyl)pyrazol-4-yl]amino]pyrimidin-5-yl]phenyl]-N-[6-methoxy-5-(trifluoromethyl)-3-pyridyl]acetamide | 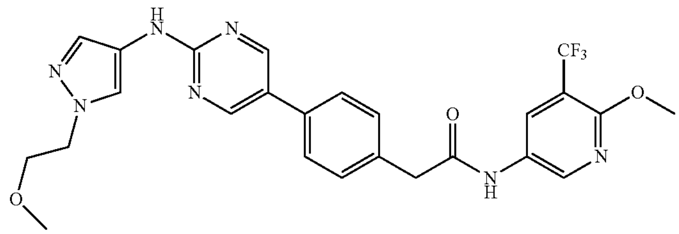 [SMILES: COCCn1cc(Nc2ncc(-c3ccc(CC(=O)Nc4cnc(OC)c(C(F)(F)F)c4)cc3)cn2)cn1] | 528.1 |
| P-0272 | N-[6-chloro-5-(trifluoromethyl)-3-pyridyl]-2-[4-[2-[[1-(2-methoxyethyl)pyrazol-4-yl]amino]pyrimidin-5-yl]phenyl]acetamide | 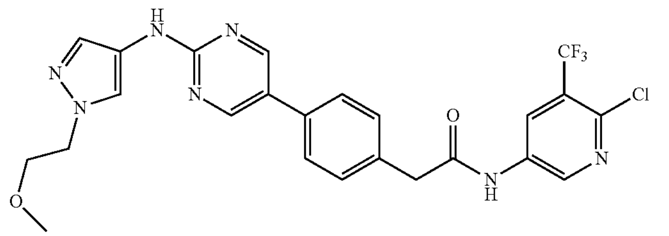 [SMILES: COCCn1cc(Nc2ncc(-c3ccc(CC(=O)Nc4cnc(Cl)c(C(F)(F)F)c4)cc3)cn2)cn1] | 532.0 |
| P-0273 | 2-[4-[2-[[1-(2-methoxyethyl)pyrazol-4-yl]amino]pyrimidin-5-yl]phenyl]-N-[6-(trifluoromethyl)-3-pyridyl]acetamide | 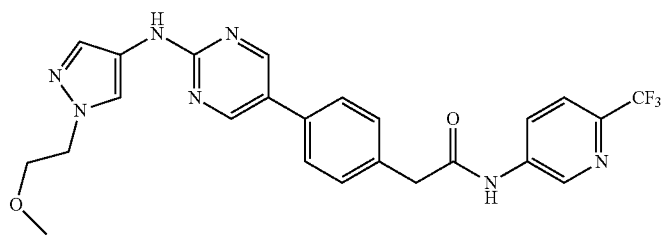 [SMILES: COCCn1cc(Nc2ncc(-c3ccc(CC(=O)Nc4ccc(C(F)(F)F)nc4)cc3)cn2)cn1] | 498.4 |
| P-0274 | 2-[4-[2-[[1-(2-methoxyethyl)pyrazol-4-yl]amino]pyrimidin-5-yl]phenyl]-N-[5-(trifluoromethyl)-2-pyridyl]acetamide | 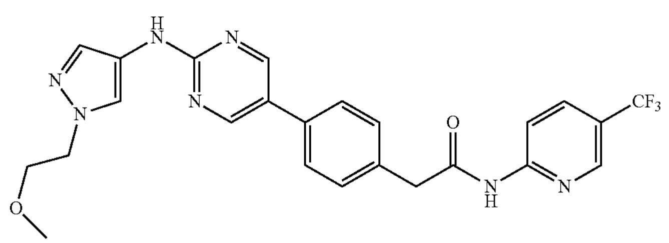 [SMILES: COCCn1cc(Nc2ncc(-c3ccc(CC(=O)Nc4ccc(C(F)(F)F)cn4)cc3)cn2)cn1] | 498.4 |

Biological Examples

Example 17

Cell-based Assays of FLT3 Kinase Activity

The FLT3 inhibitors may be assessed using the MOLM-14, Acute Myeloid Leukemia cell line that endogenously expresses FLT3 ITD or derivatives of the human FLT3 AML cell line which acquired the D835Y (activation loop) of F691L (gatekeeper) mutation after selection in escalating doses of the FLT3 Inhibitor AC220. FLT3 inhibitors may also be assessed using cells that are engineered to express mutant FLT3. For engineered cells, murine Ba/F3 cells were transfected with full-length FLT3 ITD/D835Y mutations. The parental BA/F3 cells are dependent upon Interleukin-3 (IL-3) for survival, and introduction of the FLT3 constructs rendered these cells dependent upon FLT3 kinase activity when cultured in the absences of IL-3. Engineered BA/F3 cell growth assays can be performed in either the presence or absence of IL-3, to assess the compound inhibition of FLT3 or to detect the presence of off-target activity, respectively. Inhibitors of FLT3 kinase activity reduce or eliminate the FLT3 oncogenic signaling, resulting in reduced cell proliferation. This inhibition is measured as a function of compound concentration to assess $IC_{50}$ values.

Cell lines used in proliferation assays are as follows in Table 2:

TABLE 2

| Cell line | Cell type | FLT3 expressed | Growth media |
|---|---|---|---|
| MOLM-14 | Human AML derived Cells[8] | Endogenous FLT3 ITD | IMDM media[7,] and 10% FBS[1] |
| MOLM-14 D835Y | Human AML derived Cells[8] | Endogenous FLT3 ITD and transfected FLT3 D835Y | IMDM media[7,] and 10% FBS[1] |
| MOLM-14 F691L | Human AML derived Cells[8] | Endogenous FLT3 ITD and transfected FLT3 F691L | IMDM media[7,] and 10% FBS[1] |

TABLE 2-continued

| Cell line | Cell type | FLT3 expressed | Growth media |
|---|---|---|---|
| BA/F3-FLT3-ITD + D835Y | Pro B cells[3] | Transfected FLT3-ITD + D835Y | RPMI 1640[2,] 10% FBS[1], 1% L-Glutamine[4], 1% NEAA[5], 10% WEHI-3B conditioned medium[6] (i.e. IL-3) |

[1]Fetal bovine serum (FBS), Invitrogen catalog #10438026
[2]RPMI 1640, Invitrogen catalog #11875
[3]Parental BA/F3 cells, DSMZ catalog #ACC 300
[4]L-Glutamine, Invitrogen catalog #25030
[5]Non-Essential Amino Acids (NEAA), Invitrogen catalog #11140
[6]WEHI-3B conditioned medium (CM) contains murine IL-3 that supports the growth of parental BA/F3 cells.
[7]IMDM, Invitrogen catalog #12440
[8]MOLM-14 cells obtained from Dr. Neil Shal at University of California, San Francisco.

Cells were seeded at 1×10[4] cells per well of a 96 well cell culture plate in 50 µl of cell culture medium. Compounds were dissolved in DMSO, typically at a concentration of 0.5 mM and were serially diluted 1:3 for a total of eight points and added to the cells to final concentrations of 1, 0.33, 0.11, 0.37, 0.12, 0.0041, 0.0014 and 0.00046 µM in 100 µl cell culture medium (final concentration 0.2% DMSO). Some of the more potent compounds were run at a 10× lower range. The cells were incubated at 37° C., 5% $CO_2$ for three days. CellTiter-Glo Buffer (Promega Cell Viability Assay catalog #G7573) and substrate were equilibrated to room temperature, and enzyme/substrate Recombinant Firefly Luciferase/Beetle Luciferin was reconstituted. The cell plates were equilibrated to room temperature for 30 minutes, then lysed by addition of an equivalent volume of the Celltiter-Glo Reagent. The plate was mixed for 10 minutes on a plate shaker to lyse the cells. The plates were read on a Tecan M1000 using Luminescence protocol modified to read 0.1 s per well. The luminescence reading assesses the ATP content, which correlates directly with cell number such that the reading as a function of compound concentration was used to determine the $IC_{50}$ value.

In order to determine the effect of compounds on FLT3 catalytic activity, kinase assays using recombinant enzymes and AlphaScreen® technology have been established. The catalytic activity of c-kit activity was also measured to determine selectivity of the compounds. When the kinases are catalytically active, they phosphorylate a biotinylated peptide substrate on tyrosine residues. Using AlphaScreen® technology, the ability of the compounds to affect the catalytic activity of the kinases can be measured quantitatively. The peptide substrate is immobilized by the AlphaScreen® Streptavidin Donor beads and, upon phosphorylation by a tyrosine kinase, can bind to AlphaScreen® Anti-Phosphotyrosine (PY20) Acceptor beads. Upon excitation of these beads with laser light at 680 nm, singlet oxygen is produced. This singlet oxygen is rapidly quenched, unless the AlphaScreen® Anti-Phosphotyrosine (PY20) Acceptor beads are in close proximity, in which case a proximity signal can be measured at 580 nm. In the presence of catalytic activity, there is a very strong proximity signal. Selective kinase inhibitors affect a decrease in this proximity signal through a decrease in tyrosine phosphorylation of the peptide substrate. The recombinant enzymes were purchased from the following commercial sources as summarized in Table 3:

TABLE 3

| Enzyme | Commercial Source |
|---|---|
| FLT3-ITD | Invitrogen #PV6190 |
| FLT3-D835Y | Invitrogen #PV3967 |
| c-KIT | Millipore #14-559K |

The assay was performed as summarized below. Buffers used are summarized in Table 4.

TABLE 4

| Assay | Assay Buffer | Stop/Detection Buffer |
|---|---|---|
| FLT3 | 25 mM Hepes pH 7.5<br>5 mM $MnCl_2$<br>5 mM $MgCl_2$<br>0.01% Tween-20<br>1 mM DTT<br>0.01% BSA | 25 mM Hepes pH 7.5,<br>0.01% BSA<br>100 mM EDTA |
| c-KIT | 25 mM Hepes pH 7.5<br>2 mM $MnCl_2$<br>2 mM $MgCl_2$<br>0.01% Tween-20<br>1 mM DTT<br>0.01% BSA | 25 mM Hepes pH 7.5,<br>0.01% BSA<br>100 mM EDTA |

Substrate

Poly (Glu4-Tyr) Peptide, biotin conjugate [Biotin-GG $(EEEEY)_{10}EE$] (SEQ ID NO: 4)
UBI/Millipore #12-440
Final concentration=30 nM Adenosine Triphosphate (ATP)

Sigma #A-3377
Final concentration for $IC_{50}$ determination=10 µM (FLT3-D835Y or FLT3-ITD) or 100 µM (c-KIT)

Detection Reagent

AlphaScreen® Phosphotyrosine (PY20) Assay Kit
Perkin-Elmer #6760601M
Final concentration=10 µg/mL Protocol $IC_{50}$ Dilute compounds in DMSO to 20× final concentration.
Add 1 µL of compound to each well of 384 well reaction plate (Perkin Elmer #6005359).
Mix enzyme and Poly (Glu4-Tyr) Peptide substrate at 1.33× final concentration in assay buffer.
Mix ATP at 5× final concentration in assay buffer.
Add 15 µL enzyme/substrate mixture to the reaction plate.
Add 4 µL of ATP to the reaction plate. Centrifuge 1 minute, shake to mix, and incubate as summarized in Table 5:

TABLE 5

| Assay | Reaction temperature | Reaction time |
|---|---|---|
| FLT3 | Room temperature | 60 minutes |
| c-KIT | Room temperature | 60 minutes |

Mix Streptavidin Donor beads at 6× final concentration in Stop/Detection buffer.
Add 5 µL Streptavidin Donor beads to the reaction plate. Centrifuge 1 minute, shake to mix, and incubate at room temperature for 20 minutes.

Mix Anti-Phosphotyrosine (PY20) Acceptor beads at 6× final concentration in Stop/Detection buffer.

Add 5 µL Anti-Phosphotyrosine (PY20) beads to the reaction plate.

Centrifuge 1 minute, shake to mix, and incubate at room temperature for 60 minutes.

Read plate on Wallac EnVision™ 2103 Multilabel Reader.

Cell-based Assays of c-Fms Kinase Activity

M-CSF dependent RAW264.7 cells were seeded on a 12 well plate, $2.5 \times 10^5$ cells/well and the cells were allowed to attach overnight at 37° C., 5% $CO_2$. The cells were then starved in serum-free medium overnight at 37° C., 5% $CO_2$. The cells were treated with compound for 1 hour in serum-free media (1% DMSO final concentration) and then stimulated with 20 ng/ml M-CSF for 5 minutes. After stimulation, the cells were lysed on ice, and the lysates were centrifuged at 13,000 rpm for 1 minute. The amount of protein in the sample was quantitated, sample buffer was added, and the samples were boiled at 95° C. for 10 minutes. The samples were then centrifuged at 13,000 rpm for 1 minute. The samples (15-20 µg/lane) were loaded and run on 4-12% tris-glycine gel at 75V, and then transferred onto a PVDF membrane. The membrane was blocked for 1 hour with 5% BSA in PBS/1% Tween-20 (PBST); or 5% milk, depending on the primary antibody used. Then the blots were incubated with primary antibody overnight at 4 degrees with gentle shaking. After incubation with the capture antibody, the membranes were washed 3×10 minutes with PBST; then incubated with detection antibody Goat Anti-Rabbit-HRP for 1 hour, with gentle shaking. The membranes were washed again 3×10 minutes with PBST. ECL Plus substrate was then added to the blots, the image captured with chemiluminescence camera, and the bands quantitated for pFMS and FMS levels.

The Fms inhibitors may also be assessed using M-NFS-60 mouse myelogenous leukemia cell line (ATCC catalog #CRL-1838). This cell line proliferation is stimulated by M-CSF, which binds and activates the fms tyrosine kinase receptor. Inhibitors of fms kinase activity reduce or eliminate the M-CSF stimulated kinase activity, resulting in reduced cell proliferation. This inhibition is measured as a function of compound concentration to assess $IC_{50}$ values. M-NFS-60 cells were seeded at $5 \times 10^4$ cells per well of a 96 well cell culture plate in 50 µL of cell culture medium of RPMI 1640 (CellGro Mediatech catalog #10-040-CV) supplemented with 10% FBS (HyClone catalog #SH30071.03). Compounds were dissolved in DMSO at a concentration of 1 mM and were serially diluted 1:3 for a total of eight points and added to the cells to final concentrations of 10, 3.3, 1.1, 0.37, 0.12, 0.041, 0.014 and 0.0046 µM in 100 µl cell culture medium (final concentration 0.2% DMSO). Cells were also treated with staurosporine as a positive control. The cells were stimulated by adding 20 µl of 372 ng/ml M-CSF to a final concentration of 62 ng/ml (R&D Systems catalog #216-MC). The cells were incubated at 37° C., 5% $CO_2$ for three days. CellTiter-Glo Buffer (Promega Cell Viability Assay catalog #G7573) and substrate were equilibrated to room temperature, and enzyme/substrate Recombinant Firefly Luciferase/Beetle Luciferin was reconstituted. The cell plates were equilibrated to room temperature for 30 minutes, then lysed by addition of an equivalent volume of the Celltiter-Glo Reagent. The plate was mixed for 2 minutes on a plate shaker to lyse the cells, then incubated for 10 minutes at room temperature. The plates were read on a Victor Wallac II using Luminescence protocol modified to read 0.1 s per well. The luminescence reading assesses the ATP content, which correlates directly with cell number such that the reading as a function of compound concentration was used to determine the $IC_{50}$ value.

Additional cell based assays can be correlated to the Fms activity of compounds of the invention. For example, the ability of osteoclast precursor cells (commercially available from Lonza) to differentiate into mature osteoclasts, due to stimulation by M-CSF and RANKL, in the presence of compounds, can be measured using a method analogous to that previously reported (Hudson et al., Journal of Urology, 1947, 58:89-92), where the amount of acid phosphatase in the supernatant (i.e. TRAP5b excreted by mature osteoclasts) is proportional to the number of mature osteoclasts present. In another example, the ability of M-CSF-dependent murine macrophage cells (BAC1.2F5) to proliferate in the presence of compounds can be measured by culturing cells as previously described (Morgan et al., Journal of Cellular Physiology, 1987, 130:420-427) and determining cell viability by analysis of ATP levels in the cell culture (Crouch et al., Journal of Immunological Methods, 1993, 160:81-8).

The following Table 6 provides data indicating FLT3 ITD, D835Y and F691L; c-KIT and CSF1R biochemical and/or cell inhibitory activity for exemplary compounds as described herein. In the table below, activity is provided as follows: +++=0.0001 µM<$IC_{50}$<10 µM; ++=10 µM<$IC_{50}$<50 µM, +=50 µM<$IC_{50}$<100 µM.

TABLE 6

| P # | FLT3 D835Y 8 pt GMean $IC_{50}$ (µM) | FLT3_ITD 8 pt: $IC_{50}$ (µM) | BaF3_FLT3 ITD/D835Y 3 d-Growth: $IC_{50}$ (µM) | MOLM-14 D835Y 3 d-Growth GMean $IC_{50}$ (µM) | MOLM-14 F691L 3 d-Growth GMean $IC_{50}$ (µM) | CSF1R 100 ATP 8 pt $IC_{50}$ (µM) | c-KIT 100 ATP 8 pt $IC_{50}$ (µM) |
|---|---|---|---|---|---|---|---|
| P-0001 |  | +++ | +++ | +++ | +++ |  |  |
| P-0002 | +++ | +++ | +++ |  |  |  |  |
| P-0003 | +++ | +++ | +++ | +++ | +++ |  |  |
| P-0004 | +++ | +++ | +++ | +++ | +++ |  |  |
| P-0005 | +++ | +++ | +++ | +++ | +++ |  | +++ |
| P-0006 |  |  | +++ | +++ | +++ |  |  |
| P-0007 |  |  | +++ | +++ | +++ |  |  |
| P-0008 |  |  | +++ | +++ | +++ |  |  |
| P-0009 |  |  | +++ | +++ | +++ |  |  |
| P-0010 |  |  | +++ | +++ | +++ |  |  |
| P-0011 | +++ |  | +++ | +++ | +++ |  |  |
| P-0012 |  |  | +++ | +++ | +++ |  |  |

TABLE 6-continued

| P # | FLT3 D835Y 8 pt GMean IC$_{50}$ (μM) | FLT3_ITD 8 pt: IC$_{50}$ (μM) | BaF3_FLT3 ITD/D835Y 3 d-Growth: IC$_{50}$ (μM) | MOLM-14 D835Y 3 d-Growth GMean IC$_{50}$ (μM) | MOLM-14 F691L 3 d-Growth GMean IC$_{50}$ (μM) | CSF1R 100 ATP 8 pt IC$_{50}$ (μM) | c-KIT 100 ATP 8 pt IC$_{50}$ (μM) |
|---|---|---|---|---|---|---|---|
| P-0013 | +++ |  | +++ | +++ | +++ |  | +++ |
| P-0014 | +++ |  | +++ | +++ | +++ |  |  |
| P-0015 | +++ |  | +++ | +++ | +++ |  |  |
| P-0016 | +++ |  | +++ | +++ | +++ |  |  |
| P-0017 | +++ | +++ | +++ | +++ | +++ |  | +++ |
| P-0018 | +++ | +++ | +++ | +++ |  |  | +++ |
| P-0019 | +++ | +++ | +++ | +++ | +++ |  | +++ |
| P-0020 | +++ | +++ | +++ | +++ |  |  | +++ |
| P-0021 | +++ | +++ | +++ | +++ |  |  | +++ |
| P-0022 | +++ | +++ | +++ | +++ | +++ |  | +++ |
| P-0023 | +++ | +++ | +++ | +++ | +++ |  | +++ |
| P-0024 | +++ | +++ | +++ | +++ | +++ |  | +++ |
| P-0025 | +++ | +++ | +++ | +++ | +++ |  | +++ |
| P-0026 | +++ | +++ | +++ | +++ | +++ |  | +++ |
| P-0027 | +++ | +++ | +++ | +++ | +++ |  | +++ |
| P-0028 | +++ | +++ |  |  |  |  | +++ |
| P-0029 | +++ | +++ | +++ |  |  |  | +++ |
| P-0030 |  | +++ | +++ |  | +++ |  | +++ |
| P-0031 | +++ | +++ | +++ | +++ |  |  | +++ |
| P-0032 | +++ | +++ | +++ | +++ | +++ |  | +++ |
| P-0033 | +++ | +++ | +++ | +++ | +++ |  | +++ |
| P-0034 | +++ | +++ | +++ | +++ | +++ |  | +++ |
| P-0035 | +++ | +++ | +++ | +++ | +++ |  | +++ |
| P-0036 | +++ | +++ | +++ | +++ |  |  | +++ |
| P-0037 | +++ | +++ | +++ | +++ | +++ |  | +++ |
| P-0038 |  | +++ | +++ | +++ | +++ |  |  |
| P-0039 |  |  | +++ | +++ | +++ |  |  |
| P-0040 |  |  | +++ | +++ | +++ |  |  |
| P-0041 |  |  | +++ |  |  |  |  |
| P-0042 |  |  | +++ | +++ | +++ |  |  |
| P-0043 | +++ | +++ | +++ | +++ | +++ |  | +++ |
| P-0044 | +++ | +++ | +++ | +++ | +++ |  | +++ |
| P-0045 |  | +++ | +++ |  |  |  |  |
| P-0046 |  | +++ | +++ |  |  |  |  |
| P-0047 | +++ | +++ | +++ | +++ | +++ |  | +++ |
| P-0048 | +++ |  | +++ |  |  |  | +++ |
| P-0049 |  |  | +++ | +++ | +++ |  | +++ |
| P-0050 | +++ | +++ | +++ | +++ |  |  | +++ |
| P-0051 | +++ | +++ | +++ |  |  |  | +++ |
| P-0052 | +++ | +++ |  | +++ | +++ |  | +++ |
| P-0053 | +++ | +++ | +++ | +++ | +++ |  | +++ |
| P-0054 |  |  | +++ | +++ | +++ |  |  |
| P-0055 | +++ | +++ | +++ | +++ | +++ |  | +++ |
| P-0056 |  |  | +++ | +++ | +++ |  |  |
| P-0057 | +++ | +++ | +++ | +++ | +++ |  | +++ |
| P-0058 | +++ | +++ | +++ | +++ | +++ |  | +++ |
| P-0059 | +++ | +++ | +++ | +++ | +++ |  | +++ |
| P-0060 | +++ | +++ | +++ | +++ | +++ |  | +++ |
| P-0061 | +++ | +++ | +++ | +++ | +++ |  | +++ |
| P-0062 | +++ | +++ | +++ | +++ | +++ |  | +++ |
| P-0063 | +++ | +++ | +++ | +++ | +++ |  | +++ |
| P-0064 |  | +++ | +++ | +++ |  |  | +++ |
| P-0065 | +++ | +++ | +++ | +++ | +++ |  | +++ |
| P-0066 | +++ | +++ | +++ | +++ | +++ |  | +++ |
| P-0067 | +++ | +++ | +++ | +++ | +++ |  | +++ |
| P-0068 | +++ | +++ | +++ | +++ | +++ |  | +++ |
| P-0069 |  |  | +++ | +++ |  |  |  |
| P-0070 | +++ | +++ | +++ | +++ | +++ | +++ | +++ |
| P-0071 | +++ | +++ | +++ | +++ | +++ |  | +++ |
| P-0072 | +++ | +++ | +++ | +++ | +++ | +++ | +++ |
| P-0073 | +++ | +++ | +++ | +++ | +++ | +++ | +++ |
| P-0074 | +++ | +++ | +++ | +++ | +++ |  |  |
| P-0075 | +++ | +++ | +++ | +++ |  |  |  |
| P-0076 | +++ | +++ | +++ | +++ |  |  | +++ |
| P-0077 | +++ | +++ | +++ | +++ | +++ |  | +++ |
| P-0078 | +++ | +++ | +++ | +++ | +++ |  | +++ |
| P-0079 | +++ | +++ | +++ | +++ | +++ |  | +++ |
| P-0080 | +++ | +++ |  |  |  |  | +++ |
| P-0081 | +++ | +++ | +++ | +++ | +++ |  | +++ |
| P-0082 | +++ | +++ | +++ | +++ | +++ |  | +++ |
| P-0083 | +++ | +++ | +++ | +++ | +++ |  | +++ |
| P-0084 | +++ | +++ | +++ | +++ | +++ |  | +++ |

TABLE 6-continued

| P # | FLT3 D835Y 8 pt GMean IC$_{50}$ (μM) | FLT3_ITD 8 pt: IC$_{50}$ (μM) | BaF3_FLT3 ITD/D835Y 3 d-Growth: IC$_{50}$ (μM) | MOLM-14 D835Y 3 d-Growth GMean IC$_{50}$ (μM) | MOLM-14 F691L 3 d-Growth GMean IC$_{50}$ (μM) | CSF1R 100 ATP 8 pt IC$_{50}$ (μM) | c-KIT 100 ATP 8 pt IC$_{50}$ (μM) |
|---|---|---|---|---|---|---|---|
| P-0085 | | +++ | | | | | +++ |
| P-0086 | +++ | +++ | +++ | +++ | +++ | | +++ |
| P-0087 | +++ | +++ | +++ | +++ | +++ | | +++ |
| P-0088 | | +++ | +++ | +++ | +++ | | +++ |
| P-0089 | +++ | +++ | +++ | +++ | +++ | | +++ |
| P-0090 | +++ | +++ | +++ | +++ | +++ | | +++ |
| P-0091 | +++ | +++ | +++ | +++ | +++ | | +++ |
| P-0092 | +++ | +++ | +++ | +++ | +++ | | +++ |
| P-0093 | | | +++ | +++ | +++ | | |
| P-0094 | +++ | +++ | +++ | +++ | +++ | | +++ |
| P-0095 | +++ | +++ | +++ | +++ | +++ | | +++ |
| P-0096 | +++ | +++ | +++ | +++ | +++ | | +++ |
| P-0097 | +++ | +++ | +++ | +++ | +++ | | +++ |
| P-0098 | +++ | +++ | +++ | +++ | +++ | | +++ |
| P-0099 | +++ | +++ | +++ | +++ | +++ | | +++ |
| P-0100 | +++ | +++ | +++ | +++ | +++ | | +++ |
| P-0101 | +++ | +++ | +++ | +++ | +++ | | +++ |
| P-0102 | +++ | +++ | +++ | +++ | +++ | | +++ |
| P-0103 | +++ | +++ | +++ | +++ | +++ | | +++ |
| P-0104 | +++ | +++ | +++ | +++ | +++ | | +++ |
| P-0105 | +++ | +++ | +++ | +++ | +++ | | +++ |
| P-0106 | +++ | +++ | +++ | +++ | +++ | | +++ |
| P-0107 | +++ | +++ | +++ | +++ | +++ | | +++ |
| P-0108 | +++ | +++ | +++ | +++ | +++ | | +++ |
| P-0109 | +++ | +++ | +++ | +++ | +++ | | +++ |
| P-0110 | +++ | +++ | +++ | +++ | +++ | | +++ |
| P-0111 | +++ | +++ | +++ | +++ | +++ | | +++ |
| P-0112 | | | +++ | +++ | +++ | | |
| P-0113 | | | +++ | +++ | | | |
| P-0114 | | | +++ | | +++ | | |
| P-0115 | | | | | | | |
| P-0116 | | | +++ | +++ | +++ | | |
| P-0117 | | | +++ | +++ | +++ | | |
| P-0118 | | | +++ | +++ | +++ | | |
| P-0119 | | | +++ | +++ | +++ | | |
| P-0120 | | | +++ | +++ | +++ | | |
| P-0121 | | | | | | | |
| P-0122 | | | | | | | |
| P-0123 | | | +++ | +++ | +++ | | |
| P-0124 | | | +++ | +++ | +++ | | |
| P-0125 | | | +++ | +++ | +++ | | |
| P-0126 | | | +++ | +++ | +++ | | |
| P-0127 | | | +++ | +++ | +++ | | |
| P-0128 | | | +++ | +++ | +++ | | |
| P-0129 | | | +++ | +++ | +++ | | |
| P-0130 | | | +++ | +++ | +++ | | |
| P-0131 | +++ | +++ | +++ | +++ | +++ | | +++ |
| P-0132 | | +++ | +++ | +++ | +++ | | +++ |
| P-0133 | +++ | +++ | +++ | +++ | +++ | | +++ |
| P-0134 | +++ | +++ | +++ | +++ | +++ | | +++ |
| P-0135 | +++ | +++ | +++ | +++ | +++ | | +++ |
| P-0136 | +++ | +++ | +++ | +++ | +++ | | +++ |
| P-0137 | +++ | +++ | +++ | +++ | +++ | | +++ |
| P-0138 | +++ | +++ | +++ | +++ | +++ | | +++ |
| P-0139 | +++ | +++ | +++ | +++ | +++ | | +++ |
| P-0140 | +++ | +++ | +++ | +++ | +++ | | +++ |
| P-0141 | +++ | +++ | +++ | +++ | +++ | | +++ |
| P-0142 | +++ | +++ | +++ | +++ | +++ | | +++ |
| P-0143 | +++ | +++ | +++ | +++ | +++ | | +++ |
| P-0144 | +++ | +++ | +++ | +++ | +++ | | +++ |
| P-0145 | +++ | +++ | +++ | +++ | +++ | | +++ |
| P-0146 | +++ | +++ | +++ | +++ | +++ | | +++ |
| P-0147 | | | +++ | +++ | +++ | | |
| P-0148 | | | +++ | +++ | +++ | | |
| P-0149 | +++ | +++ | +++ | +++ | +++ | | +++ |
| P-0150 | +++ | +++ | +++ | +++ | +++ | | +++ |
| P-0151 | | +++ | +++ | +++ | | | +++ |
| P-0152 | +++ | +++ | +++ | +++ | +++ | | +++ |
| P-0153 | | +++ | +++ | +++ | | | +++ |
| P-0154 | +++ | +++ | +++ | +++ | +++ | | +++ |
| P-0155 | +++ | +++ | +++ | +++ | +++ | | +++ |
| P-0156 | +++ | +++ | +++ | +++ | +++ | | +++ |

TABLE 6-continued

| P # | FLT3 D835Y 8 pt GMean IC$_{50}$ (μM) | FLT3_ITD 8 pt: IC$_{50}$ (μM) | BaF3_FLT3 ITD/D835Y 3 d-Growth: IC$_{50}$ (μM) | MOLM-14 D835Y 3 d-Growth GMean IC$_{50}$ (μM) | MOLM-14 F691L 3 d-Growth GMean IC$_{50}$ (μM) | CSF1R 100 ATP 8 pt IC$_{50}$ (μM) | c-KIT 100 ATP 8 pt IC$_{50}$ (μM) |
|---|---|---|---|---|---|---|---|
| P-0157 | +++ | +++ | +++ | +++ | +++ | | +++ |
| P-0158 | +++ | +++ | +++ | +++ | +++ | | +++ |
| P-0159 | | +++ | +++ | +++ | +++ | | +++ |
| P-0160 | | +++ | +++ | +++ | +++ | | +++ |
| P-0161 | +++ | +++ | +++ | +++ | +++ | | +++ |
| P-0162 | | +++ | +++ | | +++ | | +++ |
| P-0163 | | +++ | | | | | +++ |
| P-0164 | +++ | +++ | +++ | +++ | +++ | | |
| P-0165 | +++ | +++ | +++ | +++ | +++ | | +++ |
| P-0166 | +++ | +++ | +++ | +++ | +++ | | +++ |
| P-0167 | +++ | +++ | +++ | +++ | +++ | | +++ |
| P-0168 | +++ | +++ | +++ | +++ | +++ | | +++ |
| P-0169 | +++ | +++ | +++ | +++ | +++ | | +++ |
| P-0170 | +++ | +++ | +++ | +++ | | | +++ |
| P-0171 | | +++ | +++ | | | | +++ |
| P-0172 | +++ | +++ | +++ | +++ | | | |
| P-0173 | +++ | +++ | +++ | +++ | | +++ | +++ |
| P-0174 | +++ | +++ | +++ | +++ | | +++ | +++ |
| P-0175 | +++ | +++ | +++ | +++ | | +++ | +++ |
| P-0176 | +++ | +++ | +++ | +++ | | | +++ |
| P-0177 | +++ | +++ | +++ | +++ | | +++ | +++ |
| P-0178 | +++ | +++ | +++ | +++ | +++ | | +++ |
| P-0179 | +++ | +++ | +++ | +++ | +++ | | +++ |
| P-0180 | +++ | +++ | +++ | +++ | +++ | | +++ |
| P-0181 | +++ | +++ | +++ | +++ | +++ | | +++ |
| P-0182 | +++ | +++ | +++ | +++ | +++ | | +++ |
| P-0183 | +++ | +++ | +++ | +++ | +++ | | +++ |
| P-0184 | | | +++ | | +++ | | |
| P-0185 | | | +++ | | | | |
| P-0186 | | | +++ | +++ | | | |
| P-0187 | | | +++ | +++ | +++ | | |
| P-0188 | | | +++ | +++ | | | |
| P-0189 | | | +++ | +++ | +++ | | |
| P-0190 | | | +++ | +++ | +++ | | |
| P-0191 | | +++ | +++ | +++ | | | |
| P-0192 | +++ | +++ | +++ | +++ | +++ | | |
| P-0193 | | | +++ | +++ | +++ | | |
| P-0194 | +++ | +++ | +++ | +++ | | | +++ |
| P-0195 | +++ | +++ | +++ | +++ | | | +++ |
| P-0196 | +++ | +++ | +++ | +++ | +++ | | +++ |
| P-0197 | +++ | +++ | +++ | +++ | +++ | | |
| P-0198 | +++ | +++ | +++ | +++ | +++ | | +++ |
| P-0199 | | +++ | +++ | +++ | +++ | | +++ |
| P-0200 | | +++ | +++ | +++ | +++ | | |
| P-0201 | +++ | +++ | +++ | +++ | +++ | | +++ |
| P-0202 | +++ | +++ | +++ | +++ | +++ | | +++ |
| P-0203 | +++ | +++ | +++ | +++ | +++ | | +++ |
| P-0204 | +++ | +++ | +++ | +++ | +++ | | +++ |
| P-0205 | +++ | +++ | +++ | +++ | +++ | | +++ |
| P-0206 | +++ | +++ | +++ | +++ | +++ | | |
| P-0207 | +++ | +++ | | +++ | +++ | | +++ |
| P-0208 | +++ | | +++ | +++ | +++ | | +++ |
| P-0209 | +++ | +++ | +++ | +++ | +++ | | +++ |
| P-0210 | +++ | +++ | +++ | +++ | +++ | | +++ |
| P-0211 | +++ | +++ | +++ | +++ | +++ | | +++ |
| P-0212 | +++ | +++ | +++ | +++ | +++ | +++ | +++ |
| P-0213 | +++ | +++ | +++ | +++ | +++ | +++ | +++ |
| P-0214 | +++ | +++ | +++ | +++ | +++ | | +++ |
| P-0215 | +++ | +++ | +++ | +++ | +++ | +++ | +++ |
| P-0216 | +++ | +++ | +++ | +++ | +++ | +++ | +++ |
| P-0217 | +++ | +++ | +++ | +++ | +++ | +++ | +++ |
| P-0218 | +++ | +++ | +++ | +++ | +++ | +++ | +++ |
| P-0219 | | +++ | +++ | +++ | +++ | | |
| P-0220 | +++ | +++ | +++ | +++ | +++ | +++ | +++ |
| P-0221 | +++ | +++ | +++ | +++ | +++ | | +++ |
| P-0222 | +++ | +++ | +++ | +++ | +++ | | +++ |
| P-0223 | | | +++ | +++ | +++ | | |
| P-0224 | | | +++ | +++ | +++ | | |
| P-0225 | | | +++ | +++ | +++ | | |
| P-0226 | | | +++ | +++ | +++ | | |
| P-0227 | +++ | +++ | +++ | +++ | +++ | | |
| P-0228 | +++ | +++ | +++ | +++ | +++ | | +++ |

TABLE 6-continued

| P # | FLT3 D835Y 8 pt GMean IC$_{50}$ (μM) | FLT3_ITD 8 pt: IC$_{50}$ (μM) | BaF3_FLT3 ITD/D835Y 3 d- Growth: IC$_{50}$ (μM) | MOLM-14 D835Y 3 d- Growth GMean IC$_{50}$ (μM) | MOLM-14 F691L 3 d- Growth GMean IC$_{50}$ (μM) | CSF1R 100 ATP 8 pt IC$_{50}$ (μM) | c-KIT 100 ATP 8 pt IC$_{50}$ (μM) |
|---|---|---|---|---|---|---|---|
| P-0229 | +++ | +++ | +++ | +++ | +++ | | +++ |
| P-0230 | +++ | +++ | +++ | +++ | +++ | +++ | +++ |
| P-0231 | +++ | +++ | +++ | +++ | +++ | | +++ |
| P-0232 | +++ | +++ | +++ | +++ | +++ | | +++ |
| P-0233 | +++ | +++ | +++ | +++ | +++ | | +++ |
| P-0234 | +++ | +++ | +++ | +++ | +++ | | +++ |
| P-0235 | +++ | +++ | +++ | +++ | +++ | | +++ |
| P-0236 | +++ | +++ | +++ | +++ | +++ | | +++ |
| P-0237 | +++ | +++ | +++ | +++ | +++ | | +++ |
| P-0238 | +++ | +++ | +++ | +++ | +++ | | +++ |
| P-0239 | +++ | +++ | +++ | +++ | +++ | | +++ |
| P-0240 | +++ | +++ | +++ | +++ | +++ | | +++ |
| P-0241 | +++ | +++ | +++ | +++ | +++ | | +++ |
| P-0242 | +++ | +++ | +++ | +++ | +++ | | +++ |
| P-0243 | +++ | +++ | +++ | +++ | +++ | | +++ |
| P-0244 | +++ | +++ | +++ | +++ | +++ | | +++ |
| P-0245 | +++ | | | | | | +++ |
| P-0246 | +++ | | +++ | +++ | +++ | | +++ |
| P-0247 | +++ | | +++ | +++ | +++ | | +++ |
| P-0248 | +++ | | +++ | +++ | +++ | | +++ |
| P-0249 | +++ | | +++ | +++ | +++ | | +++ |
| P-0250 | +++ | +++ | +++ | +++ | +++ | | +++ |
| P-0251 | +++ | +++ | +++ | +++ | +++ | | +++ |
| P-0252 | +++ | +++ | +++ | +++ | +++ | | +++ |
| P-0253 | +++ | +++ | +++ | +++ | +++ | | +++ |
| P-0254 | +++ | +++ | +++ | +++ | +++ | | +++ |
| P-0255 | +++ | +++ | +++ | +++ | +++ | | +++ |
| P-0256 | +++ | +++ | +++ | +++ | +++ | | +++ |
| P-0257 | +++ | +++ | +++ | +++ | +++ | | +++ |
| P-0258 | +++ | +++ | +++ | +++ | +++ | | +++ |
| P-0259 | +++ | +++ | +++ | +++ | +++ | | +++ |
| P-0260 | +++ | +++ | +++ | +++ | +++ | | +++ |
| P-0261 | +++ | +++ | +++ | +++ | +++ | | +++ |
| P-0262 | +++ | | +++ | +++ | +++ | | +++ |
| P-0263 | +++ | | +++ | +++ | +++ | | +++ |
| P-0264 | | | +++ | +++ | +++ | | |
| P-0265 | +++ | +++ | +++ | +++ | +++ | | +++ |
| P-0266 | +++ | +++ | +++ | +++ | +++ | | +++ |
| P-0267 | +++ | +++ | +++ | +++ | +++ | | +++ |
| P-0268 | +++ | +++ | +++ | +++ | +++ | | +++ |
| P-0269 | +++ | +++ | +++ | +++ | +++ | | +++ |
| P-0270 | +++ | +++ | +++ | +++ | +++ | | +++ |
| P-0271 | +++ | +++ | +++ | +++ | +++ | | +++ |
| P-0273 | +++ | +++ | +++ | +++ | +++ | | +++ |
| P-0274 | +++ | +++ | +++ | +++ | +++ | | +++ |

Comparative Data

The BaF3 assays as developed used to generate the data in Tables 7 and 8 are identical and differ only in minor details in regards to vector design, not biological function. Both introduce the FLT3 gene with MV4-11 based ITD duplications and resistance mutations from an exogenous promoter (MSCV and CMV respectively) in the exact same cell line.

As a result of the expressed FLT3 protein, the IL3 factor dependent BaF3 cell clones become IL3-factor independent.

The compounds in Tables 7 and 8 were tested in an identical fashion by incubating such clones in with increasing concentrations. Inhibition of the FLT3 activity by an inhibitor results in factor dependency, which in the absence of IL3 results in cell death in the three day growth assays.

As shown below, the novel compounds of this disclosure exhibit superior and unexpectedly better potency against the mutated forms of the FLT3 tyroskine kinase enzymes, particularly the F691L mutation and/or D835Y mutation when compared to the compounds in WO 2011/022473.

Table 7 below lists three compounds in this disclosure and their FLT3 inhibitory activity, and Table 8 lists five compounds in WO 2011/022473 and their FLT3 inhibitory activity.

As shown below, the novel compounds of this disclosure wherein HD is defined as

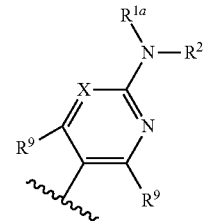

exhibit superior and unexpectedly better potency against the mutated forms of the FLT3 tyroskine kinase enzymes, particularly the F691L mutation and/or D835Y mutation when compared to the compounds in WO 2011/022473. Table 7 below lists three compounds in this disclosure and their FLT3 inhibitory activity, and Table 8 lists five compounds in WO 2011/022473 and their FLT3 inhibitory activity.

TABLE 7

| Compounds of the Disclosure | BaF3_FLT3_ITD/ D835Y (nM) | BaF3_FLT3_ITD/ F691L (nM) |
| --- | --- | --- |
| Compound P-0134 | 0.108 | 0.313 |
| Compound P-0141 | 0.462 | 1.545 |
| Compound P-0143 | 0.444 | 0.434 |

TABLE 8

| Compounds from WO 2011/022473 | Cell Assay: CS0047: BaF3-FLT3-ITD-F691L CTB:IC50 (nM) | Cell Assay: CS0048: BaF3-FLT3-ITD-D835V CTB:IC50 (nM) |
| --- | --- | --- |
|  | 73.9 | 145 |
|  | 43.2 | 92 |

TABLE 8-continued

| Compounds from WO 2011/022473 | Cell Assay: CS0047: BaF3-FLT3-ITD-F691L CTB:IC50 (nM) | Cell Assay: CS0048: BaF3-FLT3-ITD-D835V CTB:IC50 (nM) |
|---|---|---|
| [structure] | 45.4 | 94.2 |
| [structure] | 110 | 673 |
| [structure] | 77.8 | 585 |

Additionally, compounds of this disclosure wherein HD is a 9 membered fused bicyclic heterocycloalkyl group having 2-3 nitrogen atoms are structurally very distinct from the compounds disclosed in WO 2011/022473. Nevertheless, these compounds of this disclosure also exhibit unexpectedly better potency against the mutated forms of the FLT3 tyroskine kinase enzymes, particularly the F691L mutation and/or D835Y mutation.

All patents and other references cited herein are indicative of the level of skill of those skilled in the art to which the disclosure pertains, and are incorporated by reference in their entireties, including any tables and figures, to the same extent as if each reference had been incorporated by reference in its entirety individually.

One skilled in the art would readily appreciate that the present disclosure is well adapted to obtain the ends and advantages mentioned, as well as those inherent therein. The methods, variances, and compositions described herein as presently representative of the embodiments described herein are exemplary and are not intended as limitations on the scope of the disclosure. Changes therein and other uses will occur to those skilled in the art, which are encompassed within the spirit of the disclosure, are defined by the scope of the claims.

It will be readily apparent to one skilled in the art that varying substitutions and modifications may be made to the present disclosure described herein without departing from the scope and spirit of the disclosure. For example, variations can be made to provide additional compounds of Formula I(a) or I(b) and all sub-embodiments thereof, and/or various methods of administration can be used. Thus, such additional embodiments are within the scope of the present disclosure and the following claims.

The present disclosure illustratively described herein suitably may be practiced in the absence of any element or elements, limitation or limitations which is not specifically described herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the disclosure claimed. Thus, it should be understood that although the present disclosure has been specifically described by the embodiments and optional features, modification and variation of the concepts herein described may be resorted to by those skilled in the art, and that such modifications and variations are considered to be within the scope of this disclosure as defined by the appended claims.

In addition, where features or aspects of the disclosure are described in terms grouping of alternatives, those skilled in the art will recognize that the disclosure is also thereby described in terms of any individual member or subgroup of members of the groups described herein.

Also, unless indicated to the contrary, where various numerical values are provided for embodiments, additional embodiments are described by taking any 2 different values as the endpoints of a range. Such ranges are also within the scope of the present disclosure.

Thus, additional embodiments are within the scope of the disclosure and within the following claims.

SEQUENCE LISTING

SEQ ID NO: 1 Sequence NP_004110.2
MPALARDGGQLPLLVVFSAMIFGTITNQDLPVIKCVLINHKNND
SSVGKSSSYPMVSESPEDLGCALRPQSSGTVYEAAAVEVDVSASITLQVL
VDAPGNISCLWVFKHSSLNCQPHFDLQNRGVVSMVILKMTETQAGEYLLF
IQSEATNYTILFTVSIRNTLLYTLRRPYFRKMENQDALVCISESVPEPIV
EWVLCDSQGESCKEESPAVVKKEE
KVLHELFGTDIRCCARNELGRECTRLFTIDLNQTPQTTLPQLFLKVGEPL
WIRCKAVHVNHGFGLTWELENKALEEGNYFEMSTYSTNRTMIRILFAFVS
SVARNDTGYYTCSSSK
HPSQSALVTIVEKGFINATNSSEDYEIDQYEEFCFSVRFKAYPQIRCTWT
FSRKSFPCEQKGLDNGYSISKFCNHKHQPGEYIFHAENDDAQFTKMFTLN
IRRKPQVLAEASASQA
SCFSDGYPLPSWTWKKCSDKSPNCTEEITEGVWNRKANRKVFGQWVSSST
LNMSEAIK
GFLVKCCAYNSLGTSCETILLNSPGPFPFIQDNISFYATIGVCLLFIVVL
TLLICHKYKKQFRYESQLQMVQVTGSSDNEYFYVDFREYEYDLKWEFPRE
NLEFGKVLGSGAFGKV
MNATAYGISKTGVSIQVAVKMLKEKADSSEREALMSELKMMTQLGSHENI
VNLLGACT
LSGPIYLIFEYCCYGDLLNYLRSKREKFHRTWTEIFKEHNFSFYPTFQSH
PNSSMPGSREVQIHPDSDQISGLHGNSFHSEDEIEYENQKRLEEEEDLNV
LTFEDLLCFAYQVAKGMEFLEFKSCVHRDLAARNVLVTHGKVVKICDFGL
ARDIMSDSNYVVRGNARLPVKWMA
PESLFEGIYTIKSDVWSYGILLWEIFSLGVNPYPGIPVDANFYKLIQNGF
KMDQPFYATEEIYIIMQSCWAFDSRKRPSFPNLTSFLGCQLADAEEAMYQ
NVDGRVSECPHTYQNR
RPFSREMDLGLLSPQAVEDS SEQ ID NO: 2 Sequence NM_44119
    1 acctgcagcg cgaggcgcgc cgctccaggc ggcatcgcag
      ggctgggccg cgcggcctg
   61 gggaccccgg gctccggagg ccatgccggc gttggcgcgc
      gacggcggcc agctgccgct
  121 gctcgttgtt ttttctgcaa tgatatttgg gactattaca
      aatcaagatc tgcctgtgat
  181 caagtgtgtt ttaatcaatc ataagaacaa tgattcatca
      gtggggaagt catcatcata
  241 tcccatggta tcagaatccc cggaagacct cgggtgtgcg
      ttgagacccc agagctcagg
  301 gacagtgtac gaagctgccg ctgtggaagt ggatgtatct
      gcttccatca cactgcaagt
  361 gctggtcgac gccccaggga acatttcctg tctctgggtc
      tttaagcaca gctccctgaa
  421 ttgccagcca catttttgatt tacaaaacag aggagttgtt
      tccatggtca ttttgaaaat
  481 gacagaaacc caagctgtga aatacctact ttttattcag
      agtgaagcta ccaattacac
  541 aatattgttt acagtgagta taagaaatac cctgctttac
      acattaagaa gaccttactt
  601 tagaaaaatg gaaaaccagg acgccctggt ctgcatatct
      gagagccgat cagagccgat
  661 cgtggaatgg gtgctttgcg attcacaggg ggaaagctgt
      aaagaagaaa gtccagctgt
  721 tgttaaaaag gaggaaaaag tgcttcatga attatttggg
      acggacataa ggtgctgtgc
  781 cagaaatgaa ctgggcaggg aatgcaccag gctgttcaca
      atagatctaa atcaaactcc
  841 tcagaccaca ttgccacaat tatttcttaa agtagggaa
      cccttatgga taaggtgcaa
  901 agctgttcat gtgaaccatg gattcgggct cacctgggaa
      ttagaaaaca aagcactcga
  961 ggagggcaac tactttgaga tgagtaccta ttcaacaaac
      agaactatga tacggattct
 1021 gtttgctttt gtatcatcag tggcaagaaa cgacaccgga
      tactacactt gttcctcttc
 1081 aaaagcatcc agtcaatcag ctttggttac catcgtagaa
      aagggattta taaatgctac
 1141 caattcaagt gaagattatg aaattgacca atatgaagag
      ttttgttttt ctgtcaggtt
 1201 taaagcctac ccacaaatca gatgtacgtg gaccttctct
      cgaaaatcat ttccttgtga
 1261 gcaaaagggt cttgataacg gatacagcat atccaagttt
      tgcaatcata agcaccagcc
 1321 aggagaatat atattccatg cagaaaatga tgatgcccaa
      tttaccaaaa tgttcacgct
 1381 gaatataaga aggaaacctc aagtgctcgc agaagcatcg
      gcaagtcagg cgtcctgttt 1441 ctcggatgga tacccattac catcttggac ctggaagaag
      tgttcagaca agtctcccaa
 1501 ctgcacagaa gagatccaca aaggagtctg gaatagaaag
      gctaacagaa aagtgtttgg
 1561 acagtgggtg tcgagcagta ctctaaacat gagtgaagcc
      ataaaagggt tcctggtcaa
 1621 gtgctgtgca tacaattccc ttggcacatc ttgtgagacg
      atcctttaa actctccagg
 1681 ccccttccct ttcatccaag acaacatctc attctatgca
      acaattggtg tttgtctcct
 1741 cttcattgtc gttttaaccc tgctaatttg tcacaagtac
      aaaaagcaat ttaggtatga
 1801 aagccagcta cagatggtac aggtgaccgg ctcctcagat
      aatgagtact tctacgttga
 1861 tttcagaaga tatgaatatg atctcaaatg ggagtttcca
      agagaaaatt tagagtttgg
 1921 gaaggtacta ggatcaggtg cttttggaaa agtgatgaac
      gcaacagctt atggaattag
 1981 caaaacagga gtctcaatcc aggttgccgt caaaatgctg
      aaagaaaaag cagacagctc
 2041 tgaaagagag gcactcatgt cagaactcaa gatgatgacc
      cagctgggaa gccacgaaga
 2101 tattgtgaac ctgctggggg cgtgcacact gtcaggacca
      atttacttga atagaata
 2161 ctgttgctat ggtgatcttc tcaactatct aagaagtaaa
      agagaaaaat ttcacaggac
 2221 ttggacagag attttcaagg aacacaattt cagtttttac
      cccactttcc aatcacatcc
 2281 aaattccagc atgcctggtt caagagaagt tcagatacac
      ccggactcgg atcaaatctc
 2341 agggcttcat gggaattcat ttcactctga agatgaaatt
      gaatatgaaa accaaaaaag
 2401 gctggaagaa gaggaggact tgaatgtgct tacatttgaa
      gatcttcttt gctttgcata
 2461 tcaagttgcc aaaggaatgg aatttctgga atttaagtcg
      tgtgttcaca gagacctggc
 2521 cgccaggaac gtgcttgtca cccacgggaa agtggtgaag
      atatgtgact tggattggc
 2581 tcgagatatc atgagtgatt ccaactatgt tgtcaggggc
      aatgcccgtc tgcctgtaaa
 2641 atggatggcc cccgaaagcc tgtttgaagg catctacacc
      attaagagtg atgtctggtc
 2701 atatggaata ttactgtggg aaatcttctc acttggtgtg
      aatccttacc ctggcattcc
 2761 ggttgatgct aacttctaca aactgattca aaatggattt
      aaaatgggatc agccatata
 2821 tgctacagaa gaaatataca ttataatgca atcctgctgg
      gcttttgact caaggaaacg
 2881 gccatccttc cctaatttga cttcgttttt aggatgtcag
      ctggcagatg cagaagaagc
 2941 gatgtatcag aatgtggatg gccgtgtttc ggaatgtcct
      cacacctacc aaaacaggcg
 3001 accttccagc agagagatgg atttgggct actctctccg
      caggctcagg tcgaagattc
 3061 gtagaggaac aatttagttt taaggacttc atccctccac
      ctatccctaa caggctgtag
 3121 attaccaaaa caagattaat ttcatcacta aaagaaaatc
      tattatcaac tgctgcttca
 3181 ccagacttttt ctctagaagc tgtctgcgtt tactcttgtt
      ttcaaaggga cttttgtaaa
 3241 atcaaatcat cctgtcacaa ggcaggagga gctgataatg
      aactttattg gagcattgat
 3301 ctgcactccaa ggcctctca ggctggcttg agtgaattgt
      gtacctgaag tacagtatat
 3361 tcttgtaaat acataaaaca aaagcatttt gctaaggaga
      agctaatatg attttttaag
 3421 tctatgtttt aaaataatat gtaaattttt cagctatta
      gtgtatatt ttatgggtgg
 3481 gaataaaatt tctactacag aattgcccat tattgaatta
      tttacatgtt ataattaggg
 3541 caagtcttaa ctggagttca cgaaccccct gaaattgtgc
      acccatagcc acctacacat
 3601 tccttccaga gcacgtgtgc ttttacccca agatacaagg
      aatgtgtagg cagctatggt

```
3661  tgtcacagcc taagattct gcaacaacag gggttgtatt
      gggggaagtt tataatgaat
3721  aggtgttcta ccataaagag taatacatca cctagacact
      ttggcggcct tcccagactc
3781  agggccagtc agaagtaaca tggaggatta gtattttcaa
      taaagttact cttgtcccca
3841  caaaaaaa
```

What is claimed is:
1. A compound having Formula II(a) or II(b):

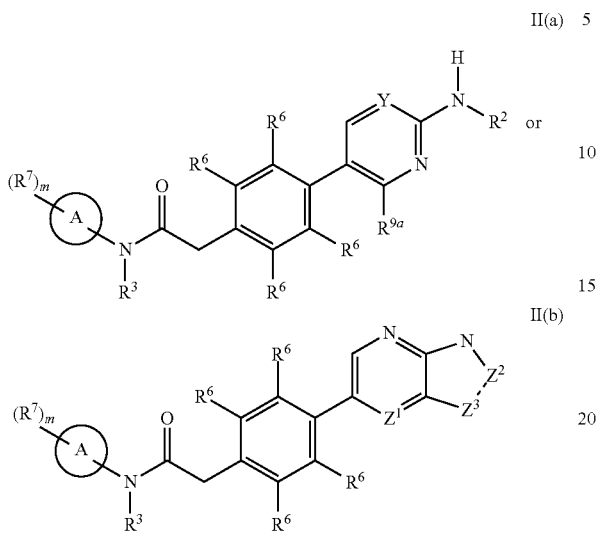

or a pharmaceutically acceptable salt, a solvate, a tautomer, a stereoisomer or a deuterated analog thereof, wherein:

Ring A is phenyl, pyridyl, pyrimidinyl, or pyridazinyl;
Y is N or $CR^9$; $R^9$ is hydrogen, halo, amino, alkyl optionally substituted with alkoxy or hydroxy, haloalkyl, or alkoxy;
(i) --- is a single bond, wherein:
$Z^1$ is CH or N, $Z^2$ is $C(R^{12})(R^{12a})$ and $Z^3$ is $C(R^{13})(R^{13a})$; or
$Z^1$ is CH, $Z^2$ is $N(R^{12})$ and $Z^3$ is $C(R^{13})(R^{13a})$; or
$Z^1$ is CH, $Z^2$ is $C(R^{12})(R^{12a})$ and $Z^3$ is $N(R^{13})$;
or
(ii) --- is a double bond, wherein:
$Z^1$ is CH or N, $Z^2$ is $C(R^{12})$ and $Z^3$ is $C(R^{13})$; or
$Z^1$ is CH, $Z^2$ is N and $Z^3$ is $C(R^{13})$; or
$Z^1$ is CH, $Z^2$ is $C(R^{12})$ and $Z^3$ is N;
$R^2$ is

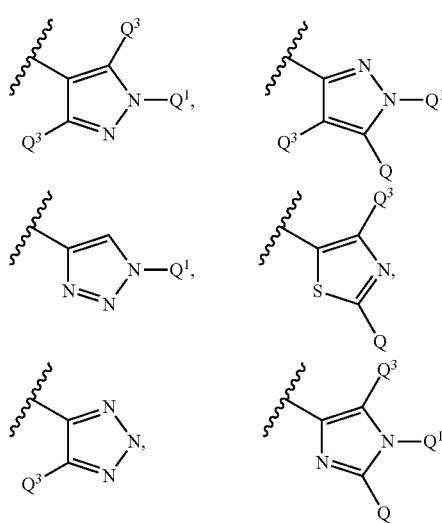

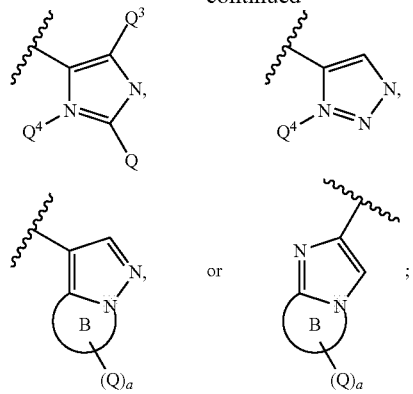

wherein:
Ring B is a 5 or 6-membered saturated or unsaturated ring having 0-3 heteroatoms selected from O, N, and S;
each Q is independently hydrogen, alkyl, halo, cyano, haloalkyl, cycloalkyl, cycloalkylalkyl, heterocycloalkyl, heterocycloalkylalkyl, oxo, —$R^{20}OR^{21}$, —$R^{20}OR^{21}$, —$R^{20}OC(O)R^{21}$, —$R^{20}C(O)N(R^{24})(R^{25})$, —$R^{20}S(O)_tR^{22}$, —$R^{20}N(R^{24})(R^{25})$, or —$R^{20}N(R^{24})(R^{25})$, or —$R^{20}N(R^{24})C(O)R^{21}$, wherein each alkyl, cycloalkyl, cycloalkylalkyl, heterocycloalkyl or heterocycloalkylalkyl is independently optionally substituted with 1 to 3 groups each independently halo, oxo, amino, alkyl, haloalkyl or —$R^{20}OR^{21}$,
$Q^1$ is hydrogen, alkyl, haloalkyl, cycloalkyl, cycloalkylalkyl, heterocycloalkyl, heterocycloalkylalkyl, —$R^{23}OR^{21}$, —$R^{23}OR^{23}OR^{21}$, —$R^{23}C(O)R^{21}$, —$R^{23}N(R^{24})(R^{25})$, —$R^{23}OC(O)R^{21}$, —$R^{23}C(O)OR^{21}$, —$R^{23}C(O)N(R^{24})(R^{25})$, or —$R^{23}S(O)_tR^{22}$, wherein each alkyl, cycloalkyl, cycloalkylalkyl, heterocycloalkyl or heterocycloalkylalkyl is independently optionally substituted with 1 to 3 groups each independently halo, oxo, amino, alkyl, haloalkyl or —$R^{20}OR^{21}$;
each $Q^3$ is independently hydrogen, cyano, —S —$C_1$-$C_2$ alkyl, halo, $C_2$-$C_3$ alkenyl, $C_2$-$C_3$ alkynyl, $C_1$-$C_3$ alkoxy, cyclopropyl, amino, —N(H)($C_1$-$C_3$alkyl), —N(H)C(O)C(H)=$CH_2$ or $C_1$-$C_3$ alkyl, wherein each $Q^3$ is optionally substituted with 1-3 substituents each independently halo, hydroxy or methoxy;
$Q^4$ is hydrogen, cyclopropyl, $C_1$-$C_4$ alkoxy, or $C_1$-$C_4$ alkyl optionally substituted with 1-3 substituents each independently halo, hydroxy or methoxy;
each $R^{20}$ is independently alkylene, alkenylene, alkynylene or a direct bond;
each $R^{21}$ is independently hydrogen, alkyl, haloalkyl, alkenyl, alkynyl or cycloalkyl;
each $R^{22}$ is independently alkyl, haloalkyl, alkenyl, alkynyl or cycloalkyl;
each $R^{23}$ is independently alkylene, alkenylene or alkynylene;
$R^{24}$ and $R^{25}$ are each independently hydrogen or alkyl;
a is an integer from 0 to 3;
each t is independently 0, 1 or 2;
$R^3$ is hydrogen or $C_1$-$C_6$ alkyl;
each $R^6$ is independently hydrogen, halo, $C_1$-$C_3$alkyl, or $C_1$-$C_3$ alkoxy;

each R⁷ is independently C₁-C₆ alkyl, C₁-C₆ haloalkyl, C₁-C₆alkoxy, C₃-C₆ cycloalkyl, 4-6 membered heterocycloalkyl, C₃-C₆cycloalkylalkyl, —S(O)₂alkyl, or a 4-6 membered heterocycloalkyl-C₁-C₆ alkyl, wherein each R⁷ is optionally substituted with 1 to 3 groups each independently hydroxy, halo, C₁-C₆ alkyl, cyano or C₁-C₆ haloalkyl;

R⁹ᵃ is hydrogen, halo, hydroxy-C₁-C₆ alkyl, C₁-C₆ alkyl, or C₁-C₆ alkoxy-C₁-C₆ alkyl;

each R¹¹ is independently a 5-6 membered heterocycloalkyl, cyano, C₁-C₆ alkoxy, C₁-C₆alkyl, C₁-C₆ haloalkyl, —C(O)OCH₃, or —C(O)OH;

R¹⁰ is C₁-C₆ alkyl, hydroxy-C₁-C₆ alkyl, C₁-C₆alkoxy-C₁-C₆ alkyl, 5-membered heteroaryl optionally substituted with alkyl, C₃-C₆ cycloalkyl, —C(O)OCH₃, or —C(O)OH;

R¹² is hydrogen, C₁-C₄ alkyl, C₁-C₄ alkoxy, —(CH₂)₀₋₂—N(R¹ᵇ)₂, halo, C₃-C₆ cycloalkyl, —C(O)—C₃-C₆cycloalkyl, phenyl optionally substituted with 1-2 R¹¹ groups, 5-6 membered heteroaryl optionally substituted with 1-2 R¹¹ groups, or alkynyl optionally substituted with R¹⁰;

R¹³ is hydrogen, C₁-C₄ alkyl, C₁-C₄ alkoxy, —C(O)—C₁-C₄ alkyl, halo, cyano, —(CH₂)₀₋₂—N(R¹ᵇ)₂, —C(O)NHCH₃, amino, —NHC(O)CF₃, C₃-C₆ cycloalkyl, —C(O)—C₃-C₆ cycloalkyl, phenyl optionally substituted with 1-2 R¹¹ groups, 5-6 membered heteroaryl optionally substituted with 1-2 R¹¹ groups, or alkynyl optionally substituted with R¹⁰;

each R¹ᵇ is independently hydrogen or alkyl;

R¹²ᵃ is hydrogen; or

R¹² and R¹²ᵃ, together with the carbon to which they are attached, join to form a C₃₋₆ spirocycloalkyl; or R¹² and R¹²ᵃ form an oxo group;

R¹³ᵃ is hydrogen; or

R¹³ and R¹³ᵃ, together with the carbon to which they are attached, join to form a C₃₋₆ spirocycloalkyl; or R¹³ and R¹³ᵃ form an oxo group; and m is 0, 1 or 2.

2. The compound of claim 1, wherein:
R³ is hydrogen;
each R⁶ is independently chloro, fluoro, methoxy, or methyl;
each R⁷ is independently C₁-C₃ alkyl, C₁-C₃ haloalkyl, C₁-C₃ alkoxy, hydroxy-C₁-C₄ alkyl, C₁-C₃alkoxy-C₁-C₃alkyl, C₃-C₆ cycloalkyl, 4-6 membered heterocycloalkyl, C₃-C₆ cycloalkylalkyl, or a 4-6 membered heterocycloalkyl-C₁-C₆ alkyl; and
m is 1 or 2.

3. The compound of claim 1 having Formula III(a):

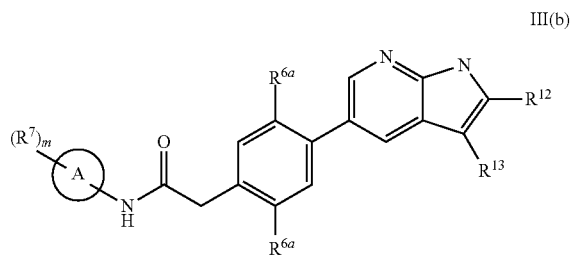

or a pharmaceutically acceptable salt, a solvate, a tautomer, a stereoisomer or a deuterated analog thereof, wherein each R⁶ᵃ is independently hydrogen or fluoro.

4. The compound of claim 1 having Formula III(b) or III(c):

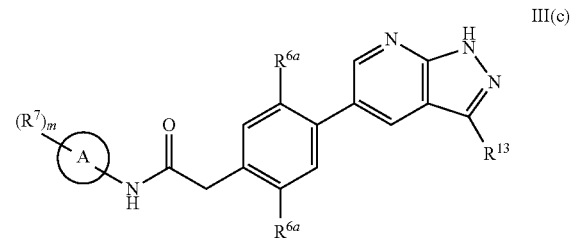

or a pharmaceutically acceptable salt, a solvate, a tautomer, a stereoisomer or a deuterated analog thereof, wherein each R⁶ᵃ is independently hydrogen or fluoro.

5. The compound of claim 1, wherein:
Ring A is pyridyl or phenyl; and
each R⁶ is hydrogen or one R⁶ is halo, alkyl or alkoxy.

6. The compound of claim 1, wherein:

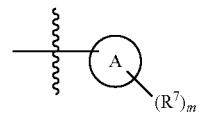

is:

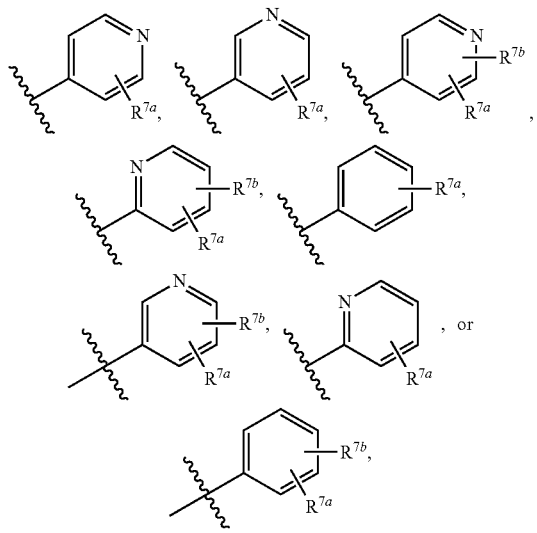

wherein:
R⁷ᵃ is C₁-C₄ alkoxy, C₁-C₄ alkyl optionally substituted with cyano, C₁-C₄ haloalkyl, cyclopropyl, halo, morpholinyl or cyano; and $R^{7b}$ is $C_1$-$C_4$ alkoxy, $C_1$-$C_4$ alkyl optionally substituted with cyano, $C_1$-$C_4$ haloalkyl, halo or cyano.

7. The compound of claim 1, wherein:

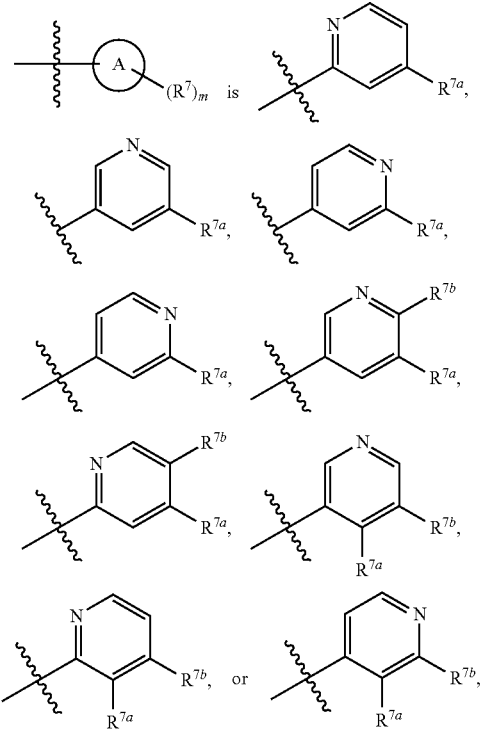

wherein:

$R^{7a}$ is cyclopropyl, —OCH$_3$, —CH$_3$, —CH$_2$F, —CHF$_2$, —CF$_3$, —OCF$_3$, —C(CH$_3$)$_3$, —C(CN)(CH$_3$)$_2$, F, Cl, Br, or cyano; and $R^{7b}$ is cyclopropyl, —OCH$_3$, —CH$_3$, —CH$_2$F, —CHF$_2$, —CF$_3$, —C(CH$_3$)$_3$, —C(CN)(CH$_3$)$_2$, —OCF$_3$, F, Cl, Br or cyano.

8. The compound of claim 1, wherein:

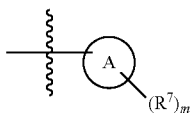

is:

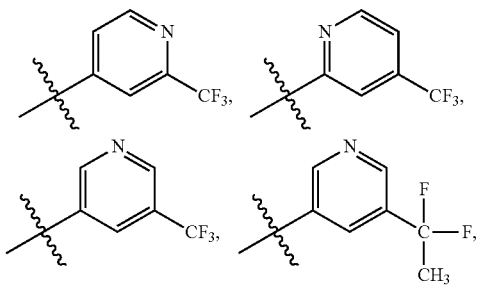

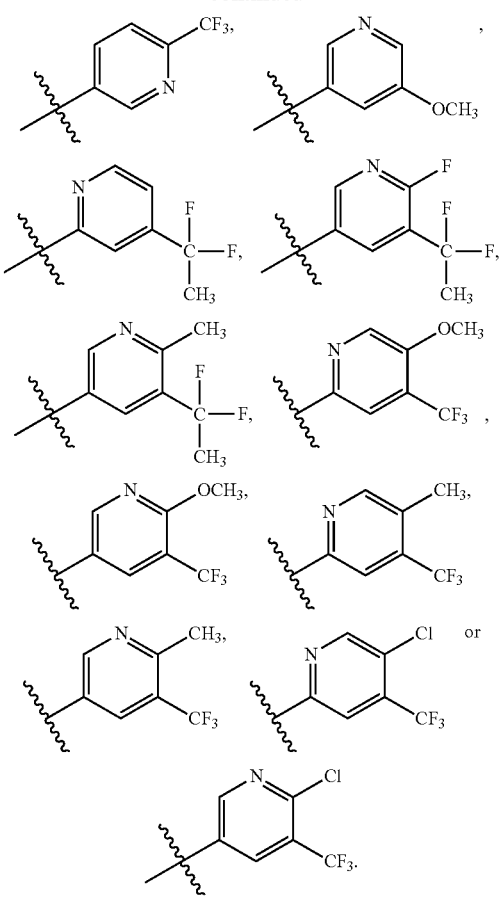

9. The compound of claim 1, wherein $R^2$ is:

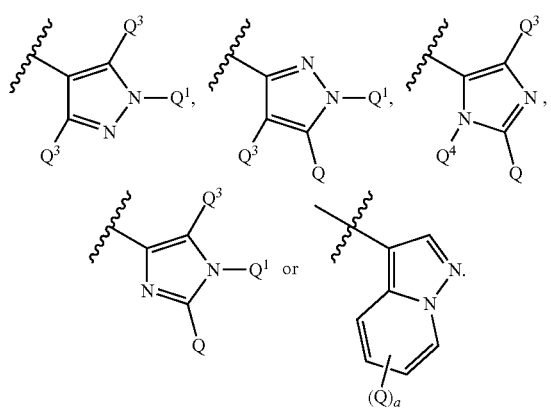

10. The compound of claim 1, wherein $R^2$ is:

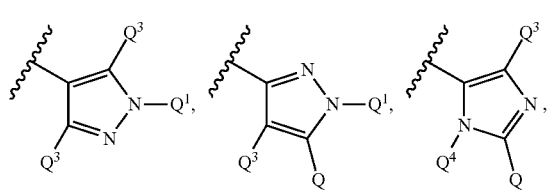

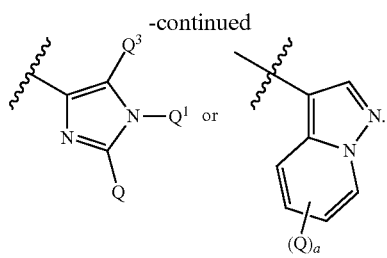

wherein:
each Q is independently hydrogen, —OCH₃, hydroxy-C₁-C₄ alkyl, —CF₃, —CHF₂, —CH₂F, —CH₂CH₃, or —CH₃;
Q¹ is hydrogen, hydroxy-C₁-C₄ alkyl, —CF₃, —CHF₂, —CH₂F, —CH₂CH₃, or —CH₃;
each Q³ is independently hydrogen, —OCH₃, hydroxy-C₁-C₃ alkyl, —CF₃, —CHF₂, —CH₂F, —CH₂CH₃, or —CH₃; and
Q⁴ is hydrogen, hydroxy-C₁-C₄ alkyl, —CF₃, —CHF₂, —CH₂F, —CH₂CH₃, or —CH₃.

11. The compound of claim 1, wherein R² is:

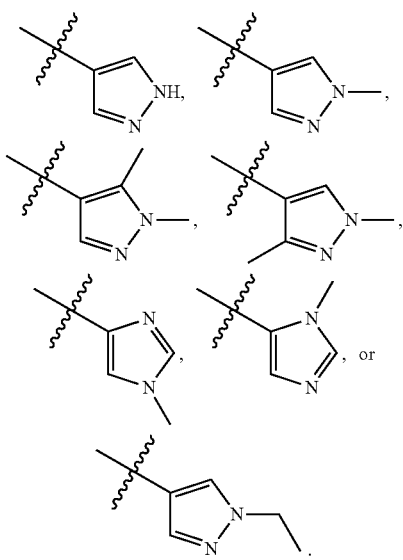

12. The compound of claim 1, wherein:
R¹² is hydrogen; —CH₃; Cl; F; Br; cyclopropyl; phenyl; pyridyl optionally substituted with morpholinyl, ethoxy, methoxy, cyano, —CF₃, —CHF₂, —CH₂F or —CH₃; ethynyl optionally substituted with —C(CH₃)₃, —C(CH₃)₂OH, cyclopropyl, —C(O)OCH₃, —C(O)OH, or methoxymethyl; or imidazolyl optionally substituted with methyl, —C(O)OCH₃, or —C(O)OH; and R¹³ is hydrogen, —C(O)CH₃, —C(O)CH₂CH₃, F, Cl, Br, cyano, cyclopropyl, —C(O)-cyclopropyl, —C(O)NHCH₃, —OCH₃, —OCH₂CH₃, —CH₂CH₃, amino, or —NHC(O)CF₃.

13. The compound of claim 1, wherein:
R¹² is phenyl; pyridyl optionally substituted with morpholinyl, ethoxy, methoxy, cyano, —CF₃, —CHF₂, —CH₂F, or —CH₃; or ethynyl optionally substituted with —C(CH₃)₃, —C(CH₃)₂OH, cyclopropyl, —C(O)OCH₃, —C(O)OH, or methoxymethyl; and
R¹³ is hydrogen, —C(O)CH₃, —C(O)CH₂CH₃, F, Cl, Br, cyano, cyclopropyl, —C(O)-cyclopropyl, —C(O)NHCH₃, —OCH₃, —OCH₂CH₃, —CH₂CH₃, amino, or —NHCOCF₃.

14. The compound of claim 4 having Formula III(b):

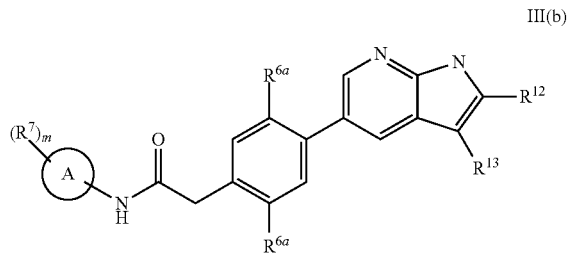

III(b)

or a pharmaceutically acceptable salt, a solvate, a tautomer, a stereoisomer or a deuterated analog thereof, wherein:
R¹² is phenyl; pyridyl optionally substituted with morpholinyl, ethoxy, methoxy, cyano, —CF₃, —CHF₂, —CH₂F, or —CH₃; or ethynyl optionally substituted with —C(CH₃)₃, —C(CH₃)₂OH, cyclopropyl, —C(O)OCH₃, —C(O)OH or methoxymethyl; and
R¹³ is hydrogen.

15. The compound of claim 4 having Formula III(c):

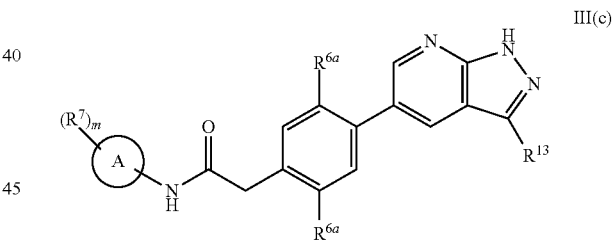

III(c)

or a pharmaceutically acceptable salt, a solvate, a tautomer, a stereoisomer or a deuterated analog thereof, wherein R¹³ is —C(O)CH₃, —C(O)CH₂CH₃, F, Cl, Br, cyano, cyclopropyl, —C(O)-cyclopropyl, —C(O)NHCH₃, —OCH₃, —OCH₂CH₃, —CH₂CH₃, amino, or —NHC(O)CF₃.

16. A compound selected from:

| No. | Compound Structure |
|---|---|
| P-0001 | 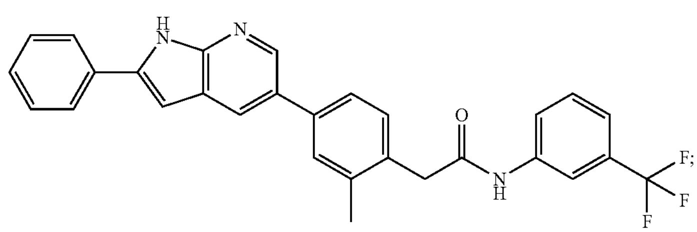 [SMILES: Cc1cc(-c2cnc3[nH]c(-c4ccccc4)cc3c2)ccc1CC(=O)Nc1cccc(C(F)(F)F)c1] |

| No. | Compound Structure |
|---|---|
| P-0002 | 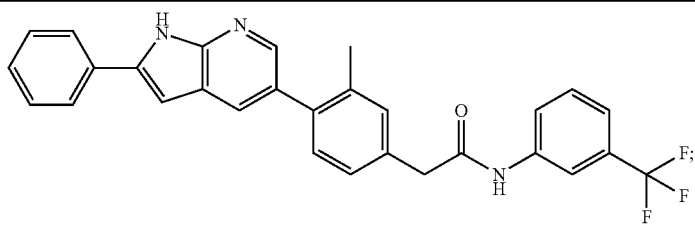 |
| P-0003 | 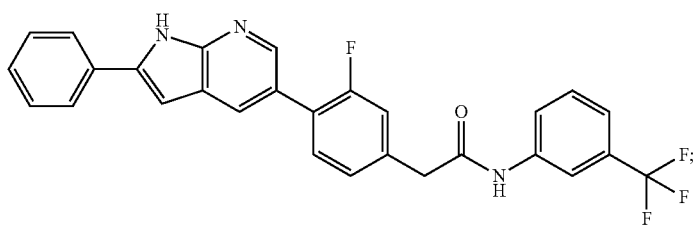 [SMILES: O=C(Cc1ccc(-c2cnc3[nH]c(-c4ccccc4)cc3c2)c(F)c1)Nc1cccc(C(F)(F)F)c1] |
| P-0004 | 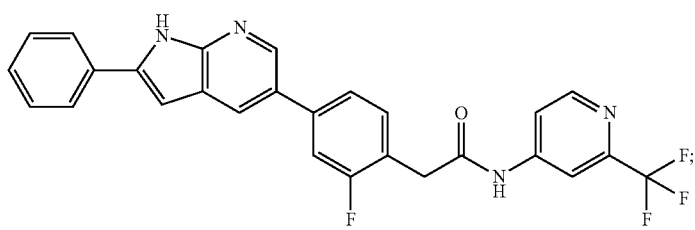 [SMILES: O=C(Cc1ccc(-c2cnc3[nH]c(-c4ccccc4)cc3c2)cc1F)Nc1ccnc(C(F)(F)F)c1] |
| P-0005 | 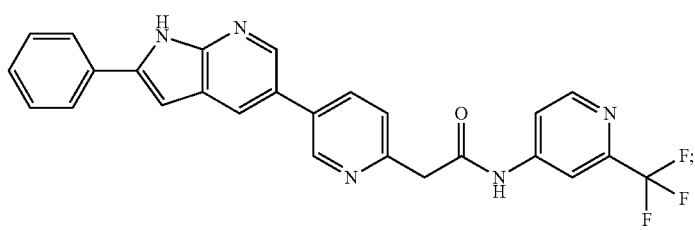 [SMILES: O=C(Cc1ccc(-c2cnc3[nH]c(-c4ccccc4)cc3c2)cn1)Nc1ccnc(C(F)(F)F)c1] |
| P-0006 | 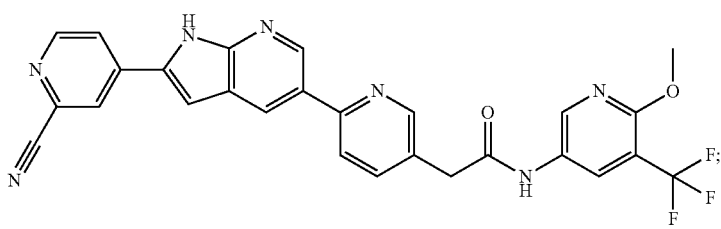 [SMILES: COc1ncc(NC(=O)Cc2ccc(-c3cnc4[nH]c(-c5ccnc(C#N)c5)cc4c3)nc2)cc1C(F)(F)F] |
| P-0007 | 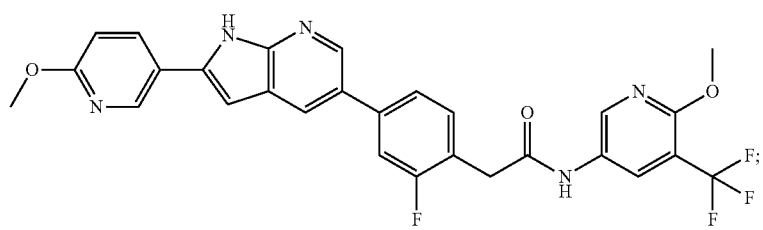 [SMILES: COc1ccc(-c2cc3cc(-c4ccc(CC(=O)Nc5cnc(OC)c(C(F)(F)F)c5)c(F)c4)cnc3[nH]2)cn1] |
| P-0008 | 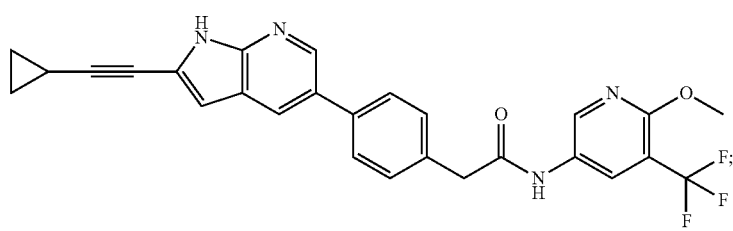 [SMILES: COc1ncc(NC(=O)Cc2ccc(-c3cnc4[nH]c(C#CC5CC5)cc4c3)cc2)cc1C(F)(F)F] |

-continued
| No. | Compound Structure |
|---|---|
| P-0009 | 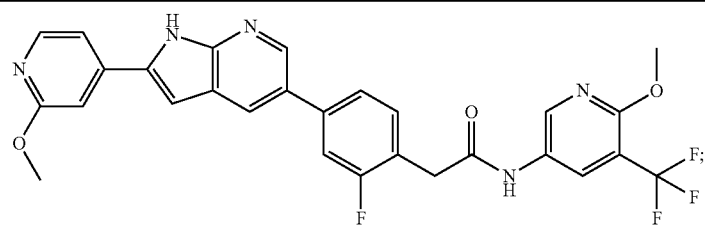 |
| P-0010 | 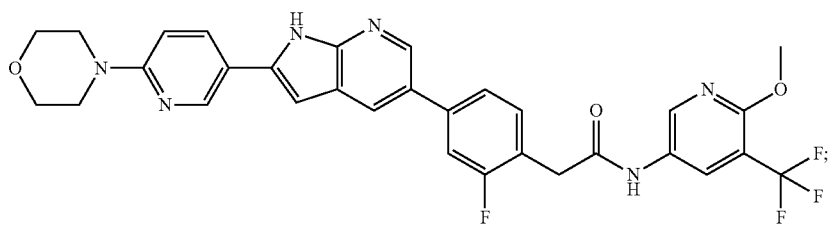 [SMILES: COc1ncc(NC(=O)Cc2ccc(-c3cnc4[nH]c(-c5ccc(N6CCOCC6)nc5)cc4c3)cc2F)cc1C(F)(F)F] |
| P-0011 | 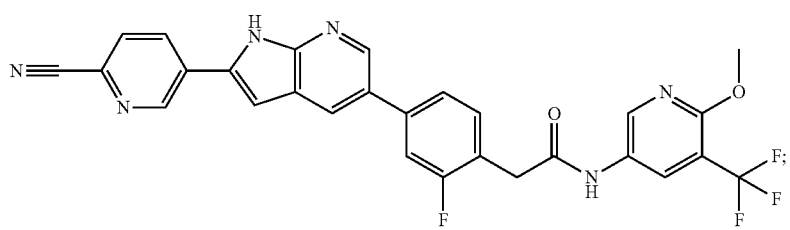 [SMILES: COc1ncc(NC(=O)Cc2ccc(-c3cnc4[nH]c(-c5ccc(C#N)nc5)cc4c3)cc2F)cc1C(F)(F)F] |
| P-0012 | 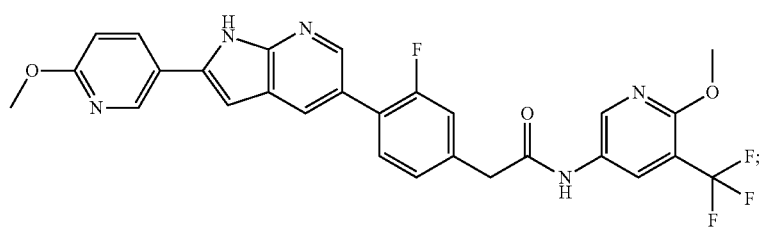 [SMILES: COc1ccc(-c2cc3cc(-c4ccc(CC(=O)Nc5cnc(OC)c(C(F)(F)F)c5)cc4F)cnc3[nH]2)cn1] |
| P-0013 | 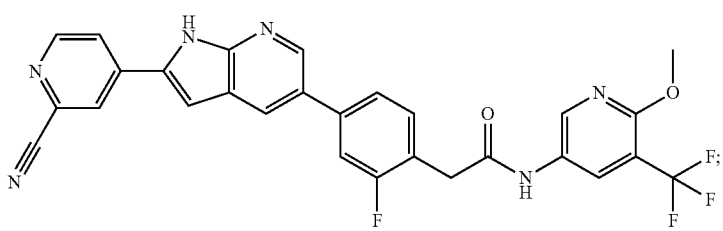 [SMILES: COc1ncc(NC(=O)Cc2ccc(-c3cnc4[nH]c(-c5ccnc(C#N)c5)cc4c3)cc2F)cc1C(F)(F)F] |
| P-0014 | 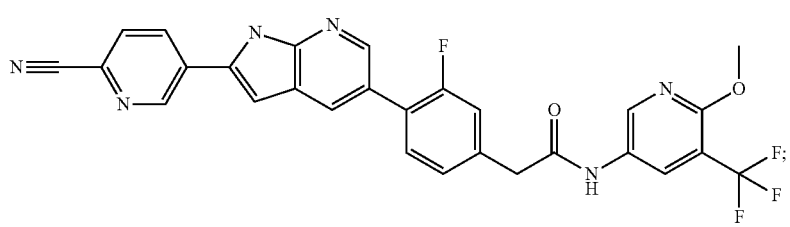 [SMILES: COc1ncc(NC(=O)Cc2ccc(-c3cnc4[nH]c(-c5ccc(C#N)nc5)cc4c3)c(F)c2)cc1C(F)(F)F] |
| P-0015 | 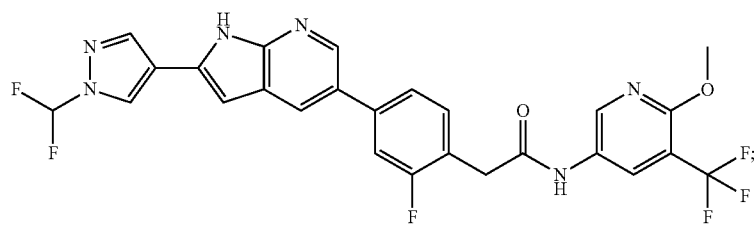 [SMILES: COc1ncc(NC(=O)Cc2ccc(-c3cnc4[nH]c(-c5cnn(C(F)F)c5)cc4c3)cc2F)cc1C(F)(F)F] |

| No. | Compound Structure |
|---|---|
| P-0016 | 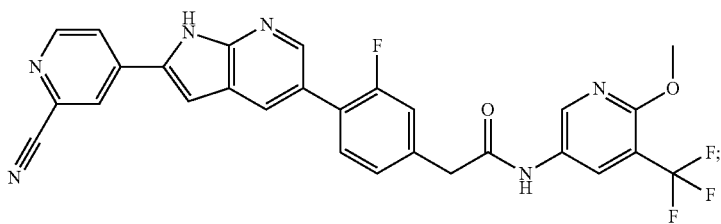 [SMILES: COc1ncc(NC(=O)Cc2ccc(-c3cnc4[nH]c(-c5ccnc(C#N)c5)cc4c3)c(F)c2)cc1C(F)(F)F] |
| P-0017 | 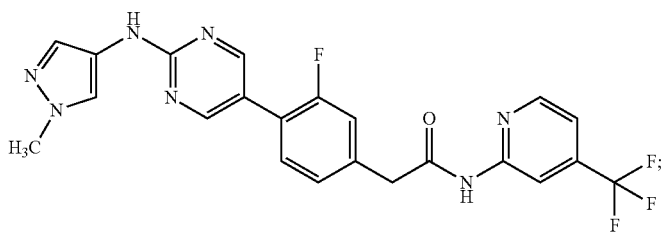 [SMILES: Cn1cc(Nc2ncc(-c3ccc(CC(=O)Nc4cc(C(F)(F)F)ccn4)cc3F)cn2)cn1] |
| P-0018 | 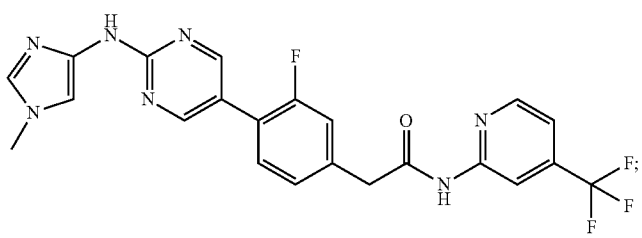 [SMILES: Cn1cnc(Nc2ncc(-c3ccc(CC(=O)Nc4cc(C(F)(F)F)ccn4)cc3F)cn2)c1] |
| P-0019 | 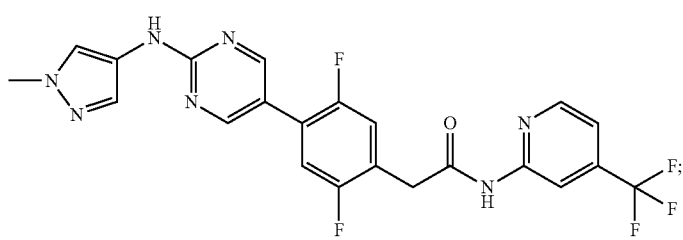 [SMILES: Cn1cc(Nc2ncc(-c3cc(F)c(CC(=O)Nc4cc(C(F)(F)F)ccn4)cc3F)cn2)cn1] |
| P-0020 | 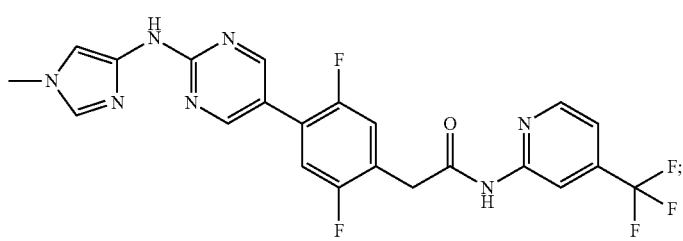 [SMILES: Cn1cnc(Nc2ncc(-c3cc(F)c(CC(=O)Nc4cc(C(F)(F)F)ccn4)cc3F)cn2)c1] |
| P-0021 | 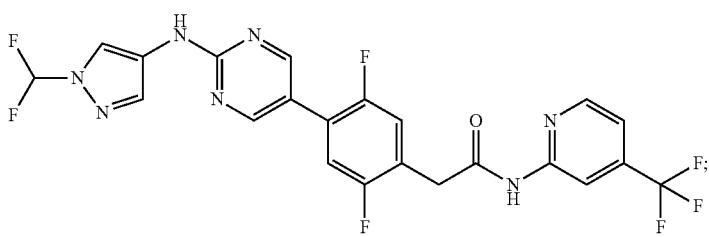 [SMILES: O=C(Cc1cc(F)c(-c2cnc(Nc3cnn(C(F)F)c3)nc2)cc1F)Nc1cc(C(F)(F)F)ccn1] |

| No. | Compound Structure |
|---|---|
| P-0022 | 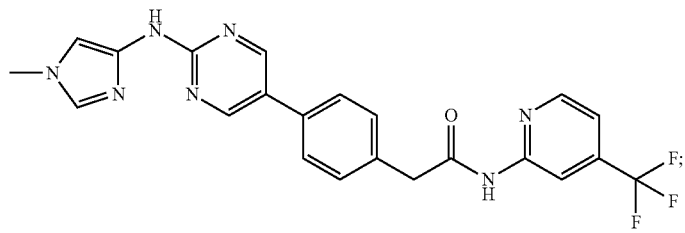 [SMILES: Cn1cnc(Nc2ncc(-c3ccc(CC(=O)Nc4cc(C(F)(F)F)ccn4)cc3)cn2)c1] |
| P-0023 | 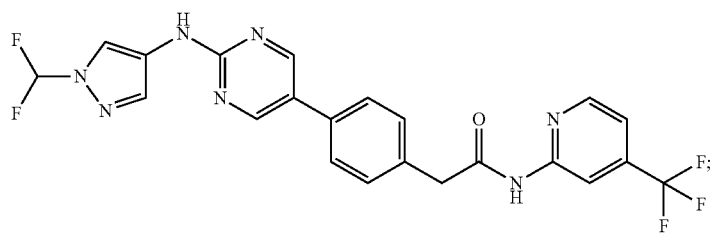 [SMILES: O=C(Cc1ccc(-c2cnc(Nc3cnn(C(F)F)c3)nc2)cc1)Nc1cc(C(F)(F)F)ccn1] |
| P-0024 | 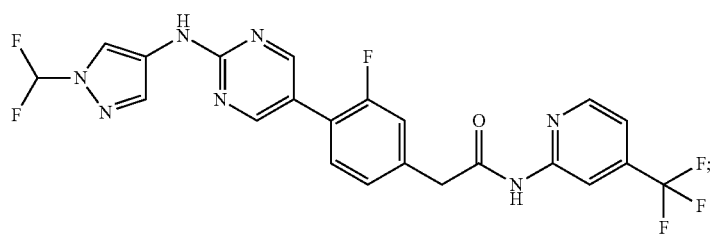 [SMILES: O=C(Cc1ccc(-c2cnc(Nc3cnn(C(F)F)c3)nc2)c(F)c1)Nc1cc(C(F)(F)F)ccn1] |
| P-0025 | 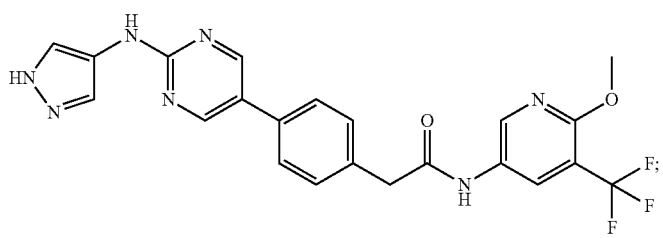 [SMILES: COc1ncc(NC(=O)Cc2ccc(-c3cnc(Nc4cn[nH]c4)nc3)cc2)cc1C(F)(F)F] |
| P-0026 | 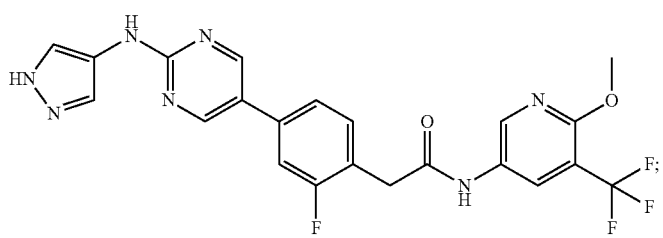 [SMILES: COc1ncc(NC(=O)Cc2ccc(-c3cnc(Nc4cn[nH]c4)nc3)cc2F)cc1C(F)(F)F] |
| P-0027 | 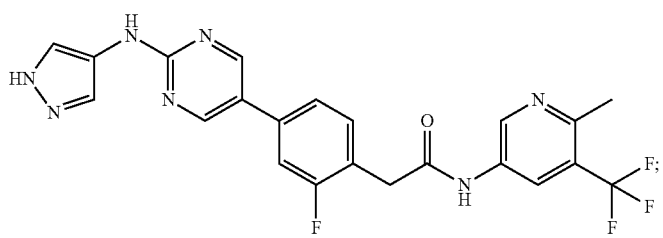 [SMILES: Cc1ncc(NC(=O)Cc2ccc(-c3cnc(Nc4cn[nH]c4)nc3)cc2F)cc1C(F)(F)F] |

| No. | Compound Structure |
|---|---|
| P-0028 | 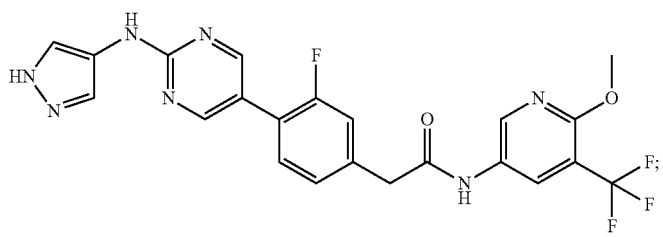 [SMILES: COc1ncc(NC(=O)Cc2ccc(-c3cnc(Nc4cn[nH]c4)nc3)c(F)c2)cc1C(F)(F)F] |
| P-0029 | 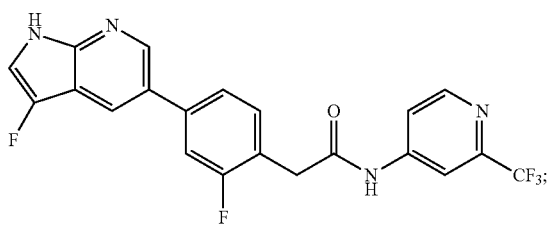 [SMILES: O=C(Cc1ccc(-c2cnc3[nH]cc(F)c3c2)cc1F)Nc1ccnc(C(F)(F)F)c1] |
| P-0030 | 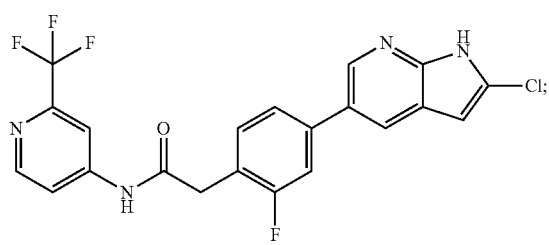 [SMILES: O=C(Cc1ccc(-c2cnc3[nH]c(Cl)cc3c2)cc1F)Nc1ccnc(C(F)(F)F)c1] |
| P-0031 | 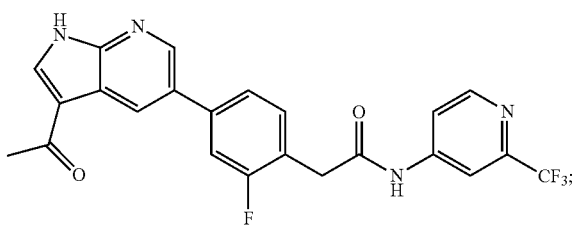 [SMILES: CC(=O)c1c[nH]c2ncc(-c3ccc(CC(=O)Nc4ccnc(C(F)(F)F)c4)c(F)c3)cc12] |
| P-0032 | 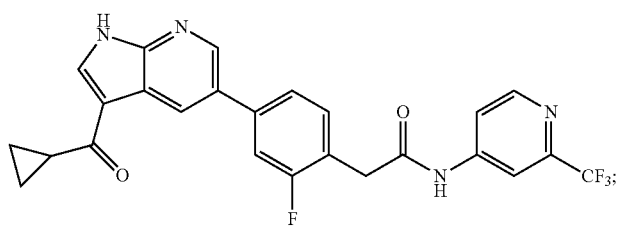 [SMILES: O=C(Cc1ccc(-c2cnc3[nH]cc(C(=O)C4CC4)c3c2)cc1F)Nc1ccnc(C(F)(F)F)c1] |
| P-0033 | 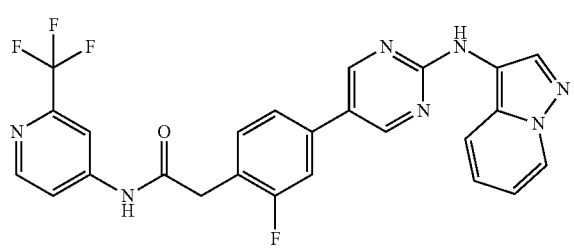 [SMILES: O=C(Cc1ccc(-c2cnc(Nc3cnn4ccccc34)nc2)cc1F)Nc1ccnc(C(F)(F)F)c1] |

| No. | Compound Structure |
|---|---|
| P-0034 | 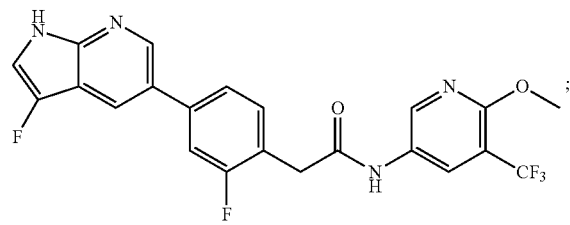 [SMILES: COc1ncc(NC(=O)Cc2ccc(-c3cnc4[nH]cc(F)c4c3)cc2F)cc1C(F)(F)F] |
| P-0035 | 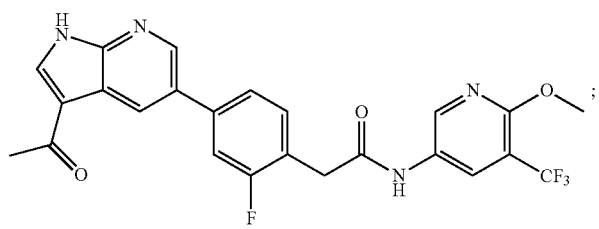 [SMILES: COc1ncc(NC(=O)Cc2ccc(-c3cnc4[nH]cc(C(C)=O)c4c3)cc2F)cc1C(F)(F)F] |
| P-0036 | 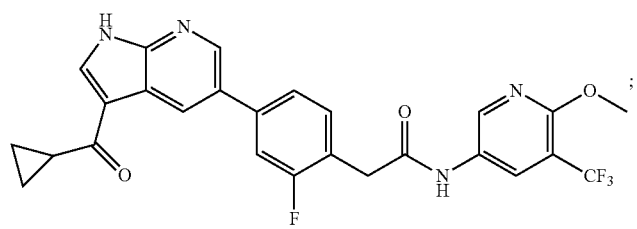 [SMILES: COc1ncc(NC(=O)Cc2ccc(-c3cnc4[nH]cc(C(=O)C5CC5)c4c3)cc2F)cc1C(F)(F)F] |
| P-0037 | 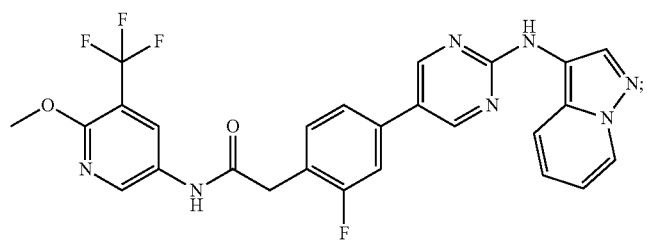 [SMILES: COc1ncc(NC(=O)Cc2ccc(-c3cnc(Nc4cnn5ccccc45)nc3)cc2F)cc1C(F)(F)F] |
| P-0038 | 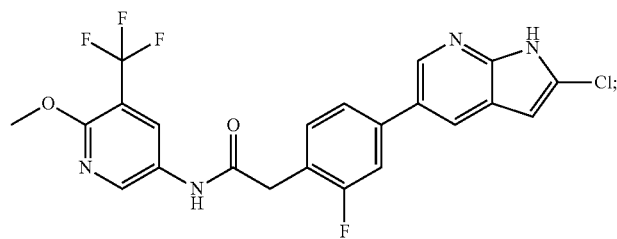 [SMILES: COc1ncc(NC(=O)Cc2ccc(-c3cnc4[nH]c(Cl)cc4c3)cc2F)cc1C(F)(F)F] |
| P-0039 | 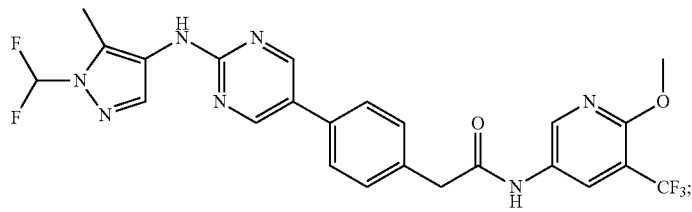 [SMILES: COc1ncc(NC(=O)Cc2ccc(-c3cnc(Nc4cnn(C(F)F)c4C)nc3)cc2)cc1C(F)(F)F] |

| No. | Compound Structure |
|---|---|
| P-0040 | 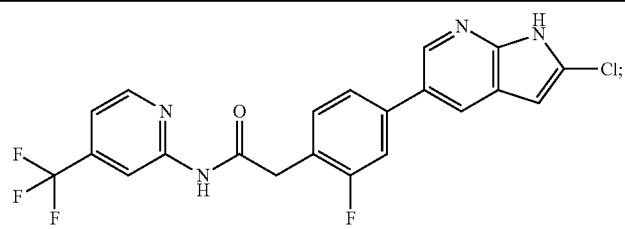 |
| P-0041 | 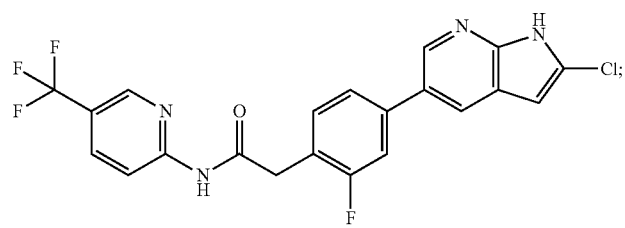 [SMILES: O=C(Cc1ccc(-c2cnc3[nH]c(Cl)cc3c2)cc1F)Nc1ccc(C(F)(F)F)cn1] |
| P-0042 | 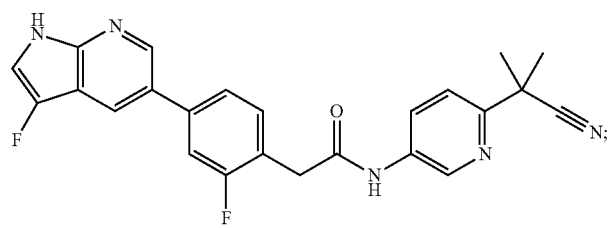 [SMILES: CC(C)(C#N)c1ccc(NC(=O)Cc2ccc(-c3cnc4[nH]cc(F)c4c3)cc2F)cn1] |
| P-0043 | 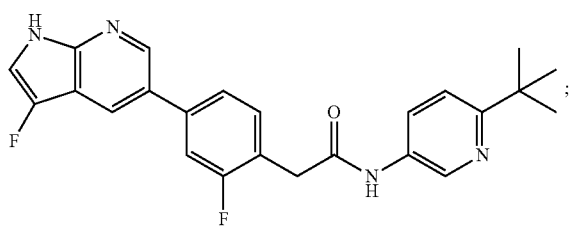 [SMILES: CC(C)(C)c1ccc(NC(=O)Cc2ccc(-c3cnc4[nH]cc(F)c4c3)cc2F)cn1] |
| P-0044 | 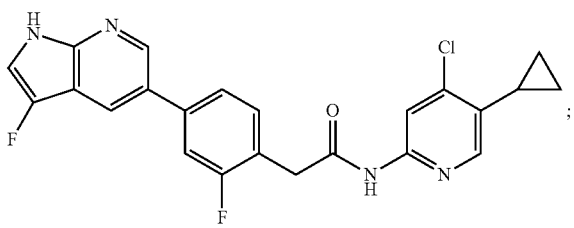 [SMILES: O=C(Cc1ccc(-c2cnc3[nH]cc(F)c3c2)cc1F)Nc1cc(Cl)c(C2CC2)cn1] |
| P-0045 | 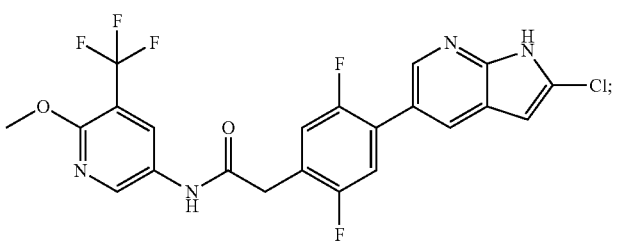 [SMILES: COc1ncc(NC(=O)Cc2cc(F)c(-c3cnc4[nH]c(Cl)cc4c3)cc2F)cc1C(F)(F)F] |
| P-0046 | 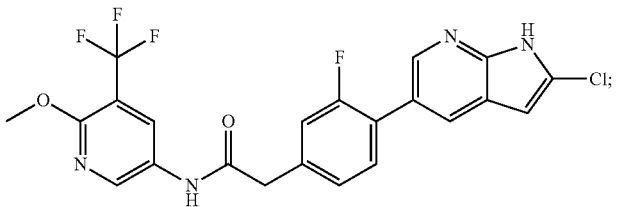 [SMILES: COc1ncc(NC(=O)Cc2ccc(-c3cnc4[nH]c(Cl)cc4c3)c(F)c2)cc1C(F)(F)F] |

-continued
| No. | Compound Structure |
|---|---|
| P-0047 | 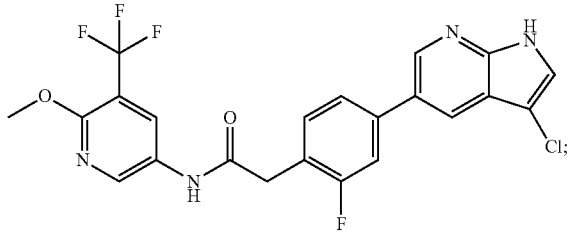 [SMILES: COc1ncc(NC(=O)Cc2ccc(-c3cnc4[nH]cc(Cl)c4c3)cc2F)cc1C(F)(F)F] |
| P-0048 | 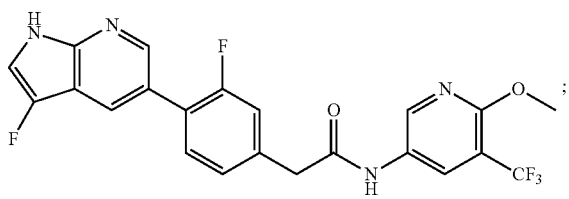 [SMILES: COc1ncc(NC(=O)Cc2ccc(-c3cnc4[nH]cc(F)c4c3)c(F)c2)cc1C(F)(F)F] |
| P-0049 | 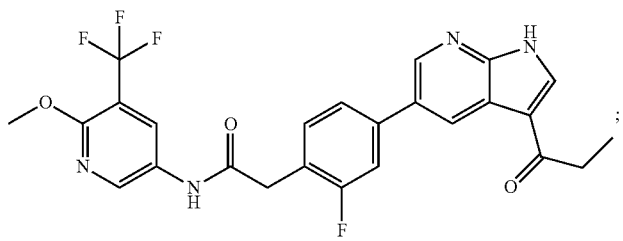 [SMILES: CCC(=O)c1c[nH]c2ncc(-c3ccc(CC(=O)Nc4cnc(OC)c(C(F)(F)F)c4)c(F)c3)cc12] |
| P-0050 | 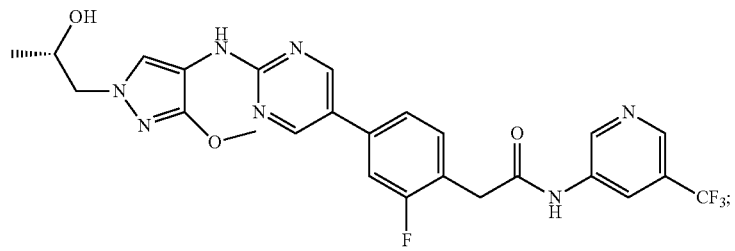 [SMILES: COc1nn(C[C@H](C)O)cc1Nc1ncc(-c2ccc(CC(=O)Nc3cncc(C(F)(F)F)c3)c(F)c2)cn1] |
| P-0051 | 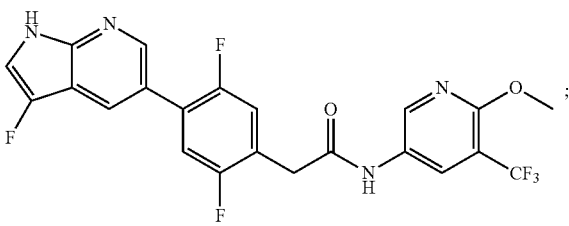 [SMILES: COc1ncc(NC(=O)Cc2cc(F)c(-c3cnc4[nH]cc(F)c4c3)cc2F)cc1C(F)(F)F] |
| P-0052 | 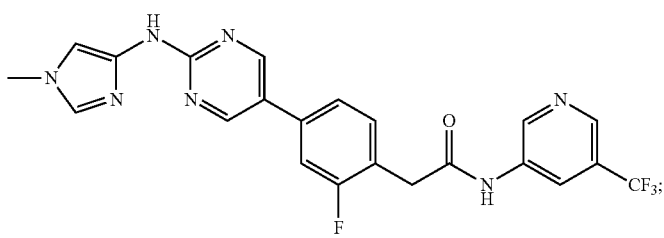 [SMILES: Cn1cnc(Nc2ncc(-c3ccc(CC(=O)Nc4cncc(C(F)(F)F)c4)c(F)c3)cn2)c1] |

-continued
| No. | Compound Structure |
|---|---|
| P-0053 | 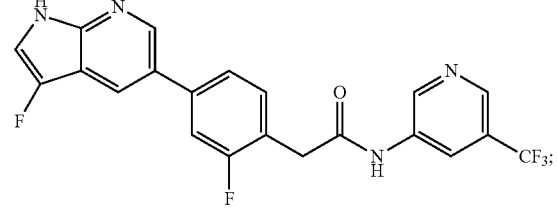 |
| P-0054 | 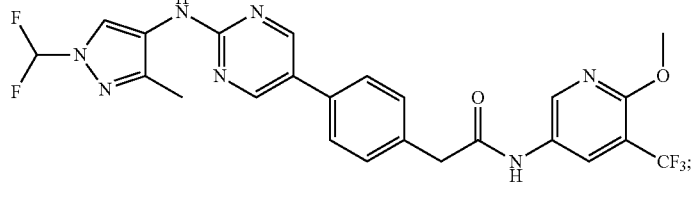 |
| P-0055 | 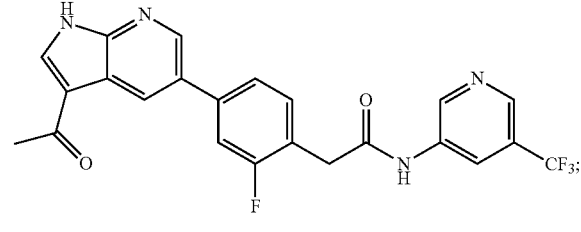 [SMILES: CC(=O)c1c[nH]c2ncc(-c3ccc(CC(=O)Nc4cncc(C(F)(F)F)c4)c(F)c3)cc12] |
| P-0056 | 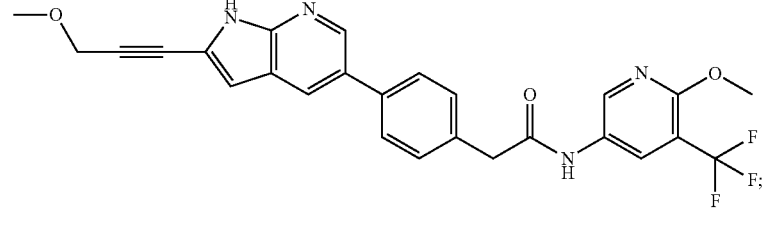 |
| P-0057 | 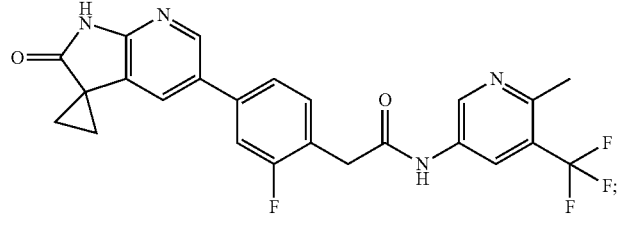 [SMILES: Cc1ncc(NC(=O)Cc2ccc(-c3cnc4c(c3)C3(CC3)C(=O)N4)cc2F)cc1C(F)(F)F] |
| P-0058 | 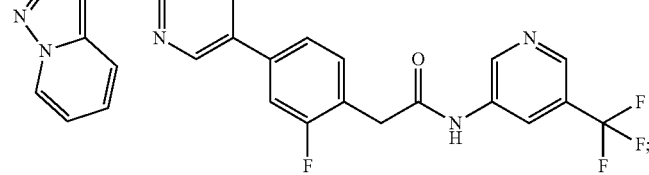 |

| No. | Compound Structure |
|---|---|
| P-0059 | 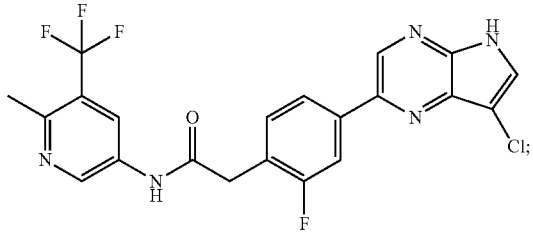 [SMILES: Cc1ncc(NC(=O)Cc2ccc(-c3cnc4[nH]cc(Cl)c4n3)cc2F)cc1C(F)(F)F] |
| P-0060 | 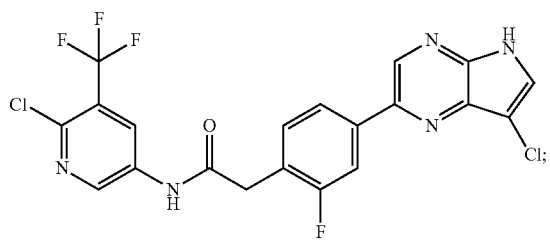 [SMILES: O=C(Cc1ccc(-c2cnc3[nH]cc(Cl)c3n2)cc1F)Nc1cnc(Cl)c(C(F)(F)F)c1] |
| P-0061 | 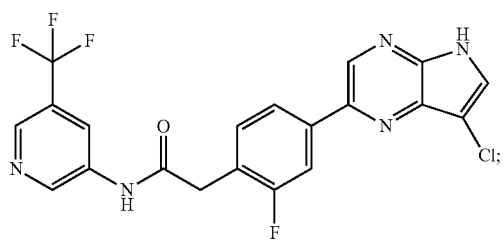 [SMILES: O=C(Cc1ccc(-c2cnc3[nH]cc(Cl)c3n2)cc1F)Nc1cncc(C(F)(F)F)c1] |
| P-0062 | 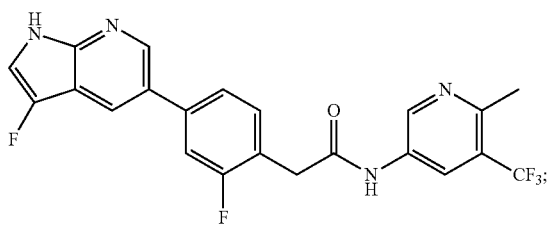 [SMILES: Cc1ncc(NC(=O)Cc2ccc(-c3cnc4[nH]cc(F)c4c3)cc2F)cc1C(F)(F)F] |
| P-0063 | 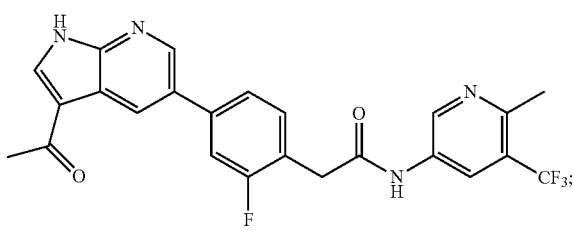 [SMILES: CC(=O)c1c[nH]c2ncc(-c3ccc(CC(=O)Nc4cnc(C)c(C(F)(F)F)c4)c(F)c3)cc12] |
| P-0064 | 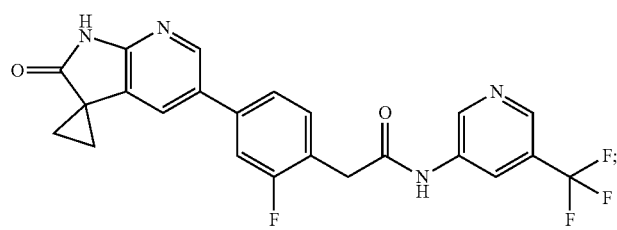 [SMILES: O=C(Cc1ccc(-c2cnc3c(c2)C2(CC2)C(=O)N3)cc1F)Nc1cncc(C(F)(F)F)c1] |

| No. | Compound Structure |
|---|---|
| P-0065 | 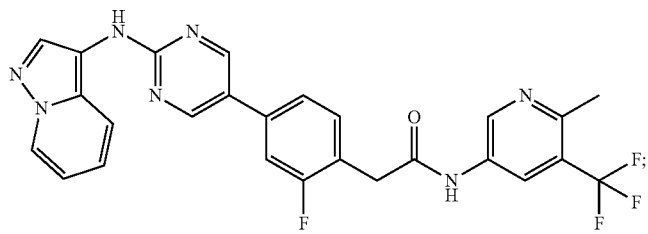 [SMILES: Cc1ncc(NC(=O)Cc2ccc(-c3cnc(Nc4cnn5ccccc45)nc3)cc2F)cc1C(F)(F)F] |
| P-0066 | 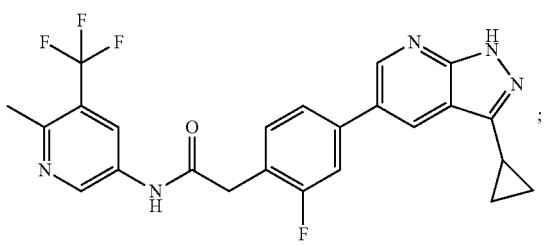 [SMILES: Cc1ncc(NC(=O)Cc2ccc(-c3cnc4[nH]nc(C5CC5)c4c3)cc2F)cc1C(F)(F)F] |
| P-0067 | 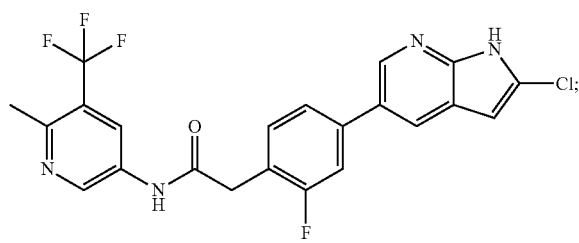 [SMILES: Cc1ncc(NC(=O)Cc2ccc(-c3cnc4[nH]c(Cl)cc4c3)cc2F)cc1C(F)(F)F] |
| P-0068 | 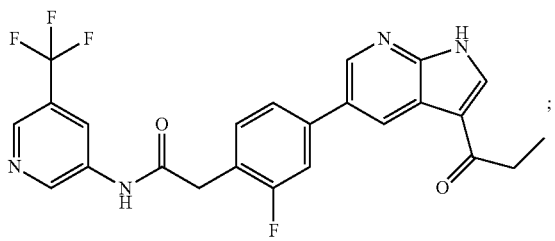 [SMILES: CCC(=O)c1c[nH]c2ncc(-c3ccc(CC(=O)Nc4cncc(C(F)(F)F)c4)c(F)c3)cc12] |
| P-0069 | 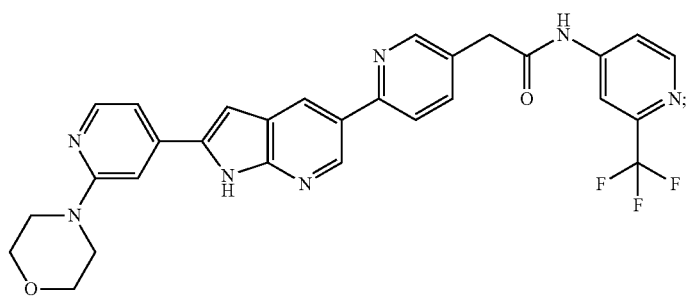 [SMILES: O=C(Cc1ccc(-c2cnc3[nH]c(-c4ccnc(N5CCOCC5)c4)cc3c2)nc1)Nc1ccnc(C(F)(F)F)c1] |
| P-0070 | 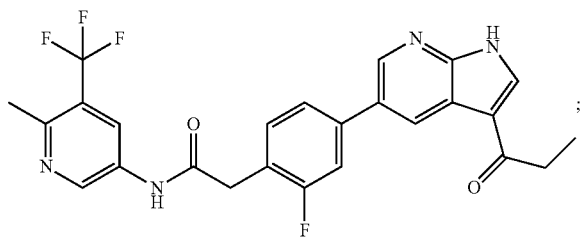 [SMILES: CCC(=O)c1c[nH]c2ncc(-c3ccc(CC(=O)Nc4cnc(C)c(C(F)(F)F)c4)c(F)c3)cc12] |

-continued

| No. | Compound Structure |
|---|---|
| P-0071 | 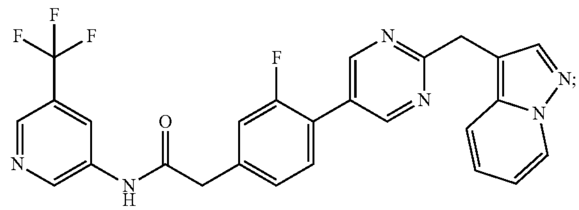 [SMILES: O=C(Cc1ccc(-c2cnc(Cc3cnn4ccccc34)nc2)c(F)c1)Nc1cncc(C(F)(F)F)c1] |
| P-0072 | 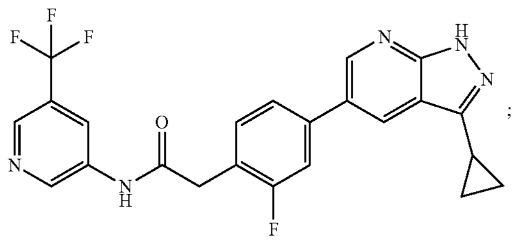 [SMILES: O=C(Cc1ccc(-c2cnc3[nH]nc(C4CC4)c3c2)cc1F)Nc1cncc(C(F)(F)F)c1] |
| P-0073 | 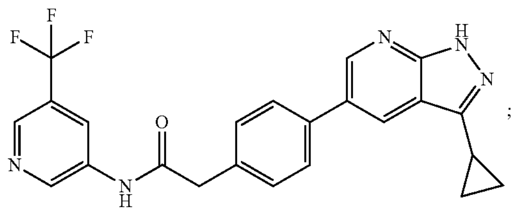 [SMILES: O=C(Cc1ccc(-c2cnc3[nH]nc(C4CC4)c3c2)cc1)Nc1cncc(C(F)(F)F)c1] |
| P-0074 | 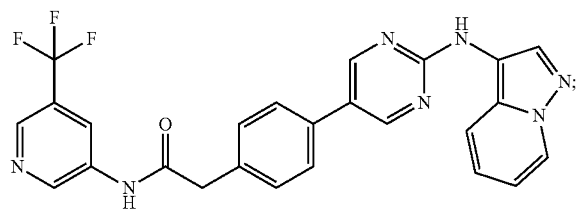 [SMILES: O=C(Cc1ccc(-c2cnc(Nc3cnn4ccccc34)nc2)cc1)Nc1cncc(C(F)(F)F)c1] |
| P-0075 | 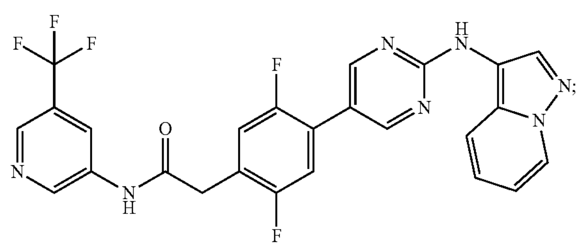 [SMILES: O=C(Cc1cc(F)c(-c2cnc(Nc3cnn4ccccc34)nc2)cc1F)Nc1cncc(C(F)(F)F)c1] |
| P-0076 | 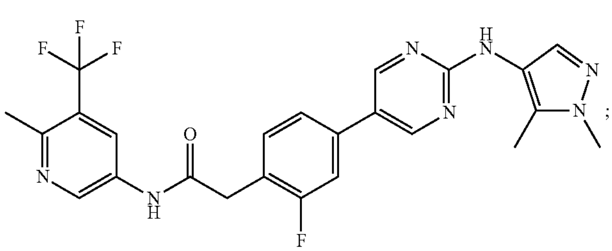 |

US 10,160,747 B2
271                                                                                            272
-continued
| No. | Compound Structure |
|---|---|
| P-0077 | 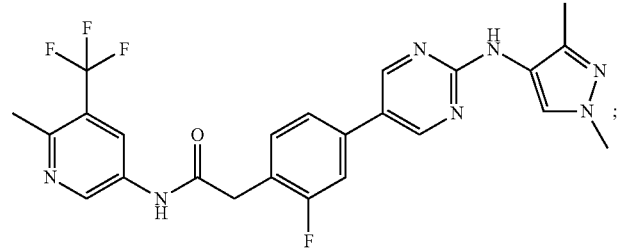 |
| P-0078 | 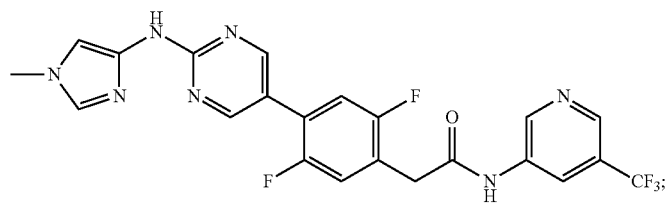 [SMILES: Cn1cnc(Nc2ncc(-c3cc(F)c(CC(=O)Nc4cncc(C(F)(F)F)c4)cc3F)cn2)c1] |
| P-0079 | 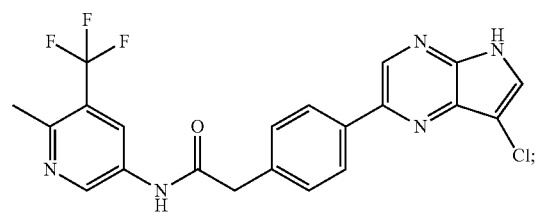 [SMILES: Cc1ncc(NC(=O)Cc2ccc(-c3cnc4[nH]cc(Cl)c4n3)cc2)cc1C(F)(F)F] |
| P-0080 | 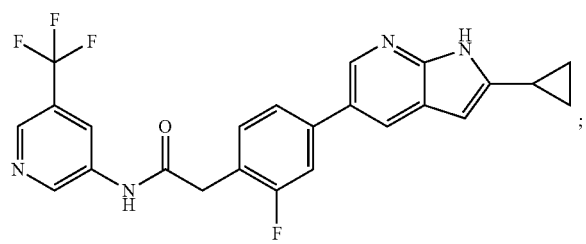 [SMILES: O=C(Cc1ccc(-c2cnc3[nH]c(C4CC4)cc3c2)cc1F)Nc1cncc(C(F)(F)F)c1] |
| P-0081 | 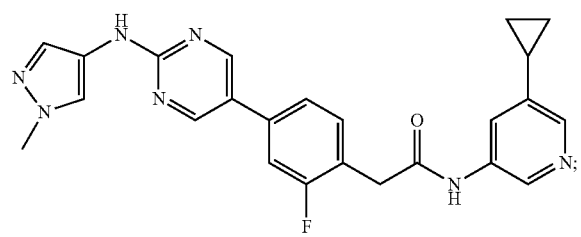 [SMILES: Cn1cc(Nc2ncc(-c3ccc(CC(=O)Nc4cncc(C5CC5)c4)c(F)c3)cn2)cn1] |
| P-0082 | 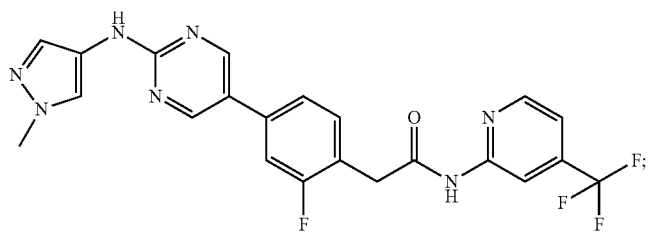 |

-continued

| No. | Compound Structure |
|---|---|
| P-0083 | 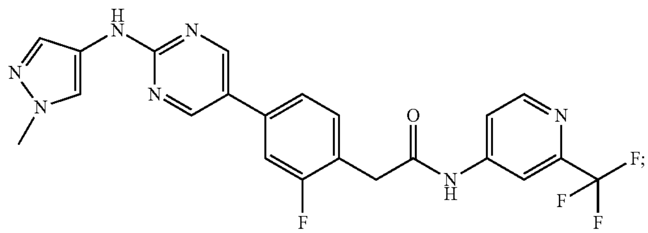 [SMILES: Cn1cc(Nc2ncc(-c3ccc(CC(=O)Nc4ccnc(C(F)(F)F)c4)c(F)c3)cn2)cn1] |
| P-0084 | 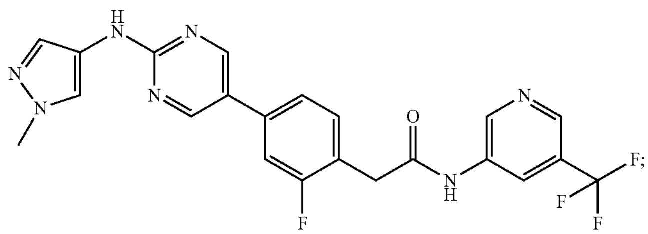 [SMILES: Cn1cc(Nc2ncc(-c3ccc(CC(=O)Nc4cncc(C(F)(F)F)c4)c(F)c3)cn2)cn1] |
| P-0085 | 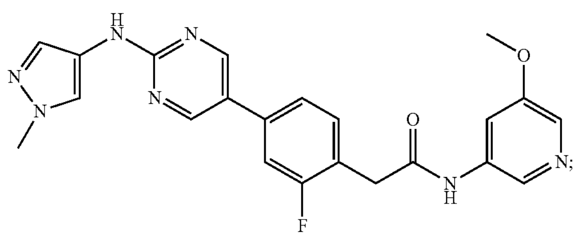 [SMILES: COc1cncc(NC(=O)Cc2ccc(-c3cnc(Nc4cnn(C)c4)nc3)cc2F)c1] |
| P-0086 | 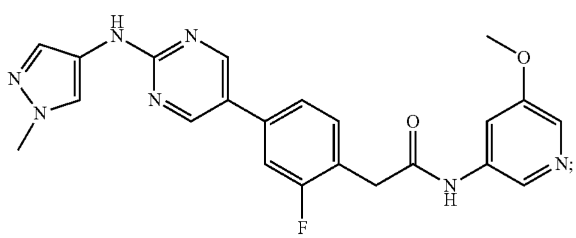 [SMILES: COc1cncc(NC(=O)Cc2ccc(-c3cnc(Nc4cnn(C)c4)nc3)cc2F)c1] |
| P-0087 | 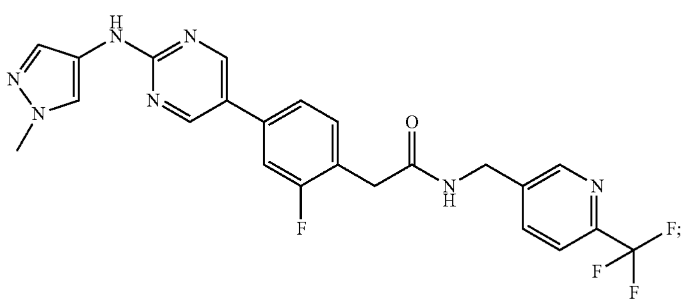 [SMILES: Cn1cc(Nc2ncc(-c3ccc(CC(=O)NCc4ccc(C(F)(F)F)nc4)c(F)c3)cn2)cn1] |
| P-0088 | 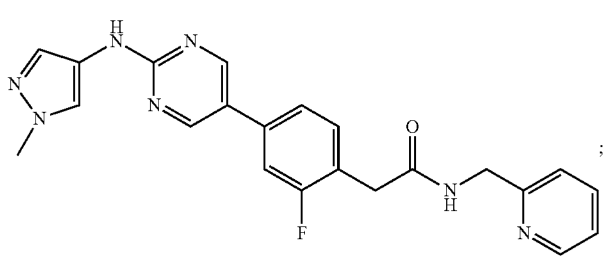 [SMILES: Cn1cc(Nc2ncc(-c3ccc(CC(=O)NCc4ccccn4)c(F)c3)cn2)cn1] |

-continued
| No. | Compound Structure |
|---|---|
| P-0089 | 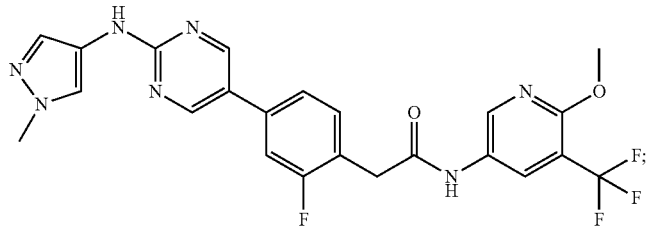 [SMILES: COc1ncc(NC(=O)Cc2ccc(-c3cnc(Nc4cnn(C)c4)nc3)cc2F)cc1C(F)(F)F] |
| P-0090 | 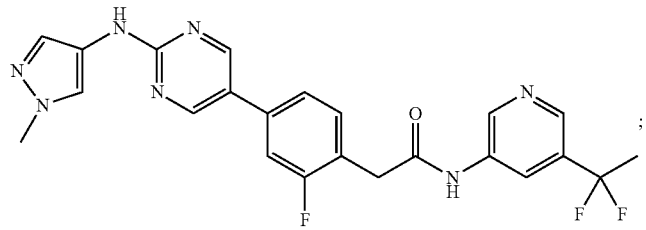 [SMILES: Cn1cc(Nc2ncc(-c3ccc(CC(=O)Nc4cncc(C(C)(F)F)c4)c(F)c3)cn2)cn1] |
| P-0091 | 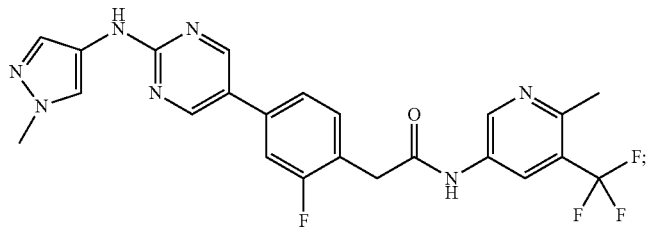 [SMILES: Cc1ncc(NC(=O)Cc2ccc(-c3cnc(Nc4cnn(C)c4)nc3)cc2F)cc1C(F)(F)F] |
| P-0092 | 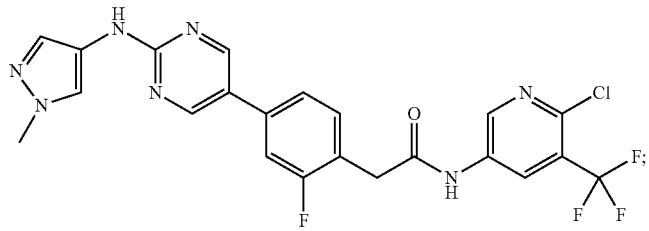 [SMILES: Cn1cc(Nc2ncc(-c3ccc(CC(=O)Nc4cnc(Cl)c(C(F)(F)F)c4)c(F)c3)cn2)cn1] |
| P-0093 | 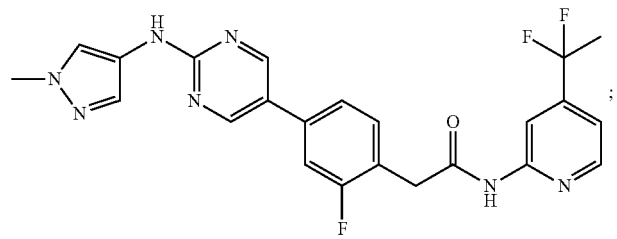 [SMILES: Cn1cc(Nc2ncc(-c3ccc(CC(=O)Nc4cc(C(C)(F)F)ccn4)c(F)c3)cn2)cn1] |
| P-0094 | 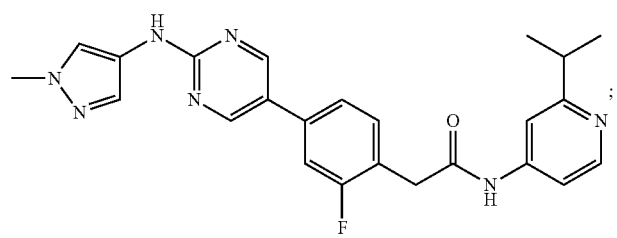 [SMILES: CC(C)c1cc(NC(=O)Cc2ccc(-c3cnc(Nc4cnn(C)c4)nc3)cc2F)ccn1] |

-continued
| No. | Compound Structure |
|---|---|
| P-0095 | 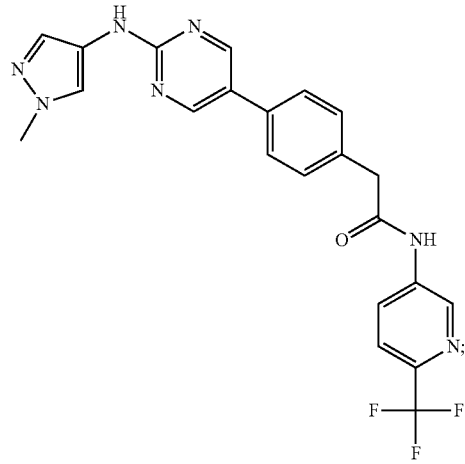 [SMILES: Cn1cc(Nc2ncc(-c3ccc(CC(=O)Nc4ccc(C(F)(F)F)nc4)cc3)cn2)cn1] |
| P-0096 | 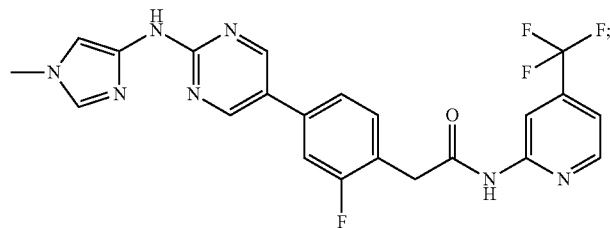 |
| P-0097 | 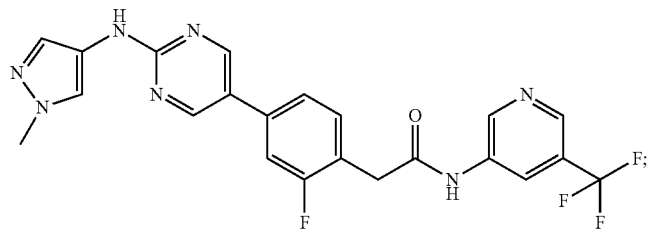 [SMILES: Cn1cc(Nc2ncc(-c3ccc(CC(=O)Nc4cncc(C(F)(F)F)c4)c(F)c3)cn2)cn1] |
| P-0098 | 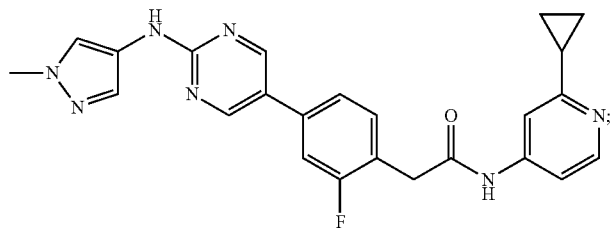 [SMILES: Cn1cc(Nc2ncc(-c3ccc(CC(=O)Nc4ccnc(C5CC5)c4)c(F)c3)cn2)cn1] |
| P-0099 | 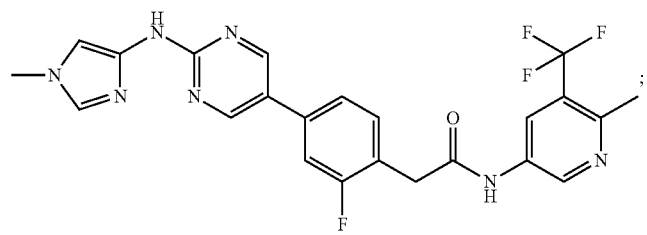 |

-continued
| No. | Compound Structure |
|---|---|
| P-0100 | 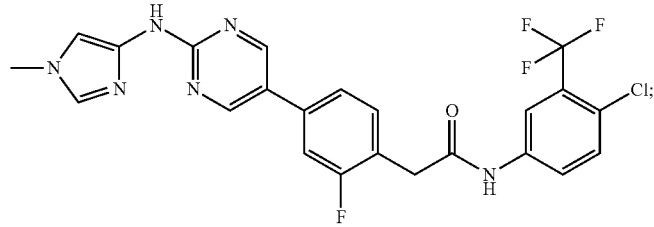 [SMILES: Cn1cnc(Nc2ncc(-c3ccc(CC(=O)Nc4ccc(Cl)c(C(F)(F)F)c4)c(F)c3)cn2)c1] |
| P-0101 | 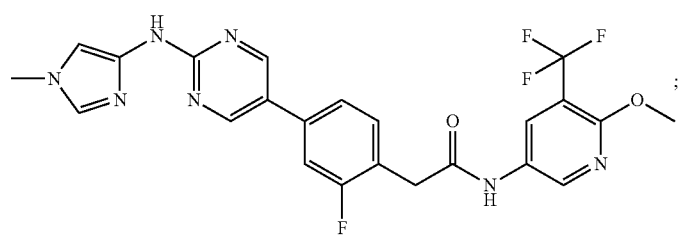 |
| P-0102 | 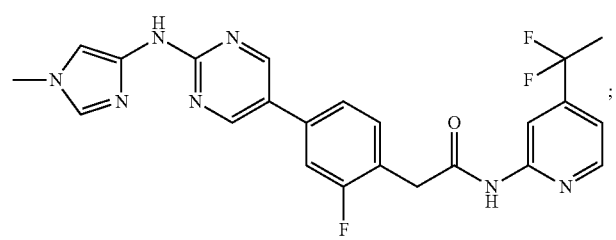 [SMILES: Cn1cnc(Nc2ncc(-c3ccc(CC(=O)Nc4cc(C(C)(F)F)ccn4)c(F)c3)cn2)c1] |
| P-0103 | 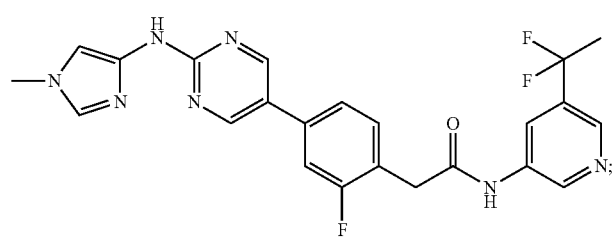 [SMILES: Cn1cnc(Nc2ncc(-c3ccc(CC(=O)Nc4cncc(C(C)(F)F)c4)c(F)c3)cn2)c1] |
| P-0104 | 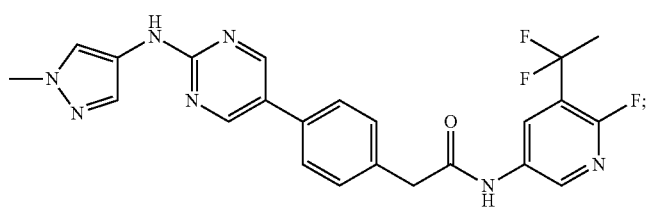 [SMILES: Cn1cc(Nc2ncc(-c3ccc(CC(=O)Nc4cnc(F)c(C(C)(F)F)c4)cc3)cn2)cn1] |
| P-0105 | 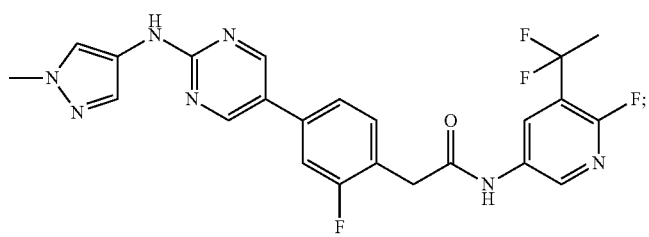 [SMILES: Cn1cc(Nc2ncc(-c3ccc(CC(=O)Nc4cnc(F)c(C(C)(F)F)c4)c(F)c3)cn2)cn1] |

| No. | Compound Structure |
|---|---|
| P-0106 | (structure) |
| P-0107 | (structure) |
| P-0108 | (structure) |
| P-0109 | (structure) |
| P-0110 | (structure) |
| P-0111 | (structure) |

-continued
| No. | Compound Structure |
|---|---|
| P-0112 | 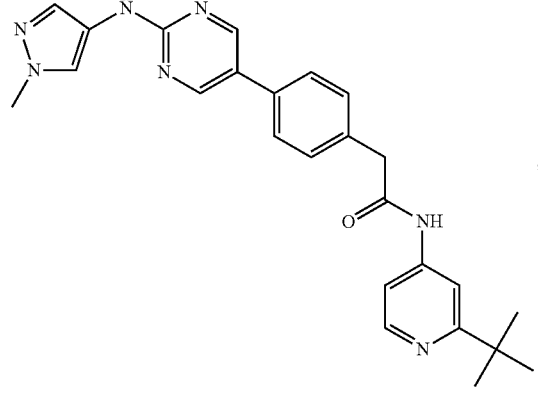 ; |
| P-0113 | 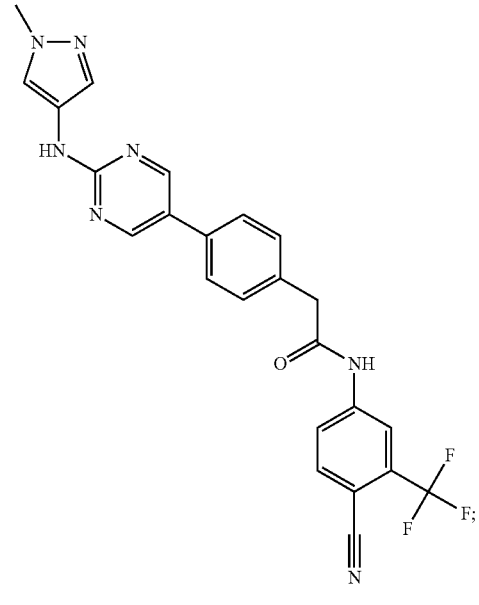 [SMILES: Cn1cc(Nc2ncc(-c3ccc(CC(=O)Nc4ccc(C#N)c(C(F)(F)F)c4)cc3)cn2)cn1] ; |
| P-0116 | 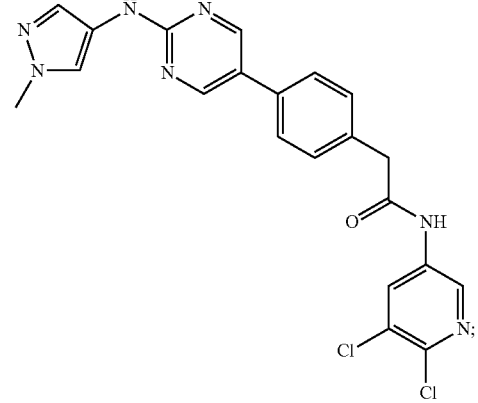 ; |

| No. | Compound Structure |
|---|---|
| P-0117 | 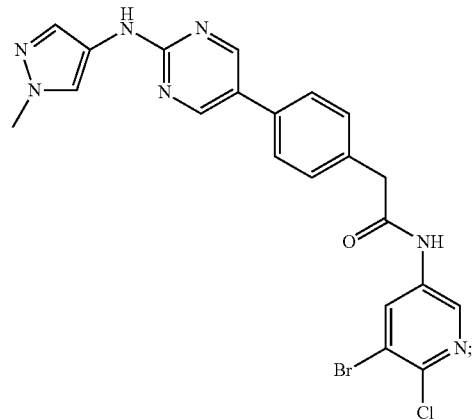 [SMILES: Cn1cc(Nc2ncc(-c3ccc(CC(=O)Nc4cnc(Cl)c(Br)c4)cc3)cn2)cn1] |
| P-0118 | 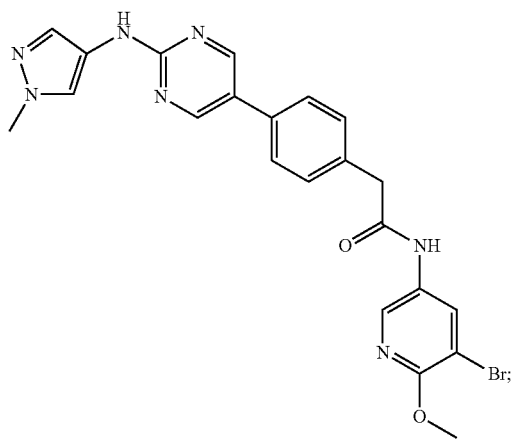 [SMILES: COc1ncc(NC(=O)Cc2ccc(-c3cnc(Nc4cnn(C)c4)nc3)cc2)cc1Br] |
| P-0119 | 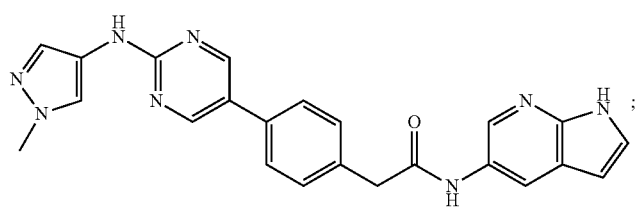 [SMILES: Cn1cc(Nc2ncc(-c3ccc(CC(=O)Nc4cnc5[nH]ccc5c4)cc3)cn2)cn1] |

-continued
| No. | Compound Structure |
|---|---|
| P-0120 | 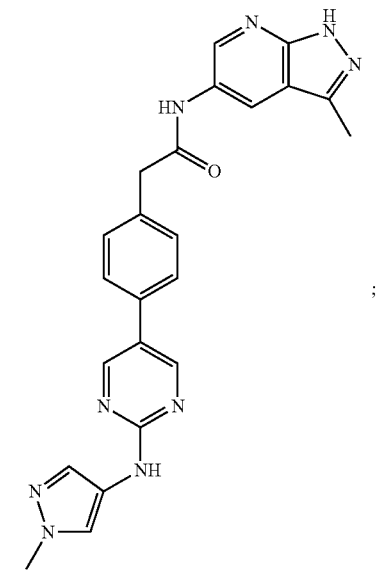 [SMILES: Cc1n[nH]c2ncc(NC(=O)Cc3ccc(-c4cnc(Nc5cnn(C)c5)nc4)cc3)cc12] |
| P-0121 | 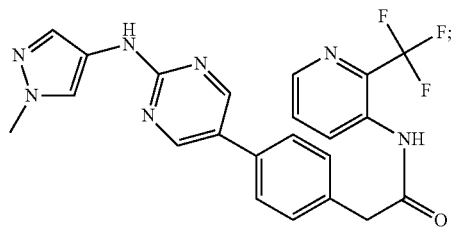 [SMILES: Cn1cc(Nc2ncc(-c3ccc(CC(=O)Nc4cccnc4C(F)(F)F)cc3)cn2)cn1] |
| P-0122 | 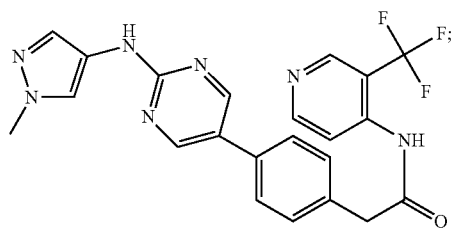 [SMILES: Cn1cc(Nc2ncc(-c3ccc(CC(=O)Nc4ccncc4C(F)(F)F)cc3)cn2)cn1] |
| P-0130 | 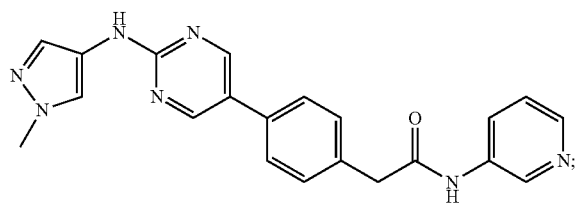 [SMILES: Cn1cc(Nc2ncc(-c3ccc(CC(=O)Nc4cccnc4)cc3)cn2)cn1] |
| P-0131 | 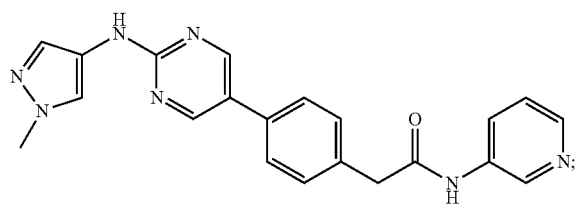 [SMILES: Cn1cc(Nc2ncc(-c3ccc(CC(=O)Nc4cccnc4)cc3)cn2)cn1] |

-continued
| No. | Compound Structure |
|---|---|
| P-0133 | 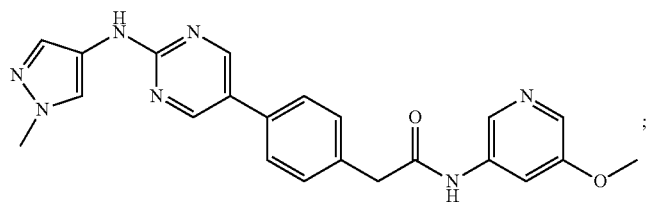 [SMILES: COc1cncc(NC(=O)Cc2ccc(-c3cnc(Nc4cnn(C)c4)nc3)cc2)c1] |
| P-0134 | 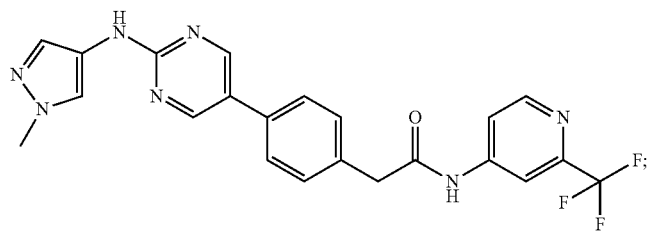 [SMILES: Cn1cc(Nc2ncc(-c3ccc(CC(=O)Nc4ccnc(C(F)(F)F)c4)cc3)cn2)cn1] |
| P-0135 | 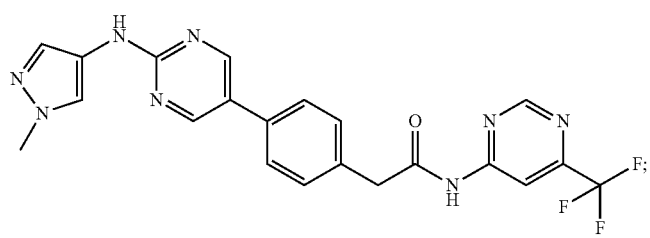 [SMILES: Cn1cc(Nc2ncc(-c3ccc(CC(=O)Nc4cc(C(F)(F)F)ncn4)cc3)cn2)cn1] |
| P-0136 | 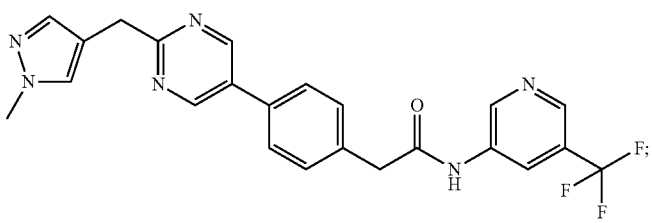 [SMILES: Cn1cc(Cc2ncc(-c3ccc(CC(=O)Nc4cncc(C(F)(F)F)c4)cc3)cn2)cn1] |
| P-0137 | 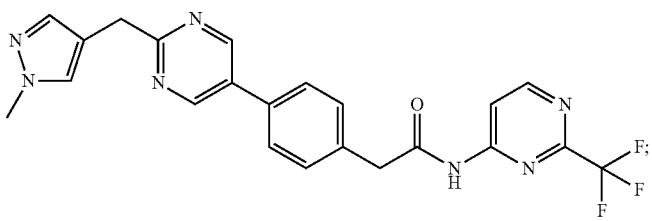 [SMILES: Cn1cc(Cc2ncc(-c3ccc(CC(=O)Nc4ccnc(C(F)(F)F)n4)cc3)cn2)cn1] |
| P-0270 | 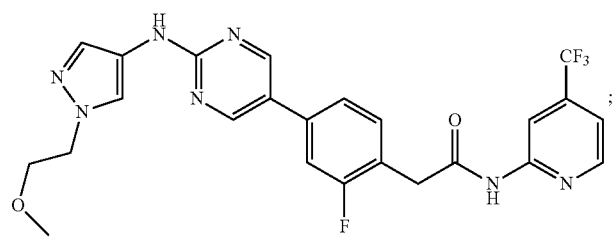 [SMILES: COCCn1cc(Nc2ncc(-c3ccc(CC(=O)Nc4cc(C(F)(F)F)ccn4)c(F)c3)cn2)cn1] |
| P-0272 | 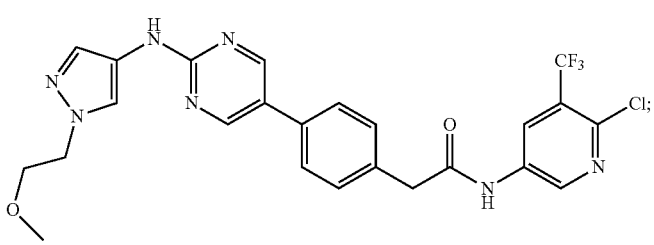 [SMILES: COCCn1cc(Nc2ncc(-c3ccc(CC(=O)Nc4cnc(Cl)c(C(F)(F)F)c4)cc3)cn2)cn1] |

| No. | Compound Structure |
|---|---|
| P-0274 | 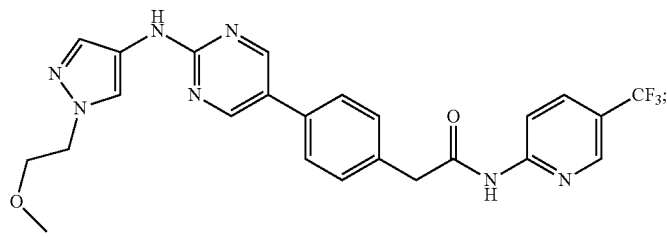 [SMILES: COCCn1cc(Nc2ncc(-c3ccc(CC(=O)Nc4ccc(C(F)(F)F)cn4)cc3)cn2)cn1] |
| P-0138 | 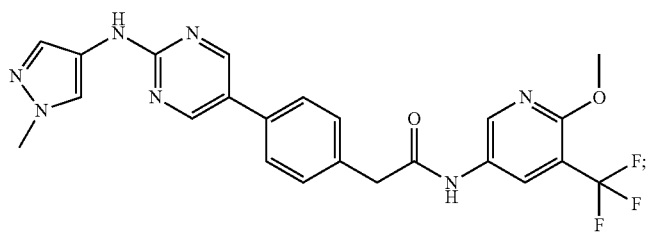 [SMILES: COc1ncc(NC(=O)Cc2ccc(-c3cnc(Nc4cnn(C)c4)nc3)cc2)cc1C(F)(F)F] |
| P-0139 | 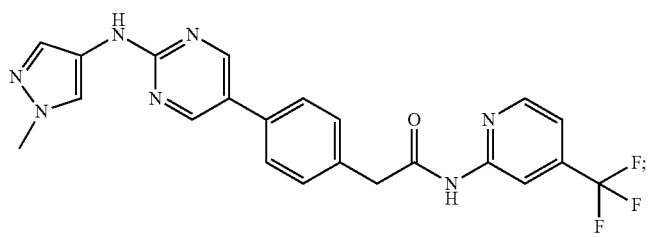 [SMILES: Cn1cc(Nc2ncc(-c3ccc(CC(=O)Nc4cc(C(F)(F)F)ccn4)cc3)cn2)cn1] |
| P-0140 | 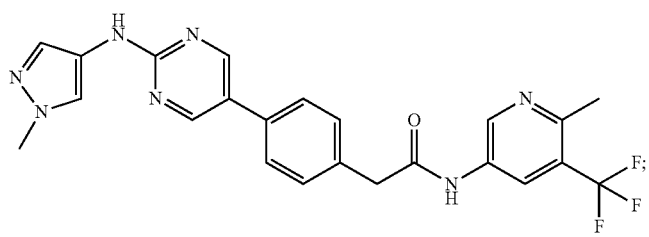 [SMILES: Cc1ncc(NC(=O)Cc2ccc(-c3cnc(Nc4cnn(C)c4)nc3)cc2)cc1C(F)(F)F] |
| P-0141 | 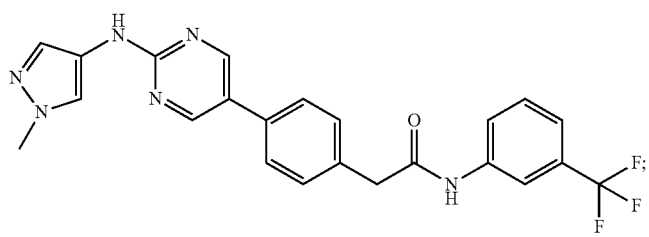 [SMILES: Cn1cc(Nc2ncc(-c3ccc(CC(=O)Nc4cccc(C(F)(F)F)c4)cc3)cn2)cn1] |
| P-0142 | 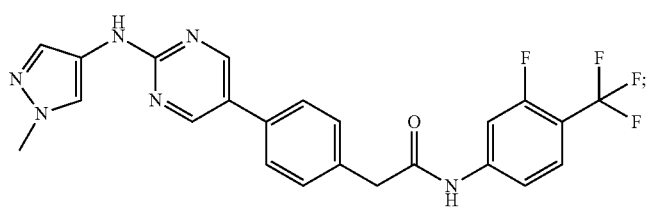 [SMILES: Cn1cc(Nc2ncc(-c3ccc(CC(=O)Nc4ccc(C(F)(F)F)c(F)c4)cc3)cn2)cn1] |

| No. | Compound Structure |
|---|---|
| P-0143 | (structure) |
| P-0144 | (structure) |
| P-0145 | (structure) |
| P-0146 | (structure) |
| P-0147 | (structure) |
| P-0148 | (structure) |
| P-0149 | (structure) |

| No. | Compound Structure |
|---|---|
| P-0150 | 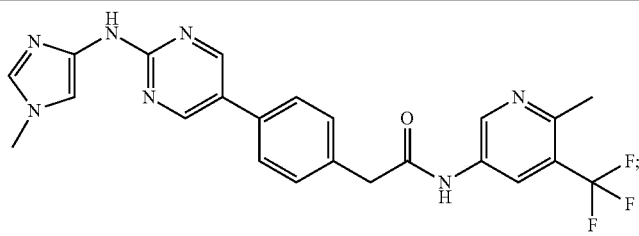 [SMILES: Cc1ncc(NC(=O)Cc2ccc(-c3cnc(Nc4cn(C)cn4)nc3)cc2)cc1C(F)(F)F] |
| P-0151 | 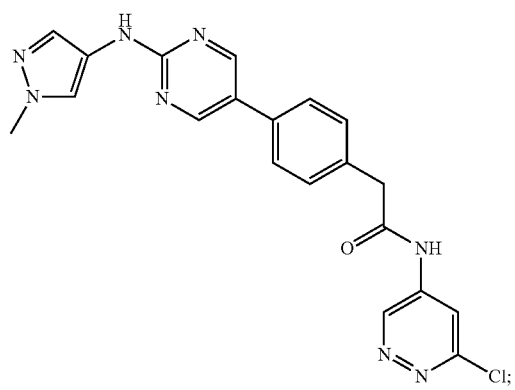 [SMILES: Cn1cc(Nc2ncc(-c3ccc(CC(=O)Nc4cnnc(Cl)c4)cc3)cn2)cn1] |
| P-0152 | 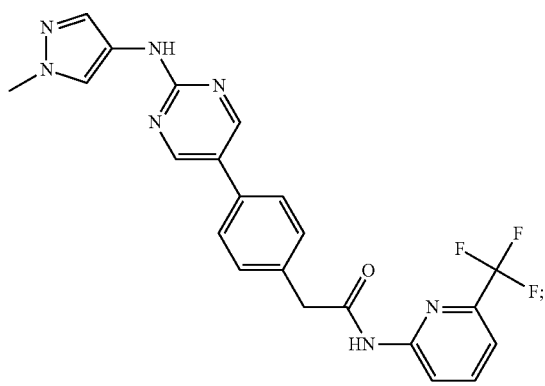 [SMILES: Cn1cc(Nc2ncc(-c3ccc(CC(=O)Nc4cccc(C(F)(F)F)n4)cc3)cn2)cn1] |
| P-0153 | 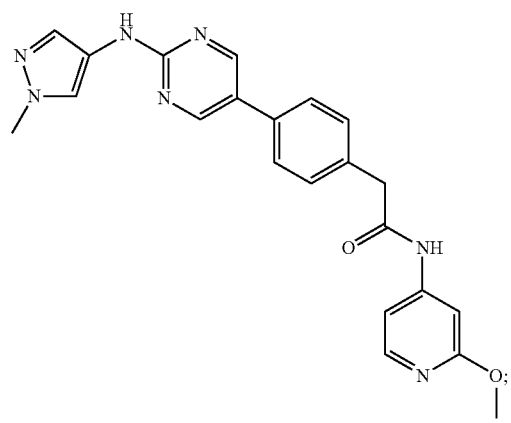 |

| No. | Compound Structure |
|---|---|
| P-0154 | 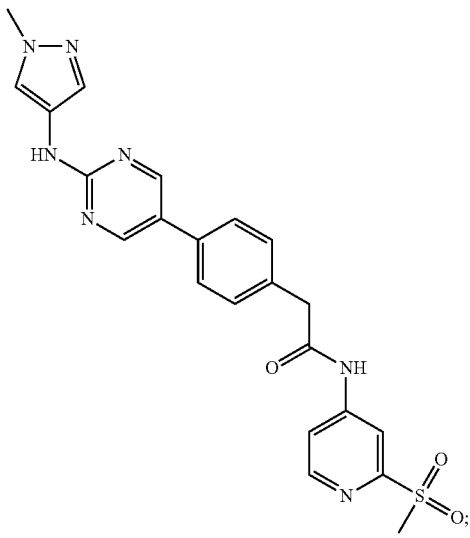 [SMILES: Cn1cc(Nc2ncc(-c3ccc(CC(=O)Nc4ccnc(S(C)(=O)=O)c4)cc3)cn2)cn1] |
| P-0155 | 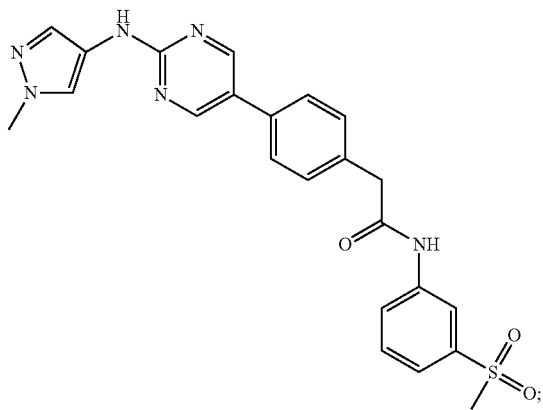 [SMILES: Cn1cc(Nc2ncc(-c3ccc(CC(=O)Nc4cccc(S(C)(=O)=O)c4)cc3)cn2)cn1] |
| P-0156 | 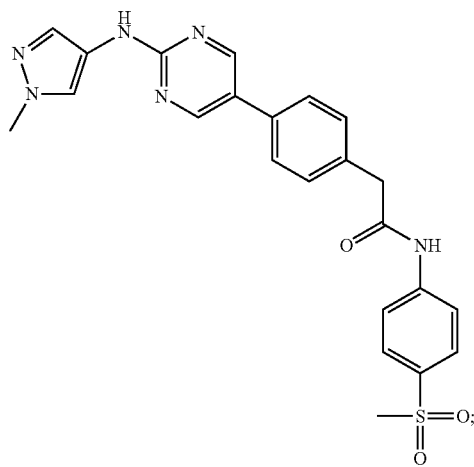 [SMILES: Cn1cc(Nc2ncc(-c3ccc(CC(=O)Nc4ccc(S(C)(=O)=O)cc4)cc3)cn2)cn1] |

| No. | Compound Structure |
|---|---|
| P-0157 | 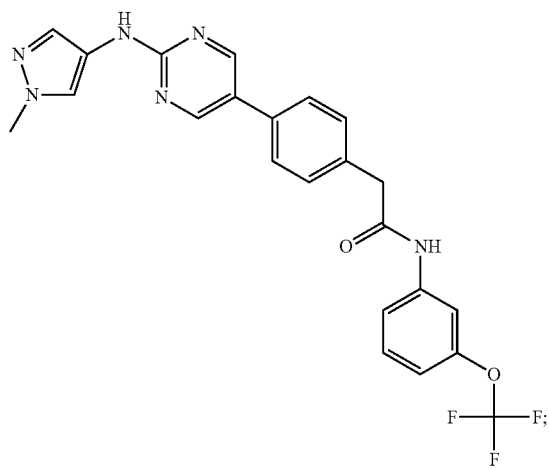 [SMILES: Cn1cc(Nc2ncc(-c3ccc(CC(=O)Nc4cccc(OC(F)(F)F)c4)cc3)cn2)cn1] |
| P-0158 | 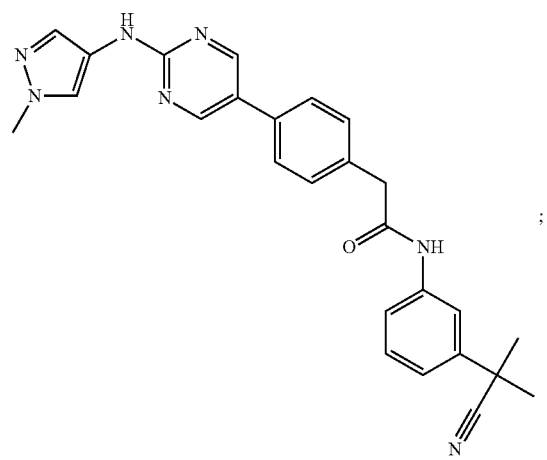 [SMILES: Cn1cc(Nc2ncc(-c3ccc(CC(=O)Nc4cccc(C(C)(C)C#N)c4)cc3)cn2)cn1] |
| P-0163 | 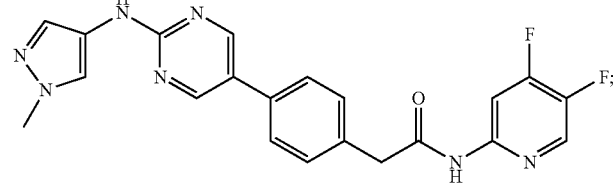 |
| P-0164 | 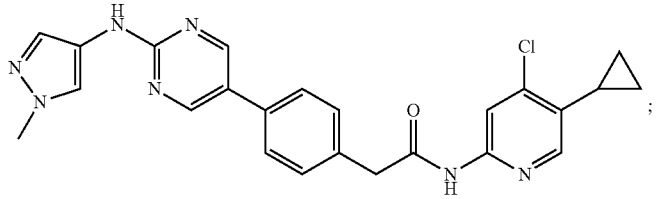 [SMILES: Cn1cc(Nc2ncc(-c3ccc(CC(=O)Nc4cc(Cl)c(C5CC5)cn4)cc3)cn2)cn1] |
| P-0165 | 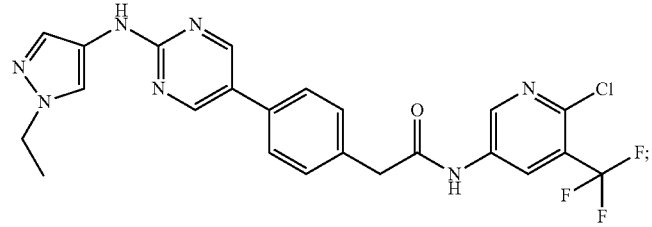 [SMILES: CCn1cc(Nc2ncc(-c3ccc(CC(=O)Nc4cnc(Cl)c(C(F)(F)F)c4)cc3)cn2)cn1] |

| No. | Compound Structure |
|---|---|
| P-0166 | 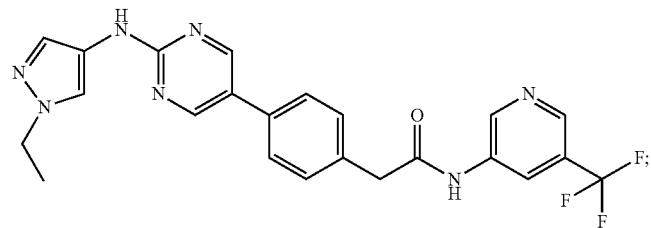 [SMILES: CCn1cc(Nc2ncc(-c3ccc(CC(=O)Nc4cncc(C(F)(F)F)c4)cc3)cn2)cn1] |
| P-0167 | 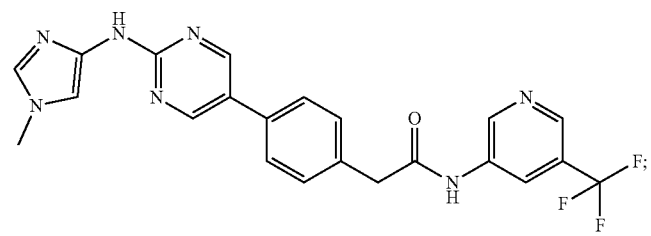 [SMILES: Cn1cnc(Nc2ncc(-c3ccc(CC(=O)Nc4cncc(C(F)(F)F)c4)cc3)cn2)c1] |
| P-0168 | 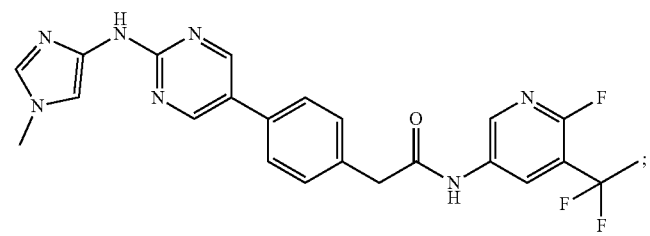 [SMILES: Cn1cnc(Nc2ncc(-c3ccc(CC(=O)Nc4cnc(F)c(C(C)(F)F)c4)cc3)cn2)c1] |
| P-0169 | 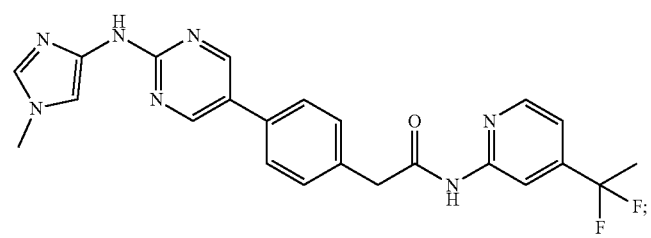 [SMILES: Cn1cnc(Nc2ncc(-c3ccc(CC(=O)Nc4cc(C(C)(F)F)ccn4)cc3)cn2)c1] |
| P-0170 | 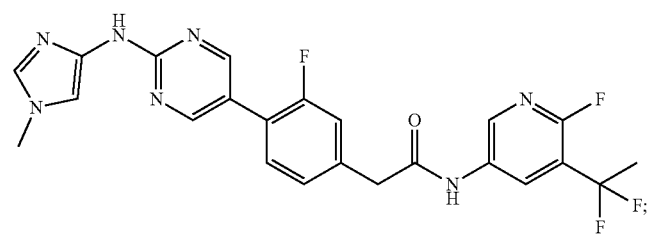 [SMILES: Cn1cnc(Nc2ncc(-c3ccc(CC(=O)Nc4cnc(F)c(C(C)(F)F)c4)cc3F)cn2)c1] |
| P-0171 | 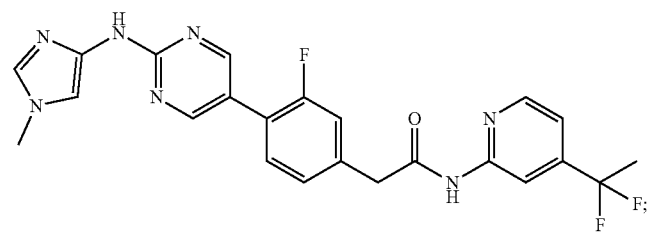 |

| No. | Compound Structure |
|---|---|
| P-0172 | 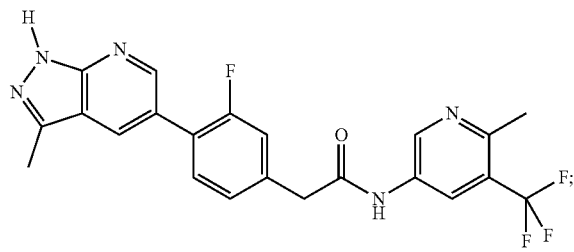 [SMILES: Cc1ncc(NC(=O)Cc2ccc(-c3cnc4[nH]nc(C)c4c3)c(F)c2)cc1C(F)(F)F] |
| P-0173 | 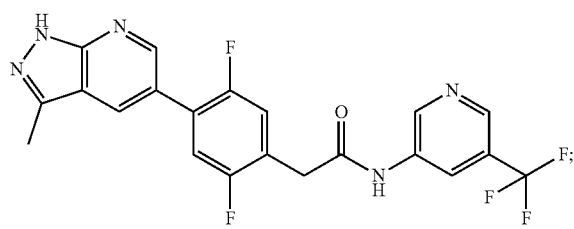 [SMILES: Cc1n[nH]c2ncc(-c3cc(F)c(CC(=O)Nc4cncc(C(F)(F)F)c4)cc3F)cc12] |
| P-0174 | 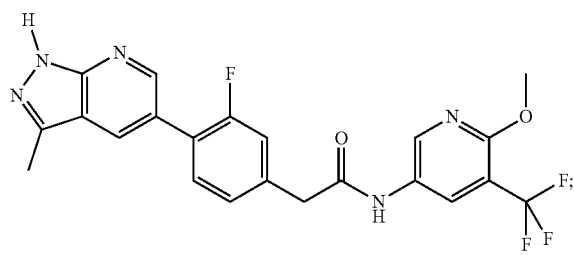 [SMILES: COc1ncc(NC(=O)Cc2ccc(-c3cnc4[nH]nc(C)c4c3)c(F)c2)cc1C(F)(F)F] |
| P-0175 | 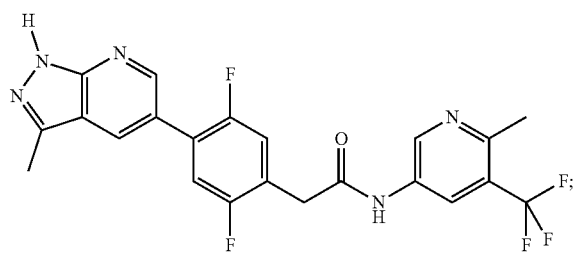 [SMILES: Cc1ncc(NC(=O)Cc2cc(F)c(-c3cnc4[nH]nc(C)c4c3)cc2F)cc1C(F)(F)F] |
| P-0176 | 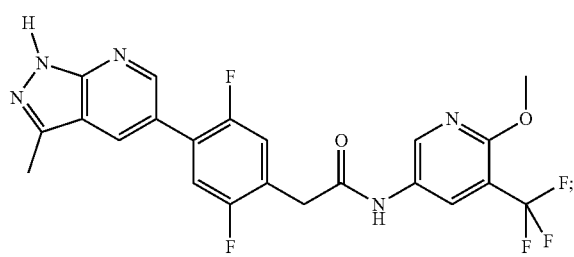 [SMILES: COc1ncc(NC(=O)Cc2cc(F)c(-c3cnc4[nH]nc(C)c4c3)cc2F)cc1C(F)(F)F] |
| P-0177 | 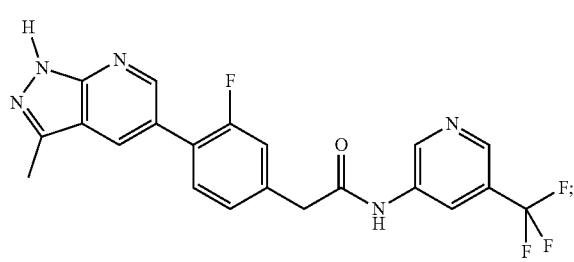 [SMILES: Cc1n[nH]c2ncc(-c3ccc(CC(=O)Nc4cncc(C(F)(F)F)c4)cc3F)cc12] |

-continued
| No. | Compound Structure |
|---|---|
| P-0178 | 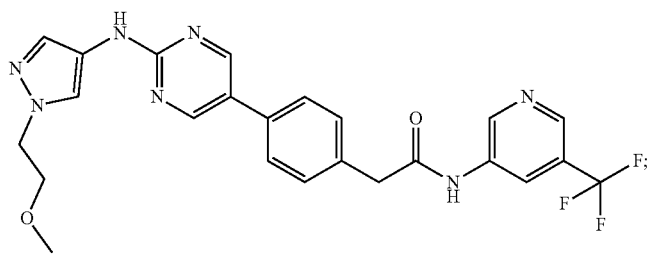 [SMILES: COCCn1cc(Nc2ncc(-c3ccc(CC(=O)Nc4cncc(C(F)(F)F)c4)cc3)cn2)cn1] |
| P-0179 | 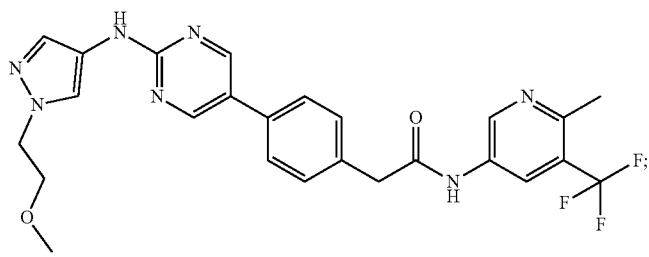 [SMILES: COCCn1cc(Nc2ncc(-c3ccc(CC(=O)Nc4cnc(C)c(C(F)(F)F)c4)cc3)cn2)cn1] |
| P-0180 | 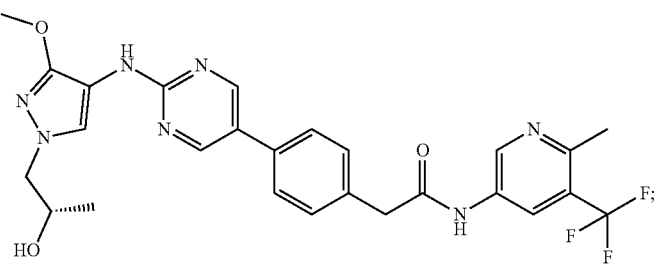 [SMILES: COc1nn(C[C@H](C)O)cc1Nc1ncc(-c2ccc(CC(=O)Nc3cnc(C)c(C(F)(F)F)c3)cc2)cn1] |
| P-0181 | 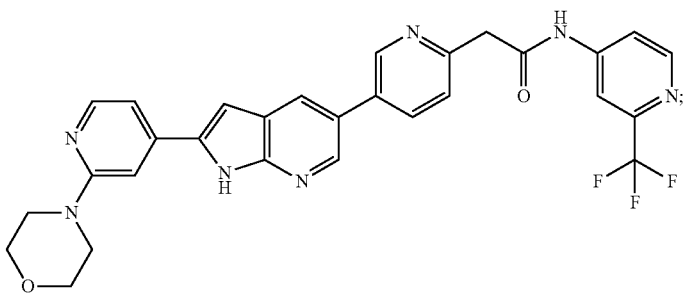 [SMILES: O=C(Cc1ccc(-c2cnc3[nH]c(-c4ccnc(N5CCOCC5)c4)cc3c2)cn1)Nc1ccnc(C(F)(F)F)c1] |
| P-0182 | 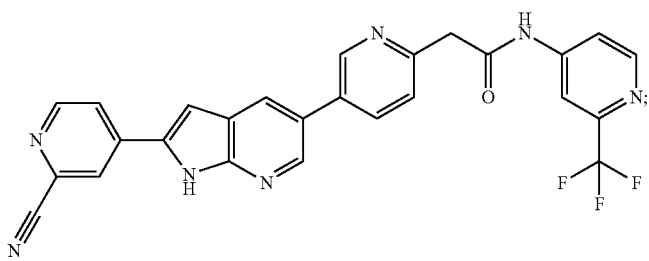 [SMILES: N#Cc1cc(-c2cc3cc(-c4ccc(CC(=O)Nc5ccnc(C(F)(F)F)c5)nc4)cnc3[nH]2)ccn1] |
| P-0183 | 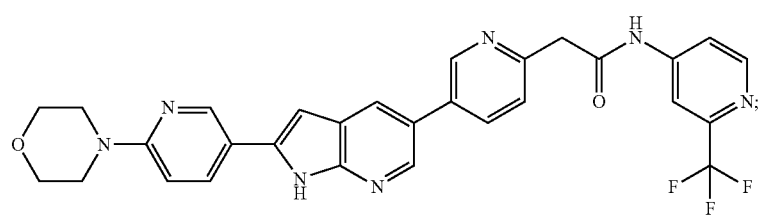 [SMILES: O=C(Cc1ccc(-c2cnc3[nH]c(-c4ccc(N5CCOCC5)nc4)cc3c2)cn1)Nc1ccnc(C(F)(F)F)c1] |

-continued

| No. | Compound Structure |
|---|---|
| P-0184 | 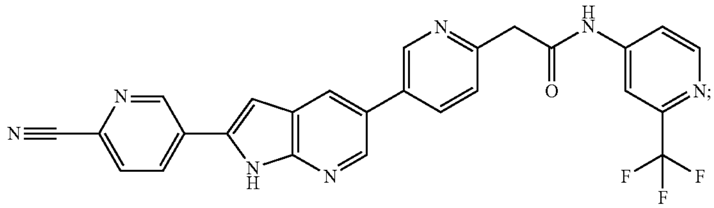 [SMILES: N#Cc1ccc(-c2cc3cc(-c4ccc(CC(=O)Nc5ccnc(C(F)(F)F)c5)nc4)cnc3[nH]2)cn1] |
| P-0185 | 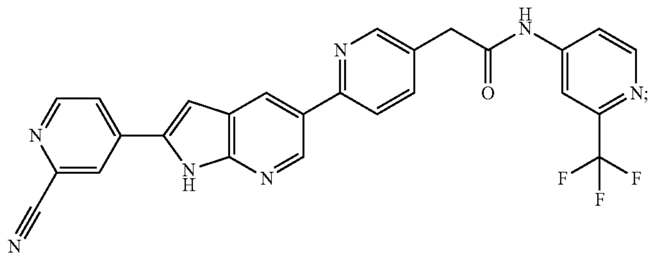 [SMILES: N#Cc1cc(-c2cc3cc(-c4ccc(CC(=O)Nc5ccnc(C(F)(F)F)c5)cn4)cnc3[nH]2)ccn1] |
| P-0186 | 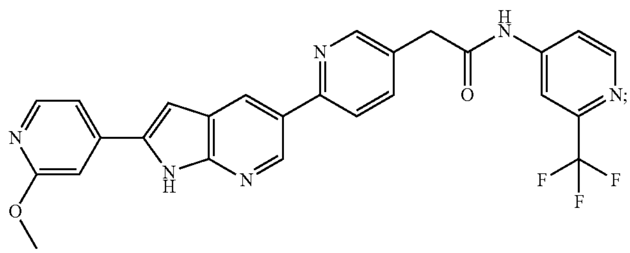 [SMILES: COc1cc(-c2cc3cc(-c4ccc(CC(=O)Nc5ccnc(C(F)(F)F)c5)cn4)cnc3[nH]2)ccn1] |
| P-0187 | 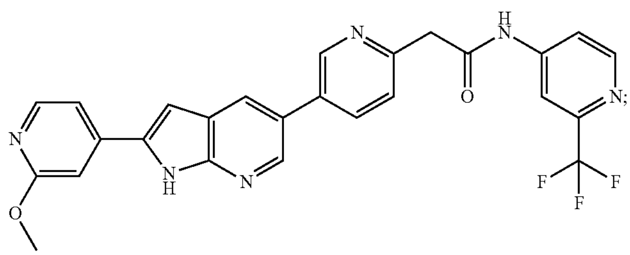 [SMILES: COc1cc(-c2cc3cc(-c4ccc(CC(=O)Nc5ccnc(C(F)(F)F)c5)nc4)cnc3[nH]2)ccn1] |
| P-0188 | 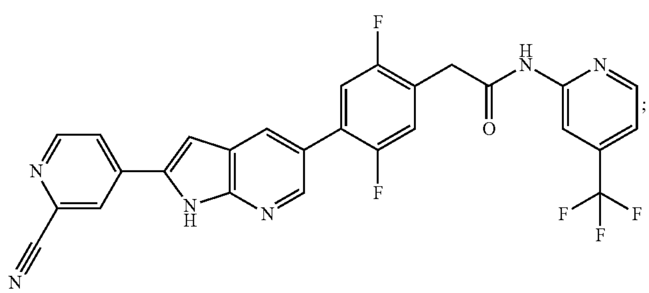 [SMILES: N#Cc1cc(-c2cc3cc(-c4cc(F)c(CC(=O)Nc5cc(C(F)(F)F)ccn5)cc4F)cnc3[nH]2)ccn1] |
| P-0189 | 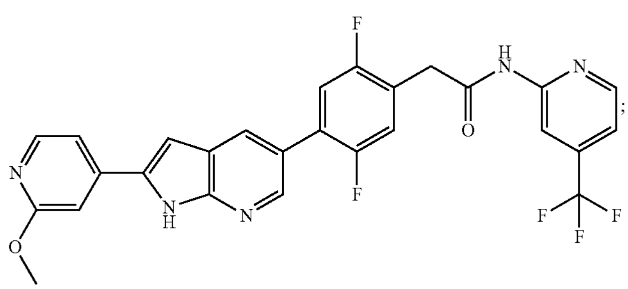 [SMILES: COc1cc(-c2cc3cc(-c4cc(F)c(CC(=O)Nc5cc(C(F)(F)F)ccn5)cc4F)cnc3[nH]2)ccn1] |

| No. | Compound Structure |
|---|---|
| P-0190 | 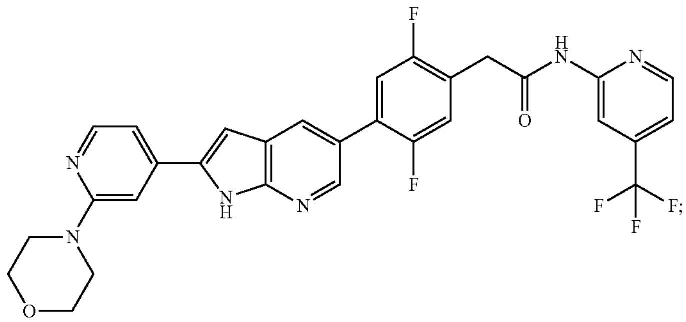 [SMILES: O=C(Cc1cc(F)c(-c2cnc3[nH]c(-c4ccnc(N5CCOCC5)c4)cc3c2)cc1F)Nc1cc(C(F)(F)F)ccn1] |
| P-0191 | 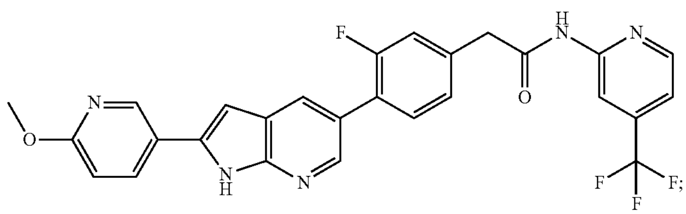 [SMILES: COc1ccc(-c2cc3cc(-c4ccc(CC(=O)Nc5cc(C(F)(F)F)ccn5)cc4F)cnc3[nH]2)cn1] |
| P-0192 | 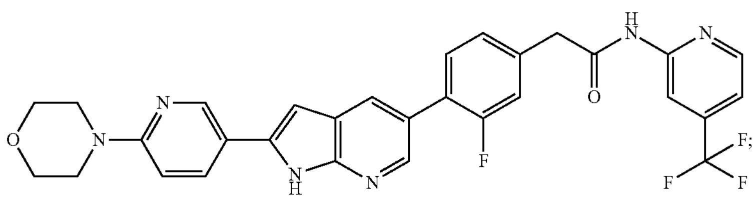 [SMILES: O=C(Cc1ccc(-c2cnc3[nH]c(-c4ccc(N5CCOCC5)nc4)cc3c2)c(F)c1)Nc1cc(C(F)(F)F)ccn1] |
| P-0193 | 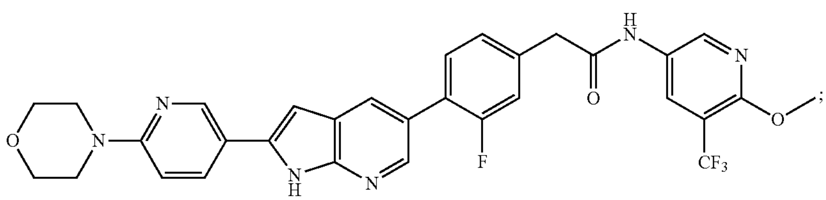 [SMILES: COc1ncc(NC(=O)Cc2ccc(-c3cnc4[nH]c(-c5ccc(N6CCOCC6)nc5)cc4c3)c(F)c2)cc1C(F)(F)F] |
| P-0194 | 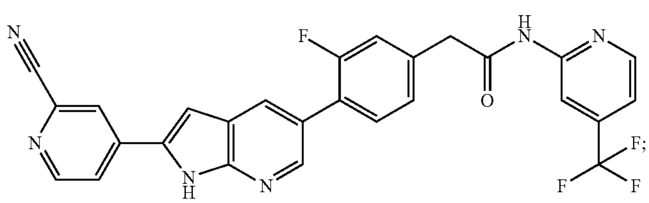 [SMILES: N#Cc1cc(-c2cc3cc(-c4ccc(CC(=O)Nc5cc(C(F)(F)F)ccn5)cc4F)cnc3[nH]2)ccn1] |
| P-0195 | 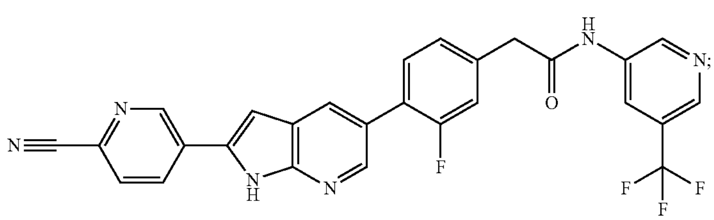 [SMILES: N#Cc1ccc(-c2cc3cc(-c4ccc(CC(=O)Nc5cncc(C(F)(F)F)c5)cc4F)cnc3[nH]2)cn1] |
| P-0196 | 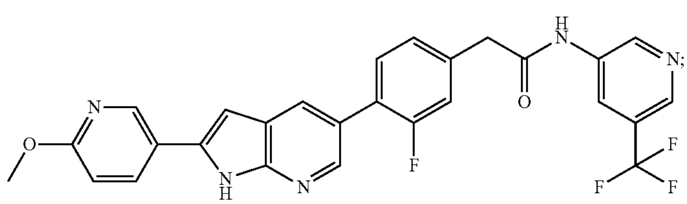 [SMILES: COc1ccc(-c2cc3cc(-c4ccc(CC(=O)Nc5cncc(C(F)(F)F)c5)cc4F)cnc3[nH]2)cn1] |

-continued
| No. | Compound Structure |
|---|---|
| P-0197 | 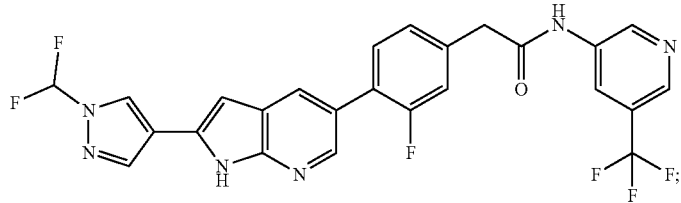 [SMILES: O=C(Cc1ccc(-c2cnc3[nH]c(-c4cnn(C(F)F)c4)cc3c2)c(F)c1)Nc1cncc(C(F)(F)F)c1] |
| P-0198 | 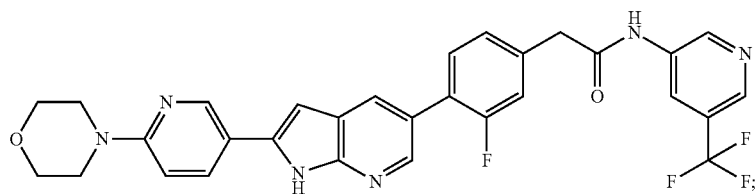 [SMILES: O=C(Cc1ccc(-c2cnc3[nH]c(-c4ccc(N5CCOCC5)nc4)cc3c2)c(F)c1)Nc1cncc(C(F)(F)F)c1] |
| P-0199 | 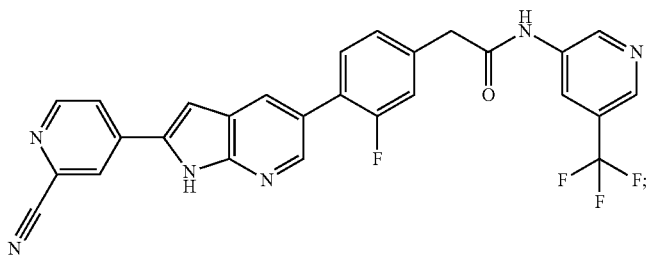 [SMILES: N#Cc1cc(-c2cc3cc(-c4ccc(CC(=O)Nc5cncc(C(F)(F)F)c5)cc4F)cnc3[nH]2)ccn1] |
| P-0200 | 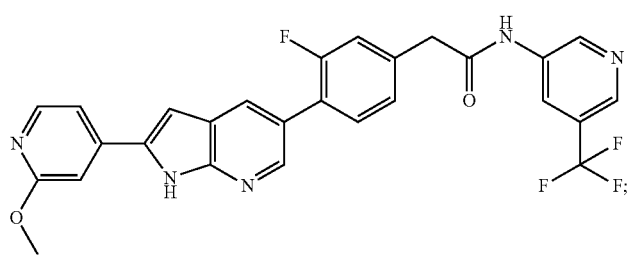 [SMILES: COc1cc(-c2cc3cc(-c4ccc(CC(=O)Nc5cncc(C(F)(F)F)c5)cc4F)cnc3[nH]2)ccn1] |
| P-0201 | 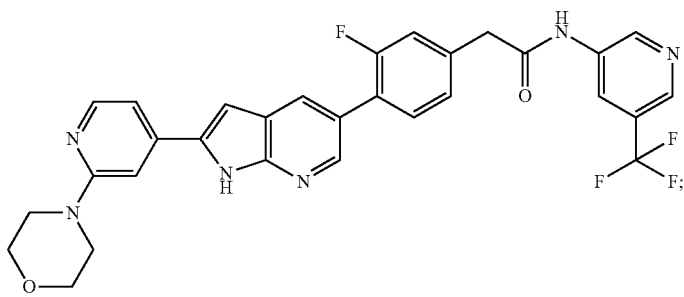 [SMILES: O=C(Cc1ccc(-c2cnc3[nH]c(-c4ccnc(N5CCOCC5)c4)cc3c2)c(F)c1)Nc1cncc(C(F)(F)F)c1] |
| P-0202 | 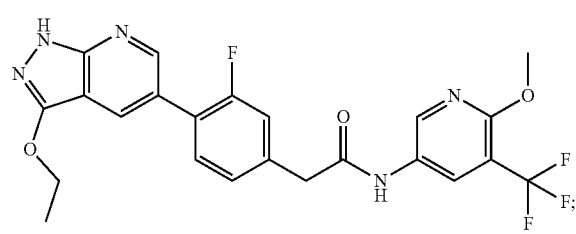 [SMILES: CCOc1n[nH]c2ncc(-c3ccc(CC(=O)Nc4cnc(OC)c(C(F)(F)F)c4)cc3F)cc12] |

-continued

| No. | Compound Structure |
|---|---|
| P-0203 | 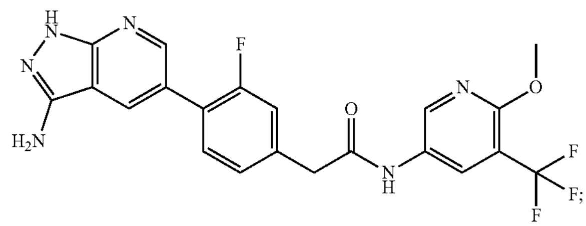 [SMILES: COc1ncc(NC(=O)Cc2ccc(-c3cnc4[nH]nc(N)c4c3)c(F)c2)cc1C(F)(F)F] |
| P-0204 | 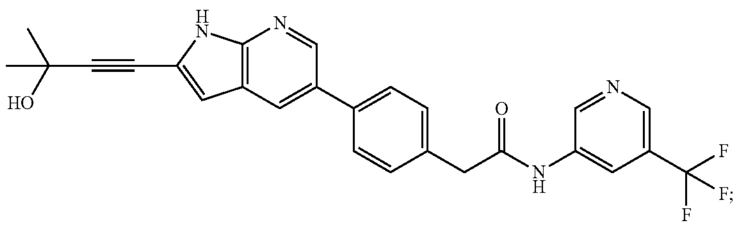 [SMILES: CC(C)(O)C#Cc1cc2cc(-c3ccc(CC(=O)Nc4cncc(C(F)(F)F)c4)cc3)cnc2[nH]1] |
| P-0205 | 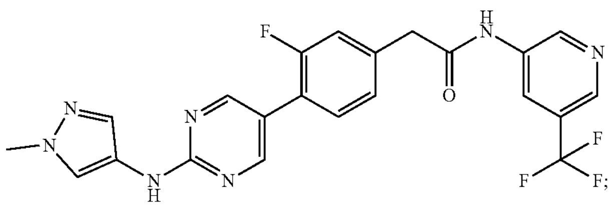 [SMILES: Cn1cc(Nc2ncc(-c3ccc(CC(=O)Nc4cncc(C(F)(F)F)c4)cc3F)cn2)cn1] |
| P-0206 | 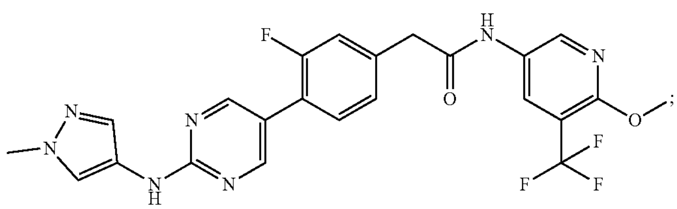 |
| P-0207 | 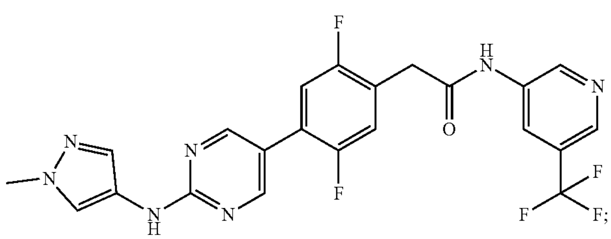 [SMILES: Cn1cc(Nc2ncc(-c3cc(F)c(CC(=O)Nc4cncc(C(F)(F)F)c4)cc3F)cn2)cn1] |
| P-0208 | 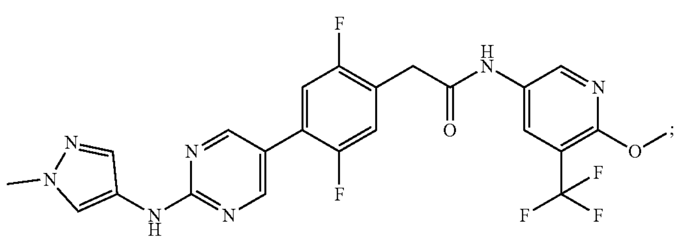 |
| P-0209 | 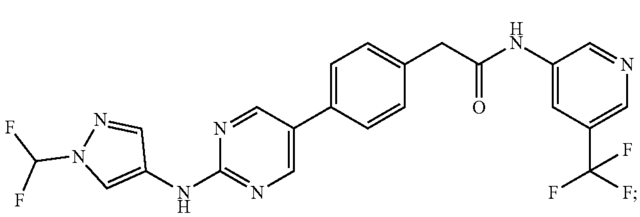 [SMILES: O=C(Cc1ccc(-c2cnc(Nc3cnn(C(F)F)c3)nc2)cc1)Nc1cncc(C(F)(F)F)c1] |

| No. | Compound Structure |
|---|---|
| P-0210 | 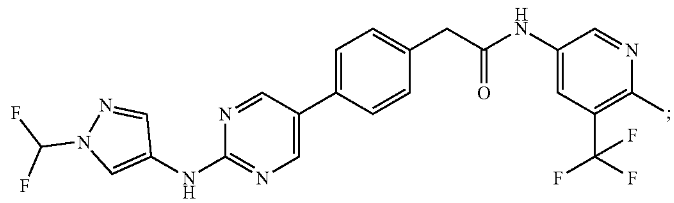 |
| P-0211 | 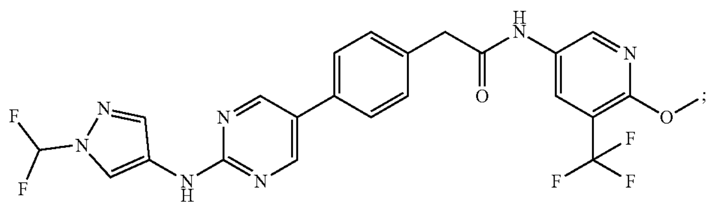 |
| P-0212 | 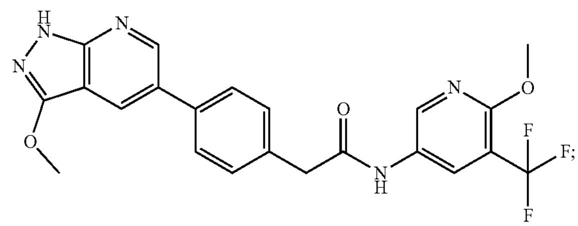 [SMILES: COc1ncc(NC(=O)Cc2ccc(-c3cnc4[nH]nc(OC)c4c3)cc2)cc1C(F)(F)F] |
| P-0213 | 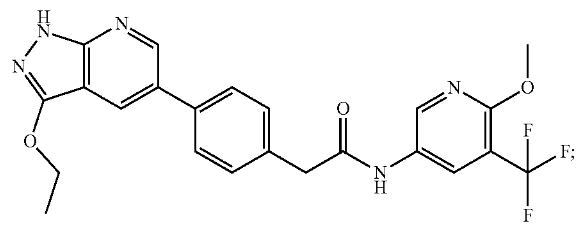 [SMILES: CCOc1n[nH]c2ncc(-c3ccc(CC(=O)Nc4cnc(OC)c(C(F)(F)F)c4)cc3)cc12] |
| P-0214 | 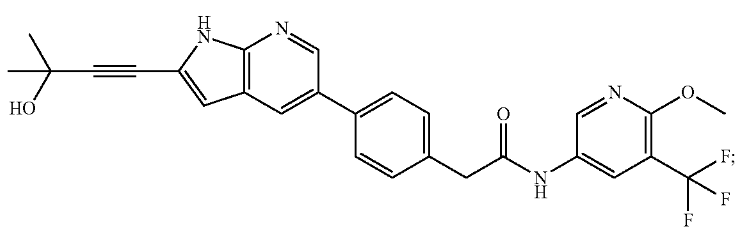 [SMILES: COc1ncc(NC(=O)Cc2ccc(-c3cnc4[nH]c(C#CC(C)(C)O)cc4c3)cc2)cc1C(F)(F)F] |
| P-0215 | 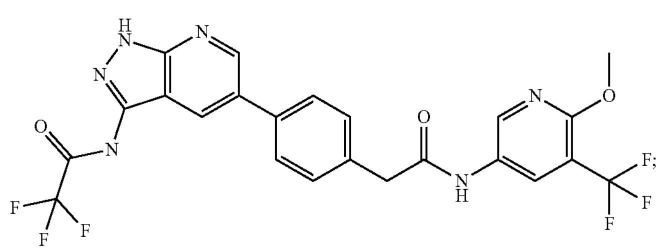 [SMILES: COc1ncc(NC(=O)Cc2ccc(-c3cnc4[nH]nc(NC(=O)C(F)(F)F)c4c3)cc2)cc1C(F)(F)F] |
| P-0216 | 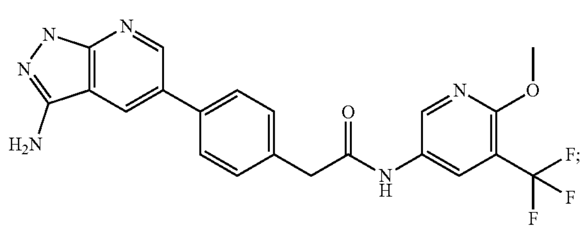 [SMILES: COc1ncc(NC(=O)Cc2ccc(-c3cnc4[nH]nc(N)c4c3)cc2)cc1C(F)(F)F] |

-continued
| No. | Compound Structure |
|---|---|
| P-0217 | 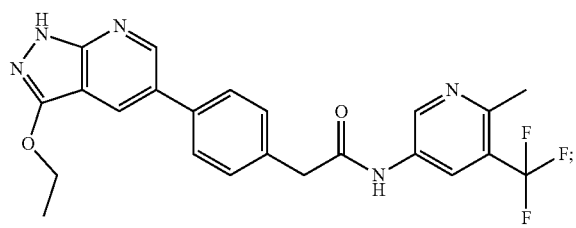 [SMILES: CCOc1n[nH]c2ncc(-c3ccc(CC(=O)Nc4cnc(C)c(C(F)(F)F)c4)cc3)cc12] |
| P-0218 | 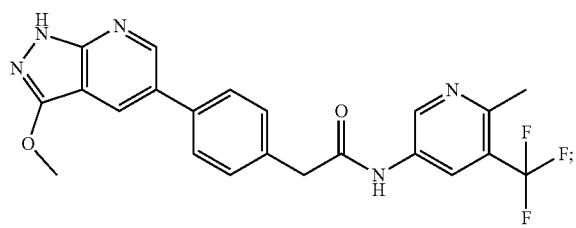 [SMILES: COc1n[nH]c2ncc(-c3ccc(CC(=O)Nc4cnc(C)c(C(F)(F)F)c4)cc3)cc12] |
| P-0219 | 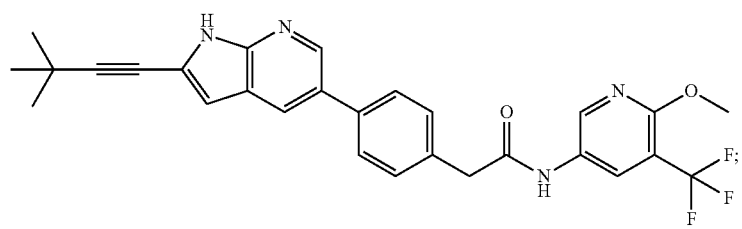 [SMILES: COc1ncc(NC(=O)Cc2ccc(-c3cnc4[nH]c(C#CC(C)(C)C)cc4c3)cc2)cc1C(F)(F)F] |
| P-0220 | 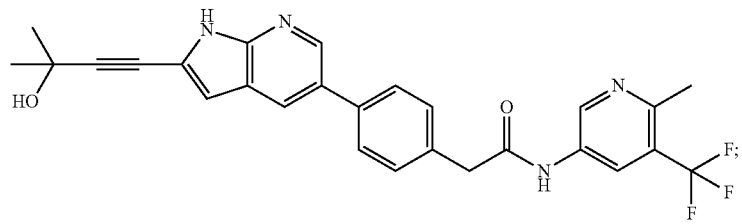 [SMILES: Cc1ncc(NC(=O)Cc2ccc(-c3cnc4[nH]c(C#CC(C)(C)O)cc4c3)cc2)cc1C(F)(F)F] |
| P-0221 | 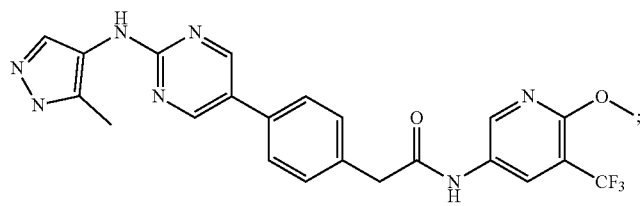 |
| P-0222 | 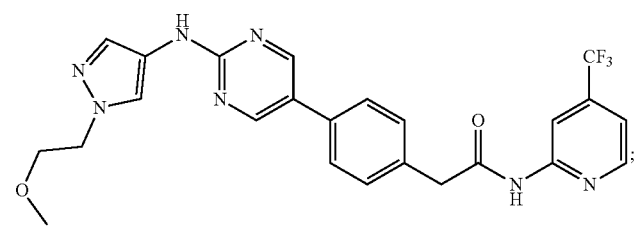 [SMILES: COCCn1cc(Nc2ncc(-c3ccc(CC(=O)Nc4cc(C(F)(F)F)ccn4)cc3)cn2)cn1] |
| P-0223 | 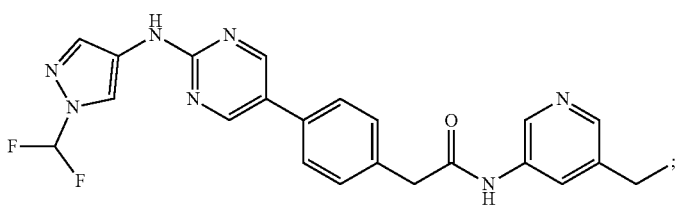 |

-continued
| No. | Compound Structure |
|---|---|
| P-0224 | 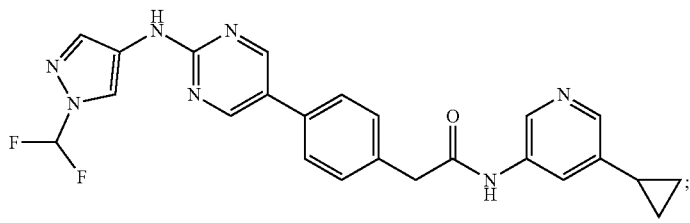 [SMILES: O=C(Cc1ccc(-c2cnc(Nc3cnn(C(F)F)c3)nc2)cc1)Nc1cncc(C2CC2)c1] |
| P-0225 | 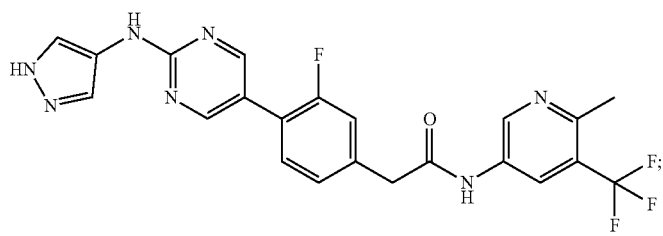 [SMILES: Cc1ncc(NC(=O)Cc2ccc(-c3cnc(Nc4cn[nH]c4)nc3)c(F)c2)cc1C(F)(F)F] |
| P-0226 | 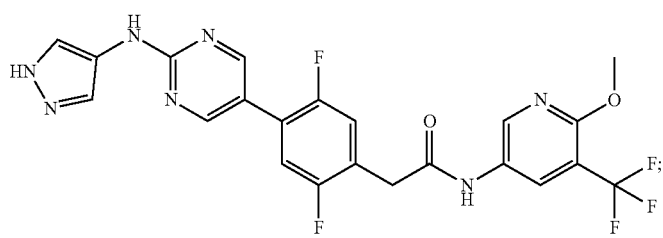 [SMILES: COc1ncc(NC(=O)Cc2cc(F)c(-c3cnc(Nc4cn[nH]c4)nc3)cc2F)cc1C(F)(F)F] |
| P-0227 | 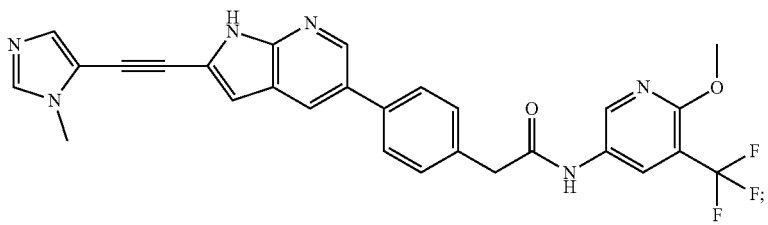 [SMILES: COc1ncc(NC(=O)Cc2ccc(-c3cnc4[nH]c(C#Cc5cncn5C)cc4c3)cc2)cc1C(F)(F)F] |
| P-0228 | 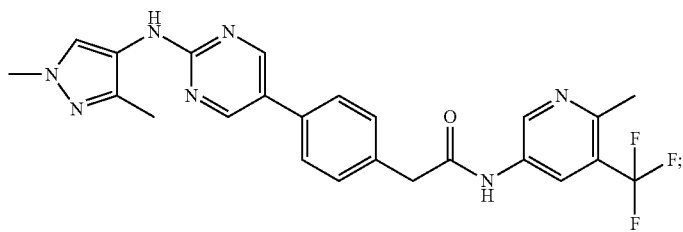 [SMILES: Cc1nn(C)cc1Nc1ncc(-c2ccc(CC(=O)Nc3cnc(C)c(C(F)(F)F)c3)cc2)cn1] |
| P-0229 | 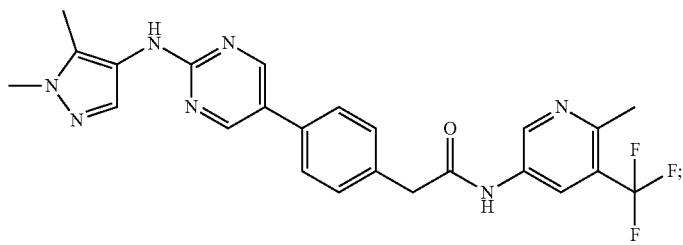 [SMILES: Cc1ncc(NC(=O)Cc2ccc(-c3cnc(Nc4cnn(C)c4C)nc3)cc2)cc1C(F)(F)F] |

| No. | Compound Structure |
|---|---|
| P-0230 | 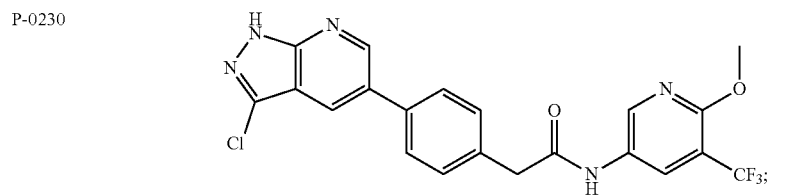 |
| P-0231 | 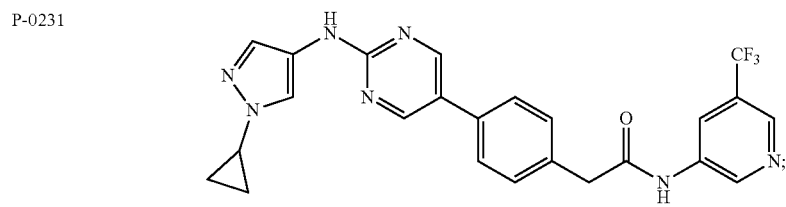 |
| P-0232 | 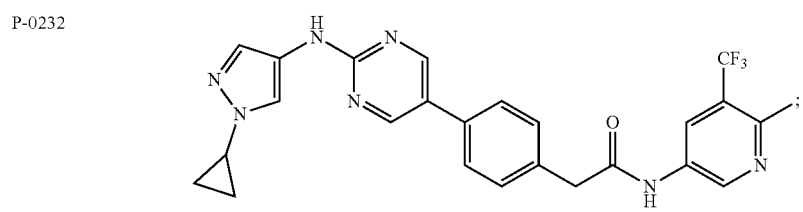 |
| P-0233 | 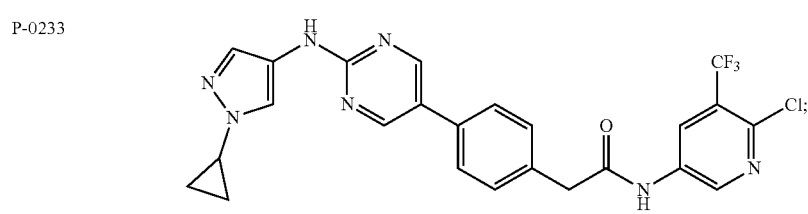 |
| P-0234 | 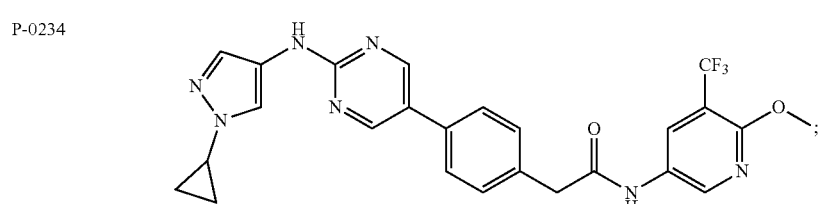 |
| P-0235 | 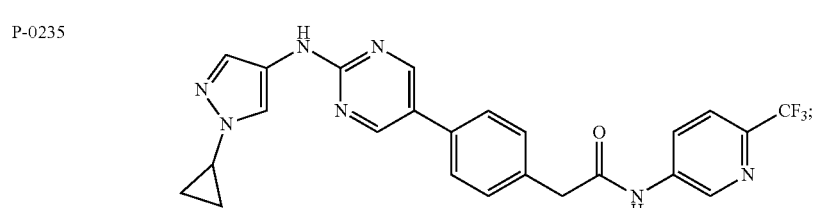 |
| P-0236 | 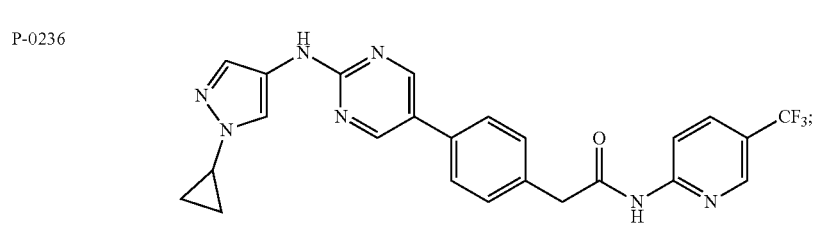 |

| No. | Compound Structure |
|---|---|
| P-0237 | (structure) |
| P-0238 | (structure) |
| P-0239 | (structure) |
| P-0240 | (structure) |
| P-0241 | (structure) |
| P-0242 | (structure) |

| No. | Compound Structure |
|---|---|
| P-0243 | 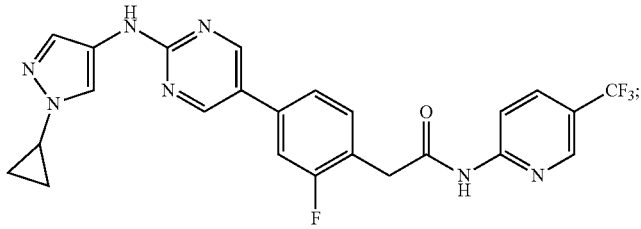 [SMILES: O=C(Cc1ccc(-c2cnc(Nc3cnn(C4CC4)c3)nc2)cc1F)Nc1ccc(C(F)(F)F)cn1] |
| P-0244 | 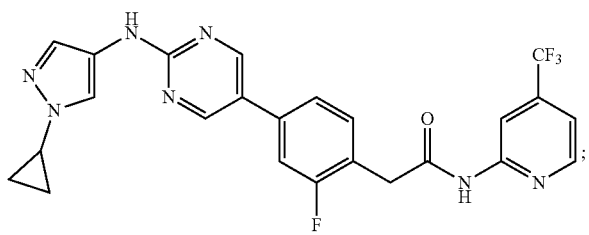 [SMILES: O=C(Cc1ccc(-c2cnc(Nc3cnn(C4CC4)c3)nc2)cc1F)Nc1cc(C(F)(F)F)ccn1] |
| P-0245 | 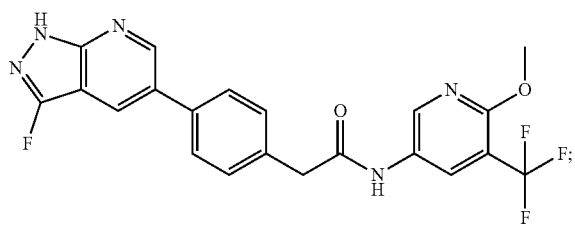 [SMILES: COc1ncc(NC(=O)Cc2ccc(-c3cnc4[nH]nc(F)c4c3)cc2)cc1C(F)(F)F] |
| P-0246 | 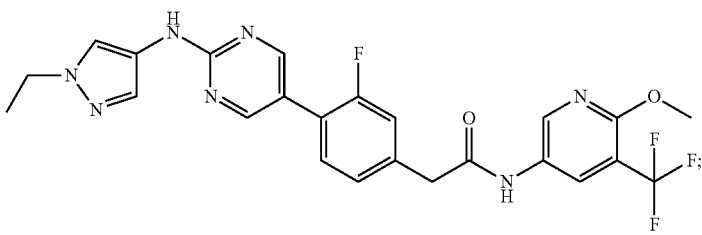 [SMILES: CCn1cc(Nc2ncc(-c3ccc(CC(=O)Nc4cnc(OC)c(C(F)(F)F)c4)cc3F)cn2)cn1] |
| P-0247 | 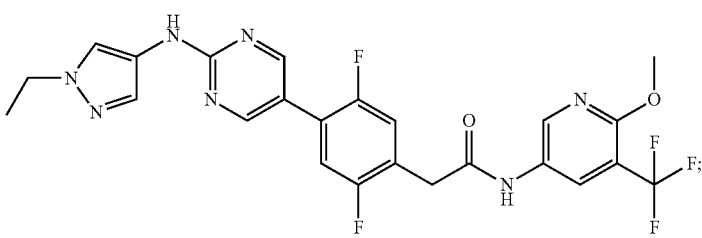 |
| P-0248 | 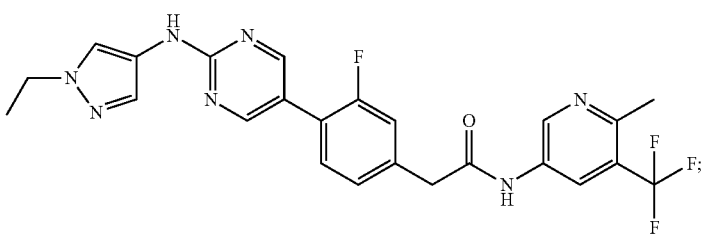 [SMILES: CCn1cc(Nc2ncc(-c3ccc(CC(=O)Nc4cnc(C)c(C(F)(F)F)c4)cc3F)cn2)cn1] |

| No. | Compound Structure |
|---|---|
| P-0249 | 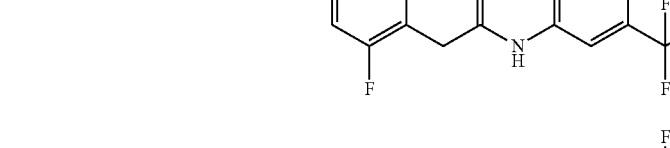 |
| P-0250 | 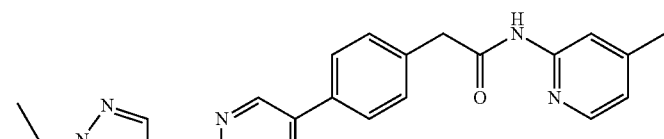 |
| P-0251 | 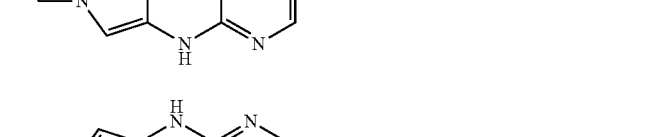 |
| P-0252 | 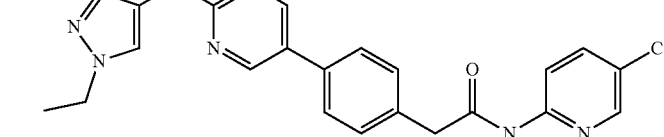 |
| P-0253 | 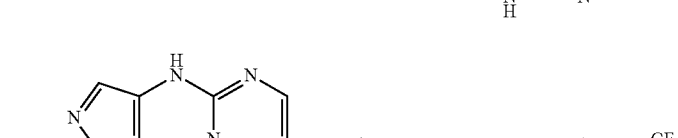 |
| P-0254 | 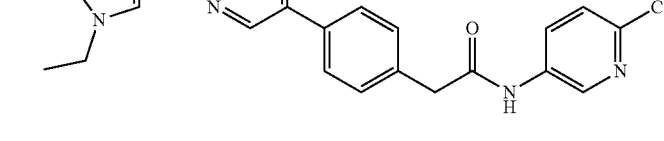 |
| P-0255 | 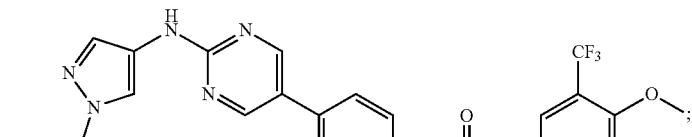 |

| No. | Compound Structure |
|---|---|
| P-0256 | 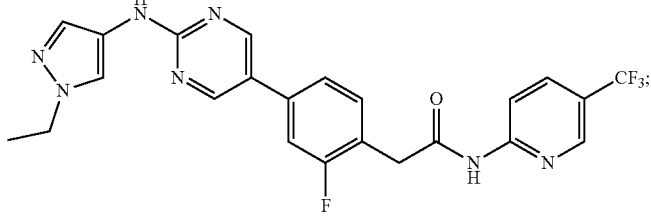 |
| P-0257 | 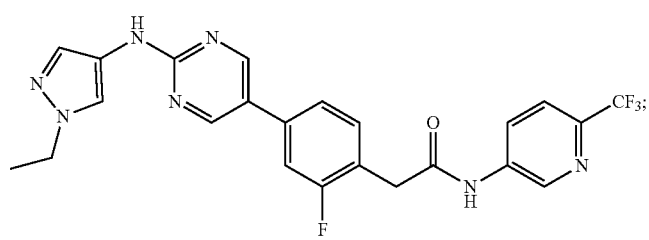 [SMILES: CCn1cc(Nc2ncc(-c3ccc(CC(=O)Nc4ccc(C(F)(F)F)nc4)c(F)c3)cn2)cn1] |
| P-0258 | 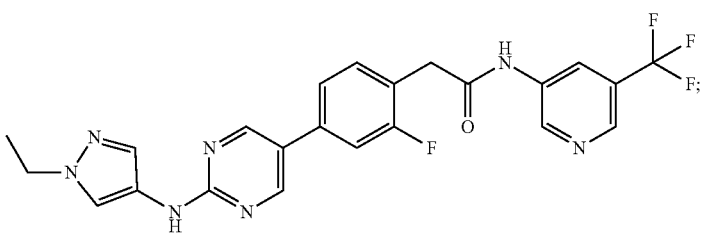 [SMILES: CCn1cc(Nc2ncc(-c3ccc(CC(=O)Nc4cncc(C(F)(F)F)c4)c(F)c3)cn2)cn1] |
| P-0259 | 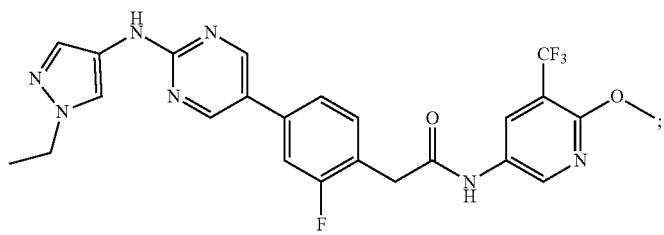 [SMILES: CCn1cc(Nc2ncc(-c3ccc(CC(=O)Nc4cnc(OC)c(C(F)(F)F)c4)c(F)c3)cn2)cn1] |
| P-0260 | 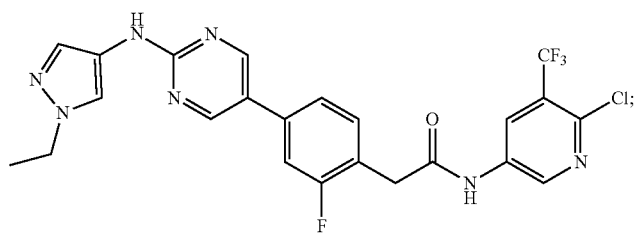 [SMILES: CCn1cc(Nc2ncc(-c3ccc(CC(=O)Nc4cnc(Cl)c(C(F)(F)F)c4)c(F)c3)cn2)cn1] |
| P-0261 | 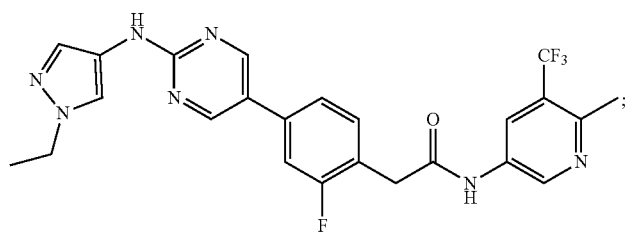 [SMILES: CCn1cc(Nc2ncc(-c3ccc(CC(=O)Nc4cnc(C)c(C(F)(F)F)c4)c(F)c3)cn2)cn1] |

| No. | Compound Structure |
|---|---|
| P-0262 | 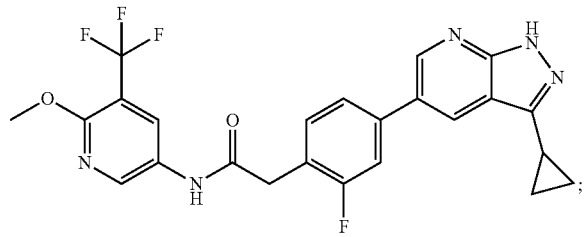 [SMILES: COc1ncc(NC(=O)Cc2ccc(-c3cnc4[nH]nc(C5CC5)c4c3)cc2F)cc1C(F)(F)F] |
| P-0263 | 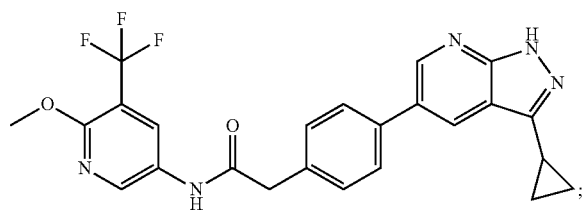 [SMILES: COc1ncc(NC(=O)Cc2ccc(-c3cnc4[nH]nc(C5CC5)c4c3)cc2)cc1C(F)(F)F] |
| P-0264 | 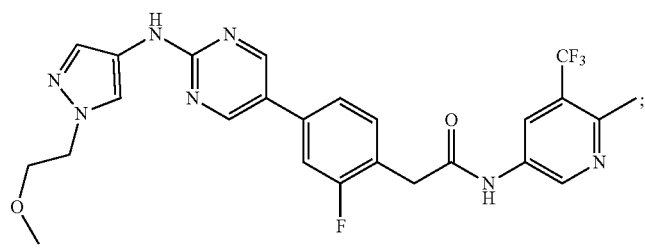 [SMILES: COCCn1cc(Nc2ncc(-c3ccc(CC(=O)Nc4cnc(C)c(C(F)(F)F)c4)c(F)c3)cn2)cn1] |
| P-0265 | 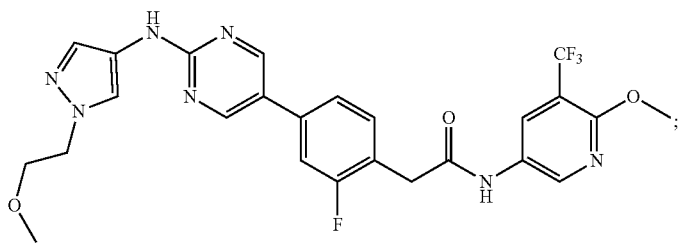 [SMILES: COCCn1cc(Nc2ncc(-c3ccc(CC(=O)Nc4cnc(OC)c(C(F)(F)F)c4)c(F)c3)cn2)cn1] |
| P-0266 | 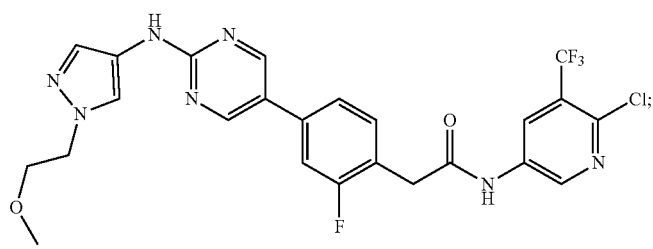 [SMILES: COCCn1cc(Nc2ncc(-c3ccc(CC(=O)Nc4cnc(Cl)c(C(F)(F)F)c4)c(F)c3)cn2)cn1] |
| P-0267 | 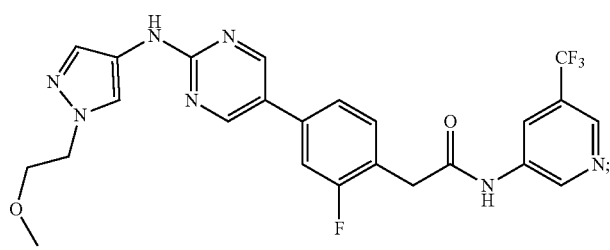 [SMILES: COCCn1cc(Nc2ncc(-c3ccc(CC(=O)Nc4cncc(C(F)(F)F)c4)c(F)c3)cn2)cn1] |

| No. | Compound Structure |
|---|---|
| P-0268 | (structure with pyrazole-NH-pyrimidine-fluorophenyl-CH2-C(O)NH-pyridine-CF3, pyrazole N-CH2CH2-O-CH3) |
| P-0269 | (structure with pyrazole-NH-pyrimidine-fluorophenyl-CH2-C(O)NH-pyridine-CF3, pyrazole N-CH2CH2-O-CH3) |
| P-0271 | (structure with pyrazole-NH-pyrimidine-phenyl-CH2-C(O)NH-pyridine with CF3 and OCH3, pyrazole N-CH2CH2-O-CH3); and |
| P-0273 | (structure with pyrazole-NH-pyrimidine-phenyl-CH2-C(O)NH-pyridine-CF3, pyrazole N-CH2CH2-O-CH3) | or a pharmaceutically acceptable salt thereof.

17. A pharmaceutical composition comprising a compound of claim 1, or a pharmaceutically acceptable salt, deuterated analog, a tautomer or a stereoisomer thereof, and a pharmaceutically acceptable carrier.

18. The pharmaceutical composition of claim 17 further comprising a second pharmaceutical agent selected from the group consisting of an anti-proliferative agent, an anti-inflammatory agent, an immunomodulatory agent and an immunosuppressive agent.

19. The pharmaceutical composition according to claim 18, wherein the second pharmaceutical agent is i) an alkylating agent selected from adozelesin, altretamine, bizelesin, busulfan, carboplatin, carboquone, carmustine, chlorambucil, cisplatin, cyclophosphamide, dacarbazine, estramustine, fotemustine, hepsulfam, ifosfamide, improsulfan, irofulven, lomustine, mechlorethamine, melphalan, oxaliplatin, piposulfan, semustine, streptozocin, temozolomide, thiotepa, and treosulfan; ii) an antibiotic selected from bleomycin, dactinomycin, daunorubicin, doxorubicin, epirubicin, idarubicin, menogaril, mitomycin, mitoxantrone, neocarzinostatin, pentostatin, and plicamycin; iii) an antimetabolite selected from the group consisting of azacitidine, capecitabine, cladribine, clofarabine, cytarabine, decitabine, floxuridine, fludarabine, 5-fluorouracil, ftorafur, gemcitabine, hydroxyurea, mercaptopurine, methotrexate, nelarabine, pemetrexed, raltitrexed, thioguanine, and trimetrexate; iv) an antibody therapy agent selected from alemtuzumab, bevacizumab, cetuximab, galiximab, gemtuzumab, nivolumab, panitumumab, pembrolizumab, pertuzumab, rituximab, tositumomab, trastuzumab, and 90 Y ibritumomab tiuxetan; v) a hormone or hormone antagonist selected from the group consisting of anastrozole, androgens, buserelin, diethylstilbestrol, exemestane, flutamide, fulvestrant, goserelin, idoxifene, letrozole, leuprolide, magestrol, raloxifene, tamoxifen, and toremifene; vi) a taxane selected from DJ-927, docetaxel, TPI 287, paclitaxel and DHA-paclitaxel; vii) a retinoid selected from alitretinoin, bexarotene, fenretinide, isotretinoin, and tretinoin; viii) an alkaloid selected from etoposide, homoharringtonine, teniposide, vinblastine, vincristine, vindesine, and vinorelbine; ix) an antiangiogenic agent selected from AE-941 (GW786034, Neovastat), ABT-510, 2-methoxyestradiol, lenalidomide, and thalidomide; x) a topoisomerase inhibitor selected from amsacrine, edotecarin, exatecan, irinotecan, SN-38 (7-ethyl-10-hydroxy-camptothecin), rubitecan, topotecan, and 9-aminocamptothecin; xi) a kinase inhibitor selected from erlotinib, gefitinib, flavopiridol, imatinib mesylate, lapatinib, sorafenib, sunitinib malate, AEE-788, AG-013736, AMG 706, AMN107, BMS-354825, BMS-599626, UCN-01 (7-hydroxystaurosporine), vemurafenib, dabrafenib, trametinib, cobimetinib selumetinib and vatalanib; xii) a targeted signal transduction inhibitor selected from bortezomib, geldanamycin, and rapamycin; xiii) a biological response modifier selected from imiquimod, interferon-α and interleukin-2; xiv) an IDO inhibitor; xv) a chemotherapeutic agent selected from 3-AP (3-amino-2-carboxyaldehyde thiosemicarbazone), altrasentan, aminoglutethimide, anagrelide, asparaginase, bryostatin-1, cilengitide, elesclomol, eribulin mesylate (E7389), ixabepilone, lonidamine, masoprocol, mitoguanazone, oblimersen, sulindac, testolactone, tiazofurin, a mTOR inhibitor, a PI3K inhibitor, a Cdk4 inhibitor, an Akt inhibitor, a Hsp90 inhibitor, a farnesyltransferase inhibitor or an aromatase inhibitor (anastrozole letrozole exemestane); xvi) a Mek inhibitor; xvii) a tyrosine kinase inhibitor; or xviii) an EGFR inhibitor.

20. A method for treatment of a disease or condition modulated by FLT3, CSF1R, or c-kit, wherein the disease is an inflammatory disease, an inflammatory condition, an autoimmune disease or cancer, said method comprising administering to a subject suffering from the disease a therapeutically effective amount of a compound of claim 1, or a pharmaceutically acceptable salt, deuterated analog, a tautomer or a stereoisomer thereof.

21. A method for treating a subject with a disease or condition mediated by FLT3, CSF1R or c-kit, said method comprising administering to the subject an effective amount of a compound of claim 1, or a pharmaceutically acceptable salt, deuterated analog, a tautomer or a stereoisomer thereof, wherein the disease or condition is acute myeloid leukemia, stem cell ablation and myelopreparation for stem cell transplant, primary progressive multiple sclerosis, Erdheim-Chester Disease, Langerhans cell histocytosis, hairy cell leukemia, HIV, glioblastoma, anterior or posterior eye disease, lysosomal storage diseases, complex regional pain syndrome, neuro-inflammation, neuroinflammatory disorders, binswager type dementia, dementia with lewy bodie, cerebral palsy, progressive supranuclear palsy, vascular dementias, multi infarct dementia, fronto temporal dementia, pseudo-dementia, bladder cancer, basal cell carcinoma, cholangiocarcinoma, colon cancer, endometrial cancer, esophageal cancer, Ewing's sarcoma, gastric cancer, glioma, hepatocellular carcinoma, Hodgkin lymphoma, laryngeal carcinoma, leukemia, liver cancer, lung cancer, melanoma, mesothelioma, pancreatic cancer, rectal cancer, renal cancer, squamous cell carcinoma, T cell lymphoma, thyroid cancer, monocytic leukemia, pheochromocytoma, malignant peripheral nerve cell tumors, malignant peripheral nerve sheath tumors (MPNST), cutaneous and plexiform neurofibromas, leiomyoadenomatoid tumor, fibroids, uterine fibroids, leiomyosarcoma, papillary thyroid cancer, anaplastic thyroid cancer, medullary thyroid cancer, follicular thyroid cancer, hurthle cell carcinoma, thyroid cancer, ascites, malignant ascites, mesothelioma, salivary gland tumors, mucoepidermoid carcinoma of the salivary gland, acinic cell carcinoma of the salivary gland, gastrointestinal stromal tumors (GIST), tumors that cause effusions in potential spaces of the body, pleural effusions, pericardial effusions, peritoneal effusions aka ascites, giant cell tumors (GCT), GCT of bone other sarcomas, tumor angiogenesis, paracrine tumor growth or tumors that express aberrantly or otherwise a FLT3 ligand, or activating mutations or translocations of any of the foregoing.

22. A method for treating a subject with a disease or condition mediated by a FLT3, CSF1R or c-kit, said method comprising administering to the subject an effective amount of a compound of claim 1, or a pharmaceutically acceptable salt, deuterated analog, a tautomer or a stereoisomer thereof, wherein the disease or condition is lysosomal storage selected from the group consisting of mucolipodosis, alpha-mannosidosis; aspartylglucosaminuria; Batten disease; beta-mannosidosis; cystinosis; Danon disease; Fabry disease; Farber disease; fucosidosis; galactosialidosis; Gaucher disease; gangliosidosis; Krabbe disease; metachromatic leukodystrophy; mucopolysaccharidoses disorders; aspartylglucosaminuria; Batten disease; beta-mannosidosis; cystinosis; Danon disease; Fabry disease; Farber disease; fucosidosis; galactosialidosis; Gaucher disease; gangliosidosis; Krabbe disease; metachromatic leukodystrophy; mucopolysaccharidoses disorders; mucolipidosis type I (Sialidosis); Mucolipidosis type II (I-Cell disease); Mucolipidosis type III (Pseudo-Hurler polydystrophy); Mucolipidosis type IV; multiple sulfatase deficiency; Niemann-Pick types A, B, C; Pompe disease (glycogen storage disease); pycnodysostosis; Sandhoff disease; Schindler disease; Salla disease/sialic acid storage disease; Tay-Sachs; and Wolman disease.

23. The method of claim 20, wherein FLT3 kinase is a mutated form comprising a FLT3 internal tandem duplication (ITD) mutation.

24. The method of claim 23, wherein mutated FLT3 kinase further comprises a D835 mutation, a F691L mutation, or both D835 and F691L mutations.

25. The method according to claim 24, wherein mutated FLT3 kinase further comprises a D835Y mutation, a F691L mutation, or both D835Y and F691L mutations.

* * * * *

UNITED STATES PATENT AND TRADEMARK OFFICE
CERTIFICATE OF CORRECTION

PATENT NO. : 10,160,747 B2
APPLICATION NO. : 15/460095
DATED : December 25, 2018
INVENTOR(S) : Jack Lin et al.

Page 1 of 1

It is certified that error appears in the above-identified patent and that said Letters Patent is hereby corrected as shown below:

In the Claims

In Claim 1, Column 241, Line 1, please replace "each $R^7$ is independently $C_1$-$C_6$ alkyl," with --each $R^7$ is independently halo, $C_1$-$C_6$ alkyl,--.

In Claim 1, Column 241, Lines 3-4, please replace "-S(O)$_2$alkyl, or a 4-6 membered heterocycoalkyl-$C_1$-$C_6$ alkyl, wherein" with -- -S(O)$_2$alkyl, 4-6 membered heterocycoalkyl-$C_1$-$C_6$ alkyl, or cyano, wherein--.

In Claim 1, Column 241, Line 5, please replace "each $R^7$ is optionally substituted" with --each $C_1$-$C_6$ alkyl, $C_1$-$C_6$ haloalkyl, $C_1$-$C_6$ alkoxy, $C_3$-$C_6$ cycloalkyl, 4-6 membered heterocycloalkyl, $C_3$-$C_6$ cycloalkylalkyl, -S(O)$_2$alkyl or 4-6 membered heterocycloalkyl- $C_1$-$C_6$ alkyl is optionally substituted--.

Signed and Sealed this
Twenty-second Day of June, 2021

Drew Hirshfeld
*Performing the Functions and Duties of the*
*Under Secretary of Commerce for Intellectual Property and*
*Director of the United States Patent and Trademark Office*

SEQUENCE LISTING

<160> NUMBER OF SEQ ID NOS: 4

<210> SEQ ID NO 1
<211> LENGTH: 993
<212> TYPE: PRT
<213> ORGANISM: Homo sapiens

<400> SEQUENCE: 1

```
Met Pro Ala Leu Ala Arg Asp Gly Gly Gln Leu Pro Leu Leu Val Val
1               5                   10                  15

Phe Ser Ala Met Ile Phe Gly Thr Ile Thr Asn Gln Asp Leu Pro Val
                20                  25                  30

Ile Lys Cys Val Leu Ile Asn His Lys Asn Asn Asp Ser Ser Val Gly
            35                  40                  45

Lys Ser Ser Ser Tyr Pro Met Val Ser Glu Ser Pro Glu Asp Leu Gly
        50                  55                  60

Cys Ala Leu Arg Pro Gln Ser Ser Gly Thr Val Tyr Glu Ala Ala Ala
65                  70                  75                  80

Val Glu Val Asp Val Ser Ala Ser Ile Thr Leu Gln Val Leu Val Asp
                85                  90                  95

Ala Pro Gly Asn Ile Ser Cys Leu Trp Val Phe Lys His Ser Ser Leu
                100                 105                 110

Asn Cys Gln Pro His Phe Asp Leu Gln Asn Arg Gly Val Val Ser Met
            115                 120                 125

Val Ile Leu Lys Met Thr Glu Thr Gln Ala Gly Glu Tyr Leu Leu Phe
        130                 135                 140

Ile Gln Ser Glu Ala Thr Asn Tyr Thr Ile Leu Phe Thr Val Ser Ile
145                 150                 155                 160

Arg Asn Thr Leu Leu Tyr Thr Leu Arg Arg Pro Tyr Phe Arg Lys Met
                165                 170                 175

Glu Asn Gln Asp Ala Leu Val Cys Ile Ser Glu Ser Val Pro Glu Pro
            180                 185                 190

Ile Val Glu Trp Val Leu Cys Asp Ser Gln Gly Glu Ser Cys Lys Glu
        195                 200                 205

Glu Ser Pro Ala Val Val Lys Lys Glu Glu Lys Val Leu His Glu Leu
    210                 215                 220

Phe Gly Thr Asp Ile Arg Cys Cys Ala Arg Asn Glu Leu Gly Arg Glu
225                 230                 235                 240

Cys Thr Arg Leu Phe Thr Ile Asp Leu Asn Gln Thr Pro Gln Thr Thr
                245                 250                 255

Leu Pro Gln Leu Phe Leu Lys Val Gly Glu Pro Leu Trp Ile Arg Cys
            260                 265                 270

Lys Ala Val His Val Asn His Gly Phe Gly Leu Thr Trp Glu Leu Glu
        275                 280                 285

Asn Lys Ala Leu Glu Glu Gly Asn Tyr Phe Glu Met Ser Thr Tyr Ser
    290                 295                 300
```

-continued

```
Thr Asn Arg Thr Met Ile Arg Ile Leu Phe Ala Phe Val Ser Ser Val
305                 310                 315                 320
Ala Arg Asn Asp Thr Gly Tyr Tyr Thr Cys Ser Ser Ser Lys His Pro
            325                 330                 335
Ser Gln Ser Ala Leu Val Thr Ile Val Glu Lys Gly Phe Ile Asn Ala
        340                 345                 350
Thr Asn Ser Ser Glu Asp Tyr Glu Ile Asp Gln Tyr Glu Glu Phe Cys
    355                 360                 365
Phe Ser Val Arg Phe Lys Ala Tyr Pro Gln Ile Arg Cys Thr Trp Thr
370                 375                 380
Phe Ser Arg Lys Ser Phe Pro Cys Glu Gln Lys Gly Leu Asp Asn Gly
385                 390                 395                 400
Tyr Ser Ile Ser Lys Phe Cys Asn His Lys His Gln Pro Gly Glu Tyr
            405                 410                 415
Ile Phe His Ala Glu Asn Asp Asp Ala Gln Phe Thr Lys Met Phe Thr
        420                 425                 430
Leu Asn Ile Arg Arg Lys Pro Gln Val Leu Ala Glu Ala Ser Ala Ser
    435                 440                 445
Gln Ala Ser Cys Phe Ser Asp Gly Tyr Pro Leu Pro Ser Trp Thr Trp
450                 455                 460
Lys Lys Cys Ser Asp Lys Ser Pro Asn Cys Thr Glu Glu Ile Thr Glu
465                 470                 475                 480
Gly Val Trp Asn Arg Lys Ala Asn Arg Lys Val Phe Gly Gln Trp Val
            485                 490                 495
Ser Ser Ser Thr Leu Asn Met Ser Glu Ala Ile Lys Gly Phe Leu Val
        500                 505                 510
Lys Cys Cys Ala Tyr Asn Ser Leu Gly Thr Ser Cys Glu Thr Ile Leu
    515                 520                 525
Leu Asn Ser Pro Gly Pro Phe Pro Phe Ile Gln Asp Asn Ile Ser Phe
530                 535                 540
Tyr Ala Thr Ile Gly Val Cys Leu Leu Phe Ile Val Val Leu Thr Leu
545                 550                 555                 560
Leu Ile Cys His Lys Tyr Lys Lys Gln Phe Arg Tyr Glu Ser Gln Leu
            565                 570                 575
Gln Met Val Gln Val Thr Gly Ser Ser Asp Asn Glu Tyr Phe Tyr Val
        580                 585                 590
Asp Phe Arg Glu Tyr Glu Tyr Asp Leu Lys Trp Glu Phe Pro Arg Glu
    595                 600                 605
Asn Leu Glu Phe Gly Lys Val Leu Gly Ser Gly Ala Phe Gly Lys Val
610                 615                 620
Met Asn Ala Thr Ala Tyr Gly Ile Ser Lys Thr Gly Val Ser Ile Gln
625                 630                 635                 640
Val Ala Val Lys Met Leu Lys Glu Lys Ala Asp Ser Ser Glu Arg Glu
            645                 650                 655
Ala Leu Met Ser Glu Leu Lys Met Met Thr Gln Leu Gly Ser His Glu
        660                 665                 670
Asn Ile Val Asn Leu Leu Gly Ala Cys Thr Leu Ser Gly Pro Ile Tyr
    675                 680                 685
Leu Ile Phe Glu Tyr Cys Cys Tyr Gly Asp Leu Leu Asn Tyr Leu Arg
690                 695                 700
Ser Lys Arg Glu Lys Phe His Arg Thr Trp Thr Glu Ile Phe Lys Glu
705                 710                 715                 720
```

His Asn Phe Ser Phe Tyr Pro Thr Phe Gln Ser His Pro Asn Ser Ser
                725                 730                 735

Met Pro Gly Ser Arg Glu Val Gln Ile His Pro Asp Ser Asp Gln Ile
            740                 745                 750

Ser Gly Leu His Gly Asn Ser Phe His Ser Glu Asp Glu Ile Glu Tyr
        755                 760                 765

Glu Asn Gln Lys Arg Leu Glu Glu Glu Asp Leu Asn Val Leu Thr
    770                 775                 780

Phe Glu Asp Leu Leu Cys Phe Ala Tyr Gln Val Ala Lys Gly Met Glu
785                 790                 795                 800

Phe Leu Glu Phe Lys Ser Cys Val His Arg Asp Leu Ala Ala Arg Asn
                805                 810                 815

Val Leu Val Thr His Gly Lys Val Val Lys Ile Cys Asp Phe Gly Leu
            820                 825                 830

Ala Arg Asp Ile Met Ser Asp Ser Asn Tyr Val Val Arg Gly Asn Ala
        835                 840                 845

Arg Leu Pro Val Lys Trp Met Ala Pro Glu Ser Leu Phe Glu Gly Ile
    850                 855                 860

Tyr Thr Ile Lys Ser Asp Val Trp Ser Tyr Gly Ile Leu Leu Trp Glu
865                 870                 875                 880

Ile Phe Ser Leu Gly Val Asn Pro Tyr Pro Gly Ile Pro Val Asp Ala
                885                 890                 895

Asn Phe Tyr Lys Leu Ile Gln Asn Gly Phe Lys Met Asp Gln Pro Phe
            900                 905                 910

Tyr Ala Thr Glu Glu Ile Tyr Ile Ile Met Gln Ser Cys Trp Ala Phe
        915                 920                 925

Asp Ser Arg Lys Arg Pro Ser Phe Pro Asn Leu Thr Ser Phe Leu Gly
    930                 935                 940

Cys Gln Leu Ala Asp Ala Glu Glu Ala Met Tyr Gln Asn Val Asp Gly
945                 950                 955                 960

Arg Val Ser Glu Cys Pro His Thr Tyr Gln Asn Arg Arg Pro Phe Ser
                965                 970                 975

Arg Glu Met Asp Leu Gly Leu Leu Ser Pro Gln Ala Gln Val Glu Asp
            980                 985                 990

Ser

<210> SEQ ID NO 2
<211> LENGTH: 3848
<212> TYPE: DNA
<213> ORGANISM: Homo sapiens

<400> SEQUENCE: 2
acctgcagcg cgaggcgcgc cgctccaggc ggcatcgcag ggctgggccg gcgcggcctg      60
gggaccccgg gctccggagg ccatgccggc gttggcgcgc gacggcggcc agctgccgct     120
gctcgttgtt ttttctgcaa tgatatttgg gactattaca aatcaagatc tgcctgtgat     180
caagtgtgtt ttaatcaatc ataagaacaa tgattcatca gtggggaagt catcatcata     240
tcccatggta tcagaatccc cggaagacct cgggtgtgcg ttgagacccc agagctcagg     300
gacagtgtac gaagctgccg ctgtggaagt ggatgtatct gcttccatca cactgcaagt     360
gctggtcgac gccccaggga acatttcctg tctctgggtc tttaagcaca gctccctgaa     420
ttgccagcca catttcgatt tacaaaaacag aggagttgtt tccatggtca ttttgaaaat     480
gacagaaacc caagctggag aatacctact ttttattcag agtgaagcta ccaattacac     540

```
aatattgttt acagtgagta taagaaatac cctgctttac acattaagaa gaccttactt      600
tagaaaaatg gaaaccagg acgccctggt ctgcatatct gagagcgttc cagagccgat       660
cgtggaatgg gtgctttgcg attcacaggg ggaaagctgt aaagaagaaa gtccagctgt      720
tgttaaaaag gaggaaaaag tgcttcatga attatttggg acggacataa ggtgctgtgc      780
cagaaatgaa ctgggcaggg aatgcaccag gctgttcaca atagatctaa atcaaactcc      840
tcagaccaca ttgccacaat tatttcttaa agtaggggaa cccttatgga taaggtgcaa      900
agctgttcat gtgaaccatg gattcgggct cacctgggaa ttagaaaaca aagcactcga      960
ggagggcaac tactttgaga tgagtaccta ttcaacaaac agaactatga tacggattct     1020
gtttgctttt gtatcatcag tggcaagaaa cgacaccgga tactacactt gttcctcttc     1080
aaagcatccc agtcaatcag ctttggttac catcgtagaa aagggattta taaatgctac     1140
caattcaagt gaagattatg aaattgacca atatgaagag ttttgttttt ctgtcaggtt     1200
taaagcctac ccacaaatca gatgtacgtg gaccttctct cgaaaatcat ttccttgtga     1260
gcaaaagggt cttgataacg gatacagcat atccaagttt tgcaatcata agcaccagcc     1320
aggagaatat atattccatg cagaaaatga tgatgcccaa tttaccaaaa tgttcacgct     1380
gaatataaga aggaaacctc aagtgctcgc agaagcatcg gcaagtcagg cgtcctgttt     1440
ctcggatgga tacccattac catcttggac ctggaagaag tgttcagaca agtctcccaa     1500
ctgcacagaa gagatcacag aaggagtctg gaatagaaag gctaacagaa aagtgtttgg     1560
acagtgggtg tcgagcagta ctctaaacat gagtgaagcc ataaaagggt tcctggtcaa     1620
gtgctgtgca tacaattccc ttggcacatc ttgtgagacg atcctttaa actctccagg      1680 cccctttcct ttcatccaag acaacatctc attctatgca acaattggtg tttgtctcct     1740
cttcattgtc gttttaaccc tgctaatttg tcacaagtac aaaaagcaat ttaggtatga     1800
aagccagcta cagatggtac aggtgaccgg ctcctcagat aatgagtact tctacgttga     1860
tttcagagaa tatgaatatg atctcaaatg ggagtttcca agagaaaatt tagagtttgg     1920
gaaggtacta ggatcaggtg cttttggaaa agtgatgaac gcaacagctt atggaattag     1980
caaaacagga gtctcaatcc aggttgccgt caaaatgctg aaagaaaaag cagacagctc     2040
tgaaagagag gcactcatgt cagaactcaa gatgatgacc cagctgggaa gccacgagaa     2100
tattgtgaac ctgctggggg cgtgcacact gtcaggacca atttacttga ttttttgaata     2160 ctgttgctat ggtgatcttc tcaactatct aagaagtaaa agagaaaaat ttcacaggac     2220
ttggacagag attttcaagg aacacaattt cagttttta ccccactttcc aatcacatcc      2280 aaattccagc atgcctggtt caagagaagt tcagatacac ccggactcgg atcaaatctc     2340
agggcttcat gggaattcat ttcactctga agatgaaatt gaatatgaaa accaaaaaag     2400
gctggaagaa gaggaggact tgaatgtgct tacatttgaa gatcttcttt gctttgcata     2460
tcaagttgcc aaaggaatgg aatttctgga atttaagtcg tgtgttcaca gagacctggc     2520
cgccaggaac gtgcttgtca cccacgggaa agtggtgaag atatgtgact ttggattggc     2580
tcgagatatc atgagtgatt ccaactatgt tgtcaggggc aatgcccgtc tgcctgtaaa     2640
atggatggcc cccgaaagcc tgtttgaagg catctacacc attaagagtg atgtctggtc     2700
atatggaata ttactgtggg aaatcttctc acttggtgtg aatccttacc ctggcattcc     2760
ggttgatgct aacttctaca aactgattca aaatggattt aaaatggatc agccattta      2820
```

```
tgctacagaa gaaatataca ttataatgca atcctgctgg gcttttgact caaggaaacg    2880
gccatccttc cctaatttga cttcgttttt aggatgtcag ctggcagatg cagaagaagc    2940
gatgtatcag aatgtggatg gccgtgtttc ggaatgtcct cacacctacc aaaacaggcg    3000
acctttcagc agagagatgg atttggggct actctctccg caggctcagg tcgaagattc    3060
gtagaggaac aatttagttt taaggacttc atccctccac ctatccctaa caggctgtag    3120
attaccaaaa caagattaat ttcatcacta aaagaaaatc tattatcaac tgctgcttca    3180
ccagactttt ctctagaagc tgtctgcgtt tactcttgtt ttcaaaggga cttttgtaaa    3240
atcaaatcat cctgtcacaa ggcaggagga gctgataatg aactttattg gagcattgat    3300
ctgcatccaa ggccttctca ggctggcttg agtgaattgt gtacctgaag tacagtatat    3360
tcttgtaaat acataaaaca aaagcatttt gctaaggaga agctaaatatg atttttttaag    3420 tctatgtttt aaaataatat gtaaatttt cagctattta gtgatatatt ttatgggtgg    3480
gaataaaatt tctactacag aattgcccat tattgaatta tttacatggt ataattaggg    3540
caagtcttaa ctggagttca cgaaccccct gaaattgtgc acccatagcc acctacacat    3600
tccttccaga gcacgtgtgc ttttacccca agatacaagg aatgtgtagg cagctatggt    3660
tgtcacagcc taagatttct gcaacaacag gggttgtatt gggggaagtt tataatgaat    3720
aggtgttcta ccataaagag taatacatca cctagacact ttggcggcct tcccagactc    3780
agggccagtc agaagtaaca tggaggatta gtattttcaa taaagttact cttgtcccca    3840
caaaaaaa                                                             3848
```

<210> SEQ ID NO 3
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 3

His His His His His His
1               5

<210> SEQ ID NO 4
<211> LENGTH: 54
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Gly Gly Glu Glu Glu Glu Tyr Glu Glu Glu Glu Tyr Glu Glu Glu Glu
1               5                   10                  15

Tyr Glu Glu Glu Glu Tyr Glu Glu Glu Glu Tyr Glu Glu Glu Glu Tyr
                20                  25                  30

Glu Glu Glu Glu Tyr Glu Glu Glu Glu Tyr Glu Glu Glu Glu Tyr Glu
        35                  40                  45

Glu Glu Glu Tyr Glu Glu
    50